(12) United States Patent
Shacham et al.

(10) Patent No.: US 8,513,230 B2
(45) Date of Patent: Aug. 20, 2013

(54) NUCLEAR TRANSPORT MODULATORS AND USES THEREOF

(75) Inventors: Sharon Shacham, Newton, MA (US); Michael Kauffman, Newton, MA (US); Vincent P. Sandanayaka, Northboro, MA (US); Sharon Shechter, Andover, MA (US)

(73) Assignee: Karyopharm Therapeutics, Inc., Newton, MA (US)

( * ) Notice: Subject to any disclaimer, the term of this patent is extended or adjusted under 35 U.S.C. 154(b) by 0 days.

(21) Appl. No.: 13/041,377

(22) Filed: Mar. 5, 2011

(65) Prior Publication Data

US 2011/0275607 A1    Nov. 10, 2011

Related U.S. Application Data

(60) Provisional application No. 61/310,810, filed on Mar. 5, 2010, provisional application No. 61/383,275, filed on Sep. 15, 2010.

(51) Int. Cl.
*A61K 31/4245* (2006.01)
*A61P 9/10* (2006.01)
*C07D 413/06* (2006.01)
*C07D 413/14* (2006.01)

(52) U.S. Cl.
USPC ............... 514/210.2; 514/383; 548/262.2; 548/268.4

(58) Field of Classification Search
USPC ........................... 514/383; 548/262.2
See application file for complete search history.

(56) References Cited

U.S. PATENT DOCUMENTS

| 5,153,201 | A | 10/1992 | Aono et al. |
| 2003/0018025 | A1 | 1/2003 | Thurkauf et al. |
| 2012/0258986 | A1 | 10/2012 | Sandanayaka et al. |

FOREIGN PATENT DOCUMENTS

| EP | 2 090 570 A1 | 8/2009 |
| WO | WO 2011/109799 A1 | 9/2011 |
| WO | WO 2012/099807 | 7/2012 |
| WO | WO 2013/019548 | 2/2013 |
| WO | WO 2013/019561 A1 | 2/2013 |

OTHER PUBLICATIONS

Modzelewska-Banachiewicz, et al., Eur. J. Med. Chem., 39(2004), pp. 873-877 (published online Sep. 2004).*
Modzelewska-Banachiewicz, et al., Monatsh. Chem., 2009, 140, pp. 439-444 (published online Oct. 2008).*
Patani et al., Chem Rev, 1996, vol. 96 (8), especially p. 3149.*
Van Neck, et al., Bioorgan. Med. Chem., 16, 2008, 9487-9497.*
International Search Report for PCT/US11/27328 mailed Apr. 29, 2011.
Written Opinion for PCT/US11/27328 mailed Apr. 29, 2011.
Van Neck et al., "Inhibition of the CRM-1-mediated nucleocytoplasmic transport by N-azolylacrylates: Structure-activity relationship and mechanism of action", Bioorganic & Medicinal Chemistry, 16: 9487-9497, 2008.
Kau et al., "A chemical genetic screen identifies inhibitors of regulated nuclear export of a Forkhead transcription factor in PTEN-deficient tumor cells", Cancer Cell, pp. 463-476, 2003.
Monecke et al., "Crystal Structure of the Nuclear Export Receptor CRM-1 in Complex with Snurportin1 and RanGTP", Science, 324: 1087-1091, 2009.
Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Cai, X., et al., "Inhibition of Thr-55 phosphorylation restores p53 nuclear localization and sensitizes cancer cells to DNA damage", PNAS, 105(44):16958-16963 (Nov. 4, 2008).
Cronshaw, J.M., et al., "The nuclear pore complex: disease associations and functional correlations", TRENDS Endocrin Metab. 15:34-39 (2004).
Daelemans, D., et al., "A synthetic HIV-1 Rev inhibitor interfering with the CRM1-mediated nuclear export", PNAS, 99(22):14440-14445 (Oct. 29, 2002).
Davis, J.R., et al., "Controlling protein compartmentalization to overcome disease" Pharmaceut Res., 24:17-27 (2007).
Falini, B., et al., "Both carboxy-terminus NES motif and mutated tryptophan(2) are crucial for aberrant nuclear export of nucleophosmin leukemic mutants in NPMc+ AML", Blood Journal, 107(11):45144523, (Jun. 1, 2006).
Freundt, E.C., et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R., et al., "The Respiratory Syncytial Virus Matrix Protein Possesses a Crm1-Mediated Nuclear Export Mechanism", Journal of Virology, 83(11):5353-5362 (Jun. 2009).
Ghosh, C.C., et al., "Analysis of nucleocytoplasmic shuttling of NF kappa B proteins in human leukocytes", Methods Mol. Biol. 457:279-92. (2008).
Gupta, N., et. al., "Retinal tau pathology in human glaucomas" Can J Ophthalmol. 43(1):53-60 (Feb. 2008).

(Continued)

Primary Examiner — Susannah Chung
(74) Attorney, Agent, or Firm — Hamilton, Brook, Smith & Reynolds, PC

(57) ABSTRACT

The invention generally relates to the field of nuclear transport modulators, e.g., CRM1 inhibitors, and more particularly to new substituted-heterocyclic azole compounds, the synthesis and use of these compounds and their pharmaceutical compositions, e.g., in the treatment, modulation and/or prevention of physiological conditions associated with CRM1 activity such as in treating cancer and other neoplastic disorders, inflammatory diseases, disorders of abnormal tissue growth and fibrosis including cardiomyopathy, pulmonary fibrosis, hepatic fibrosis, glomerulonephritis, and other renal disorders, and for the treatment of viral infections (both acute and chronic).

7 Claims, 7 Drawing Sheets

(56) References Cited

OTHER PUBLICATIONS

Hoshino, L., et al., "Combined effects, of p53 gene therapy and leptomyein B in human esophageal squamous cell carcinoma", *Oncology*, 75:113-119 ((2008).

International Search Report for International Application No. PCT/US2012/048368 dated Sep. 21, 2009.

International Search Report for International Application No. PCT/US2012/048319 dated Jul. 29, 2011.

Lain, S. et al., "An inhibitor of nuclear export activates the p53 response and induces the localization of HDM2 and p53 to U1A-positive nuclear bodies associated with the PODs", *Exp Cell Res.* 248:457-472 (1999).

Lain, S. et al., "Accumulating active p53 in the nucleus by inhibition of nuclear export: a novel strategy to promote the p53 tumor suppressor function", *Exp Cell Res.* 253:315 (1999).

Modzelewska-Banachiewicz, B., et al., "Synthesis and biological activity of (Z) and (E) isomers of 3-(3,4-diaryl-1-1,2,4-triazole-5-yl)prop-2-enoic acid" *Monatsh Chem.* 140:439-444 (2009).

Modzelewska-Banachiewicz, B., et al., "Synthesis and biological activity of new derivatives of 3-(3,4-diaryl-1-1,2,4-triazole-5-yl)propenoic acid" *European Journal of Medicinal Chemistry*, 39:873-877 (2004).

Muller, P.A.J., et al., "Nuclear-Cytosolic Transport of COMMD1 Regulates NF-κB and HIF-1 Activity", *Traffic*, 10:514-527 (2009).

Mutka, S., et al., "Nuclear export inhibitors (NEIs) as novel cancer therapeutics", *98th AACr Ann. Mtg.*, 2 pgs (Apr. 14-18, 2007).

Nakahara, J., et al., "Abnormal expression of TIP30 and arrested nucleocytoplasmic transport within oligodendrocyte precursor cells in multiple sclerosis", *Journal of Clinical Investigation*, 119(1):169-181 (Jan. 2009).

Noske, A., et al., "Expression of the Nuclear Export Protein Chromosomal Region Maintenance/Exportin 1/Xpo1 Is a Prognostic Factor in Human Ovarian Cancer", *Cancer*, 112(8):1733-1743 (Apr. 15, 2008).

Notification of Transmittal of the International Search Report and The Written Opinion of the International Searching Authority, or the Declaration for International Application No. PCT/US2012/021406 dated Apr. 30, 2012.

Patani, G.A., et al., "Bioisosterism: A Rational Approach in Drug Design", *Amer. Chem. Soc.*, 96:3147-3176 (1996).

Rawlinson, S.M., et al., "CRM1-mediated Nuclear Export of Dengue Virus RNA Polymerase NS5 Modulates Interleukin-8 Induction and Virus Production", *Journal of Biological Chemistry*, 284(23):15589-15597 (Jun. 5, 2009).

Sanchez, V., et al., "Nuclear Export of the Human Cytomegalovirus Tegument Protein pp65 Requires Cyclin-Dependent Kinase Activity and the Crm1 Exporter", *Journal of Virology*, 81(21):11730-11736 (Nov. 2007).

Sorokin, A.V., et al., "Nucleocytoplasmic Transport of Proteins", *Biochemistry*, 72(13):1439-1457 (2007).

Terry, L.J., et al., "Crossing the Nuclear Envelope: Hierarchical Regulation of Nucleocytoplasmic Transport", *Science*, 318:1412-1416(Nov. 30, 2007).

van der Watt, P.J., et al., "The Karyopherin proteins, Crm1 and Karyopherin β1, are overexpressed in cervical cancer and are critical for cancer cell survival and proliferation", *Int. J. Cancer*, 124:1829-1840 (2009).

Walsh, Jr., M.D., et al., Exportin 1 Inhibition Attenuates Nuclear Factor-κB-Dependent Gene Expression, *Shock*, 29(2):160-166 (2008).

Williams, P., et al., "Characterization of a CRM1-Dependent Nuclear Export Signal in the C Terminus of Herpes Simplex Virus Type 1 Tegument Protein UL47", *Journal of Virology*, 82(21):10946-10952 (Nov. 2008).

Yao, Y., et al., "The expression of CRM1 is associated with prognosis in human osteosarcoma", *Oncology Reports*, 21:229-235 (2009).

Zimmerman, T.L., et al., "Nuclear Export of Retinoid X Receptor α in Response to Interleukin-1β-mediated Cell Signaling", *The Journal of Biological Chemistry*, 281(22):15434-15440 (Jun. 2, 2006.).

\* cited by examiner

FIGURE 2, continued
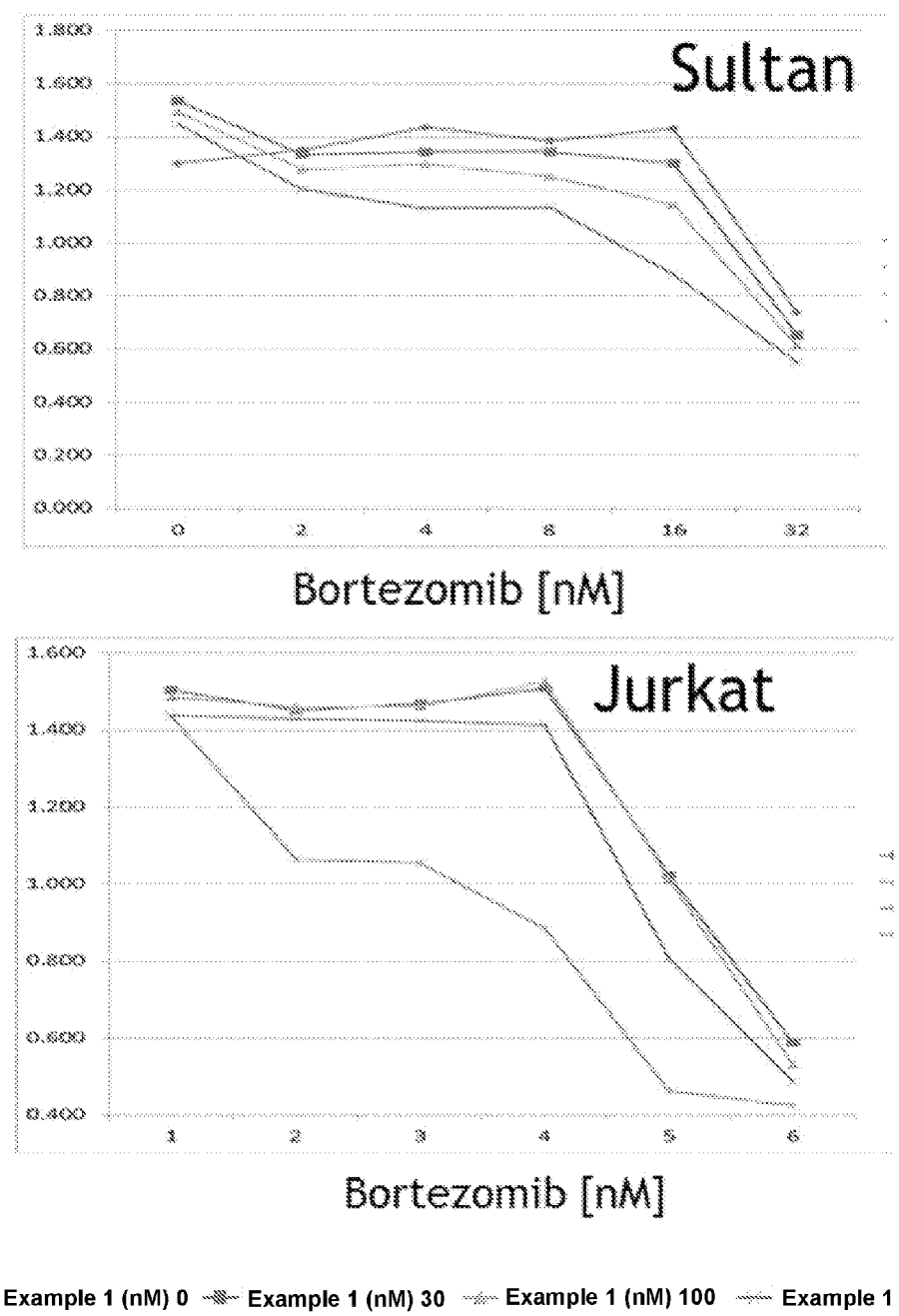

Example 3 Induced Cytotoxicity in Cancer Cell Lines

NUCLEAR TRANSPORT MODULATORS AND USES THEREOF

RELATED APPLICATIONS

The present application claims priority to U.S. provisional application Ser. Nos. 61/310,810, filed Mar. 5, 2010 and 61/383,275, filed Sep. 15, 2010, the entirety of each of which is hereby incorporated herein by reference.

TECHNICAL FIELD OF THE INVENTION

The present invention relates to compounds useful as nuclear transport modulators. The invention also provides pharmaceutically acceptable compositions comprising compounds of the present invention and methods of using said compositions in the treatment of various disorders.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al, 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al, 2008; Hoshino et al 2008; Lain et al 1999a; Lain et al 1999b; Smart et al 1999), can restore sensitivity of cancer cells to DNA damaging agents (Cai et al, 2008), and can lead to regression of established tumors (Sharpless & DePinho 2007, Xue et al, 2007). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009). Crm1 inhibition may provide particularly interesting utility in familial cancer syndromes (e.g., Li-Fraumeni Syndrome due to loss of one p53 allele, BRCA1 or 2 cancer syndromes), where specific tumor suppressor proteins (TSP) are deleted or dysfunctional and where increasing TSP levels by systemic (or local) administration of Crm1 inhibitors could help restore normal tumor suppressor function.

Specific proteins and RNAs are carried into and out of the nucleus by specialized transport molecules, which are classified as importins if they transport molecules into the nucleus, and exportins if they transport molecules out of the nucleus (Terry et al, 2007; Sorokin et al 2007). Proteins that are transported into or out of the nucleus contain nuclear import/localization (NLS) or export (NES) sequences that allow them to interact with the relevant transporters. Chromosomal Region Maintenance 1 (Crm1), which is also called exportin-1 or Xpo1, is a major exportin.

Overexpression of Crm1 has been reported in several tumors, including human ovarian cancer (Noske et al, 2008), cervical cancer (van der Watt et al, 2009), pancreatic cancer (Huang et al, 2009), hepatocellular carcinoma (Pascale et al, 2005) and osteosarcoma (Yao et al, 2009) and is independently correlated with poor clinical outcomes in these tumor types.

Inhibition of Crm1 blocks the exodus of tumor suppressor proteins and/or growth regulators such as p53, c-Abl, p21, p2'7, pRB, BRCA1, IkB, ICp27, E2F4, KLF5, YAP1, ZAP, KLF5, HDAC4, HDAC5 or forkhead proteins (e.g. FOXO3a) from the nucleus that are associated with gene expression, cell proliferation, angiogenesis and epigenetics. Crm1 inhibitors have been shown to induce apoptosis in cancer cells even in the presence of activating oncogenic or growth stimulating signals, while sparing normal (untransformed) cells. Most studies of Crm1 inhibition have utilized the natural product Crm1 inhibitor Leptomycin B (LMB). LMB itself is highly toxic to neoplastic cells, but poorly tolerated with marked gastrointestinal toxicity in animals (Roberts et al, 1986) and humans (Newlands et al, 1996). Derivatization of LMB to improve drug-like properties leads to compounds that retain antitumor activity and are better tolerated in animal tumor models (Yang et al, 2007, Yang et al, 2008, Mutka et al, 2009). Therefore, nuclear export inhibitors could have beneficial effects in neoplastic and other proliferative disorders. To date, however, small-molecule, drug-like Crm1 inhibitors for use in vitro and in vivo are uncommon.

In addition to tumor suppressor proteins, Crm1 also exports several key proteins that are involved in many inflammatory processes. These include IkB, NF-kB, Cox-2, RXRα, Commd1, HIF1, HMGB1, FOXO, FOXP and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (Phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LMB not only results in accumulation of transcriptionally inactive, nuclear IkBa-NF-kB complex but also prevents the initial activation of NF-kB even upon cell stimulation (Ghosh 2008, Huang 2000). In a different study, treatment with LMB inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB amd hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

CRM1 Inhibition affects gene expression by inhibiting/activating a series of transcription factors like ICp27, E2F4, KLF5, YAP1, ZAP Crm1 inhibition has potential therapeutic effects across many opthamologic indications including macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Crm1 inhibition has potential therapeutic effects across many dermatologic syndromes including inflammatory dermatoses (atopy, allergic dermatitis, chemical dermatitis, psoriasis), sun-damage (Ultraviolet/UV damage), and infections. CRM1 inhibition, best studied with LMB, showed minimal effects on normal keratinocytes, and exerted anti-inflammatory activity on keratinocytes subjected to UV, TNFa, or other inflammatory stimuli (Kobayashi & Shinkai 2005, Kannan & Jaiswal 2006). Crm1 inhibition also upregulates NRF2 (nuclear factor erythroid-related factor 2) activity, which protects keratinocytes (Schafer et al, 2010, Kannan & Jaiswal 2006) and other cell types (Wang et al, 2009) from oxidative damage. LMB induces apoptosis in keratinocytes infected with oncogenic human papillomavirus (HPV) strains such as HPV16, but not in uninfected keratinocytes (Jolly et al, 2009). Together, these data suggest that Crm1 inhibition could Crm1 also mediates Retinoid X receptor α (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. Lep B is able to prevent IL-1β induced cytoplasmic increase in RXRα levels in human liver derived cells (Zimmerman 2006). NOTE: This result strongly suggests that inflammation itself stimulates Crm1 mediated nuclear export, and therefore, blocking nuclear export can be potentially beneficial in many inflammatory processes across multiple tissues and organs including the vasculature (vasculitis, arteritis, polymyalgia rheumatic, atherosclerosis), dermatologic (see above), rheumatologic (rheumatoid and related arthridities, psoriatic arthritis, spondyloarthropathies, crystal arthropathies, systemic lupus erythematosus, mixed connective tissue disease, myositis syndromes, dermatomyositis, inclusion body myositis, undifferentiated connective tissue disease, Sjogren's syndrome, scleroderma and overlap syndromes, etc.).

Crm1 also mediates the transport of key neuroprotectant proteins that may be useful in neurodegenerative diseases including Parkinson's Disease (PD), Alzheimer's Disease, and Amytrophic Lateral Sclerosis. For example, (1) forcing nuclear retention of key neuroprotective regulators such as NRF2 (Wang 2009), FOXA2 (Kittappa et al, 2007), parkin in neuronal cells and/or by (2) inhibiting NFκB transcriptional activity by sequestering IκB to the nucleus in glial cells, Crm1 inhibition could slow or prevent neuronal cell death found in these disorders. There is also evidence linking abnormal glial cell proliferation to abnormalities in CRM1 levels or CR1 function (Shen 2008).

Intact nuclear export, primarily mediated through Crm1, is also required for the intact maturation of many viruses. Viruses where nuclear export, and/or Crm1 itself, has been implicated in their lifecycle include human immunodeficiency virus (HIV), adenovirus, simian retrovirus type 1, Borna disease virus, influenza (usual strains as well as H1N1 and avian H5N1 strains), hepatitis B (HBV) and C(HCV) viruses, human papilomavirus (HPV), respiratory syncytial virus (RSV), Dungee, Severe Acute Respiratory Syndrome coronavirus, yellow fever virus, West Nile Virus, herpes simplex virus (HSV), cytomegalovirus (CMV), and Merkel cell polyomavirus (MCV). (Bhuvanakantham 2010, Cohen 2010, Whittaker 1998). It is anticipated that additional viral infections reliant on intact nuclear export will be uncovered in the near future.

The HIV-1 Rev protein, which traffics through nucleolus and shuttles between the nucleus and cytoplasm, facilitates export of unspliced and singly spliced HIV transcripts containing Rev Response Elements (RRE) RNA by the Crm1 export pathway. Inhibition of Rev-mediated RNA transport using Crm1 inhibitors such as LepB or PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, dengue fever (DF), and its more severe and potentially deadly dengue hemorrhagic fever (DHF). DHF appears to be the result of an over exuberant inflammatory response to DENV. NS5 is the largest and most conserved protein of DENV. Crm1 regulates the transport of NS5 from the nucleus to the cytoplasm, where most of the NS5 functions are mediated Inhibition of Crm1 mediated export of NS5 results in altered kinetics of virus production and reduces induction of the inflammatory chemokine interleukin-8 (IL-8), presenting a new avenue for the treatment of diseases caused by DENV and other medically important flaviviruses including Hepatitis C virus (Rawlinson 2009).

Other virus-encoded RNA-binding proteins that use Crm1 to exit the nucleus include the HSV type 1 tegument protein (VP13/14, or hUL47), human CMV protein pp 65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. Crm1 inhibitors could therefore have beneficial effects on both the viral infectious process as well as on the process of neoplastic transformation due to these viruses.

Crm1 controls the nuclear localization and therefore activity of multiple DNA metabolizing enzymes including histone deacetylases (HDAC), histone acetyltransferases (HAT), and histone methyltransferases (HMT). Suppression of cardiomyocyte hypertrophy with irreversible Crm1 inhibitors has been demonstrated and is believed to be linked to nuclear retention (and activation) of HDAC 5, an enzyme known to suppress a hypertrophic genetic program (Monovich et al, 2009). Thus, Crm1 inhibition may have beneficial effects in hypertrophic syndromes, including certain forms of congestive heart failure and hypertrophic cardiomyopathies.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

SUMMARY OF THE INVENTION

It has now been found that compounds of this invention, and pharmaceutically acceptable compositions thereof, are effective as nuclear transport modulators. Such compounds have the general formula I:

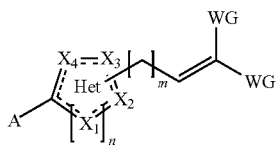

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with abnormal cellular responses triggered by improper nuclear transport. Such diseases, disorders, or conditions include those described herein.

Compounds provided by this invention are also useful for the study of nuclear transport modulation in biological and pathological phenomena; the study of intracellular signal transduction pathways mediated by such kinases; and the comparative evaluation of new nuclear transport modulators.

DETAILED DESCRIPTION OF CERTAIN EMBODIMENTS

Figure 1:
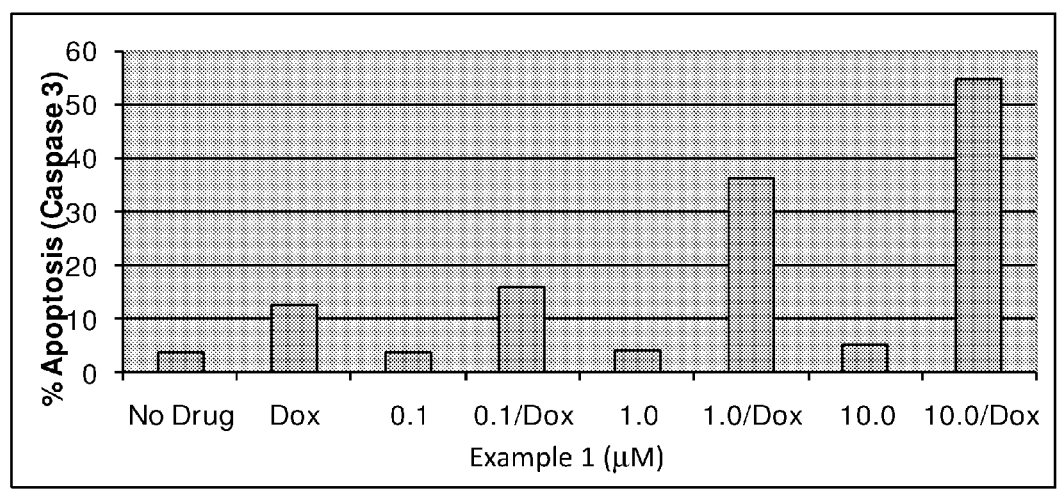
FIG. 1 is a bar graph demonstrating that Example 1 sensitizes non-Cyclin resistant Myeloma H929 cells to Topo II inhibitor Doxorubicin (16 hrs) by trapping Topo II in the nucleus allowing doxorubicin to act on Topo II.
Figure 2:
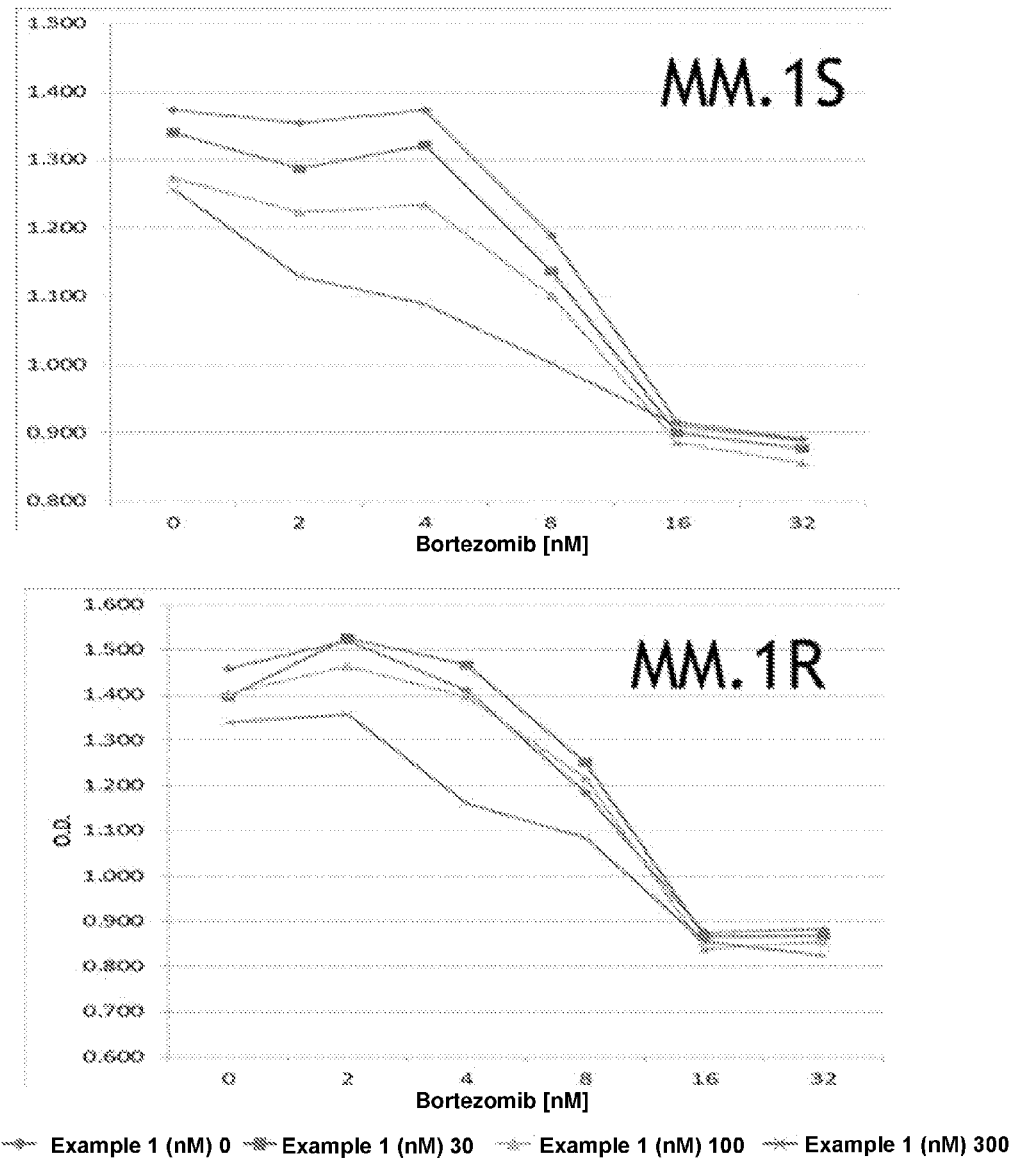
FIG. 2 depicts Example 1's (KPT-127) synergistic interactions with Bortezomib in four myeloma, lymphoma and leukemia cell lines. Isobologram analysis of the interaction between KPT-0127 and Bortezomib in MM.1S, MM.1R, Jurkat and HS-Sultan cells.

1. General Description of Compounds of the Invention

In certain embodiments, the present invention provides a compound of formula I:

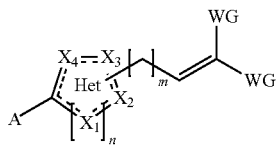

or a pharmaceutically acceptable salt thereof, wherein:
each ---  is independently a double or single bond with the proviso that two adjacent double bonds do not exist;
n=1 or 2;
m=0, 1
A is aryl or heteroaryl, wherein A is optionally substituted with one or more $R_1$ substituents;
each $R_1$ is independently selected from the group of halogen (Br, F, I, Cl), or an optionally substituted group selected from alkyl, alkenyl, alkynyl, haloalkyl, alkyl-alkoxy, alkyl-thioalkyl, alkyl-sulfinylalkyl, alkyl-sulfonylalkyl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryloxy, aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl;
Het is a five- or six-membered heteroaryl ring having 1-4 nitrogens, wherein each of $X_1$, $X_2$, $X_3$ and $X_4$ is independently selected from N, N($R_2$), O, S, C($R_2$)C($R_2$) and, as valency permits;
each $R_2$ is independently selected from H,

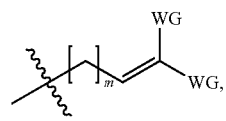

halogen (Br, F, Cl), or an optionally substituted group selected from alkyl, alkyl-alkoxy, alkyl-thioalkyl, alkyl-sulfinylalkyl, alkyl-sulfonylalkyl, alkyl-aryl, alkyl-heteroaryl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl;
each WG is independently selected from the group consisting of H, F, $CF_3$, $NO_2$, CN, C(O)$R_3$, C(O)O$R_3$, $SO_2R_3$, C(O)N$R_3R_4$ and C(NO$R_3$)$R_4$; and
each $R_3$ and $R_4$ is independently an optionally substituted group selected from alkyl, alkyl-alkoxy, alkyl-thioalkyl, alkyl-sulfinylalkyl, alkyl-sulfonylalkyl, alkyl-aryl, alkyl-heteroaryl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl.

In certain embodiments, the present invention provides a compound of formula I':

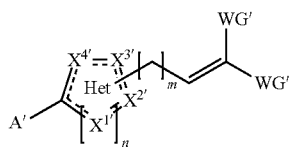

or a pharmaceutically acceptable salt thereof, wherein:
each ----- is independently a double or single bond with the proviso that two adjacent double bonds do not exist;
n=1 or 2;
m=0, 1
each of $X^{1'}$, $X^{2'}$, $X^{3'}$ and $X^{4'}$ is independently selected from N, N($R^{2'}$), O, S, and C($R^{2'}$), as valency permits, wherein at least one of $X^{1'}$, $X^{2'}$, $X^{3'}$ and $X^{4'}$ is either N or N($R^{2'}$);
A' is phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur, wherein A' is optionally substituted with one or more $R^{1'}$ substituents;
each $R^{1'}$ is independently selected from the group of halogen (F, Cl, Br, I), —$NO_2$, —CN, —$OR^a$, —$SR^a$, —$N(R^a)_2$, —$N_3$, or -$L^1$-R;
each $R^{2'}$ is independently selected from —H,

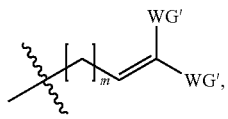

halogen (F, Cl, Br, I), —$NO_2$, —CN, —$OR^a$, —$SR^a$, —$N(R^a)_2$, —$N_3$, or -$L^1$-R;
each WG' is independently selected from the group consisting of —H, —F, —$CF_3$, —$NO_2$, —CN, —C(O)$R^{3'}$, —C(O)O$R^{3'}$, —S(O)$R^{3'}$, —$SO_2R^{3'}$, —C(O)N($R^{3'}$)$_2$ and —C(NO$R^{3'}$)$R^{4'}$;
each $R^{3'}$ and $R^{4'}$ is independently -$L^1$-R;
each R is independently optionally substituted $C_{1-8}$ alkyl, $C_{2-8}$ alkenyl, $C_{2-8}$ alkynyl, haloalkyl, phenyl, a 3-7 membered saturated or partially unsaturated cycloalkyl ring, an 8-10 membered bicyclic saturated, partially unsaturated or aryl carbocyclic ring, a 4-7-membered saturated or partially unsaturated heterocycloalkyl ring having 1-4 heteroatoms independently selected from nitrogen, oxygen, or sulfur; a 5-6 membered monocyclic heteroaryl ring having 1-3 heteroatoms independently selected from nitrogen, oxygen, or sulfur; or an 8-10 membered bicyclic heteroaryl ring having 1-4 heteroatoms independently selected from nitrogen, oxygen, or sulfur; or:
two R on the same nitrogen are taken together with their intervening atoms to form a 4-7 membered heterocyclic ring having 1-2 heteroatoms independently selected from nitrogen, oxygen, and sulfur
$L^1$ is a covalent bond or an optionally substituted bivalent $C_{1-6}$ hydrocarbon chain, wherein one or more methylene units of $L^1$ is optionally and independently replaced by —Cy—, —O—, —S—, —N($R^a$)—, —C(O)—, —C(S)—, —C(O)N($R^a$)—, —N($R^a$)C(O)N($R^a$)—, —N($R^a$)C(O)—, —N($R^a$)C(O)O—, —OC(O)N($R^a$)—, —S(O)—, —S(O)$_2$—, —S(O)$_2$N($R^a$)—, —N($R^a$)S(O)$_2$—, —OC(O)— or —C(O)O—;
—Cy— is an optionally substituted bivalent ring selected from a 3-7 membered saturated or partially unsaturated cycloalkylene ring, a 4-7-membered saturated or partially unsaturated heterocycloalkylene ring having 1-4 heteroatoms independently selected from nitrogen, oxygen, or sulfur, phenylene, a 5-6 membered monocyclic heteroarylene having 1-3 heteroatoms independently selected from nitrogen, oxygen, or sulfur, an 8-10 membered bicyclic arylene, or an 8-10 membered bicyclic heteroarylene having 1-4 heteroatoms independently selected from nitrogen, oxygen, or sulfur; and
each $R^a$ is independently —H, —R or —C(O)R.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

Generally, reference to a certain element such as hydrogen or H is meant to, if appropriate, include all isotopes of that element, for example, deuterium and tritium for hydrogen.

The term "alkyl" as used herein means a straight- or branched-chain hydrocarbon radical; in one aspect, having from one to eight carbon atoms, and includes, for example, and without being limited thereto, methyl, ethyl, propyl, isopropyl, t-butyl and the like. As noted above, "alkyl" encompasses substituted alkyl. Substituted alkyl includes, for example, and without being limited thereto, haloalkyl, hydroxyalkyl, cyanoalkyl, and the like. This is applied to any of the groups mentioned herein. Groups such as "alkenyl", "alkynyl", "aryl", etc. encompass substituted "alkenyl", "alkynyl", "aryl", etc.

The term "alkenyl" as used herein means a straight- or branched-chain alkenyl radical; in one aspect, having from two to eight carbon atoms, and includes, for example, and without being limited thereto, ethenyl, 1-propenyl, 1-butenyl and the like. The term "alkenyl" encompass radicals having "cis" and "trans" orientations, or alternatively, "E" and "Z" orientations.

The term "alkynyl" as used herein means a straight- or branched-chain alkynyl radical; in one aspect, having from two to eight carbon atoms, and includes, for example, and without being limited thereto, 1-propynyl (propargyl), 1-butynyl and the like.

The term "cycloalkyl" as used herein means a carbocyclic system (which may be unsaturated) containing one or more rings wherein such rings may be attached together in a pendent manner or may be fused. In one aspect, the ring(s) may have from three to seven carbon atoms, and includes, for example, and without being limited thereto, cyclopropyl, cyclohexyl, cyclohexenyl and the like.

The term "heterocycloalkyl" as used herein means a heterocyclic system (which may be unsaturated) having at least one heteroatom selected from N, S and/or O and containing one or more rings wherein such rings may be attached together in a pendent manner or may be fused. In one aspect, the ring(s) may have a three- to seven-membered cyclic group and includes, for example, and without being limited thereto, piperidinyl, piperazinyl, pyrrolidinyl, tetrahydrofuranyl and the like.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy" as used herein means a straight- or branched-chain alkoxy radical; in one aspect, having from one to eight carbon atoms and includes, for example, and without being limited thereto, methoxy, ethoxy, propyloxy, isopropyloxy, t-butoxy and the like.

The term "halo" as used herein means halogen and includes, for example, and without being limited thereto, fluoro, chloro, bromo, iodo and the like, in both radioactive and non-radioactive forms.

The term "alkylene" as used herein means a difunctional branched or unbranched saturated hydrocarbon radical; in one aspect, having one to eight carbon atoms, and includes, for example, and without being limited thereto, methylene, ethylene, n-propylene, n-butylene and the like.

The term "alkenylene" as used herein means a difunctional branched or unbranched hydrocarbon radical; in one aspect, having two to eight carbon atoms, and having at least one double bond, and includes, for example, and without being limited thereto, ethenylene, n-propenylene, n-butenylene and the like.

The term "alkynylene" as used herein means a difunctional branched or unbranched hydrocarbon radical; in one aspect, having two to eight carbon atoms, and having at least one triple bond, and includes, for example, and without being limited thereto, ethynylene, n-propynylene, n-butynylene and the like.

The term "aryl", alone or in combination, as used herein means a carbocyclic aromatic system containing one or more rings wherein such rings may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl or acenaphthyl. The "aryl" group may have 1 to 4 substituents such as lower alkyl, hydroxyl, halo, haloalkyl, nitro, cyano, alkoxy, lower alkylamino and the like.

The term "heteroaryl", alone or in combination, as used herein means an aromatic system having at least one heteroatom selected from N, S and/or O and containing one or more rings wherein such rings may be attached together in a pendent manner or may be fused. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, tetrazolyl, pyridyl, indolyl, furyl, benzofuryl, thienyl, benzothienyl, quinolyl, oxazolyl and the like. The "heteroaryl" group may have 1 to 4 substituents such as lower alkyl, hydroxyl, halo, haloalkyl, nitro, cyano, alkoxy, lower alkylamino and the like.

It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon or on different carbons, as long as a stable structure results.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH$ $(OR^o)_2$; —$(CH_2)_{0-4}SR^o$; —$(CH_2)_{0-4}$Ph, which may be substituted with $R^o$; —$(CH_2)_{0-4}O(CH_2)_{0-1}$Ph which may be substituted with $R^o$; —CH=CHPh, which may be substituted with $R^o$; —$(CH_2)_{0-4}O(CH_2)_{0-1}$-pyridyl which may be substituted with $R^o$; —$NO_2$; —CN; —$N_3$; —$(CH_2)_{0-4}N(R^o)_2$; —$(CH_2)_{0-4}N(R^o)C(O)R^o$; —$N(R^o)C(S)R^o$; —$(CH_2)_{0-4}N(R^o)C(O)NR^o_2$; —$N(R^o)C(S)NR^o_2$; —$(CH_2)_{0-4}N(R^o)C(O)OR^o$; —$N(R^o)N(R^o)C(O)R^o$; —$N(R^o)N(R^o)C(O)NR^o_2$; —$N(R^o)N(R^o)C(O)OR^o$; —$(CH_2)_{0-4}C(O)R^o$; —$C(S)R^o$; —$(CH_2)_{0-4}C(O)OR^o$; —$(CH_2)_{0-4}C(O)SR^o$; —$(CH_2)_{0-4}C(O)OSiR^o_3$; —$(CH_2)_{0-4}C(O)R^o$; —$OC(O)(CH_2)_{0-4}SR$—, $SC(S)SR^o$; —$(CH_2)_{0-4}SC(O)R^o$; —$(CH_2)_{0-4}C(O)NR^o_2$; —$C(S)NR^o_2$; —$C(S)SR^o$; —$SC(S)SR^o$, —$(CH_2)_{0-4}OC(O)NR^o_2$; —$C(O)N(OR^o)R^o$; —$C(O)C(O)R^o$; —$C(O)CH_2C(O)R^o$; —$C(NOR^o)R^o$; —$(CH_2)_{0-4}SSR^o$; —$(CH_2)_{0-4}S(O)_2R^o$; —$(CH_2)_{0-4}S(O)_2OR^o$; —$(CH_2)_{0-4}OS(O)_2R^o$; —$S(O)_2NR^o_2$; —$(CH_2)_{0-4}S(O)R^o$; —$N(R^o)S(O)_2NR^o_2$; —$N(R^o)S(O)_2R^o$; —$N(OR^o)R^o$; —$C(NH)NR^o_2$; —$P(O)_2R^o$; —$P(O)R^o_2$; —$OP(O)R^o_2$; —$OP(O)(OR^o)_2$; $SiR^o_3$; —$(C_{1-4}$ straight or branched alkylene)O—$N(R^o)_2$; or —$(C_{1-4}$ straight or branched)alkylene)$C(O)O$—$N(R^o)_2$, wherein each $R^o$ may be substituted as defined below and is independently hydrogen, $C_{1-6}$ aliphatic, —$CH_2$Ph, —$O(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, —$(CH_2)_{0-2}R^•$, —(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)$C(O)OR^•$, or —$SSR^•$ wherein each $R^•$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, -(haloR$^•$), —OH, —$OR^•$, —O(haloR$^•$), —CN, —$C(O)OH$, —$C(O)OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(haloR$^•$), —OH, —$OR^•$, —O(haloR$^•$), —CN, —$C(O)OH$, —$C(O)OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "pharmaceutically acceptable salt" means either an acid addition salt or a basic addition salt which is compatible with the treatment of patients.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating or lessening the severity of one or more symptoms of a disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is pharmaceutically acceptable oil typically used for parenteral administration.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

3. Description of Exemplary Compounds

According to one aspect, the present invention provides a compound of formula I,

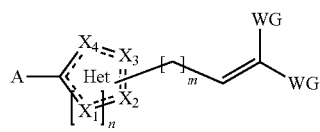

or a pharmaceutically acceptable salt thereof, wherein:
each ---- is independently a double or single bond with the proviso that two adjacent double bonds do not exist;
n=1 or 2;
m=0 or 1;
A is aryl or heteroaryl, wherein A is optionally substituted with one or more $R_1$ substituents;
each $R_1$ is independently selected from the group of halogen (Br, F, I, Cl), or an optionally substituted group selected from alkyl, alkenyl, alkynyl, haloalkyl, alkyl-alkoxy, alkyl-thioalkyl, alkyl-sulfinylalkyl, alkyl-sulfonylalkyl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryloxy, aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl;

Het is a five- or six-membered heteroaryl ring having 1-4 nitrogens, wherein each of $X_1$, $X_2$, $X_3$ and $X_4$ is independently selected from N, N($R_2$), O, S, C(R2)C($R_2$) and, as valency permits;

each $R_2$ is independently selected from H,

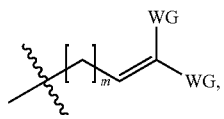

halogen (Br, F, Cl), or an optionally substituted group selected from alkyl, alkyl-alkoxy, alkyl-thioalkyl, alkyl-sulfinylalkyl, alkyl-sulfonylalkyl, alkyl-aryl, alkyl-heteroaryl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl;

each WG is independently selected from the group consisting of H, F, $CF_3$, $NO_2$, CN, C(O)$R_3$, C(O)O$R_3$, $SO_2R_3$, C(O)N$R_3R_4$ and C(NO$R_3$)$R_4$; and each $R_3$ and $R_4$ is independently an optionally substituted group selected from alkyl, alkyl-alkoxy, alkyl-thioalkyl, alkyl-sulfinylalkyl, alkyl-sulfonylalkyl, alkyl-aryl, alkyl-heteroaryl, alkyl-thioaryl, alkyl-sulfinylaryl, alkyl-sulfonylaryl, alkyl-thioheteroaryl, alkyl-sulfinylheteroaryl, alkyl-sulfonylheteroaryl, cycloalkyl, heterocycloalkyl, bicycloalkyl, hetero-bicycloalkyl, aryl, and heteoaryl; aryl-thioalkyl, aryl-sulfinylalkyl, aryl-sulfonylalkyl, aryl-thioaryl, aryl-sulfinylaryl, aryl-sulfonylaryl, aryl-thioheteroaryl, aryl-sulfinylheteroaryl, aryl-sulfonylheteroaryl, heteroaryl-thioalkyl, heteroaryl-sulfinylalkyl, heteroaryl-sulfonylalkyl, heteroaryl-thioaryl, heteroaryl-sulfinylaryl, heteroaryl-sulfonylaryl, heteroaryl-thioheteroaryl, heteroaryl-sulfinylheteroaryl, and heteroaryl-sulfonylheteroaryl.

In one embodiment, any cyclic group is substituted with one or more R1, R1 being selected from F, Cl, Br and I.

In some embodiments, the exocyclic double bond in Formula I is either Trans or Cis. Alternatively, it may be referred to as either E or Z. In some embodiments, the exocyclic double bond in Formula I is in the E configuration. In other embodiments, the exocyclic double bond of formula I is in the Z configuration.

In a further embodiment, the acid addition salt is formed from hydrochloric acid, hydrobromic acid, sulfuric acid, phosphoric acid, acid metal salt, monocarboxylic acids, dicarboxylic acids, or tricarboxylic acids.

In some embodiments, the compound has the following structure:

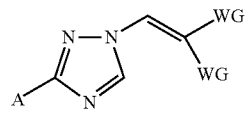

or a pharmaceutically acceptable salt thereof, wherein each of A and WG is as defined above and described herein.

In some embodiments, A is a mono-substituted aryl (e.g., a mono-substituted phenyl). In other embodiments, A is phenyl substituted with one or two $R_1$ groups. In some embodiments, each $R_1$ is independently halogen, —O-4-chlorophenyl, —OR°, or —N(R°)$_2$. In certain embodiments, A is phenyl substituted with one or two groups selected from chloro, —O-isopropyl, —OCH$_3$, or —NH(CH$_3$).

In some embodiments, the compound has the following structure:

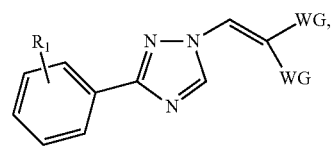

or a pharmaceutically acceptable salt thereof, wherein each of $R_1$ and WG is as defined above and described herein.

In some embodiments, $R_1$ is halo. In certain embodiments, $R_1$ is chloro.

In some embodiments, one WG is hydrogen and the other is C(O)O$R_2$. In some embodiments, $R_2$ is substituted or unsubstituted alkyl (e.g., unsubstituted alkyl such as ethyl, isopropyl or tert-butyl). In some embodiments, $R_2$ is substituted or unsubstituted aryl (e.g., phenyl). In some embodiments, one WG is hydrogen and the other is C(O)N$R_2R_3$. In some embodiments, one of $R_2$ and $R_3$ is hydrogen and the other is substituted or unsubstituted aryl (e.g., substituted or unsubstituted phenyl). In some embodiments, one of $R_2$ and $R_3$ is substituted or unsubstituted alkyl (e.g., methyl) and the other is substituted or unsubstituted aryl (e.g., substituted or unsubstituted phenyl).

In some embodiments, the compound has the following structure:

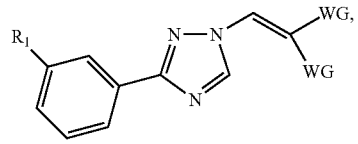

In some embodiments, $R_1$ is halo (e.g., chloro). In some embodiments, one WG is hydrogen and the other is C(O)O$R_2$. In some embodiments, $R_2$ is substituted or unsubstituted alkyl (e.g., unsubstituted alkyl such as ethyl, isopropyl or tert-butyl). In some embodiments, $R_2$ is substituted or unsubstituted aryl (e.g., phenyl). In some embodiments, one WG is hydrogen and the other is C(O)N$R_2R_3$. In some embodiments, one of $R_2$ and $R_3$ is hydrogen and the other is substituted or unsubstituted aryl (e.g., substituted or unsubstituted phenyl). In some embodiments, one of $R_2$ and $R_3$ is substituted or unsubstituted alkyl (e.g., methyl) and the other is substituted or unsubstituted aryl (e.g., substituted or unsubstituted phenyl).

In certain embodiments, the present invention provides a compound of formula I':

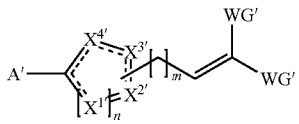

or a pharmaceutically acceptable salt thereof, wherein:
each ----- is independently a double or single bond with the proviso that two adjacent double bonds do not exist;
n=1 or 2;
m=0, 1
each of $X^{1'}, X^{2'}, X^{3'}$ and $X^{4'}$ is independently selected from N, $N(R^{2'})$, O, S, and $C(R^{2'})$, as valency permits, wherein at least one of $X^{1'}, X^{2'}, X^{3'}$ and $X^{4'}$ is either N or $N(R^{2'})$;
A' is phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur, wherein A' is optionally substituted with one or more $R^{1'}$ substituents;
each $R^{1'}$ is independently selected from the group of halogen (F, Cl, Br, I), —$NO_2$, —CN, —$OR^a$, —$SR^a$, —$N(R^a)_2$, —$N_3$, or -$L^1$-R;
each $R^{2'}$ is independently selected from —H,

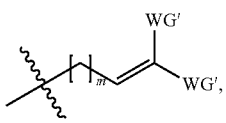

halogen (F, Cl, Br, I), —$NO_2$, —CN, —$OR^a$, —$SR^a$, —$N(R^a)_2$, —$N_3$, or -$L^1$-R;
each WG' is independently selected from the group consisting of —H, —F, —$CF_3$, —$NO_2$, —CN, —$C(O)R^{3'}$, —$C(O)OR^{3'}$, —$S(O)R^{3'}$, —$SO_2R^{3'}$, —$C(O)N(R^{3'})_2$ and —$C(NOR^{3'})R^{4'}$;
each $R^{3'}$ and $R^{4'}$ is independently -$L^1$-R;
each R is independently optionally substituted $C_{1-8}$ alkyl, $C_{2-8}$ alkenyl, $C_{2-8}$ alkynyl, haloalkyl, phenyl, a 3-7 membered saturated or partially unsaturated cycloalkyl ring, an 8-10 membered bicyclic saturated, partially unsaturated or aryl carbocyclic ring, a 4-7-membered saturated or partially unsaturated heterocycloalkyl ring having 1-4 heteroatoms independently selected from nitrogen, oxygen, or sulfur; a 5-6 membered monocyclic heteroaryl ring having 1-3 heteroatoms independently selected from nitrogen, oxygen, or sulfur; or an 8-10 membered bicyclic heteroaryl ring having 1-4 heteroatoms independently selected from nitrogen, oxygen, or sulfur; or:
two R on the same nitrogen are taken together with their intervening atoms to form a 4-7 membered heterocyclic ring having 1-2 heteroatoms independently selected from nitrogen, oxygen, and sulfur
$L^1$ is a covalent bond or an optionally substituted bivalent $C_{1-6}$ hydrocarbon chain, wherein one or more methylene units of $L^1$ is optionally and independently replaced by —Cy—, —O—, —S—, —$N(R^a)$—, —C(O)—, —C(S)—, —$C(O)N(R^a)$—, —$N(R^a)C(O)N(R^a)$—, —$N(R^a)C(O)$—, —$N(R^a)C(O)O$—, —$OC(O)N(R^a)$—, —S(O)—, —$S(O)_2$—, —$S(O)_2N(R^a)$—, —$N(R^a)S(O)_2$—, —OC(O)— or —C(O)O—;
—Cy— is an optionally substituted bivalent ring selected from a 3-7 membered saturated or partially unsaturated cycloalkylene ring, a 4-7-membered saturated or partially unsaturated heterocycloalkylene ring having 1-4 heteroatoms independently selected from nitrogen, oxygen, or sulfur, phenylene, a 5-6 membered monocyclic heteroarylene having 1-3 heteroatoms independently selected from nitrogen, oxygen, or sulfur, an 8-10 membered bicyclic arylene, or an 8-10 membered bicyclic heteroarylene having 1-4 heteroatoms independently selected from nitrogen, oxygen, or sulfur; and
each $R^a$ is independently —H, —Ror —C(O)R.

In some embodiments of Formula I', n is 1. In some embodiments of Formula I', at least one of $X^{1'}, X^{2'}, X^{3'}$ and $X^{4'}$ are N. In some embodiments of Formula I', at least two of $X^{1'}, X^{2'}, X^{3'}$ and $X^{4'}$ are N. In some embodiments of Formula I', $X^{1'}$ and $X^{4'}$ are N. In some embodiments of Formula I', $X^{2'}$ is $C(R^{2'})$. In some embodiments of Formula I', $X^{2'}$ is CH. In some embodiments of Formula I', at least one of $X^{2'}$ and $X^{3'}$ is $N(R^{2'})$. In some embodiments of Formula I', one of $X^{2'}$ or $X^{3'}$ is $NR^{2'}$, wherein $R^{2'}$ is

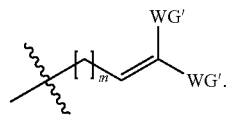

In some embodiments of Formula I', $R^{2'}$ is

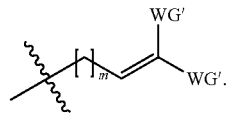

In some embodiments of Formula I', at least one WG' is —$C(O)OR^{3'}$. In some embodiments of Formula I', one WG' is —H and the other WG' is —$C(O)OR^{3'}$. In some embodiments of Formula I', one WG' is —H and the other WG' is —$C(O)OR^{3'}$, wherein $R^{3'}$ is $C_{1-8}$ alkyl. In some embodiments of Formula I', one WG' is —H and the other WG' is —$C(O)OR^{3'}$, wherein $R^{3'}$ is $C_{1-3}$ alkyl. In some embodiments of Formula I', one WG' is —H and the other WG' is —$C(O)OR^{3'}$, wherein $R^{3'}$ is —$CH_3$. In some embodiments of Formula I', one WG' is —H and the other WG' is —$C(O)OR^{3'}$, wherein $R^{3'}$ is —$CH_2CH_3$. In some embodiments of Formula I', one WG' is —H and the other WG' is —$C(O)OR^{3'}$, wherein $R^{3'}$ is —$CH(CH_3)_2$.

In some embodiments of Formula I', one WG' is —H and the other WG' is —$C(O)OR^{3'}$, wherein $R^{3'}$ is $C_{1-4}$ alkyl. In some embodiments of Formula I', one WG' is —H and the other WG' is —$C(O)OR^{3'}$, wherein $R^{3'}$ is —$C(CH_3)_3$.

In some embodiments of Formula I', one WG' is —H and the other WG' is —$C(O)OR^{3'}$, wherein $R^{3'}$ is $C_{1-5}$ alkyl. In some embodiments of Formula I', one WG' is —H and the other WG' is —$C(O)OR^{3'}$, wherein $R^{3'}$ is $C_{1-6}$ alkyl.

In some embodiments of Formula I', one WG' is —H and the other WG' is —$C(O)OR^{3'}$, wherein $R^{3'}$ is a 4-7-membered saturated or partially unsaturated heterocycloalkyl ring having 1-4 heteroatoms independently selected from nitrogen, oxygen, or sulfur. In some embodiments of Formula I', one WG' is —H and the other WG' is —$C(O)OR^{3'}$, wherein $R^{3'}$ is a 4-7-membered saturated or partially unsaturated heterocycloalkyl ring having 1 heteroatom selected from nitrogen, oxygen, or sulfur. In some embodiments of Formula I', one WG' is —H and the other WG' is —C(O)OR$^{3'}$, wherein R$^{3'}$ is a 4-membered saturated or partially unsaturated heterocycloalkyl ring having 1 heteroatom selected from nitrogen, oxygen, or sulfur. In some embodiments of Formula I', one WG' is —H and the other WG' is —C(O)OR$^{3'}$, wherein R$^{3'}$ is tetrahydrofuranyl. In some embodiments of Formula I', one WG' is —H and the other WG' is —C(O)OR$^{3'}$, wherein R$^{3'}$ is dihydrofurna-2(3H)-onyl. In some embodiments of Formula I', one WG' is —H and the other WG' is —C(O)OR$^{3'}$, wherein R$^{3'}$ is tetrahydro-2H-pyranyl. In some embodiments of Formula I', one WG' is —H and the other WG' is —C(O)OR$^{3'}$, wherein R$^{3'}$ is oxetanyl. In some embodiments of Formula I', one WG' is —H and the other WG' is —C(O)OR$^{3'}$, wherein R$^{3'}$ is azetindinyl.

In some embodiments of Formula I', one WG' is —H and the other WG' is —C(O)OR$^{3'}$, wherein R$^{3'}$ is a 3-7 membered saturated or partially unsaturated cycloalkyl ring. In some embodiments of Formula I', one WG' is —H and the other WG' is —C(O)OR$^{3'}$, wherein R$^{3'}$ is a 3-7 membered saturated cycloalkyl ring. In some embodiments of Formula I', one WG' is —H and the other WG' is —C(O)OR$^{3'}$, wherein R$^{3'}$ is cyclobutyl. In some embodiments of Formula I', one WG' is —H and the other WG' is —C(O)OR$^{3'}$, wherein R$^{3'}$ is cyclopentyl. In some embodiments of Formula I', one WG' is —H and the other WG' is —C(O)OR$^{3'}$, wherein R$^{3'}$ is cyclohexyl.

In some embodiments of Formula I', one WG' is —H and the other WG' is —C(O)OR$^{3'}$, wherein R$^{3'}$ is a 5-6 membered monocyclic heteroaryl ring having 1-3 heteroatoms independently selected from nitrogen, oxygen, or sulfur. In some embodiments of Formula I', one WG' is —H and the other WG' is —C(O)OR$^{3'}$, wherein R$^{3'}$ is a 5-6 membered monocyclic heteroaryl ring having 1-3 nitrogen atoms. In some embodiments of Formula I', one WG' is —H and the other WG' is —C(O)OR$^{3'}$, wherein R$^{3'}$ is pyridinyl.

In some embodiments of Formula I', one WG' is —H and the other WG' is —C(O)OR$^{3'}$, wherein R$^{3'}$ is phenyl.

In some embodiments of Formula I', one WG' is —H and the other WG' is —C(O)OR$^{3'}$, wherein R$^{3'}$ is L$^1$-R, wherein L$^1$ is —CH$_2$— and R is pyrrolidinyl. In some embodiments of Formula I', one WG' is —H and the other WG' is —C(O)OR$^{3'}$, wherein R$^{3'}$ is L$^1$-R, wherein L$^1$ is —CH$_2$— and R is imidazolyl. In some embodiments of Formula I', one WG' is —H and the other WG' is —C(O)OR$^{3'}$, wherein R$^{3'}$ is L$^1$-R, wherein L$^1$ is —CH$_2$— and R is pyridinyl.

In some embodiments of Formula I', one WG' is —H and the other WG' is —C(O)N(R$^{3'}$)$_2$. In some embodiments of Formula I', one WG' is —H and the other WG' is —C(O)N(H)R$^{3'}$. In some embodiments of Formula I', one WG' is —H and the other WG' is —C(O)N(H)R$^{3'}$, wherein R$^{3'}$ is a 3-7 membered saturated or partially unsaturated cycloalkyl ring. In some embodiments of Formula I', one WG' is —H and the other WG' is —C(O)N(H)R$^{3'}$, wherein R$^{3'}$ is a 3-7 membered saturated cycloalkyl ring. In some embodiments of Formula I', one WG' is —H and the other WG' is —C(O)N(H)R$^{3'}$, wherein R$^{3'}$ is cyclopentyl.

In some embodiments of Formula I', one WG' is —H and the other WG' is —C(O)N(H)R$^{3'}$, wherein R$^{3'}$ is phenyl. In some embodiments of Formula I', one WG' is —H and the other WG' is —C(O)N(CH$_3$)R$^{3'}$, wherein R$^{3'}$ is phenyl.

In some embodiments of Formula I', one WG' is —H and the other WG' is —C(O)N(R$^{3'}$), wherein both R$^{3'}$ groups are taken together to form a 4-7 membered saturated heterocyclic ring. In some embodiments of Formula I', one WG' is —H and the other WG' is —C(O)N(R$^{3'}$), wherein both R$^{3'}$ groups are taken together to form a 4-membered saturated heterocyclic ring.

In some embodiments of Formula I', one WG' is —H and the other WG' is —CN.

In some embodiments of Formula I', one WG' is —H and the other WG' is —CF$_3$.

In some embodiments of Formula I', one WG' is —H and the other WG' is —S(O)R$^{3'}$. In some embodiments of Formula I', one WG' is —H and the other WG' is —S(O)CH$_3$. In some embodiments of Formula I', one WG' is —H and the other WG' is —SO$_2$R$^{3'}$. In some embodiments of Formula I', one WG' is —H and the other WG' is —SO$_2$CH$_3$.

In some embodiments of Formula I', R$^{1'}$ is optionally substituted C$_{1-8}$ alkyl. In some embodiments of Formula I', R$^{1'}$ is optionally substituted C$_{1-3}$ alkyl. In some embodiments of Formula I', R$^{1'}$ is —CH$_3$. In some embodiments of Formula I', R$^{1'}$ is —CF$_3$.

In some embodiments of Formula I', R$^{1'}$ is halogen. In some embodiments of Formula I', R$^{1'}$ is —F. In some embodiments of Formula I', R$^{1'}$ is —Cl. In some embodiments of Formula I', R$^{1'}$ is —Br.

In some embodiments of Formula I', R$^{1'}$ is —CN.

In some embodiments of Formula I', R$^{1'}$ is —N(R$^a$)$_2$. In some embodiments of Formula I', R$^{1'}$ is —NH$_2$. In some embodiments of Formula I', R$^{1'}$ is —N(H)CH$_3$. In some embodiments of Formula I', R$^{1'}$ is —N(CH$_3$)$_2$. In some embodiments of Formula I', R$^{1'}$ is —N(H)CH(CH$_3$)$_2$.

In some embodiments of Formula I', R$^{1'}$ is —OR$^a$. In some embodiments of Formula I', R$^{1'}$ is —OH. In some embodiments of Formula I', R$^{1'}$ is —OC$_{1-8}$ alkyl. In some embodiments of Formula I', R$^{1'}$ is —OC$_{1-3}$ alkyl. In some embodiments of Formula I', R$^{1'}$ is —OCH$_3$. In some embodiments of Formula I', R$^{1'}$ is —OCH(CH$_3$)$_2$.

In some embodiments of Formula I', R$^{1'}$ is L$^1$-R. In some embodiments of Formula I', L$^1$-R is —OC$_{1-8}$ alkyl. In some embodiments of Formula I', L$^1$-R is —OCH$_3$. In some embodiments of Formula I', L$^1$-R is —OCF$_3$. In some embodiments of Formula I', L$^1$-R is —O$^i$Pr. In some embodiments of Formula I', L$^1$-R is —N(R$^a$)C$_{1-8}$ alkyl. In some embodiments of Formula I', L$^1$-R is —N(R$^a$)CH$_3$. In some embodiments of Formula I', L$^1$-R is —N(H)CH$_3$. In some embodiments of Formula I', L$^1$-R is —N(CH$_3$)$_2$. In some embodiments of Formula I', L$^1$-R is —N(H)CH(CH$_3$)$_2$. In some embodiments of Formula I', L$^1$-R is —OPh. In some embodiments of Formula I', L$^1$-R is —OCH$_2$CH$_2$N(CH$_3$). In some embodiments of Formula I', L$^1$-R is phenyl.

In some embodiments, A' is optionally substituted phenyl. In some embodiments of formula I', A' is phenyl optionally substituted with one or more R$^{1'}$.

In some embodiments, A' is a 5-membered monocyclic heteroaryl ring having 1 heteroatom selected from nitrogen, oxygen, or sulfur. In some embodiments, A' is pyrrolyl, furanyl or thiophenyl.

In some embodiments, A' is a 5-membered monocyclic heteroaryl ring having 2 heteroatoms independently selected from nitrogen, oxygen, or sulfur. In some embodiments, A' is oxazolyl, isoxazolyl, thiazolyl, pyrazolyl, imidazolyl or isothiazolyl.

In some embodiments, A' is a 5-membered monocyclic heteroaryl ring having 3 heteroatoms independently selected from nitrogen, oxygen, or sulfur. In some embodiments, A' is oxadiazolyl, thiadiazolyl or triazolyl.

In some embodiments, A' is a 6-membered monocyclic heteroaryl ring having 1 nitrogens. In some embodiments, A' is pyridyl.

In some embodiments, A' is a 6-membered monocyclic heteroaryl ring having 2 nitrogens. In some embodiments, A' is pyrimidinyl, pyrazinyl, or pyridizinyl.

In some embodiments, A' is a 6-membered monocyclic heteroaryl ring having 3 nitrogens. In some embodiments, A' is triazinyl.

In some embodiments of Formula I', $L^1$ is a covalent bond.

In some embodiments of Formula I', $L^1$ is —O—. In some embodiments of Formula I', $L^1$ is —OCH$_2$CH$_2$—. In some embodiments of Formula I', $L^1$ is —OCH$_2$CH$_2$O—. In some embodiments of Formula I', $L^1$ is —OCH$_2$CH$_2$N(R$^a$)—. In some embodiments of Formula I', $L^1$ is —OCH$_2$CH$_2$N(CH$_3$)—. In some embodiments of Formula I', $L^1$ is —O—C(H)=C(H)—C(O)O—. In some embodiments of Formula I', $L^1$ is —N(R$^a$)—. In some embodiments of Formula I', $L^1$ is —N(H)—. In some embodiments of Formula I', $L^1$ is —S—. In some embodiments of Formula I', $L^1$ is —S(O)$_2$—.

In some embodiments of Formula I', R is $C_{1-8}$ alkyl, $C_{1-8}$ alkenyl, or $C_{1-8}$ alkynyl. In some embodiments of Formula I', R is $C_{1-8}$ alkyl, $C_{1-8}$ alkenyl, or $C_{1-8}$ alkynyl. In some embodiments of Formula I', R is $C_{1-8}$ alkyl. In some embodiments of Formula I', R is $C_{1-3}$ alkyl. In some embodiments of Formula I', R is methyl. In some embodiments of Formula I', R is ethyl. In some embodiments of Formula I', R is isopropyl.

In some embodiments of Formula I', R is a 3-7-membered saturated or partially unsaturated cycloalkyl ring. In some embodiments of Formula I', R is a 3-7-membered saturated cycloalkyl ring. In some embodiments of Formula I', R is a cyclobutyl ring.

In some embodiments of Formula I', R is optionally substituted phenyl.

In some embodiments of Formula I', R is a 4-7-membered saturated or partially unsaturated heterocycloalkylene ring having 1-4 heteroatoms independently selected from nitrogen, oxygen, or sulfur. In some embodiments of Formula I', R is a 5-membered saturated or partially unsaturated heterocycloalkylene ring having 1-4 heteroatoms independently selected from nitrogen, oxygen, or sulfur. In some embodiments of Formula I', R is a 5-membered saturated heterocycloalkylene ring having 1 heteroatom independently selected from nitrogen, oxygen, or sulfur. In some embodiments of Formula I', R is pyrrolidinyl.

In some embodiments of formula I', A' is phenyl optionally substituted with one or more $R^{1'}$. In some embodiments, A' is phenyl optionally substituted with one or more halogens. In some such embodiments, $R^{1'}$ is —Cl.

In some embodiments, A' is phenyl substituted with one or more —OR$^a$. In some embodiments, A' is phenyl substituted with one or more —OR$^a$, wherein R$^a$ is $C_{1-8}$ alkyl. In some embodiments, A' is phenyl substituted with one or more —OR$^a$, wherein R$^a$ is $C_{1-3}$ alkyl. In some embodiments, A' is phenyl substituted with one or more —OMe. In some embodiments, A' is phenyl substituted with one or more —OCF$_3$. In some embodiments, A' is phenyl substituted with one or more —O$^i$Pr.

In some embodiments, A' is phenyl substituted with one or more $L^1$-R. In some embodiments, A' is phenyl substituted with $L^1$-R, wherein $L^1$ is a covalent bond. In some embodiments, A' is phenyl substituted with $L^1$-R, wherein $L^1$ is a covalent bond and R is $C_{1-8}$ alkyl. In some embodiments, A' is phenyl substituted with $L^1$-R, wherein $L^1$ is a covalent bond and R is optionally substituted $C_{1-8}$ alkyl. In some embodiments, A' is phenyl substituted with $L^1$-R, wherein $L^1$ is a covalent bond and R is optionally substituted $C_{1-3}$ alkyl. In some embodiments, A' is phenyl substituted with $L^1$-R, wherein $L^1$ is a covalent bond and R is —CF$_3$.

In some embodiments, the present invention provides a compound of formula II':

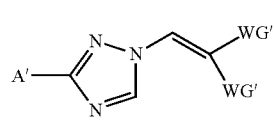

II' or a pharmaceutically acceptable salt thereof, wherein each of A' and WG' is as defined above and described herein.

In some embodiments, the present invention provides a compound of formulae III' or IV':

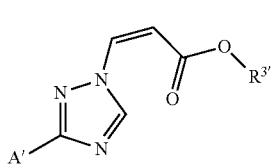

III'

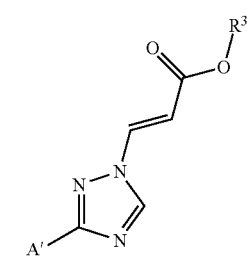

IV' or a pharmaceutically acceptable salt thereof, wherein each of A' and $R^{3'}$ is as defined above and described herein.

In some embodiments of formulae III' or IV', $R^{3'}$ is $C_{1-8}$ alkyl. In some embodiments of formulae III' or IV', $R^{3'}$ is $C_{1-6}$ alkyl. In some embodiments of formulae III' or IV', $R^{3'}$ is $C_{1-4}$ alkyl. In some embodiments of formulae III' or IV', $R^{3'}$ is —C(CH$_3$)$_3$. In some embodiments of formulae III' or IV', $R^{3'}$ is $C_{1-3}$ alkyl. In some embodiments of formulae III' or IV', $R^{3'}$ is —CH(CH$_3$)$_2$. In some embodiments of formulae III' or IV', $R^{3'}$ is —CF(CH$_3$)$_2$. In some embodiments of formulae III' or IV', $R^{3'}$ is $C_{1-2}$ alkyl. In some embodiments of formulae III' or IV', $R^{3'}$ is —CH$_2$CH$_3$. In some embodiments of formulae III' or IV', $R^{3'}$ is —CH$_3$.

In some embodiments of formulae III' or IV', $R^{3'}$ is a 3-7 membered saturated or partially unsaturated cycloalkyl ring. In some embodiments of formulae III' or IV', $R^{3'}$ is a 3-7 membered saturated cycloalkyl ring. In some embodiments of formulae III' or IV', $R^{3'}$ is cyclopropyl. In some embodiments of formulae III' or IV', $R^{3'}$ is cyclobutyl. In some embodiments of formulae III' or IV', $R^{3'}$ is cyclopropyl. In some embodiments of formulae III' or IV', $R^{3'}$ is syclopentyl. In some embodiments of formulae III' or IV', $R^{3'}$ is cyclopropyl. In some embodiments of formulae III' or IV', $R^{3'}$ is cyclohexyl.

In some embodiments of formulae III' or IV', $R^{3'}$ is a 4-7 membered saturated or partially unsaturated heterocycloalkyl ring having 1-4 heteroatoms selected from nitrogen, oxygen or sulfur. In some embodiments of formulae III' or IV', $R^{3'}$ is a 4-7 membered saturated heterocycloalkyl ring having 1-4 heteroatoms independently selected from nitrogen, oxygen or sulfur. In some embodiments of formulae III' or IV', $R^{3'}$ is a 4-7 membered saturated heterocycloalkyl ring having 1 heteroatom selected from nitrogen, oxygen or sulfur. In some In some embodiments of formulae III' or IV', $R^{3'}$ is a tetrahydrofuranyl ring. In some embodiments of formulae III' or IV', $R^{3'}$ is a dihydrofuran-2-onyl ring. In some embodiments of formulae III' or IV', $R^{3'}$ is a tetrahydropyranyl ring. In some embodiments of formulae III' or IV', $R^{3'}$ is an azetindinyl ring. In some embodiments of formulae III' or IV', $R^{3'}$ is an oxepanyl ring.

In some embodiments of formulae III' or IV', $R^{3'}$ is $L^1$-R. In some embodiments of formulae III' or IV', $R^{3'}$ is $L^1$-R, wherein $L^1$ is —$CH_2$—. In some embodiments of formulae III' or IV', $R^{3'}$ is $L^1$-R, wherein $L^1$ is —$CH_2$— and R is a 5-6 membered monocyclic heterocyclic ring having 1-3 heteroatoms independently selected from nitrogen, oxygen or sulfur. In some embodiments of formulae III' or IV', $R^{3'}$ is $L^1$-R, wherein $L^1$ is —$CH_2$— and R is a 5-membered monocyclic heterocyclic ring having 1-3 heteroatoms independently selected from nitrogen, oxygen or sulfur. In some embodiments of formulae III' or IV', $R^{3'}$ is $L^1$-R, wherein $L^1$ is —$CH_2$— and R is triazolyl. In some embodiments of formulae III' or IV', $R^{3'}$ is $L^1$-R, wherein $L^1$ is —$CH_2$— and R is thiadiazolyl. In some embodiments of formulae III' or IV', $R^{3'}$ is $L^1$-R, wherein $L^1$ is —$CH_2$— and R is a 5-membered monocyclic heterocyclic ring having 1-2 heteroatoms independently selected from nitrogen, oxygen or sulfur. In some embodiments of formulae III' or IV', $R^{3'}$ is $L^1$-R, wherein $L^1$ is —$CH_2$— and R is a 5-membered monocyclic heterocyclic ring having 1-2 nitrogens. In some embodiments of formulae III' or IV', $R^{3'}$ is $L^1$-R, wherein $L^1$ is —$CH_2$— and R is imidazolyl. In some embodiments of formulae III' or IV', $R^{3'}$ is $L^1$-R, wherein $L^1$ is —$CH_2$— and R is pyrrolidinyl. In some embodiments of formulae III' or IV', $R^{3'}$ is $L^1$-R, wherein $L^1$ is —$CH_2$— and R is a 5-membered monocyclic heterocyclic ring having 1 heteroatom selected from nitrogen, oxygen or sulfur.

In some embodiments of formulae III' or IV', $R^{3'}$ is $L^1$-R, wherein $L^1$ is —$CH_2$— and R is a 6-membered monocyclic heterocyclic ring having 1-3 nitrogens. In some embodiments of formulae III' or IV', $R^{3'}$ is $L^1$-R, wherein $L^1$ is —$CH_2$— and R is pyridyl. In some embodiments of formulae III' or IV', $R^{3'}$ is $L^1$-R, wherein $L^1$ is —$CH(CH_3)$— and R is pyridyl.

In some embodiments of formulae III' or IV', $R^{3'}$ is phenyl.

In some embodiments, the present invention provides a compound of formula V' or VI':

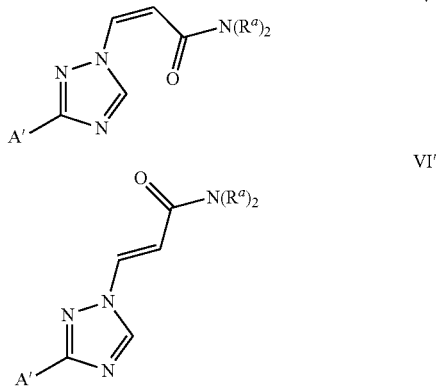

or a pharmaceutically acceptable salt thereof, wherein each of A' and $R^a$ is as defined above and described herein.

In some embodiments of formulae V' or VI', one $R^a$ is hydrogen. In some embodiments of formulae V' or VI', $R^a$ is a 3-7 membered saturated or partially unsaturated cycloalkyl ring. In some embodiments of formulae V' or VI', $R^a$ is a 3-7 membered saturated cycloalkyl ring. In some embodiments of formulae V' or VI', $R^a$ is cyclopropyl. In some embodiments of formulae V' or VI', $R^a$ is cyclobutyl. In some embodiments of formulae V' or VI', $R^a$ is cyclopropyl. In some embodiments of formulae V' or VI', $R^a$ is syclopentyl. In some embodiments of formulae V' or VI', $R^a$ is cyclopropyl. In some embodiments of formulae V' or VI', $R^a$ is cyclohexyl.

In some embodiments of formulae V' or VI', one $R^a$ is hydrogen and the other is optionally substituted phenyl. In some embodiments of formulae V' or VI', one $R^a$ is $C_{1-8}$ alkyl and the other is phenyl. In some embodiments of formulae V' or VI', one $R^a$ is —$CH_3$ and the other is phenyl.

In some embodiments of formulae V' or VI', $R^a$ is $C_{1-8}$ alkyl. In some embodiments of formulae V' or VI', one $R^a$ is —$CH_3$ and the other $R^a$ is —$CH(CH_3)_2$.

In some embodiments of formulae V' or VI', both $R^a$ groups are taken together with their intervening atoms to form a 4-7 membered heterocyclic ring having 1-2 heteroatoms independently selected from nitrogen, oxygen or sulfur. In some embodiments of formulae V' or VI', both $R^a$ groups are taken together with their intervening atoms to form a 4-membered heterocyclic ring having 1-2 heteroatoms independently selected from nitrogen, oxygen or sulfur. In some embodiments of formulae V' or VI', both $R^a$ groups are taken together with their intervening atoms to form a 4-membered heterocyclic ring having 1 nitrogen atom. In some embodiments of formulae V' or VI', the heterocyclic ring formed by two $R^a$ groups is

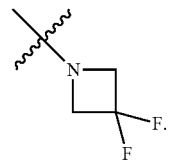 [SMILES: *N1CC(F)(F)C1]

In some embodiments of formulae V' or VI', the heterocyclic ring formed by two $R^a$ groups is

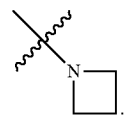

In some embodiments of formulae III', IV', V' or VI', A' is phenyl substituted with one or more $R^{1'}$ groups. In some embodiments of formulae III', IV', V' or VI', $R^{1'}$ is halogen. In some embodiments of formulae III', IV', V' or VI', $R^{1'}$ is —Cl. In some embodiments of formulae III', IV', V' or VI', $R^{1'}$ is —F. In some embodiments of formulae III', IV', V' or VI', $R^{1'}$ is —$CF_3$. In some embodiments of formulae III', IV', V' or VI', $R^{1'}$ is —$C_{1-8}$ alkyl. In some embodiments of formulae III', IV', V' or VI', $R^{1'}$ is —$CH_3$. In some embodiments of formulae III', IV', V' or VI', $R^{1'}$ is —$OR^a$. In some embodiments of formulae III', IV', V' or VI', $R^{1'}$ is —$OCH_3$. In some embodiments of formulae III', IV', V' or VI', $R^{1'}$ is —$OCH(CH_3)_2$. In some embodiments of formulae III', IV', V' or VI', $R^{1'}$ is —$OCF(CH_3)_2$. In some embodiments of formulae III', IV', V' or VI', $R^{1'}$ is —OPh. In some embodiments of formulae III', IV', V' or VI', $R^{1'}$ is —$OCF_3$. In some embodiments of formulae III', IV', V' or VI', $R^{1'}$ is —CN. In some embodiments of formulae III', IV', V' or VI', $R^{1'}$ is —$N(R^a)_2$. In some embodiments of formulae III', IV', V' or VI', $R^{1'}$ is —NH$_2$. In some embodiments of formulae III', IV', V' or VI', $R^{1'}$ is —N(H)R$^a$. In some embodiments of formulae III', IV', V' or VI', $R^{1'}$ is —N(H)CH$_3$. In some embodiments of formulae III', IV', V' or VI', $R^{1'}$ is —N(H)CH(CH$_3$)$_2$.

In some embodiments of formulae III', IV', V' or VI', $R^{1'}$ is phenyl.

In some embodiments of formulae III', IV', V' or VI', $R^{1'}$ is a 5-6 membered monocyclic heterocyclic ring having 1-3 heteroatoms independently selected from nitrogen, oxygen or sulfur. In some embodiments of formulae III', IV', V' or VI', $R^{1'}$ is a 5-membered monocyclic heterocyclic ring having 1-3 heteroatoms independently selected from nitrogen, oxygen or sulfur. In some embodiments of formulae III', IV', V' or VI', $R^{1'}$ is a 5-membered monocyclic heterocyclic ring having 1 heteroatom selected from nitrogen, oxygen or sulfur. In some embodiments of formulae III', IV', V' or VI', $R^{1'}$ is thiophenyl. In some embodiments of formulae III', IV', V' or VI', $R^{1'}$ is thiazolyl.

In some embodiments of formulae III', IV', V' or VI', A' is a 5-6 membered monocyclic heterocyclic ring having 1-3 heteroatoms independently selected from nitrogen, oxygen or sulfur. In some embodiments of formulae III', IV', V' or VI', A' is a 6-membered monocyclic heterocyclic ring having 1-3 nitrogen atoms. In some embodiments of formulae III', IV', V' or VI', A' is pyridinyl.

In some embodiments of formulae III', IV', V' or VI', A' is a 8-10 membered bicyclic aryl ring. In some embodiments of formulae III', IV', V' or VI', A' is naphthyl.

In some embodiments of formulae III', IV', V' or VI', A' is a 8-10 membered bicyclic heteroaryl ring having 1-4 heteroatoms independently selected from nitrogen, oxygen or sulfur. In some embodiments of formulae III', IV', V' or VI', A' is a 8-10 membered bicyclic heteroaryl ring having 1 heteroatom selected from nitrogen, oxygen or sulfur. In some embodiments of formulae III', IV', V' or VI', A' is indolyl.

In some embodiments, the compound is selected from:

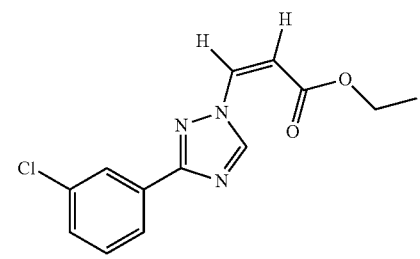

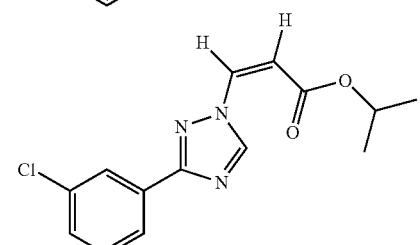

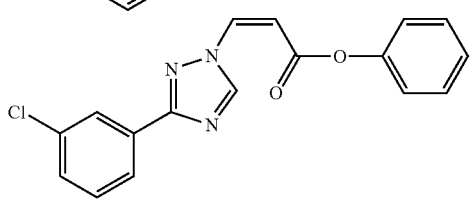

-continued

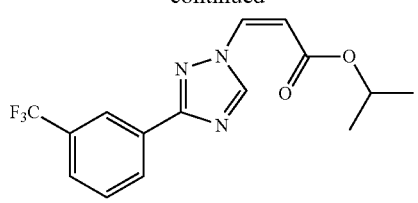

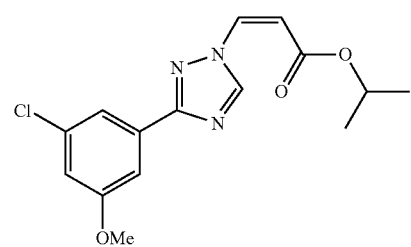

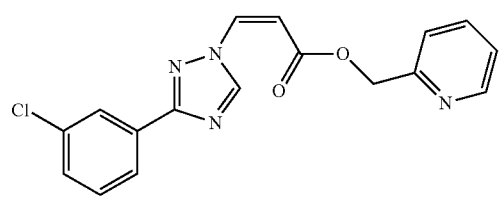

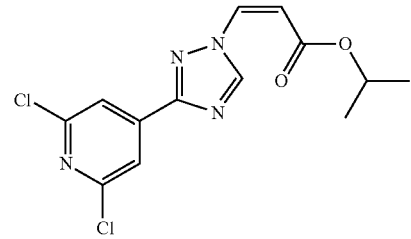

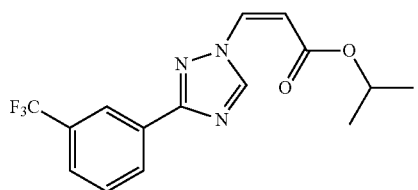

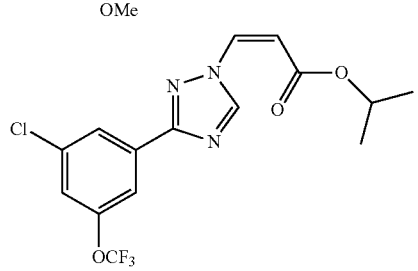

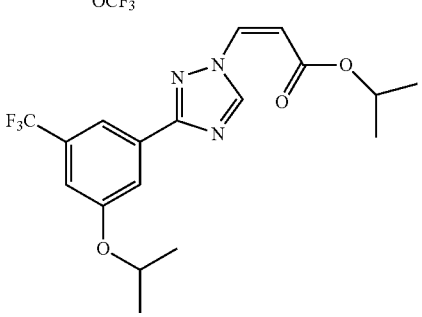

[Structures of several compounds shown, including triazole derivatives with F₃C-phenyl-OMe, F₃C-phenyl with dimethylaminoethoxy, NC-phenyl with isopropoxy, Cl-pyridine with isopropylamino, and F₃C-phenyl-OMe with difluoroazetidine amide groups]

or a pharmaceutically acceptable salt thereof.

In some embodiments, the present invention provides a compound of formula II:

II or a pharmaceutically acceptable salt thereof, wherein each of A and WG is as defined above and described herein.

In some embodiments, the present invention provides a compound of formula III:

III or a pharmaceutically acceptable salt thereof, wherein each of A and WG is as defined above and described herein In some embodiments, A is a mono-substituted aryl (e.g., a mono-substituted phenyl).

In some embodiments, the present invention provides a compound of formula IV:

IV or a pharmaceutically acceptable salt thereof, wherein each of $R_1$ and WG is as defined above and described herein.

In some embodiments, $R_1$ is halo (e.g., chloro). In some embodiments, one WG is hydrogen and the other is C(O)OR₂. In some embodiments, R2 is substituted or unsubstituted alkyl (e.g., unsubstituted alkyl such as isopropyl).

In some embodiments, the present invention provides a compound of formula V:

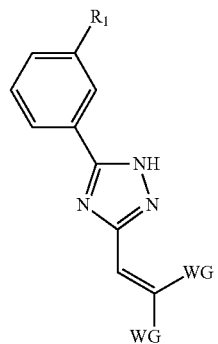

V

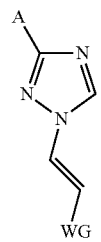

VIII

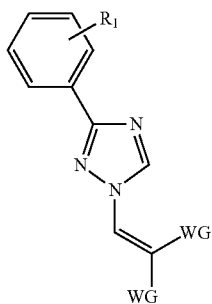

VI

IX or a pharmaceutically acceptable salt thereof, wherein each of R₁ and WG is as defined above and described herein.

In some embodiments, R₁ is halo (e.g., chloro). In some embodiments, one WG is hydrogen and the other is C(O)OR₂. In some embodiments, R2 is substituted or unsubstituted alkyl (e.g., unsubstituted alkyl such as isopropyl).

In some embodiments, the present invention provides a compound of formula VI:

or a pharmaceutically acceptable salt thereof, wherein each of A and WG is as defined above and described herein.

In some embodiments, the compound is:

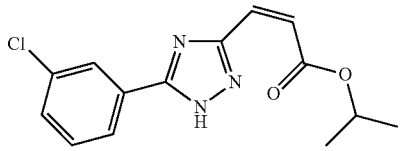 [SMILES: CC(C)OC(=O)/C=C\c1n[nH]c(-c2cccc(Cl)c2)n1]

or a pharmaceutically acceptable salt thereof, wherein each of R₁ and WG is as defined above and described herein.

In some embodiments, the present invention provides a compound of formula VII:

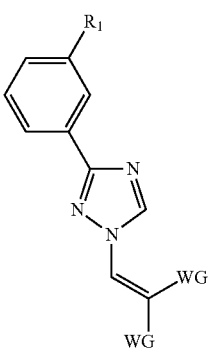

VII or a pharmaceutically acceptable salt thereof.

In some embodiments, a provided compound is not one that is disclosed in Van Neck et al. Bioorgan. Med. Chem. 16 (2008) 9487-9497.

In one aspect, the invention features a pharmaceutical composition comprising a compound described herein, or a pharmaceutically acceptable salt or N-oxide thereof, and a pharmaceutically acceptable carrier.

In another aspect, the invention features a method of treating a neoplastic or inflammatory or viral disorder in a subject, comprising administering a pharmaceutically effective amount of a compound or composition described herein.

Also provided herein are methods of treating a disease associated with expression or activity of p53, p73, p21, pRB, p27, IκB, NFκB, c-Abl, FOXO proteins, Cox-2 in a subject comprising administering to the patient a therapeutically effective amount of a compound described herein. For example, provided herein are methods of treating various cancers in mammals specifically including humans, dogs, cats, and farm animals, including hematologic malignancies (leukemias, lymphomas, myelomas, myelodysplastic and myeloproliferative syndromes) and solid tumors (carcinomas such as prostate, breast, lung, colon, pancreatic, renal, ovarian as well as soft tissue and osteo-sarcomas, and stromal tumors), inflammatory disorders such as rheumatoid arthritis, systemic lupus, systemic sclerosis, vasculitis syndromes (small, medium and large vessel), atherosclerosis, psoriasis and other dermatological inflammatory disorders (such as pemphigous, pemphigoid, allergic dermatitis), and urticarial syndromes comprising administering a compound represented by formula I.

or a pharmaceutically acceptable salt thereof, wherein each of R₁ and WG is as defined above and described herein.

In some embodiments, the present invention provides a compound of formula VIII or formula IX:

Also provided are compounds represented by formula I for use in therapy and/or for the manufacture of a medicament for the treatment of a disease associated with expression or activity of p53, p73, p21, pRB, p27, IκB, NFκB, c-Abl, FOXO proteins or Cox-2 in a subject.

In yet another aspect, the compound or composition is administrable intravenously and/or intraperitoneally.

In some embodiments, the present invention provides a compound selected from:

(Z)-3-[3-(3-Chloro-phenyl)[1,2,4]-triazol-1-yl]-acrylic acid ethyl ester
(E)-3-[3-(3-Chloro-phenyl)[1,2,4]-triazol-1-yl]-acrylic acid ethyl ester
(Z)-3-[3-(3-Chloro-phenyl)-[1,2,4]-triazol-1-yl]-acrylic acid isopropyl ester
(E)-3-[3-(3-Chloro-phenyl)-[1,2,4]-triazol-1-yl]-acrylic acid isopropyl ester
(Z)-3-[3-(3-Chloro-phenyl)-[1,2,4]-triazol-1-yl]-acrylic acid tert-butyl ester
(Z)-3-[3-(3-Chloro-phenyl)-[1,2,4]-triazol-1-yl]-acrylic acid tert-butyl ester
(E)-3-[3-(3-Chloro-phenyl)-[1,2,4]-triazol-1-yl]-N-phenyl-acryl amide
(E)-N-(2-Chloro-phenyl)-3-[3-(3-chloro-phenyl)-[1,2,4]-triazol-1-yl]-acryl amide
(4-{(E)-3-[3-(3-Chloro-phenyl)[1,2,4]-triazol-1-yl]-acryloylamino}-phenyl)-carbamic acid tert-butyl ester
(E)-3-[3-(3-Chloro-phenyl)-[1,2,4]-triazol-1-yl]-N-(4-methoxy-phenyl)-acryl amide
(E)-3-[3-(3-Chloro-phenyl)-[1,2,4]-triazol-1-yl]-N-methyl-N-phenyl-acryl amide
(E)-3-[3-(3-Chloro-phenyl)-[1,2,4]-triazol-1-yl]-N-methyl-N-phenyl-acryl amide
(E)-N-(4-Amino-phenyl)-3-[3-(3-chloro-phenyl)-[1,2,4]-triazol-1-yl]-acryl amide and/or a pharmaceutically-acceptable salt thereof.

In some embodiments, the present invention provides a compound selected from:

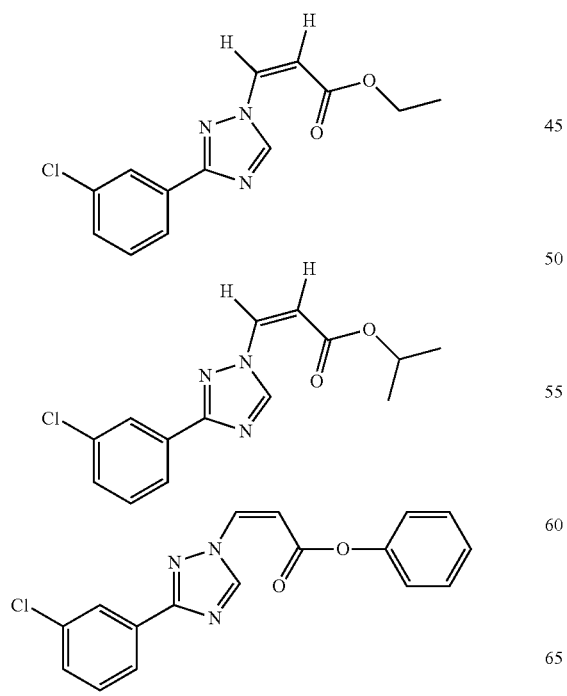
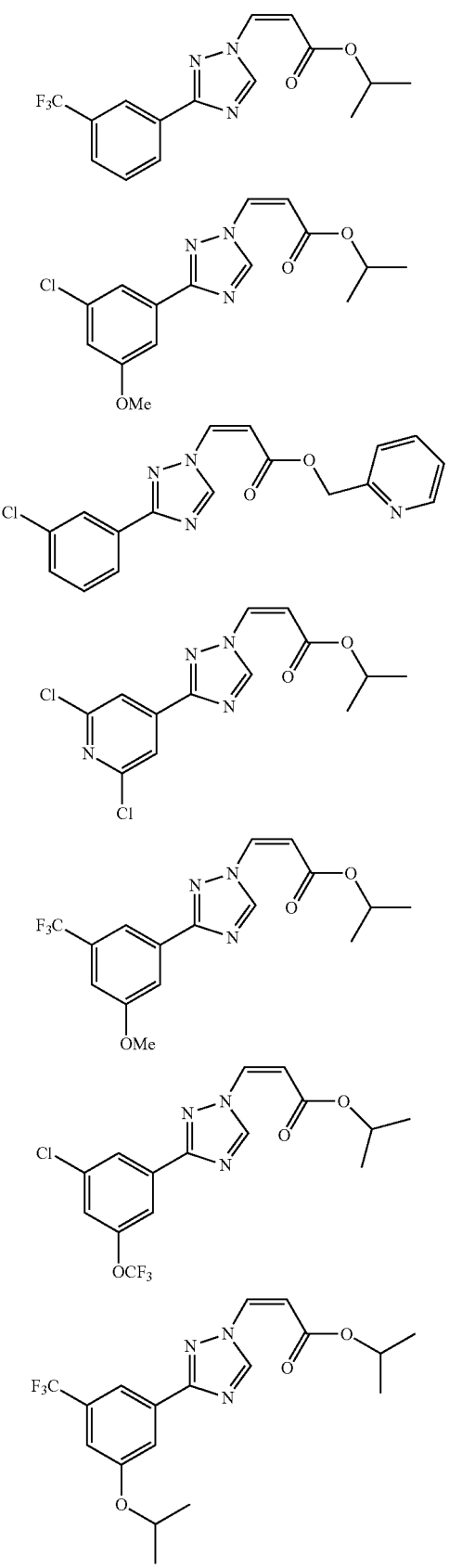

or a pharmaceutically acceptable salt thereof.

In some embodiments, the present invention provides a pharmaceutically acceptable composition comprising any of the compounds set forth in Table A, below, or a pharmaceutically acceptable salt thereof, and a pharmaceutically acceptable carrier, adjuvant, or vehicle:

TABLE A

TABLE A-continued
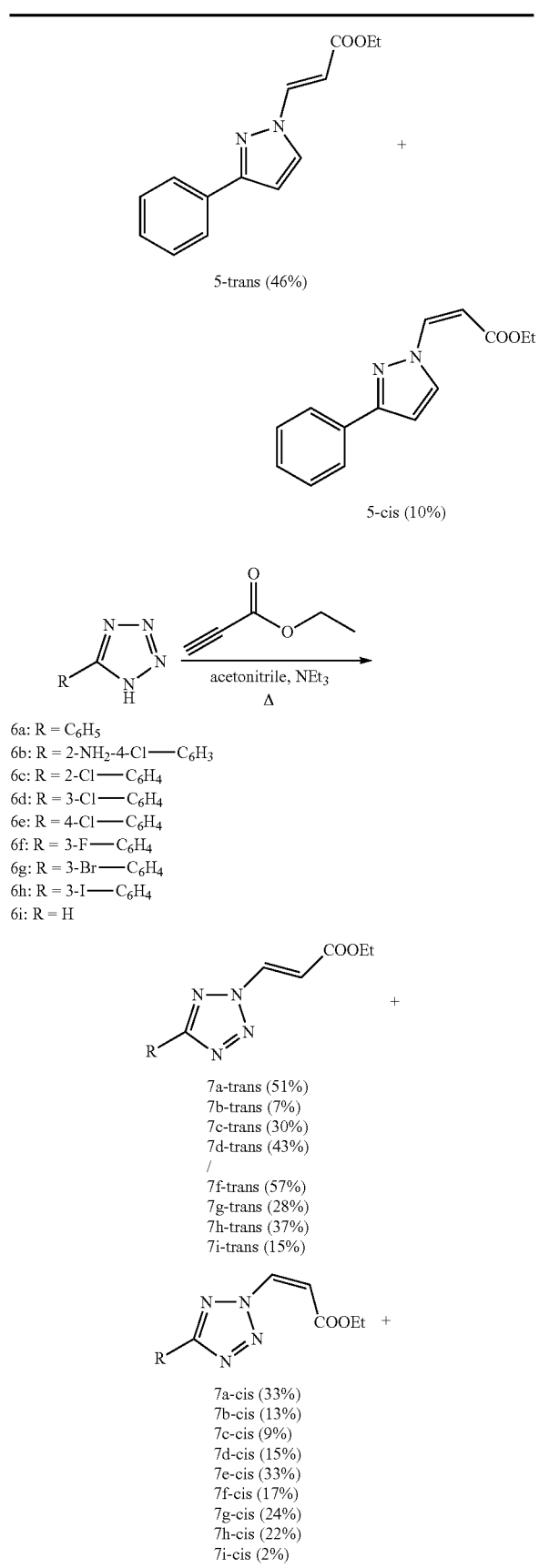
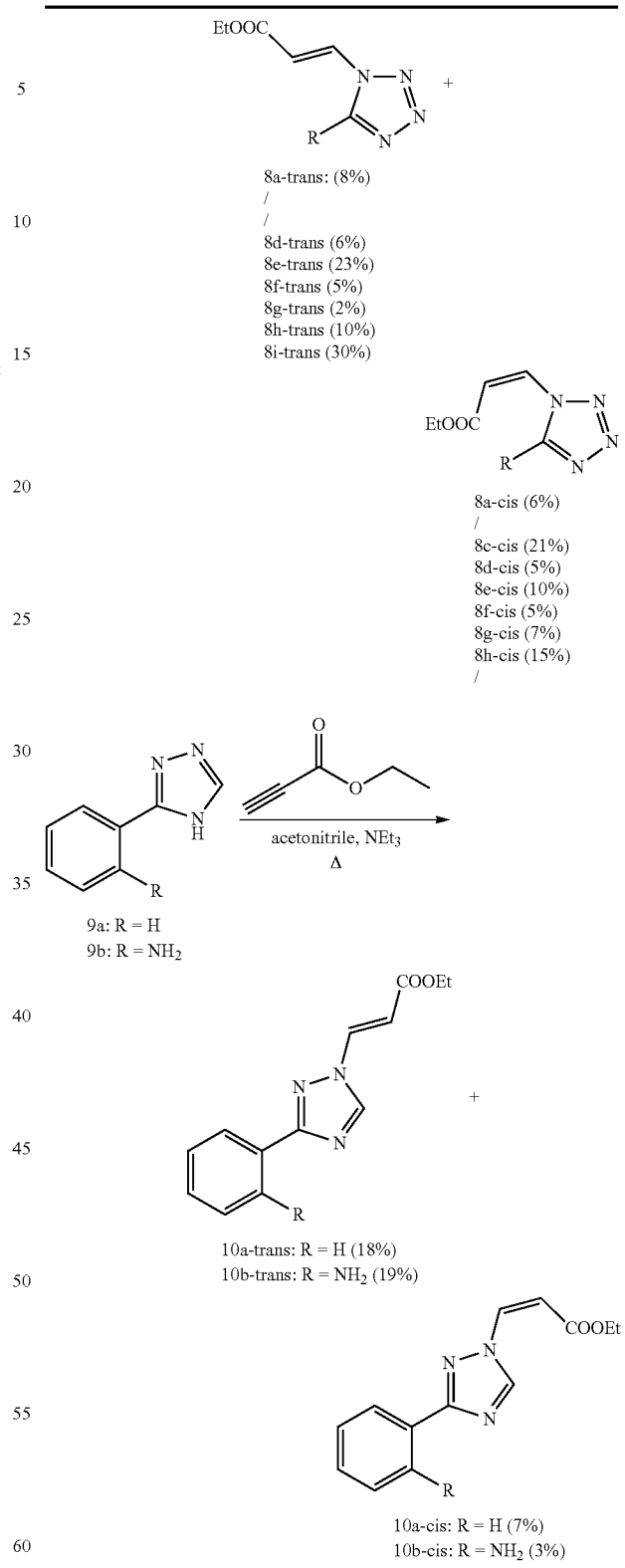
Compounds set forth in Table A, above, are described in Van Neck, et al., *Bioorg. Med. Chem.* 16 (2008) 9487-9497 ("Van Neck"), the entirety of which is hereby incorporated herein by reference. It will be appreciated that, although the compounds of Table A are disclosed in Van Neck, there is no disclosure whatsoever of addition salts of such compounds or pharmaceutical compositions comprising such compounds, or a pharmaceutically acceptable salt thereof. Nor is there any disclosure of administration of such compositions to a patient for treating a CRM1-mediated disorder or condition. Accordingly, in some embodiments, the present invention provides a pharmaceutically acceptable composition comprising a compound set forth in Table A, or a pharmaceutically acceptable salt thereof, and a pharmaceutically acceptable carrier, adjuvant, or vehicle:

In certain embodiments, the present invention provides a method for treating a CRM1-mediated disorder or condition in a patient, comprising administering to the patient a pharmaceutically acceptable composition comprising a compound set forth in Table A, or a pharmaceutically acceptable salt thereof, and a pharmaceutically acceptable carrier, adjuvant, or vehicle:

In some embodiments, the present invention provides a method for inhibiting CRM1 in a biological sample or in a patient, comprising contacting the biological sample with, or administering to the patient, a pharmaceutically acceptable salt of a compound det forth in Table A or pharmaceutically acceptable composition thereof.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CRM1, in a biological sample or in a patient. In certain embodiments, the amount of compound in compositions of this invention is such that is effective to measurably inhibit CRM1 in a biological sample or in a patient. In certain embodiments, a composition of this invention is formulated for administration to a patient in need of such composition. In some embodiments, a composition of this invention is formulated for oral administration, intravenous, subcutaneous, intraperitoneal or dramatological application to a patient.

The term "patient", as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, a provided oral formulation is formulated for immediate release or sustained/delayed release. Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

A provided compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms a provided compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for oral administration may be designed to protect the active ingredient against degradation as it passes through the alimentary tract, for example by an outer coating of the formulation on a tablet or capsule.

In another embodiment, a provided compound is be provided in an extended (or "delayed" or "sustained") release composition. This delayed release composition comprises a provided compound in combination with a delayed release component. This composition allows targeted release of a provided compound into the lower gastrointestinal tract; for example into the small intestine, the large intestine, the colon and/or the rectum. In certain embodiments, the delayed release composition comprising a provided compound further comprises an enteric or pH dependent coating such as cellulose acetate phthalates and other phthalates (e.g. polyvinyl acetate phthalate, methacrylates (Eudragits)). Alternatively, the delayed release composition provides controlled release to the small intestine and/or colon by the provision of pH sensitive methacrylate coatings, pH sensitive polymeric microspheres, or polymers which undergo degradation by hydrolysis. The delayed release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time dependent hydrogel coatings and/or by acrylic acid linked to azoaromatic bonds coatings.

In certain embodiments, the delayed release compositions of the present invention comprise hypromellose, microcrystalline cellulose, and a lubricant. The mixture of a provided compound, hypromellose and microcrystalline cellulose may be formulated into a tablet or capsule for oral administration. In certain embodiments, the mixture is granulated and pressed into tablets.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

In some embodiments, pharmaceutically acceptable compositions of this invention are formulated for topical administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water and penetration enhancers. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, intraocularly, intravitreally, subdermally or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms Uses of Compounds and Pharmaceutically Acceptable Compositions Compounds and compositions described herein are generally useful for the inhibition of CRM1.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Examples below.

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc, and companion animals (dog, cat, horse etc).

Provided compounds are inhibitors of CRM1 and are therefore useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable composition thereof.

As used herein, the term "CRM1-mediated" disorder or condition, as used herein, means any disease or other deleterious condition in which CRM1 is known to play a role. Accordingly, another embodiment of the present invention relates to treating or lessening the severity of one or more diseases in which CRM1 is known to play a role. Specifically, the present invention relates to a method of treating or lessening the severity of a disease or condition selected from a proliferative disorder, wherein said method comprises administering to a patient in need thereof a compound or composition according to the present invention. Such disorders are set forth in detail below.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, brain, bone, colon, lung, breast, ovarian, and liver origin), hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, kinase inhibitors, immunotherapy, and hormonal therapy, and anti-angiogenic therapies. Examples of each of these treatments are provided below.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g. Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs)

eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g. VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

As previously mentioned, DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including $O^6$-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Figure 3:
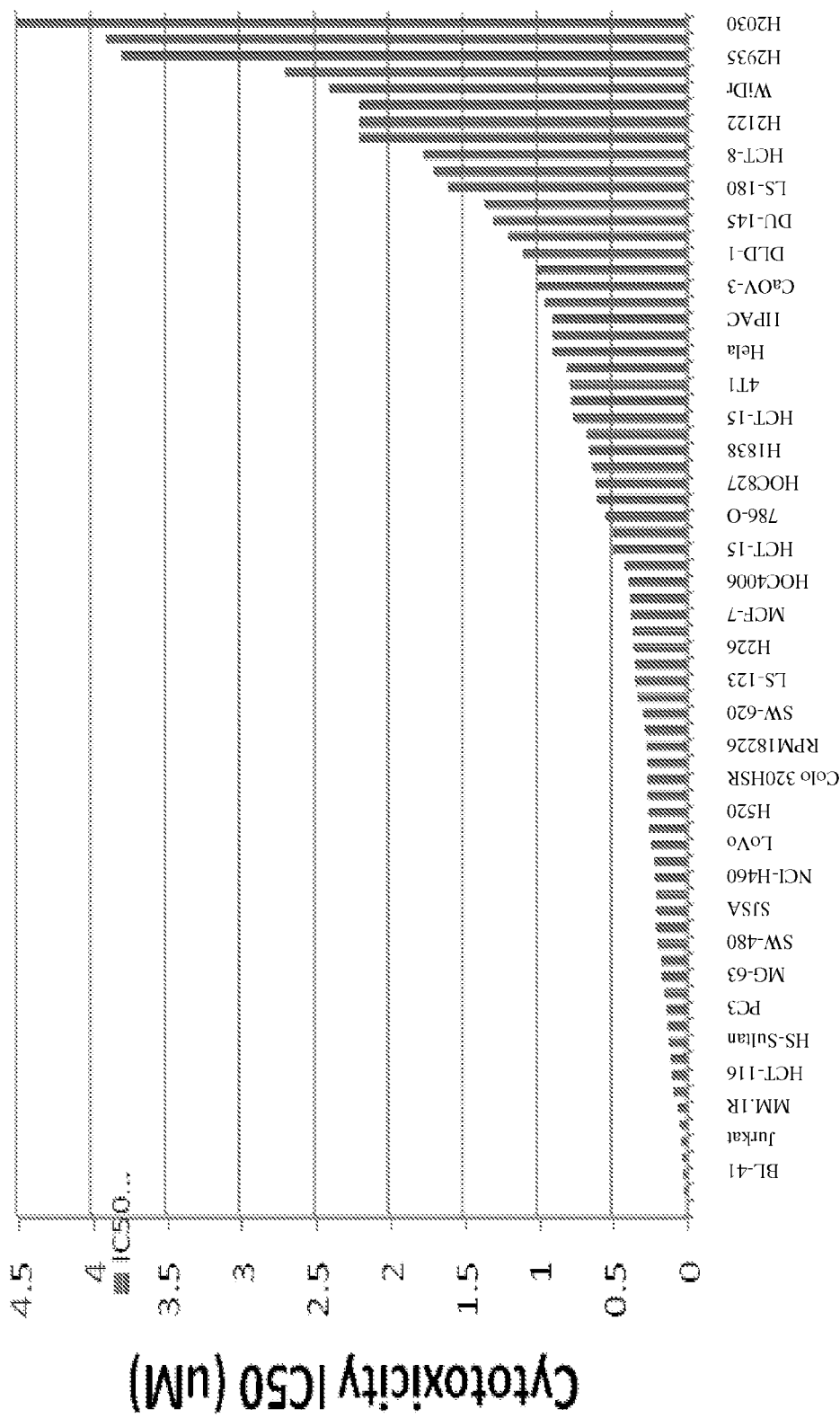
FIG. 3 is a bar graph which depicts Example 1's (KPT-0127) demonstrated potent and selective cytotoxicity in hematologic and solid tumor cell lines with minimal effect on normal cells. A panel of ~570 solid and hematologic cancer cell lines was exposed to KPT-0127 for 72 hours IC50 was determined by MTS assay.
Figure 4A:
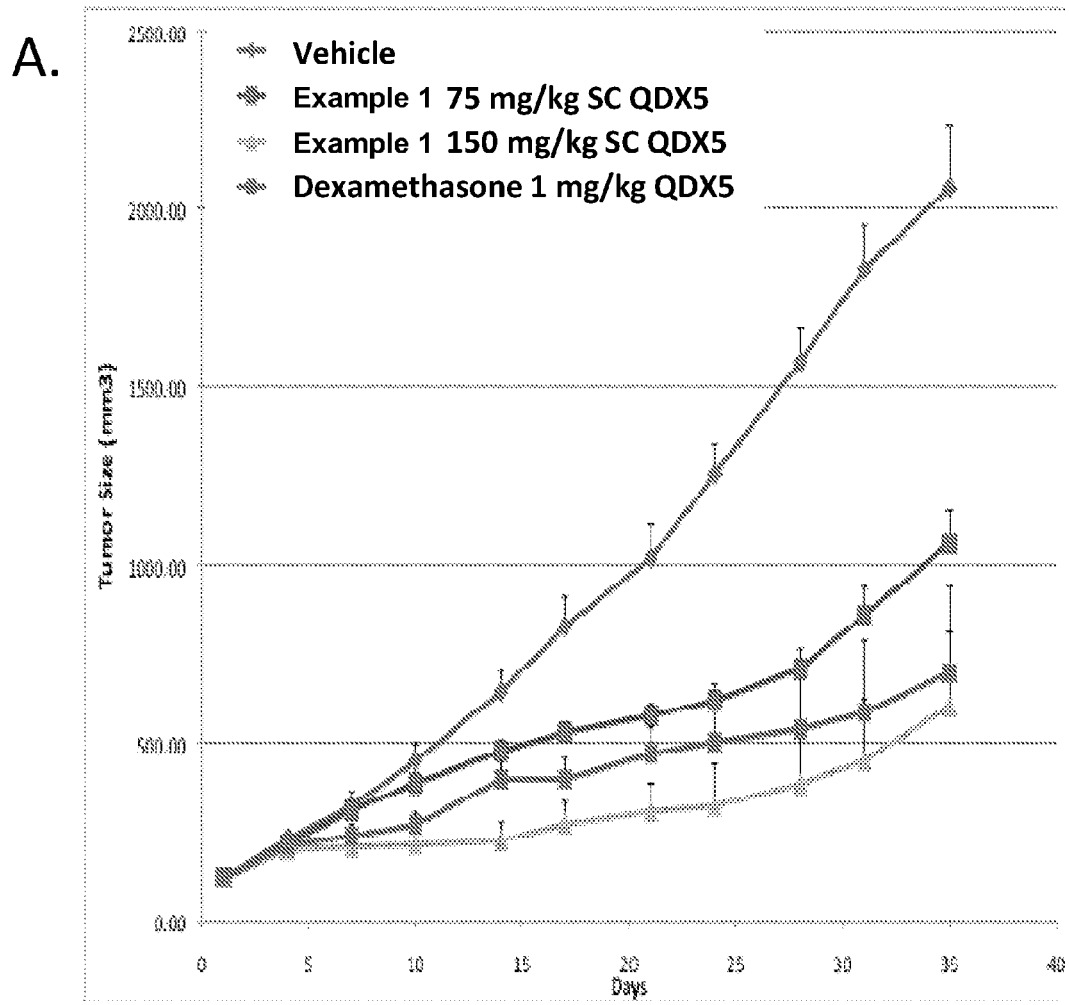
FIG. 4 presents activity data for Example 1 (KPT-0127) administered at 150 mg/kg QD×5. KPT-0127 inhibits growth of small (130 mm$^3$) and large (1300 mm$^3$) MM1.S xenografts. (A) MM1.S cells were grown as xenografts to 130 mm$^3$ (small) or (B) 1350 mm$^3$ (large) sizes and were treated with KPT-0127 SC or dexamethasone IP daily×5 and growth was assessed. Treatment of large xenografts is ongoing (data shown after 5 doses of KPT-0127).
Figure 4B:
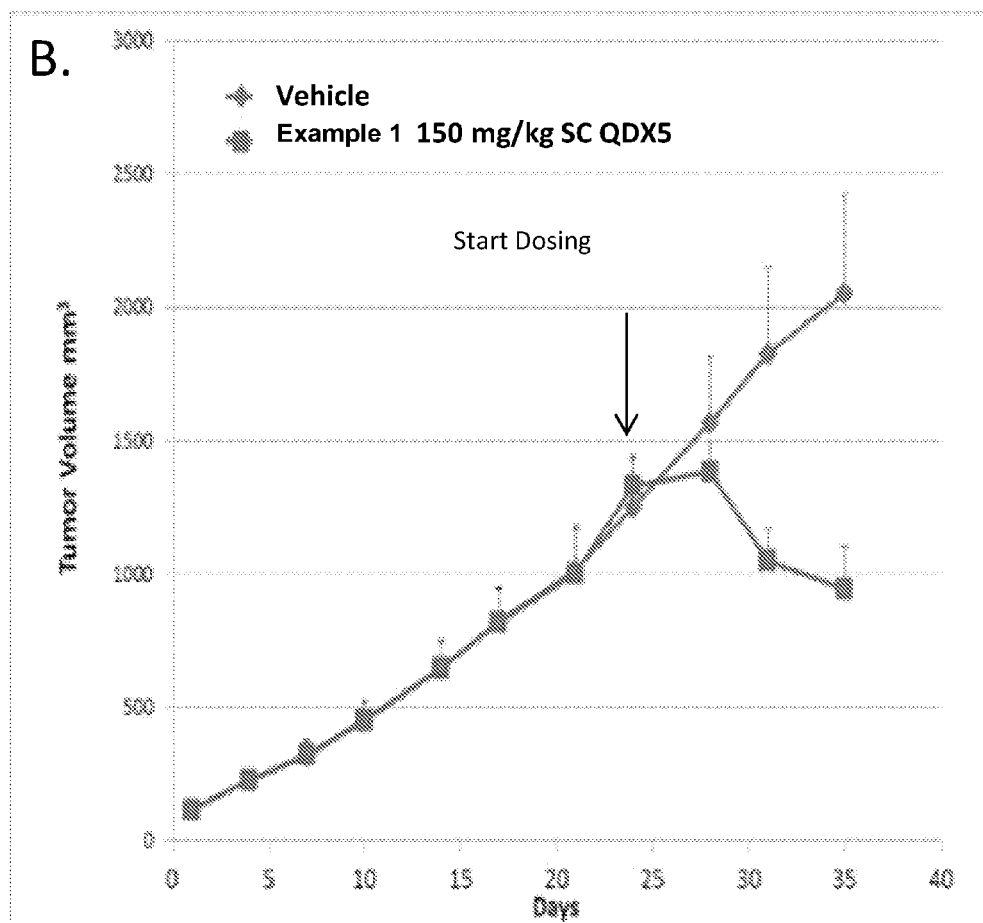
Figure 5:
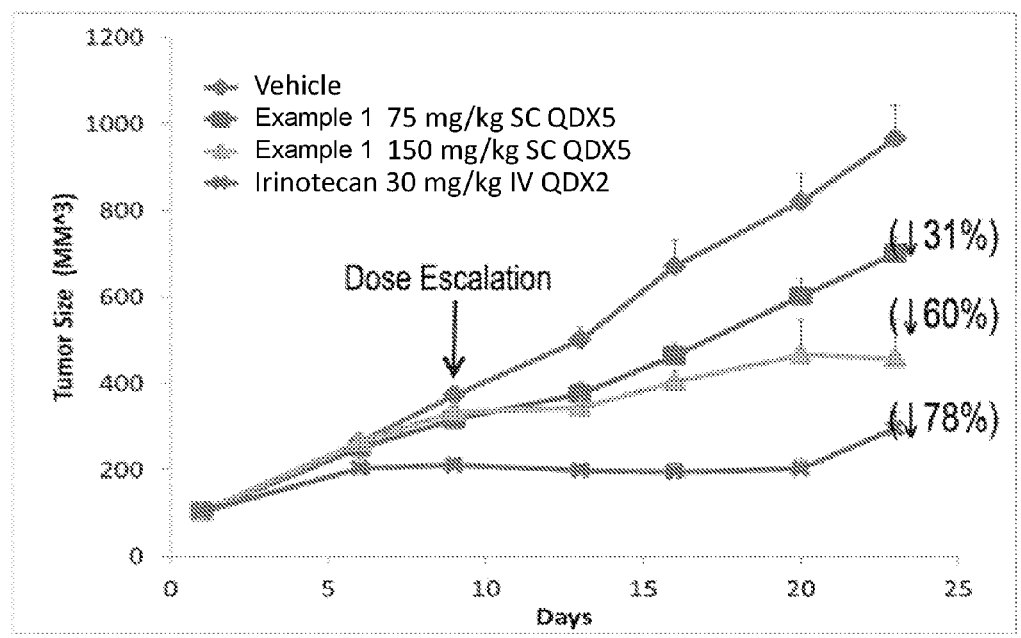
FIG. 5 presents activity data for Example 1 (KPT-127) administered at 150 mg/kg QD×7. KPT-0127 inhibits moderate HCT-116 xenografts. HCT-116 xenografts were grown to ~150 mm$^3$ and low dose KPT0127 administered. On day 9, when the tumors were ~350 mm$^3$, KPT-127 dose was escalated to 150 mg/kg sc daily. Irinotecan was used as a control. KPT-127 150 mg/kg sc daily is well tolerated, and showed similar anti-tumor effect (day 9 through day 24) as irinotecan. Clinical chemistries and CBCs were not significantly affected by KPT-127 treatment.

Fragile X syndrome gets its name from the way the part of the X chromosome that contains the gene abnormality looks under a microscope; it usually appears as if it is hanging by a thread and easily breakable (FIG. 3). The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligoncloetides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Inflammation and Autoimmune Disease

The compounds and methods described herein may be used to treat or prevent a disease or disorder associated with inflammation in humans as well as other mammals. A compound described herein may be administered prior to the onset of, at, or after the initiation of inflammation. When used prophylactically, the compounds are preferably provided in advance of any inflammatory response or symptom. Administration of the particles may prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g. giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In another embodiment, a particle or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The particles may be used to treat chronic hepatitis infection, including hepatitis B and hepatitis C.

Additionally, a particle or method described herein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacyl-morphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a particle described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection humans as well as other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT)), and inhibition of the release of virus (e.g., zanamivir and oseltamivir).

Ophthamology

Compounds and methods described herein may be used to treat or prevent an ophthamology disorder. Exemplary ophthamology disorders include macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFCATION

Abbreviations:

| | |
|---|---|
| atm | Atmosphere |
| aq. | Aqueous |
| BINAP | 2,2'-bis(diphenylphosphino)-1,1'-binaphthyl |
| Boc | tert-butoxycarbonyl |
| CDI | N,N'-Carbonyldiimidazole |
| DCC | N,N-Dicyclohexylcarbodiimide |
| DCM | Dichloromethane |
| DBU | Diaza(1,3)bicyclo[5.4.0]undecane |
| DEA | N,N-Diisopropyl ethylamine |
| DIBAL-H | Diisobutylaluminium hydride |
| DIC | N,N'-Diisopropylcarbodiimide |
| DMAP | N,N-Dimethyl-4-aminopyridine |
| DMF | Dimethylformamide |
| DMSO | Dimethylsulfoxide |
| DPPF | Diphenylphosphinoferrocene |
| EA | Ethyl acetate |
| EDCI | N-[3-(dimethylamino)propyl]-N'-ethylcarbodiimide hydrochloride |
| EDC | 1-Ethyl-3-(3-dimethylaminopropyl)-carbodiimide |
| $Et_2O$ | Diethylether |
| EtOAc | Ethyl acetate |
| EtOH | Ethanol |
| EtI | Iodoethane |
| Et | Ethyl |
| Fmoc | 9-fluorenylmethyloxycarbonyl |
| h | hour(s) |
| HetAr | Heteroaryl |
| HOBt | N-Hydroxybenzotriazole |
| HBTU | O-(Benzotriazol-1-yl)-N,N,N',N'-tetramethyluronium hexafluorophosphate |
| HPLC | High performance liquid chromatography |
| LAH | Lithium aluminium hydride |
| LCMS | HPLC mass spec |
| MCPBA | m-Chlorbenzoic acid |
| MeCN | Acetonitrile |
| MeOH | Methanol |
| min | Minutes |
| MeI | Iodomethane |
| MeMgCl | Methyl magnesium chloride |
| Me | Methyl |
| n-BuLi | 1-Butyllithium |
| NaOAc | Sodium acetate |
| NMR | Nuclear magnetic resonance |
| NMP | N-Methyl pyrrolidinone |
| nBuLi | 1-Butyl lithium |
| o.n. | Over night |
| RT, rt, r.t. | Room temperature |
| TEA | Triethylamine |
| THF | Tetrahydrofurane |

-continued

| | |
|---|---|
| nBu | normal Butyl |
| OMs | Mesylate or methane sulfonate ester |
| OTs | Tosylate, toluene sulfonate or 4-methylbenzene sulfonate ester |
| PCC | Pyridinium chlorochromate |
| PPTS | Pyridinium p-toluenesulfonate |
| TBAF | Tetrabutylammonium fluoride |
| pTsOH | p-Toluenesulfonic acid |
| SPE | Solid phase extraction (usually containing silica gel for mini-chromatography) |
| sat. | Saturated |
| GP | Protecting group |
| mins | minutes |

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

In a similar manner the following compounds were synthesized:
A=<1 uM; B=1-10 uM; C=>10 uM; NT=Not Tested.

TABLE 1

| Example | Structure | Name | Rev Export (%)/[IC$_{50}$] OR Cytotoxicity[EC$_{50}$] |
|---|---|---|---|
| 1 | 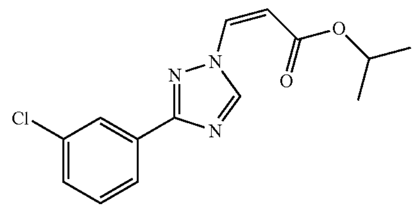 [SMILES: CC(C)OC(=O)/C=C\n1cnc(-c2cccc(Cl)c2)n1] | (Z)-3-[3-(3-Chloro-phenyl)-[1,2,4]-triazol-1-yl]-acrylic acid isopropyl ester | A |
| 2 | 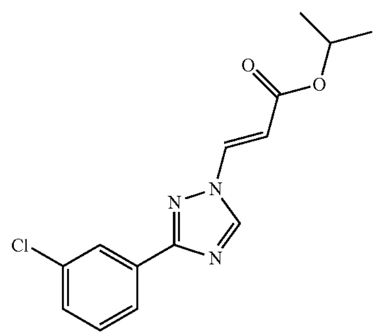 [SMILES: CC(C)OC(=O)/C=C/n1cnc(-c2cccc(Cl)c2)n1] | (E)-3-[3-(3-Chloro-phenyl)-[1,2,4]-triazol-1-yl]-acrylic acid isopropyl ester | C |
| 3 | 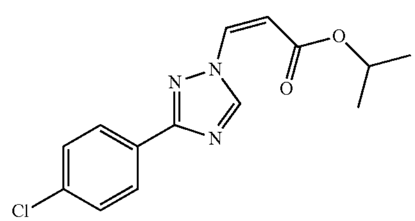 [SMILES: CC(C)OC(=O)/C=C\n1cnc(-c2ccc(Cl)cc2)n1] | (Z)-isopropyl 3-(3-(4-chlorophenyl)-1H-1,2,4-triazol-1-yl)acrylate | A |
| 4 | 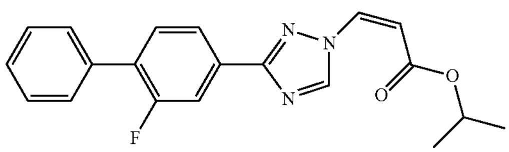 [SMILES: CC(C)OC(=O)/C=C\n1cnc(-c2ccc(-c3ccccc3)c(F)c2)n1] | (Z)-isopropyl 3-(3-(2-fluoro-[1,1'-biphenyl]-4-yl)-1H-1,2,4-triazol-1-yl)acrylate | C |
| 5 | 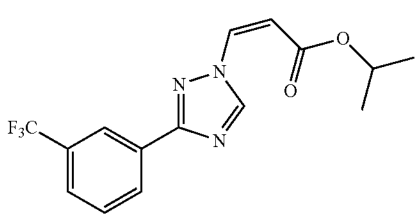 [SMILES: CC(C)OC(=O)/C=C\n1cnc(-c2cccc(C(F)(F)F)c2)n1] | (Z)-isopropyl 3-(3-(3-(trifluoromethyl)phenyl)-1H-1,2,4-triazol-1-yl)acrylate | A |
| 6 | 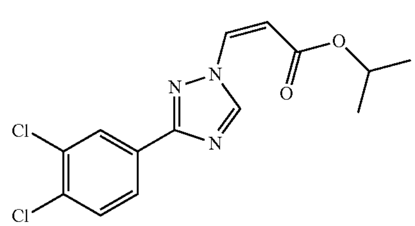 [SMILES: CC(C)OC(=O)/C=C\n1cnc(-c2ccc(Cl)c(Cl)c2)n1] | (Z)-isopropyl 3-(3-(3,4-dichlorophenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 7 | 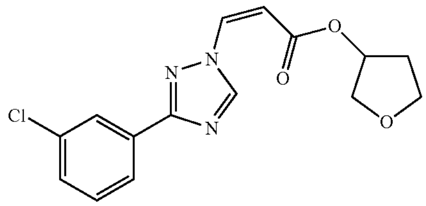 [SMILES: O=C(/C=C\n1cnc(-c2cccc(Cl)c2)n1)OC1CCOC1] | (Z)-tetrahydrofuran-3-yl 3-(3-(3-chlorophenyl)-1H-1,2,4-triazol-1-yl)acrylate | A |
| 8 | 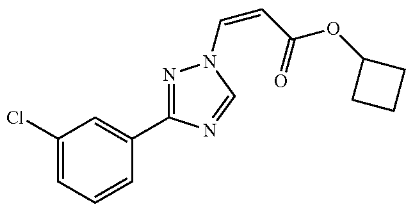 [SMILES: O=C(/C=C\n1cnc(-c2cccc(Cl)c2)n1)OC1CCC1] | (Z)-cyclobutyl 3-(3-(3-chlorophenyl)-1H-1,2,4-triazol-1-yl)acrylate | A |
| 9 | 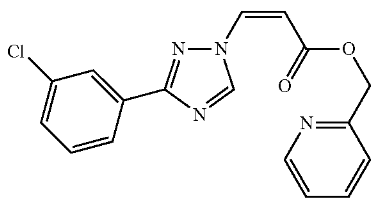 [SMILES: O=C(/C=C\n1cnc(-c2cccc(Cl)c2)n1)OCc1ccccn1] | (Z)-pyridin-2-ylmethyl 3-(3-(3-chlorophenyl)-1H-1,2,4-triazol-1-yl)acrylate | A |
| 10 | 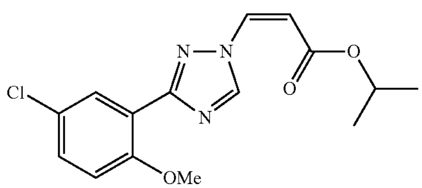 [SMILES: COc1ccc(Cl)cc1-c1ncn(/C=C\C(=O)OC(C)C)n1] | (Z)-isopropyl 3-(3-(5-chloro-2-methoxyphenyl)-1H-1,2,4-triazol-1-yl)acrylate | A |
| 11 | 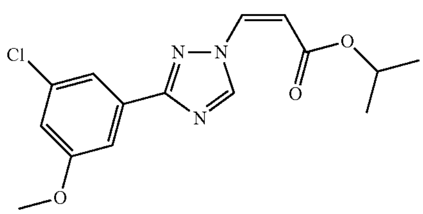 [SMILES: COc1cc(Cl)cc(-c2ncn(/C=C\C(=O)OC(C)C)n2)c1] | (Z)-isopropyl -(3-(3-chloro-5-methoxyphenyl)-1H-1,2,4-triazol-1-yl)acrylate | A |
| 12 | 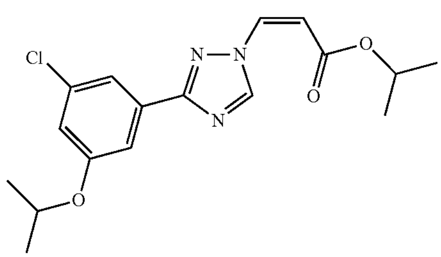 [SMILES: CC(C)OC(=O)/C=C\n1cnc(-c2cc(Cl)cc(OC(C)C)c2)n1] | (Z)-isopropyl 3-(3-(3-chloro-5-isopropoxyphenyl)-1H-1,2,4-triazol-1-yl)acrylate | A |
| 13 | 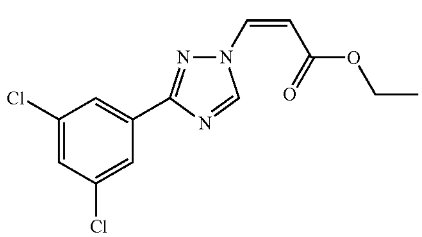 [SMILES: CCOC(=O)/C=C\n1cnc(-c2cc(Cl)cc(Cl)c2)n1] | (Z)-3-[3-(3,5-Dichloro-phenyl)-[1,2,4]triazol-1-yl]-acrylic acid ethyl ester | A |

TABLE 1-continued

| Example | Structure | Name | Rev Export (%)/[IC$_{50}$] OR Cytotoxicity[EC$_{50}$] |
|---|---|---|---|
| 14 | 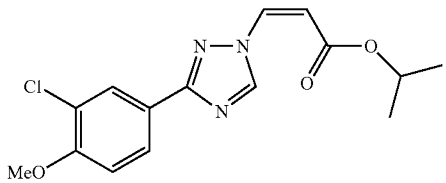 [SMILES: COc1ccc(-c2ncn(/C=C\C(=O)OC(C)C)n2)cc1Cl] | (Z)-isopropyl 3-(3-(3-chloro-4-methoxyphenyl)-1H-1,2,4-triazol-1-yl)acrylate | B |
| 15 | 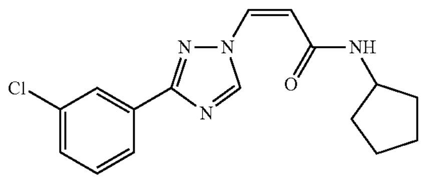 [SMILES: O=C(/C=C\n1cnc(-c2cccc(Cl)c2)n1)NC1CCCC1] | (Z)-3-(3-(3-chlorophenyl)-1H-1,2,4-triazol-1-yl)-N-cyclopentylacrylamide | C |
| 16 | 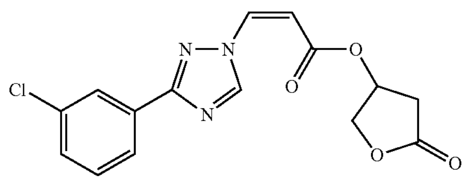 [SMILES: O=C(/C=C\n1cnc(-c2cccc(Cl)c2)n1)OC1COC(=O)C1] | (Z)-5-oxotetrahydrofuran-3-yl 3-(3-(3-chlorophenyl)-1H-1,2,4-triazol-1-yl)acrylate | B |
| 17 | 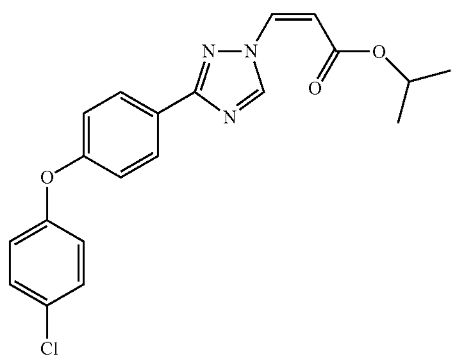 [SMILES: CC(C)OC(=O)/C=C\n1cnc(-c2ccc(Oc3ccc(Cl)cc3)cc2)n1] | (Z)-isopropyl 3-(3-(4-(4-chlorophenoxy)phenyl)-1H-1,2,4-triazol-1-yl)acrylate | B |
| 18 | 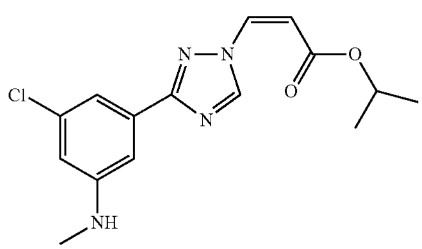 [SMILES: CNc1cc(Cl)cc(-c2ncn(/C=C\C(=O)OC(C)C)n2)c1] | (Z)-isopropyl 3-(3-(3-chloro-5-(methylamino)phenyl)-1H-1,2,4-triazol-1-yl)acrylate | A |
| 19 | 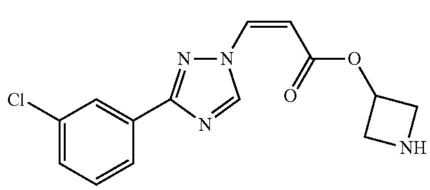 [SMILES: O=C(/C=C\n1cnc(-c2cccc(Cl)c2)n1)OC1CNC1] | (Z)-azetidin-3-yl 3-(3-(3-chlorophenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 20 | 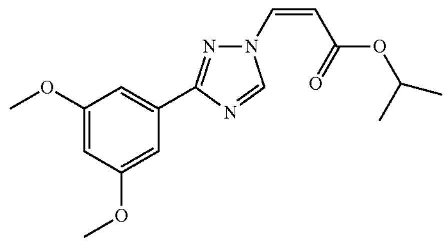 [SMILES: COc1cc(OC)cc(-c2ncn(/C=C\C(=O)OC(C)C)n2)c1] | (Z)-isopropyl 3-(3-(3,5-dimethoxyphenyl)-1H-1,2,4-triazol-1-yl)acrylate | A |
| 21 | 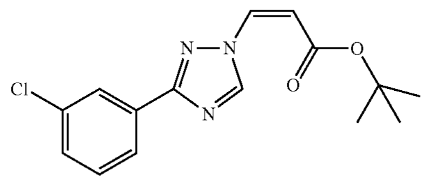 [SMILES: CC(C)(C)OC(=O)/C=C\n1cnc(-c2cccc(Cl)c2)n1] | (Z)-tert-butyl 3-(3-(3-chlorophenyl)-1H-1,2,4-triazol-1-yl)acrylate | B |
| 22 | 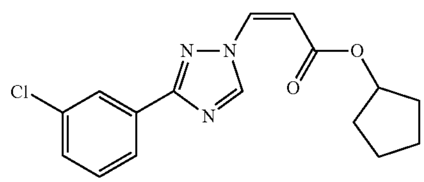 [SMILES: O=C(/C=C\n1cnc(-c2cccc(Cl)c2)n1)OC1CCCC1] | (Z)-cyclopentyl 3-(3-(3-chlorophenyl)-1H-1,2,4-triazol-1-yl)acrylate | A |
| 23 | 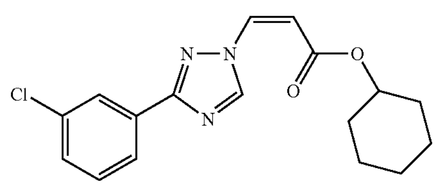 [SMILES: O=C(/C=C\n1cnc(-c2cccc(Cl)c2)n1)OC1CCCCC1] | (Z)-cyclohexyl 3-(3-(3-chlorophenyl)-1H-1,2,4-triazol-1-yl)acrylate | A |
| 24 | 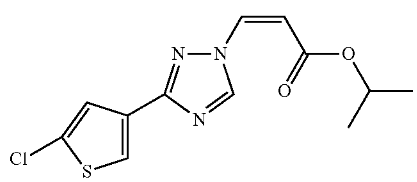 [SMILES: CC(C)OC(=O)/C=C\n1cnc(-c2csc(Cl)c2)n1] | (Z)-isopropyl 3-(3-(5-chlorothiophen-3-yl)-1H-1,2,4-triazol-1-yl)acrylate | A |
| 25 | 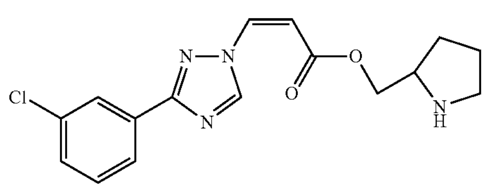 [SMILES: O=C(/C=C\n1cnc(-c2cccc(Cl)c2)n1)OCC1CCCN1] | (Z)-pyrrolidin-2-ylmethyl 3-(3-(3-chlorophenyl)-1H-1,2,4-triazol-1-yl)acrylate | B |
| 26 | 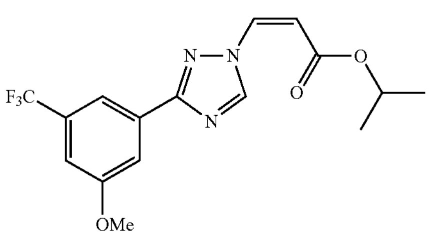 [SMILES: COc1cc(-c2ncn(/C=C\C(=O)OC(C)C)n2)cc(C(F)(F)F)c1] | (Z)-isopropyl 3-(3-(3-methoxy-5-(trifluoromethyl)phenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 27 | 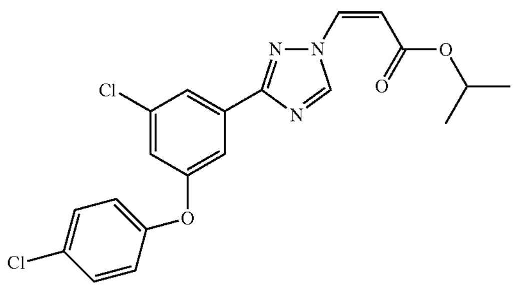 [SMILES: CC(C)OC(=O)/C=C\n1cnc(-c2cc(Cl)cc(Oc3ccc(Cl)cc3)c2)n1] | (Z)-isopropyl 3-(3-(3-chloro-5-(4-chlorophenoxy)phenyl)-1H-1,2,4-triazol-1-yl)acrylate | B |
| 28 | 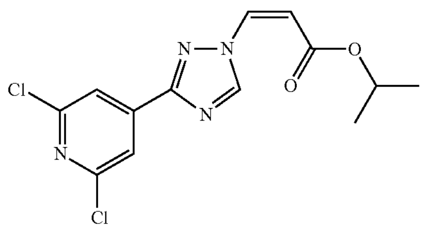 [SMILES: CC(C)OC(=O)/C=C\n1cnc(-c2cc(Cl)nc(Cl)c2)n1] | (Z)-isopropyl 3-(3-(2,6-dichloropyridin-4-yl)-1H-1,2,4-triazol-1-yl)acrylate | A |
| 29 | 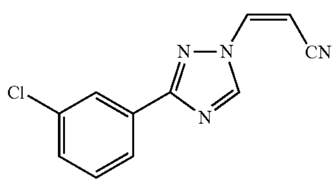 [SMILES: N#C/C=C\n1cnc(-c2cccc(Cl)c2)n1] | (Z)-3-(3-(3-chlorophenyl)-1H-1,2,4-triazol-1-yl)acrylonitrile | A |
| 30 | 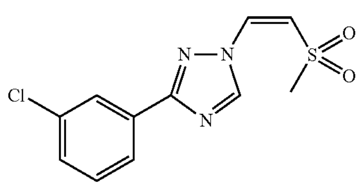 [SMILES: CS(=O)(=O)/C=C\n1cnc(-c2cccc(Cl)c2)n1] | (Z)-3-(3-chlorophenyl)-1-(2-(methylsulfonyl)vinyl)-1H-1,2,4-triazole | A |
| 31 | 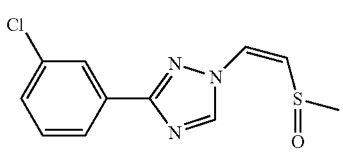 [SMILES: CS(=O)/C=C\n1cnc(-c2cccc(Cl)c2)n1] | (Z)-ethyl 3-(3-(3-chloro-5-methoxyphenyl)-1H-1,2,4-triazol-1-yl)acrylate | B |
| 32 | 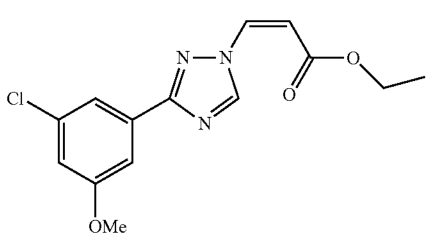 [SMILES: CCOC(=O)/C=C\n1cnc(-c2cc(Cl)cc(OC)c2)n1] | (Z)-methyl 3-(3-(3-chloro-5-methoxyphenyl)-1H-1,2,4-triazol-1-yl)acrylate | A |
| 33 | 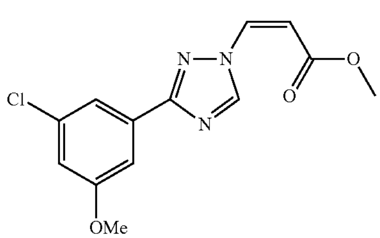 [SMILES: COC(=O)/C=C\n1cnc(-c2cc(Cl)cc(OC)c2)n1] | (Z)-methyl 3-(3-(3-chloro-5-methoxyphenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 34 | 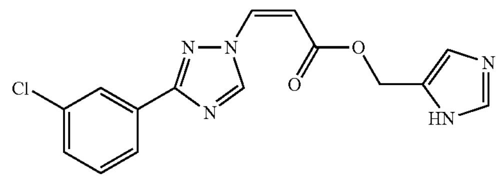 [SMILES: O=C(/C=C\n1cnc(-c2cccc(Cl)c2)n1)OCc1cnc[nH]1] | (Z)-(1H-imidazol-5-yl)methyl 3-(3-(3-chlorophenyl)-1H-1,2,4-triazol-1-yl)acrylate | B |
| 35 | 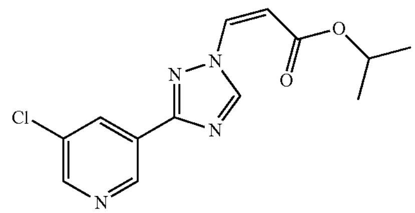 [SMILES: CC(C)OC(=O)/C=C\n1cnc(-c2cncc(Cl)c2)n1] | (Z)-isopropyl 3-(3-(5-chloropyridin-3-yl)-1H-1,2,4-triazol-1-yl)acrylate | A |
| 36 | 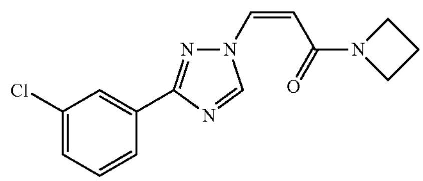 [SMILES: O=C(/C=C\n1cnc(-c2cccc(Cl)c2)n1)N1CCC1] | (Z)-1-(azetidin-1-yl)-3-(3-(3-chlorophenyl)-1H-1,2,4-triazol-1-yl)prop-2-en-1-one | A |
| 37 | 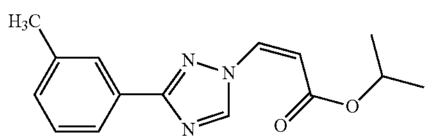 [SMILES: Cc1cccc(-c2ncn(/C=C\C(=O)OC(C)C)n2)c1] | (Z)-isopropyl 3-(3-(m-tolyl)-1H-1,2,4-triazol-1-yl)acrylate | A |
| 38 | 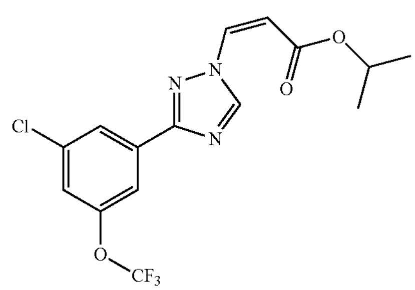 [SMILES: CC(C)OC(=O)/C=C\n1cnc(-c2cc(Cl)cc(OC(F)(F)F)c2)n1] | (Z)-isopropyl 3-(3-(3-chloro-5-(trifluoromethoxy)phenyl)-1H-1,2,4-triazol-1-yl)acrylate | A |
| 39 | 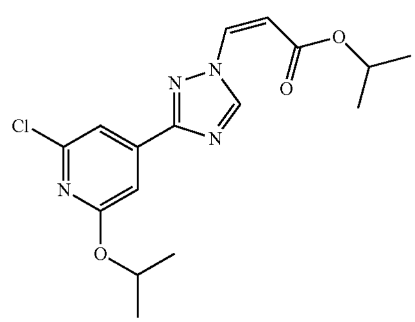 [SMILES: CC(C)OC(=O)/C=C\n1cnc(-c2cc(Cl)nc(OC(C)C)c2)n1] | (Z)-isopropyl 3-(3-(2-chloro-6-isopropoxypyridin-4-yl)-1H-1,2,4-triazol-1-yl)acrylate | A |
| 40 | 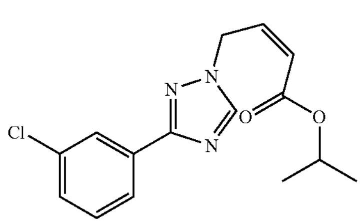 [SMILES: CC(C)OC(=O)/C=C\Cn1cnc(-c2cccc(Cl)c2)n1] | (Z)-isopropyl 4-(3-(3-chlorophenyl)-1H-1,2,4-triazol-1-yl)but-2-enoate | B |

TABLE 1-continued

| Example | Structure | Name | Rev Export (%)/[IC$_{50}$] OR Cytotoxicity[EC$_{50}$] |
|---|---|---|---|
| 41 | 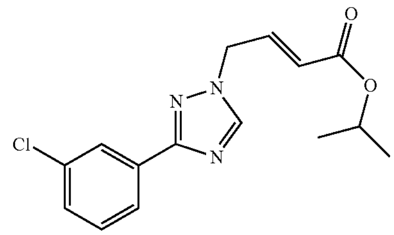 [SMILES: CC(C)OC(=O)/C=C/Cn1cnc(-c2cccc(Cl)c2)n1] | (E)-isopropyl 4-(3-(3-chlorophenyl)-1H-1,2,4-triazol-1-yl)but-2-enoate | B |
| 42 | 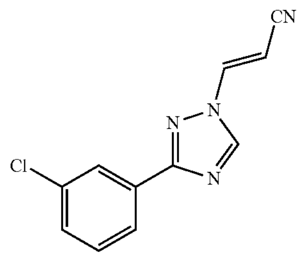 [SMILES: N#C/C=C/n1cnc(-c2cccc(Cl)c2)n1] | (E)-3-(3-(3-chlorophenyl)-1H-1,2,4-triazol-1-yl)acrylonitrile | B |
| 43 | 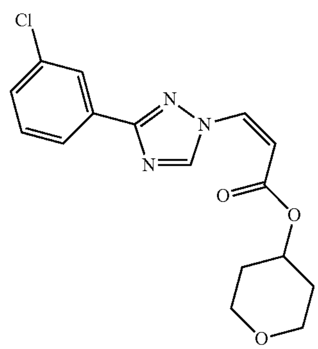 [SMILES: O=C(/C=C\n1cnc(-c2cccc(Cl)c2)n1)OC1CCOCC1] | (Z)-tetrahydro-2H-pyran-4-yl 3-(3-(3-chlorophenyl)-1H-1,2,4-triazol-1-yl)acrylate | A |
| 44 | 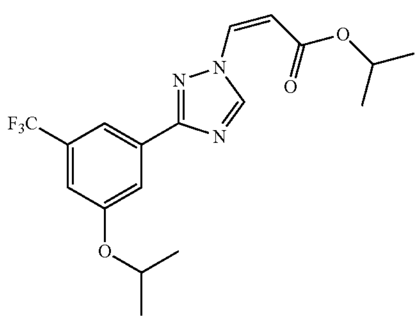 [SMILES: CC(C)OC(=O)/C=C\n1cnc(-c2cc(OC(C)C)cc(C(F)(F)F)c2)n1] | (Z)-isopropyl 3-(3-(3-isopropoxy-5-(trifluoromethyl)phenyl)-1H-1,2,4-triazol-1-yl)acrylate | A |
| 45 | 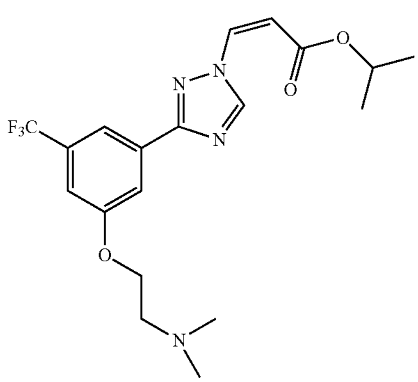 [SMILES: CC(C)OC(=O)/C=C\n1cnc(-c2cc(OCCN(C)C)cc(C(F)(F)F)c2)n1] | (Z)-isopropyl 3-(3-(3-(2-(dimethylamino)ethoxy)-5-(trifluoromethyl)phenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 46 | 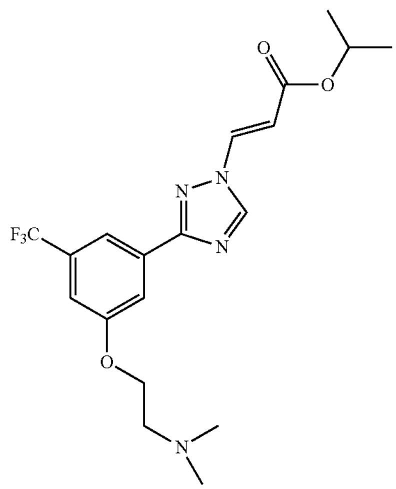 [SMILES: CC(C)OC(=O)/C=C/n1cnc(-c2cc(OCCN(C)C)cc(C(F)(F)F)c2)n1] | (E)-isopropyl 3-(3-(3-(2-(dimethylamino)ethoxy)-5-(trifluoromethyl)phenyl)-1H-1,2,4-triazol-1-yl)acrylate | B |
| 47 | 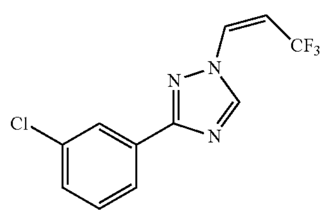 [SMILES: FC(F)(F)/C=C\n1cnc(-c2cccc(Cl)c2)n1] | (Z)-3-(3-chlorophenyl)-1-(3,3,3-trifluoroprop-1-en-1-yl)-1H-1,2,4-triazole | B |
| 48 | 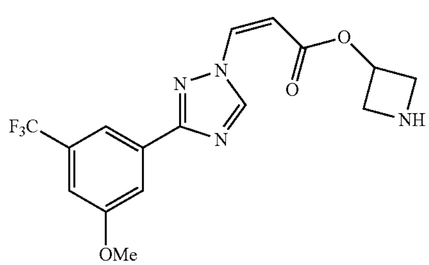 [SMILES: COc1cc(-c2ncn(/C=C\C(=O)OC3CNC3)n2)cc(C(F)(F)F)c1] | (Z)-azetidin-3-yl 3-(3-(3-methoxy-5-(trifluoromethyl)phenyl)-1H-1,2,4-triazol-1-yl)acrylate | A |
| 49 | 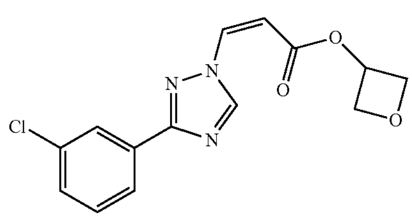 [SMILES: O=C(/C=C\n1cnc(-c2cccc(Cl)c2)n1)OC1COC1] | (Z)-oxetan-3-yl 3-(3-(3-chlorophenyl)-1H-1,2,4-triazol-1-yl)acrylate | A |
| 50 | 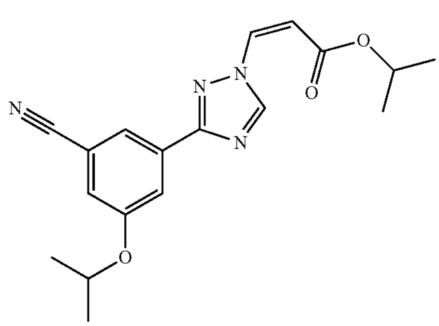 [SMILES: CC(C)OC(=O)/C=C\n1cnc(-c2cc(C#N)cc(OC(C)C)c2)n1] | (Z)-isopropyl 3-(3-(3-cyano-5-isopropoxyphenyl)-1H-1,2,4-triazol-1-yl)acrylate | A |

TABLE 1-continued
| Example | Structure | Name | Rev Export (%)/[IC$_{50}$] OR Cytotoxicity[EC$_{50}$] |
|---|---|---|---|
| 51 | 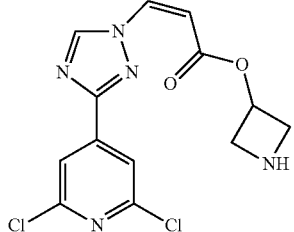 [SMILES: O=C(/C=C\n1cnc(-c2cc(Cl)nc(Cl)c2)n1)OC1CNC1] | (Z)-azetidin-3-yl 3-(3-(2,6-dichloropyridin-4-yl)-1H-1,2,4-triazol-1-yl)acrylate | A |
| 52 | 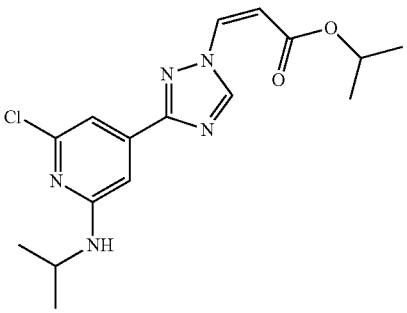 [SMILES: CC(C)Nc1cc(-c2ncn(/C=C\C(=O)OC(C)C)n2)cc(Cl)n1] | (Z)-isopropyl 3-(3-(2-chloro-6-(isopropylamino)pyridin-4-yl)-1H-1,2,4-triazol-1-yl)acrylate | A |
| 53 | 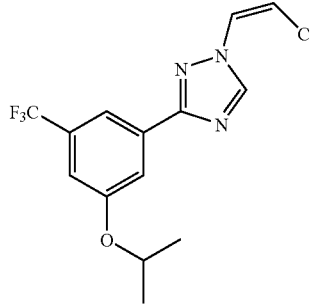 | (Z)-3-(3-(3-isopropoxy-5-(trifluoromethyl)phenyl)-1H-1,2,4-triazol-1-yl)acrylonitrile | A |
| 54 | 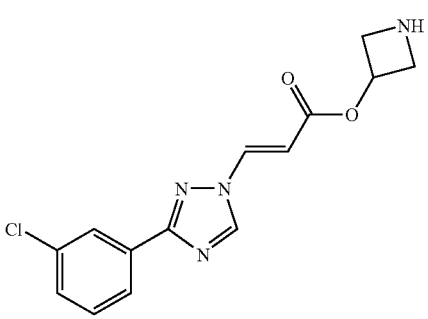 [SMILES: O=C(/C=C/n1cnc(-c2cccc(Cl)c2)n1)OC1CNC1] | (E)-azetidin-3-yl 3-(3-(3-chlorophenyl)-1H-1,2,4-triazol-1-yl)acrylate | B |

TABLE 1-continued

| Example | Structure | Name | Rev Export (%)/[IC$_{50}$] OR Cytotoxicity[EC$_{50}$] |
|---|---|---|---|
| 55 | 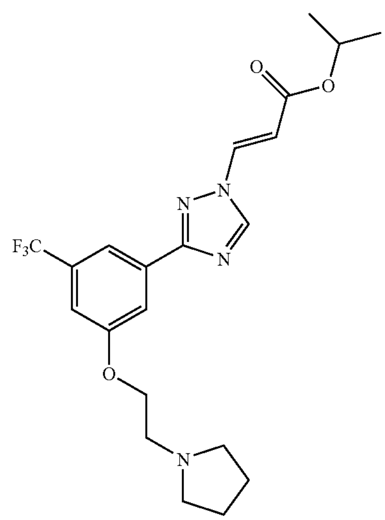 [SMILES: CC(C)OC(=O)/C=C/n1cnc(-c2cc(OCCN3CCCC3)cc(C(F)(F)F)c2)n1] | (E)-isopropyl 3-(3-(3-(2-(pyrrolidin-1-yl)ethoxy)-5-(trifluoromethyl)phenyl)-1H-1,2,4-triazol-1-yl)acrylate | C |
| 56 | 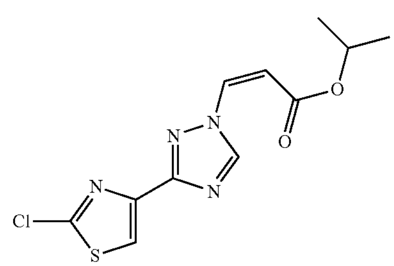 | (Z)-isopropyl 3-(3-(2-chlorothiazol-4-yl)-1H-1,2,4-triazol-1-yl)acrylate | B |
| 57 | 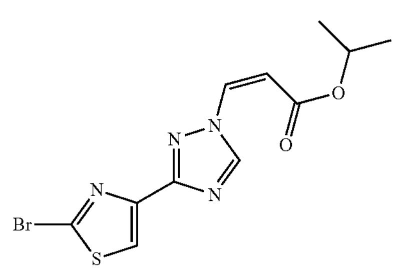 [SMILES: CC(C)OC(=O)/C=C\n1cnc(-c2csc(Cl)n2)n1] | (Z)-isopropyl 3-(3-(2-bromothiazol-4-yl)-1H-1,2,4-triazol-1-yl)acrylate | B |
| 58 | 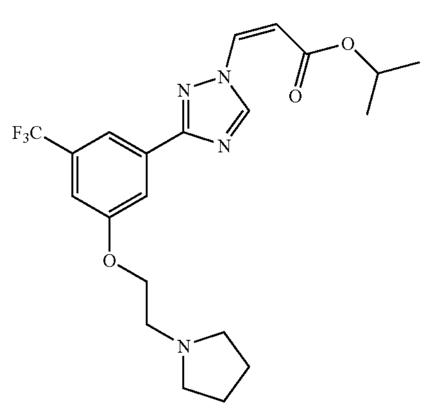 [SMILES: CC(C)OC(=O)/C=C\n1cnc(-c2cc(OCCN3CCCC3)cc(C(F)(F)F)c2)n1] | (Z)-isopropyl 3-(3-(3-(2-(pyrrolidin-1-yl)ethoxy)-5-(trifluoromethyl)phenyl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---------|-----------|------|------|
| 59 | 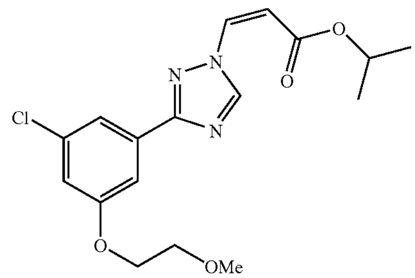 [SMILES: COCCOc1cc(Cl)cc(-c2ncn(/C=C\C(=O)OC(C)C)n2)c1] | (Z)-isopropyl 3-(3-(3-chloro-5-(2-methoxyethoxy)phenyl)-1H-1,2,4-triazol-1-yl)acrylate | A |
| 60 | 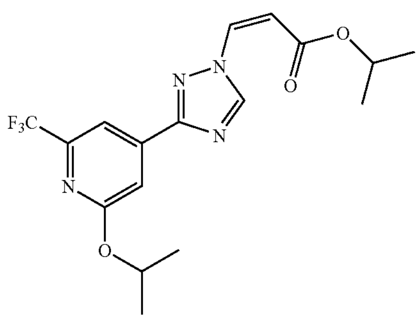 | (Z)-isopropyl 3-(3-(2-isopropoxy-6-(trifluoromethyl)pyridin-4-yl)-1H-1,2,4-triazol-1-yl)acrylate | A |
| 61 | 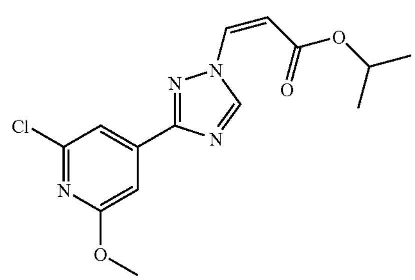 [SMILES: COc1cc(-c2ncn(/C=C\C(=O)OC(C)C)n2)cc(Cl)n1] | (Z)-isopropyl 3-(3-(2-chloro-6-methoxypyridin-4-yl)-1H-1,2,4-triazol-1-yl)acrylate | A |
| 62 | 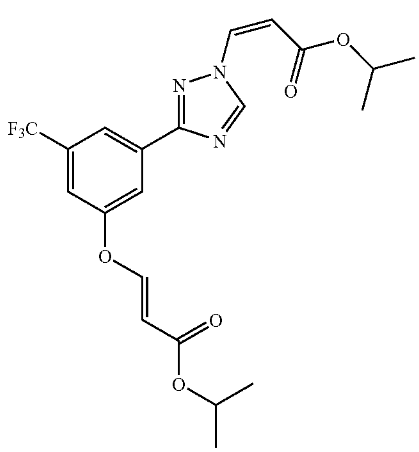 [SMILES: CC(C)OC(=O)/C=C\n1cnc(-c2cc(O/C=C/C(=O)OC(C)C)cc(C(F)(F)F)c2)n1] | (E)-isopropyl 3-(3-(1-((Z)-3-isopropoxy-3-oxoprop-1-en-1-yl)-1H-1,2,4-triazol-3-yl)-5-(trifluoromethyl)phenoxy)acrylate | B |

TABLE 1-continued

| Example | Structure | Name | Rev Export (%)/[IC$_{50}$] OR Cytotoxicity[EC$_{50}$] |
|---|---|---|---|
| 63 | 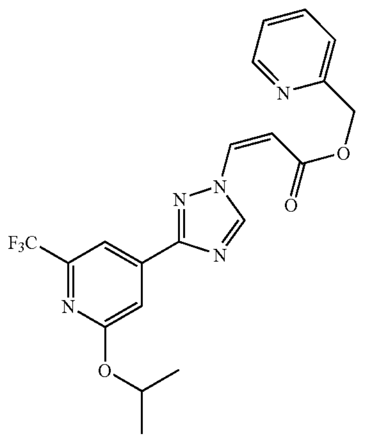 | (Z)-pyridin-2-ylmethyl 3-(3-(2-isopropoxy-6-(trifluoromethyl)pyridin-4-yl)-1H-1,2,4-triazol-1-yl)acrylate | A |
| 64 | 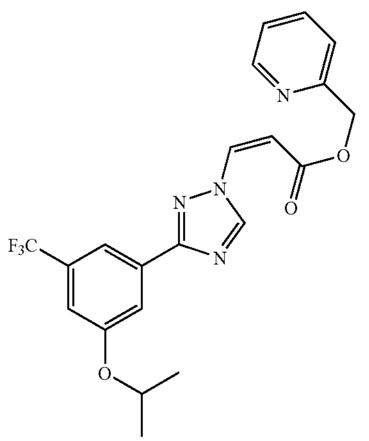 [SMILES: CC(C)Oc1cc(-c2ncn(/C=C\C(=O)OCc3ccccn3)n2)cc(C(F)(F)F)n1] | (Z)-pyridin-2-ylmethyl 3-(3-(3-isopropoxy-5-(trifluoromethyl)phenyl)-1H-1,2,4-triazol-1-yl)acrylate | A |
| 65 | 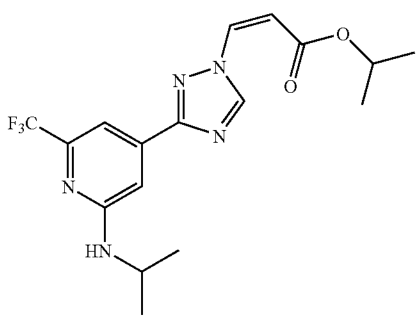 [SMILES: CC(C)Nc1cc(-c2ncn(/C=C\C(=O)OC(C)C)n2)cc(C(F)(F)F)n1] | (Z)-isopropyl 3-(3-(2-(isopropylamino)-6-(trifluoromethyl)pyridin-4-yl)-1H-1,2,4-triazol-1-yl)acrylate | A |
| 66 | 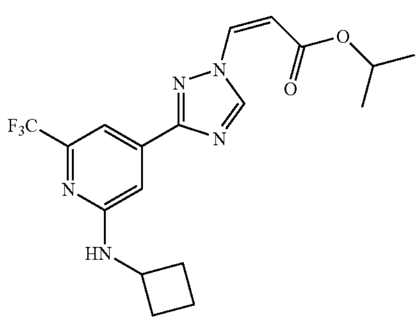 [SMILES: CC(C)OC(=O)/C=C\n1cnc(-c2cc(NC3CCC3)nc(C(F)(F)F)c2)n1] | (Z)-isopropyl 3-(3-(2-(cyclobutylamino)-6-(trifluoromethyl)pyridin-4-yl)-1H-1,2,4-triazol-1-yl)acrylate | A |

TABLE 1-continued

| Example | Structure | Name | Rev Export (%)/[IC$_{50}$] OR Cytotoxicity[EC$_{50}$] |
|---|---|---|---|
| 67 | 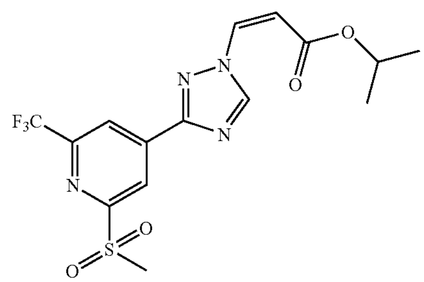 [SMILES: CC(C)OC(=O)/C=C\n1cnc(-c2cc(C(F)(F)F)nc(S(C)(=O)=O)c2)n1] | (Z)-isopropyl 3-(3-(3-(methylsulfonyl)-5-(trifluoromethyl)phenyl)-1H-1,2,4-triazol-1-yl)acrylate | A |
| 68 | 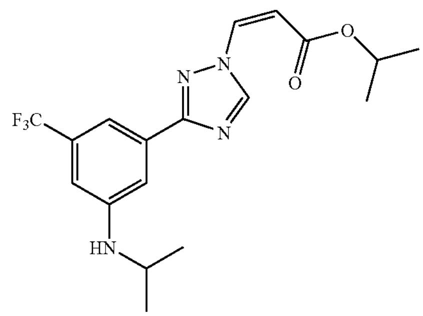 | (Z)-isopropyl 3-(3-(3-(isopropylamino)-5-(trifluoromethyl)phenyl)-1H-1,2,4-triazol-1-yl)acrylate | NT |
| 69 | 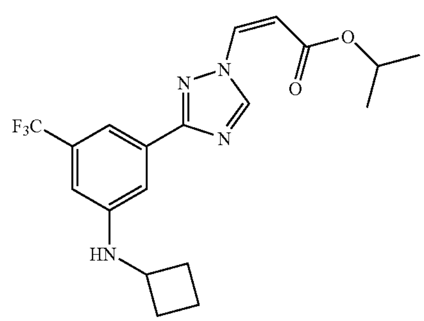 | (Z)-isopropyl 3-(3-(3-(cyclobutylamino)-5-(trifluoromethyl)phenyl)-1H-1,2,4-triazol-1-yl)acrylate | NT |
| 70 | 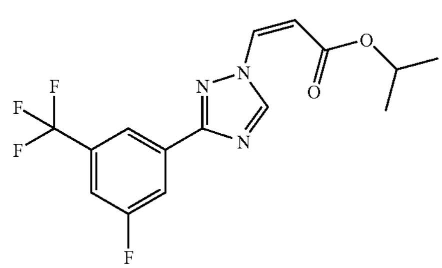 [SMILES: CC(C)OC(=O)/C=C\n1cnc(-c2cc(F)cc(C(F)(F)F)c2)n1] | (Z)-isopropyl 3-(3-(3-fluoro-5-(trifluoromethyl)phenyl)-1H-1,2,4-triazol-1-yl)acrylate | NT |
| 71 | 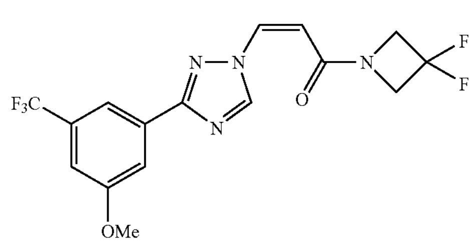 [SMILES: COc1cc(-c2ncn(/C=C\C(=O)N3CC(F)(F)C3)n2)cc(C(F)(F)F)c1] | (Z)-1-(3,3-difluoroazetidin-1-yl)-3-(3-(3-methoxy-5-(trifluoromethyl)phenyl)-1H-1,2,4-triazol-1-yl)prop-2-en-1-one | NT |

TABLE 1-continued

| Example | Structure | Name | Rev Export (%)/[IC$_{50}$] OR Cytotoxicity[EC$_{50}$] |
|---|---|---|---|
| 72 | 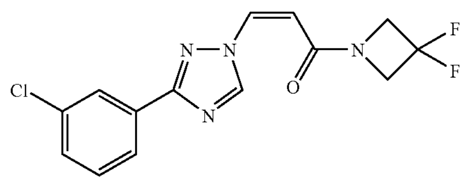 [SMILES: O=C(/C=C\n1cnc(-c2cccc(Cl)c2)n1)N1CC(F)(F)C1] | (Z)-3-(3-(3-chlorophenyl)-1H-1,2,4-triazol-1-yl)-1-(3,3-difluoroazetidin-1-yl)prop-2-en-1-one | NT |
| 73 | 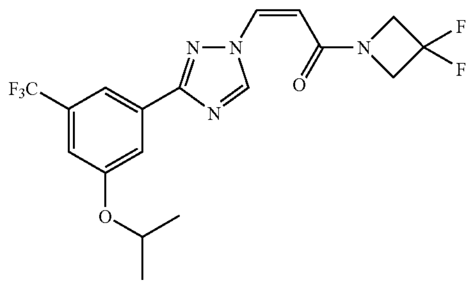 [SMILES: CC(C)Oc1cc(-c2ncn(/C=C\C(=O)N3CC(F)(F)C3)n2)cc(C(F)(F)F)c1] | (Z)-1-(3,3-difluoroazetidin-1-yl)-3-(3-(3-isopropoxy-5-(trifluoromethyl)phenyl)-1H-1,2,4-triazol-1-yl)prop-2-en-1-one | NT |
| 74 | 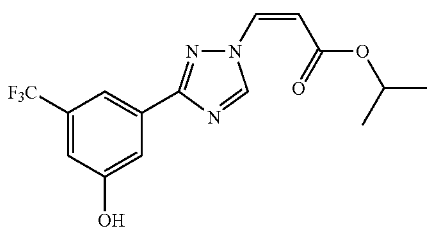 [SMILES: CC(C)OC(=O)/C=C\n1cnc(-c2cc(O)cc(C(F)(F)F)c2)n1] | (Z)-isopropyl 3-(3-(3-hydroxy-5-(trifluoromethyl)phenyl)-1H-1,2,4-triazol-1-yl)acrylate | NT |
| 75 | 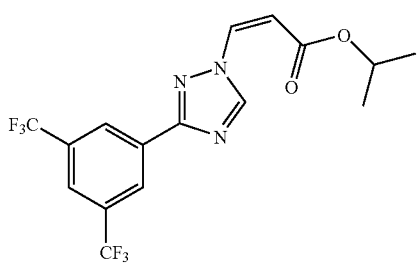 [SMILES: CC(C)OC(=O)/C=C\n1cnc(-c2cc(C(F)(F)F)cc(C(F)(F)F)c2)n1] | (Z)-isopropyl 3-(3-(3,5-bis(trifluoromethyl)phenyl)-1H-1,2,4-triazol-1-yl)acrylate | NT |
| 76 | 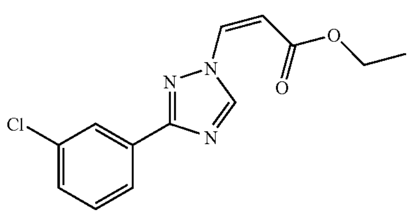 [SMILES: CCOC(=O)/C=C\n1cnc(-c2cccc(Cl)c2)n1] | (Z)-3-[3-(3-Chloro-phenyl)-[1,2,4]-triazol-1-yl]-acrylic acid ethyl ester | A |
| 77 | 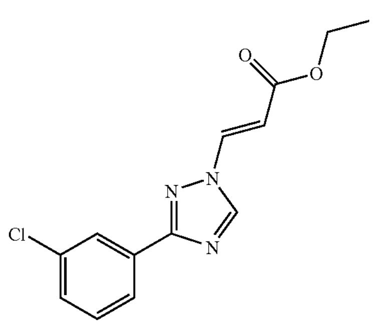 [SMILES: CCOC(=O)/C=C/n1cnc(-c2cccc(Cl)c2)n1] | (E)-3-[3-(3-Chloro-phenyl)-[1,2,4]-triazol-1-yl]-acrylic acid ethyl ester | C |

TABLE 1-continued

| Example | Structure | Name | Rev Export (%)/[IC$_{50}$] OR Cytotoxicity[EC$_{50}$] |
|---|---|---|---|
| 78 | 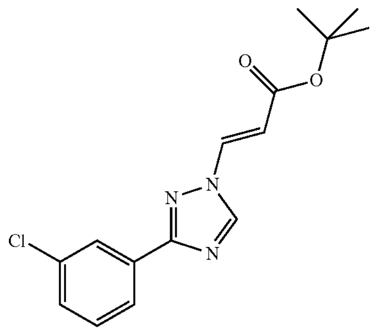 [SMILES: CC(C)(C)OC(=O)/C=C/n1cnc(-c2cccc(Cl)c2)n1] | (E)-3-[3-(3-Chloro-phenyl)-[1,2,4]-triazol-1-yl]-acrylic acid tert-butyl ester | C |
| 79 | 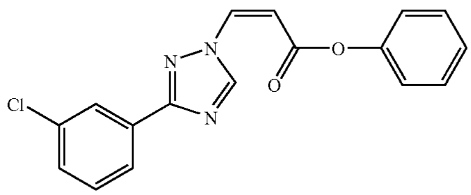 [SMILES: O=C(/C=C\n1cnc(-c2cccc(Cl)c2)n1)Oc1ccccc1] | (Z)-3-[3-(3-Chloro-phenyl)-[1,2,4]triazol-1-yl]-acrylic acid phenyl ester | A |
| 80 | 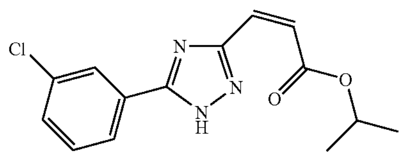 [SMILES: CC(C)OC(=O)/C=C\c1n[nH]c(-c2cccc(Cl)c2)n1] | (Z)-3-[5-(3-Chloro-phenyl)-1H-[1,2,4]triazol-3-yl]-acrylic acid isopropyl ester | A |
| 81 | 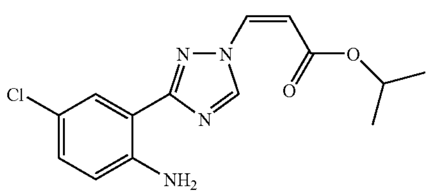 [SMILES: CC(C)OC(=O)/C=C\n1cnc(-c2cc(Cl)ccc2N)n1] | 3-[3-(2-Amino-5-chloro-phenyl)-[1,2,4]triazol-1-yl]-acrylic acid isopropyl ester | A |
| 82 | 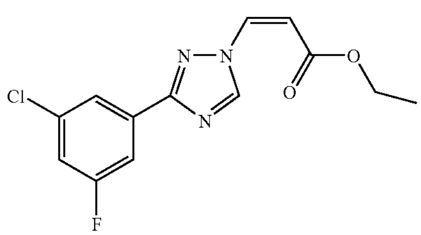 [SMILES: CCOC(=O)/C=C\n1cnc(-c2cc(F)cc(Cl)c2)n1] | 3-[3-(3-Chloro-5-fluoro-phenyl)-[1,2,4]triazol-1-yl]-acrylic acid ethyl ester | B |
| 83 | 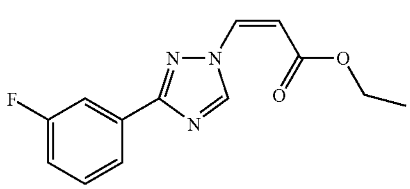 [SMILES: CCOC(=O)/C=C\n1cnc(-c2cccc(F)c2)n1] | 3-[3-(3-Fluoro-phenyl)-[1,2,4]triazol-1-yl]-acrylic acid ethyl ester | NT |
| 84 | 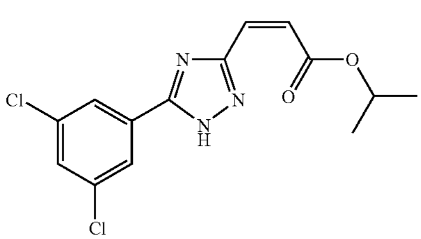 [SMILES: CC(C)OC(=O)/C=C\c1n[nH]c(-c2cc(Cl)cc(Cl)c2)n1] | (Z)-isopropyl 3-(5-(3,5-dichlorophenyl)-1H-1,2,4-triazol-3-yl)acrylate | B |

TABLE 1-continued

| Example | Structure | Name | Rev Export (%)/[IC$_{50}$] OR Cytotoxicity[EC$_{50}$] |
|---|---|---|---|
| 85 | 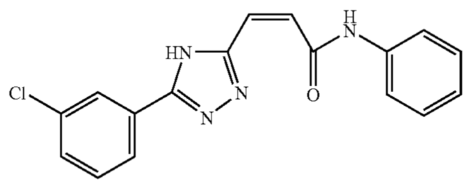 [SMILES: O=C(/C=C\c1nnc(-c2cccc(Cl)c2)[nH]1)Nc1ccccc1] | (Z)-3-(5-(3-chlorophenyl)-4H-1,2,4-triazol-3-yl)-N-phenylacrylamide | C |
| 86 | 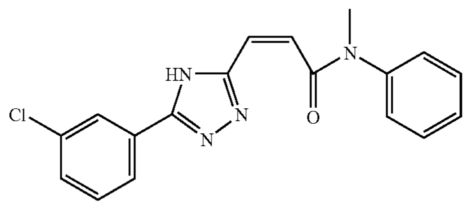 [SMILES: CN(C(=O)/C=C\c1nnc(-c2cccc(Cl)c2)[nH]1)c1ccccc1] | (Z)-3-(5-(3-chlorophenyl)-4H-1,2,4-triazol-3-yl)-N-methyl-N-phenylacrylamide | C |
| 87 | 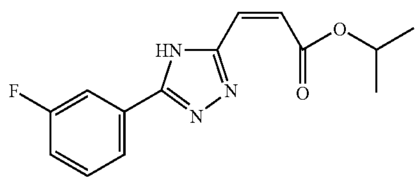 [SMILES: CC(C)OC(=O)/C=C\c1nnc(-c2cccc(F)c2)[nH]1] | (Z)-isopropyl 3-(5-(3-fluorophenyl)-4H-1,2,4-triazol-3-yl)acrylate | B |
| 88 | 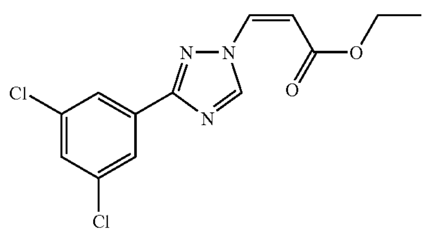 [SMILES: CCOC(=O)/C=C\n1cnc(-c2cc(Cl)cc(Cl)c2)n1] | (Z)-ethyl 3-(3-(3,5-dichlorophenyl)-1H-1,2,4-triazol-1-yl)acrylate | A |
| 89 | 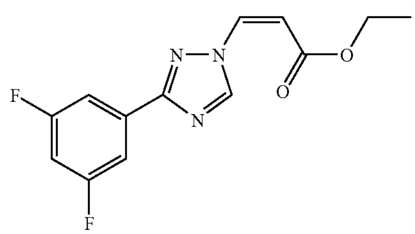 [SMILES: CCOC(=O)/C=C\n1cnc(-c2cc(F)cc(F)c2)n1] | (Z)-ethyl 3-(3-(3,5-difluorophenyl)-1H-1,2,4-triazol-1-yl)acrylate | B |
| 90 | 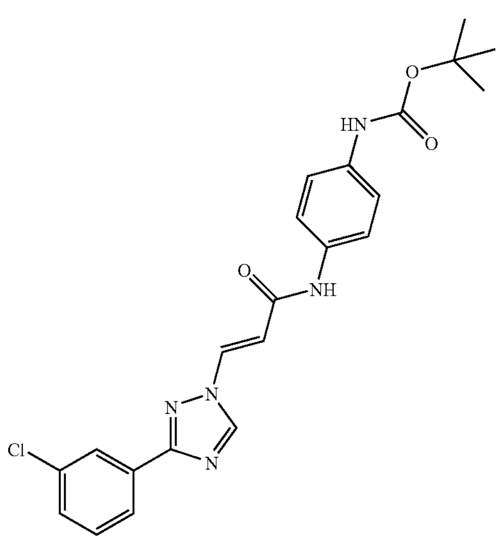 [SMILES: CC(C)(C)OC(=O)Nc1ccc(NC(=O)/C=C/n2cnc(-c3cccc(Cl)c3)n2)cc1] | (E)-tert-butyl (4-(3-(3-(3-chlorophenyl)-1H-1,2,4-triazol-1-yl)acrylamido)phenyl)carbamate | C |

TABLE 1-continued

| Example | Structure | Name | Rev Export (%)/[IC$_{50}$] OR Cytotoxicity[EC$_{50}$] |
|---|---|---|---|
| 92 | 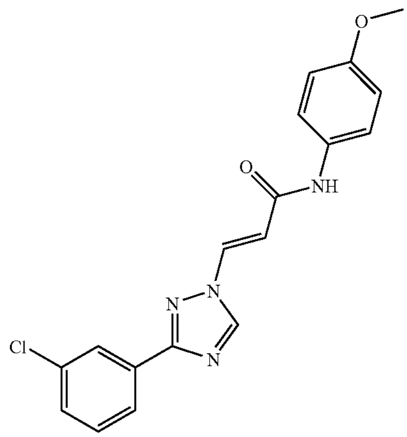 [SMILES: COc1ccc(NC(=O)/C=C/n2cnc(-c3cccc(Cl)c3)n2)cc1] | (E)-3-(3-(3-chlorophenyl)-1H-1,2,4-triazol-1-yl)-N-(4-methoxyphenyl)acrylamide | C |
| 93 | 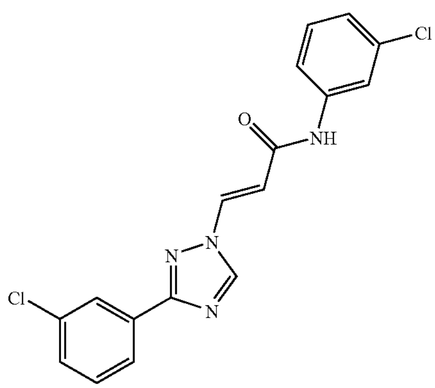 [SMILES: O=C(/C=C/n1cnc(-c2cccc(Cl)c2)n1)Nc1cccc(Cl)c1] | (E)-N-(3 Chloro-phenyl)-3-[3-(3-chloro-phenyl)-[1,2,4]-triazol-1-yl]-acryl amide | C |
| 94 | 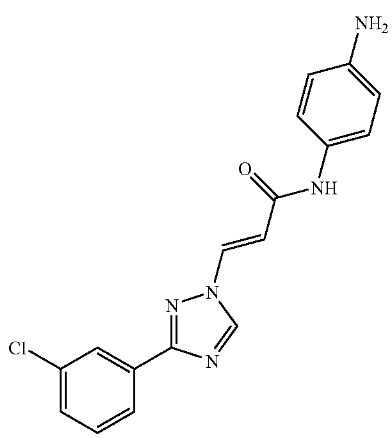 [SMILES: Nc1ccc(NC(=O)/C=C/n2cnc(-c3cccc(Cl)c3)n2)cc1] | (E)-N-(4-Amino-phenyl)-3-[3-(3-chloro-phenyl)-[1,2,4]-triazol-1-yl]-acryl amide | C |
| 95 | 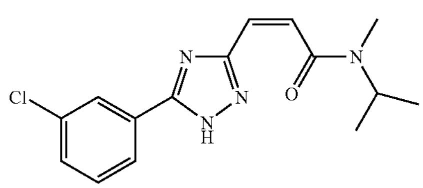 [SMILES: CC(C)N(C)C(=O)/C=C\c1n[nH]c(-c2cccc(Cl)c2)n1] | 3-[5-(3-Chloro-phenyl)-1H-[1,2,4]triazol-3-yl]-N-isopropyl-N-methyl-acrylamide | C |

TABLE 1-continued

| Example | Structure | Name | Rev Export (%)/[IC$_{50}$] OR Cytotoxicity[EC$_{50}$] |
|---|---|---|---|
| 96 | 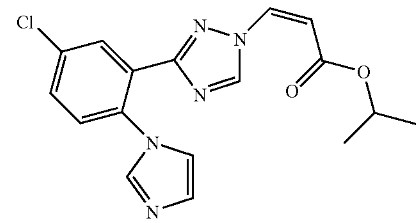 [SMILES: CC(C)OC(=O)/C=C\n1cnc(-c2cc(Cl)ccc2-n2ccnc2)n1] | (Z)-isopropyl 3-(3-(5-chloro-2-(1H-imidazol-1-yl)phenyl)-1H-1,2,4-triazol-1-yl)acrylate | NT |
| 97 | 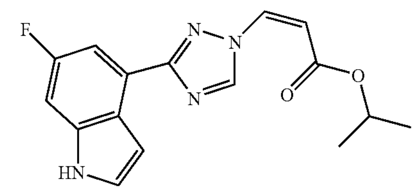 [SMILES: CC(C)OC(=O)/C=C\n1cnc(-c2cc(F)cc3[nH]ccc23)n1] | (Z)-isopropyl 3-(3-(6-fluoro-1H-indol-4-yl)-1H-1,2,4-triazol-1-yl)acrylate | NT |
| 98 | 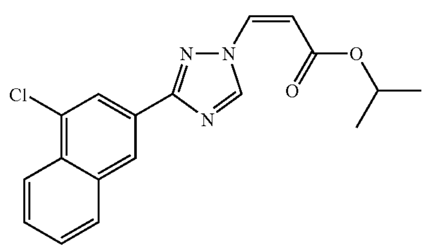 [SMILES: CC(C)OC(=O)/C=C\n1cnc(-c2cc(Cl)c3ccccc3c2)n1] | (Z)-isopropyl 3-(3-(4-chloronaphthalen-2-yl)-1H-1,2,4-triazol-1-yl)acrylate | NT |
| 99 | 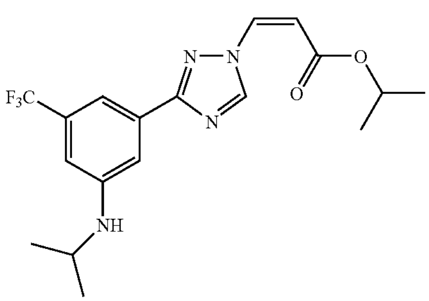 [SMILES: CC(C)Nc1cc(-c2ncn(/C=C\C(=O)OC(C)C)n2)cc(C(F)(F)F)c1] | (Z)-isopropyl 3-(3-(3-(isopropylamino)-5-(trifluoromethyl)phenyl)-1H-1,2,4-triazol-1-yl)acrylate | NT |
| 100 | 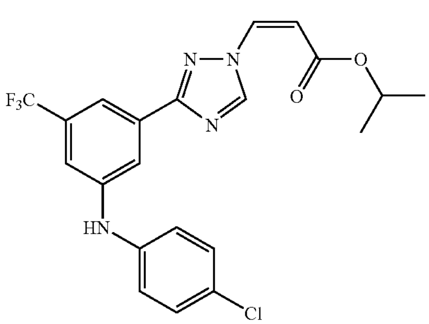 [SMILES: CC(C)OC(=O)/C=C\n1cnc(-c2cc(Nc3ccc(Cl)cc3)cc(C(F)(F)F)c2)n1] | (Z)-isopropyl 3-(3-(3-((4-chlorophenyl)amino)-5-(trifluoromethyl)phenyl)-1H-1,2,4-triazol-1-yl)acrylate | NT |

TABLE 1-continued

| Example | Structure | Name | Rev Export (%)/[IC$_{50}$] OR Cytotoxicity[EC$_{50}$] |
|---|---|---|---|
| 101 | 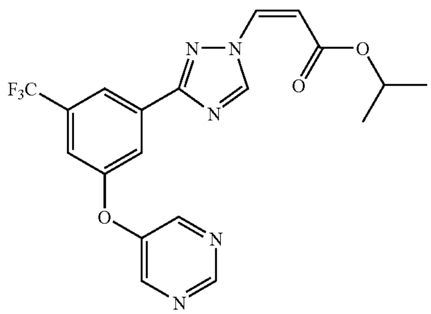 [SMILES: CC(C)OC(=O)/C=C\n1cnc(-c2cc(Oc3cncnc3)cc(C(F)(F)F)c2)n1] | (Z)-isopropyl 3-(3-(3-(pyrimidin-5-yloxy)-5-(trifluoromethyl)phenyl)-1H-1,2,4-triazol-1-yl)acrylate | NT |
| 102 | 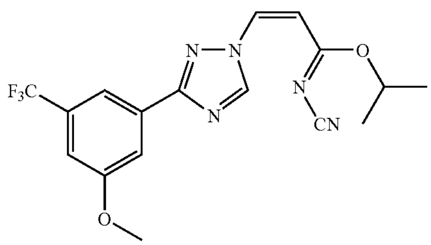 [SMILES: COc1cc(-c2ncn(/C=C\C(=N\C#N)OC(C)C)n2)cc(C(F)(F)F)c1] | (1Z,2Z)-isopropyl N-cyano-3-(3-(3-methoxy-5-(trifluoromethyl)phenyl)-1H-1,2,4-triazol-1-yl)acrylimidate | NT |
| 103 | 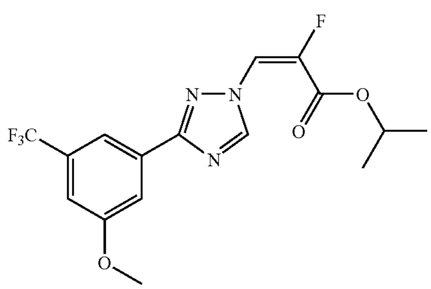 [SMILES: COc1cc(-c2ncn(/C=C(/F)C(=O)OC(C)C)n2)cc(C(F)(F)F)c1] | (E)-isopropyl 2-fluoro-3-(3-(3-methoxy-5-(trifluoromethyl)phenyl)-1H-1,2,4-triazol-1-yl)acrylate | NT |
| 104 | 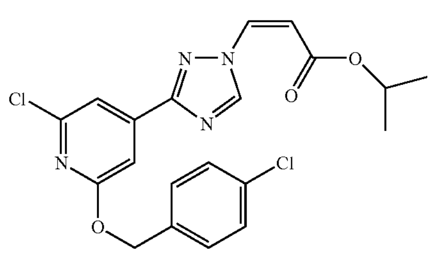 [SMILES: CC(C)OC(=O)/C=C\n1cnc(-c2cc(Cl)nc(OCc3ccc(Cl)cc3)c2)n1] | (Z)-isopropyl 3-(3-(2-chloro-6-((4-chlorobenzyl)oxy)pyridin-4-yl)-1H-1,2,4-triazol-1-yl)acrylate | NT |
| 105 | 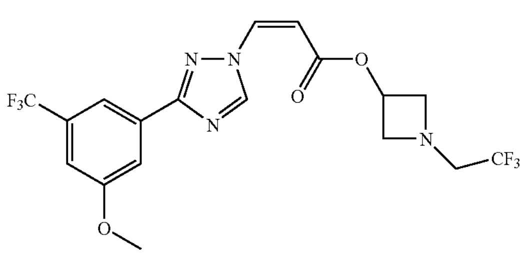 [SMILES: COc1cc(-c2ncn(/C=C\C(=O)OC3CN(CC(F)(F)F)C3)n2)cc(C(F)(F)F)c1] | (Z)-1-(2,2,2-trifluoroethyl)azetidin-3-yl 3-(3-(3-methoxy-5-(trifluoromethyl)phenyl)-1H-1,2,4-triazol-1-yl)acrylate | NT |

TABLE 1-continued

| Example | Structure | Name | Rev Export (%)/[IC$_{50}$] OR Cytotoxicity[EC$_{50}$] |
|---|---|---|---|
| 106 | 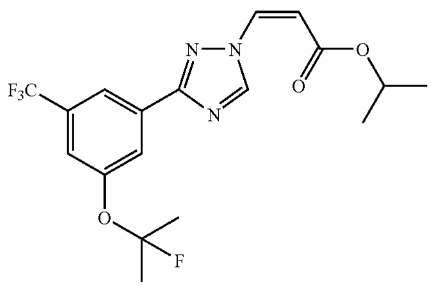 [SMILES: CC(C)OC(=O)/C=C\n1cnc(-c2cc(OC(C)(C)F)cc(C(F)(F)F)c2)n1] | (Z)-isopropyl 3-(3-(3-((2-fluoropropan-2-yl)oxy)-5-(trifluoromethyl)phenyl)-1H-1,2,4-triazol-1-yl)acrylate | NT |
| 107 | 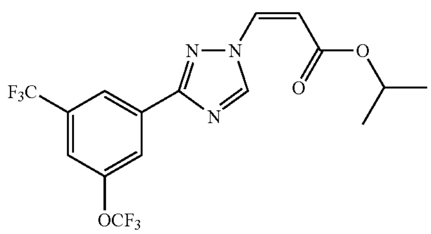 [SMILES: CC(C)OC(=O)/C=C\n1cnc(-c2cc(OC(F)(F)F)cc(C(F)(F)F)c2)n1] | (Z)-isopropyl 3-(3-(3-(trifluoromethoxy)-5-(trifluoromethyl)phenyl)-1H-1,2,4-triazol-1-yl)acrylate | NT |
| 108 | 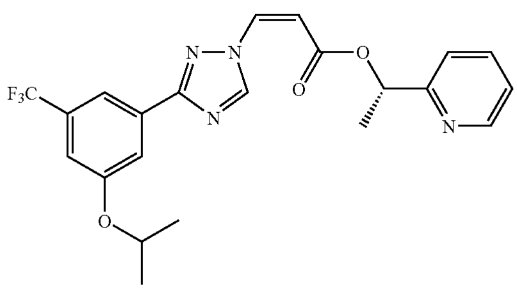 [SMILES: CC(C)Oc1cc(-c2ncn(/C=C\C(=O)O[C@@H](C)c3ccccn3)n2)cc(C(F)(F)F)c1] | (S,Z)-1-(pyridin-2-yl)ethyl 3-(3-(3-isopropoxy-5-(trifluoromethyl)phenyl)-1H-1,2,4-triazol-1-yl)acrylate | NT |
| 109 | 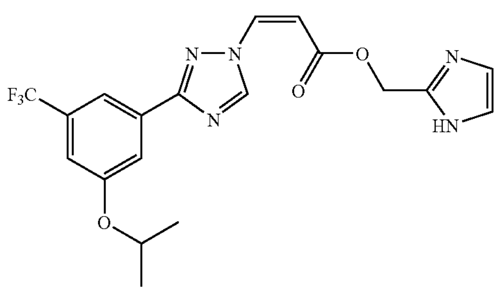 [SMILES: CC(C)Oc1cc(-c2ncn(/C=C\C(=O)OCc3ncc[nH]3)n2)cc(C(F)(F)F)c1] | (Z)-(1H-imidazol-2-yl)methyl 3-(3-(3-isopropoxy-5-(trifluoromethyl)phenyl)-1H-1,2,4-triazol-1-yl)acrylate | NT |
| 110 | 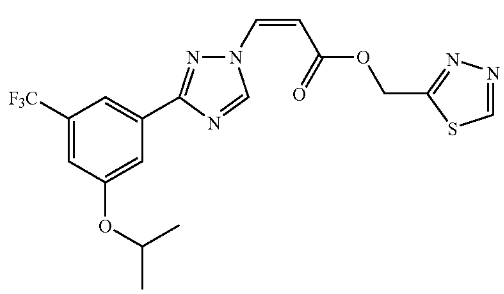 [SMILES: CC(C)Oc1cc(-c2ncn(/C=C\C(=O)OCc3nncs3)n2)cc(C(F)(F)F)c1] | (Z)-(1,3,4-thiadiazol-2-yl)methyl 3-(3-(3-isopropoxy-5-(trifluoromethyl)phenyl)-1H-1,2,4-triazol-1-yl)acrylate | NT |

TABLE 1-continued

| Example | Structure | Name | Rev Export (%)/[IC$_{50}$] OR Cytotoxicity[EC$_{50}$] |
|---|---|---|---|
| 111 | 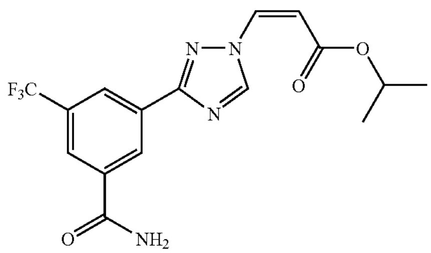 [SMILES: CC(C)OC(=O)/C=C\n1cnc(-c2cc(C(N)=O)cc(C(F)(F)F)c2)n1] | (Z)-isopropyl 3-(3-(3-carbamoyl-5-(trifluoromethyl)phenyl)-1H-1,2,4-triazol-1-yl)acrylate | NT |
| 112 | 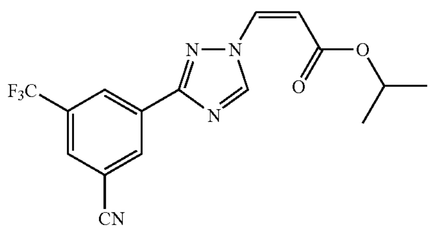 | (Z)-isopropyl 3-(3-(3-cyano-5-(trifluoromethyl)phenyl)-1H-1,2,4-triazol-1-yl)acrylate | NT |
| 113 | 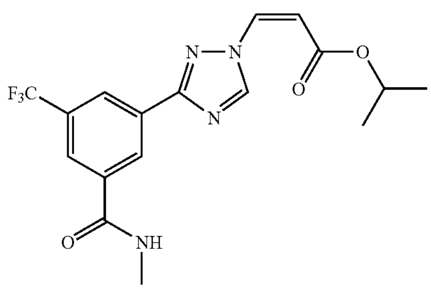 [SMILES: CNC(=O)c1cc(-c2ncn(/C=C\C(=O)OC(C)C)n2)cc(C(F)(F)F)c1] | (Z)-isopropyl 3-(3-(3-(methylcarbamoyl)-5-(trifluoromethyl)phenyl)-1H-1,2,4-triazol-1-yl)acrylate | NT |
| 114 | 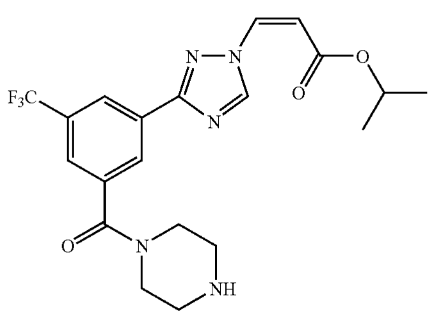 [SMILES: CC(C)OC(=O)/C=C\n1cnc(-c2cc(C(=O)N3CCNCC3)cc(C(F)(F)F)c2)n1] | (Z)-isopropyl 3-(3-(3-(piperazine-1-carbonyl)-5-(trifluoromethyl)phenyl)-1H-1,2,4-triazol-1-yl)acrylate | NT |
| 115 | 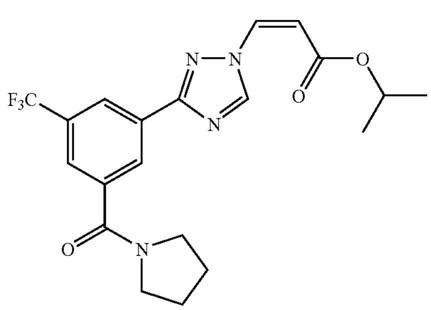 [SMILES: CC(C)OC(=O)/C=C\n1cnc(-c2cc(C(=O)N3CCCC3)cc(C(F)(F)F)c2)n1] | (Z)-isopropyl 3-(3-(3-(pyrrolidine-1-carbonyl)-5-(trifluoromethyl)phenyl)-1H-1,2,4-triazol-1-yl)acrylate | NT |

TABLE 1-continued

| Example | Structure | Name | Rev Export (%)/[IC$_{50}$] OR Cytotoxicity[EC$_{50}$] |
|---|---|---|---|
| 116 | 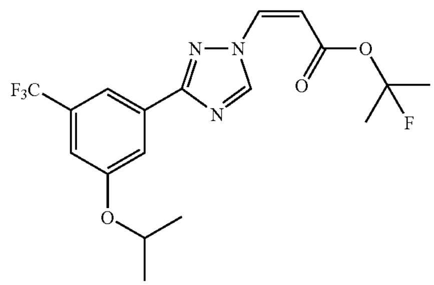 [SMILES: CC(C)Oc1cc(-c2ncn(/C=C\C(=O)OC(C)(C)F)n2)cc(C(F)(F)F)c1] | (Z)-2-fluoropropan-2-yl 3-(3-(3-isopropoxy-5-(trifluoromethyl)phenyl)-1H-1,2,4-triazol-1-yl)acrylate | NT |
| 117 | 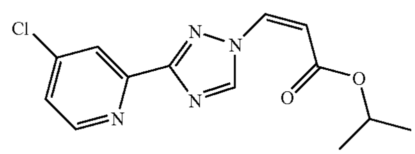 [SMILES: CC(C)OC(=O)/C=C\n1cnc(-c2cc(Cl)ccn2)n1] | (Z)-isopropyl 3-(3-(4-chloropyridin-2-yl)-1H-1,2,4-triazol-1-yl)acrylate | NT |
| 118 | 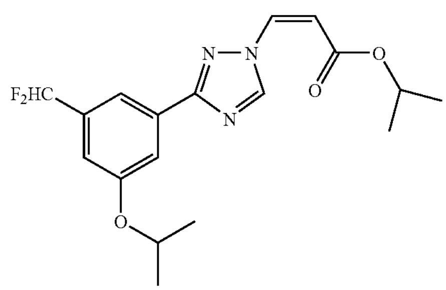 [SMILES: CC(C)OC(=O)/C=C\n1cnc(-c2cc(OC(C)C)cc(C(F)F)c2)n1] | (Z)-isopropyl 3-(3-(3-(difluoromethyl)-5-isopropoxyphenyl)-1H-1,2,4-triazol-1-yl)acrylate | NT |
| 119 | 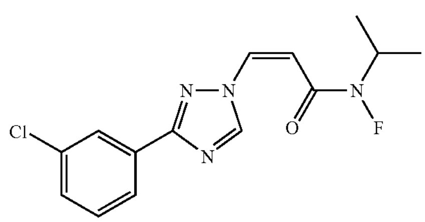 [SMILES: CC(C)N(F)C(=O)/C=C\n1cnc(-c2cccc(Cl)c2)n1] | (Z)-3-(3-(3-chlorophenyl)-1H-1,2,4-triazol-1-yl)-N-fluoro-N-isopropylacrylamide | NT |
| 120 | 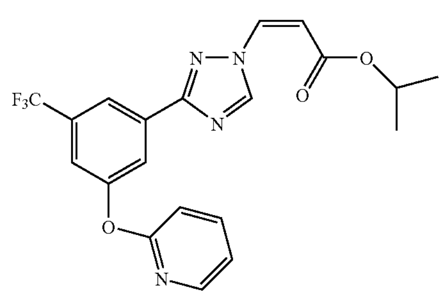 [SMILES: CC(C)OC(=O)/C=C\n1cnc(-c2cc(Oc3ccccn3)cc(C(F)(F)F)c2)n1] | (Z)-isopropyl 3-(3-(3-(pyridin-2-yloxy)-5-(trifluoromethyl)phenyl)-1H-1,2,4-triazol-1-yl)acrylate | NT |
| 121 | 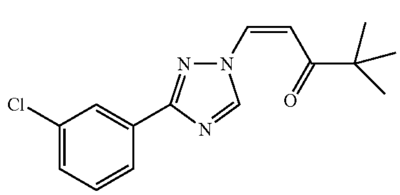 [SMILES: CC(C)(C)C(=O)/C=C\n1cnc(-c2cccc(Cl)c2)n1] | (Z)-1-(3-(3-chlorophenyl)-1H-1,2,4-triazol-1-yl)-4,4-dimethylpent-1-en-3-one | NT |

TABLE 1-continued

| Example | Structure | Name | Rev Export (%)/[IC$_{50}$] OR Cytotoxicity[EC$_{50}$] |
|---|---|---|---|
| 122 | 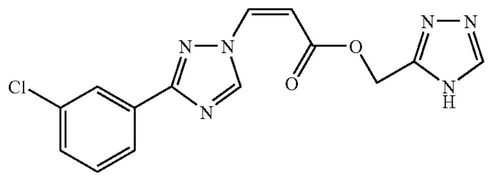 [SMILES: O=C(/C=C\n1cnc(-c2cccc(Cl)c2)n1)OCc1nnc[nH]1] | (Z)-(4H-1,2,4-triazol-3-yl)methyl 3-(3-(3-chlorophenyl)-1H-1,2,4-triazol-1-yl)acrylate | NT |
| 123 | 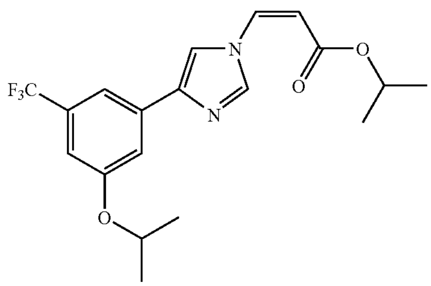 | (Z)-isopropyl 3-(4-(3-isopropoxy-5-(trifluoromethyl)phenyl)-1H-imidazol-1-yl)acrylate | NT |
| 124 | 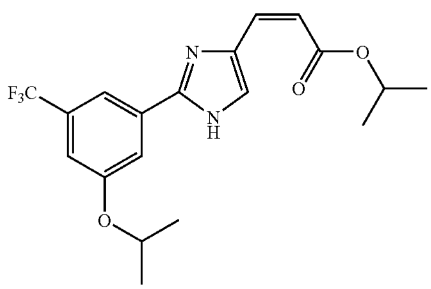 [SMILES: CC(C)OC(=O)/C=C\c1c[nH]c(-c2cc(OC(C)C)cc(C(F)(F)F)c2)n1] | (Z)-isopropyl 3-(2-(3-isopropoxy-5-(trifluoromethyl)phenyl)-1H-imidazol-4-yl)acrylate | NT |
| 125 | 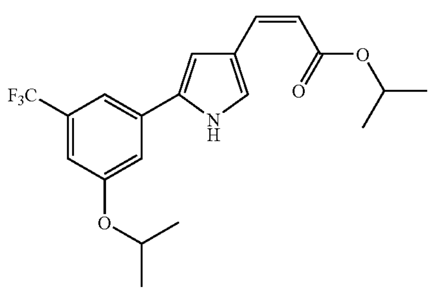 | (Z)-isopropyl 3-(5-(3-isopropoxy-5-(trifluoromethyl)phenyl) 1H-pyrrol-3-yl)acrylate | NT |
| 126 | 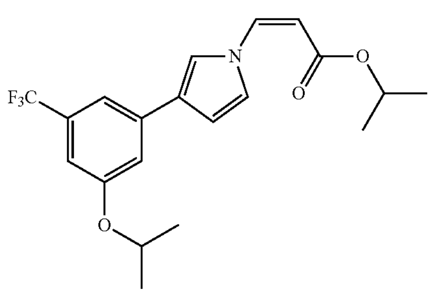 [SMILES: CC(C)OC(=O)/C=C\n1ccc(-c2cc(OC(C)C)cc(C(F)(F)F)c2)c1] | (Z)-isopropyl 3-(3-(3-isopropoxy-5-(trifluoromethyl)phenyl)-1H-pyrrol-1-yl)acrylate | NT |

TABLE 1-continued

| Example | Structure | Name | Rev Export (%)/[IC$_{50}$] OR Cytotoxicity[EC$_{50}$] |
|---|---|---|---|
| 127 | 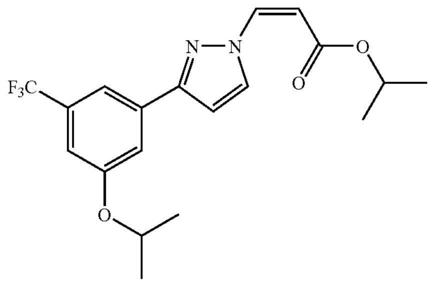 | (Z)-isopropyl 3-(3-(3-isopropoxy-5-(trifluoromethyl)phenyl)-1H-pyrazol-1-yl)acrylate | NT |
| 128 | 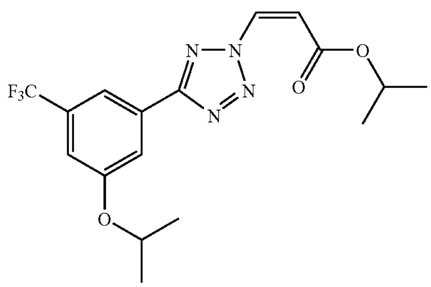 [SMILES: CC(C)OC(=O)/C=C\n1nnc(-c2cc(OC(C)C)cc(C(F)(F)F)c2)n1] | (Z)-isopropyl 3-(5-(3-isopropoxy-5-(trifluoromethyl)phenyl)-2H-tetrazol-2-yl)acrylate | NT |

General Synthetic Methods

Several general methods for preparing compounds of Formula I are illustrated in the following Schemes and Examples. Starting materials and the requisite intermediates are in some cases commercially available or can be prepared according to literature procedures (Bioorg. Med. Chem. 16, 2008, 9487-9497; Bioorg. Med. Chem. 16, 2008, 10031-10310; Synthetic Comm. 35, 2005, 761-764) or as illustrated herein.

Certain azole compounds of Formula I, wherein the group A is selected from aryl and heteroaryl optionally substituted with one or more substituents and the Het is a triazole group with the double bond substituted at one N, and one WG is hydrogen while the other is either carboxylic acid, carboxylic ester, carboxylic amides, cyano, etc., can be prepared in accordance with general Scheme 1. In the steps where product was obtained as a mixture of cis- and trans-isomers of the double bond, pure isomers can be easily separated using chromatographic methods in the literature.

It is understood that the functional groups present in compounds described in the Schemes below can be further manipulated, when appropriate, using the standard functional group transformation techniques available to those skilled in the art, to provide desired compounds described in this invention. Other variations or modifications, which will be obvious to those skilled in the art, are within the scope and teachings of this invention.

Scheme 1

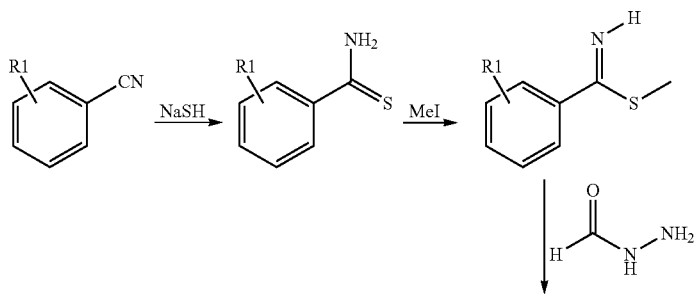

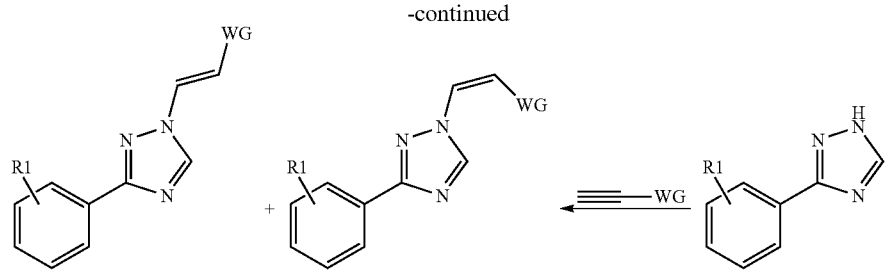

In Scheme 2, a general method is described for the preparation of certain azoles compounds of Formula I, wherein the group A is selected from aryl and heteroaryl optionally substituted with one or more substituents and the Het is a triazole group with the double bond substituted at one C, one WG is hydrogen and the other is either carboxylic acid, carboxylic ester, carboxylic amides, cyano, etc., and the group —CH=C(WG)$_2$ is attached to X$_1$, can be prepared in accordance with general Scheme 2 and Scheme 3.

Scheme 2

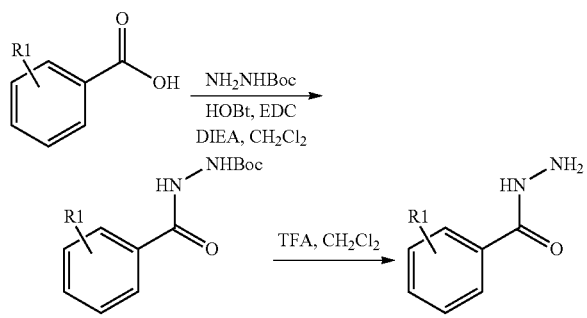

In accordance with Scheme 2, carboxylic acid derivatives are coupled with t-butyl carbazate by activation with HOBt (Hydroxybenzotriazole) in the presence of a suitable carbodiimide such as EDC [1-(3-dimethylaminopropyl-3(ethylcarbodiimide)] in presence of diisopropylethylamine (DIEA) as base in dichloromethane to provide hydrazide intermediate (Advance Org. Chem. 5$^{th}$ ed., John Wiley & Sons, New York, pp. 506-512, 2001).

As shown in Scheme 3, hydrazide intermediate was used to construct the 1,2,4-Triazole cores, wherein the substitution of the double-bond is made via a carbon atom and can be ester, acid, amide etc. In the steps where product was obtained as a mixture of cis- and trans-isomers of the double bond, pure isomers can be easily separated using chromatographic methods known for those skilled in the art in the literature.

Scheme 3

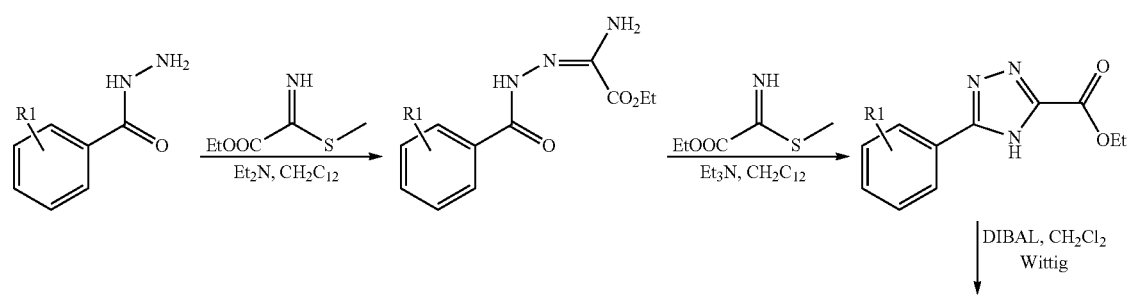

General Procedure for the Synthesis of Isopropyl Propiolate:

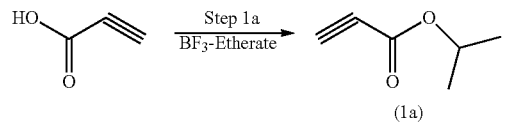

(1a)

In 3-neck 2 L round-bottomed flask, Propiolic acid (50 g, 0.713 mmol) was dissolved in IPA (400 mL, 8 Vol) and added BF$_3$-etherate (202.71 g, 1.427 mmol) and reaction mixture was refluxed to 90° C. for 2 h. Reaction completion was monitored on TLC using ethyl acetate:hexane (2:8) as mobile phase and absence of starting material was observed with Bromocresols green. Reaction mixture was brought to room temperature and quenched into the ice-water slurry (1 L) and compound was extracted in the dichloromethane (500 mL×3). Organic layer was washed with brine solution followed by drying using anhydrous sodium sulphate. Organic layer was concentrated under reduced pressure to afford 30.5 g of pure compound, yield (61%).

Example 1

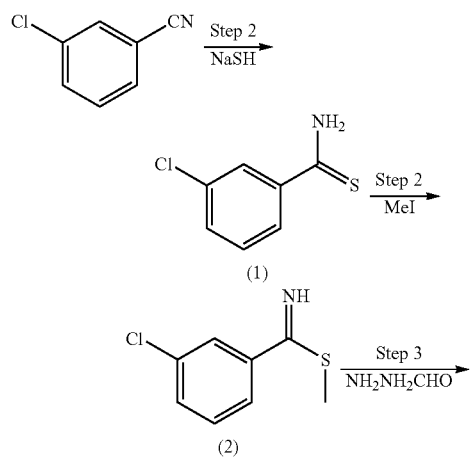

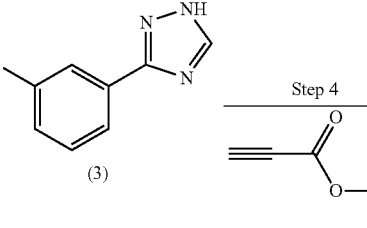

CH$_3$CN/TEA

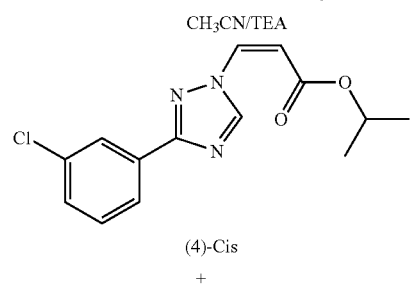

(4)-Cis

+

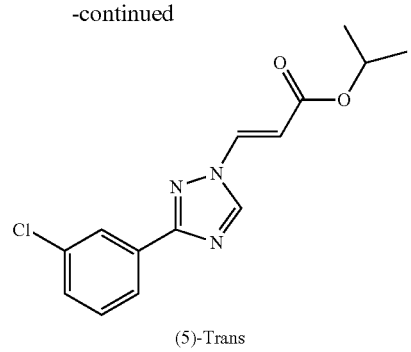

(5)-Trans

Synthesis of Intermediate (1)

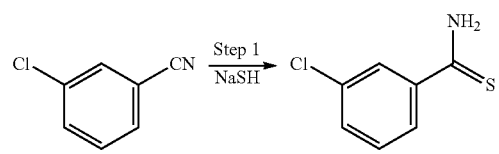

Molecular Weight: 137.6      (1)

Molecular Weight: 171.6

In a 3-neck 2 L round-bottomed flask, equipped with an overhead mechanical stirrer, slurry of sodium hydrosulfide hydrate (90.9 g, 1.226 mmol) and magnesium chloride hexahydrate (125.86 g, 0.620 mmol) in 1 L of DMF was added 3-Chlorobenzonitrile (85 g, 0.620 mmol) in one portion, and the reaction mixture was stirred at room temperature for 2 h. The progress of reaction was followed by TLC analysis on silica gel using ethyl acetate:hexane (1:1) as mobile phase. The resulting green slurry was poured in 5000 mL water, and the resulting precipitates were collected by filtration. The crude product was re-suspended in 1 N HCl and stirred for 45 min, then filtered and washed with water to give intermediate-1 (63 g, 75%). Mass/LCMS: 180.0; NMR confirmed.

Synthesis of Intermediate (2)

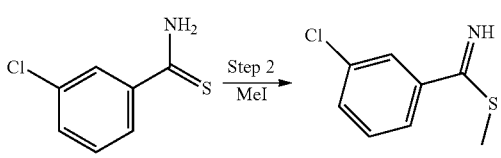

(1)      (2)

Molecular Weight: 171.6    Molecular Weight: 185.7

In a 3-neck 2 L round-bottomed flask, equipped with an overhead mechanical stirrer, a solution of intermediate-1 (50.0 g, 0.292 mmol) in 750 mL diethyl ether was treated with methyl iodide (155.8 g, 1.1052 mmol). Reaction was stirred for 24 h and completion of reaction was monitored on TLC using ethyl acetate:hexane (1:1) as mobile phase. Reaction mixture was filtered, precipitates washed with diethyl ether and dried under vacuum to give intermediate-2 (41 g, 76%). Mass/LCMS: 180.0; NMR: Confirmed.

Synthesis of Intermediate (3)

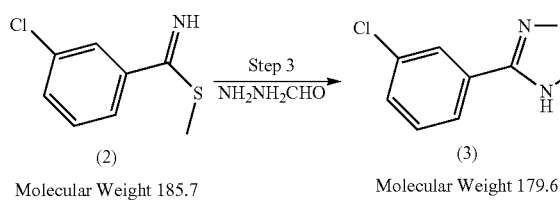

(2)
Molecular Weight 185.7

(3)
Molecular Weight 179.6

In a 3-neck 1 L round-bottomed flask, equipped with an water condenser, a solution of intermediate-2 (25.0 g, 0.135 mmol) in 250 mL DMF was added formic hydrazide (16.21 g, 0.270 mmol) under nitrogen atmosphere. The reaction mixture was stirred for 16 h and then heated at 90° C. for 3 h. Completion of reaction was monitored on TLC using ethyl acetate:hexane (1:1) as mobile phase. Cooled reaction mixture was poured into water and, extracted with ethyl acetate, dried over sodium sulfate, and evaporated under vacuum to obtain the intermediate-3 (19 g, 79%). Compound was used as such without further purification. Mass/LCMS: 180.0; NMR: Confirmed.

Synthesis of Example 3

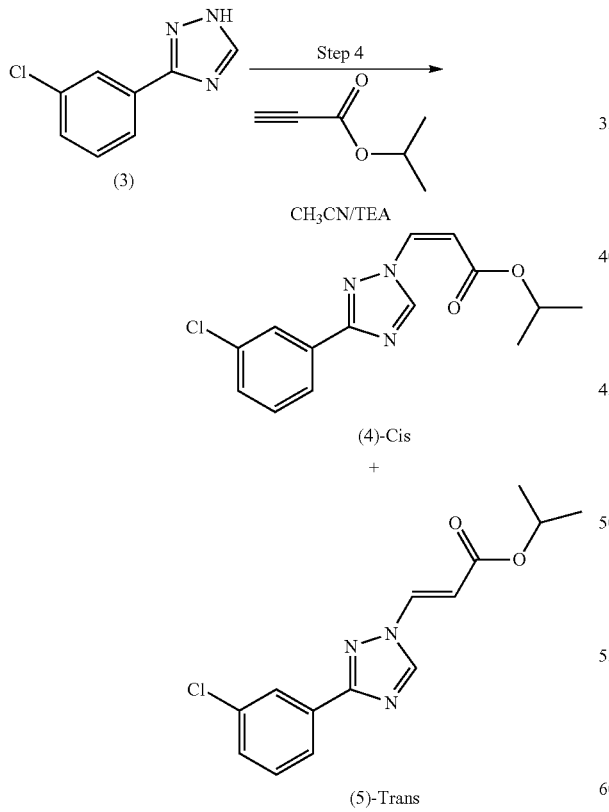

In 3-neck 250 mL round-bottomed flask, Intermediate-3 (10 g, 0.0556 mmol) was dissolved in acetonitrile (100 mL, 10 Vol), added TEA (5.62 g, 0.0556 mmol) and isopropyl propiolate (9.36 g, 0.0835 mmol) in cooling condition under nitrogen atmosphere. Reaction mixture was reflux overnight at 90° C. and completion of reaction was monitored on TLC using ethyl acetate:hexane (2:8) as mobile phase. Acetonitrile was removed under reduced pressure to give crude product. Compound was purified by column chromatography using silica 60/120 and ethylacetate:hexane as mobile phase. Compound was eluted at 0.25% ethyl acetate in hexane which further purified by combiflash to give 2.5 g of the product; $^1$H NMR (400 MHz, CDCl$_3$) δ 9.72 (S, 1H), 7.39-8.16 (m, 4H), 7.27-7.29 (d, J=10.8 Hz, 1H), 5.69-5.71 (d, J=10.8 Hz, 1H), 5.10-5.19 (m, 1H), 1.28-1.34 (d, 6H): LCMS for C$_{14}$H$_{14}$ClN$_3$O$_2$ [M+1]$^+$ 291.1 found 291.19 at RT 7.391 min (LCMS 98.92%).

Example 2

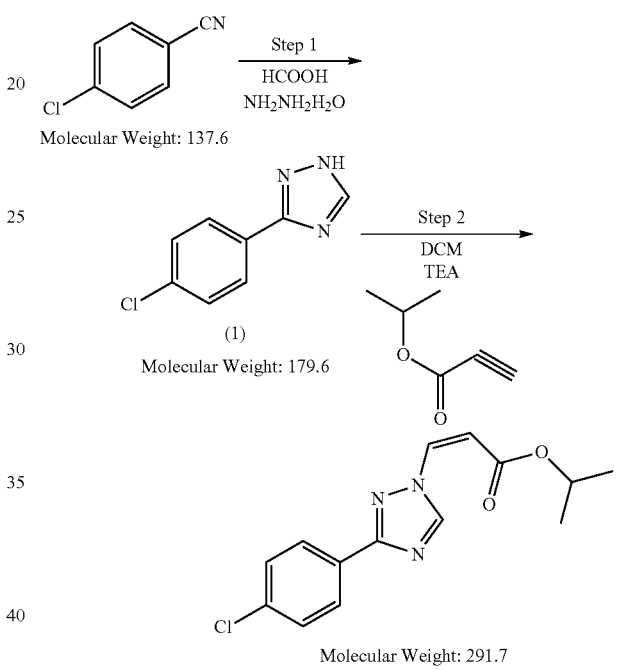

Synthesis of Intermediate (1)

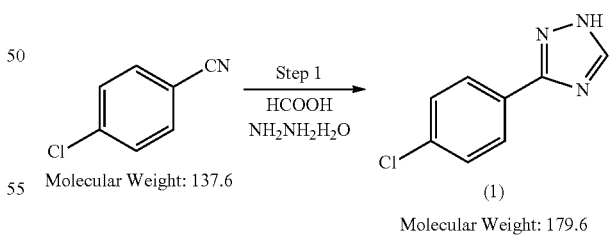

In 3-neck 50 mL round-bottomed flask, 4-chlorobenzonitrile (5.0, 1 eq.) was mixed with formic acid (25 mL, 5 Vol) and hydrazine hydrate (25 mL, 5 Vol) and reaction mixture was refluxed to 110° C. for 12 h. Reaction was clear solution once it attained 90° C. Reaction remained yellow colored clear solution throughout the reaction. Reaction completion was monitored on TLC using ethyl acetate:hexane (4:6) mobile phase. After 12 h reaction was completed and worked up. Reaction mixture was brought to room temperature and quenched into the ice-water slurry (100 mL) and compound was extracted in the ethylacetate (50 mL×3). Organic layer was washed with brine solution (50 mL×3) followed by drying using anhydrous sodium sulphate. Organic layer was concentrated under reduced pressure to afford 5.5 g of crude compound. Crude compound was further purified by column chromatography using silica 60/120 and ethylacetate:hexane as mobile phase. Column purification was started with 5% EtOAc in hexane upto 35%. Compound started eluting in 30% ethylacetate and continued till 35% EtOAc. Fractions containing compound was distilled out using rotary evaporation at 45° C./250 mm Hg to obtain 0.430 g of pure compound, yield (6.6%). Mass/LCMS: 180.0; NMR: Confirmed.

Trans-isomer (5; major isomer): $^1$H NMR (400 MHz, CDCl$_3$) δ 8.53 (s, 1H), 8.23 (s, 1H), 8.09-8.11 (m, 1H), 7.43-7.58 (m, 2H), 6.74-6.76 (d, J=13.8 Hz, 1H), 5.10-5.19 (m, 1H), 1.28-1.34 (d, 6H): LCMS for C$_{14}$H$_{14}$ClN$_3$O$_2$ [M+1]$^+$ 291.1 found 291.19 at RT 7.391 min (LCMS 98.92%).

Synthesis of Example 3

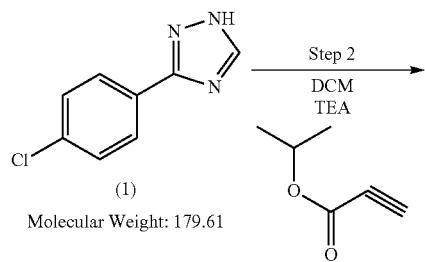

(1)
Molecular Weight: 179.61

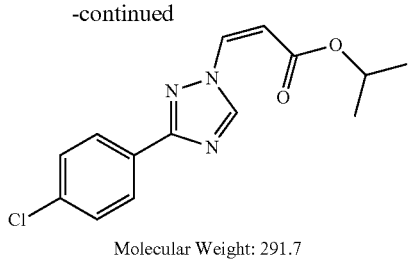

Molecular Weight: 291.7

In 3-neck 50 mL round-bottomed flask, Intermediate-1 (0.4 g, 1.0 eq.) was dissolved in DCM (10 mL, 25 Vol), added isopropyl propiolate (0.35 g, 1.4 eq) and TEA (0.334 g, 1.5 eq) and reaction mixture was stirred at RT for 30 mins. Reaction completion was monitored on TLC using ethyl acetate: hexane (2:8) mobile phase. After 30 mins reaction mixture was concentrated under reduced pressure to afford 0.6 g of crude compound. Compound was further purified by column chromatography using silica 60/120 and ethylacetate:hexane as mobile phase. Column purification was started with 5% EtOAc in hexane upto 20%. Compound started eluting in 11% ethylacetate and continued till 15% EtOAc. Fractions containing compound was distilled out using rotary evaporation at 45° C./250 mm Hg to obtain 0.021 g of pure compound. HPLC/LCMS: 99.58%; Mass/LCMS: 292.2; $^1$H NMR (400 MHz, CDCl$_3$) δ=8.36 (s, 1H), 8.11 (s, 1H), 7.99-8.01 (d, J=8 Hz, 1H), 7.44-7.46 (d, J=8 Hz, 2H), 7.22-7.24 (d, J=8 Hz, 1H), 6.23-6.25 (d, J=8, 1H) 3.03 (s, 3H) LCMS: Calculated C$_{11}$H$_{10}$ClN$_3$OS (M+H)$^+$ 267.73. Found 267.84; Retention time 2.836 min (95.23%)

Example 4

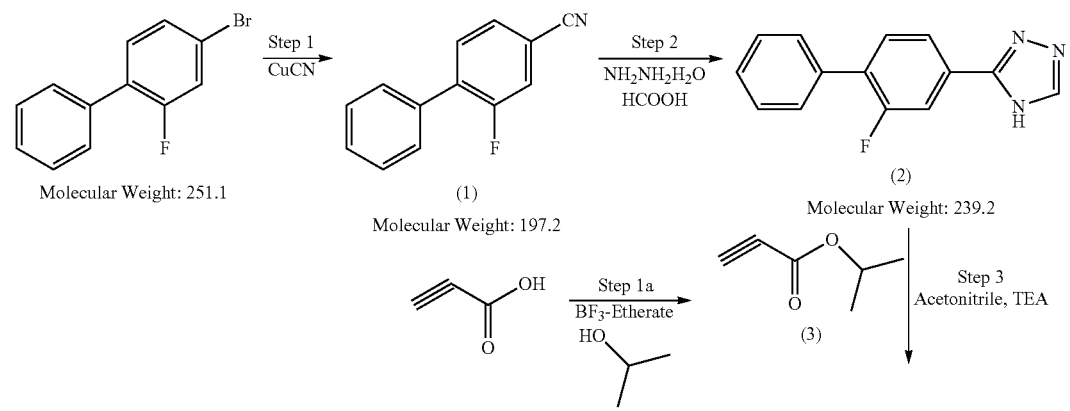

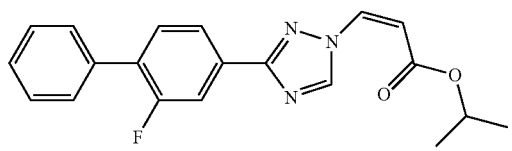

Molecular Weight: 351.4

Synthesis of Intermediate (1)

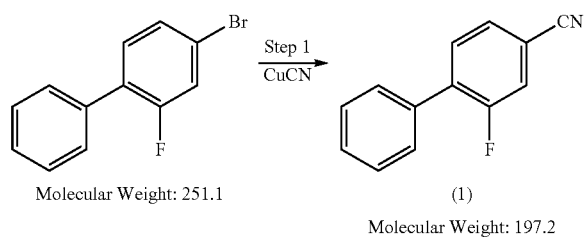

Molecular Weight: 251.1

(1)

Molecular Weight: 197.2

In 3-neck 50 mL round-bottomed flask, 4-bromo-2-fluoro bi phenyl (4.0, 1 eq.) was mixed with cuprous cyanide (4.3 g, 3 eq.), potassium iodide (3.2 g, 1.2 eq.) and pyridine (40 mL, 10 V). Reaction mixture was refluxed to 140-150° C. for 12 h. Reaction completion was monitored on TLC using ethyl acetate:hexane (2:8) mobile phase. After 12 h reaction was completed and worked up. Reaction mixture was brought to room temperature and quenched into the ice-water slurry (150 mL) and compound was extracted in the ethylacetate (50 mL×3). Organic layer was washed with brine solution (50 mL×3) followed by drying using anhydrous sodium sulphate. Organic layer was concentrated under reduced pressure to afford 5.0 g of crude compound. Crude compound was further purified by column chromatography using silica 60/120 and ethylacetate:hexane as mobile phase. Column purification was started with 1% EtOAc in hexane upto 10%. Compound started eluting in 6% ethylacetate and continued till 10% EtOAc. Fractions containing compound was distilled out using rotary evaporation at 45° C./250 mm Hg to obtain 1.0 g of pure compound, yield (31.8%). NMR: Confirmed.

Synthesis of Intermediate (2)

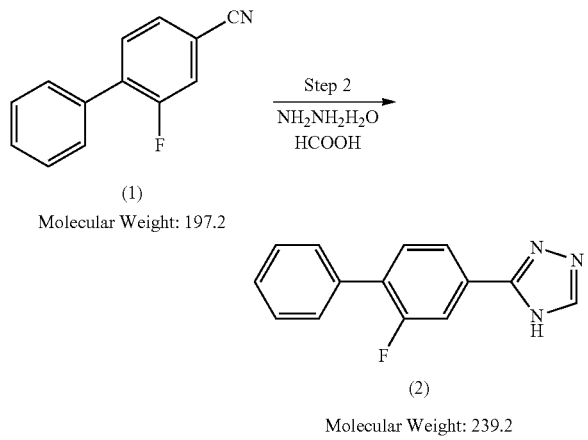

(1)

Molecular Weight: 197.2

(2)

Molecular Weight: 239.2

In 3-neck 50 mL round-bottomed flask, Intermediate-1 (1.0, 1 eq.) was mixed with formic acid (5.0 mL, 5 Vol) and hydrazine hydrate (5.0 mL, 5 Vol) and reaction mixture was refluxed to 110° C. for 12 h. Reaction was clear solution once it attained 90° C. Reaction remained yellow colored clear solution throughout the reaction. Reaction completion was monitored on TLC using ethyl acetate:hexane (5:5) mobile phase. After 12 h reaction was completed and worked up. Reaction mixture was brought to room temperature and quenched into the ice-water slurry (100 mL) and compound was extracted in the ethylacetate (50 mL×3). Organic layer was washed with brine solution (50 mL×3) followed by drying using anhydrous sodium sulphate. Organic layer was concentrated under reduced pressure to afford 1.2 g of crude compound. Crude compound was further purified by column chromatography using silica 60/120 and ethylacetate:hexane as mobile phase. Column purification was started with 5% EtOAc in hexane upto 35%. Compound started eluting in 30% ethylacetate and continued till 35% EtOAc. Fractions containing compound was distilled out using rotary evaporation at 45° C./250 mm Hg to obtain 0.135 g of pure compound, yield (11.2%). Mass/LCMS: 86.96%; NMR: Confirmed.

Synthesis of Example 4

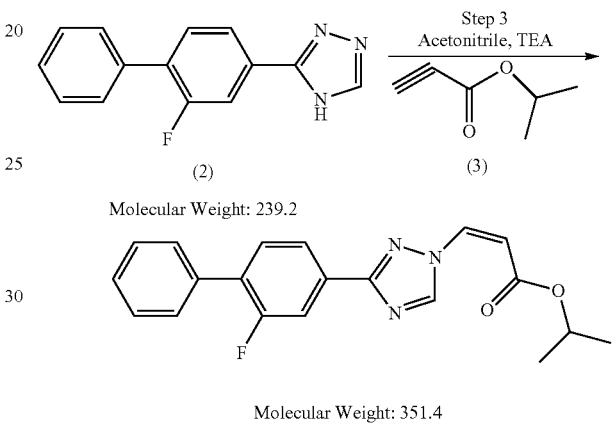

(2)

Molecular Weight: 239.2

(3)

Molecular Weight: 351.4

In 3-neck 50 mL round-bottomed flask, Intermediate-2 (0.5 g, 1.0 eq.) was dissolved in DCM (12.5 mL, 25 Vol), added isopropyl propiolate (0.329 g, 1.4 eq) and TEA (0.319 g, 1.5 eq) and reaction mixture was stirred at RT for 30 mins. Reaction completion was monitored on TLC using ethyl acetate:hexane (2:8) mobile phase. After 30 mins reaction mixture was concentrated under reduced pressure to afford 0.6 g of crude compound. Compound was further purified by column chromatography using silica 60/120 and ethylacetate: hexane as mobile phase. Column purification was started with 5% EtOAc in hexane upto 15%. Compound started eluting in 10% ethylacetate and continued till 15% EtOAc. Fractions containing compound was distilled out using rotary evaporation at 45° C./250 mm Hg to obtain 0.020 g of pure compound, Yield (2.7%). HPLC/LCMS: 99.73%; Mass/LCMS: 352.2; $^1$H NMR (400 MHz, CDCl$_3$) δ 9.75 (s, 1H), 7.94-8.01 (m, 2H), 7.28-7.64 (m, 7H), 5.70-5.72 (d, J=10.8 Hz, 1H), 5.14-5.17 (t, J=12.4 Hz, J'=6.4 Hz, 1H), 1.33-1.35 (d, 6H). LCMS-ESI calcd for $C_{20}H_{18}FN_3O_2[M+1]^+$ 351.14. found 352.23 at 6.13 min. (LCMS 99.73%).

Example 5

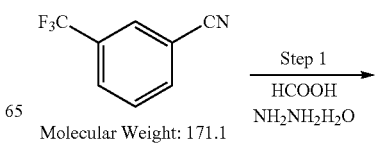

Molecular Weight: 171.1

Step 1
HCOOH
NH$_2$NH$_2$H$_2$O

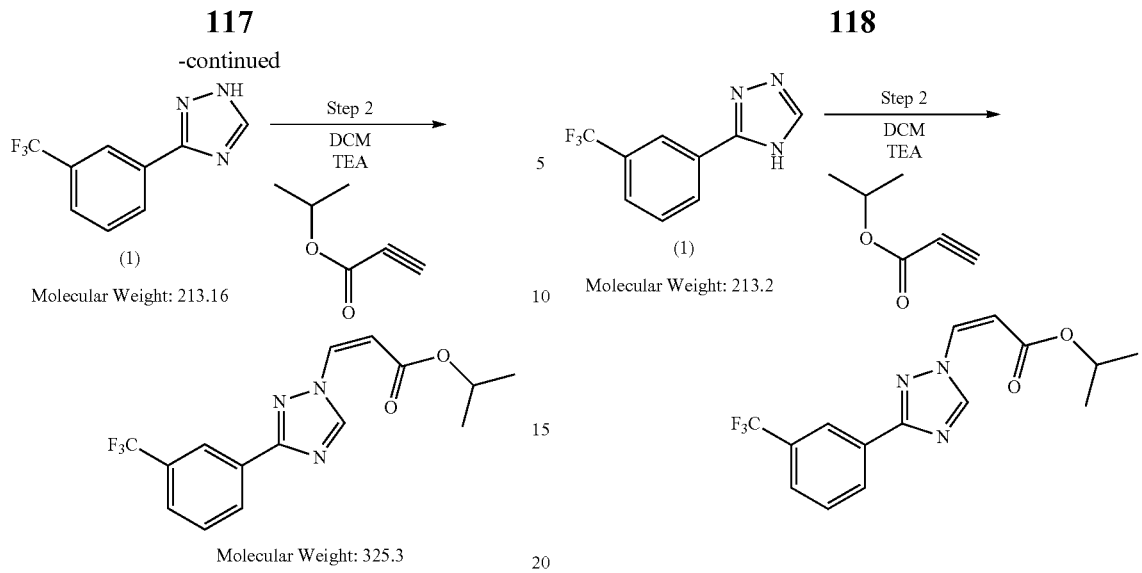

Synthesis of Intermediate (1)

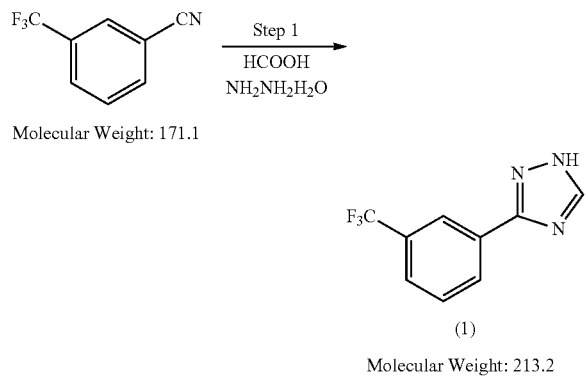

In 3-neck 50 mL round-bottomed flask, (trifluoromethyl) benzonitrile (5.0, 1 eq.) was mixed with formic acid (25 mL, 5 Vol) and hydrazine hydrate (25 mL, 5 Vol) and reaction mixture was refluxed to 110° C. for 12 h. Reaction was clear solution once it attained 90° C. Reaction remained yellow colored clear solution throughout the reaction. Reaction completion was monitored on TLC using ethyl acetate:hexane (5:5) mobile phase. After 12 h reaction was completed and worked up. Reaction mixture was brought to room temperature and quenched into the ice-water slurry (100 mL) and compound was extracted in the ethylacetate (50 mL×3). Organic layer was washed with brine solution (50 mL×3) followed by drying using anhydrous sodium sulphate. Organic layer was concentrated under reduced pressure to afford 5.6 g of crude compound. Crude compound was further purified by column chromatography using silica 60/120 and ethylacetate:hexane as mobile phase. Column purification was started with 5% EtOAc in hexane upto 35%. Compound started eluting in 28% ethylacetate and continued till 35% EtOAc. Fractions containing compound was distilled out using rotary evaporation at 45° C./250 mm Hg to obtain 0.6 g of pure compound yield (9.6%).

In 3-neck 50 mL round-bottomed flask, Intermediate-1 (0.6 g, 1.0 eq.) was dissolved in DCM (15 mL, 25 Vol), added isopropyl propiolate (0.442 g, 1.4 eq) and TEA (0.425 g, 1.5 eq) and reaction mixture was stirred at RT for 30 mins. Reaction completion was monitored on TLC using ethyl acetate: hexane (2:8) mobile phase. After 30 mins reaction mixture was concentrated under reduced pressure to afford 0.6 g of crude compound. The compound was further purified by column chromatography using silica 60/120 and ethylacetate: hexane as mobile phase. Column purification was started with 5% EtOAc in hexane upto 20%. Compound started eluting in 15% ethylacetate and continued till 20% EtOAc. Fractions containing compound was distilled out using rotary evaporation at 45° C./250 mm Hg to obtain 0.025 g of pure compound. $^1$H NMR (400 MHz, CDCl$_3$) δ 9.73 (s, 1H), 7.59-8.44 (m, 4H), 7.29-7.31 (d, J=10.4 Hz, 1H), 5.71-5.74 (d, J=10.8 Hz, 1H), 5.10-5.18 (m, 1H), 1.29-1.35 (d, 6H): LCMS for $C_{15}H_{14}F_3N_3O_2$ 325.29 found 326.27 at 7.370 min (LCMS 97.63%).

Example 6

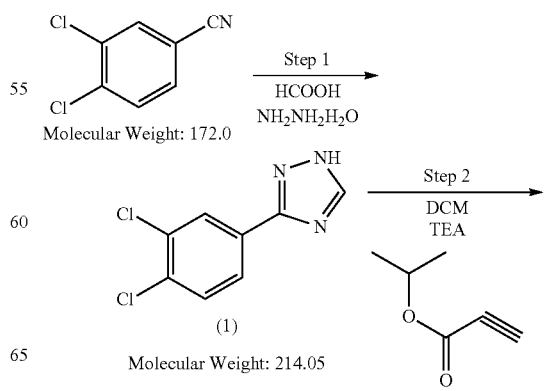

Synthesis of Example 6

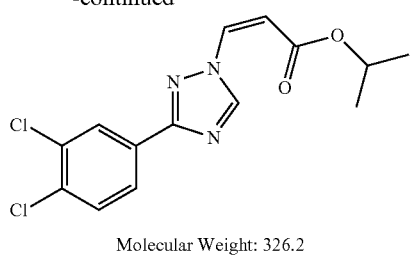

Molecular Weight: 326.2

Synthesis of Intermediate (1)

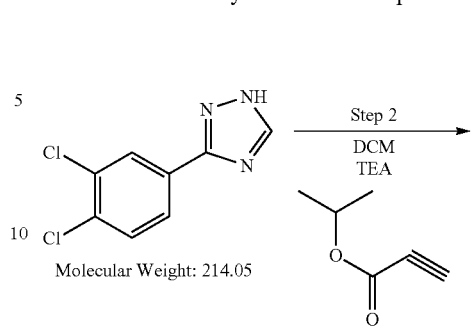

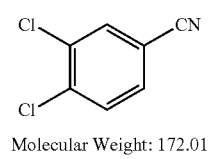

(1)
Molecular Weight: 214.05

In 3-neck 50 mL round-bottomed flask, (Trifluoromethyl) benzonitrile (5.0, 1 eq.) was mixed with formic acid (25 mL, 5 Vol) and hydrazine hydrate (25 mL, 5 Vol) and reaction mixture was refluxed to 110° C. for 12 h. Reaction was clear solution once it attained 90° C. Reaction remained yellow colored clear solution throughout the reaction. Reaction completion was monitored on TLC using ethyl acetate:hexane (5:5) mobile phase. After 12 h reaction was completed and worked up. Reaction mixture was brought to room temperature and quenched into the ice-water slurry (100 mL) and compound was extracted in the ethylacetate (50 mL×3). Organic layer was washed with brine solution (50 mL×3) followed by drying using anhydrous sodium sulphate. Organic layer was concentrated under reduced pressure to afford 5.6 g of crude compound. Crude compound was further purified by column chromatography using silica 60/120 and ethylacetate:hexane as mobile phase. Column purification was started with 5% EtOAc in hexane upto 35%. Compound started eluting in 28% ethylacetate and continued till 35% EtOAc. Fractions containing compound was distilled out using rotary evaporation at 45° C./250 mm Hg to obtain 0.650 g of pure compound, yield (10.5%). HPLC/LCMS: 85.99%.

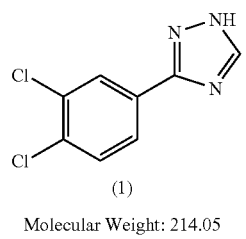

Molecular Weight: 326.2

In 3-neck 50 mL round-bottomed flask, intermediate-1 (0.65 g, 1.0 eq.) was dissolved in DCM (16 mL, 25 Vol), added isopropyl propiolate (0.471 g, 1.4 eq) and TEA (0.455 g, 1.5 eq). reaction mixture was stirred at RT for 30 mins. Reaction completion was monitored on TLC using ethyl acetate:hexane (3:7) mobile phase. After 30 mins reaction mixture was concentrated under reduced pressure to afford 0.8 g of crude compound. The Compound was further purified by column chromatography using silica 60/120 and ethylacetate:hexane as mobile phase. Column purification was started with 5% EtOAc in hexane upto 25%. Compound started eluting in 20% ethylacetate and continued till 25% EtOAc. Fractions containing compound was distilled out using rotary evaporation at 45° C./250 mm Hg to obtain 0.055 g of pure compound, yield (5.6%). HPLC/LCMS: 98.01%; $^1$H NMR (400 MHz, CDCl$_3$): δ 9.71 (s, 1H), 8.26-8.27 (d, J=2 Hz, 1H), 7.97-8 (dd, 1H), 7.54-7.56 (d, J=8.4 Hz, 1H), 7.25-7.28 (d, J=10.8 Hz, 1H), 5.7-5.73 (d, J=10.8 Hz, 1H), 5.11-5.17 (m, 1H), 1.27-1.34 (d, 6H): LCMS for C$_{14}$H$_{13}$Cl$_2$N$_3$O$_2$ [M]$^+$ 326.18 found 326.16 at 6.237 min.

Example 7

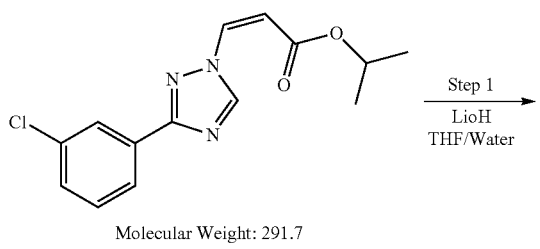

Molecular Weight: 291.7

121

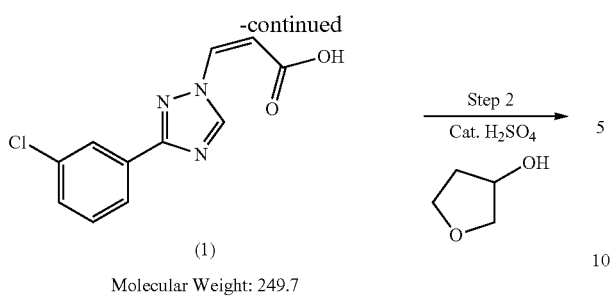

Synthesis of Intermediate (1)

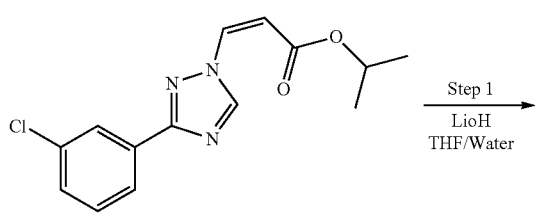

In 3-neck 100 mL round-bottomed flask, Example 1 (1.0 g, 1 eq.) was mixed with THF-Water (1:1) (20 mL, 20 Vol.) and LiOH (0.288 g, 2.0 eq.) was added. The reaction mixture was stirred at RT for 2-3 h. Reaction completion was monitored on TLC using neat ethyl acetate as mobile phase. Reaction mixture was quenched into the ice-water slurry (50 mL) and acidified with approximately 5 N HCl to 4 PH. Compound was extracted in the ethylacetate (50 mL×3) and organic layer was washed with brine solution (50 mL×3) followed by drying using anhydrous sodium sulphate. Organic layer was concentrated under reduced pressure to afford 0.7 g of pure compound. Yield (81.8%). Mass/LCMS: 250.0, Confirmed. NMR: Confirmed.

122

Synthesis of Example 7

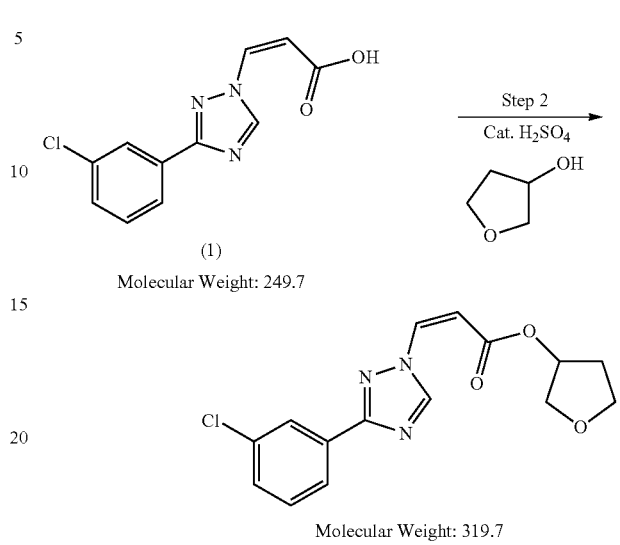

In 3-neck 50 mL round-bottomed flask, Intermediate 1 (0.05 g, 1 eq.) was mixed with 3-hyroxy tetrahydrofuran (0.035 g, 2.0 eq.) using THF (2.0 mL, 40 Vol.) as solvent. $H_2SO_4$ was added into the above reaction mixture in catalytic amount (1-2 drops). Reaction mixture was refluxed for 3-4 h at 80° C. Reaction completion was monitored on TLC using ethyl acetate:hexane (2:8) mobile phase. Reaction mixture was brought to room temperature and quenched into the ice-water slurry (100 mL) and compound was extracted in the Ethyl acetate (25 mL×3). Compound was further purified by column chromatography using silica 60/120 and ethylacetate:hexane as mobile phase. Column purification was started with 1% EtOAc in hexane upto 10% Ethylacetate. Compound started eluting in 3% ethylacetate and continued till 5% EtOAc. Fractions containing compound was distilled out using rotary evaporation at 45° C./250 mm Hg to obtain 14 mg of compound with some aliphatic impurity. The compound was further purified by preparative TLC to get 5 mg of pure final compound. Yield (7.81%). $^1$HNMR (400 MHz, $CDCl_3$) δ 9.70 (s, 1H), 9.16 (s, 1H), 8.05-8.02 (d, J=10.4 Hz, 1H), 7.44-7.42 (d, 2H), 7.34-7.31 (d, 1H), 5.75-5.72 (d, J=11.2 Hz, 1H), 5.46-5.43 (m, 1H), 4.00-3.88 (m, 4H), 2.32-2.23 (m, 1H), 2.13-2.07 (m, 1H): LCMS for $C_{15}H_{14}ClN_3O_3$ $[M+H]^+$ 319.7 found at 320.22 at RT 6.461 min.

Example 8

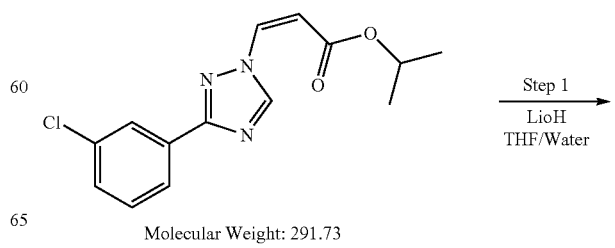

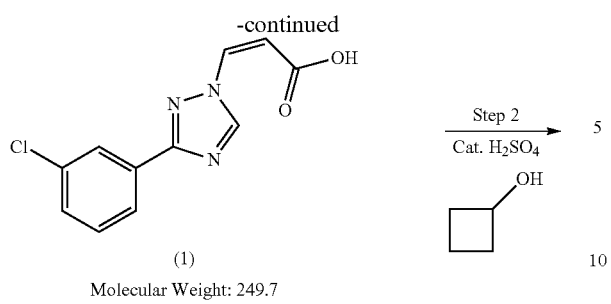
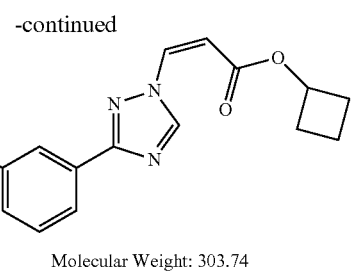

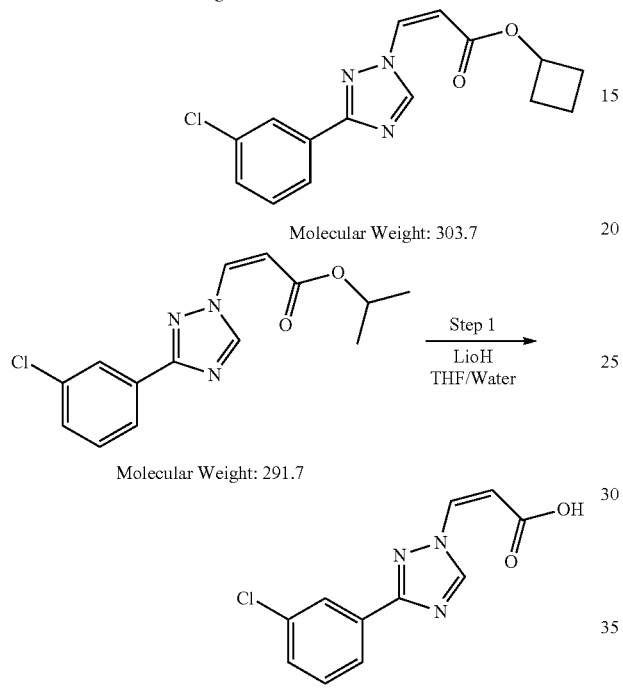

In a 3-neck 100 mL round-bottomed flask, Example 1 (1.0 g, 1 eq.) was mixed with THF-Water acid (20 mL, 20 Vol) and LiOH (0.288 g, 2.0 eq) was added. Reaction mixture was stirred at RT for 2-3 h. Reaction completion was monitored on TLC using neat ethyl acetate as mobile phase. Reaction mixture was quenched into the ice-water slurry (50 mL) and acidified with approximately 5 N HCl to 4 PH. Compound was extracted in the ethylacetate (50 mL×3) and organic layer was washed with brine solution (50 mL×3) followed by drying using anhydrous sodium sulphate. Organic layer was concentrated under reduced pressure to afford 0.7 g of pure compound, Yield (81.8%). Mass/LCMS: 250.0, Confirmed. NMR: Confirmed.

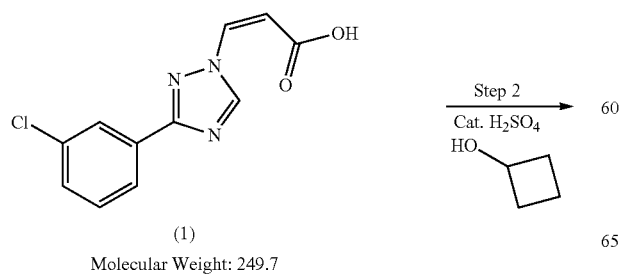

In a 3N 50 mL round-bottomed flask, Intermediate 1 (0.1 g, 1 eq.) was mixed with Cyclobutanol (0.058 g, 2.0 eq) and $H_2SO_4$ was added into the above reaction mixture in catalytic amount (1-2 drops). Reaction mixture was refluxed for overnight at 80° C. Reaction completion was monitored on TLC using ethyl acetate: n-hexane (2:8) as mobile phase. Reaction mixture was brought to room temperature and quenched into the ice-water slurry (25 mL) and compound was extracted in the Ethyl acetate (10 mL×3). Compound was further purified by column chromatography using silica 60/120 and ethylacetate:n-hexane as mobile phase. Column purification was started with 5% EtOAc in hexane upto 10% Ethylacetate. Compound started eluting in 6% ethylacetate and continued till 7% EtOAc. Fractions containing compound was distilled out using rotary evaporation at 45° C./250 mm Hg to obtain 23 mg of pure final compound. Yield (18.9%) ($^1$H NMR, 400 MHz, CDCl$_3$) δ 9.7 (s, 1H), 68.16 (s, 1H), δ 8.02-8.05 (t, 1H), 67.41-7.44 (d, 2H), δ 7.28-7.31 (d, J: 11.2 Hz, 1H), 5.69-5.72 (d, J: 10.8 Hz, 1H), δ 5.08-5.16 (m, 1H), 62.39-2.47 (qt, 2H), δ 2.12-2.21 (qt, 2H), δ 1.85-1.91 (m, 2H). LCMS of $C_{15}H_{14}ClN_3O_2$ (M+1)$^+$:303.74 found 304.30 at 7.640 min (LCMS 98.75%).

Example 9

Synthesis of Intermediate (1)

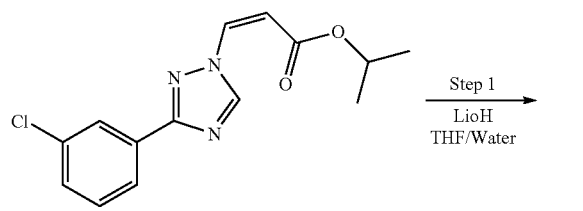

Molecular Weight: 291.7

Step 1
LiOH
THF/Water

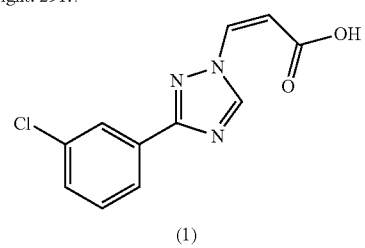

(1)
Molecular Weight: 249.7

In a 3-neck 100 mL round-bottomed flask, Example 1 (1.0 g, 1 eq.) was mixed with THF-Water acid (1:1) (20 mL, 20 Vol.) and LiOH (0.288 g, 2.0 eq.) was added to this mixture. Reaction mixture was stirred at RT for 2-3 h. Reaction completion was monitored on TLC using neat ethyl acetate as a mobile phase. Reaction mixture was quenched into the ice-water slurry (50 mL) and acidified with approximately 5 N HCl to pH 4. Compound was extracted in the ethylacetate (50 mL×3) and organic layer was washed with brine solution (50 mL×3) followed by drying using anhydrous sodium sulphate. Organic layer was concentrated under reduced pressure to afford 0.7 g of pure compound. Yield (81.8%). Mass/LCMS: 250.0, Confirmed. NMR: Confirmed.

Synthesis of Example 9

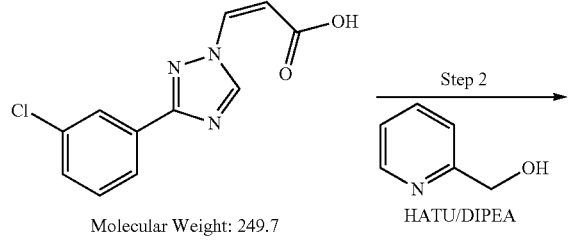

Molecular Weight: 249.7

Step 2
HATU/DIPEA

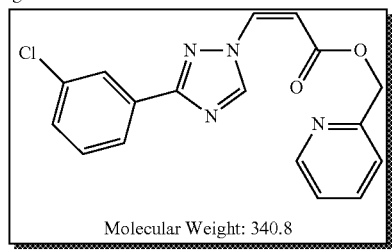

Molecular Weight: 340.8

In a 3-neck 25 mL round-bottomed flask, Intermediate 1 (0.15 g, 1 eq.) was dissolved in DCM (6 mL, 40 Vol.) and HATU (0.251 g, 1.1 eq.) and DIPEA (0.085 g, 1.1 eq.) was added. Reaction mixture was stirred at RT for 3-4 h. Reaction completion was monitored on TLC using ethyl acetate:hexane (4:6) mobile phase. Reaction mixture was quenched into the ice-water slurry (20 mL) and the compound was extracted in the DCM (10 mL×3). Compound was further purified by column chromatography using silica 60/120 and ethylacetate:hexane as mobile phase. Column purification was started with 5% EtOAc in hexane upto 30%. Compound started eluting in 10% ethyl acetate and continued till 12% EtOAc. Fractions containing compound was distilled out using rotary evaporation at 45° C./250 mm Hg to obtain 0.020 g of pure compound. Yield (9.76%); Compound was also easily converted to its hydrochloride salt using dioxane-HCl by conventional method and characterized by NMR. $^1$H NMR (400 MHz, CDCl$_3$) δ 9.76 (s, 1H, D2O Exchangeable), 7.31-8.66 (m, 8H), 7.36-7.38 (d, J=10.8 Hz, 1H), 5.84-5.87 (d, J=11.2 Hz, 1H), 5.39 (s, 2H): LCMS for C$_{17}$H$_{13}$ClN$_4$O$_2$ 340.76 found 341.18 at R.T. 6.185 min LCMS (purity-97.42%). NMR spectrum of HCl salt: $^1$H NMR (400 MHz, CDCl$_3$) δ 9.24 (s, 1H, D2O Exchangeable), 8.61-8.62 (d, 1H, J=4 Hz), 7.84-7.95 (m, 3H), 7.43-7.6 (m, 4H), 6.11-6.14 (d, 1H, J=12 Hz), 5.37 (s, 2H): LCMS for C$_{17}$H$_{14}$Cl$_2$N$_4$O$_2$ 377.22 found 341.18 LCMS (purity-99%).

Example 10

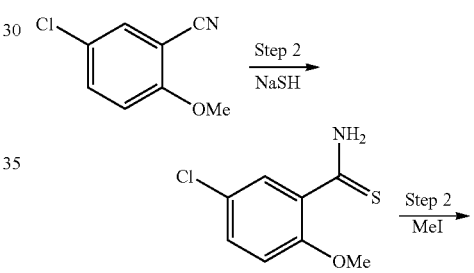

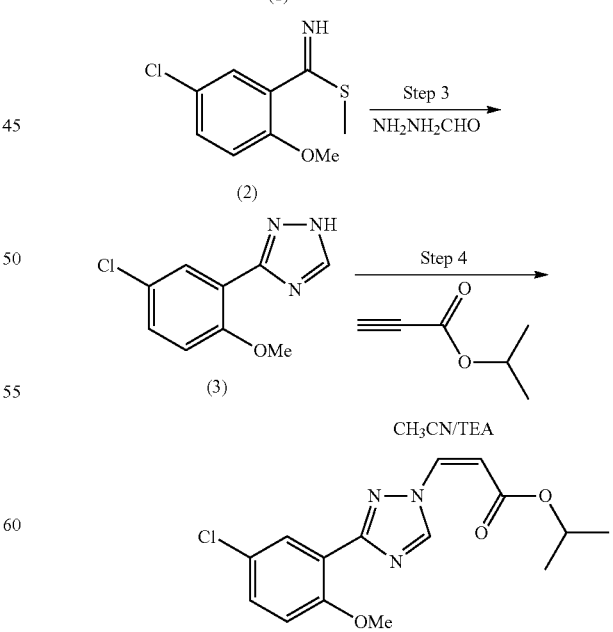

Synthesis of Intermediate (1)

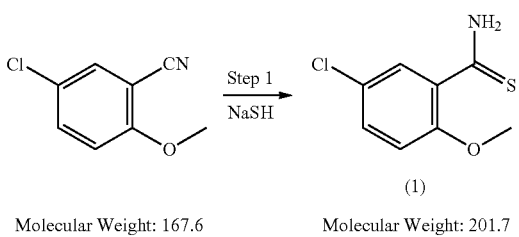

(1)
Molecular Weight: 167.6   Molecular Weight: 201.7

In a 3-neck 100 mL round-bottomed flask, on magnetic stirrer, slurry of sodium hydrosulfide hydrate (4.33 g, 2.0 eq) and magnesium chloride hexahydrate (1.52 g, 1.0 eq.) in DMF (15 mL) was added. 3-Chloro-5-methoxybenzonitrile (1.25 g, 1.0 eq) was added in one portion and the reaction mixture was stirred at room temperature for 1-2 h. The progress of reaction was followed by TLC using ethyl acetate:hexane (1:1) as mobile phase. The resulting green slurry was poured in 150 mL water and the resulting precipitates were collected by filtration. The crude product was re-suspended in 1 N HCl and stirred for 45 min., then filtered and washed with water to give intermediate-1 (1.2 g, 80%). Mass/LCMS: 202.0.

Synthesis of Intermediate (2)

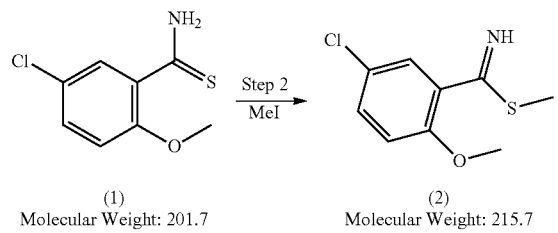

(1)                        (2)
Molecular Weight: 201.7    Molecular Weight: 215.7

In a 3-neck 100 mL round-bottomed flask, on magnetic stirrer, a solution of intermediate-1 (1.2 g, 1.0 eq.) in diethyl ether (24 mL) was treated with methyl iodide (3.36 g, 4.0 eq.). Reaction was stirred for 12 h during which white colored solid separated. The completion of reaction was monitored on TLC using ethyl acetate:hexane (1:1) as mobile phase. Reaction mixture was filtered, precipitates washed with diethyl ether and dried under vacuum to give intermediate-2 (1.0 g, 78.13%). Mass/LCMS: 216.0.

Synthesis of Intermediate (3)

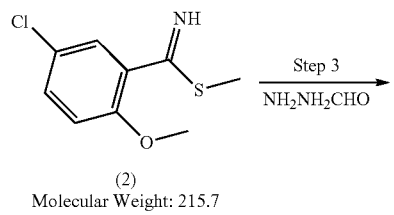

(2)
Molecular Weight: 215.7

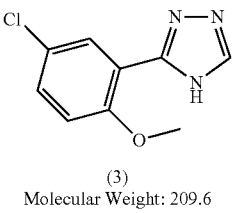

(3)
Molecular Weight: 209.6

In a 3-neck 100 mL round-bottomed flask, equipped with water condenser, a solution of intermediate-2 (1.0 g, 1.0 eq.) in DMF (10 mL) was added. To this reaction, Formic hydrazide (0.556 g, 2.0 eq.) was added under nitrogen atmosphere. The reaction mixture was stirred for 3 h and then heated at 90° C. for 3 h. Completion of the reaction was monitored on TLC using ethyl acetate:hexane (1:1) as mobile phase. Cooled reaction mixture was poured into water and extracted with ethyl acetate, dried over sodium sulfate and evaporated under vacuum to obtain the intermediate-3 (0.2 g, 21.6%). Compound was used as such without further purification. Mass/LCMS: 209.9.

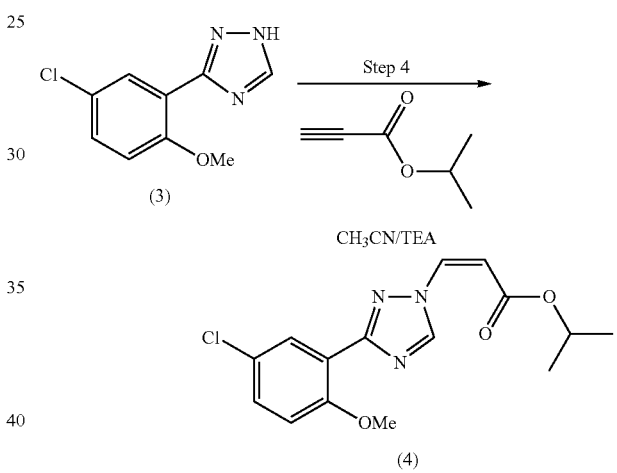

(4)

In a 3-neck 25 mL round-bottomed flask, Intermediate-3 (0.2 g, 1.0 eq.) was dissolved in DCM (100 mL, 20 Vol.). To this reaction mixture TEA (0.096 g, 1.0 eq.) and isopropyl propiolate (0.160 g, 1.5 eq.) was added in cooling condition under nitrogen atmosphere. Reaction mixture stirred at RT for 30 mins. Reaction was monitored on TLC using ethyl acetate: hexane (2:8) as mobile phase for completion. DCM was removed under reduced pressure to give crude product. The crude reaction mixture was purified by column chromatography using silica 60/120 using ethylacetate:hexane as mobile phase. The column was packed in hexane and started eluting in ethyl acetate in gradient manner starting from 5% to 10% ethyl acetate in hexane. Column purification was started with 5% EtOAc in hexane upto 10% Ethylacetate. Compound started eluting in 5% ethylacetate and continued till 7% EtOAc. Fractions containing compound was distilled out using rotary evaporation at 45° C./250 mm Hg to obtain 12 mg of pure final compound. Yield (3.9%). (Z)-isopropyl 3-(3-(5-chloro-2-methoxyphenyl)-1H-1,2,4-triazol-1-yl)acrylate (VS-107): $^1$H NMR (400 MHz, CDCl$_3$) δ 9.78 (s, 1H), 6.97-8.03 (m, 3H), 7.33-7.36 (d, J=11.4 Hz, 1H), 5.67-5.70 (d, J=11.4 Hz, 1H), 5.13-5.16 (m, 1H), 3.96 (s, 3H), 1.32-1.34 (d, 6H): LCMS for C$_{15}$H$_{16}$ClN$_3$O$_3$ 321.76 found 322.17 at R.T. 5.052 min (LCMS 95.81%).

Example 11

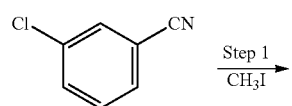

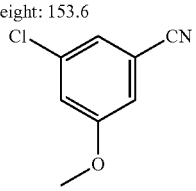

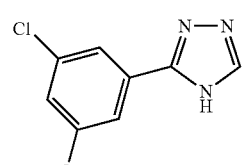

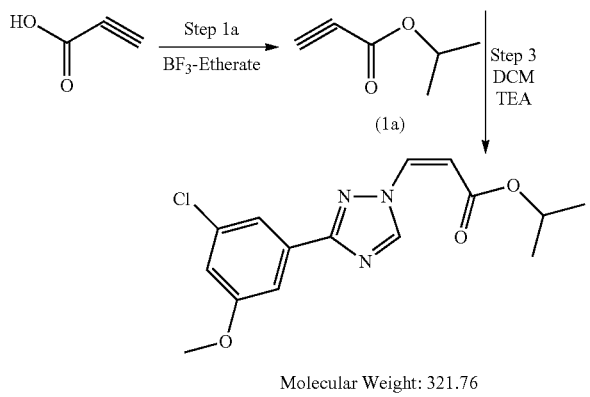

Synthesis of Intermediate (1)

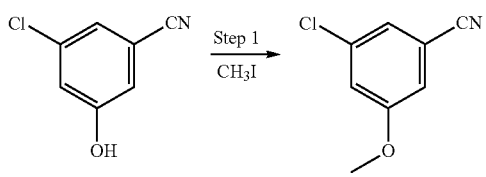

In a 3-neck 100 mL round-bottomed flask, 3-Chloro-5-hydroxy benzonitrile (5.0 g, 1.0 eq) was dissolved in Acetone (50 mL). $CH_3I$ (9.27 g, 2.0 eq) and $K_2CO_3$ (6.68 g, 1.5 eq) was added to this reaction mixture. Reaction mixture was heated at 70° C. for 3-4 h. The progress of reaction was followed by TLC using ethyl acetate:hexane (1:1) as mobile phase. The resulting slurry was poured in 100 mL water and compound was extracted in the Ethyl acetate (25 mL×3). Organic layer was washed with brine solution (25 mL×3) followed by drying using anhydrous sodium sulphate. Organic layer was concentrated under reduced pressure to afford 5 g of crude compound. Yield (92.08%). Mass/LCMS: Confirmed.

Synthesis of Intermediate (2)

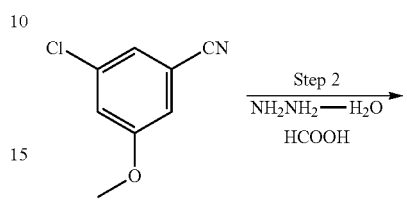

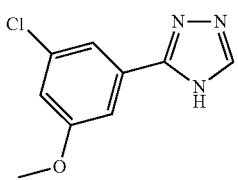

In a 3-neck 100 mL round-bottomed flask, a solution of intermediate-1 (5.0 g, 0.0298 mmol) in formic acid (25 mL) and Hydrazine hydrate (25 mL) was refluxed at 110° C. for 12 h. Reaction completion was monitored on TLC using ethyl acetate:hexane (1:1) as mobile phase. Reaction was clear solution once it attained 90° C. Reaction remained yellow colored clear solution throughout the reaction. Reaction completion was monitored on TLC using ethyl acetate:hexane (4:6) mobile phase. After 12 h reaction was completed and worked up. Reaction mixture was brought to room temperature and quenched into the ice-water slurry (100 mL) and compound was extracted in the ethylacetate (50 mL×3). Organic layer was washed with brine solution (50 mL×3) followed by drying using anhydrous sodium sulphate. Organic layer was concentrated under reduced pressure to afford 6.43 g of crude compound. Crude compound was further purified by column chromatography using silica 60/120 and ethylacetate:hexane as mobile phase. Column purification was started with 5% EtOAc in hexane upto 35%. Compound started eluting in 30% ethylacetate and continued till 35% EtOAc. Fractions containing compound was distilled out using rotary evaporation at 45° C./250 mm Hg to obtain 0.9 g of pure compound yield. Mass/LCMS: 210.

Synthesis of Example 11

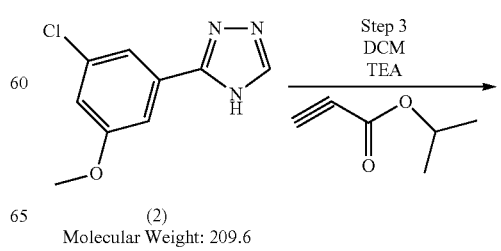

-continued

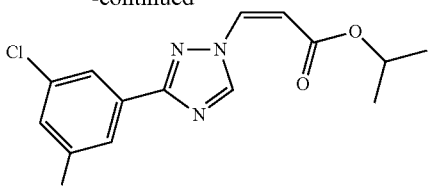

Molecular Weight: 321.8

In a 3-neck 50 mL round-bottomed flask, Intermediate-2 (0.4 g) was dissolved in DCM (4 mL, 10 Vol.). To this reaction mixture TEA (0.269 g, 1.4 eq.) and isopropyl propiolate (0.258 g, 1.2 eq.) was added at room temperature reaction. Reaction mixture was stirred at RT for 30 mins. Reaction completion was monitored on TLC using ethyl acetate:hexane (2:8) mobile phase. After 30 mins reaction mixture was concentrated under reduced pressure to afford 0.5 g of crude compound. Compound was further purified by column chromatography using silica 60/120 and ethylacetate:hexane as mobile phase. Column purification was started with 1% EtOAc in hexane upto 10%. Compound started eluting in 6% ethylacetate and continued till 10% EtOAc. Fractions containing compound was distilled out using rotary evaporation at 45° C./250 mm Hg to obtain 0.020 g of pure compound. Yield (3.25%). $^1$H NMR (400 MHz, CDCl$_3$) δ=9.72 (s, 1H), 7.76 (s, 1H), 7.58 (s, 1H) 7.26-7.28 (d, J=10.2 Hz, 1H), 6.99 (s, 1H), 5.69-5.72 (d, J=10.8 Hz, 1H), 5.11-5.17 (m, 1H), 3.89 (s, 3H), 1.32-1.34 (d, 6H). LCMS: Calculated for $C_{15}H_{16}ClN_3O_3$ (M+H)$^+$ 321.76 Found: 322.3 at 5.666 min (LCMS 95.07%).

Example 12

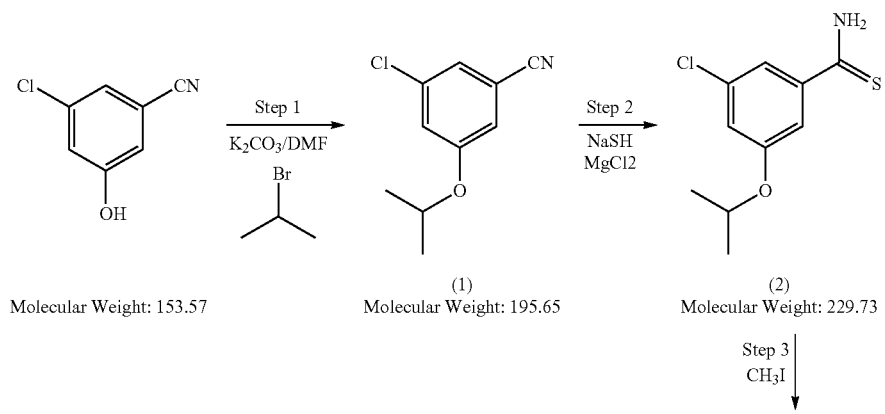

(1) Molecular Weight: 195.65

(2) Molecular Weight: 229.73

Molecular Weight: 153.57

Step 3
CH$_3$I

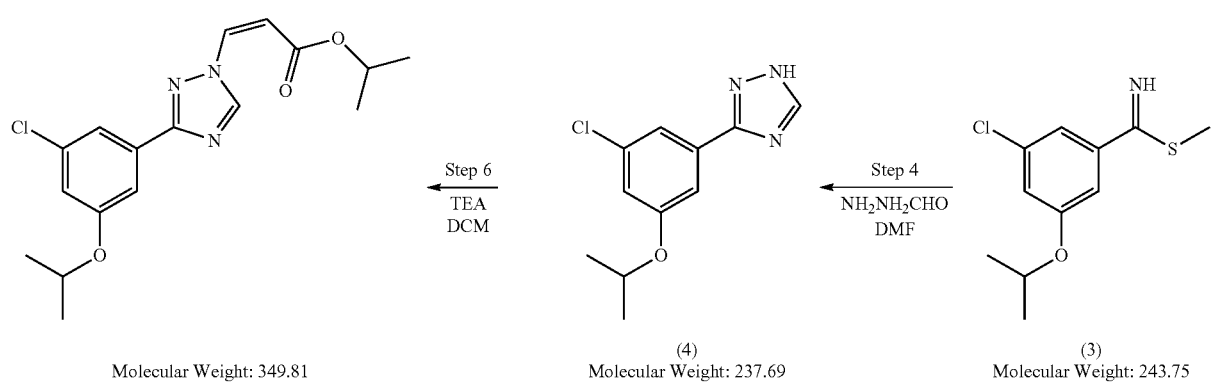

(4) Molecular Weight: 349.81

(4) Molecular Weight: 237.69

(3) Molecular Weight: 243.75

Synthesis of Intermediate (1)

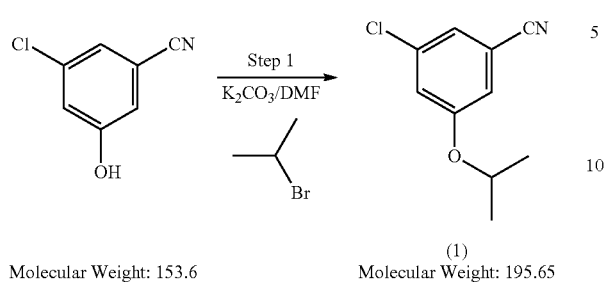

(1)
Molecular Weight: 153.6     Molecular Weight: 195.65

In a 3-neck 100 mL round-bottomed flask, 3-Chloro-5-hydroxy benzonitrile (1.0 g, 1.0 eq) was dissolved in 10 ml of DMF and 2-Bromo Propane (2.0 g, 2.0 eq) and $K_2CO_3$ (1.35 g, 1.5 eq) was added. Reaction mixture was heated at 90° C. for 3-4 h. The progress of reaction was followed by TLC using ethyl acetate:hexane (1:1) as mobile phase. The resulting slurry was poured in 100 mL water and compound was extracted in the Ethyl acetate (25 mL×3). Organic layer was washed with brine solution (25 mL×3) followed by drying using anhydrous sodium sulphate. Organic layer was concentrated under reduced pressure to afford 1.1 g of pure compound. Yield (86.61%).

Synthesis of Intermediate (2)

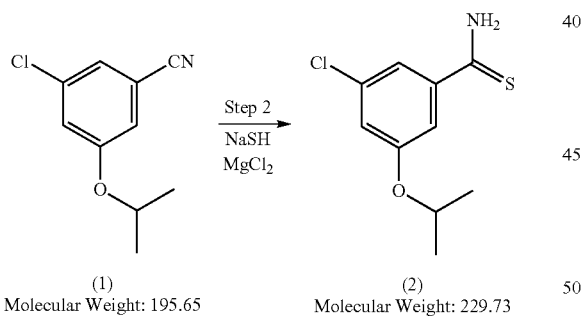

(1)           (2)
Molecular Weight: 195.65    Molecular Weight: 229.73

In a 3-neck 100 mL round-bottomed flask, equipped with an overhead mechanical stirrer, slurry of sodium hydrosulfide hydrate (0.630 g, 2.0 eq.) and magnesium chloride hexahydrate (1.14 g, 1.0 eq) made in DMF (13.2 mL) was added. Intermediate-1 (1.1 g, 1.0 eq) was added in one portion and the reaction mixture was stirred at room temperature for 1-2 h. The progress of reaction was followed by TLC using ethyl acetate:hexane (1:1) as mobile phase. The resulting green slurry was poured in water (130 mL) and the resulting precipitates were collected by filtration. The crude product was re-suspended in 1 N HCl and stirred for 45 min. and solid was filtered and washed with excess water to give intermediate-2 (1.0 g, 77.52%). Mass/LCMS: 230.0

Synthesis of Intermediate (3)

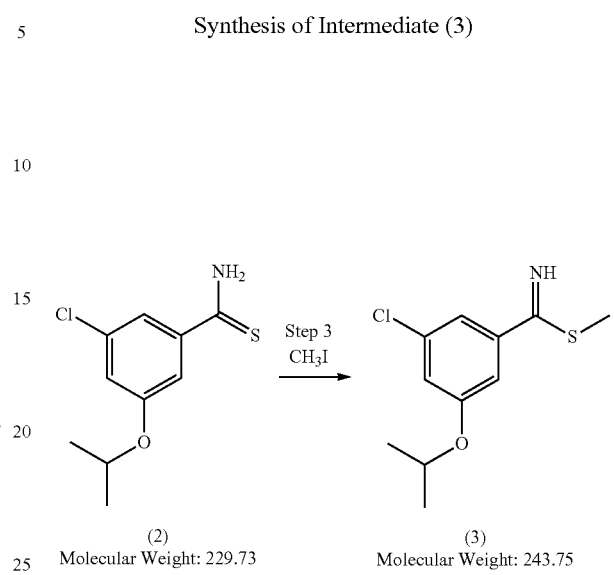

(2)           (3)
Molecular Weight: 229.73    Molecular Weight: 243.75

In a 3-neck 100 mL round-bottomed flask equipped with water condenser, a solution of intermediate-2 (1.0 g, 1.0 eq.) in 20 mL Diethyl ether was added. Methyl iodide (3.06 g, 5.0 eq.) was added under nitrogen atmosphere at room temperature for 12 h during which white solid was separated from the reaction mixture. Completion of the reaction was monitored on TLC using ethyl acetate:hexane (1:1) as mobile phase. Reaction mixture was filtered and dried over vacuum to obtain the intermediate-3 (1 g). Compound was used as such without further purification. Yield (94.3%). Mass/LCMS: 244.0

Synthesis of Intermediate (4)

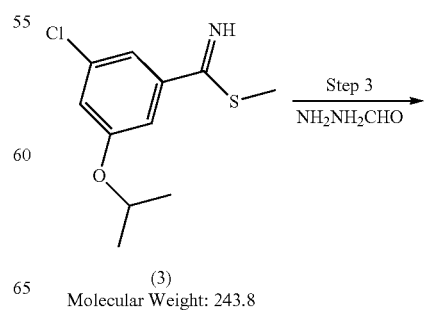

(3)
Molecular Weight: 243.8

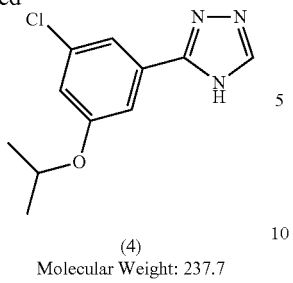

(4)
Molecular Weight: 237.7

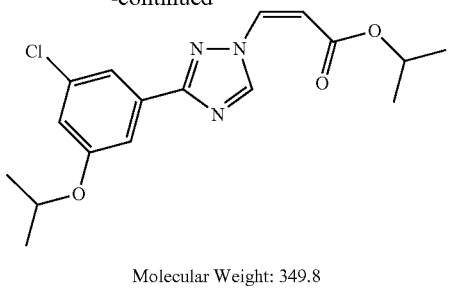

Molecular Weight: 349.8

In a 3-neck 100 mL, round-bottomed flask, a solution of intermediate-3 (1.6 g, 1.0 eq.) dissolved in DMF (16 mL, 10 Vol) and formic hydrazide (0.79 g, 2.0 eq.) was added to it at room temperature in one portion. Reaction was stirred for 1 h at RT and then at 90° C. for 12 h. The completion of reaction was monitored on TLC using ethyl acetate:hexane (1:1) as mobile phase. The reaction mixture was poured into ice-water slurry and white solid obtained was filtered and dried over vacuum to obtain intermediate-4 (1.3 g, 83%). Mass/LCMS: 238.0

In a 3-neck 100 mL round-bottomed flask, Intermediate-4 (1.3 g) was dissolved in DCM (15 mL, 10 Vol.). To this reaction mixture TEA (0.55 g, 1.0 eq.) was added at room temperature. isopropyl propiolate (0.92 g, 1.5 eq.) was added into it dropwise at room temperature under nitrogen atmosphere. Reaction completion was monitored on TLC using ethyl acetate:hexane (2:8) as mobile phase. DCM was removed under reduced pressure to give crude product. The crude reaction mixture was purified by column chromatography using silica 60/120 using ethylacetate:hexane as mobile phase. The column was packed in hexane and started eluting in ethyl acetate in gradient manner starting from 5% to 10% ethyl acetate in hexane. Compound started eluting at 5% ethylacetate in hexane. Fraction containing such TLC profile was collected together to obtain 50 mg of pure compound, Yield (2.6%). $^1$H NMR (400 MHz, CDCl$_3$): δ 9.71 (s, 1H), 7.72 (s, 1H), 7.57 (s, 1H), 7.26-7.26 (d, J=9.2 Hz, 1H), 6.96-6.97 (t, 1H), 5.68-5.71 (d, 1H), 5.11-5.17 (m, 1H), 4.61-4.68 (m, 1H), 0.89-1.39 (double doublet, 6H): LCMS for C$_{17}$H$_{20}$ClN$_3$O$_3$ [M+H]$^+$ 349.81 found 350.38 at 8.337 min.

Synthesis of Example 12

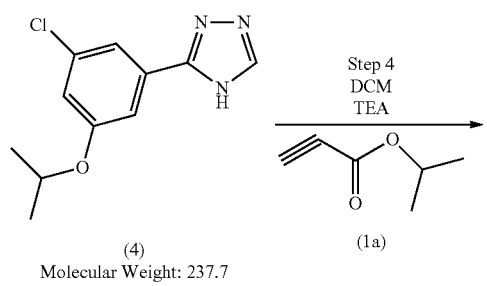

Example 13

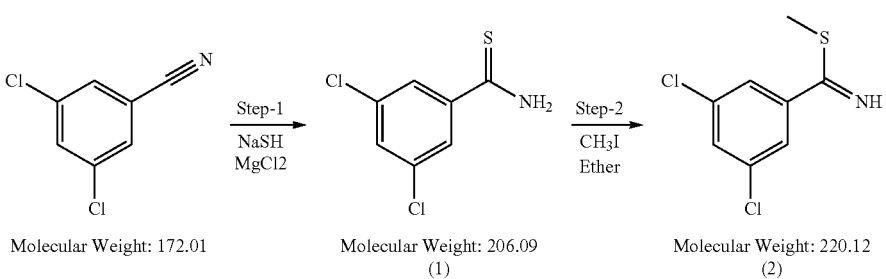

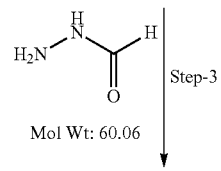

Mol Wt: 60.06

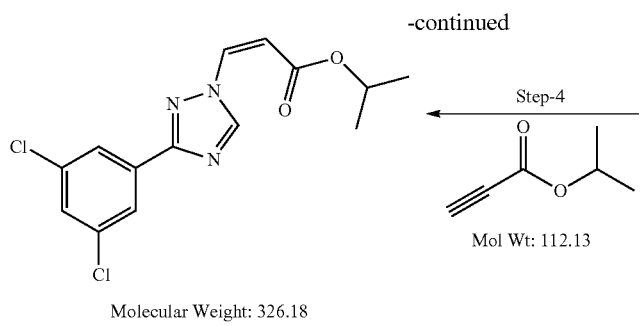

Molecular Weight: 326.18

← Step-4

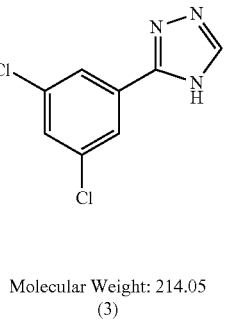

Mol Wt: 112.13

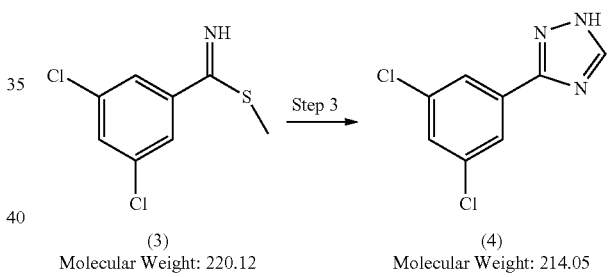

Molecular Weight: 214.05
(3)

Synthesis of Intermediate (1)

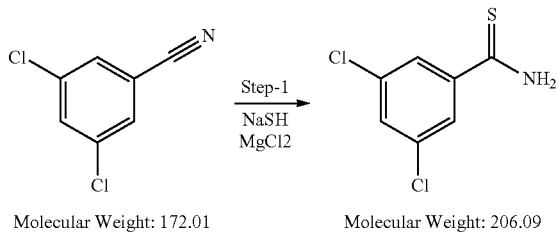

Molecular Weight: 172.01     Molecular Weight: 206.09
(1)

In a single necked 250 mL round-bottomed flask, Intermediate-3 (5.0 g, 1.0 eq.) was dissolved in DMF (50 mL, 10 V) (3.26 g, 2.0 eq.)NaSH was added and $MgCl_2$ (6.50 g, 1.1 eq.) in reaction mixture. The reaction mixture was stirred for 4-5 h at RT. The progress of the reaction was followed by TLC analysis on silica gel with 40% ethyl acetate: n-hexane as mobile phase and visualization with UV, SM $R_f$=0.30 and Product $R_f$=0.20. Reaction mixture was quenched into the ice-water slurry (300 mL) and compound extracted in the ethyl acetate (100 mL×3). Organic layer was washed with brine solution (100 mL) followed by drying using anhydrous sodium sulphate. Organic layer was concentrated under reduced pressure to afford 5.5 g of crude compound as high viscous yellow oil, yield (90%). This crude material was directly used for next step without purification. Mass: (ES+) 207.2 (M+1).

Synthesis of Intermediate (2)

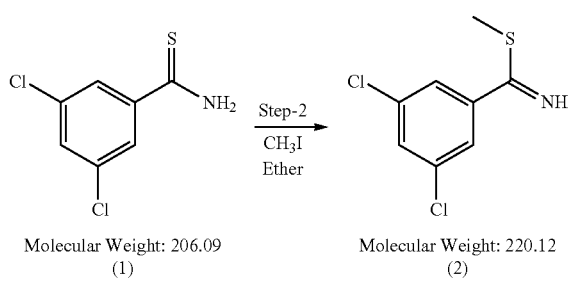

Molecular Weight: 206.09     Molecular Weight: 220.12
(1)     (2)

In a 3-neck 100 mL round-bottomed flask, Intermediate 1 (5.5 g, 1 eq.) was dissolved in diethyl ether (32 mL, 10 Vol) and Iodo methane (2.27 mL, 4.0 eq.) was added dropwise and reaction mixture was stirred at room temperature for 12 h. The progress of reaction was followed by TLC the reaction was followed by TLC analysis on silica gel with ethyl acetate: n-hexane (2:8) as mobile phase and visualization with UV, SM $R_f$=0.30 and Product $R_f$=0.20. Reaction mixture was brought to room temperature and solid was filtered and washed with ether. Solid was dried under reduced pressure to afford 5.0 g of crude compound, yield (85.0%). LCMS (%): Confirmed.

Synthesis of Intermediate (3)

Molecular Weight: 220.12     Molecular Weight: 214.05
(3)     (4)

In a 3-neck 100 mL round-bottomed flask, Intermediate 2 (5.0 g, 1 eq.) and formic hydrazide (2.8 g, 2.0 eq.) was dissolved in DMF (50 mL, 10 Vol) and reaction mixture was heated at 140° C. for 2 h. The progress of reaction was followed by TLC analysis on silica gel with 10% methanol: DCM as mobile phase and visualization with UV, SM $R_f$=0.20 and Product $R_f$=0.35. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 4.5 g of crude compound. The resulting crude compound (4.5 g) was subjected to column purification. The crude reaction mixture was purified by column chromatography using silica 60/120 using methanol: DCM as mobile phase. The column (2×10 cm) was packed in DCM and started eluting in Methanol in gradient manner starting with fraction collection (25-mL fractions) from 1.5% to 2.5% methanol in DCM. Compound started eluting with 1.5% methanol in DCM. Fraction containing such TLC profile was collected together to obtain pure compound (3.4 g), Yield (69.95%). Mass: (ES−) 213.81 (M−1).

139

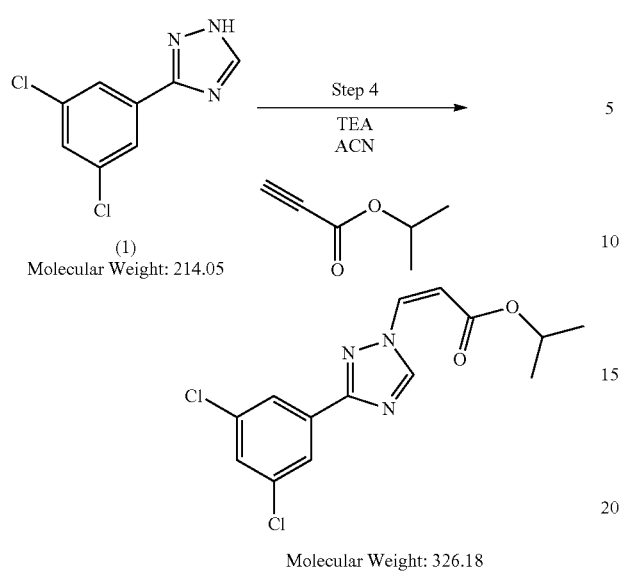

In a 3-neck 50 mL round-bottomed flask, Intermediate 1a (1.0 g, 1 eq.) and TEA (0.85 mL, 1.3 eq.) was dissolved in DCM (10 mL, 10 Vol) and added Isopropyl propiolate (0.680 g, 1.3 eq.) and reaction mixture was stirred at 15° C. for 30 min. The progress of the reaction was followed by TLC analysis on silica gel with 20% ethyl acetate:hexane as mobile phase and visualization with UV, SM $R_f$=0.35 and Product $R_f$=0.15. Reaction mixture was brought to room temperature and quenched into the ice-water slurry (100 mL) and compound was extracted in the DCM (50 mL×3). Organic layer was washed with brine solution (50 mL×3) followed by drying using anhydrous sodium sulphate. Organic layer was concentrated under reduced pressure to afford 1.0 g of crude compound. The crude reaction mixture was purified by column chromatography using silica 60/120 using ethyl acetate: hexane as mobile phase. The column (2×10 cm) was packed in DCM and started eluting in ethyl acetate in gradient manner starting with fraction collection (25 mL fractions) from 5-8% ethyl acetate in hexane. Compound started eluting with 5% ethyl acetate in hexane. Fraction containing such TLC profile was collected together to obtain 0.05 g of pure compound. Yield (03.28%). $^1$H NMR (400 MHz, CDCl$_3$) δ 9.72 (S, 1H), 7.43-8.05 (m, 3H), 7.25-7.28 (d, J=10.8, 1H), 5.71-5.74 (d, J=11.2 Hz, 1H), 5.10-5.18 (m, 1H), 1.33-1.35 (d, 6H); LCMS for C$_{14}$H$_{13}$Cl$_2$N$_3$O$_2$ [M−H]$^+$ 326.2 found 325.84 at RT 6.592 min purity (98.73%).

Example 14

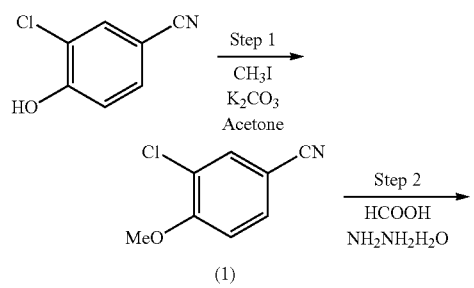

140
-continued

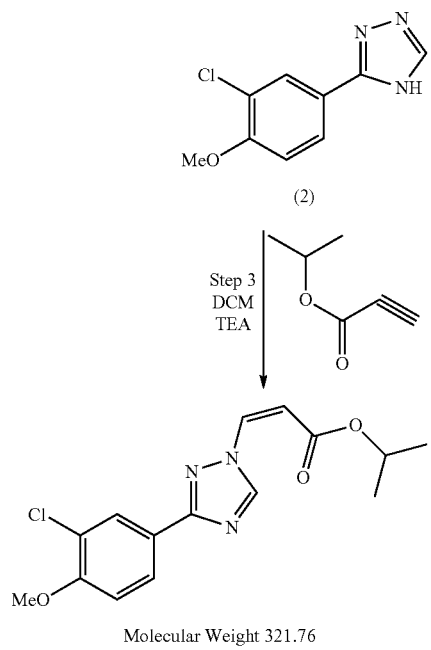

Synthesis of Intermediate (1)

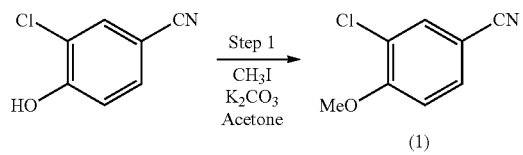 [SMILES: N#Cc1ccc(O)c(Cl)c1 ; COc1ccc(C#N)cc1Cl]

In a 3-neck 100 mL round-bottomed flask, 3-Chloro-5-hydroxy benzonitrile (3.5 g, 1 eq.) was mixed with potassium carbonate (4.71 g, 1.5 eq.) using acetone (70 mL, 20 Vol.) as solvent. To this reaction mixture methyl Iodide (6.46 g, 2.0 eq.) was added drop-wise at room temperature and reaction was further stirred at RT for 3-4 h. Reaction completion was monitored on TLC using ethyl acetate: n-hexane (2:8) mobile phase. The reaction mixture was quenched into ice-water slurry (150 mL) and compound was extracted in the ethyl acetate (50 mol×3). Organic layer was washed with brine solution (50 mol×3) followed by drying using anhydrous sodium sulphate. Organic layer was concentrated under reduced pressure to afford 3.5 g of crude compound, Yield (92.1%).

Synthesis of Intermediate (2)

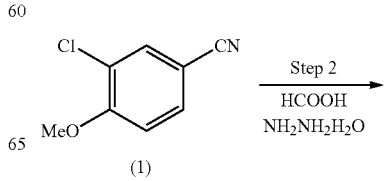

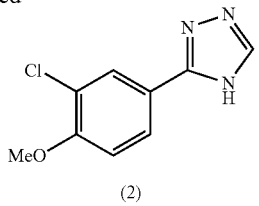

In a 3-neck 50 mL round-bottomed flask, Intermediate-1 (3.5 g, 1 eq.) was dissolved in DMF (70 mL, 20 Vol.). Formic acid (18 mL, 5.1 Vol.) and Hydrazine hydrate (18 mL, 5.1 Vol.) was added to this reaction mixture. Reaction mixture was refluxed to 90° C. for 12 h. Reaction completion was monitored on TLC using ethyl acetate: n-hexane (5:5) as mobile phase. Reaction mixture was brought to room temperature after completion and quenched into the ice-water slurry (350 mL) and compound was extracted in the Ethyl acetate (100 mL×3). Organic layer was washed with brine solution (100 mL×3) followed by drying using anhydrous sodium sulphate. Organic layer was concentrated under reduced pressure to afford 4.0 g of crude compound. Compound was purified by column chromatography using silica 60/120 and ethylacetate:hexane as mobile phase. Column purification was started with 5% EtOAc in hexane up to 30% EtOAc. Compound started eluting in 25% ethylacetate and continued till 30% EtOAc. Fractions containing compound was distilled out using rotary evaporation at 45° C./250 mm Hg to obtain 0.7 g of pure compound, Yield (16.2%).

Synthesis of Example 14

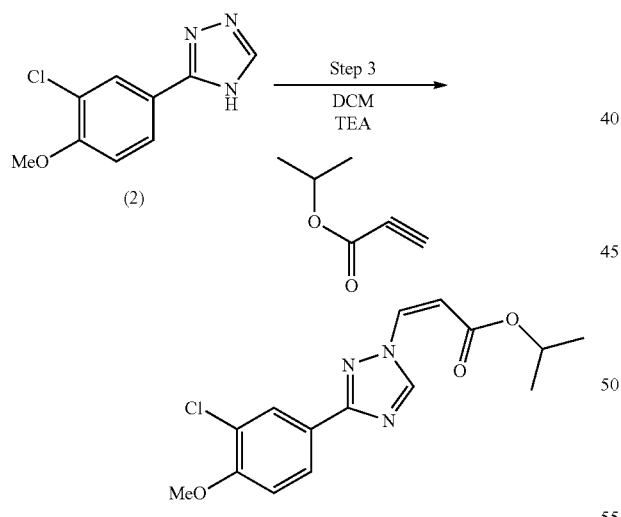

Molecular Weight: 321.76

In 3-neck 50 mL round-bottomed flask, Intermediate-2 (0.9 g, 1.0 eq.) was dissolved in DCM (18 mL, 20 Vol.), added TEA (1.3 g, 3.0 eq.) and isopropyl propiolate (0.722 g, 1.5 eq.). The reaction mixture was stirred at RT for 30 mins. Reaction completion was monitored on TLC using ethyl acetate:hexane (2:8) mobile phase. After 30 min. reaction mixture was concentrated under reduced pressure to afford 1.3 g of crude compound. Compound was purified by column chromatography using silica 60/120 and ethylacetate:n-hexane as mobile phase. Column purification was started with 5% EtOAc in hexane upto 20%. Compound started eluting in 11% ethylacetate and continued till 15% EtOAc. Fractions containing compound were distilled out using rotary evaporation at 45° C./250 mm Hg to obtain 0.128 g of pure compound. Yield (9.27%). $^1$H NMR (400 MHz, CDCl$_3$) δ 9.70 (S, 1H), 8.7.25-8.2 (m, 3H), 7.01-7.03 (d, J=8.4 Hz, 1H), 5.66-5.68 (d, J=11.2 Hz, 1H), 5.11-5.17 (m, 1H), 3.98 (S, 3H), 1.32-1.34 (d, 6H): LCMS for C$_{15}$H$_{16}$ClN$_3$O$_3$ [M+1]$^+$ 321.1.

Example 15

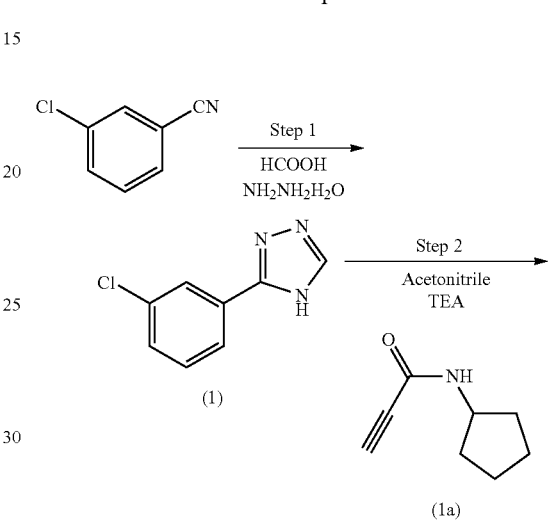

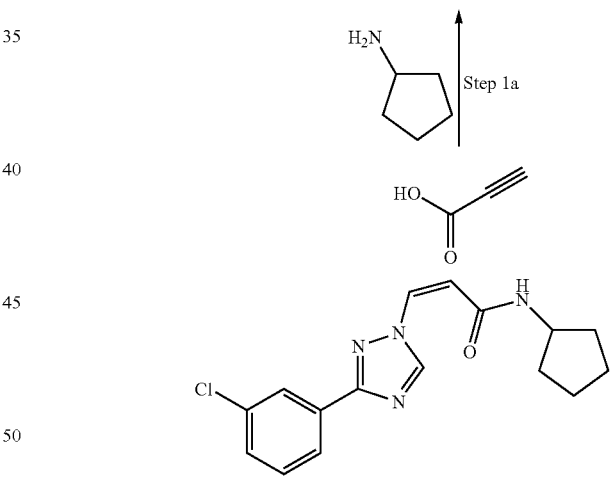

Synthesis of Intermediate (1)

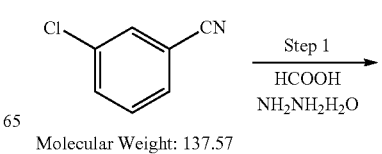

Molecular Weight: 137.57

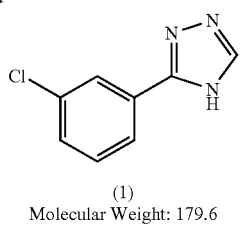

(1)
Molecular Weight: 179.6

In a 3-neck 50 mL round-bottomed flask, Intermediate-1 (5.0 g, 1 eq.) was dissolved in DMF (10 mL, 10 Vol.) and formic acid (50 mL, 10 Vol.) and Hydrazine hydrate mono hydrate (50 mL, 10 Vol.) was added to this reaction mixture. Reaction mixture was refluxed to 90° C. for 12 h. Reaction completion was monitored on TLC using ethyl acetate: n-hexane (5:5) mobile phase. Reaction mixture was brought to room temperature and quenched into the ice-water slurry (500 mL). The compound was extracted in the Ethyl acetate (100 mL×3). Organic layer was washed with brine solution (100 mL×3) followed by drying using anhydrous sodium sulphate. Organic layer was concentrated under reduced pressure to afford 5.2 g of crude compound. Compound was purified by column chromatography using silica 60/120 and ethyl acetate:hexane as mobile phase. Column purification was started with 5% EtOAc in hexane up to 30%. Compound started eluting in 25% ethyl acetate and continued till 30% EtOAc. Fractions containing compound was distilled out using rotary evaporation at 45° C./250 mm Hg to obtain 0.7 g of pure compound, Yield (10.8%).

Synthesis of Intermediate (1a)

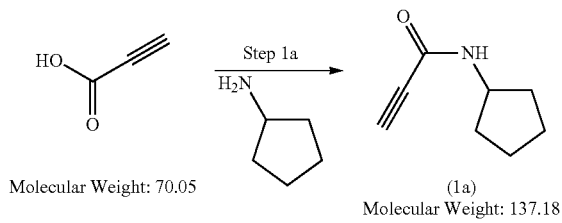

In 3-neck 25 mL round-bottomed flask, Propiolic acid (0.3 g, 1 eq.) was dissolved in DCM (5 mL, 20 Vol.), added DCC (0.1.15 g, 1.1 eq.), DMAP (0.052 g, 0.1 eq.) and cyclopentyl amine (0.546 g, 1.5 eq.). The reaction mixture was stirred at RT for 3-4 h. Reaction completion was monitored on TLC using ethyl acetate:hexane (3:7) mobile phase. Reaction mixture was filtered through celite bed and filtered was distilled off to get 0.468 g crude compound. Yield (79.75%).

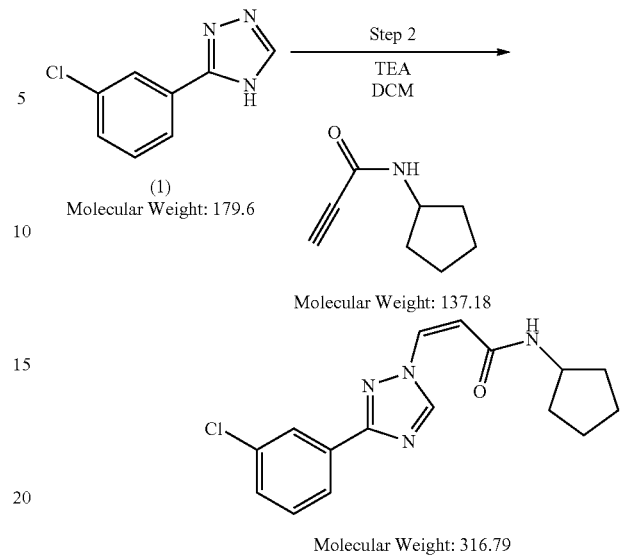

In a 3-neck 50 mL round-bottomed flask, Intermediate 1 (0.05 g, 1 eq.) was dissolved in DCM (2.5 mL, 50 Vol.) and added cyclopentyl ester (0.058 g, 1.5 eq.) and TEA (0.042 g, 1.5 eq.). The reaction mixture was stirred at RT for 30 min. Reaction completion was monitored on TLC using ethyl acetate: n-hexane (2:8) mobile phase. Reaction mixture was concentrated under reduced pressure to afford 0.06 g of crude compound; The compound was purified by column chromatography using silica 60/120 and ethyl acetate: n-hexane as mobile phase. Column purification was started with 5% EtOAc in hexane up to 7%. Compound started eluting in 5% ethyl acetate and continued till 7% EtOAc. Fractions containing compound was distilled out using rotary evaporation at 45° C./250 mm Hg to obtain 0.008 g of pure compound, Yield (9.09%). $^1$HNMR (400 MHz, CDCl$_3$) δ 9.39 (s, 1H), 8.14 (S, 1H), 8.04-8.01 (t, 1H), 7.44-7.39 (d, 2H), 7.09-7.06 (d, J=10.8 Hz, 1H), 5.63-5.60 (d, J=10.8 Hz, 1H), 4.35-4.29 (m, 1H), 2.10-2.07 (m, 2H), 1.73-1.66 (q, 4H), 1.65-1.59 (m, 1H), 1.50-1.46 (m, 2H): LCMS for $C_{16}H_{17}ClN_4O[M+H]^+$ 316.8 found at 317.18 at RT 6.642 min.

Example 16

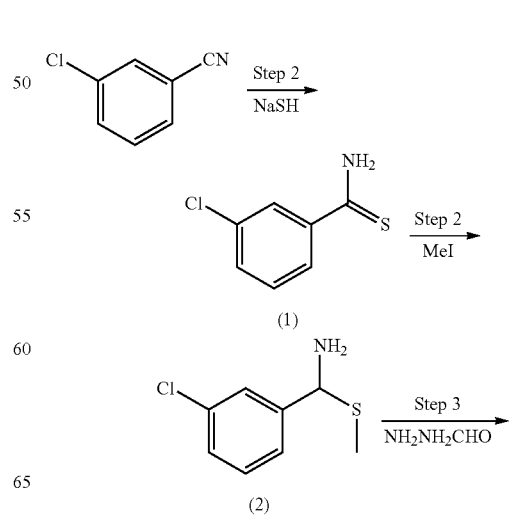

145

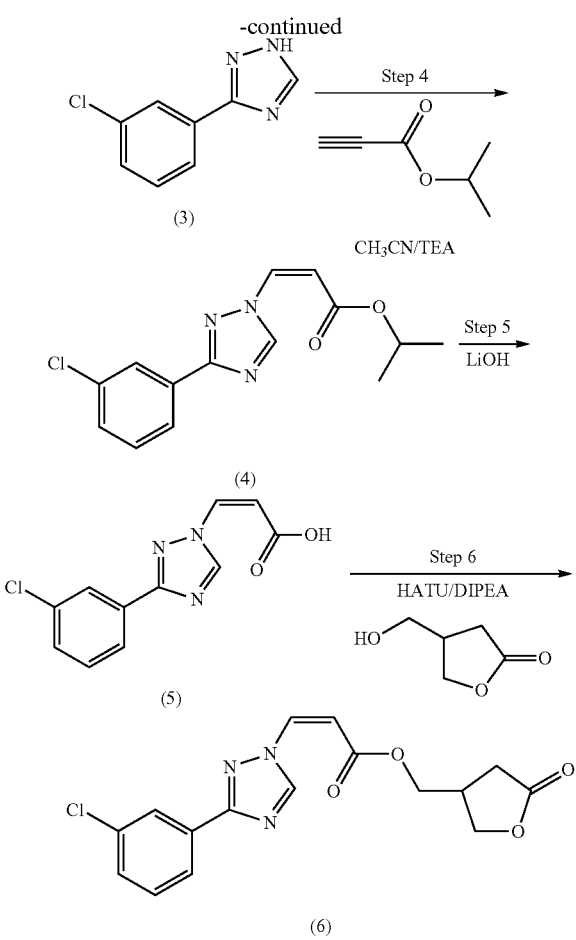

Synthesis of Intermediate (1)

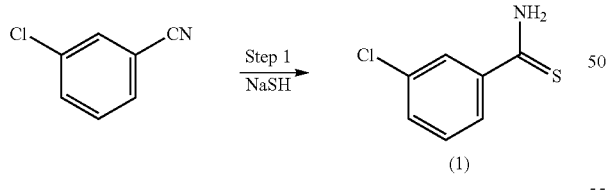

In a 3-neck 2 L round-bottomed flask, equipped with an overhead mechanical stirrer, slurry of sodium hydrosulfide hydrate (107.58 g, 1.453 mmol) and magnesium chloride hexahydrate (147.56 g, 0.726 mmol) in 1.2 L of DMF was added 3-Chlorobenzonitrile (100 g, 0.726 mmol) in one portion, and the reaction mixture was stirred at room temperature for 2 h. The progress of the reaction was followed by TLC using ethyl acetate:hexane (1:1) as mobile phase. The resulting green slurry was poured in 6000 mL water, and the resulting precipitates were collected by filtration. The crude product was re-suspended in 1 N HCl and stirred for 45 min, then filtered and washed with water to give intermediate-1 (120 g, 96%). Mass: 172.1.

Synthesis of Intermediate (2)

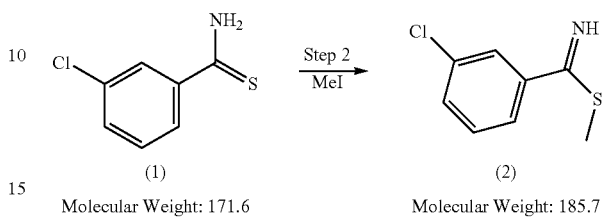

In a 3-neck 3 L round-bottomed flask, equipped with an overhead mechanical stirrer, a solution of intermediate-1 (100.0 g, 0.584 mmol) in 1.5 L diethyl ether was treated with methyl iodide (329.8 g, 2.339 mmol). Reaction was stirred for 24 h and completion of reaction was monitored on TLC using ethyl acetate:hexane (1:1) as mobile phase. Reaction mixture was filtered, precipitates washed with diethyl ether and dried under vacuum to give intermediate-2 (100, 92%). Mass: 186.1.

Synthesis of Intermediate (3)

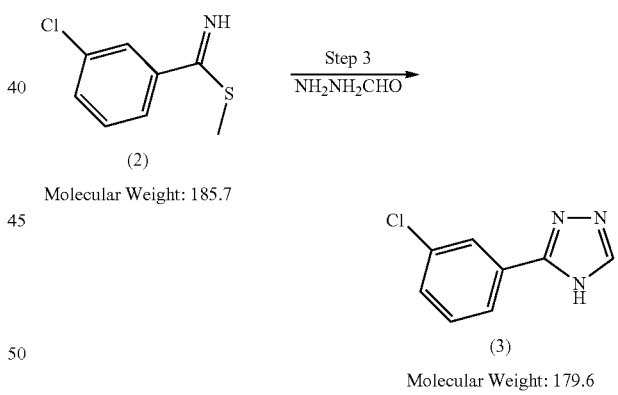

In a 3-neck 3 L round-bottomed flask, equipped with water condenser, a solution of intermediate-2 (100.0 g, 0.540 mmol) in 1 L DMF was added formic hydrazide (64.86 g, 1.081 mmol) under nitrogen atmosphere. The reaction mixture was stirred for 3 h and then heated at 90° C. for 3 h. Completion of reaction was monitored on TLC using ethyl acetate:hexane (1:1) as mobile phase. Cooled reaction mixture was poured into water and, extracted with ethyl acetate, dried over sodium sulfate, and evaporated under vacuum to obtain the intermediate-3 (90 g, 92%). Compound was used as such without further purification. Mass: 180.1.

Synthesis of Intermediate (4)

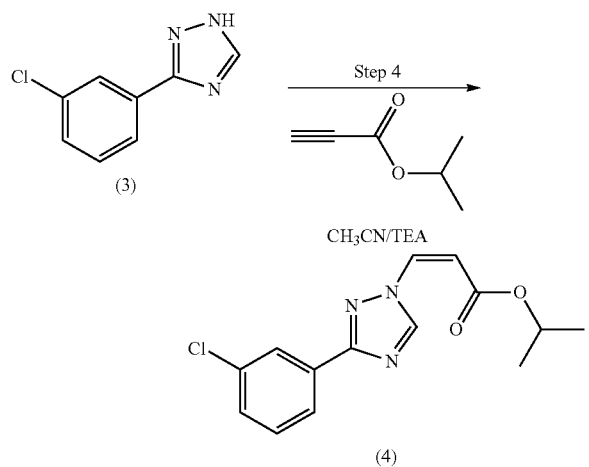

In a 3-neck 250 mL round-bottomed flask, Intermediate-3 (10 g, 0.0556 mmol) was dissolved in acetonitrile (100 mL, 10 Vol), added TEA (5.62 g, 0.0556 mmol) and isopropyl propiolate (9.36 g, 0.0835 mmol) in cooling condition under nitrogen atmosphere. Reaction mixture was reflux overnight at 90° C. and completion of reaction was monitored on TLC using ethyl acetate:hexane (2:8) as mobile phase. Acetonitrile was removed under reduced pressure to give crude product. Compound was purified by column chromatography using silica 60/120 and ethyl acetate:hexane as mobile phase. Compound was eluted at 0.25% ethyl acetate in hexane which further purified by comb flash to give 500 mg of KPT-0127 according the method described in the attached file below. Mass/LCMS: 292.2, NMR: Confirmed.

Synthesis of Intermediate (5)

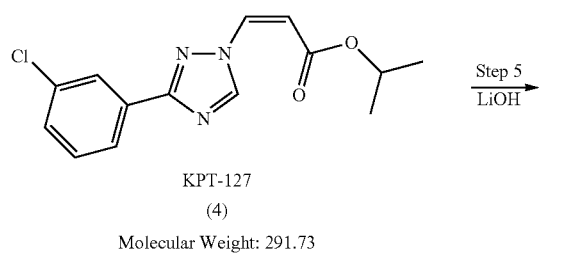

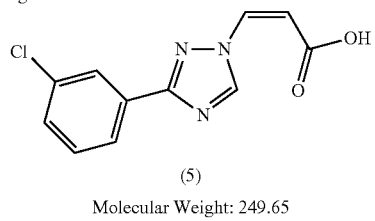

In a 3-neck 100 mL round-bottomed flask, KPT 127 (1, 1 .eq.) was dissolved in THF (10 mL) and Water (10 mL) added LiOH (0.28 g, 2 eq) portion wise in reaction mixture. Stirred the reaction mixture at RT for 3 hr. Reaction completion was monitored on TLC using Dichlormethane:MeOH (9:1) mobile phase. Reaction mixture quenched into the ice-water slurry (250 mL), acidify with dil. HCl and compound was extracted in the ethyl acetate (50 mL×3). Organic layer was washed with brine solution (50 mL×3) followed by drying using anhydrous sodium sulphate. Organic layer was concentrated under reduced pressure to afford 0.73 g of crude compound, Yield (86%). Mass: 249.9

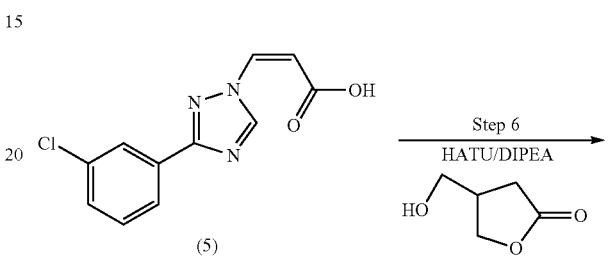

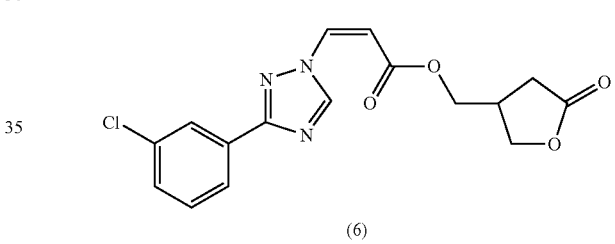

In a 3-neck 25 mL round-bottomed flask, Intermediate-5 (0.1 g, 0.4 mmol) was dissolved in THF (2.0 mL, 20 V), 4-Hydroxydihydrofuran-2 (3H)-one (0.082 g, 0.8 eq.) and Cat. $H_2SO_4$ (2-3 drop). Reaction mixture was refluxed for 12 h. The Reaction was monitored on TLC using ethyl acetate: n-hexane (2:8) as mobile phase. Reaction mixture was poured into the ice-water slurry (5 L) and compound was extracted in the DCM (5 mL×3). Organic layer was washed with brine solution followed by drying using anhydrous sodium sulphate. Organic layer was concentrated under reduced pressure to afford 0.1 g of Crude compound, yield (61%). Compound was purified by column chromatography using silica 60/120 and ethyl acetate: n-hexane as mobile phase. Compound was eluted at 0.25% ethyl acetate in hexane which further purified by comb flash to give 10 mg of VS-086. $^1$HNMR (400 MHz, CDCl$_3$) δ 9.67 (s, 1H), 8.16 (s, 1H), 8.04 (m, 1H), 7.44 (m, 3H), 5.74-5.72 (d, J=10.8 Hz, 1H), 5.60 (m, 1H), 4.60 (m, 1H), (d, J=10.8 Hz, 1H), 4.50-4.47 (d, J=11.2 Hz, 1H), 2.99-2.97 (d, J=6.8 Hz, 1H), 2.94-2.92 (d, J=6.8 Hz, 1H): LCMS for $C_{16}H_{14}ClN_3O_3$ [M+H]$^+$ 331.75 found at 10.554 min.

149 150
Example 17
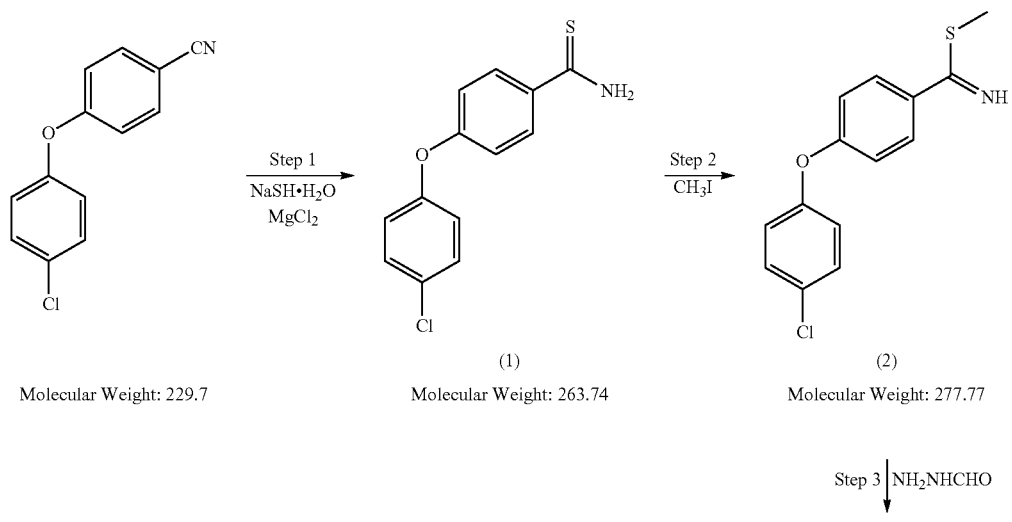
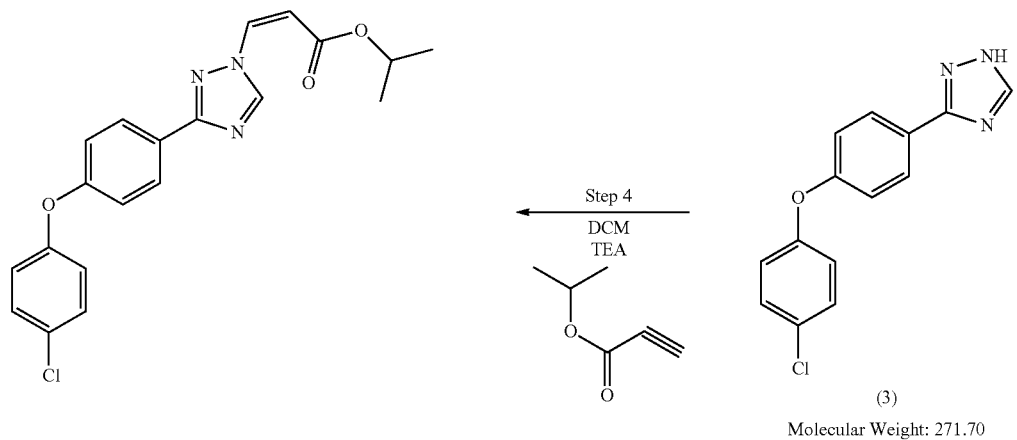
Synthesis of Intermediate (1)
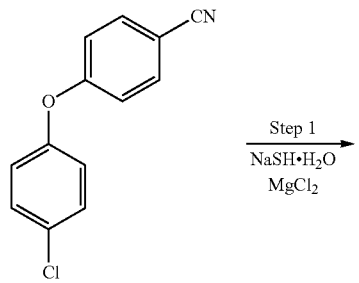
-continued
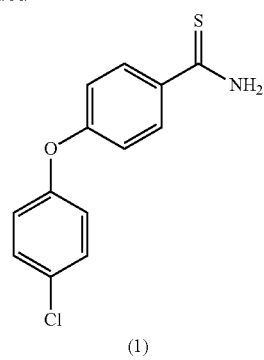

In a 3-neck 100 mL round-bottomed flask 4 (4-Chlorophenoxy)benzonitrile (1.3 g, 1 eq.) was dissolved in DMF (26 mL, 20 Vol) and NaSH (0.837 g, 2.0 eq.) was added followed by MgCl$_2$ (1.13 g, 1.0 eq). Reaction mixture was stirred at RT for 2 h. Reaction completion was monitored on TLC using ethyl acetate:n-hexane (1:9) as mobile phase. Reaction mixture was brought to room temperature and quenched into the water (200 mL) and compound was extracted in the Ethyl acetate (50 mL×3). Organic layer was washed with brine solution (30 mL×3) followed by drying using anhydrous sodium sulphate. Organic layer was concentrated under reduced pressure to afford 1.3 g of crude compound, yield (87.24%). Mass: 263.9.

Synthesis of Intermediate (2)

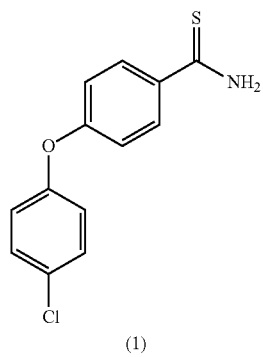

(1)
Molecular Weight: 263.74

Step 2
CH$_3$I

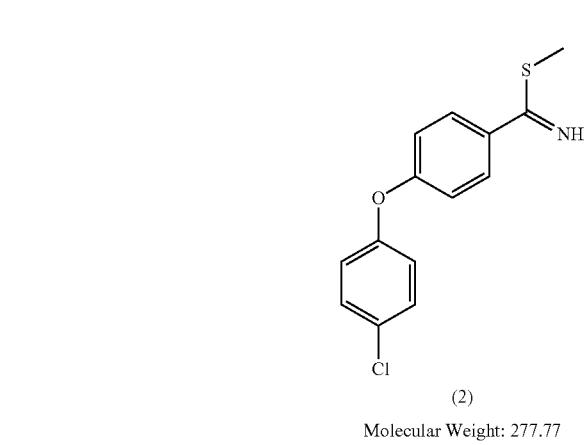

(2)
Molecular Weight: 277.77

In a 3-neck 100 mL round-bottomed flask, Intermediate-1 (1.3 g, 1 eq.) was dissolved in diethyl ether (13 mL, 10 Vol) and reaction mixture was cooled to 0° C. and methyl iodide (3.49 g, 5.0 eq) was added dropwise in reaction mixture. Reaction mixture was stirred at RT for overnight. Reaction completion was monitored on TLC using ethyl acetate:n-hexane (1:9) as mobile phase. Product was filtered and washed with diethyl ether (3×20 mL). Compound was dried under reduced pressure to afford 1.20 g of crude compound, yield (88.23%). Mass: 278.1.

Synthesis of Intermediate (3)

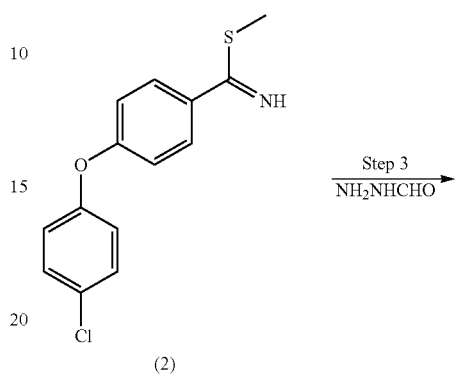

(2)
Molecular Weight: 277.77

Step 3
NH$_2$NHCHO

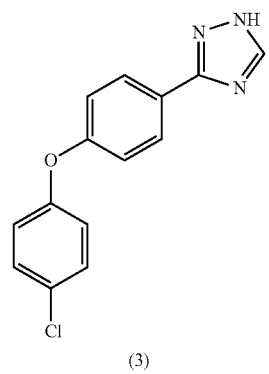

(3)
Molecular Weight: 271.70

In a 3-neck 100 mL round-bottomed flask, Intermediate-2 (1.2 g, 1 eq.) was dissolved in DMF (12 mL, 10 Vol) and Formic hydrazide (0.518 g, 2.0 eq) was added. Reaction mixture was refluxed for 2 h and reaction completion was monitored on TLC using ethyl acetate: n-hexane (2:8) mobile phase. Reaction mixture was brought to room temperature and poured into the water (200 mL) and compound was extracted in the Ethyl acetate (50 mL×3). Organic layer was again washed with water (50 mL×3) and dried over anhydrous sodium sulphate. Organic layer was concentrated under reduced pressure to afford 1.3 g of crude compound and crude compound was further purified by column chromatography using silica 60/120 and ethylacetate: n-hexane as mobile phase. Column purification was started with 5% EtOAc in hexane up to 18%. Compound started eluting in 17% ethyl acetate and continued till 18% EtOAc. Fractions containing compound was distilled out using rotary evaporation at 35° C./250 mm Hg to obtain 1.0 g of pure compound yield (85.47%). Mass: 272.1.

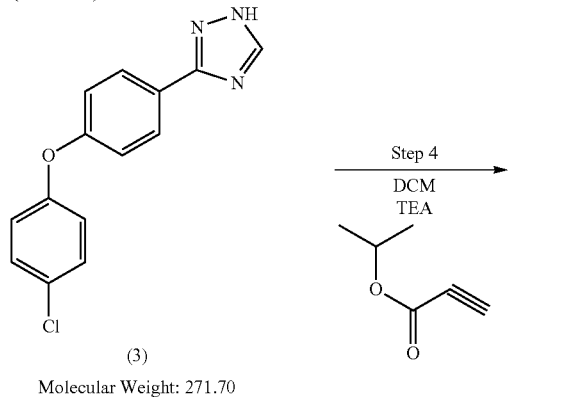

(3)
Molecular Weight: 271.70

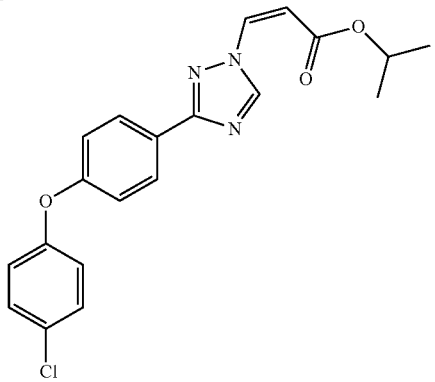

In a 3-neck 100 mL round-bottomed flask Intermediate-3 (1.4 g, 1 eq.) was dissolved in DCM (14 mL, 10 Vol) and added TEA (0.667 g, 1.3 eq.). Reaction mixture was cool at 15-20° C. and drop wise added isopropyl propiolate (0.750 g, 1.3 eq.). And reaction mixture was stirred at 15-20° C. for 1 h. Reaction completion was monitored on TLC using Ethyl acetate:Hexane (1:9) mobile phase. Reaction mixture was poured into the water (300 mL) and compound was extracted in DCM (100 mL×3). Organic layer was dried over anhydrous sodium sulphate. Organic layer was concentrated under reduced pressure to afford 1.2 g of crude compound; Crude compound was further purified by column chromatography using silica 60/120 and ethylacetate:hexane as mobile phase. Column purification was started in hexane up to 6%. Compound started eluting in 4% ethyl acetate and continued till 6% EtOAc. Fractions containing compound was distilled out using rotary evaporation at 35° C./250 mm Hg to obtain 0.05 g of pure compound yield (2.53%). $^1$H NMR (400 MHz, CDCl$_3$) δ 9.72 (s, 1H), 7.00-8.13 (m, 8H), 7.27-7.30 (d, J=10.8 Hz, 1H), 5.66-5.69 (d, J=10.8 Hz, 1H), 5.11-5.17 (m, 1H), 1.32-1.34 (d, 6H): LCMS for C$_{20}$H$_{18}$ClN$_3$O$_3$ 383.8 found 384.51 at R.T. 6.254 min (LCMS 99.47%).

Example 18

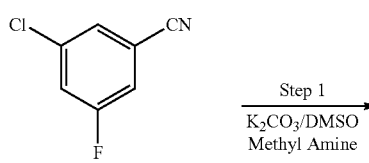

Molecular Weight: 155.56

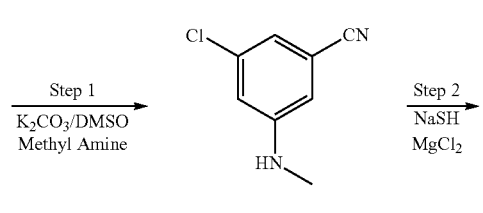

(1)
Molecular Weight: 166.61

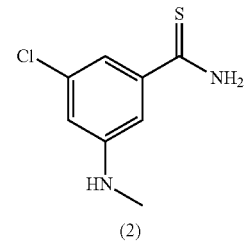

(2)
Molecular Weight: 200.69

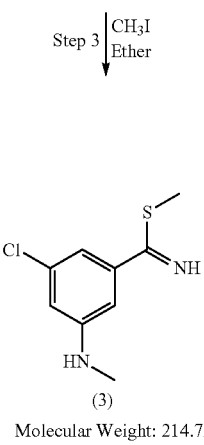

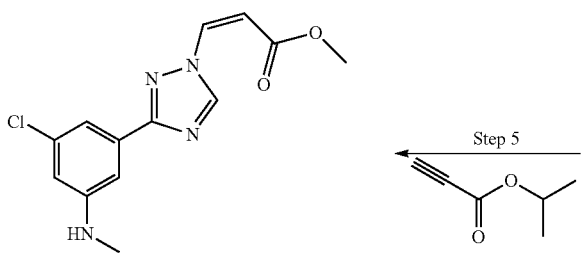

Molecular Weight: 320.77

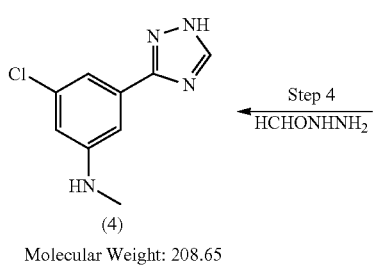

(4)
Molecular Weight: 208.65

(3)
Molecular Weight: 214.72

155
Synthesis of Intermediate (1)

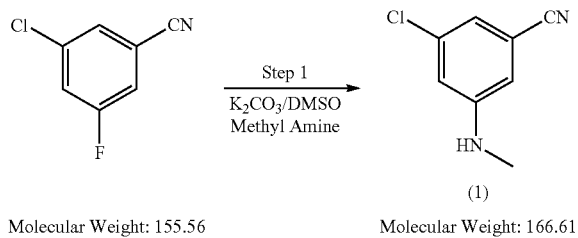

In a 35 mL microwave vial, 3-chloro-5-fluoro benzonitrile (0.5 g, 1 eq.), Methyl amine (0.2 g, 2.0 eq.), $K_2CO_3$ (1.55 g, 3.5 eq.) was mixed with DMSO (10 mL, 20 Vol). The reaction mixture was stirred at 125° C. in microwave for 30 min. Reaction completion was monitored on TLC using ethyl acetate:hexane (5:5) mobile phase. After 30 minutes reaction was completed and worked up. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 0.5 g of crude compound. Mass/LCMS: 167.0, NMR: Confirmed.

Synthesis of Intermediate (2)

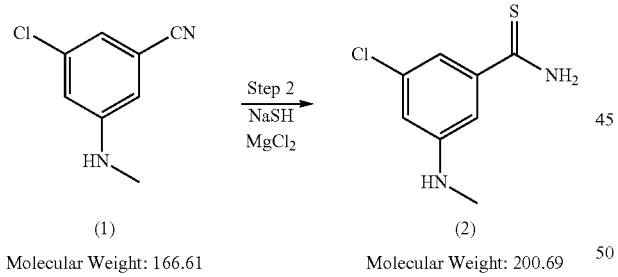

In a 3-neck 100 mL round-bottomed flask, Intermediate 1 (0.5 g, 1 eq.) was mixed with DMF (5 mL, 13 Vol.), $MgCl_2 6H_2O$ (0.610 g, 1.0 eq.) and sodium thiol (0.445 g, 2.0 eq.) was stirred at room temperature for 2 h. The reaction remained green colored clear solution throughout the reaction. Reaction completion was monitored on TLC using ethyl acetate:hexane (5:5) mobile phase. After 2 h, the reaction was completed and worked up. Reaction mixture was brought to room temperature and poured into water (100 mL) and compound was extracted in the ethyl acetate (100 mL×3). Organic layer was again washed with water (100 mL×3) followed by drying using anhydrous sodium sulphate. Organic layer was concentrated under reduced pressure to afford 0.5 g of crude compound. Crude compound was carry forward in next step. yield (82.91%).

156
Synthesis of Intermediate (3)

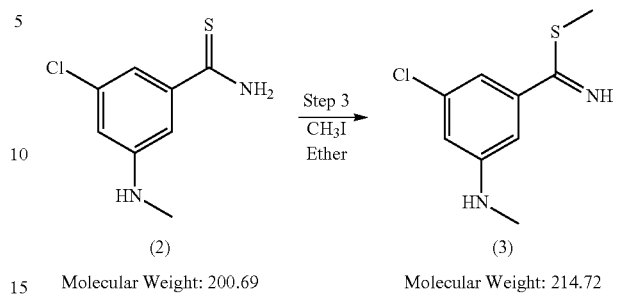

In a 3-neck 100 mL round-bottomed flask, Intermediate 1 (1.0 g, 1 eq.) was dissolved in Diethyl ether (15 mL, 8 Vol.) and reaction mixture was cooled at 0° C. and methyl iodide was added dropwise (2.82 g, 4.0 eq.) in reaction mixture and reaction mixture was stirred at RT for overnight. Reaction completion was monitored on TLC using ethyl acetate:hexane (3:7) mobile phase. Product was filtered and washed with diethyl ether (3×50 mL). Product was dried under reduced pressure to afford 0.720 g of crude compound, yield (67.92%). NMR: Confirmed.

Synthesis of Intermediate (4)

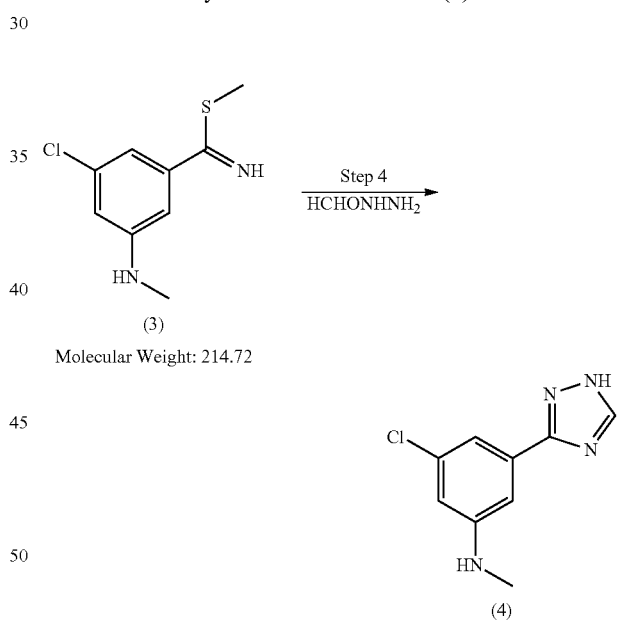

In a 3-neck 100 mL round-bottomed flask, Int-2 (0.72 g, 1 eq.) and Formic hydrazide (0.403 g, 2 eq.) were dissolved in DMF (10 mL, 12 Vol.) and reaction mixture was stirred at reflux temperature for 2 h. Reaction completion was monitored on TLC using ethylacetate:MDC (1:9) mobile phase. Reaction mixture was brought to room temperature and poured into the water (100 mL) and compound was extracted in the Ethyl acetate (100 mL×3). Organic layer was washed with water (100 mL×3) followed by drying using anhydrous sodium sulphate. Organic layer was concentrated under reduced pressure to afford 0.9 g of crude compound. NMR: Confirmed.

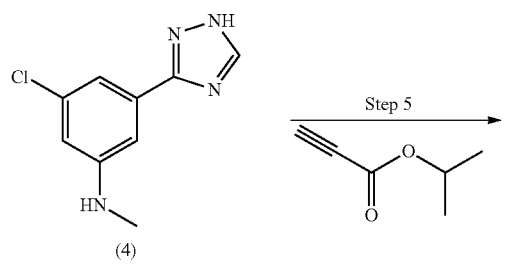

(50 mL×3). Organic layer was again washed with water (50 mL×3) followed by drying using anhydrous sodium sulphate. Organic layer was concentrated under reduced pressure to afford 0.9 g of crude compound, Product was purified by flash chromatography using ethyl acetate and Hexane to afford 0.040 g pure compound. Yield (2.9%). $^1$H NMR (400 MHz, CDCl$_3$): δ 9.12 (s, 1H), 7.43-7.46 (d, J=10 Hz, 1H), 7.14-7.16 (dd, 2H), 6.61-6.62 (t, 1H), 6.28-6.30 (m, 1H), 5.92-5.94 (d, J=10 Hz, 1H), 5.03-5.06 (m, 1H), 2.70-2.72 ((d, 3H), 1.23-1.24 (d, 6H). LCMS for $C_{15}H_{17}ClN_4O_2$.

Example 19

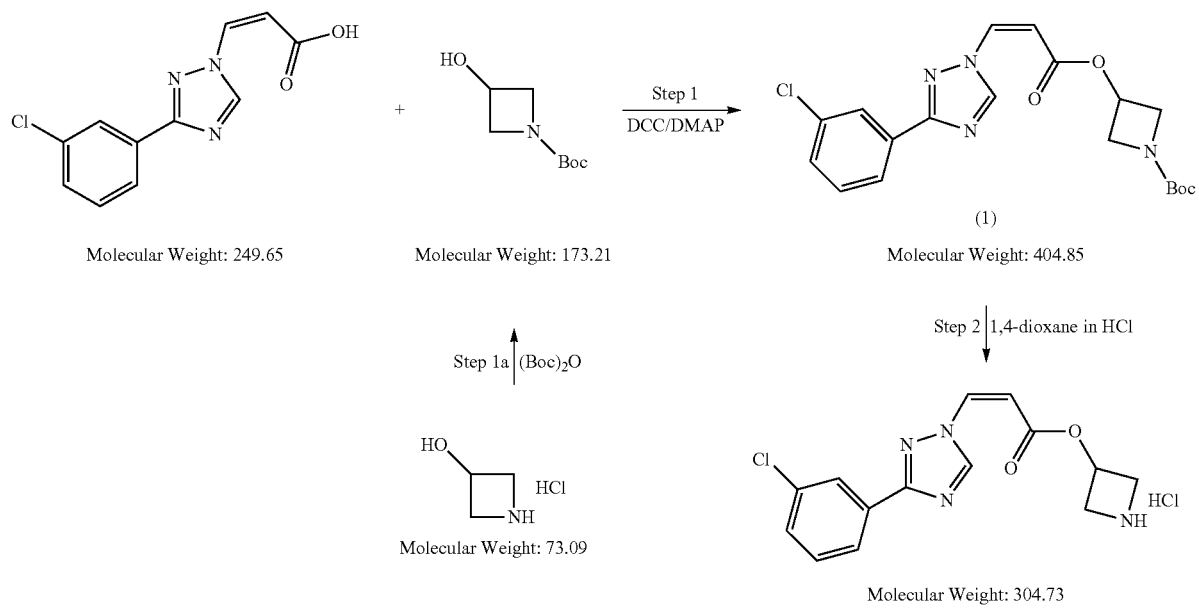

Synthesis of Intermediate (1)

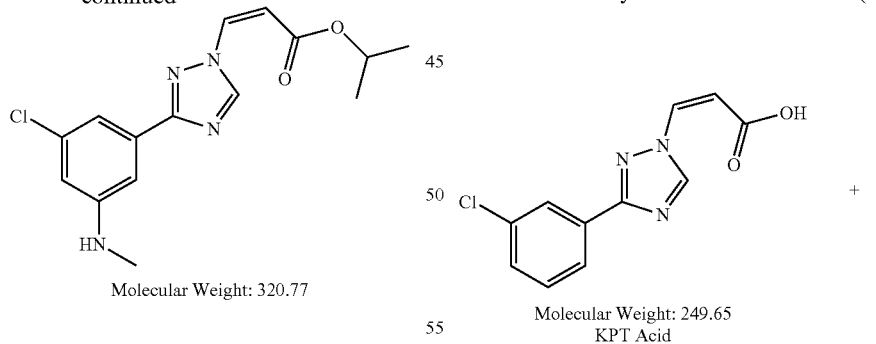

In a 1-neck 50 mL round-bottomed flask, Intermediate 3 (0.9 g, 1 eq.), TEA (0.61 g, 1.4 eq.) was dissolved in MDC (10 mL, 10 vol.). Reaction mixture was cooled to 20° C. and isopropyl propionate (0.667 g, 1.4 eq.) was added drop-wise and reaction mixture was stirred at 15-20° C. for 30 minutes. Reaction completion was monitored on TLC using Ethyl acetate:Hexane (2:8) mobile phase. Reaction mixture was brought to the room temperature and poured into the water (100 mL) and compound was extracted in the Ethyl acetate

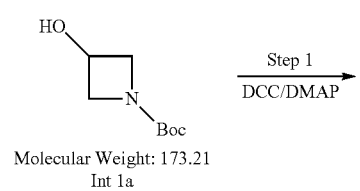

-continued

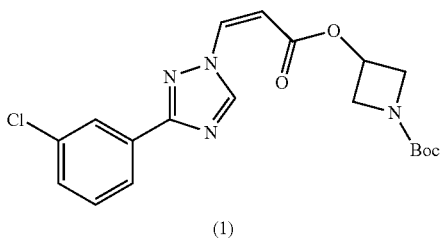

(1)

Molecular Weight: 404.85

In a 3-neck 25 mL round-bottomed flask, acid from Example 1 (2.0 g, 1 eq.) was dissolved in DCM (40 mL, 20 Vol.). DCC (0.1.81 g, 1.1 eq.), DMAP (0.098 g, 1.1 eq.) and Intermediate 1a (1.52 g, 1.1 eq.) was added to this reaction mixture and reaction mixture was stirred at RT for 3-4 h. Reaction completion was monitored on TLC using ethyl acetate:hexane (3:7) mobile phase. Reaction mixture was filtered through celite bed and filtered was distilled off to get crude compound. The crude compound was purified using silica 60/120 and ethylacetate:hexane as mobile phase. Column purification was started with 5% EtOAc in hexane up to 30%. Compound started eluting in 10% ethyl acetate and continued till 12% EtOAc. Fractions containing compound was distilled out using rotary evaporation at 45° C./250 mm Hg to obtain 2.0 g of pure compound, Yield (51.95%). LCMS: Confirmed.

Synthesis of Intermediate (1a)

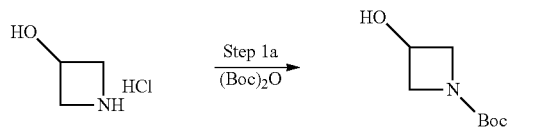

Molecular Weight: 109.55

Molecular Weight: 173.21

In a 3-neck 50 mL round-bottomed flask, Azitidine HCl (5.0 g, 1 eq.) was dissolved in DCM (100 mL, 20 Vol.) and cooled the reaction mixture to 0° C. TEA (6.68 g, 1.5 eq.) and Boc anhydride (10.9 g, 1.1 eq.) was added to this reaction mixture. Reaction mixture was stirred at 0° C. for 1 h. Reaction completion was monitored on TLC using ethyl acetate:hexane (5:5) mobile phase. Reaction mixture was brought to room temperature and quenched into the ice-water slurry (100 mL) and compound was extracted in the DCM (100 mL×3). Organic layer was washed with brine solution (150 mL×3) followed by drying using anhydrous sodium sulphate. Organic layer was concentrated under reduced pressure to afford 7.0 g of crude compound, yield (88.60%). Mass/LCMS: Confirmed.

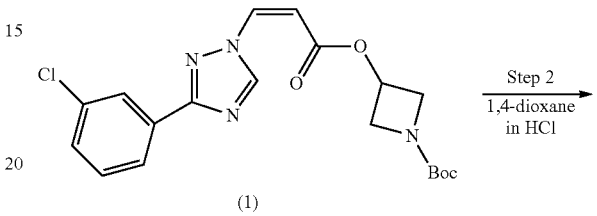

(1)

Molecular Weight: 404.85

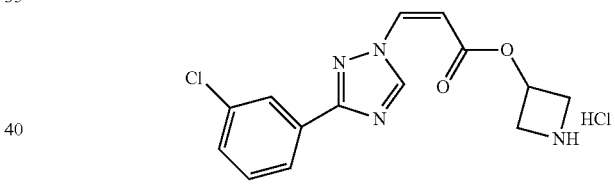

Molecular Weight: 304.73

In a 3-neck 25 mL round-bottomed flask, Intermediate-1 (0.5 g, 1 eq.) was dissolved in 1,4-dioxane (5.0 mL, 10 Vol.) and added 1,4-Dioxane HCl (2.0 mL, 4 Vol.). Reaction mixture was stirred at RT for 12 h. Reaction completion was monitored on TLC using Methanol:DCM (2:8) mobile phase. Reaction mixture was concentrated under reduced pressure to afford 0.5 g of crude compound which was triturated with diethyl ether to get 0.213 g compound, Yield (50.23%). $^1$H NMR [400 MHz DMSO-d6] δ 9.24 (s, 1H), 8.22 (s, 1H), 7.97-8.00 (m, 2H), 7.60-7.63 (m, 3H), 6.01-6.06 (d, J=10, 1H), 5.34-5.38 (m, 1H), 4.32-4.33 (m, 2H), 4.29-4.30 (m, 2H): LCMS for $C_{14}H_{14}Cl_2N_4O_2$ [M+1]$^+$ 341.2 found 304.88 at 2.60 min.

Mesylate salt: $^1$H NMR δ 9.23 (s, 1H), 8.99 (broad s, $D_2O$ exchangeable, 1H), 8.76 (broad s, $D_2O$ exchangeable, 1H), 7.54-7.97 (m, 4H), 7.59-7.62 (d, J=10.4 Hz, 1H), 6.04-6.06 (d, J=10.0 Hz, 1H), 5.34-5.38 (m, 1H), 4.32-4.36 (m, 2H), 4.07-4.10 (m, 2H): LCMS for $C_{15}H_{17}ClN_4O_5S$ 400.84.

Example 20

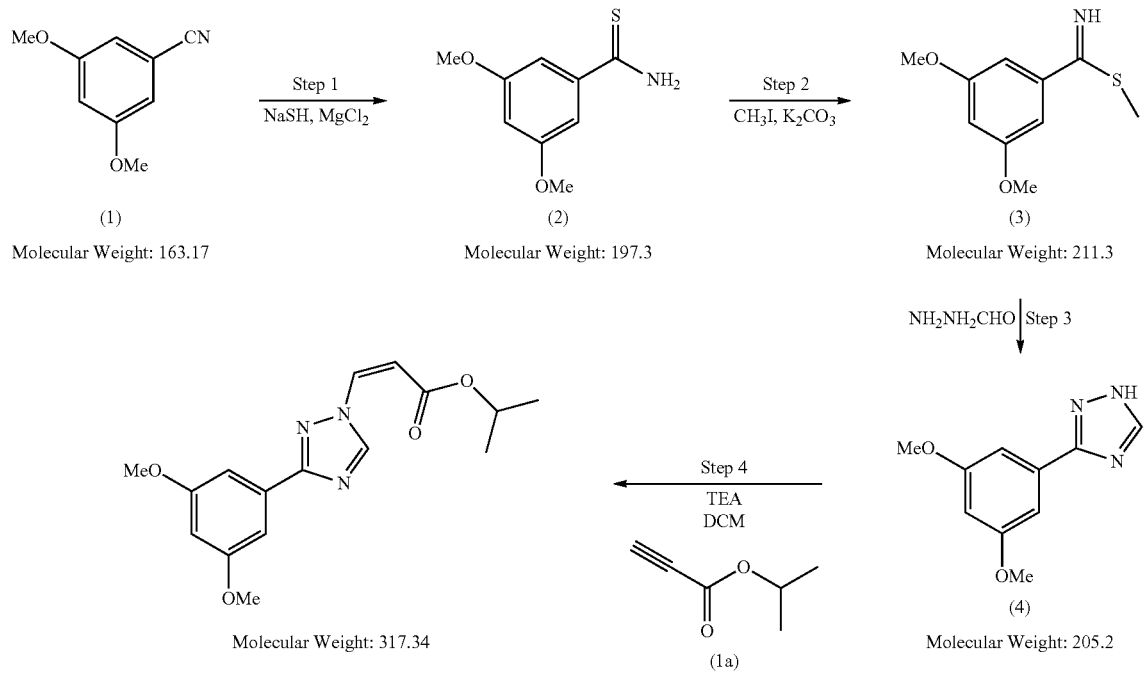

Synthesis of Intermediate (1)

Synthesis of Intermediate (2)

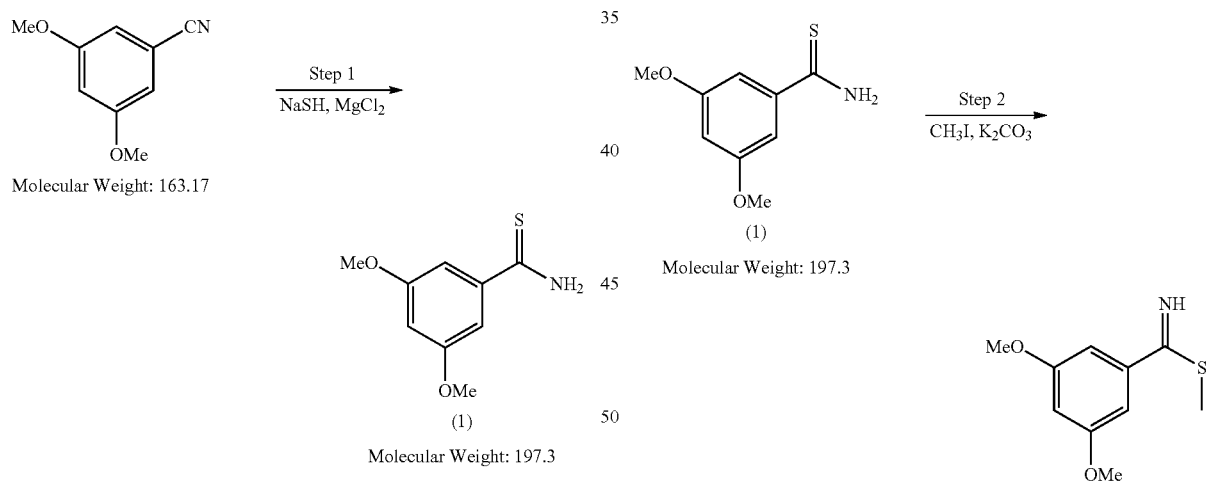

In a 3-neck 100 mL round-bottomed flask, 3,5-dimethoxy benzonitrile (10.0 g, 1 eq.), NaSH H$_2$O (9.43 g, 2.0 eq.) and MgCl$_2$6H$_2$O (12.43 g, 1.0 eq.) were dissolved in DMF (100 mL, 10 Vol.). The reaction mixture was stirred at room temperature for 2 h. Reaction completion was monitored on TLC using ethyl acetate: n-hexane (2:8) as mobile phase. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 2.5 g of crude compound, yield (20.68%). Mass/LCMS: 197.0 NMR: Confirmed.

In a 3-neck 100 mL round-bottomed flask, Intermediate 1 (2.5 g, 1 eq.) was dissolved in diethyl ether (25 mL, 10 Vol.) and Iodomethane (3.17 mL, 4.0 eq.) was added drop-wise. The reaction mixture was stirred at room temperature for 12 h. Reaction completion was monitored on TLC using ethyl acetate: n-hexane (2:8) as mobile phase. Reaction mixture was brought to room temperature and solid was filtered and washed with ether. Solid was dried under reduced pressure to afford 2.4 g of crude compound. Yield (89.62%). Mass/LCMS: 197.0 NMR: Confirmed.

Synthesis of Intermediate (3)

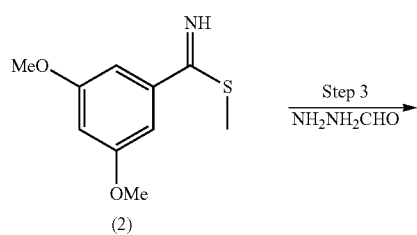
Molecular Weight: 211.3

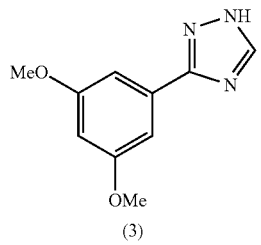
Molecular Weight: 205.2

In 3-neck 100 mL round-bottomed flask, Intermediate 2 (2.38 g, 1 eq.) and formic hydrazide (1.47 g, 2.0 eq.) was dissolved in DMF (24 mL, 20 Vol) and reaction mixture was heated at 140° C. for 2 h. Reaction completion was monitored on TLC using ethyl acetate: n-hexane (2:8) as mobile phase. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 2.3 g of crude compound and the compound was purified by column chromatography using ethyl acetate and Hexane as mobile phase. Product was eluted in 10% ethyl acetate in Hexane to afford 0.184 g of pure compound. Yield (07.36%). Mass/LCMS: 197 NMR: Confirmed.

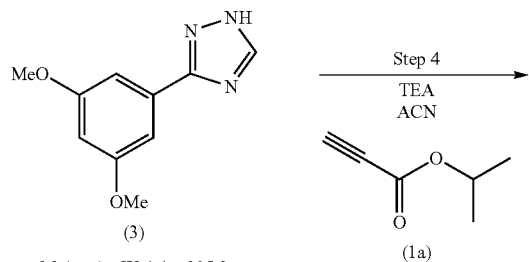

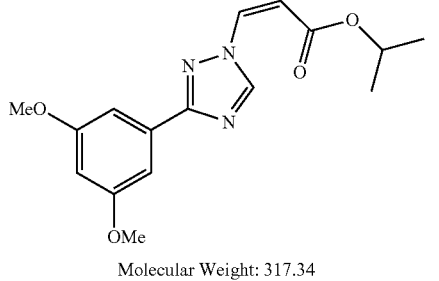
Molecular Weight: 317.34

In a 3-neck 50 mL round-bottomed flask, Intermediate 3 (0.184 g, 1 eq.) and TEA (0.18 mL, 1.5 eq.) was dissolved in DCM (5 mL, 25 Vol) and isopropyl propiolate (0.150 g, 1.5 eq.) was added dropwise. The reaction mixture was stirred at 15° C. for 30 min. Reaction completion was monitored on TLC using ethyl acetate: n-hexane (2:8) mobile phase. Reaction mixture was brought to room temperature and quenched into the ice-water slurry (100 mL) and compound was extracted in the DCM (50 mL×3). Organic layer was washed with brine solution (50 mL×3) followed by drying using anhydrous sodium sulphate. Organic layer was concentrated under reduced pressure to afford 0.120 g of crude compound and the compound was purified by column chromatography using ethyl acetate and hexane as mobile phase. Product was eluted in 4-5% ethyl acetate in hexane to afford 0.039 g of pure compound. Yield (13.73%). $^1$H NMR (400 MHz, CDCl$_3$): δ 9.72 (s, 1H), 7.33 (d, 2H), 7.25-7.30 (s, 1H), 6.56-6.57 (t, 1H), 5.67-5.69 (d, 1H), 5.11-5.17 (m, 1H), 3.86-3.89 (s, 6H), 1.58 (d, 6H). LCMS for $C_{16}H_{19}N_3O_4$ [M+H]$^+$ 317.3 found 318.41 at 6.671 min (LCMS 99.12%).

General method for Example 21, Example 22, Example 23: A mixture of 5-(3-Chlorophenyl)-1,2,4-triazole (0.50 g, 3.4 mmol), respective propiolate (0.52 ml, 5.1 mmol) and some drops of triethylamine in acetonitrile under nitrogen was stirred at room temperature for 12-16 h. Acetonitrile was removed under reduced pressure to give a residual oil, which was purified by flash chromatography (3-5% EtOAc/hexanes) to afford the both cis and trans isomers. Cis isomer was isolated 10-30% and trans was isolated in 30-50% with overall yield of 50-80%.

Example 21

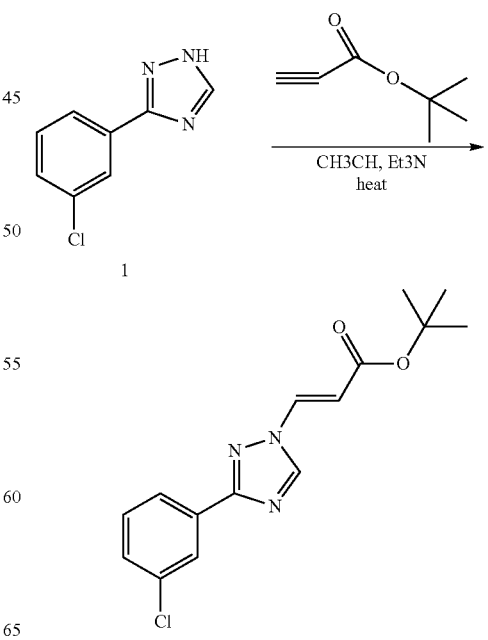

-continued

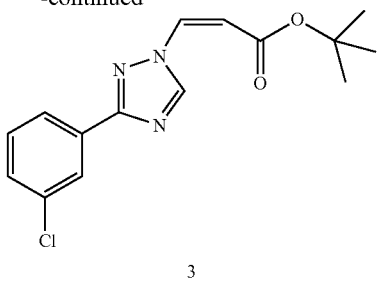

3

Cis-isomer: ¹H NMR (CDCl₃, 300 MHz): 1.58 (s, 9H), 5.64 (d, 1H), 7.22 (d, 1H), 7.43 (m, 2H), 8.0 (m, 1H), 9.62 (s, 1H), 8.22 (s, 1H). Mass (ESI): 306.3 (M+H).

Trans-isomer: ¹H NMR (CDCl₃, 300 MHz): 1.59 (s, 9H), 6.61 (d, 1H), 7.41 (m, 2H), 7.89 (d, 1H), 8.05 (d, 1H), 8.15 (s, 1H), 8.31 (s, 1H). Mass (ESI): 306.3 (M+H).

Example 22

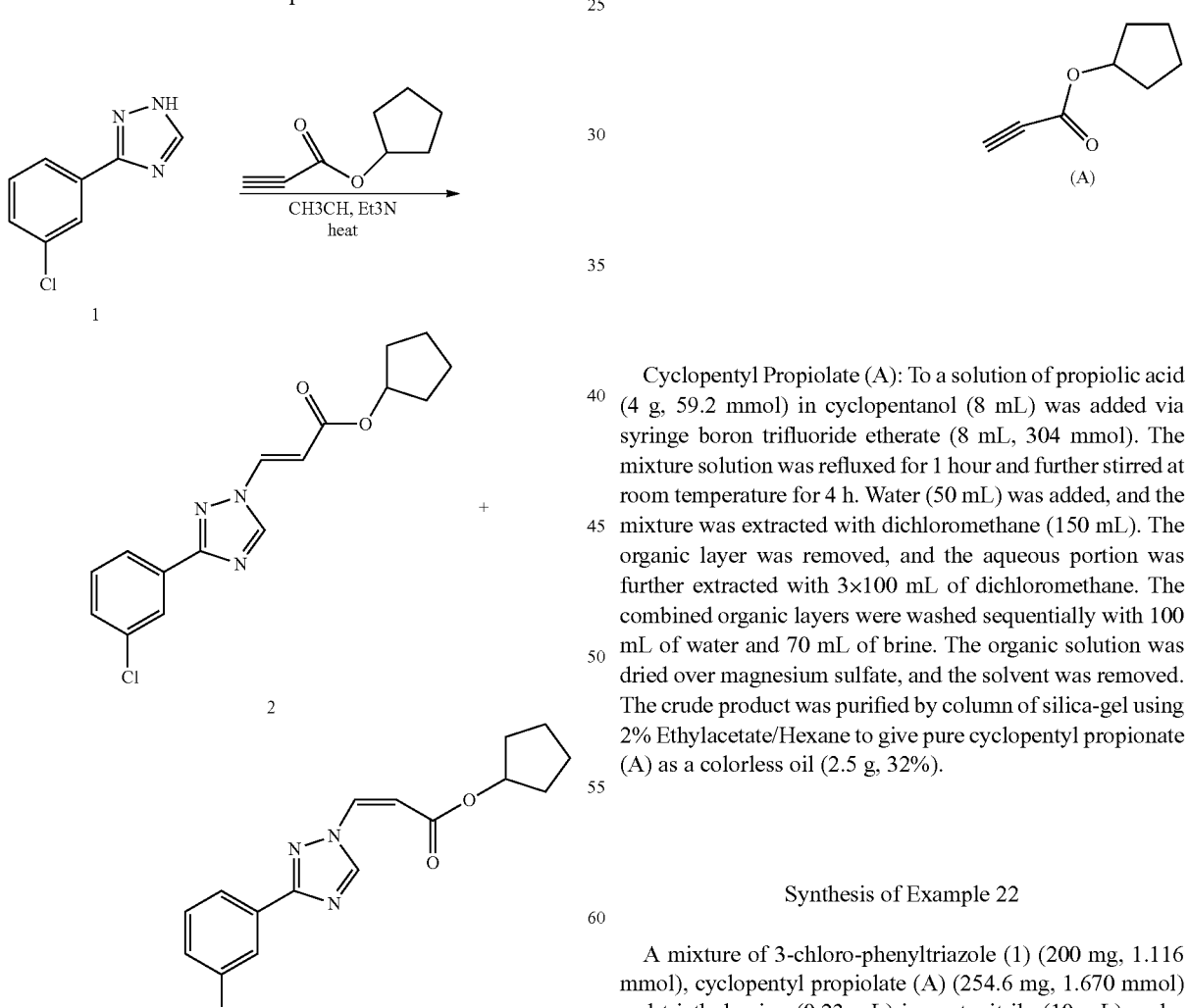

Synthesis of Cyclopentyl Propiolate (A)

Scheme 2: Synthesis scheme of the key intermediate (A)

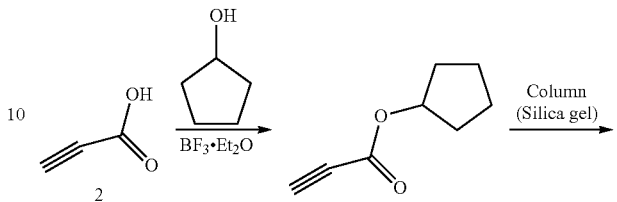

Cyclopentyl Propiolate (A): To a solution of propiolic acid (4 g, 59.2 mmol) in cyclopentanol (8 mL) was added via syringe boron trifluoride etherate (8 mL, 304 mmol). The mixture solution was refluxed for 1 hour and further stirred at room temperature for 4 h. Water (50 mL) was added, and the mixture was extracted with dichloromethane (150 mL). The organic layer was removed, and the aqueous portion was further extracted with 3×100 mL of dichloromethane. The combined organic layers were washed sequentially with 100 mL of water and 70 mL of brine. The organic solution was dried over magnesium sulfate, and the solvent was removed. The crude product was purified by column of silica-gel using 2% Ethylacetate/Hexane to give pure cyclopentyl propionate (A) as a colorless oil (2.5 g, 32%).

Synthesis of Example 22

A mixture of 3-chloro-phenyltriazole (1) (200 mg, 1.116 mmol), cyclopentyl propiolate (A) (254.6 mg, 1.670 mmol) and triethylamine (0.23 mL) in acetonitrile (10 mL) under nitrogen was heated overnight at reflux (~90° C. Acetonitrile was removed under reduced pressure to leave a dark yellow oil. The mixture was separated by column chromatography (silica gel, using Ethyl acetate/Hexane, 25/75 as eluant). This process was repeated three (3) times to get 75 mg of Example 22 and 130 mg of its trans isomer as pure materials.
Example 23
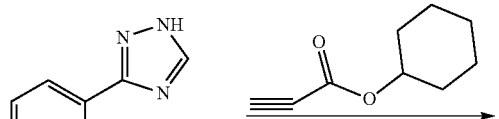
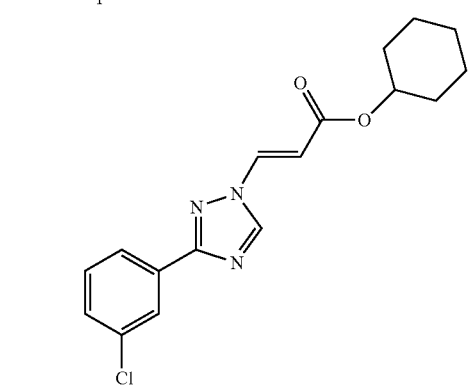
+
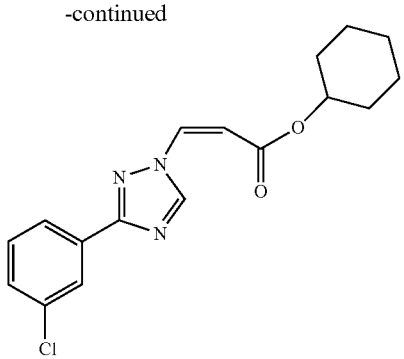
3
Synthesis of B
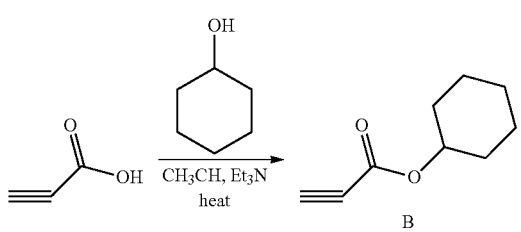
Example 24
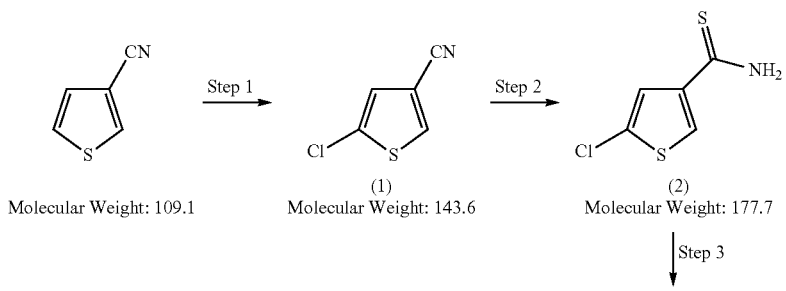
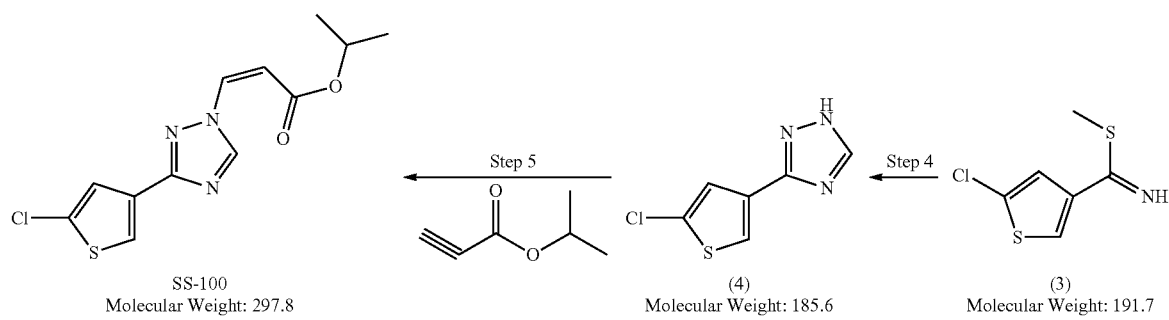

Synthesis of Intermediate 1

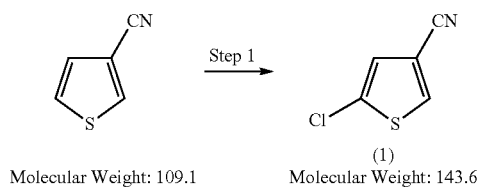 [SMILES: N#Cc1ccsc1 ; N#Cc1csc(Cl)c1]

In a 3-neck 100 mL round-bottomed flask, 3-Cyanothiophene (5.0 g, 1 eq.) was dissolved in Acetic acid (50 mL, 10 Vol.) and Added N-chloro succinamide (6.73 g, 1.1 eq.). Reaction mixture was stirred at reflux temperature for 2-3 h. Reaction completion was monitored on TLC using ethyl acetate: n-hexane (1:9) as mobile phase. Reaction mixture was brought to room temperature and poured into ice-water slurry (250 mL) and neutralized with sodium bicarbonate solution. Compound was extracted in the EtOAc (100 mL×3). Organic layer was washed with brine solution (100 mL×2) followed by drying using anhydrous sodium sulphate. Organic layer was concentrated under reduced pressure to afford 5.0 g of crude compound. Compound was purified by flash chromatography using ethyl acetate and Hexane to afford 2.4 g pure compound. Yield (36.5%). Mass/LCMS: 177.0' NMR: Confirmed.

Synthesis of Intermediate (2)

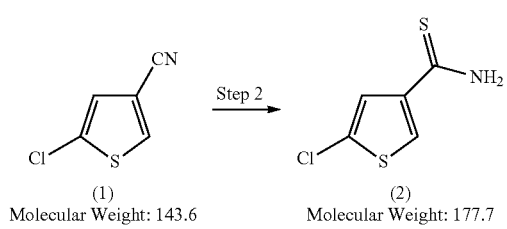 [SMILES: N#Cc1csc(Cl)c1 ; NC(=S)c1csc(Cl)c1]

In a 3-neck 100 mL round-bottomed flask, Intermediate 1 (2.4 g, 1 eq.) was mixed with DMF (24 mL, 10 Vol.), $MgCl_2 6H_2O$ (3.39 g, 1.0 eq.) and NaSH $H_2O$ (2.47 g, 2.0 eq.). The reaction mixture was stirred at room temperature for 2 h. Reaction remained as a green colored clear solution throughout the reaction. Reaction completion was monitored on TLC using ethyl acetate: n-hexane (3:7) as mobile phase. After 2 h reaction was completed and worked up. Reaction mixture was brought to room temperature and poured into ice-water slurry (100 mL). Compound was extracted in the EtOAc (100 mL×3). Organic layer was washed with brine solution (100 mL×2) followed by drying using anhydrous sodium sulphate. Organic layer was concentrated under reduced pressure to afford 0.7 g of crude compound. Crude compound was carried forward without further purification, Yield (23.6%). Mass/LCMS: 177.0 Confirmed.

Synthesis of Intermediate (3)

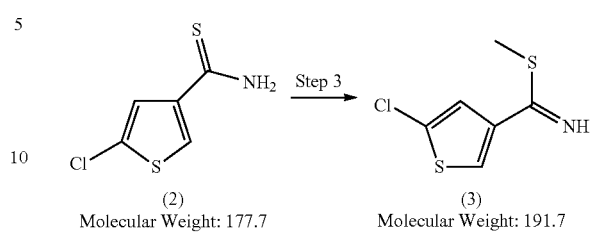

In a 3-neck 100 mL round-bottomed flask, Intermediate-1 (0.7 g, 1 eq.) was dissolved in diethyl ether (14 mL, 20 Vol.). To this reaction mixture methyl iodide (1.23 mL, 5 eq.) was added drop-wise at 0 C. The reaction mixture was further stirred at RT for overnight. Reaction completion was monitored on TLC using ethyl acetate: n-hexane (3:7) as mobile phase. Product was filtered and washed with diethyl ether (3×10 mL). Product was dried under reduced pressure to afford 0.5 g of crude compound, Yield (66.23%). Mass/LCMS: Confirmed, NMR: confirmed.

Synthesis of Intermediate (4)

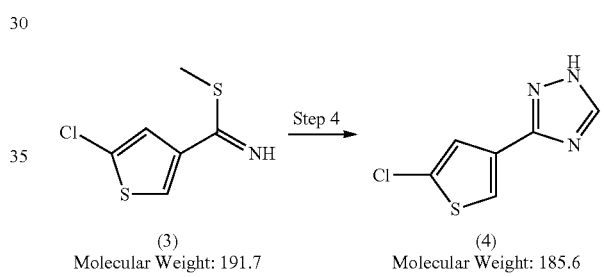

In 3-neck 100 mL round-bottomed flask, Int-2 (0.5 g, 1 eq.) and Formic hydrazide (0.313 g, 2 eq.) were dissolved in DMF (10 mL, 20 Vol.) and the reaction mixture was stirred at reflux temperature for 2 h. The reaction completion was monitored on TLC using MeOH:MDC (1:9) mobile phase. Reaction mixture was brought to room temperature and poured into the water (50 mL) and compound was extracted in the Ethyl acetate (25 mL×3). Organic layer was again washed with water (25 mL×3) followed by drying using anhydrous sodium sulphate. Organic layer was concentrated under reduced pressure to afford 0.4 g of crude compound, and the crude product was purified by flash chromatography using ethyl acetate and hexane as mobile phase. Weight of pure product 0.230 g. Yield (47.52%). Mass/LCMS: Confirmed, NMR: Confirmed.

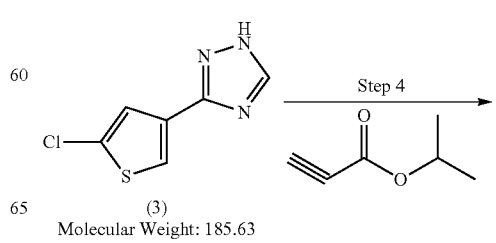

-continued

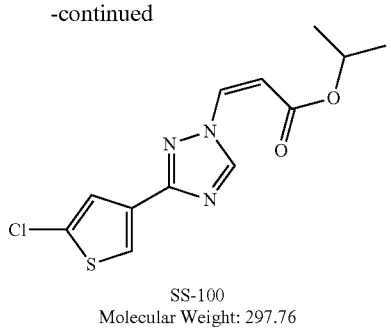

SS-100
Molecular Weight: 297.76

In a 1-neck 50 mL round-bottomed flask, Intermediate-3 (0.23 g, 1 eq.) was dissolved in MDC (5.75 mL, 25 Vol.). TEA (0.163 g, 1.3 eq.) was added to the reaction mixture and the mixture was cooled to 15-20° C. Isopropyl propiolate (0.180 g, 1.3 eq.) was added drop-wise and the reaction mixture was stirred at 15-20° C. for 30 minutes. Reaction completion was monitored on TLC using Ethyl acetate:Hexane (2:8) mobile phase. Reaction mixture was concentrated under reduced pressure to afford 0.250 g of crude compound and the product was purified by flash chromatography using ethyl acetate and Hexane to afford 0.035 g pure compound. Yield (9.4%). $^1$H NMR (400 MHz, CDCl$_3$) δ=9.69 (s, 1H), 7.79 (s, 1H), 7.50 (s, 1H), 7.22-7.25 (d, J=11.2 Hz, 1H), 5.67-5.69 (d, J=11.2 Hz, 1H), 5.12-5.17 (m, 1H), 1.32-1.34 (d, 6H). LC-MS: Calculated $C_{12}H_{12}N_3ClO_2S$, (M+1)$^+$ 297.76. Found 297.86 at RT 4.220 min (LCMS 97.62

Example 25

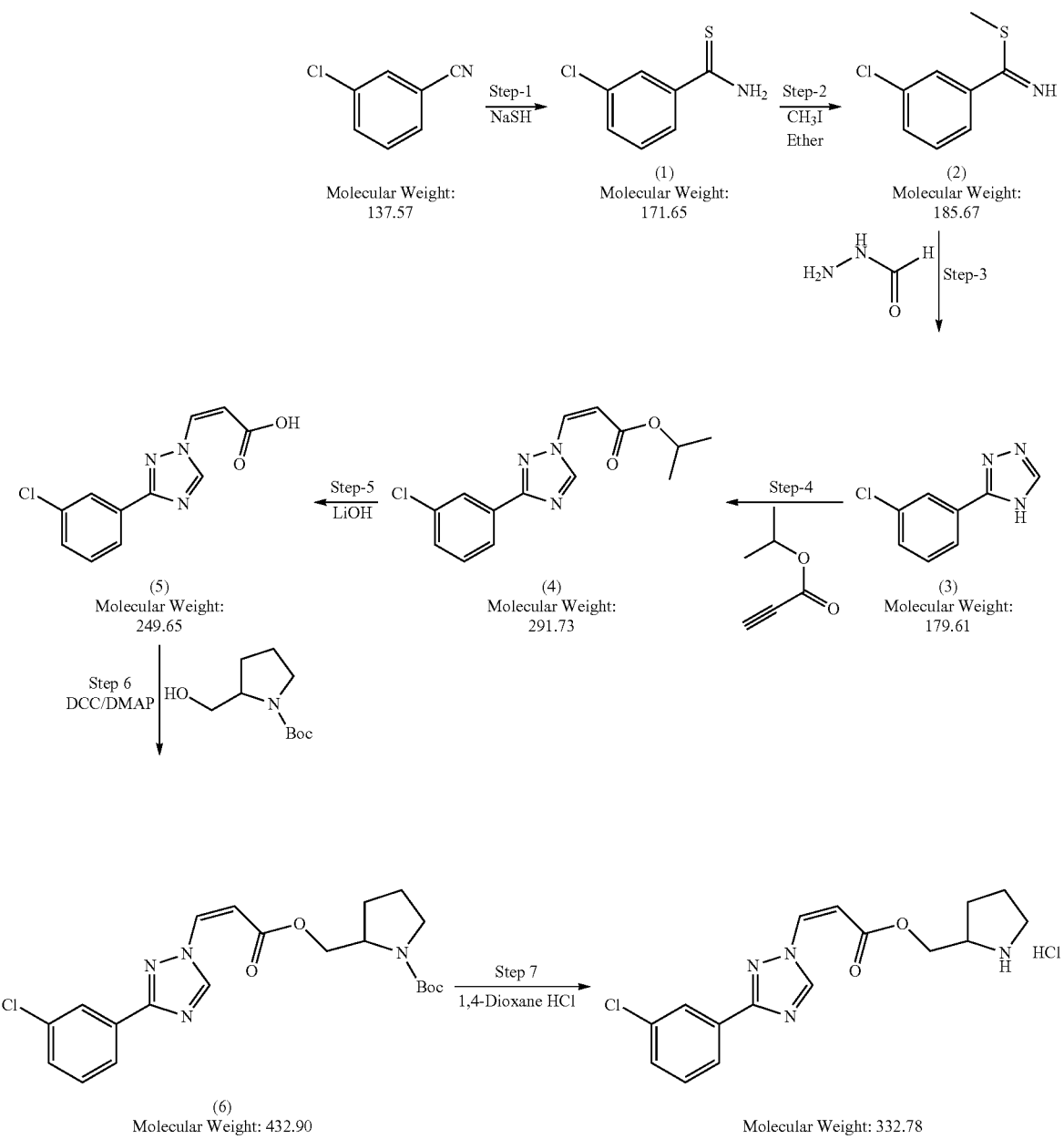

Synthesis of Intermediate (6)

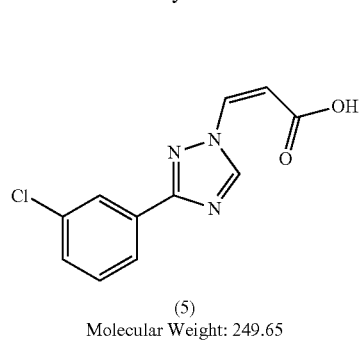

(5)
Molecular Weight: 249.65

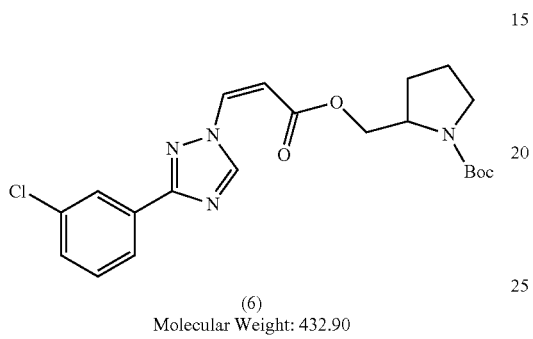

(6)
Molecular Weight: 432.90

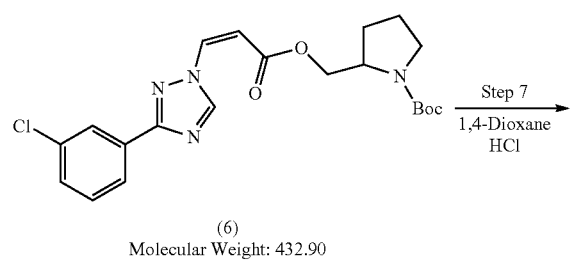

(6)
Molecular Weight: 432.90

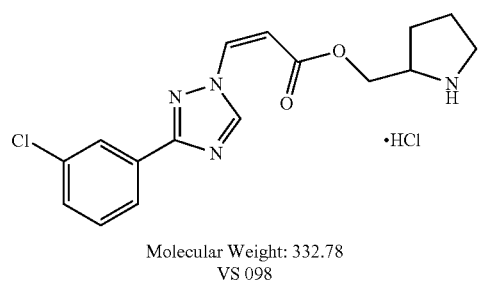

Molecular Weight: 332.78
VS 098

In a 3-neck 25 mL round-bottomed flask, Intermediate 5 (from Example 1) (0.25 g, 1 eq.) was dissolved in DCM (5 mL, 20 Vol.) and DCC (0.226 g, 1.1 eq.), DMAP (0.012 g, 1.1 eq.) and N-Boc Prolinol (0.221 g, 1.1 eq.) were added to this reaction mixture. Reaction mixture was stirred at RT for 3-4 h. Reaction completion was monitored on TLC using ethyl acetate: n-hexane (3:7) mobile phase. Reaction mixture was filtered through celite bed and filtrate was distilled off to get crude compound. The crude compound was purified using silica 60/120 and ethylacetate:hexane as mobile phase. Column purification was started with 5% EtOAc in hexane up to 30% EtOAc. Compound started eluting in 10% ethyl acetate and continued till 12% EtOAc. Fractions containing compound was distilled out using rotary evaporation at 45° C./250 mm Hg to obtain 0.130 g of pure compound. Yield (30%). LCMS: Confirmed. NMR: Confirmed.

In a 3-neck 25 mL round-bottomed flask, Intermediate-6 (0.13 g, 1 eq.) was dissolved in 1,4-dioxane (5.2 mL, 40 Vol.) and 1,4-Dioxane HCl (0.5 mL, 5 Vol.) was added drop-wise. Reaction mixture was stirred at RT for 40 h. Reaction completion was monitored on TLC using methanol:DCM (2:8) as mobile phase to see absence of free base. Reaction mixture was concentrated to dryness under reduced pressure to afford 0.13 g of crude compound which was triturated with diethyl ether to get 0.04 g compound, Yield (40.4%). $^1$H NMR (400 MHz, DMSO) β=9.54 (Broad s, 1H, $D_2O$ exchangeable), 9.30 (s, 1H), 9.06 (Broad s, 1H $D_2O$ exchangeable), 7.97-7.99 (m, 2H), 7.55-7.61 (m, 2H), 6.02-6.04 (d, 2H, J=8 Hz), 4.32-4.46 (m, 2H), 3.78-3.79 (d, 2H), 3.12-3.19 (m, 1H), 1.81-2.09 (m, 3H). LCMS: Calculated for $C_{16}H_{17}ClN_4O_2$ $(M+H)^+$ 332.78 Found: 332.86 Retention time: 2.658 min (96.64%).

Example 26

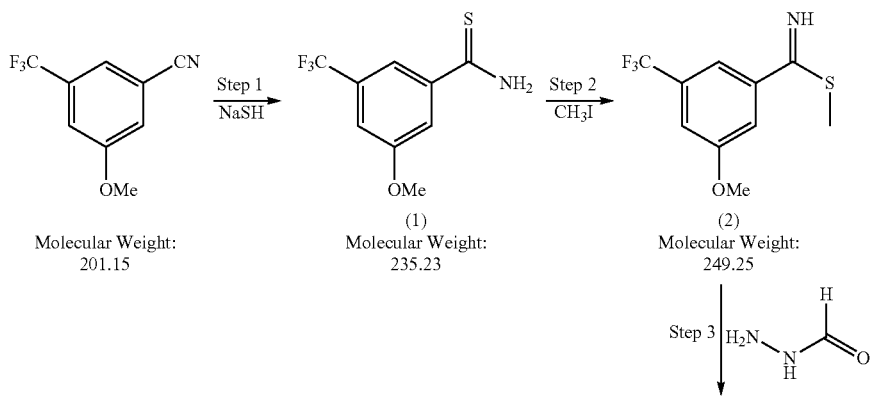

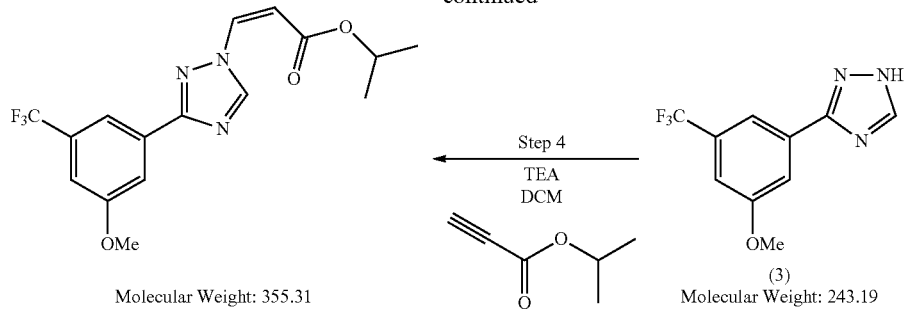

Synthesis of Intermediate (1)

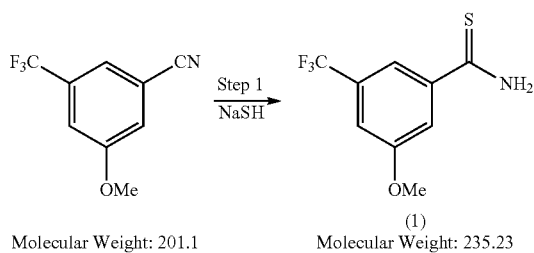

In a 3-neck 100 mL round-bottomed flask, 3-methoxy-5-(trifluoromethyl)benzonitrile (5.0 g, 1 eq.), NaSH H$_2$O (3.68 g, 2.0 eq.) and MgCl$_2$6H$_2$O (5.05 g, 1.0 eq.) was dissolved in DMF (50 mL, 10 Vol) and reaction mixture was stirred at room temperature for 2 h. Reaction completion was monitored on TLC using ethyl acetate:hexane (4:6) mobile phase. Reaction mixture was brought to room temperature and quenched into the ice-water slurry (500 mL) and compound was extracted in the ethyl acetate (150 mL×3). Organic layer was washed with brine solution (150 mL×3) followed by drying using anhydrous sodium sulphate. Organic layer was concentrated under reduced pressure to afford 5.5 g of crude compound, yield (94.8%). Mass/LCMS: 235.8.

Synthesis of Intermediate (2)

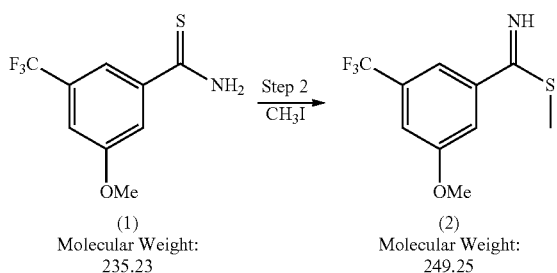

In a 3-neck 100 mL round-bottomed flask, Intermediate 1 (5.5 g, 1 eq.) was dissolved in diethyl ether (55 mL, 10 Vol) and dropwise added Iodomethane (13.27, 4.0 eq.) and reaction mixture was stirred at room temperature for 12 h. Reaction completion was monitored on TLC using ethyl acetate:hexane (4:6) mobile phase. Reaction mixture was brought to room temperature and solid was filtered and washed with ether. Solid was dried under reduced pressure to afford 5.2 g of crude compound, yield (89.35%). LCMS: 61.3%.

Synthesis of Intermediate (3)

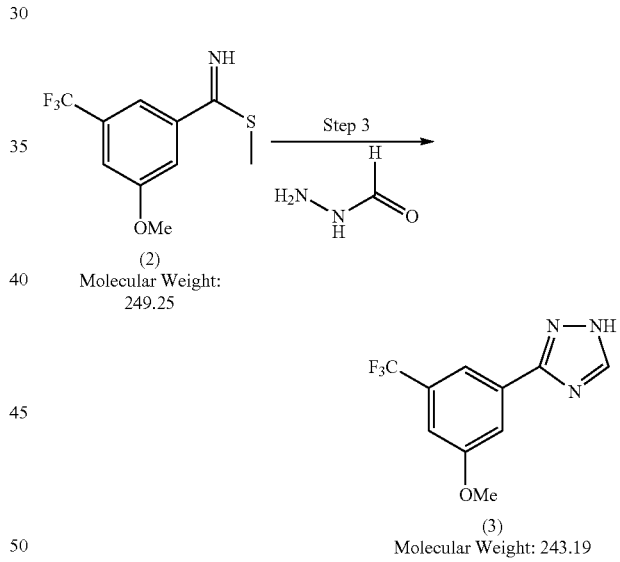

In a 3-neck 100 mL round-bottomed flask, Int-2 (5.5 g, 1 eq.) and formic hydrazide (2.91 g, 2.0 eq.) was dissolved in DMF (55 mL, 10 Vol) and reaction mixture was heated at 90° C. for 2 h. Reaction completion was monitored on TLC using ethyl acetate:hexane (4:6) mobile phase. Reaction mixture was brought to room temperature and quenched into the ice-water slurry (500 mL) and compound was extracted in the ethyl acetate (150 mL×3). Organic layer was washed with brine solution (150 mL×3) followed by drying using anhydrous sodium sulphate. Organic layer was concentrated under reduced pressure to afford 5.0 g of crude compound and the compound was purified by column chromatography using ethyl acetate and Hexane as mobile phase. Product was eluted in 10% ethyl acetate in Hexane to afford 3.4 g of pure compound. Yield (63.43%). LCMS: 99.84%.

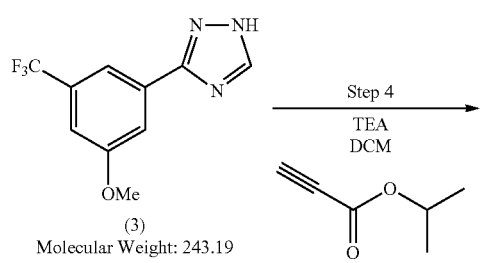

(3)
Molecular Weight: 243.19 hexane (3:7) mobile phase. Reaction mixture was concentrated under reduced pressure to afford 2.6 g of crude compound and the compound was purified by column chromatography using ethyl acetate and Hexane as mobile phase. Product was eluted in 4-5% ethyl acetate in Hexane to afford 0.15 g of pure compound. Yield (4.11%). $^1$H NMR (400 MHz, CDCl$_3$) δ 9.72 (s, 1H), 8.02 (s, 1H), 7.86 (s, 1H), 7.30 (s, 1H), 7.28 (d, J=8.8 Hz, 1H), 5.71-5.73 (d, J=10.8 Hz, 1H), 5.12-5.18 (m, 1H), 3.94 (s, 3H), 1.34 (d, 6H): LCMS for $C_{16}H_{16}F_3N_3O_3$ [M+1]$^+$ 355.31 found 355.92 at 4.317 min (LCMS 99.82%).

Example 27

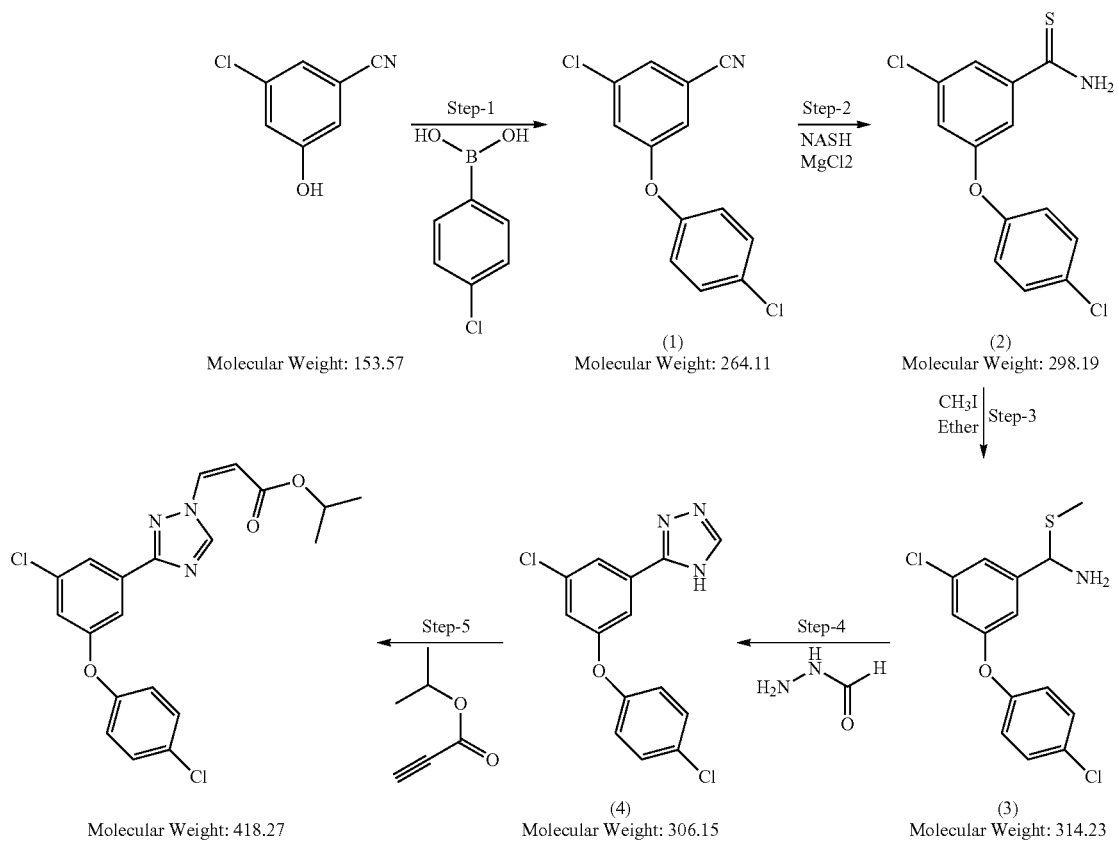

-continued

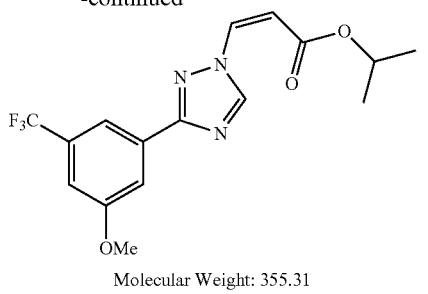

Molecular Weight: 355.31

In a 3-neck 50 mL round-bottomed flask, Intermediate 3 (2.5 g, 1 eq.) was dissolved in DCM (25 mL, 10 Vol), added TEA (1.35 g, 1.3 eq) and Isopropyl propiolate (1.49 g, 1.3 eq.) and reaction mixture was stirred at 15° C. for 30 min. Reaction completion was monitored on TLC using ethyl acetate:

Synthesis of Intermediate (1)

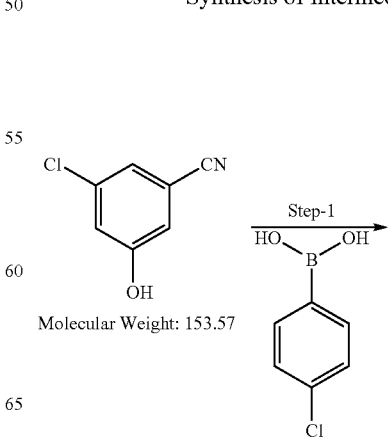

Molecular Weight: 153.57

-continued

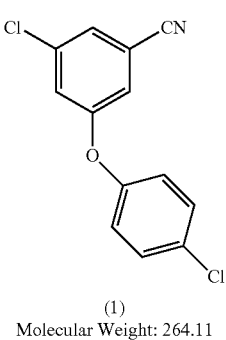

(1)
Molecular Weight: 264.11

In a 3-neck 50 mL round-bottomed flask, 3-chlorobenzonitrile (1.5 g, 1 eq.), 4-Chlorophenyl boronic acid (1.53 g, 1 eq.) znc Copper acetate (1.77 g, 1 eq.) were mixed with TEA (6.8 mL, 5 eq.) and DCM (45 mL, 30 Vol.) was added to this mixture. The reaction mixture was stirred at room temperature for 12 h. Reaction remained brown colored clear solution throughout the reaction. Reaction completion was monitored on TLC using ethyl acetate: n-hexane (2:8) mobile phase. After 12 h reaction was completed and worked up. Reaction mixture was brought to room temperature and quenched into the ice-water slurry (100 mL) and emulsion was filtered through celite pad. The compound was extracted in the MDC (50 mL×3). Organic layer was washed with brine solution (50 mL×3) followed by drying using anhydrous sodium sulphate. Organic layer was concentrated under the reduced pressure to afford 3.0 g of crude compound. Crude compound was further purified by column chromatography using silica 60/120 and ethylacetate:n-hexane as mobile phase. Column purification was started with hexane upto 5% EtOAc. Compound started eluting in 1% ethylacetate and continued till 5% EtOAc. Fractions containing compound were distilled out using rotary evaporation at 45° C./250 mm Hg to obtain 1.7 g of pure compound, yield (28.24%). Mass/LCMS: not confirmed, NMR: Confirmed.

Synthesis of Intermediate (2)

In a 3-neck 50 mL round-bottomed flask, Int-1 (1.7 g, 1 eq.), NaSH.H$_2$O (0.952 g, 2.0 eq.) and MgCl$_2$. 6H$_2$O (1.3 g, 1.0 eq.) were dissolved in DMF (34 mL, 20 Vol.). Reaction was stirred at room temperature for 2 h. Reaction completion was monitored on TLC using ethyl acetate:hexane (3:7) mobile phase. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 2.5 g of crude compound, yield (78.8%).

Synthesis of Intermediate (3)

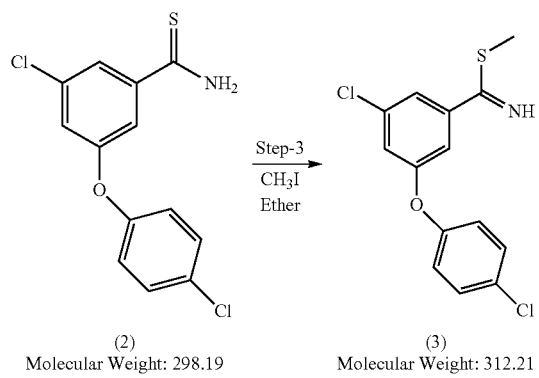 [SMILES: NC(=S)c1cc(Cl)cc(Oc2ccc(Cl)cc2)c1 ; CSC(=N)c1cc(Cl)cc(Oc2ccc(Cl)cc2)c1]

(2)
Molecular Weight: 298.19

(3)
Molecular Weight: 312.21

In a 1-neck 50 mL round-bottomed flask, Intermediate 2 (2.5 g, 1 eq.) was dissolved in Diethyl ether (25 mL, 10 Vol.) and added Iodo methene (2.6 mL, 5.0 eq.) at 0° C. The reaction mixture was stirred at room temperature overnight. Reaction completion was monitored on TLC using ethyl acetate: n-hexane (3:7) mobile phase. The reaction mixture was brought to room temperature and Solid product was filtered and washed with ether. Product was dried under reduced pressure to afford 1.9 g of pure compound, yield (72.8%). Mass/LCMS: Mass was not confirmed for this compound, NMR: Confirmed.

Synthesis of Intermediate (4)

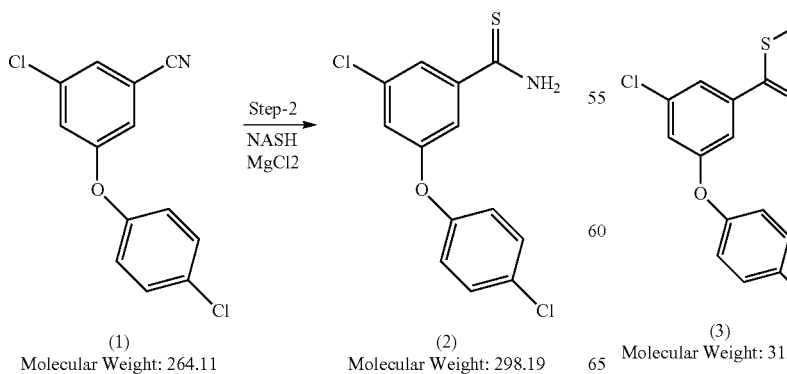

(1)
Molecular Weight: 264.11

(2)
Molecular Weight: 298.19

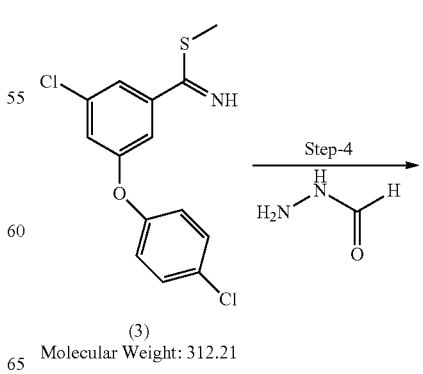

(3)
Molecular Weight: 312.21

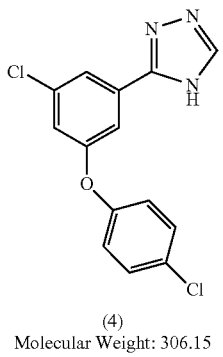

(4)
Molecular Weight: 306.15

In a 3-neck 50 mL round-bottomed flask, Intermediate 3 (1.9 g, 1 eq.) and Formic hydride (0.736 g, 2.0 eq.) were dissolved in DMF (19 mL, 10 Vol.) reaction mixture was refluxed to 140° C. for 2 h. Reaction completion was monitored on TLC using ethyl acetate:hexane (3:7) mobile phase. Reaction mixture was brought to room temperature and quenched into the ice-water slurry (100 mL) and compound was extracted in the ethyl acetate (50 mL×3). Organic layer was washed with brine solution (50 mL×3) followed by drying using anhydrous sodium sulphate. Organic layer was concentrated under reduced pressure to afford 1.5 g of crude compound and product was purified by combiflash to afford 1.19 g of pure compound. yield (53.5%). Mass/LCMS: Confirmed, NMR: Confirmed.

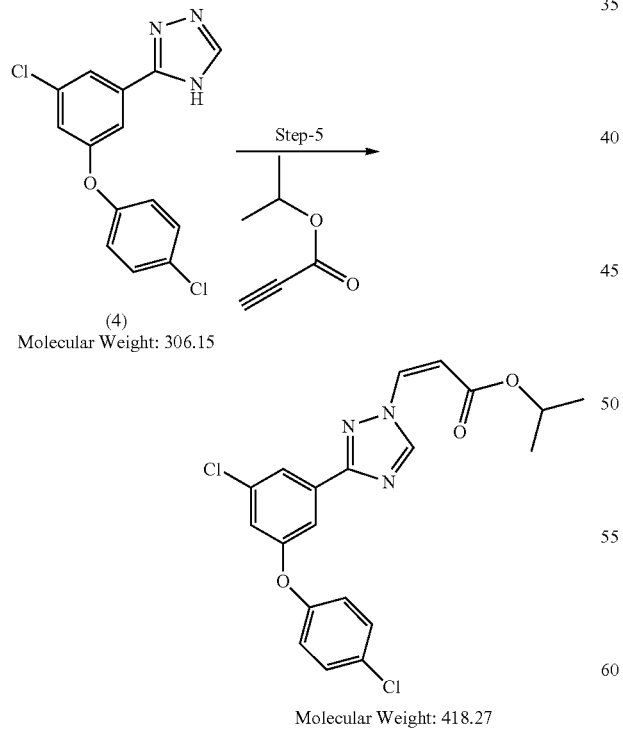

In a 3-neck 50 mL round-bottomed flask and TEA (1.0 g, 1 eq.) were dissolved in DCM (20 mL, 20 Vol.) and isopropyl propiolate (0.440 g, 1.2 eq.) was drop-wise added in the reaction mixture at 10-15° C. The reaction mixture was stirred at 10-15° C. for 30 minutes. Reaction completion was monitored on TLC using ethyl acetate: n-hexane (0.5:9.5) as mobile phase. Reaction mixture was brought to room temperature and quenched into the ice-water slurry (100 mL) and compound was extracted in the DCM (50 mL×3). Organic layer was washed with brine solution (50 mL×3) followed by drying using anhydrous sodium sulphate. Organic layer was concentrated under the reduced pressure to afford 1.0 g of crude compound. Product was purified by column chromatography to afford 0.174 g of pure compound. Yield (12.8%).
$^1$H NMR (400 MHz, CDCl$_3$) δ 9.69 (s, 1H), 7.01-7.92 (m, 7H), 7.24-7.27 (d, J=10.8 Hz, 1H), 5.69-5.72 (d, J=11.2 Hz, 1H), 5.10-5.12 (m, 1H), 1.32-1.34 (d, 6H). LC-MS calculated for C$_{20}$H$_{17}$Cl$_2$N$_3$O$_3$ [M+1]$^+$ 418.3. Found 417.7 and 419.7 at 4.670 min.

Example 28

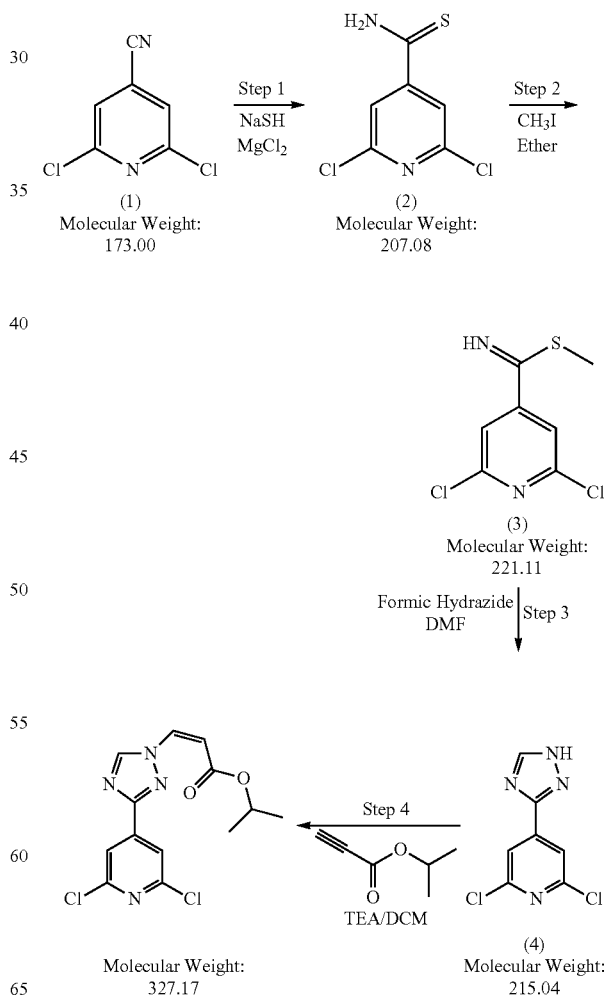

Synthesis of Intermediate (2)

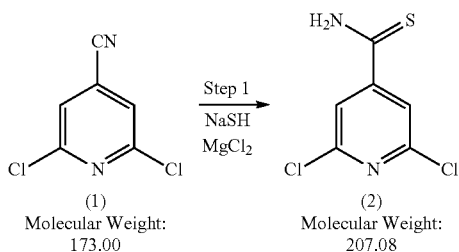 [SMILES: N#Cc1cc(Cl)nc(Cl)c1 ; NC(=S)c1cc(Cl)nc(Cl)c1]

In a 3-neck 250 mL round-bottomed flask, NaSH (8.55 g, 2.0 eq.) and $MgCl_2.6H_2O$ (11.73 g, 1.0 eq.) were dissolved in DMF (120 mL). The reaction mixture was stirred for 10 min. 2,6-Dichloro isonicotinonitrile (10 g, 1.0 eq.) was then added to the above reaction mixture. Reaction mixture was stirred for 2 h. The completion of reaction was monitored on TLC using Ethyl acetate:hexane (4:6) as mobile phase.

The reaction mixture was dumped in water (1 L). Solid product that separated, was filtered and dried under vacuum. As we found that the aqueous layer also contained some product which was extracted with Ethyl acetate (3×250 mL). Organic layer was dried over sodium sulphate. Solvent was evaporated to dryness under reduced pressure to obtain the crude product. Mass/LCMS: 180.0, NMR Confirmed, HPLC: 99.96%.

Synthesis of Intermediate (3)

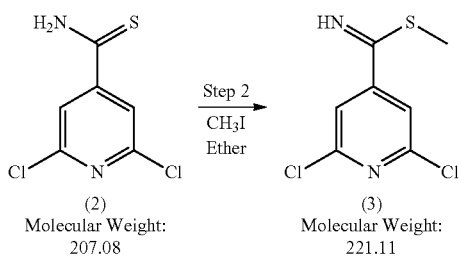

In a 3-neck 100 mL round-bottomed flask, Intermediate-2 (7.0 g, 1.0 eq.) was dissolved in Diethyl ether (70 mL, 10 Vol.). Reaction mixture was cooled at 0° C. and Methyl iodide (14.36 mL, 4.0 eq.) was added drop-wise to the above reaction mixture. Reaction mixture was stirred at RT for overnight. Reaction completion was monitored on TLC using ethyl acetate:hexane (4:6) as mobile phase. The reaction mixture was dumped in water (250 mL). Aqueous layer was extracted with diethyl ether (3×250 mL) and Organic layer was dried over sodium sulphate. Solvent was evaporated to dryness under the reduced pressure to obtain crude material.

Synthesis of Intermediate (4)

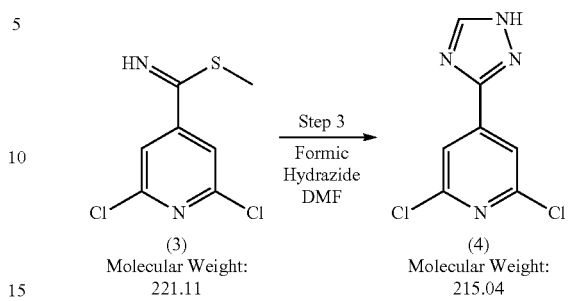

In a 3-neck 250 mL round-bottomed flask, Intermediate 3 (9.4 g, 1.0 eq.) was dissolved in DMF (100 mL, 10 Vol.) and added Formic Hydrazide (5.10 g, 2.0 eq.) and the reaction mixture was stirred at RT for 1 h. Reaction mixture was then heated at 100° C. for 3-4 h. Reaction completion was monitored on TLC using ethyl acetate:hexane (8:2) mobile phase. The reaction mixture was dumped in water (250 mL). Aqueous layer was extracted with Ethyl Acetate (3×250 mL). Organic layer was dried over sodium sulphate. Solvent was evaporated to dryness under the reduced pressure to obtain crude product. Concentrated filtrate was purified by Column chromatography using 8% Ethyl acetate in Hexane. Yield: 6.86%

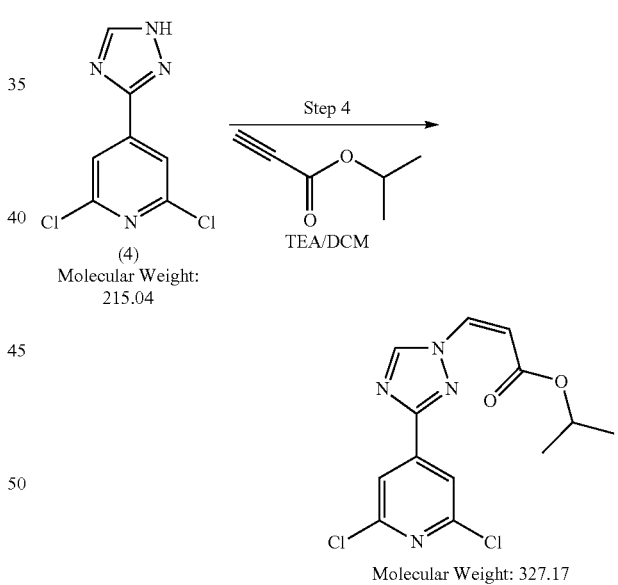

In a 3-neck 50 mL round-bottomed flask, Intermediate 4 (1.0 g, 1.0 eq.) was dissolved in DCM (15 mL). The reaction mixture was cooled at 0° C. and TEA (0.84 mL, 1.3 eq.) was added to the reaction mixture drop-wise. Isopropyl propiolate was also added drop-wise into the above reaction mixture at 0° C. Reaction mixture was stirred for 30 min. Reaction completion was monitored on TLC using ethyl acetate:hexane (5:5) mobile phase. The reaction mixture was dumped in water (50 mL). Aqueous layer was extracted with DCM (3×50 mL). Organic layer was dried over sodium sulphate. Solvent was evaporated to dryness under reduced pressure to obtain crude material. $^1$H NMR (400 MHz, $CDCl_3$) δ 9.75 (S, 1H), 8.00 (S, 1H), 7.26-7.29 (d, J=10.8 Hz, 1H), 5.78-5.81 (d, J=10.8 Hz, 1H), 5.12-5.18 (m, 1H), 1.33-1.35 (d, 6H): LCMS for $C_{13}H_{12}Cl_2N_4O_2$ [M−1]⁻ 327.2 found 326.78 at 4.352 min.

Example 29

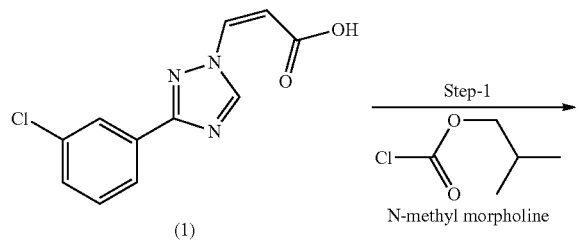

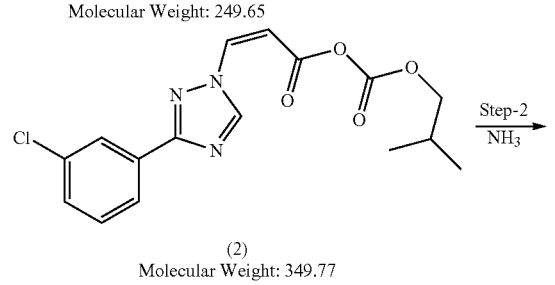

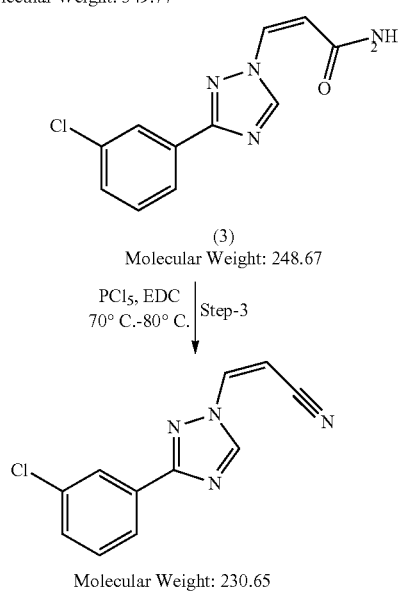

Synthesis of Intermediate (2)

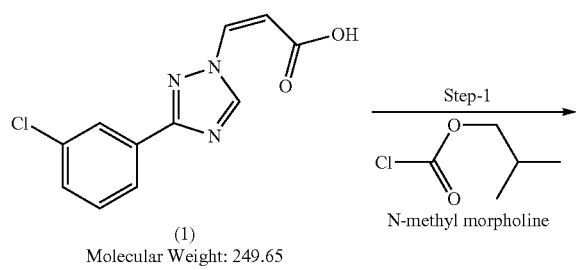

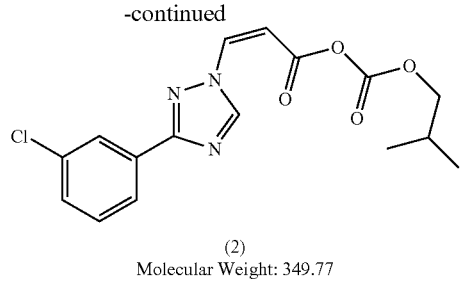

In a 50 mL 3-neck round bottom flask equipped with septum, nitrogen bubbler and thermometer pocket, Intermediate 1 (0.400 g) was dissolved in THF (15 mL). N-methyl morpholine (0.227 g, 1.4 eq.) was added into the reaction mixture at 0° C. The reaction mixture was stirred at same temperature for further 5 min. Isobutyl chloroformate (0.32 mL, 1.56 eq.) was added drop-wise to the above reaction mixture. The reaction mixture was stirred at 0° C. for 1 h. The completion of reaction was monitored on TLC using Ethyl acetate: n-hexane (5:5) as mobile phase. The reaction is carried forward without purification.

Synthesis of Intermediate (3)

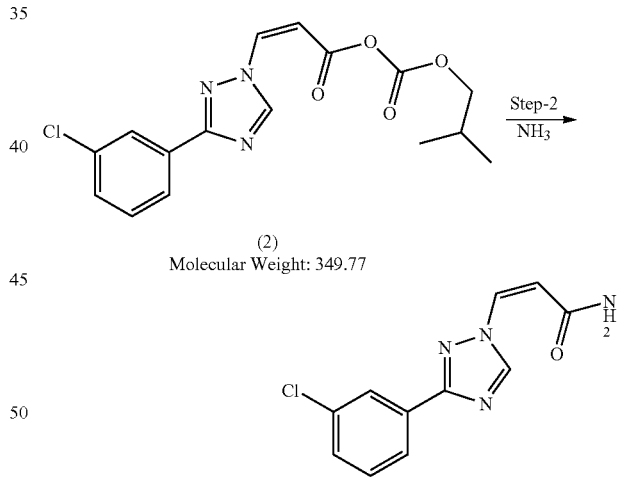

In a 50 mL 3-neck round bottom flask equipped with septum, Nitrogen bubbler and thermometer pocket, intermediate 2 (0.400 g) and THF (15 mL) were added. Then NH₃ gas was passed into the above reaction mixture for 5 minutes. The completion of reaction was monitored on TLC using Ethyl acetate:Hexane (5:5) as mobile phase.

The reaction mixture was dumped in water (100 mL). Aqueous layer was extracted with Ethyl acetate (3×50 mL). Organic layer was dried over sodium sulphate. Solvent was evaporated to dryness under reduced pressure to obtain crude material. Mass: Confirmed.

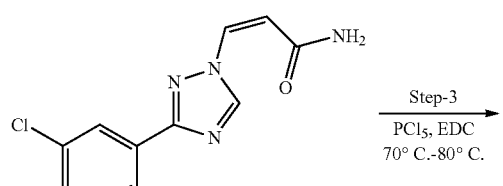

(3)
Molecular Weight: 248.67

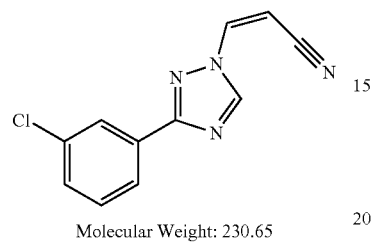

Molecular Weight: 230.65

In a 100 mL 3-neck round bottom flask equipped with Condenser, Nitrogen bubbler and thermometer pocket intermediate 3 (0.569 g, 0.0023 mol) and EDC (10 mL) were added. Then PCl$_5$ (0.524 g, 0.0025 mol) was added to the reaction mixture. The reaction was allowed to reflux for 2-3 hours. The completion of reaction was monitored on TLC using Ethyl acetate:Hexane (4:6) as mobile phase. The reaction mixture was dumped in water (100 mL). Aqueous layer was extracted with Ethyl acetate (3×50 mL). Organic layer was dried over sodium sulphate. Solvent was evaporated to dryness under reduced pressure to obtain crude material. $^1$H NMR (400 MHz, CDCl$_3$) δ 8.84 (s, 1H), 7.49-8.19 (m, 4H), 7.43-7.45 (d, J=8.14, 1H), 5.31-5.33 (d, J=9.6, 1H), LCMS-ESI calculated for C$_{11}$H$_7$ClN$_4$ [M+H]$^+$ 230.65. found 230.93 at 3.77 min (LCMS 70.21%).

Example 30

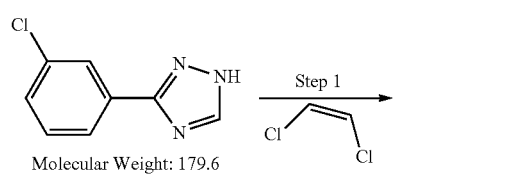

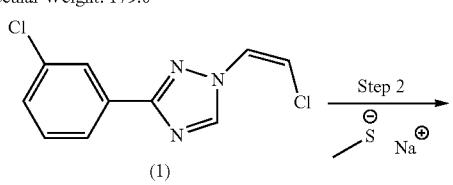

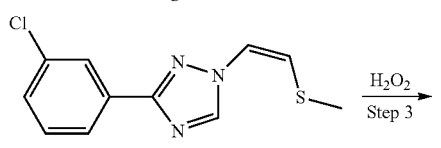

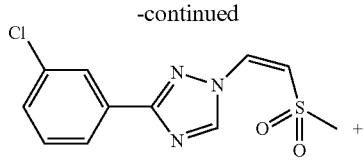

Molecular Weight: 283.73

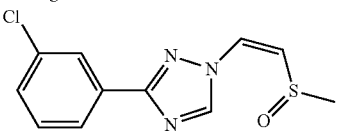

Molecular Weight: 267.73

Synthesis of Intermediate (1)

In a 3-neck 25 mL round-bottomed flask, 3-(3-chlorophenyl)-1H-1,2,4-triazole (3.0 g, 1 eq.) was mixed with DMF (40 mL, 13 Vol.), sodium hydride (1.0 g, 1.5 eq.) and reaction mixture was stirred at room temperature for 1 h. To this reaction mixture, c is 1,2-dichloro ethylene (1.5 mL, 1.2 eq.) was added drop-wise and the reaction mixture was heated at 125° C. for 12 h. Reaction remained black colored solution throughout the reaction time. Reaction completion was monitored on TLC using ethyl acetate:n-hexane (3:7) as mobile phase. After completion of the reaction (12 h), the reaction mixture was brought to room temperature and quenched into the ice-water slurry (100 mL) and compound was extracted in the ethylacetate (50 mL×3). Organic layer was washed with brine solution (50 mL×3) and dried over anhydrous sodium sulphate. Organic layer was concentrated under reduced pressure to afford 4.0 g of crude compound. The crude compound was further purified by flash chromatography using ethylacetate:hexane as mobile phase. Column purification was started with neat hexane and polarity was increased upto 5% ethylacetate. Compound started eluting in 5% ethylacetate and polarity was maintained till product elution was completed. Fractions containing compound was concentrated under reduced pressure using rotary evaporation at 45° C./250 mmHg to obtain 0.237 g of pure compound, Yield (59%). Mass/LCMS: 240.0, NMR: Confirmed.

Synthesis of Intermediate (2)

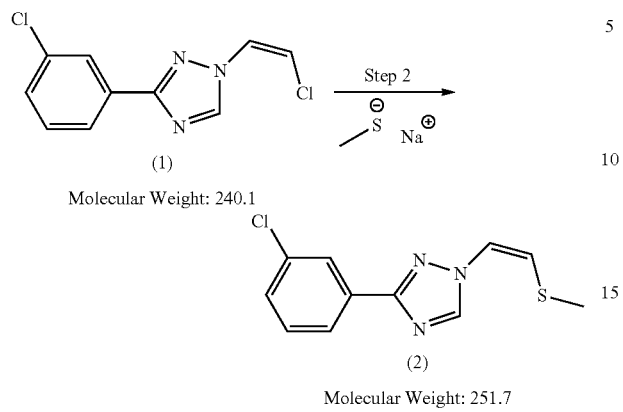

(1)
Molecular Weight: 240.1

(2)
Molecular Weight: 251.7

In a 1-neck 25 mL round-bottomed flask, Intermediate) (0.187 g, 1 eq.) was dissolved in HMPA (32 mL, 27 Vol.) and Sodium thiomethoxide (0.082 g, 1.5 eq.) was added drop-wise. The reaction mixture was stirred at RT for 30 min. Reaction completion was monitored on TLC using ethyl acetate:hexane (3:7) mobile phase. Reaction mixture was brought to room temperature and quenched into the ice-water slurry (100 mL) and compound was extracted in the Ethyl acetate (50 mL×3). Organic layer was washed with brine solution (50 mL×3) followed by drying using anhydrous sodium sulphate. Organic layer was concentrated under reduced pressure to afford 0.333 g of crude compound. NMR: confirmed

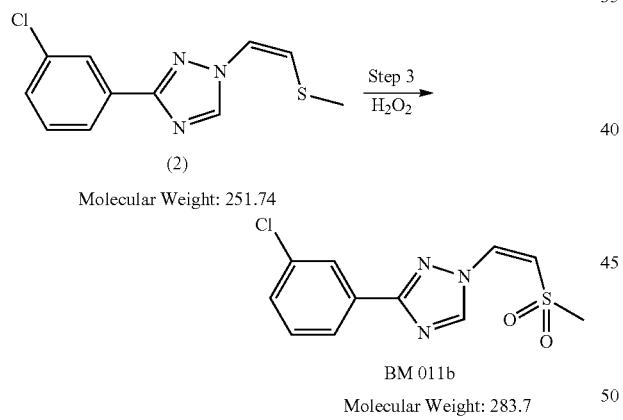

(2)
Molecular Weight: 251.74

BM 011b
Molecular Weight: 283.7

In a 3-neck 50 mL round-bottomed flask, Int-2 (0.333 g, 1 eq.) was dissolved in acetic acid (3 mL, 9 Vol) and $H_2O_2$ was added drop-wise. The reaction mixture was stirred at room temperature for 2-3 h. Reaction completion was monitored on TLC using ethyl MeOH:MDC (1:9) mobile phase. Reaction mixture was brought to room temperature and poured into the ice-water (100 mL) and compound was extracted in the Ethyl acetate (50 mL×3). Organic layer was washed with brine solution (50 mL×3) followed by drying using anhydrous sodium sulphate. Organic layer was concentrated under reduced pressure to afford 0.010 g of crude compound. 1H NMR (400 MHz, CDCl$_3$) δ=8.99 (s, 1H), 8.15 (s, 1H), 8.04-8.05 (d, J=7.2 Hz, 1H), 7.37-7.47 (m, 3H), 6.24-6.26 (d, J=8, 1H), 3.30 (s, 3H). LCMS: Calculated $C_{11}H_{10}ClN_3O_2S$ (M+H)$^+$ 283.73 Found: 283.94 at 3.193 min (94.75%).

Example 31

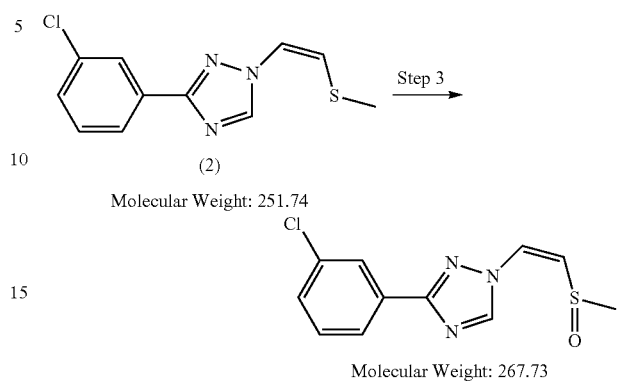

(2)
Molecular Weight: 251.74

Molecular Weight: 267.73

In a 3-neck 50 mL round-bottomed flask, Intermediate 2 (0.333 g, 1 eq.) was dissolved in acetic acid (3 mL, 9 Vol.) and $H_2O_2$ (2.0 mL, 6 Vol.) was added drop-wise. The reaction mixture was stirred at room temperature for 2-3 h. Reaction completion was monitored on TLC using ethyl MeOH:MDC (1:9) mobile phase. Reaction mixture was brought to room temperature and poured into the ice-water slurry (100 mL) and compound was extracted in the Ethyl acetate (50 mL×3). Organic layer was further washed with brine solution (50 mL×3) followed by drying using anhydrous sodium sulphate. Organic layer was concentrated under reduced pressure to afford 0.109 g of crude compound. $^1$H NMR (400 MHz, CDCl$_3$) δ=8.36 (s, 1H), 8.11 (s, 1H), 7.99-8.01 (d, J=8 Hz, 1H), 7.44-7.46 (d, J=8 Hz, 2H), 7.22-7.24 (d, J=8 Hz, 1H), 6.23-6.25 (d, J=8, 1H) 3.03 (s, 3H) LCMS: Calculated $C_{11}H_{10}ClN_3OS$ (M+H)$^+$ 267.73. Found 267.84 at 2.836 min (95.23%).

Example 32

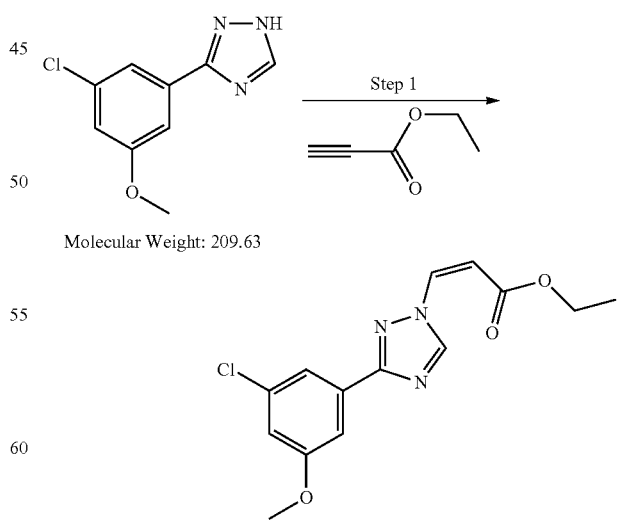

Molecular Weight: 209.63

VS-108b
Molecular Weight: 307.73

In a 3-neck 250 mL round-bottomed flask, Intermediate-1 (0.300 g, 1.43 mmol) was dissolved in DCM (9 mL, 10 Vol.). Then reaction mixture was cooled to 0° C. and TEA (0.26 mL, 1.86 mmol) was added drop-wise in the above reaction mixture. Intermediate-2 (0.182 g, 1.86 mmol) was added in the reaction mixture. Completion of reaction was monitored on TLC using ethyl acetate:hexane (4:6) as mobile phase. Organic layer was concentrated under reduced pressure. Concentrated crude material was purified through Column chromatography using 4% Ethyl acetate: n-hexane as mobile phase. $^1$H NMR [400 MHz CDCl$_3$] δ 9.70-9.72 (s, 1H), 8.18 (s, 1H), 8.01-8.04 (s, 1H), 7.27-7.30 (s, 1H), 7.01-7.03 (d, J=8.8, 1H), 5.69-5.71 (d, J=10.8, 1H), 4.26-4.31 (m, 2H), 3.98 (s, 3H), 1.30 (m, 3H): LCMS for C$_{14}$H$_{14}$ClN$_3$O$_3$ [M+1]$^+$ 307.7 found 307.8 at 3.90 min (LCMS 98.71%).

Example 33

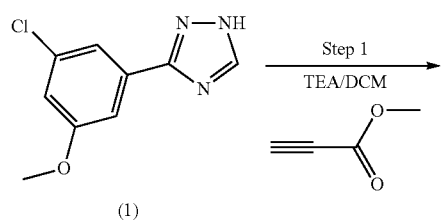

(1)
Molecular Weight: 209.63

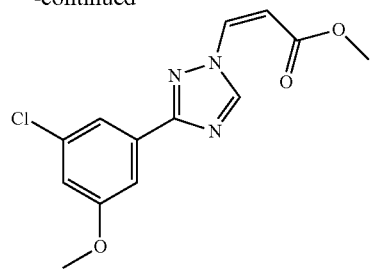

Molecular Weight: 293.71

In a 1 neck 25 mL round-bottomed flask, Intermediate-1 (0.271 g) was dissolved in DCM (5 mL, 10 Vol.). TEA (0.23 mL, 1.3 eq.) and Intermediate-2 (0.141 g, 1.3 eq.) was added to the above reaction mixture. Reaction mixture was stirred at RT for 30 minutes. Completion of reaction was monitored on TLC using ethyl acetate:hexane (4:6) as mobile phase. The reaction mixture was dumped in water (25 mL). Aqueous layer was extracted with DCM (3×25 mL). Organic layer was dried over sodium sulphate. Solvent was evaporated to dryness under reduced pressure to obtain crude material. Concentrated filtrate was purified by Column chromatography using 4% Ethyl acetate in Hexane. Yield: 13.18% $^1$H NMR [400 MHz CDCl$_3$] δ 9.71 (s, 1H), 8.18 (s, 1H), 8.04-8.06 (d, J=8, 1H), 7.28-7.31 (d, J=12, 1H), 7.01-7.03 (d, J=12, 1H), 5.70-5.73 (d, J=12, 1H), 3.98 (s, 3H), 3.83 (s, 3H): LCMS for C$_{13}$H$_{12}$ClN$_3$O$_3$ [M+1]$^+$ 293.7 found 293.86 at 3.71 min (LCMS 97.79%).

Example 34

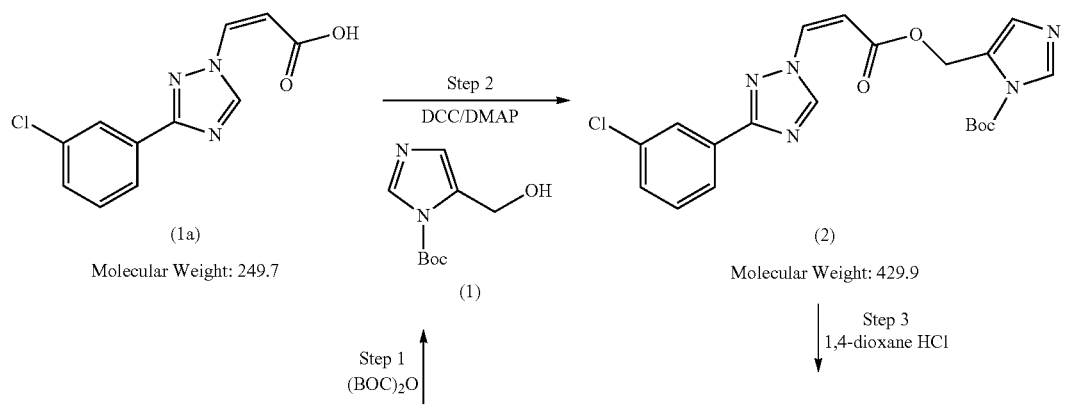

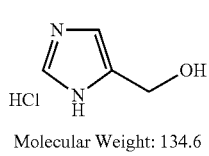

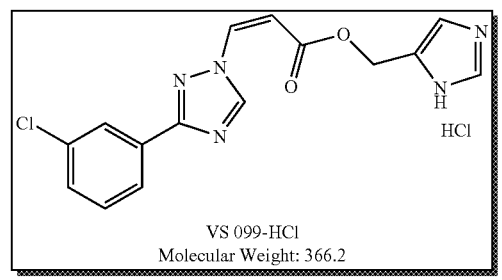

Synthesis of Intermediate (1)

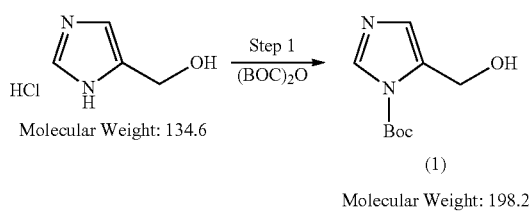

(1)
Molecular Weight: 198.2

In a 3-neck 50 mL round-bottomed flask, (1H-pyrazol-5-yl)methanol hydrochloride (1.0, 1 eq.) was dissolved in DCM (25 mL, 25 Vol.). The reaction mixture was cooled to 0-5° C. To this reaction mixture, TEA (1.49 g, 2.0 eq.) and Boc anhydride (1.72 g, 1.1 eq.) was added drop-wise and stirred the reaction mixture at RT for 3-4 h. Reaction completion was monitored on TLC using ethyl acetate: n-hexane (5:5) mobile phase. Reaction mixture was quenched into the ice-water slurry (50 mL) and compound was extracted in the DCM (50 mL×3). Organic layer was washed with brine solution (50 mL×3) followed by drying using anhydrous sodium sulphate. Organic layer was concentrated under reduced pressure to afford 2.5 g of crude compound. Crude compound was further purified by column chromatography using silica 60/120 and ethylacetate:n-hexane as mobile phase. Compound started eluting in 25% ethylacetate and continued till 35% EtOAc. Fractions containing compound was distilled out using rotary evaporation at 45° C./250 mmHg to obtain 0.50 g of pure compound, yield (34.01%). NMR: Confirmed.

Synthesis of Intermediate (2)

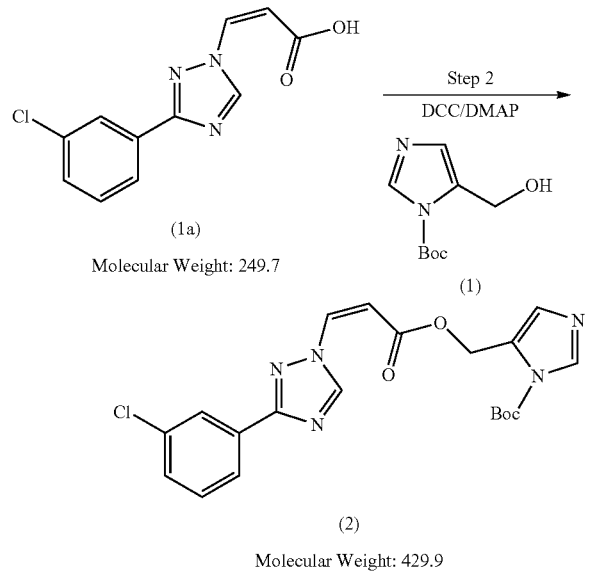

(2)
Molecular Weight: 429.9

In a 3-neck 50 mL round-bottomed flask, Intermediate 1 (0.5 g, 1.0 eq.) was mix with intermediate 1a (0.692 g, 1.1 eq.) using DCM (10 mL, 20 Vol.) as solvent. Reaction mixture was cooled to 0-5° C. and DCC (0.578 g, 1.1 eq.) was added using DMAP (0.031 g, 0.1 eq.) in catalytic amount. The reaction mixture was stirred at RT for 2-3 h. Reaction completion was monitored on TLC using ethyl acetate: n-hexane (5:5) as mobile phase. Reaction mixture was filtered through celite bed to remove dicyclohexyl urea. Crude compound was further purified by column chromatography using silica 60/120 and ethylacetate:n-hexane as mobile phase. Column purification was started with 5% EtOAc in hexane upto 25% EtOAc. Compound started eluting in 22% ethylacetate and continued till 25% EtOAc. Fractions containing compound was distilled out using rotary evaporation at 45° C./250 mm Hg to obtain 0.2 g of pure compound yield (18.45%). Mass/LCMS: 87.17%, NMR: recorded.

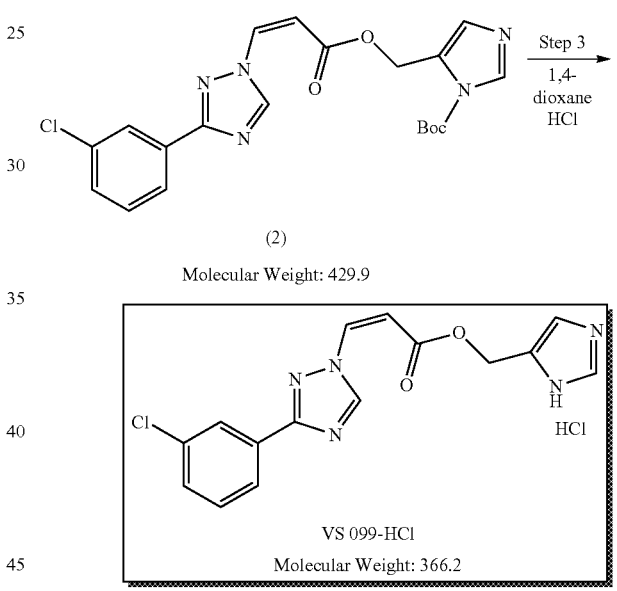

(2)
Molecular Weight: 429.9

VS 099-HCl
Molecular Weight: 366.2

In a 3-neck 50 mL round-bottomed flask, Intermediate-2 (0.12 g, 1.0 eq.) was dissolved in 1,4-dioxane (2 mL, 17 Vol.) and added 1,4-Dioxane HCl (0.5 mL, 4.2 Vol.). The reaction mixture was stirred at RT for overnight. Reaction completion was monitored on TLC using neat ethyl acetate as a mobile phase and worked up. The reaction mixture was concentrated under reduced pressure to afford 0.13 g of crude compound. The Compound was triturated using ether and dried under reduced pressure to afforded pure compound. Yield (43%). $^1$H NMR (400 MHz, DMSO-$d_6$) δ 14.65 (broad s, 1H, $D_2O$ exchangeable), 9.24 (S, 1H), 9.10 (S, 1H), 7.96 (S, 1H), 7.31 (S, 1H), 7.93-7.90 (m, 1H), 7.77 (S, 1H), 7.60-7.56 (m, 3H), 6.04-6.02 (d, J=10.0 Hz, 1H), 5.76 (s, 1H): LCMS for $C_{15}H_{13}Cl_2N_5O_2$ [M−H]$^+$ 365.2 found 329.8 at 5.872 min (LCMS 92.06%).

Example 35

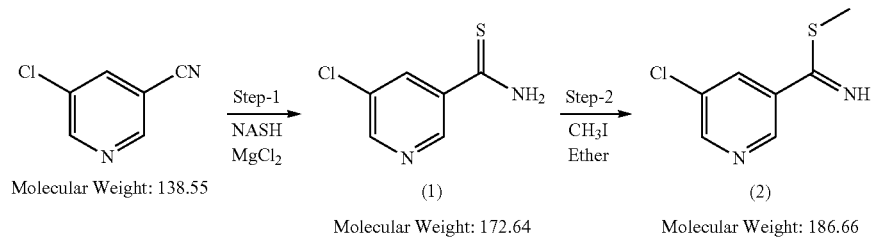

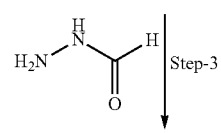

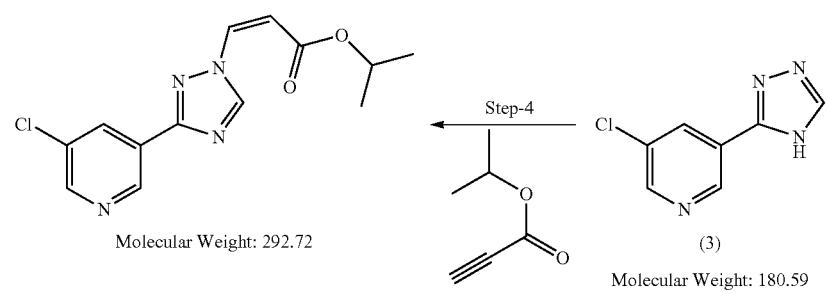

Synthesis of Intermediate (1)

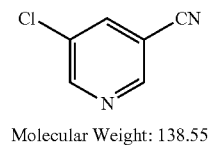

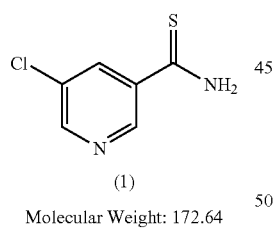

In a 3-neck 100 mL round-bottomed flask, 5-Chloro-3-Cyanopyridine (5.0 g, 1 eq.) was mixed with DMF (50 mL, 10 Vol.) and added Sodium hydrosulfide (5.34 g, 2 eq.) and Magnesium Chloride (8.03 g 1.12 eq.) Reaction mixture was stirred at room temperature for 3 h. Reaction remained yellow colored clear solution throughout the reaction. Reaction completion was monitored on TLC using ethyl acetate:hexane (4:6) mobile phase. After 3 hr reaction was completed and worked up. Reaction mixture was brought to room temperature and quenched into the ice-water slurry (250 mL) and compound was extracted in the ethylacetate (100 mL×3). Organic layer was washed with brine solution (100 mL×3) followed by drying using anhydrous sodium sulphate. Organic layer was concentrated under reduced pressure to afford 5.0 g of crude compound.

Synthesis of Intermediate (2)

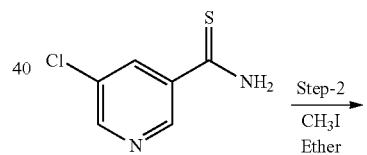

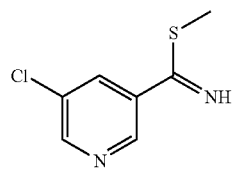

In a 1-neck 100 mL round-bottomed flask, (1) (5.0 g, 1 eq.) was dissolved in Diethyl Ether (50 mL, 10 Vol.) and Methyl Iodide (7.3 mL, 4.0 eq.) were added drop-wise and reaction mixture was stirred at room temperature for 42 h. Reaction completion was monitored on TLC using ethyl acetate: n-hexane (5:5) mobile phase. Reaction mixture was filtered on Buckner funnel and 20 mL diethyl ether wash given to 6 g of compound.

Synthesis of Intermediate (3)

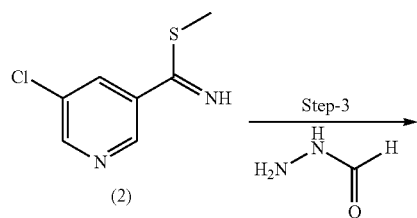

Molecular Weight: 188.68

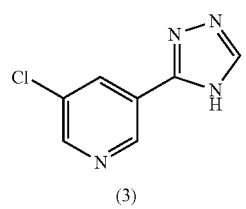

Molecular Weight: 180.59

In a 3-neck 100 mL round-bottomed flask, intermediate (2) (6.0 g, 1 eq.) was dissolved in DMF (30 mL, 5 Vol.) and Formic Hydrazide (3.85 g, 2.0 eq.) was added into this. Reaction mixture was stirred at room temperature for 1 h and then refluxed to 90° C. for 3-4 h. Reaction completion was monitored on TLC using ethyl acetate: n-hexane (5:5) mobile phase. Reaction mixture was brought to room temperature and quenched into the ice-water slurry (500 mL) and the compound was extracted in the ethyl acetate (50 mL×3). Organic layer was washed with brine solution (50 mL×3) followed by drying using anhydrous sodium sulphate. Organic layer was concentrated under reduced pressure to afford 5.5 g of crude compound. Crude compound was further purified by column chromatography using silica 60/120 and ethylacetate:n-hexane as mobile phase. Column purification was started with 5% EtOAc in hexane up to 35%. Compound started eluting in 30% ethyl acetate and continued till 35% EtOAc. Fractions containing compound were distilled out using rotary evaporation at 45° C./250 mm Hg to obtain 2 g of crude compound yield (34%).

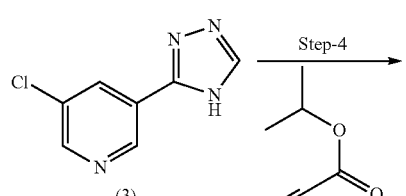

Molecular Weight: 180.59

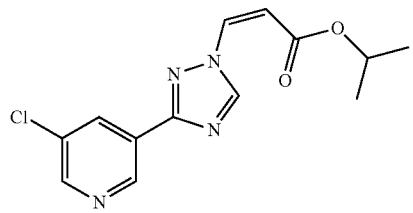

In a 1-neck 100 mL round-bottomed flask, (3) (1.0 g, 1 eq.) was dissolved in DCM (40 mL, 4 Vol.) and added TEA (0.99 g, 1.3 eq.). The reaction mixture was cooled to 15° C. for 20 min and isopropyl propiolate was added (0.0795 g, 1.3 eq.) to reaction mixture. The nitrogen atmosphere was maintained throughout the reaction. Reaction completion was monitored on TLC using ethyl acetate:hexane (2:8) mobile phase. Organic layer was concentrated under reduced pressure to afford 1 g of crude compound. Crude compound was further purified by column chromatography using silica 60/120 and ethylacetate:n-hexane as mobile phase. Column purification was started with 5% EtOAc in hexane up to 20%. Compound started eluting in 20% ethylacetate and continued till 25% EtOAc. Fractions containing compound was distilled out using rotary evaporation at 45° C./250 mm Hg to obtain 0.130 g of crude compound yield (8.02%). $^1$HNMR (400 MHz, CDCl$_3$) δ 9.74 (s, 1H), 9.24 (s, 1H), 8.64 (s, 1H), 8.42 (s, 1H), 7.28 (d, J=10.8 Hz, 1H), 5.76 (d, J=11.2 Hz, 1H), 5.166 (m, 1H), 1.347 (d, 6H): LCMS for C$_{13}$H$_{13}$ClN$_4$O$_2$ [M+H]$^+$ 292.72 found at 292.90 at 6.489 min (LCMS 97.72%).

Example 36

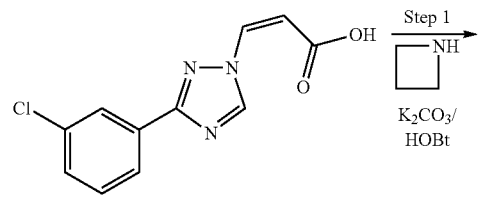

Molecular Weight: 249.7

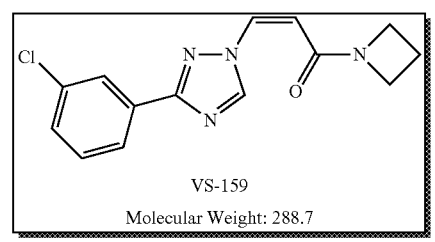

VS-159
Molecular Weight: 288.7

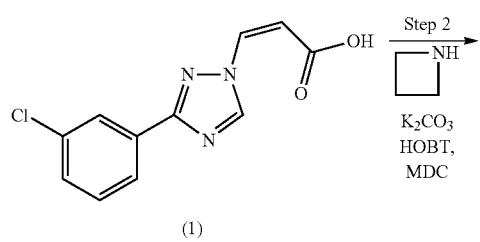

(1)
Molecular Weight: 249.7 compound was distilled out using rotary evaporation at 45° C./250 mm Hg to obtain 0.012 g of pure compound. Yield (20.75%). $^1$H NMR (400 MHz, CDCl$_3$) δ 9.77 (S, 1H), 8.16 (S, 1H), 8.02-8.05 (m, 1H), 7.38-7.43 (m, 2H), 7.15-7.18 (d, J=10.8 Hz, 1H), 5.59-5.62 (d, J=10.8 Hz, 1H), 4.23-4.27 (t, 2H), 4.15-4.19 (t, 2H), 2.32-2.40 (m, 2H): LCMS for C$_{15}$H$_{14}$ClN$_3$O [M+H]$^+$ 288.7 found 288.85 at 3.183 min (LCMS 99.15%).

Example 37

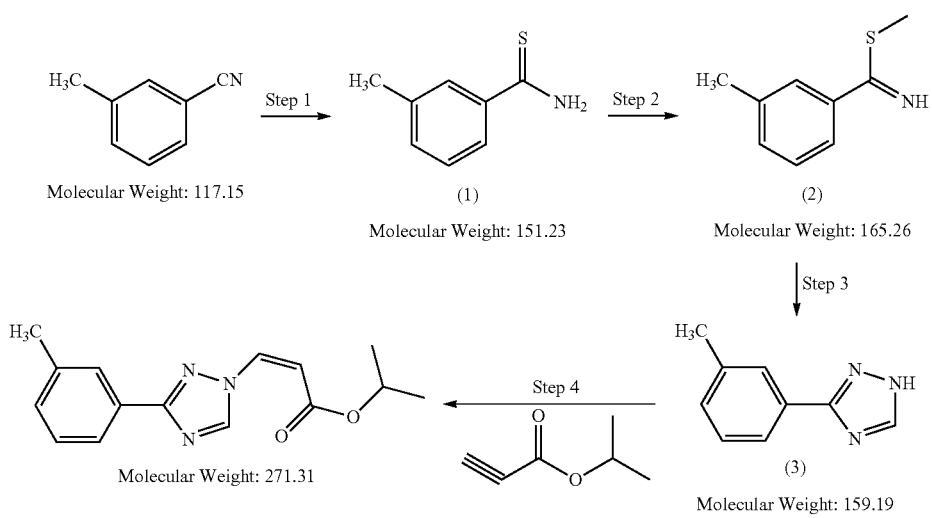

Synthesis of Intermediate (1)

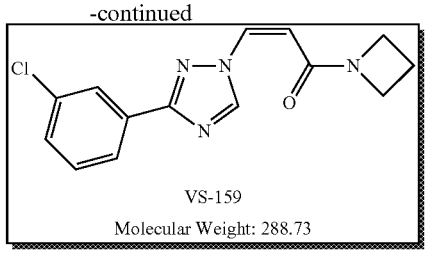

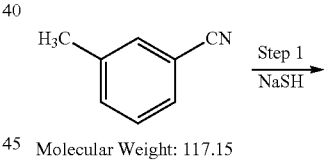

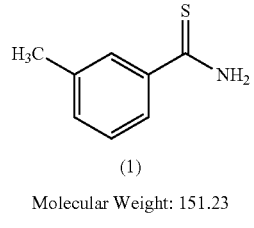

(1)
Molecular Weight: 151.23

In a 3-neck 25 mL round-bottomed flask, Intermediate 1 (from Example 7) (0.05 g, 1 eq.) was dissolved in DCM (5 mL, 10 Vol.). To this reaction mixture, DIPEA (0.031 g, 1.2 eq.), EDC HCl (0.057 g, 1.5 eq.) and azitinde (0.017 g, 1.5 eq) was added at 0° C. temperature followed by the addition of HOBT (0.036 g, 1.2 eq.). Reaction mixture was stirred at 0° C. for 2 h. Reaction completion was monitored on TLC using ethyl acetate:hexane (4:6) mobile phase. Reaction mixture was quenched into the ice-water slurry (20 mL) and compound was extracted in the Ethylacetate (10 mL×3). Compound was further purified by column chromatography using silica 60/120 and ethylacetate: n-hexane as mobile phase. Column purification was started with 5% EtOAc in hexane up to 15% EtOAc. Compound started eluting in 10% ethylacetate and continued till 12% EtOAc. Fractions containing In a 3-neck 100 mL round-bottomed flask, 3-methyl benzonitrile (4.0 g, 1 eq.) was mixed with DMF (48 mL, 13 Vol.), MgCl$_2$6H$_2$O (7.0 g, 1.0 eq.) and sodium thiol (5.05 g, 2.0 eq.). The reaction mixture was stirred at room temperature for 2 h. Reaction remained green colored clear solution throughout the reaction. Reaction completion was monitored on TLC using ethyl acetate: n-hexane (3:7) mobile phase. After 2 h reaction was completed and worked up. Reaction mixture was brought to room temperature and poured into water (100 mL) and compound was extracted in the ethylacetate (100 mL×3). Organic layer was again washed with water (100 mL×3) followed by drying using anhydrous sodium sulphate.

Organic layer was concentrated under reduced pressure to afford 5.2 g of crude compound. Crude compound was carry forward in next step. Yield (95.0%). Mass/LCMS: 152.0 Confirmed.

Synthesis of Intermediate (2)

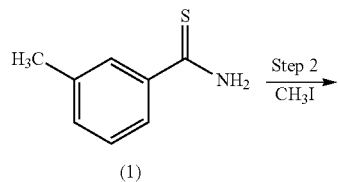

(1)
Molecular Weight: 151.23

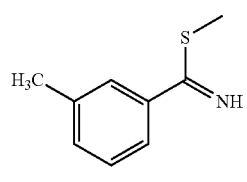

(2)
Molecular Weight: 165.26

In a 3-neck 100 ml, round-bottomed flask, Int-1 (5.2 g, 1 eq.) was dissolved in Diethyl ether (40 mL, 8 Vol.) and the reaction mixture was cooled at 0° C. and methyl iodide was added drop-wise in reaction mixture and reaction mixture was stirred at RT for overnight. Reaction completion was monitored on TLC using ethyl acetate:hexane (3:7) mobile phase. Product was filtered and washed with diethyl ether (3×50 mL). Product was dried under reduced pressure to afford 9.2 g of crude compound. Mass/LCMS: Confirmed, NMR: confirmed.

Synthesis of Intermediate (3)

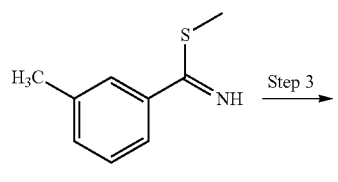

(2)
Molecular Weight: 165.26

-continued

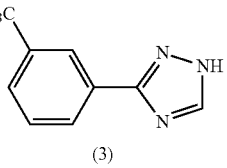

(3)
Molecular Weight: 159.19

In a 3-neck 100 mL round-bottomed flask, Intermediate 2 (9.0 g, 1 eq.) and formic hydrazide (6.5 g, 2 eq) were dissolved in DMF (54 mL, 6 Vol.) and reaction mixture was stirred at reflux temperature for 2 h. Reaction completion was monitored on TLC using ethyl MeOH:MDC (1:9) mobile phase. Reaction mixture was brought to room temperature and poured on to the ice-water (100 mL) and compound was extracted in the Ethyl acetate (100 mL×3). Organic layer was again washed with water (100 mL×3) followed by drying using anhydrous sodium sulphate. Organic layer was concentrated under reduced pressure to afford 5.0 g of crude compound and the crude product was purified by flash chromatography using ethyl acetate and hexane as mobile phase. Weight of pure product 1.3 g. Yield (15.0%). Mass/LCMS: Confirmed, NMR: Confirmed.

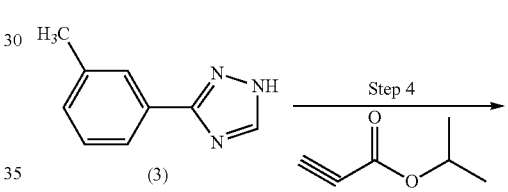

(3)
Molecular Weight: 159.19

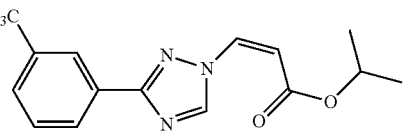

Molecular Weight: 271.31

In a 1-neck 50 mL round-bottomed flask, Int-3 (1.3 g, 1 eq.), TEA (1.44 mL, 1.2 eq.) was dissolved in MDC (15 mL, 11 Vol.). The reaction mixture was cooled to 15-20° C. and isopropyl propiolate (1.16 g, 1.2 eq.) was added drop-wise. The reaction mixture was stirred at 15-20° C. for 30 minutes. Reaction completion was monitored on TLC using Ethyl acetate:Hexane (2:8) mobile phase. Reaction mixture was brought to room temperature and poured into the water (100 mL) and compound was extracted in the Ethyl acetate (50 mL×3). Organic layer was again washed with water (50 mL×3) followed by drying using anhydrous sodium sulphate. Organic layer was concentrated under reduced pressure to afford 1.2 g of crude compound, Product was purified by flash chromatography using ethyl acetate and Hexane to afford 0.140 g pure compound. Yield (6.3%). $^1$H NMR (400 MHz, CDCl$_3$) δ 9.72 (S, 1H), 7.98 (S, 1H), 7.94-7.96 (d, J=8.0 Hz, 1H), 7.35-7.39 (t, 1H), 7.28-7.26 (d, 2H), 5.66-5.68 (d, J=10.8 Hz, 1H), 5.11-5.18 (m, 1H), 2.44 (d, 6H), 1.32-1.34 (d, 61H): LCMS for C$_{15}$H$_{17}$N$_3$O$_2$ [M+H]$^+$ 271.3 found 271.98 at 4.102 min.

Example 38

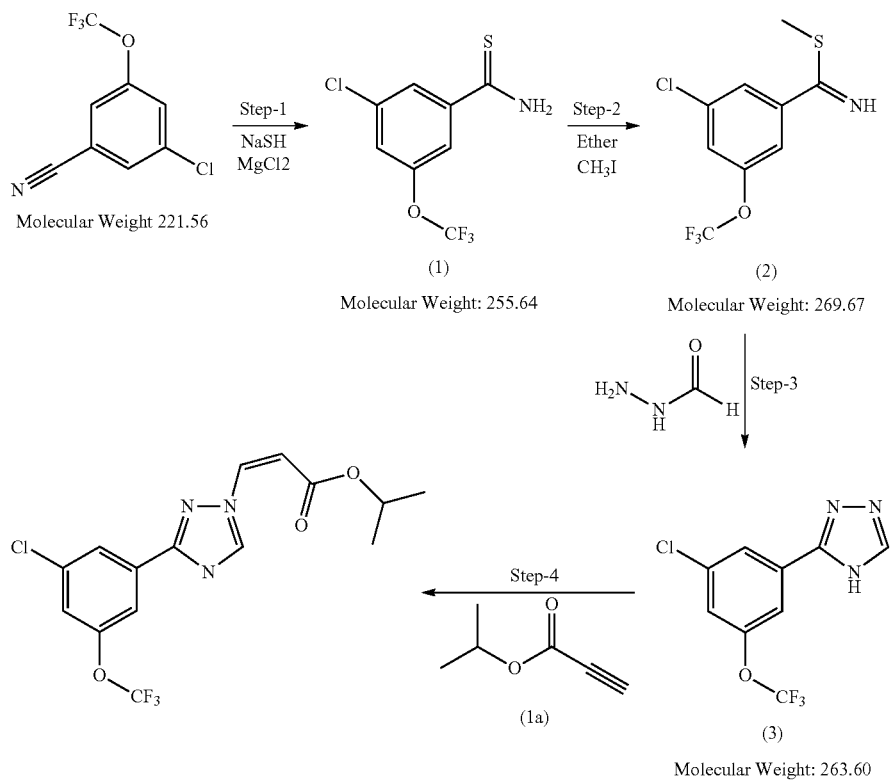

Synthesis of Intermediate (1)

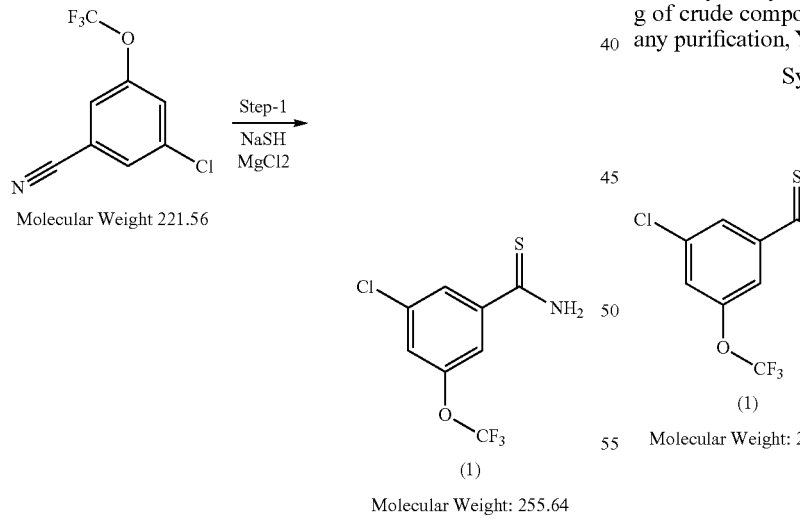

In a 250-mL, 3N round-bottomed flask equipped with nitrogen inlet, and a rubber septum, 3-chloro-5-(trifluoromethoxy)Benzonitrile (5.0 g, 1.0 eq) was dissolved in DMF (100 mL, 20V) and NaSH (3.33 g, 2.0 eq) and MgCl$_2$ (5.04 g, 1.1 eq) was added. Reaction mixture was stirred at RT for 2-3 h. The progress of the reaction was followed by TLC analysis on silica gel with 40% EtOAc-n-hexane as mobile phase. SM R$_f$=0.5 and Product R$_f$=0.3. Reaction mixture was poured into ice water (500 mL) and extracted with EtOAc (3×100 mL). The combined organic layers were washed with brine solution (3×100 mL), dried over MgSO$_4$, filtered, and concentrated by rotary evaporation (25° C., 20 mmHg) to afford 5.0 g of crude compound which was used for next step without any purification, Yield (86.8%). Mass: 256.1.

Synthesis of Intermediate (2)

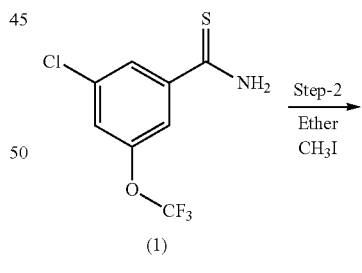

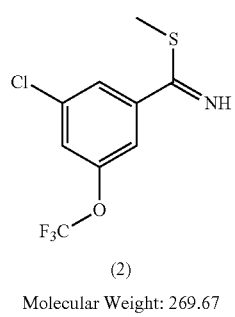

In a 250-mL, 3N round-bottomed flask equipped with nitrogen inlet, and a rubber septum, Intermediate-1 (1.8 g, 1.0 eq) was dissolved in Diethyl ether (50 mL, 10V), and Methyl Iodide (13.88 g, 5.0 eq) was added dropwise. Reaction mixture was stirred at RT for 12 h. The progress of the reaction was followed by TLC analysis on silica gel with 20% EtOAc-n-hexane as mobile phase. SM $R_f$=0.5 and Product $R_f$=0.3. Reaction mixture was filtered and concentrated using rotary evaporation (25° C., 20 mmHg) to afford 5.0 g of crude compound which was used for next step without any purification, Yield (94.87). Mass: 269.9.

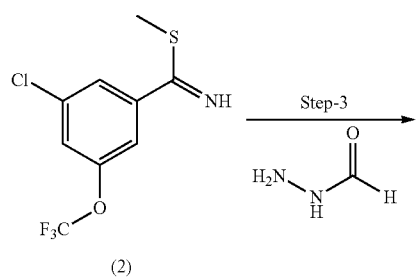

(2)

Molecular Weight: 269.67

In a 250-mL, 3N round-bottomed flask equipped with nitrogen inlet, and a rubber septum, Intermediate-2 (5.0 g, 1.0 eq.) was dissolved in DMF (100 mL, 20V) and NH$_2$NH$_2$.H$_2$O (25.0 mL, 5V) was added into it. The reaction mixture was stirred at RT for 1 h. Reaction mixture was refluxed at 90° C. for 2-3 h and HCOOH (25.0 mL, 5V) was added to this reaction mixture. The progress of the reaction was followed by TLC analysis on silica gel with 50% Ethyl acetate-n-Hexane as mobile phase. SM $R_f$=0.50 and Product $R_f$=0.3. Reaction mixture was poured into ice-water (500 mL) and neutralized with Saturated Sodium bicarbonate solution. The reaction mixture was extracted with EtOAc (3×100 mL). The combined organic layers were washed with brine solution (3×100 mL), dried over MgSO$_4$, filtered, and concentrated by rotary evaporation (25° C., 20 mmHg) to afford 4.0 g of Crude compound, which was used for next step without any purification Yield (81.9%). Mass: 264.1.

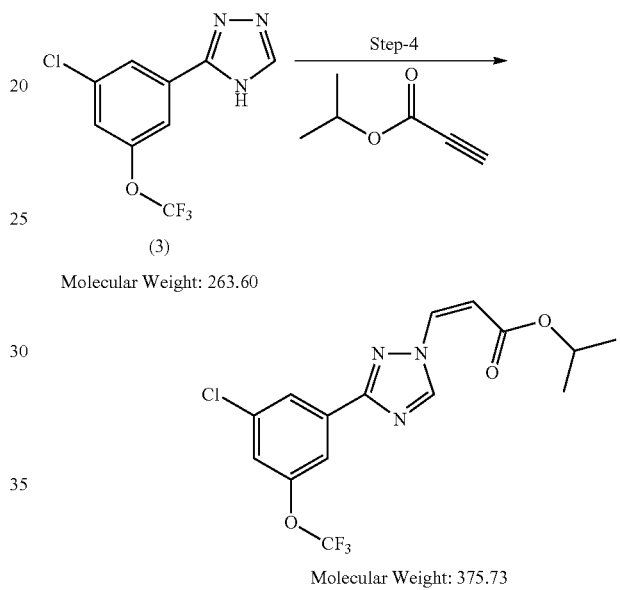

Molecular Weight: 263.60

Molecular Weight: 375.73

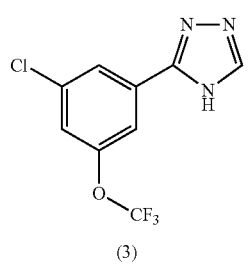

(3)

Molecular Weight: 263.60

In a 250-mL, 3N round-bottomed flask equipped with nitrogen inlet, and a rubber septum, Intermediate-3 (4.0 g, 1.0 eq.) was dissolved in DCM (80 mL, 20V), added TEA (1.99 g, 1.3 eq) and isopropyl propiolate (2.21 g, 1.3 eq) was added. The Reaction mixture was stirred at RT for 30 min. The progress of the reaction was followed by TLC analysis on silica gel with 50% Ethyl acetate-Hexane as mobile phase. SM $R_f$=0.30 and Product $R_f$=0.5. Reaction mixture was concentrated by rotary evaporation (25° C., 20 mmHg) to afford 4.12 g of Crude compound. The crude reaction mixture was purified by column chromatography using silica 60/120 using Ethyl acetate:Hexane as mobile phase. The column (5×10 cm) was packed in Hexane and started eluting in Ethyl acetate in gradient manner starting with fraction collection (100-mL fractions) from 5% to 20% Ethyl acetate in hexane. Compound started eluting with 20% Ethyl acetate in Hexane. Fraction containing such TLC profile was collected together to obtain pure compound (0.750 mg), Yield (13.16%). $^1$H NMR (400 MHz, CDCl$_3$) δ 9.72 (S, 1H), 8.11 (S, 1H), 7.92 (S, 1H), 7.31 (S, 1H), 7.26-7.28 (d, J=10.8 Hz, 1H), 5.72-5.75 (d, J=10.8 Hz, 1H), 5.11-5.16 (m, 1H), 1.34-1.36 (d, 6H): LCMS for C$_{15}$H$_{13}$ClF$_3$N$_3$O$_3$ [M+H]$^+$ 375.7 found 375.78 at RT 4.900 min (LCMS 99.41%).

207
Example 39
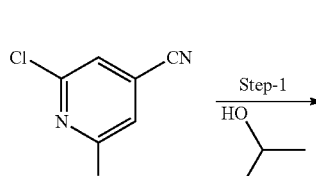
Molecular Weight: 173.00
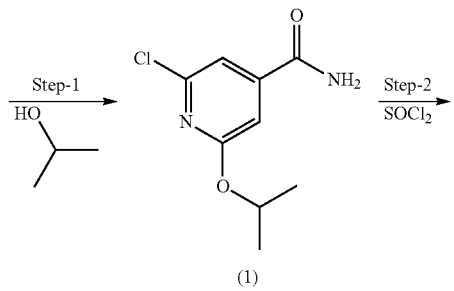
(1)
Molecular Weight: 214.65
208
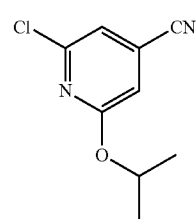
(2)
Molecular Weight: 196.63
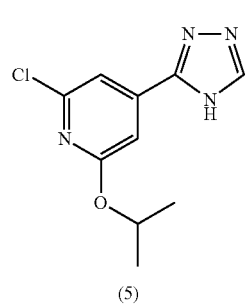
(5)
Molecular Weight: 238.67
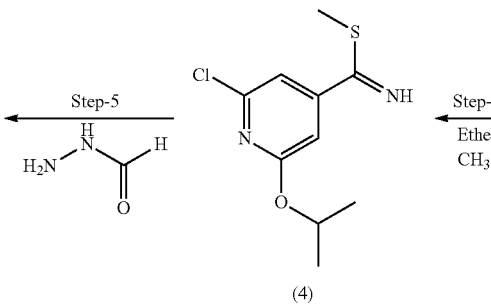
(4)
Molecular Weight: 244.74
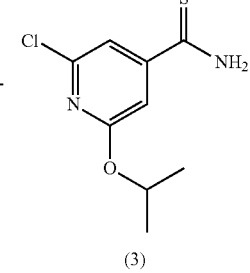
(3)
Molecular Weight: 230.71
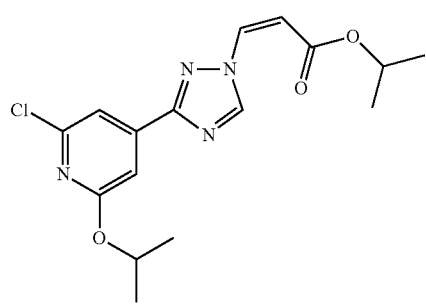
Molecular Weight: 350.80

Synthesis of Intermediate (1)

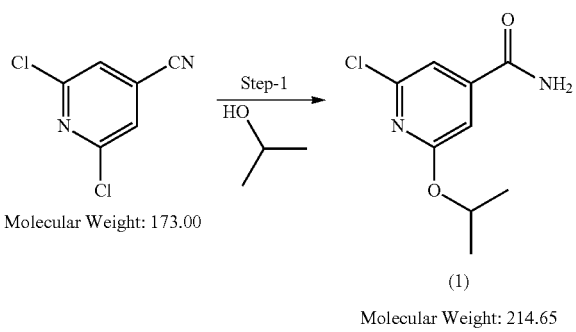

Molecular Weight: 173.00

Molecular Weight: 214.65

In a 3-neck 100 mL round-bottomed flask, Iso propyl alcohol (2.0, 1.2 eq.) was dissolved in THF (50 mL, 10 Vol), added NaH portion wise in reaction mixture. Stirred the reaction mixture at RT for 1 hr. Cooled the reaction mixture at 0° C. and added 2,6-dichloroisonicotinonitrile (5.0 q, 1.0 eq) Portion wise in reaction mixture. Reaction mixture was refluxed for overnight. Reaction completion was monitored on TLC using ethyl acetate:hexane (3:7) mobile phase. Reaction mixture was brought to room temperature and quenched into the ice-water slurry (250 mL) and compound was extracted in the ethyl acetate (50 mL×3). Organic layer was washed with brine solution (50 mL×3) followed by drying using anhydrous sodium sulphate. Organic layer was concentrated under reduced pressure to afford 5 g of crude compound, Yield (88.18%). This crude material was directly used for next step without purification. Mass: 214.9.

Synthesis of Intermediate (2)

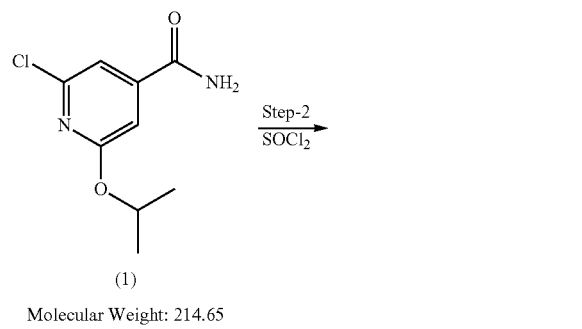

Molecular Weight: 214.65

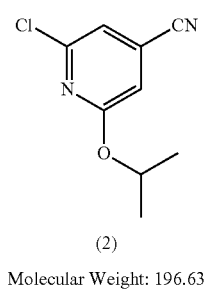

Molecular Weight: 196.63

In a 3-neck 100 mL round-bottomed flask, Intermediate 1 (5.0 g, 1 eq.) was dissolved in Toluene (50 mL, 10 Vol) and added $SOCl_2$ (5.54 g, 2.0 eq.) and reaction mixture was refluxed to 90° C. for Overnight. Reaction completion was monitored on TLC using ethyl acetate:hexane (2:8) mobile phase. Reaction mixture was brought to room temperature and quenched into the ice-water slurry (300 mL) and Neutralized with sodium bi carbonate solution. Compound was extracted in the E.A (100 mL×3). Organic layer was washed with brine solution (100 mL×3) followed by drying using anhydrous sodium sulphate. Organic layer was concentrated under reduced pressure to afford 4.12 g of crude compound, yield (89.76%). This crude material was directly used for next step without purification. Mass/LCMS: Mass was not confirmed for this compound.

Synthesis of Intermediate (3)

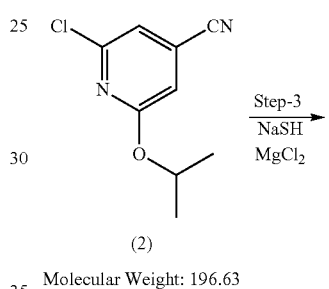

Molecular Weight: 196.63

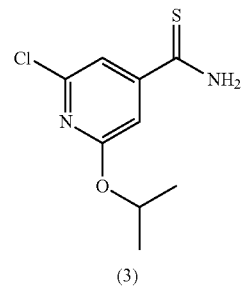

Molecular Weight: 230.71

In a 1-neck 100 mL round-bottomed flask, Intermediate-2 (4.12 g, 1.0 eq.) was dissolved in DMF (40 mL, 10 V) added (3.1 g, 2.0 eq) and $MgCl_2$ (4.67 g, 1.1 eq) in reaction mixture. The reaction mixture was stirred for 3-4 h at RT. Reaction completion was monitored on TLC using ethyl acetate:hexane (2:8) mobile phase. Reaction mixture was brought to room temperature and quenched into the ice-water slurry (250 mL) and compound was extracted in the E.A (100 mL×3). Organic layer was washed with brine solution (100 mL×3) followed by drying using anhydrous sodium sulphate. Organic layer was concentrated under reduced pressure to afford 3.8 g of crude compound, yield (79.16%). This crude material was directly used for next step without purification. Mass/LCMS: 230.8.

Synthesis of Intermediate (4)

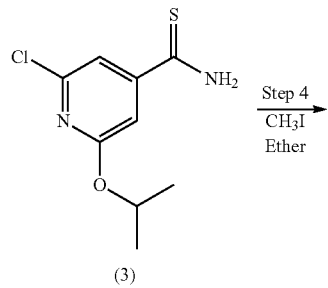

(3)
Molecular Weight: 230.71

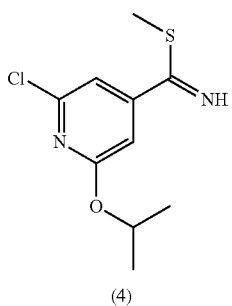

(4)
Molecular Weight: 244.74

In a 1-neck 100 mL round-bottomed flask, Intermediate-3 (3.8 g, 1 eq.) was dissolved in Diethyl ether (38 mL, 10V) and added Methyl Iodide (11.6 g, 5.0 eq.) and reaction mixture was stirred at RT for overnight. Reaction completion was monitored on TLC using ethyl acetate:hexane (3:7) mobile phase. In reaction mixture yellow solid material was obtained, filtered and wash with Diethyl ether (10 mL×2). Dried over Vacuum to afford 3.0 g of crude compound, yield (75.0%). This crude material was directly used for next step without further purification. Mass/LCMS: 244.9.

Synthesis of Intermediate (5)

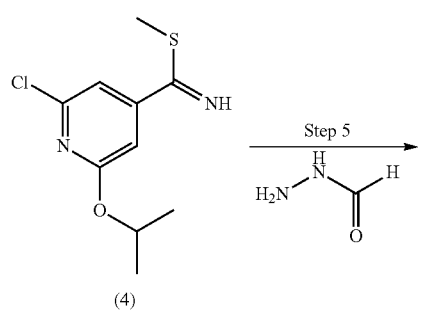

(4)
Molecular Weight: 244.74

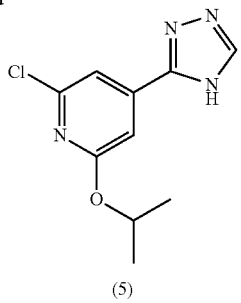

(5)
Molecular Weight: 238.67

In 3-neck 50 mL round-bottomed flask, Intermediate 4 (3.0 g, 1.0 eq.) was dissolved DMF (30 mL, 10) and added formic hydrazide (1.47 g, 2.0 eq.) and reaction mixture was refluxed to 90° C. for 3-4 h. Reaction completion was monitored on TLC using ethyl acetate:hexane (5:5) mobile phase. Reaction mixture was brought to room temperature and quenched into the ice-water slurry (150 mL) and compound was extracted in the Ethyl acetate (50 mL×3). Organic layer was washed with brine solution (50 mL×3) followed by drying using anhydrous sodium sulphate. Organic layer was concentrated under reduced pressure to afford 3.2 g of crude compound. Product was purified by flash chromatography using ethyl acetate and Hexane to afford 0.700 g pure compound, Yield (23.97%). Mass/LCMS: 238.8.

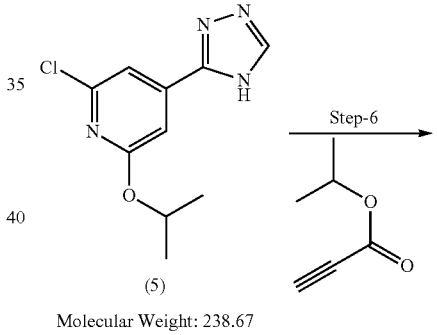

(5)
Molecular Weight: 238.67

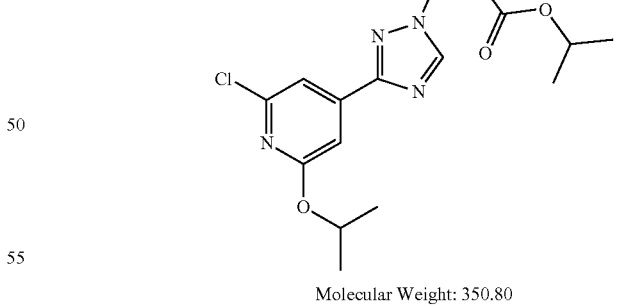

Molecular Weight: 350.80

In 1-neck 25 mL round-bottomed flask, Intermediate-5 (0.6 g, 1.0 eq.), was dissolved in DCM (10 mL, 10 vol.), added TEA (0.279 g, 11 eq) and added Isopropyl propionate (0.309 g, 1.1 eq.). Reaction mixture was stirred at RT for 30 minutes. Reaction completion was monitored on TLC using Ethyl acetate:Hexane (2:8) mobile phase. Reaction mixture was concentrated under reduced pressure to afford 0.7 g of crude compound; Product was purified by flash chromatography using ethyl acetate and Hexane to afford 0.130 g pure compound, Yield (14.73%). ¹H NMR (400 MHz, CDCl₃) δ 9.72 (s, 1H), 7.59 (s, 1H), 7.33 (s, 1H), 7.25-7.28 (d, J=11.2 Hz, 1H), 5.72-5.75 (d, J=10.8 Hz, 1H), 5.31-5.72 (m, 1H), 5.11-5.17 (m, 1H), 1.37-1.39 (d, 6H), 1.32-1.34 (d, 6H). LCMS-ESI calcd for $C_{16}H_{19}ClN_4O_3$ [M+1]⁺ 350.80. found 350.87 at 5.25 min (LCMS 98.32%).

Example 40

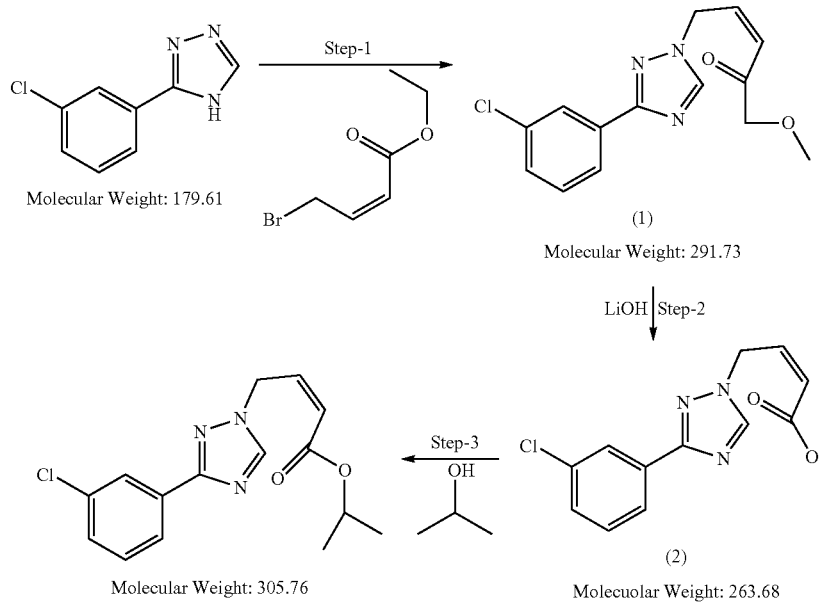

Synthesis of Intermediate (1)

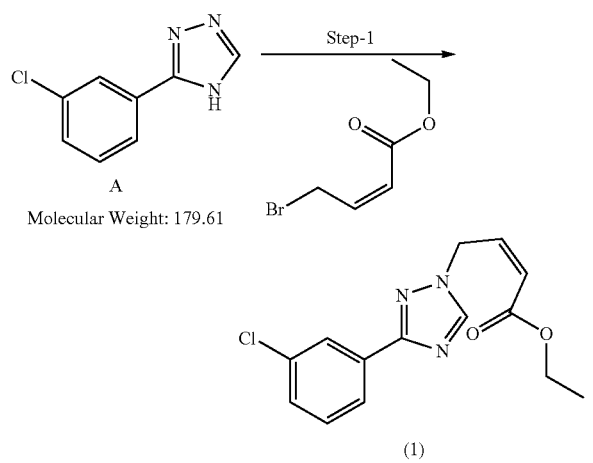

In a 3-neck 100 mL round-bottomed flask, Intermediate-A (5.0 g, 1 eq.) and NaH (0.737 g, 1.1 eq.) were mixed with DMF (50 mL, 10 Vol.). The reaction mixture was stirred at 0° C. for 1 h and Ethyl 4-bromo crotonate (6.4 mL, 1.2 eq.) was added drop-wise in reaction mixture at 0° C. The reaction mixture was stirred at room temperature for 15 min. and then heated at 80° C. for 1 h. Reaction completion was monitored on TLC using ethyl acetate: n-hexane (5:5) as mobile phase. After the reaction was completed, it was worked up. Reaction mixture was brought to room temperature and quenched into the ice-water slurry (100 mL) and compound was extracted in the ethyl acetate (100 mL×3). Organic layer was washed with brine solution (50 mL×3) followed by drying using anhydrous sodium sulphate. Organic layer was concentrated under reduced pressure to afford 5.5 g of crude compound. Mass/LCMS: 292.0, NMR: Confirmed.

Synthesis of Intermediate (2)

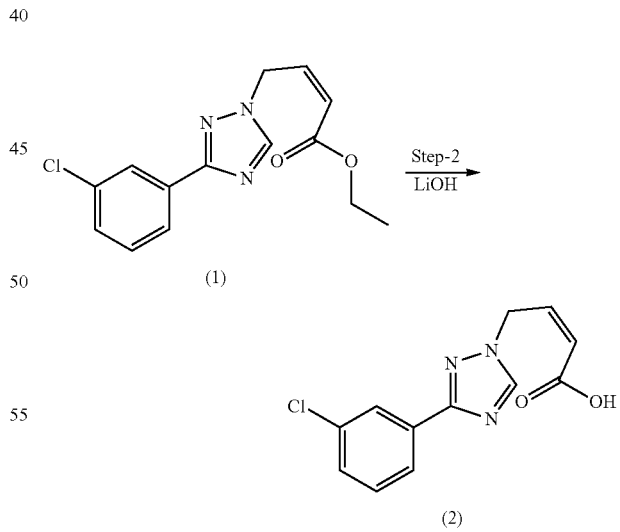

In a 3-neck 50 mL round-bottomed flask, Intermediate-1 (2.15 g, 1 eq.) and LiOH (0.622 g, 2 eq.) were dissolved in THF (6 mL) and H₂O (6 mL) and the reaction mixture was stirred at room temperature for 45 min. Reaction completion was monitored on TLC using ethyl acetate: n-hexane (5:5) mobile phase. Reaction mixture was quenched into the ice-water and adjusted the pH to 2.0 with Conc. HCl (2 mL) and compound was extracted in the ethyl acetate (50 mL×3). Organic layer was washed with brine solution (50 mL×3) followed by drying using anhydrous sodium sulphate. Organic layer was concentrated under reduced pressure to afford 2.2 g of crude compound, yield (57.8%). NMR: Confirmed

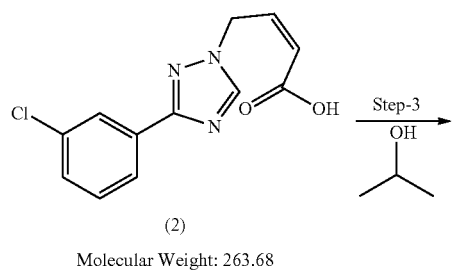

(2)
Molecular Weight: 263.68 tored on TLC using ethyl acetate:hexane (2:8) as mobile phase. Reaction mixture was brought to the room temperature and quenched into the ice-water slurry (100 mL). The compound was extracted in the DCM (50 mL×3). Organic layer was washed with brine solution (50 mL×3) followed by drying using anhydrous sodium sulphate. Organic layer was concentrated under reduced pressure to afford 3.7 g of crude compound. Crude compound was further purified by column chromatography using silica 60/120 and ethyl acetate:hexane as mobile phase. Column purification was started with 2% EtOAc in hexane up to 7%. Compound started eluting in 5% ethyl acetate and continued till 7% EtOAc. Fractions containing compound were distilled out using rotary evaporation at 45° C./250 mm Hg to obtain 0.082 g of pure compound yield (3.2%). $^1$H NMR (400 MHz, CDCl$_3$) δ 8.14-8.18 (d, 2H), 8.00-8.02 (t, 1H), 7.40-7.45 (t, 2H), 7.02-7.09 (m, 1H), 5.84-5.88 (d, 1H), 5.04-5.12 (m, 1H), 5.01-5.02 (d, 2H), 1.27-1.28 (d, 8H) LCMS-ESI calculated for C$_{15}$H$_{16}$ClN$_3$O$_2$ [M+H]$^+$ 305.76. found 305.85 at 3.96 min. (93.76).

Example 41

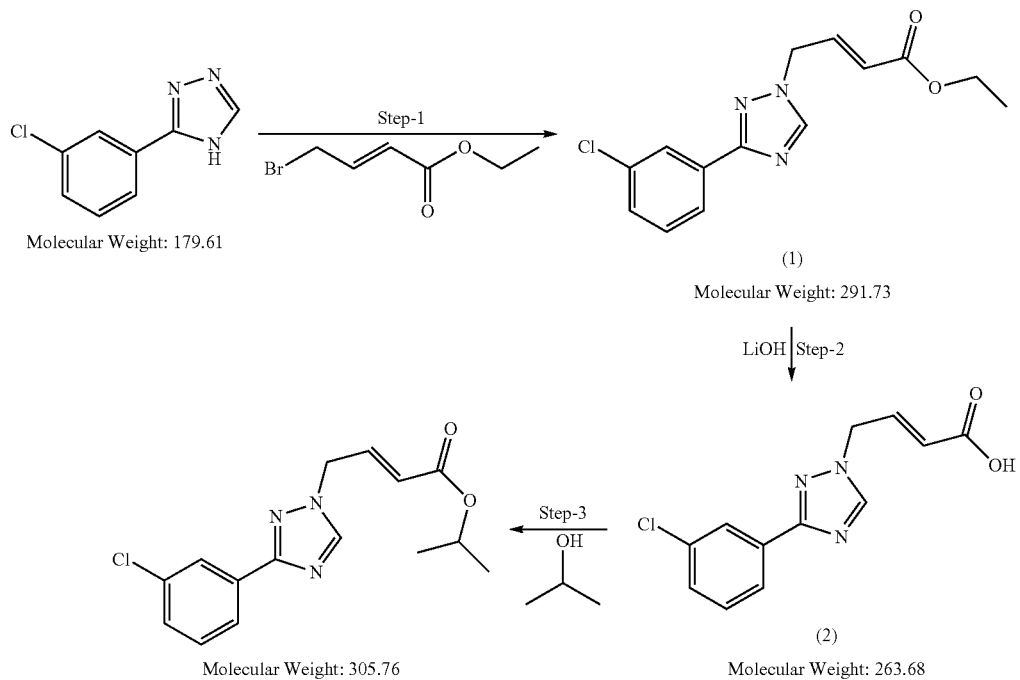

-continued

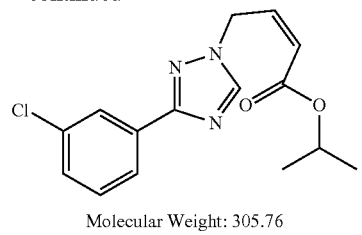

Molecular Weight: 305.76

In a 3-neck 50 mL round-bottomed flask, Intermediate-2 (2.2 g, 1 eq.) was dissolved in IPA (10 mL, 5 Vol.) and added BF$_3$-etherate (2.1 mL, 2.0 eq.) and the reaction mixture was refluxed to 90° C. for 3-4 h. Reaction completion was moni- Synthesis of Intermediate (1)

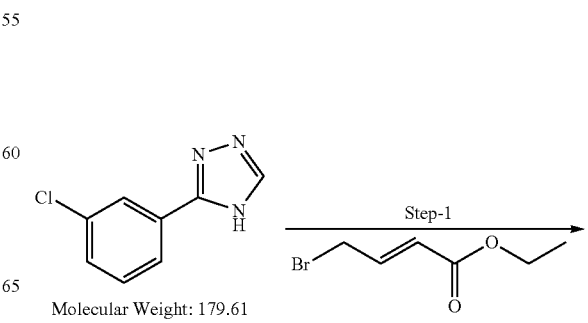

Molecular Weight: 179.61

-continued

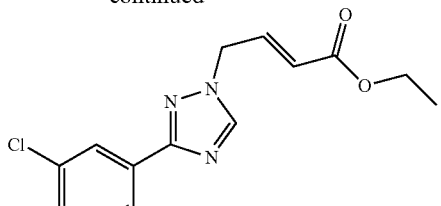

(1)
Molecular Weight: 291.73

In a 3-neck 100 mL round-bottomed flask, Intermediate-A (5.0 g, 1 eq.) and NaH (0.737 g, 1.1 eq.) were mixed with DMF (50 mL, 10 Vol.). The reaction mixture was stirred at 0° C. for 1 h and Ethyl 4-bromo crotonate (6.4 mL, 1.2 eq.) was added drop-wise in reaction mixture at 0° C. The reaction mixture was stirred at room temperature for 15 min. and then heated at 80° C. for 1 h. Reaction completion was monitored on TLC using ethyl acetate: n-hexane (5:5) as mobile phase. After the reaction was completed, reaction mixture was brought to room temperature and quenched into the ice-water slurry (100 mL) and compound was extracted in the ethyl acetate (100 mL×3). Organic layer was washed with brine solution (50 mL×3) followed by drying using anhydrous sodium sulphate. Organic layer was concentrated under reduced pressure to afford 5.5 g of crude compound. Mass/LCMS: 292.0, NMR: Confirmed.

Synthesis of Intermediate (2)

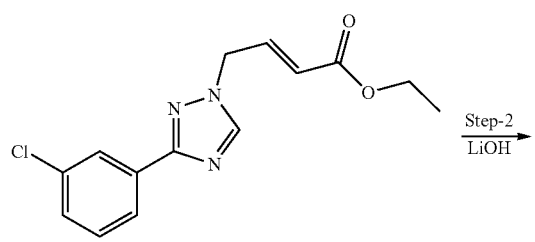

(1)
Molecular Weight: 291.73

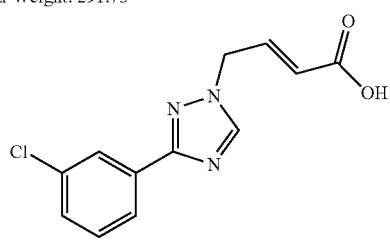

(2)
Molecular Weight: 263.68

In a 3-neck 50 mL round-bottomed flask, Intermediate-1 (2.15 g, 1 eq.) and LiOH (0.622 g, 2 eq.) were dissolved in THF (6 mL): H$_2$O (6 mL) (1:1) and the reaction mixture was stirred at room temperature for 45 min. Reaction completion was monitored on TLC using ethyl acetate: n-hexane (5:5) as mobile phase. Reaction mixture was quenched into the ice-water slurry and pH was adjusted to 2.0 with Conc. HCl (2 mL) and compound was extracted in the ethyl acetate (50 mL×3). Organic layer was washed with brine solution (50 mL×3) followed by drying using anhydrous sodium sulphate. Organic layer was concentrated under reduced pressure to afford 2.2 g of crude compound, yield (57.8%). for this compound. NMR: Confirmed.

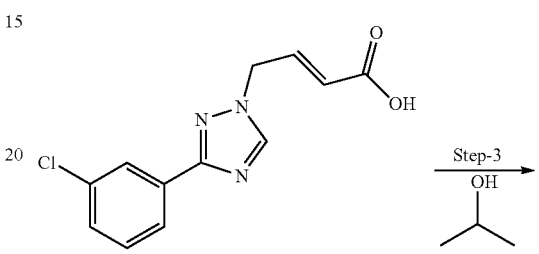

(2)
Molecular Weight: 263.68

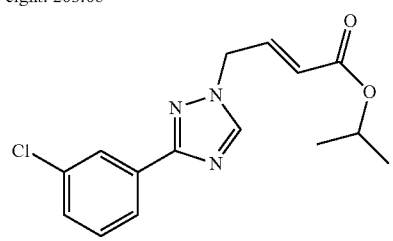

Molecular Weight: 305.76

In a 3-neck 50 mL round-bottomed flask, Intermediate-2 (2.2 g, 1 eq.) was dissolved in IPA (10 mL, 5 Vol.) and BF$_3$-etherate (2.1 mL, 2.0 eq.) was added to the reaction mixture and the reaction mixture was refluxed to 90° C. for 3-4 h. Reaction completion was monitored on TLC using ethyl acetate: n-hexane (2:8) as mobile phase. Reaction mixture was brought to the room temperature and quenched into the ice-water slurry (100 mL). The compound was extracted in the DCM (50 mL×3). Organic layer was washed with brine solution (50 mL×3) followed by drying using anhydrous sodium sulphate. Organic layer was concentrated under reduced pressure to afford 3.7 g of crude compound. Crude compound was further purified by column chromatography using silica 60/120 and ethyl acetate: n-hexane as mobile phase. Column purification was started with 2% EtOAc in hexane up to 7%. Compound started eluting in 5% ethyl acetate and continued till 7% EtOAc. Fractions containing compound were distilled out using rotary evaporation at 45° C./250 mm Hg to obtain 0.082 g of pure compound yield (3.2%). $^1$H NMR (400 MHz, CDCl$_3$) δ 8.16-8.23 (m, 1H), 8.02-8.05 (m, 1H), 7.98-7.41 (m, 2H), 7.00-7.04 (d, J=16.0, 1H), 6.48-6.55 (m, 1H), 5.05-5.11 (m, 1H), 3.23-3.25 (d, 2H), 1.29-1.30 (d, 6H) LCMS-ESI calculated for C$_{15}$H$_{16}$ClN$_3$O$_2$ [M+H]$^+$ 305.76. found 305.85 at 4.15 min. (LCMS 99.17%).

Example 42

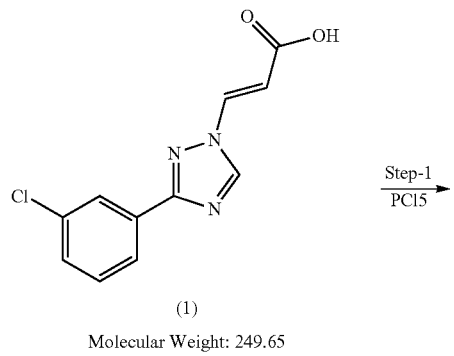

(1)
Molecular Weight: 249.65

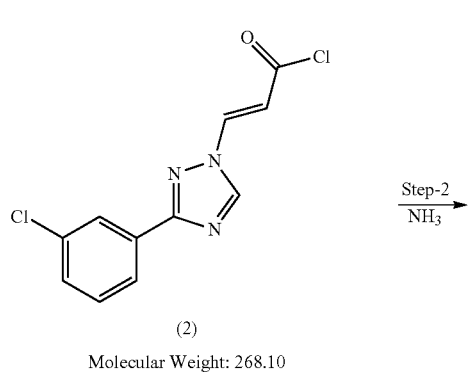

(2)
Molecular Weight: 268.10

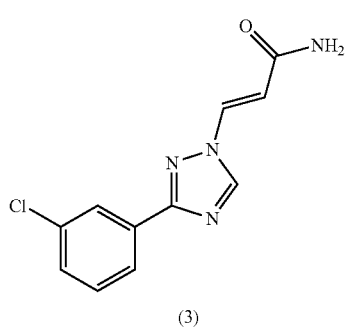

(3)
Molecular Weight: 248.67

PCl₅, EDC
70° C.-80° C. | Step-3

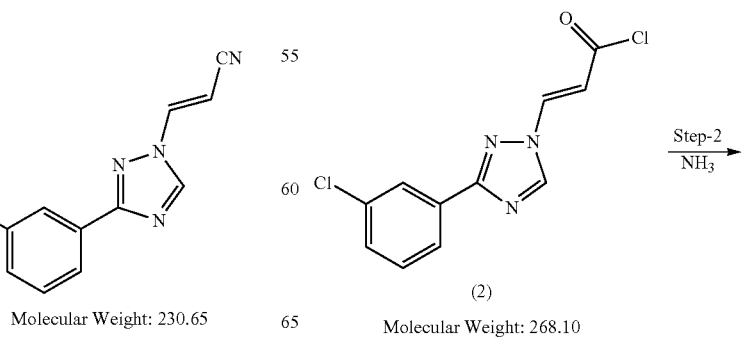

Molecular Weight: 230.65

Synthesis of Intermediate (2)

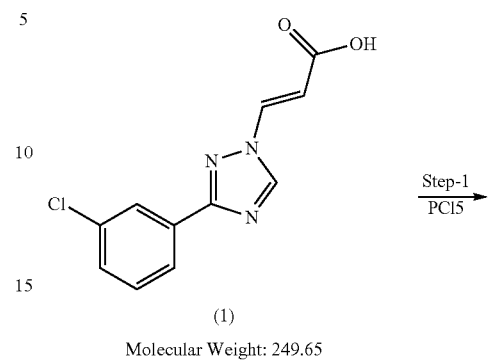

(1)
Molecular Weight: 249.65

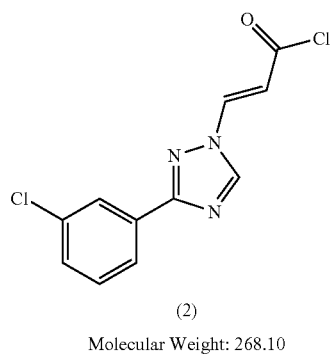

(2)
Molecular Weight: 268.10

In a 50 ml, 3-neck round bottom flask equipped with septum, nitrogen bubbler and thermometer pocket, Intermediate 1 (0.500 g) was dissolved in DCM (10 mL), PCl5 (0.625 g, 1.5 eq.) was added into the reaction mixture at RT. The reaction mixture was stirred at same temperature for further 2-3 hr.min. The completion of reaction was monitored on TLC using Ethyl acetate: n-hexane (5:5) as mobile phase. The reaction is carried forward without purification.

Synthesis of Intermediate (3)

221
-continued

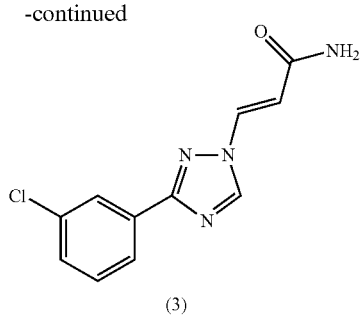

(3)
Molecular Weight: 248.67

222
-continued

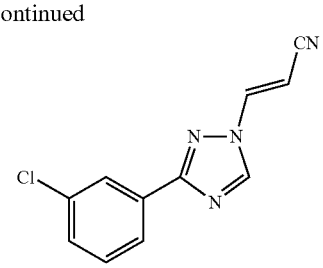

Molecular Weight: 230.65

In a 50 mL 3-neck round bottom flask equipped with septum, Nitrogen bubbler and thermometer pocket, intermediate 2 (0.500 g) and DCM (15 mL) were added. Then $NH_3$ gas was passed into the above reaction mixture for 5 minutes. The completion of reaction was monitored on TLC using Ethyl acetate:Hexane (5:5) as mobile phase. The reaction mixture was dumped in water (50 mL). Aqueous layer was extracted with Ethyl acetate (3×25 mL). Organic layer was dried over sodium sulphate. Solvent was evaporated to dryness under reduced pressure to obtain 0.25 g of crude material. Yield (54%). Mass: Confirmed.

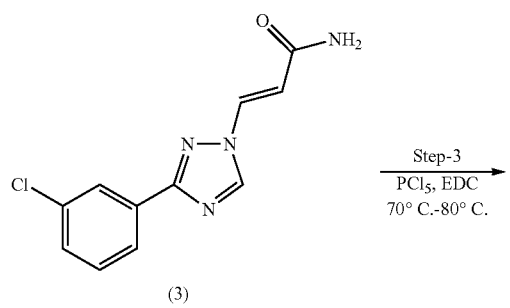

(3)
Molecular Weight: 248.67

In a 25 mL 3-neck round bottom flask equipped with condenser, nitrogen bubbler and thermometer pocket intermediate 2 (0.25 g, 1.0 eq.) and EDC (10 mL) were added. Then $PCl_5$ (0.314 g, 1.5 eq.) was added to the reaction mixture. The reaction was allowed to reflux for 2-3 h. The completion of reaction was monitored on TLC using Ethyl acetate: n-Hexane (4:6) as mobile phase. The reaction mixture was dumped in water (100 mL). Aqueous layer was extracted with Ethyl acetate (3×50 mL). Organic layer was dried over sodium sulphate. Solvent was evaporated to dryness under reduced pressure to obtain crude material. The crude reaction mixture was purified by column chromatography using silica 60/120 using Ethyl acetate:Hexane as mobile phase. Fraction containing such TLC profile was collected together to obtain pure compound (25 mg), Yield (10.82%). $^1$H NMR (400 MHz, $CDCl_3$) δ 8.33 (s, 1H), 7.49-8.19 (m, 4H), 7.68-7.72 (d, J=14.0 Hz, 1H), 6.28-6.31 (d, J=14.0 Hz, 1H), LCMS-ESI calculated for $C_{11}H_7ClN_4$ $[M+1]^+$ 230.65. found 230.93. (LCMS 98%).

Example 43

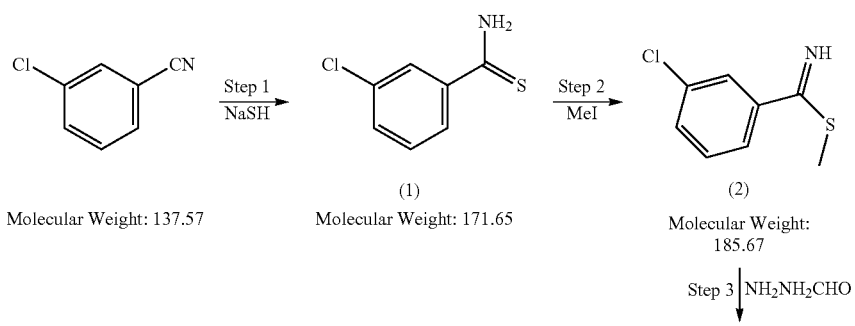

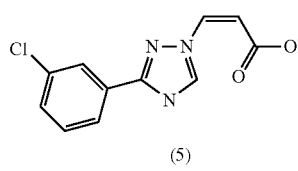
(5)
Molecular Weight: 249.65

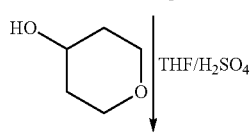
THF/H$_2$SO$_4$

← LiOH

-continued

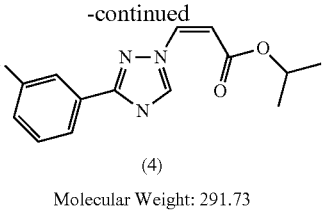
(4)
Molecular Weight: 291.73

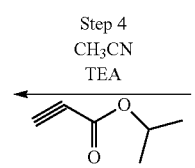
Step 4
CH$_3$CN
TEA

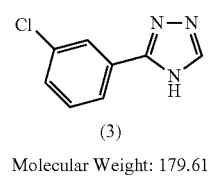
(3)
Molecular Weight: 179.61

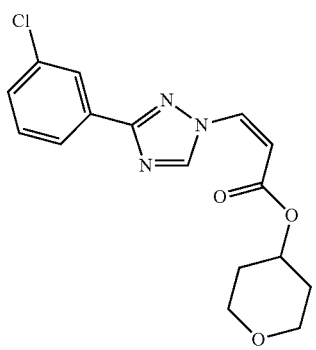
Molecular Weight: 333.77

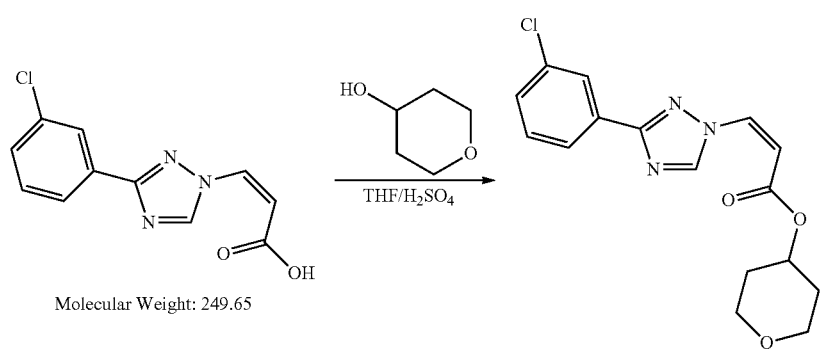
Molecular Weight: 249.65

In a 50-mL, 3N round-bottomed flask equipped with a condenser fitted with a nitrogen inlet, and a rubber septum, intermediate 5 (from Example 7) (0.49 g, 1.2 eq.) was dissolved in THF (5 mL) and catalytic amount of H$_2$SO$_4$ (0.04 g, 0.1 eq.) was added to this reaction mixture. The reaction mixture was stirred at room temperature for 15 min and refluxed for 15-16 h. The progress of the reaction was followed by TLC analysis on silica gel with 30% EtOAc-hexane as mobile phase and visualization with UV Radiation. Reaction mixture was brought to room temperature and quenched into the ice-water slurry (50 mL) and Neutralized with sodium bicarbonate solution. Compound was extracted in the ethylacetate (20 mL×3). Organic layer was washed with brine solution (50 mL×3) followed by drying using anhydrous sodium sulphate. Organic layer was concentrated under reduced pressure to afford 1.5 g of crude compound. The crude reaction mixture was purified by column chromatography using silica 60/120 using ethyl acetate: n-hexane as mobile phase. The column was packed in hexane and started eluting in ethyl acetate in gradient manner starting with fraction collection (25 mL fractions) from 5-10% ethyl acetate in hexane. Compound started eluting with 30% ethyl acetate in hexane. Fraction containing such TLC profile was collected together to obtain pure compound (33 mg), Yield (2.47%). $^1$H NMR (400 MHz, DMSO) δ 9.11 (s, 1H), 8.35-8.39 (d, J=14 Hz, 1H), 8.4-8.07 (s, 2H), 7.59 (s, 2H), 6.55-6.58 (d, J=12 Hz, 1H), 5 (m, 1H), 3.83-3.86 (t, 2H), 3.48-3.53 (t, 2H), 1.8-1.9 (t, 2H), 1.61-1.63 (t, 2H): LCMS for C$_{16}$H$_{16}$ClN$_3$O$_3$ [M]$^+$ 333.77 found 333.88 at R.T. 3.987 min Example 44
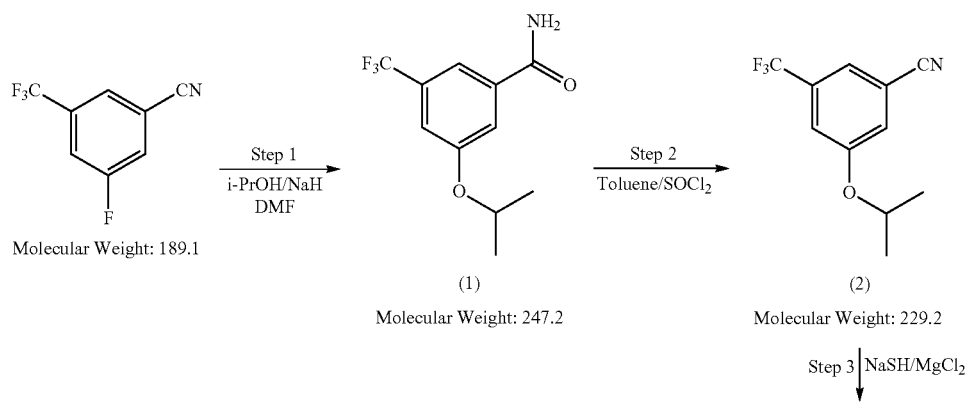
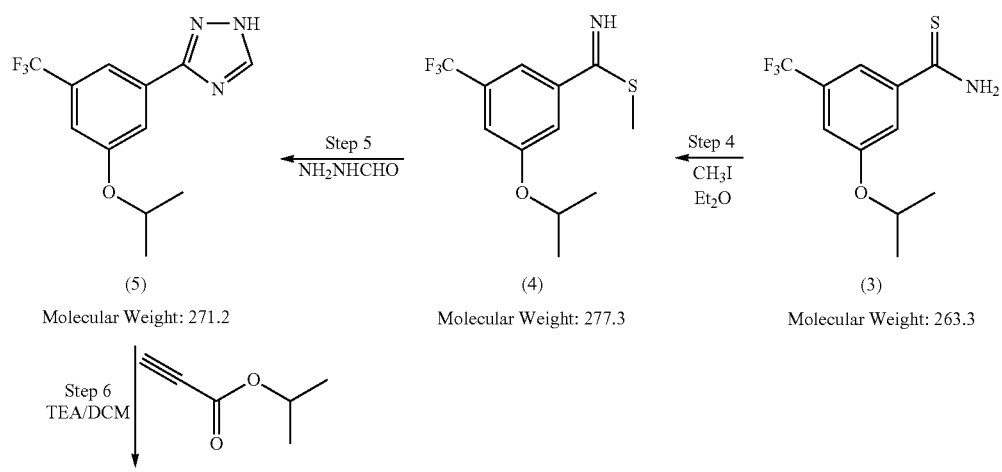
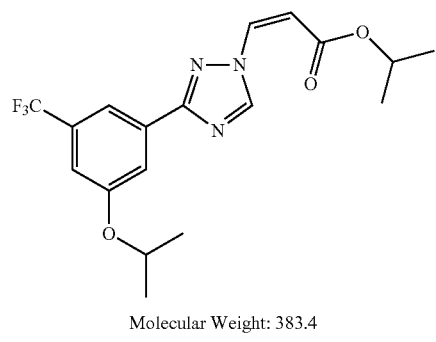
Molecular Weight: 383.4

Synthesis of Intermediate (1)

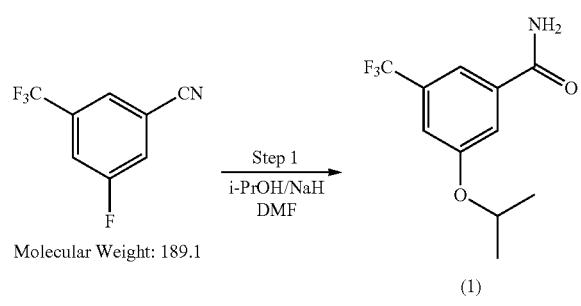

In a 3-neck 100 mL round-bottomed flask, to a solution of propan-2-ol (1.6 mL, 1 eq.) in DMF (25 mL, 5 V) at 0° C. was added 60% NaH in mineral oil (1.5 g, 3 eq.). The reaction mixture was stirred at 0° C. for 1 h and then 3-fluoro-5-(trifluoromethyl)benzonitrile (5 g, 1.25 eq.) was added and reaction was heated to 60° C. for 2 h an further stirred for 12 h at room temp. Reaction completion was monitored on TLC using ethyl acetate:hexane (2:8) as mobile phase. The reaction mixture was quenched into the ice-water slurry (250 mL) and was extracted with ethyl acetate (50 mL×3). Organic layer was washed with brine solution (50 mL×3). The organic layer was dried using anhydrous sodium sulfate, filtered, and concentrated under reduced pressure to provide the 5.8 g crude titled compound, yield (96%). This crude material was directly used for next step without purification.

Synthesis of Intermediate (2)

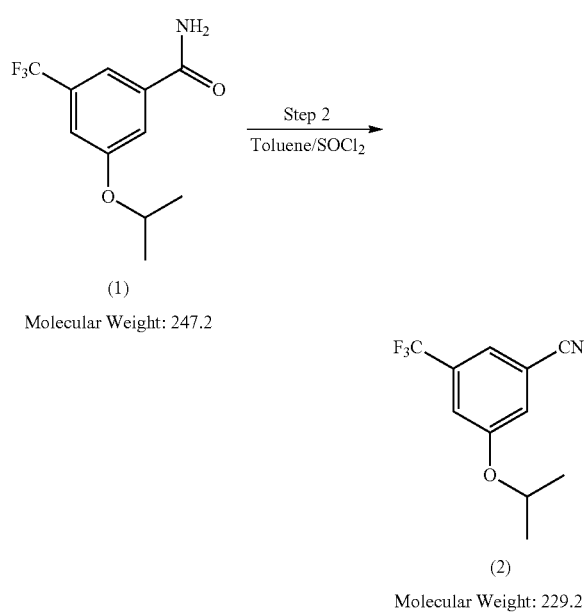

In a 3-neck 100 mL round-bottomed flask, 3-Isopropoxy-5-(trifluoromethyl)benzamide (5.8 g, 1 eq.) was dissolved in toluene (58 mL, 10 V) and thionyl chloride (3.4 mL, 2 eq.) was added and reaction mixture was refluxed to 90° C. for 2-3 h. Reaction completion was monitored on TLC using ethyl acetate:hexane (2:8) mobile phase. The reaction mixture was quenched into the ice-water slurry (250 mL) and was extracted with ethyl acetate (50 mL×3). Organic layer was washed with brine solution (50 mL×3). The organic layer was dried using anhydrous sodium sulfate, filtered, and concentrated under reduced pressure to provide the 5.3 g crude titled compound, yield (98.6%). This crude material was directly used for next step without purification. Mass/LCMS: Confirmed.

Synthesis of Intermediate (3)

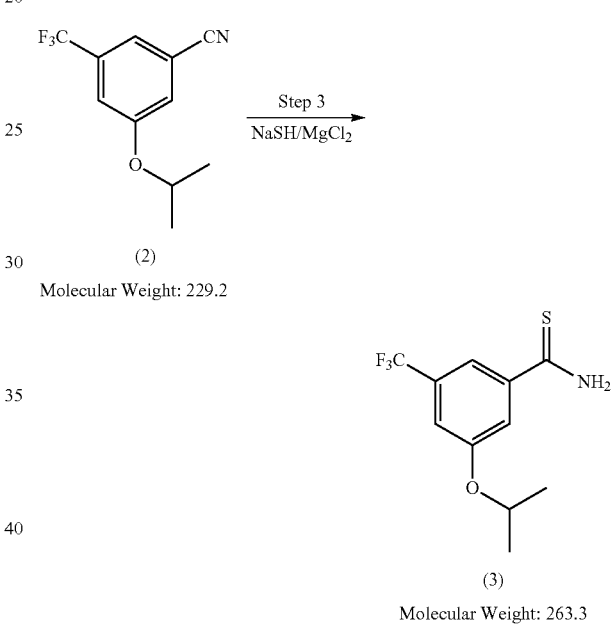

In a 1-neck 100 mL round-bottomed flask, 3-isopropoxy-5-(trifluoromethyl)benzonitrile (5.8 g, 1 eq.) was dissolved in DMF (53 mL, 10 V) and sodium hydrogensulfide hydrate (3.4 g, 2 eq.) was added followed by magnesium chloride hexahydrate (5.2 g, 1.1 eq.) in reaction mixture. The reaction mixture was stirred for 3-4 h at room temperature. Reaction completion was monitored on TLC using ethyl acetate:hexane (2:8) mobile phase. The reaction mixture was quenched into the ice-water slurry (250 mL) and was extracted with ethyl acetate (50 mL×3). Organic layer was washed with brine solution (50 mL×3). The organic layer was dried using anhydrous sodium sulfate, filtered, and concentrated under reduced pressure to provide the 6 g crude titled compound, yield (98.5%). This crude material was directly used for next step without purification. LCMS: Confirmed.

Synthesis of Intermediate (4)

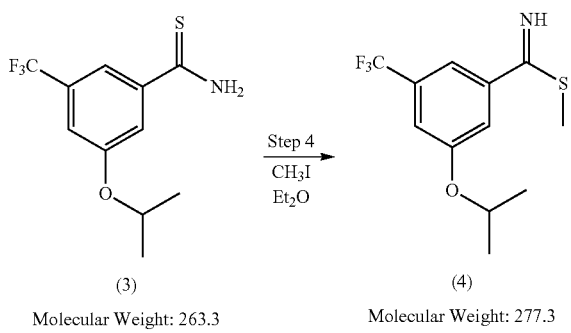 [SMILES: CC(C)Oc1cc(C(N)=S)cc(C(F)(F)F)c1 ; CSC(=N)c1cc(OC(C)C)cc(C(F)(F)F)c1]

(3)
Molecular Weight: 263.3

(4)
Molecular Weight: 277.3

In a 3-neck 100 mL round-bottomed flask, 3-isopropoxy-5-(trifluoromethyl)benzothioamide (6 g, 1 eq.) was dissolved in diethyl ether (60 mL, 10 V) and iodomethane (5.7 mL, 4 eq.) was added dropwise and reaction mixture was stirred at room temperature for 12 h. The reaction mixture was stirred for 3-4 h at room temperature. Reaction completion was monitored on TLC using ethyl acetate:hexane (2:8) mobile phase. The reaction mixture was quenched into the ice-water slurry (250 mL) and was extracted with DCM (50 mL×3). Organic layer was washed with brine solution (50 mL×3). The organic layer was dried using anhydrous sodium sulfate, filtered, and concentrated under reduced pressure to provide the 5 g crude titled compound, yield (79.1%). This crude material was directly used for next step without purification. LCMS: Confirmed

Synthesis of Intermediate (5)

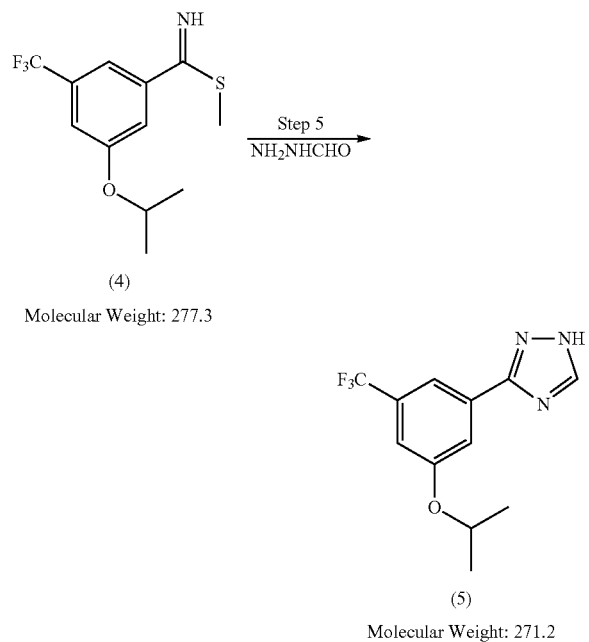

(4)
Molecular Weight: 277.3

(5)
Molecular Weight: 271.2

In a 3-neck 100 mL round-bottomed flask, methyl 3-isopropoxy-5-(trifluoromethyl)benzimidothioate (5 g, 1 eq.) and formylhydrazine (2.2 g, 2.0 eq.) was dissolved in DMF (25 mL, 5 Vol) and reaction mixture was refluxed for 2 h. Reaction completion was monitored on TLC using ethyl acetate:hexane (2:8) as mobile phase. The reaction mixture was quenched into the ice-water slurry (250 mL) and was extracted with ethyl acetate (50 mL×3). Organic layer was washed with brine solution (50 mL×3). The organic layer was dried using anhydrous sodium sulfate, filtered, and concentrated under reduced pressure to provide the 5.3 g crude compound was purified by column chromatography using ethyl acetate and hexane as mobile phase. Product was eluted in 35% ethyl acetate in hexane to afford 2.26 g of pure titled compound, yield (46.2%). LCMS: Confirmed.

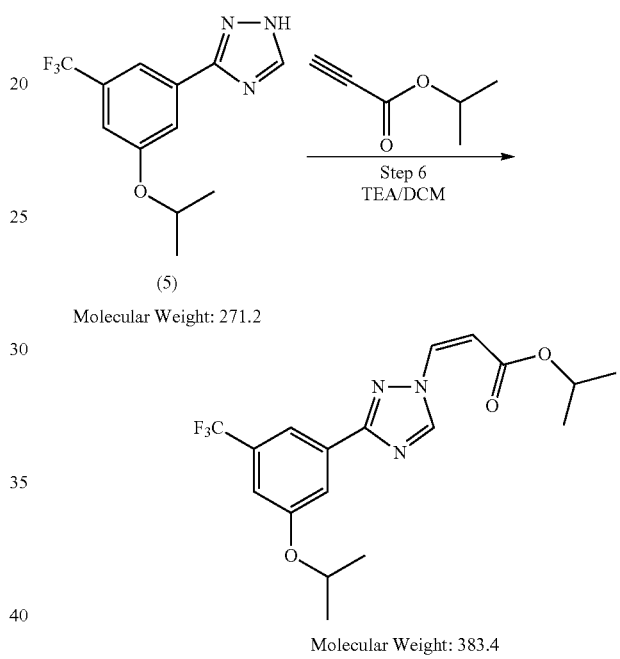

(5)
Molecular Weight: 271.2

Molecular Weight: 383.4

In a 3-neck 50 mL round-bottomed flask, intermediate 5 (1.6 mL, 1.4 eq.) was dissolved in DCM (11 mL, 5 Vol) and isopropyl propiolate (1.3 g, 1.4 eq.) was added at 15° C. and reaction mixture was stirred for 30 min. Reaction completion was monitored on TLC using ethyl acetate: n-hexane (2:8) mobile phase. The reaction mixture was quenched into the ice-water slurry (50 mL) and was extracted with DCM (20 mL×3). Organic layer was washed with brine solution (50 mL×3). The organic layer was dried using anhydrous sodium sulfate, filtered, and concentrated under reduced pressure to provide the 3.0 crude compounds was purified by column chromatography using ethyl acetate and hexane as mobile phase. Product was eluted in 4% ethyl acetate in hexane to afford 0.1 g of pure titled compound. $^1$H NMR (400 MHz, CDCl$_3$) δ 9.76 (s, 1H), 8 (s, 1H), 7.87 (s, 1H), 7.28 (d, J=12 Hz, 1H), 7.20 (s, 1H), 5.74 (d, J=10.8 Hz, 1H), 5.12-5.18 (m, 1H), 4.69-4.76 (m, 1H), 1.17-1.59 (double doublet, 12H): LCMS for C$_{18}$H$_{20}$F$_3$N$_3$O$_3$ MW 383.36 found 229.99 at 4.767 min (LCMS 91.05%).

Example 45
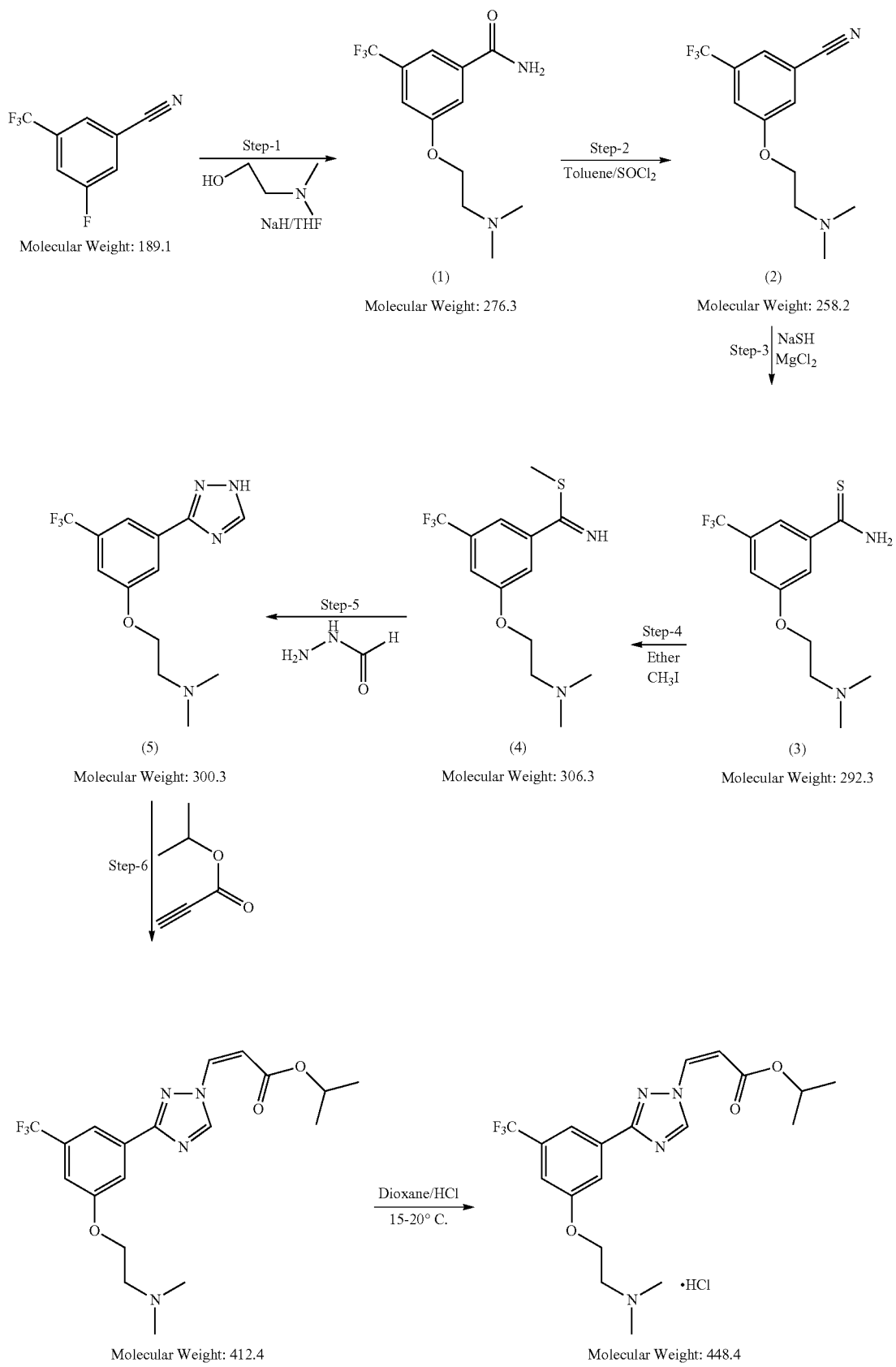

Synthesis of Intermediate (1)

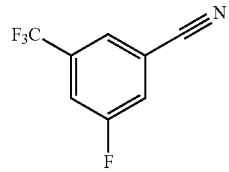
Molecular Weight: 189.1

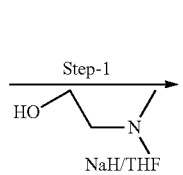
NaH/THF

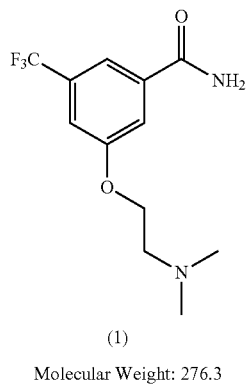
(1)
Molecular Weight: 276.3

In a 3-neck 100 mL round-bottomed flask, 2-(dimethylamino)ethanol (2.925, 1.2 eq.) was dissolved in THF (50 mL, 10 Vol), added NaH portion wise in reaction mixture at −25° C. Stirred the reaction mixture at −25° C. for 1 hr. Added 3-fluoro-5-(trifluoromethyl)benzonitrile (5.0 g, 1.0 eq) Portion wise in reaction mixture. Reaction mixture was stirred at this temp for 2 hrs and then at RT overnight. Reaction completion was monitored on TLC using ethyl acetate:hexane (3:7) mobile phase. Reaction mixture was quenched into the ice-water slurry (250 mL) and compound was extracted in the ethyl acetate (50 mL×3). Organic layer was washed with brine solution (50 mL×3) followed by drying using anhydrous sodium sulphate. Organic layer was concentrated under reduced pressure to afford 6.5 g of crude compound, Yield (89.18%). This crude material was directly used for next step without purification. Mass: 276.3.

Synthesis of Intermediate (2)

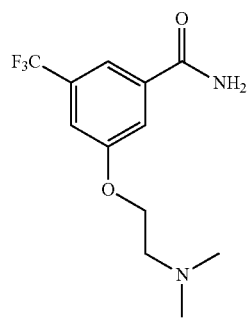
(1)
Molecular Weight: 276.3

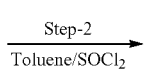
Step-2
Toluene/SOCl$_2$

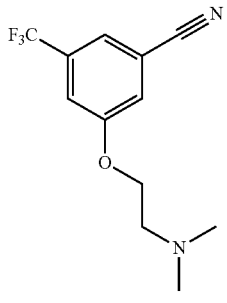
(2)
Molecular Weight: 258.2

In a 3-neck 100 mL round-bottomed flask, Intermediate 1 (6.5 g, 1 eq.) was dissolved in Toluene (65 mL, 10 Vol) and added SOCl (5.6 g, 2.0 eq.) and reaction mixture was refluxed to 90° C. for Overnight. Reaction completion was monitored on TLC using ethyl acetate:hexane (2:8) mobile phase. Reaction mixture was brought to room temperature and quenched into the ice-water slurry (300 mL) and Neutralized with sodium bi carbonate solution. Compound was extracted in the E.A (100 mL×3). Organic layer was washed with brine solution (100 mL×3) followed by drying using anhydrous sodium sulphate. Organic layer was concentrated under reduced pressure to afford 6.0 g of crude compound, yield (95.0%). This crude material was directly used for next step without purification. Mass/LCMS: 258.9.

Synthesis of Intermediate (3)

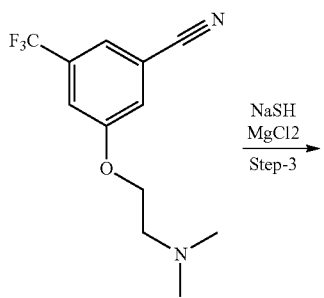
(2)
Molecular Weight: 258.2

NaSH
MgCl2
Step-3

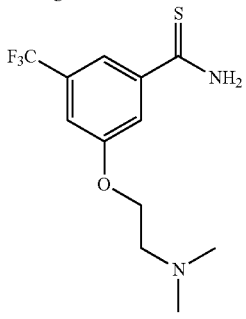
(3)
Molecular Weight: 292.3

In 1-neck 100 mL round-bottomed flask, Intermediate-2 (6.0 g, 1.0 eq.) was dissolved in DMF (60 mL, 10 V) added (3.43 g, 2.0 eq) and MgCl$_2$ (5.20 g, 1.1 eq). in reaction mixture. The reaction mixture was stirred for 6-8 h at RT. Reaction completion was monitored on TLC using ethyl acetate: hexane (4:6) mobile phase. Reaction mixture was brought to room temperature and quenched into the ice-water slurry (250 mL) and compound was extracted in the E.A (100 mL×3). Organic layer was washed with brine solution (100 mL×3) followed by drying using anhydrous sodium sulphate. Organic layer was concentrated under reduced pressure to afford 6.0 g of crude compound, yield (88.2%). This crude material was directly used for next step without purification. Mass/LCMS: 292.8.

Synthesis of Intermediate (4)

Synthesis of Intermediate (5)

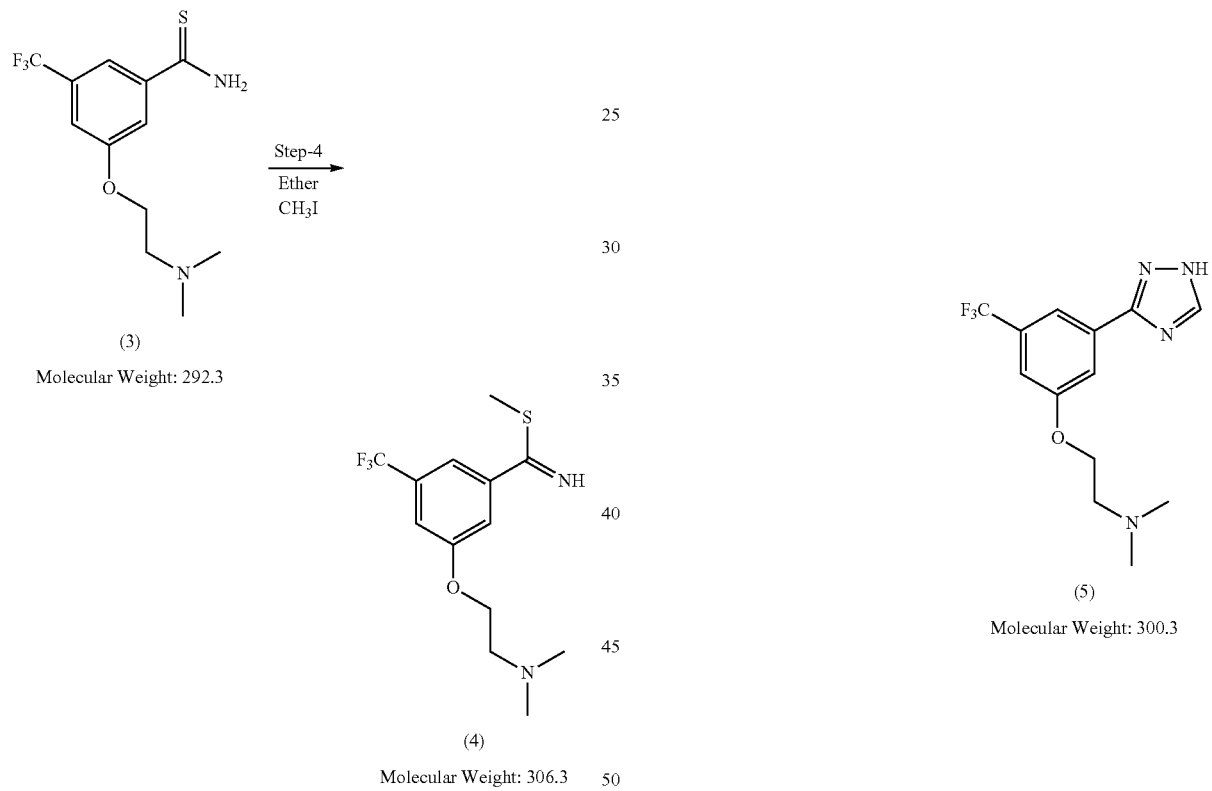

In a 1-neck 100 mL round-bottomed flask, Intermediate-3 (6.0 g, 1 eq.) was dissolved in Diethyl ether (60 mL, 10V) and added methylIodide (14.5 g, 5.0 eq.) and reaction mixture was stirred at RT for overnight. Reaction completion was monitored on TLC using ethyl acetate:hexane (4:6) mobile phase. In reaction mixture yellow solid material was obtained, filtered and wash with Diethyl ether (10 mL×2). Dried over Vacuum to afford 5.9 g of crude compound, yield (90.0%). This crude material was directly used for next step without purification.

Mass/LCMS: 306.9.

In a 3-neck 50 mL round-bottomed flask, Intermediate 4 (5.9 g, 1.0 eq.) was dissolved DMF (30 mL, 10) and added formic hydrazide (2.31 g, 2.0 eq.) and reaction mixture was refluxed to 90° C. for 12-15 h. Reaction completion was monitored on TLC using methanol:DCM (1:9) mobile phase. Reaction mixture was brought to room temperature and quenched into the ice-water slurry (150 mL) and compound was extracted in the Ethyl acetate (50 mL×3). Organic layer was washed with brine solution (50 mL×3) followed by drying using anhydrous sodium sulphate. Organic layer was concentrated under reduced pressure to afford 3.2 g of crude compound. Product was purified by column chromatography using methanol and DCM to afford 0.700 g pure compound, Yield (12.10%). Mass/LCMS: 300.9.

Synthesis of Intermediate (6)

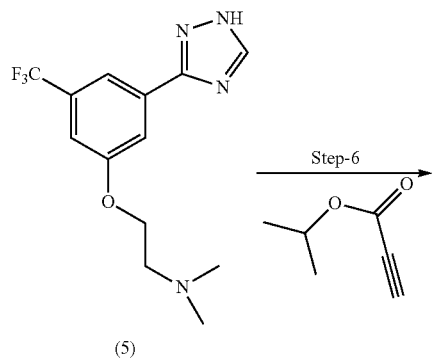

(5)
Molecular Weight: 300.3

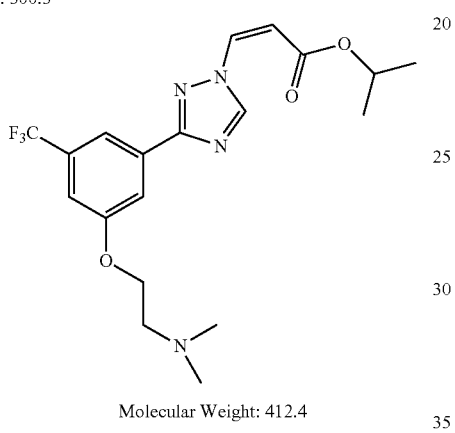

Molecular Weight: 412.4

In 1-neck 25 mL round-bottomed flask, Intermediate-5 (0.175 g, 1.0 eq.), was dissolved in DCM (5 mL, 10 vol.), added TEA (0.065 g, 11 eq) and added Isopropyl propionate (0.071 g, 1.1 eq.). Reaction mixture was stirred under lamp at 0° C. for 2-3 hrs. Reaction completion was monitored on TLC using Ethyl acetate:Hexane (2:8) mobile phase. Reaction mixture was concentrated under reduced pressure to afford 0.250 g of crude compound; Product was purified by flash chromatography using ethyl acetate and Hexane to afford 0.008 g pure compound, Yield (3.3%). LCMS: Confirmed, NMR: Confirmed.

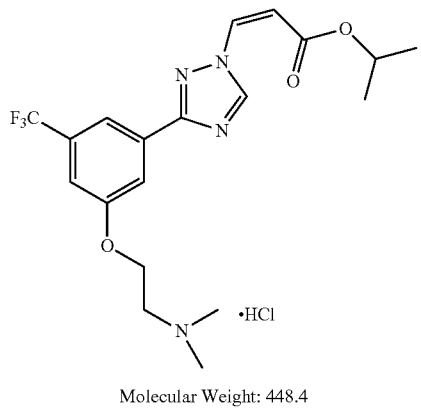

Molecular Weight: 448.4

In a 1-neck 25 mL round-bottomed flask, Intermediate-5 (0.020 g, 1.0 eq.), was dissolved in DMSO (2 mL, 10 vol.), added Dioxane/HCl (0.1 mL, 15V) at 15-20° C. and stirred overnight. Reaction completion was monitored on TLC using Ethyl acetate:Hexane (2:8) mobile phase. Reaction mixture was concentrated under reduced pressure to afford 0.035 g of crude compound. Product was purified by tituration with diethyl ether to afford 0.008 g pure compound. $^1$H NMR (400 MHz, D$_2$O Exchange): 610.55 (Broad s, 1H D$_2$O Exchangeable), 9.13 (s, 1H), 7.85-7.88 (d, J=12 Hz, 2H), 7.46 (s, 2H), 5.98-6.02 (d, J=9.6 Hz, 1H), 5.01-5.03 (m, 1H), 4.48 (broad s, 2H), 3.56-3.67 (t, 2H), 2.86-2.87 (d, 6H), 1.22 (s, 6H): LCMS for C$_{19}$H$_{24}$ClF$_3$N$_4$O$_3$ [M+1]$^+$ 448.87 found 413.05 at 3.015 min (LCMS 96.95%).

Example 46

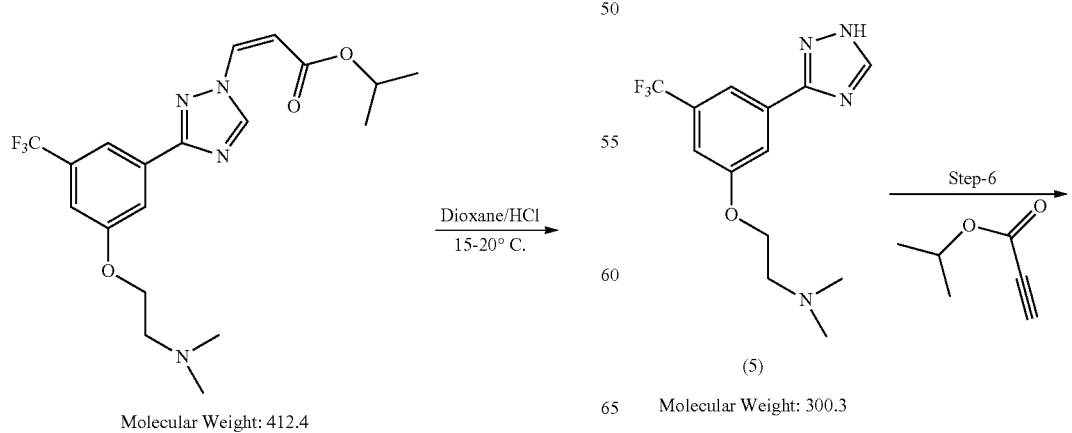

(5)
Molecular Weight: 300.3

239 -continued

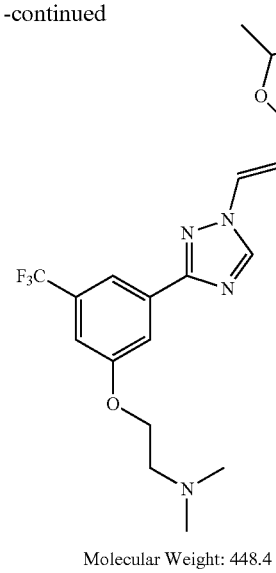

Molecular Weight: 448.4

Trans isomer of Example 45; $^1$H NMR (400 MHz, D$_2$O Exchange): 610.33 (Broad s, 1H D$_2$O Exchangeable), 9.15 (s, 1H), 8.32-8.36 (d, J=14 Hz, 1H), 7.47-8.22 (m, 3H), 6.59-6.56 (d, J=14 Hz, 1H), 5.01-5.08 (m, 1H), 4.55 (broad s, 2H), 3.55 (Broad S, 2H), 2.86-2.87 (d, 6H), 1.21 (s, 6H): LCMS for C$_{19}$H$_{24}$ClF$_3$N$_4$O$_3$ [M+1]$^+$ 448.87 found 413.05 at 3.016 min (LCMS 90%).

Example 47

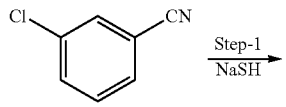

Molecular Weight: 137.57

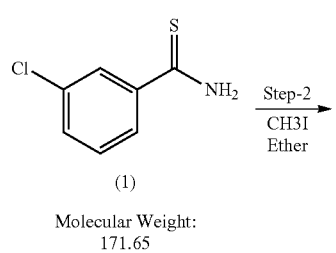

(1)

Molecular Weight: 171.65

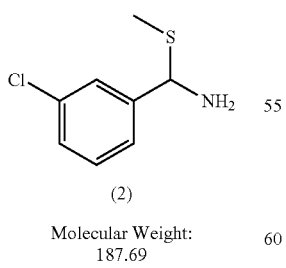

(2)

Molecular Weight: 187.69

240 -continued

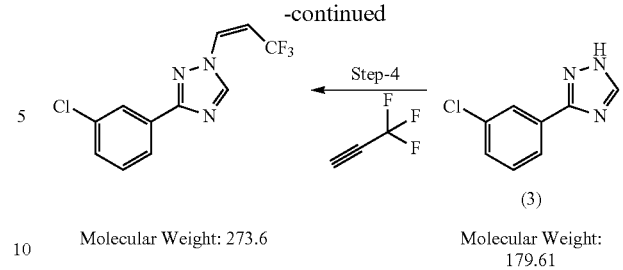

(3)

Molecular Weight: 273.6    Molecular Weight: 179.61

Synthesis of Example 47

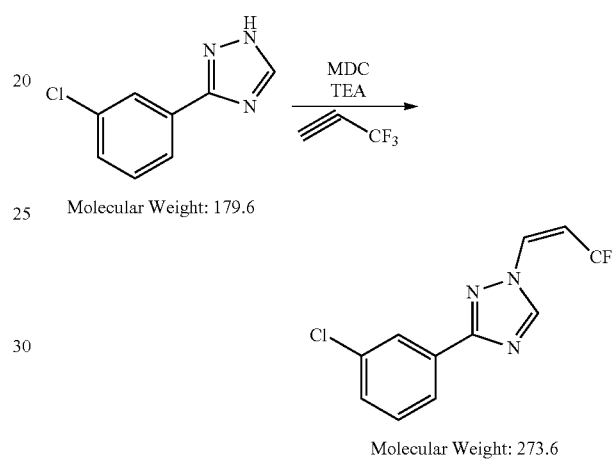

Molecular Weight: 179.6

Molecular Weight: 273.6

In a 3-neck 50 ml round-bottomed flask, intermediate 3 (from Example 1) (0.340 g, 1 eq.) was dissolved in MDC (3.4 ml, 10 Vol) and TEA was added (0.362, 2.0 eq.). Then 1,1,1-trifluoropropyne gas purged in the reaction mixture between temp 30 to 35° C. Reaction was monitored on TLC. 20 ml MDC added in the reaction mixture. Organic layer was washed with Water (50 ml×3) Organic layer was washed with brine solution (50 mL×3) followed by drying using anhydrous sodium sulphate. Organic layer was concentrated under reduced pressure to afford 0.120 g of crude compound, yield (35.29%). $^1$H NMR (400 MHz, CDCl$_3$) δ 8.5 (s, 1H), 8.03-8.05 (d, J=8.0 Hz, 1H), 7.23-7.54 (m, 3H), 5.70-5.61 (m, 1H), −57.97-57.99 (d, J=8.0 Hz, 1H): LCMS C$_{11}$H$_7$ClF$_3$N$_3$ (273.64)[M+1] found 273.85.

Example 48

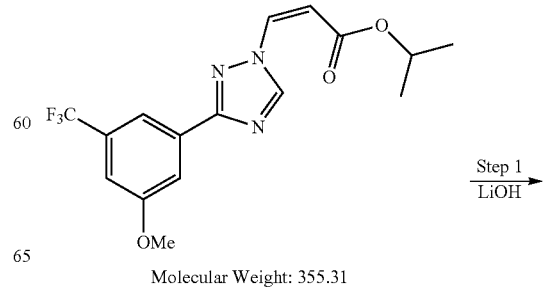

Molecular Weight: 355.31

Synthesis of Intermediate (1)

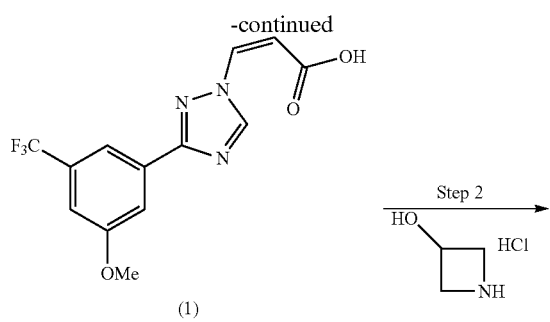

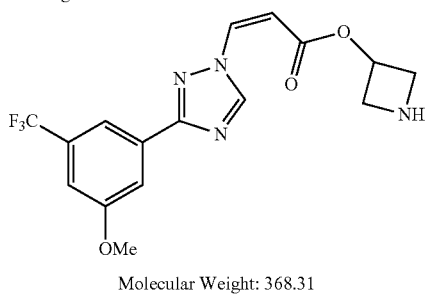

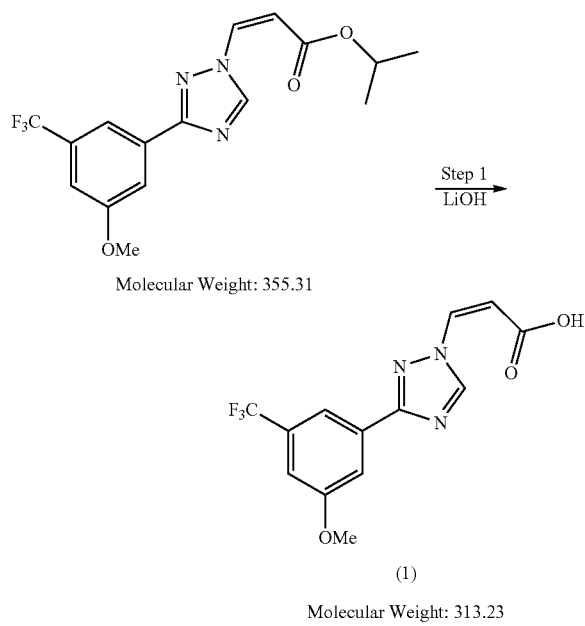

In a 3-neck 100 mL round-bottomed flask, Example 26 (0.7 g, 1 eq.) was dissolved in THF (15 mL): Water (15 mL), LiOH (0.32 g, 4 eq) was added portion wise in reaction mixture. Reaction mixture was stirred at RT for 3 h. Reaction completion was monitored on TLC using DCM:MeOH (9:1) as mobile phase. Reaction mixture quenched into the ice-water slurry (250 mL) and acidified it with dil. HCl and compound was extracted in the ethyl acetate (50 mL×3). Organic layer was washed with brine solution (50 mL×3) followed by drying using anhydrous sodium sulphate. Organic layer was concentrated under reduced pressure to afford 0.65 g of crude compound, Yield (96%); Mass: 314.1.

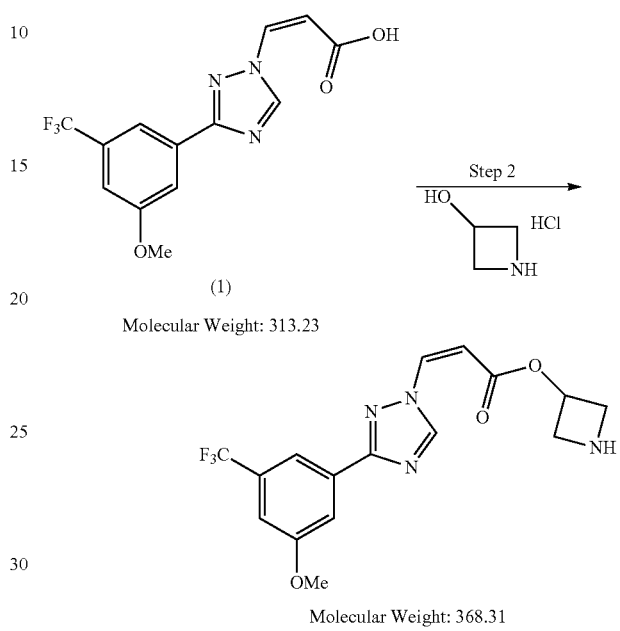

In a 3-neck 50 mL round-bottomed flask, intermediate 1 (0.65 g, 1 eq.) was dissolved in DCM (50 mL) and DMAP (0.025 g, 0.1 eq.) was added followed by DCC (0.55, 1.3 eq.) and 3-OH azitidine (0.46, 1.3 eq.) at −20° C. under stirring at 0° C. for 2 h. Reaction completion was monitored on TLC using DCM:MeOH (9:1) as mobile phase. Reaction mixture was brought to room temperature and quenched into the ice-water slurry (100 mL) and compound was extracted in the Ethylacetate (100 mL×3). Organic layer was washed with brine solution (100 mL×3) followed by drying using anhydrous sodium sulphate. Organic layer was concentrated under reduced pressure to afford 0.09 g of crude compound which was purified by column to give 0.06 g of pure compound yield (7.85%). $^1$H NMR (400 MHz, D$_2$O Exchange) δ 9.72 (s, 1H), 8.02 (s, 1H), 7.86 (s, 1H), 7.28 (d, 1H), 7.21 (s, 1H), 5.62-5.65 (d, J=10.8 Hz, 1H), 4.75 (m, 1H), 4.39-4.44 (m, 1H), 3.94 (s, 3H), 1.27-1.42 (m, 4H): LCMS for C$_{16}$H$_{15}$F$_3$N$_4$O$_3$ [M]+368.31 found 368.76 at R.T. 3.02 min.

Example 49

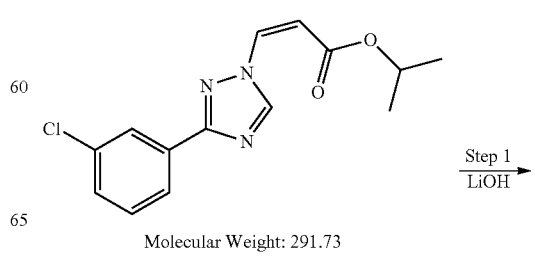

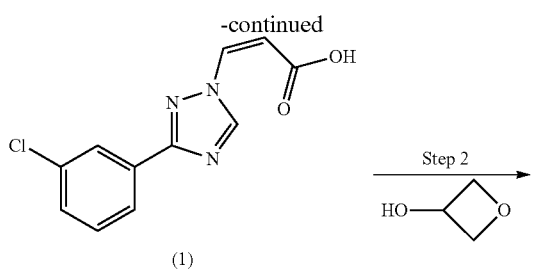

Molecular Weight: 249.65

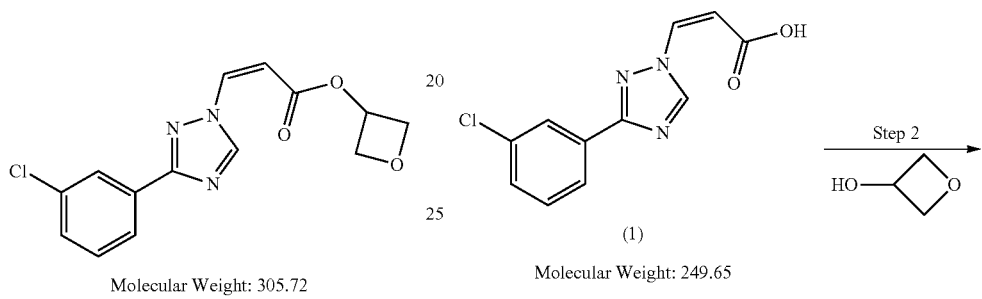

Synthesis of Intermediate (1)

In a 3-neck 100 mL round-bottomed flask, Example 1 (0.37, 1 .eq.) was dissolved in THF (30 mL) and Water (30 mL)(1:1). LiOH (0.642 g, 2.0 eq) was added portionwise in reaction mixture. Reaction mixture was stirred at RT for 3 hr. Reaction completion was monitored on TLC using DCM: MeOH (9:1) as mobile phase. Reaction mixture was quenched into the ice-water slurry (250 mL) and acidified with dil. HCl. Compound was extracted in the ethyl acetate (50 mL×3). Organic layer was washed with brine solution (50 mL×3) followed by drying using anhydrous sodium sulphate. Organic layer was concentrated under reduced pressure to afford 2.05 g of crude compound, Yield (80.07%). Mass: 250.1.

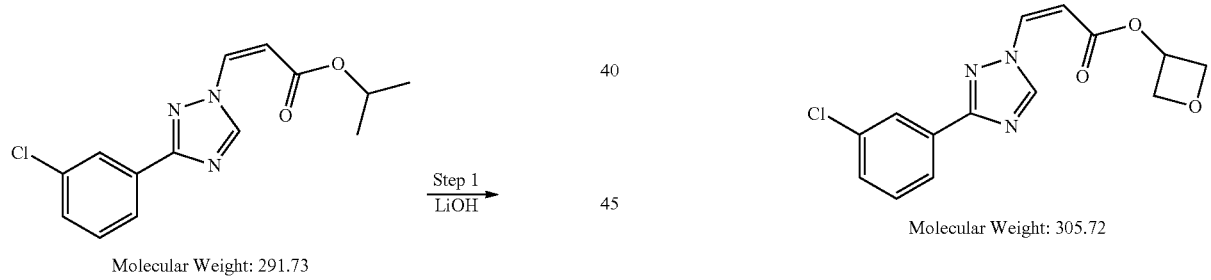

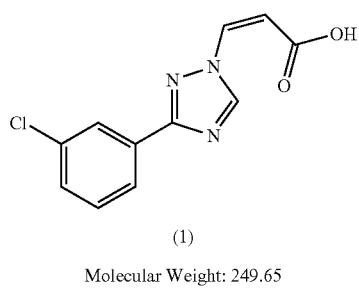

Molecular Weight: 249.65

In a 3-neck 25 mL round-bottomed flask, Intermediate-1 (0.250 g, 1 eq.) was dissolved in DCM (7 mL, 28V) and DMAP (0.012 g, 0.1 eq.) added, DCC (0.227 g, 1.3 eq.) and Oxetan-3-ol (0.096 g, 1.3 eq.) at 0° C. The reaction mixture was stirred at RT for 1-2 h. Reaction completion was monitored on TLC using Ethyl acetate: n-Hexane (5:5) as mobile phase. Reaction mixture was filtered through celite-bed and the filtered was concentrated under reduced pressure to afford 0.44 g of crude compound which was purified by column to give 123 mg of pure compound yield (40.19%). $^1$H NMR (400 MHz, DMSO-$d_6$) δ 9.19 (S, 1H), 7.58-7.97 (m, 4H), 7.55-7.57 (d, J=10.2 Hz, 1H), 6.05-6.08 (d, J=11.0 Hz, 1H), 5.52-5.58 (m, 1H), 4.82-4.86 (d, 2H), 4.56-4.59 (d, 2H): LCMS for $C_{14}H_{12}ClN_3O_3$ [M+1]$^+$ 305.72 found 306.54 at 3.62 min (LCMS 98.17%).

Example 50

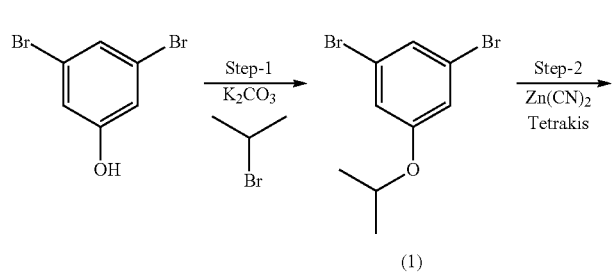
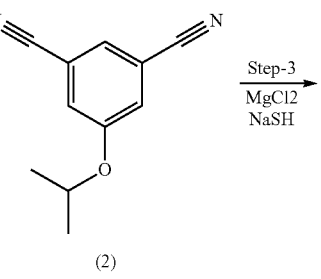
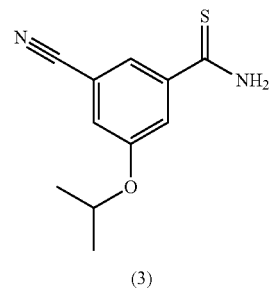
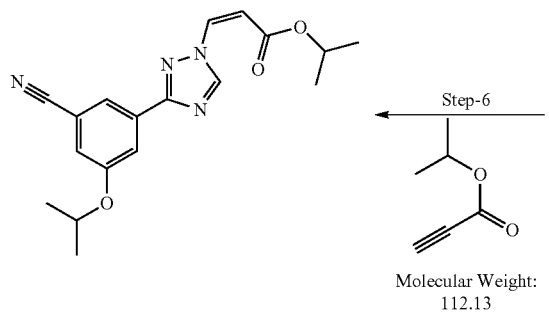

Synthesis of Intermediate (1)

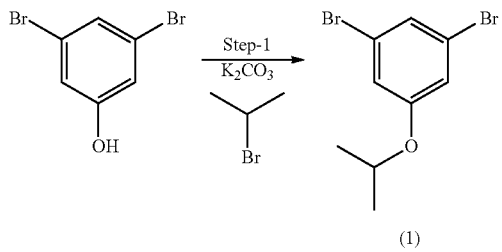

In a 3-neck 100 mL round-bottomed flask, 3,5-dibromo phenol (5 g, 1 eq.) and K$_2$CO$_3$ (5.478 g, 2 eq.) was stirred at room temperature for 30-40 min. To this reaction mixture isopropyl bromide (2.2 mL, 1.2 eq.) was added dropwise. Resulting reaction mixture was stirred at 80-90° C. and reaction was monitored by TLC using Ethyl acetate: n-hexane (1:9) as mobile phase, which shows starting material was consumed after 5 h. Reaction was quenched in ice-water slurry and compound was extracted by ethyl acetate (50 mL×3). Combined organic layer were dried over anhydrous sodium sulfate and concentrated under reduce pressure to obtain crude reaction mass. The crude compound was subjected to column chromatography using silica 60/120 as stationary phase and ethyl acetate:Hexane as mobile phase. Compound was eluted in 5% ethyl acetate in Hexane as mobile phase. Fractions containing compound was distilled out using rotary evaporation at 40° C./250 mmHg to obtain 3.591 g (61.56%). NMR: Confirmed.

Synthesis of Intermediate (2)

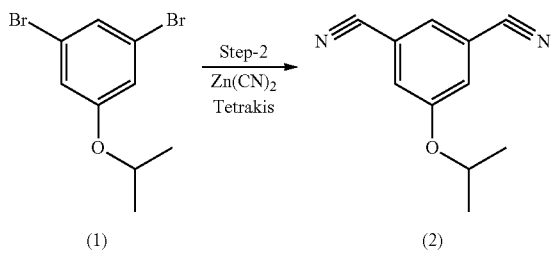

(1)
Molecular Weight: 293.98

(2)
Molecular Weight: 186.21

In a 3-neck 100 mL round-bottomed flask, intermediate-1 (3.5 g, 1 eq.) was dissolved in DMF and degassed it for 20-30 min. To this reaction mixture, Zinc Cyanide (1.72 g, 1.2 eq.) and tetrakis (0.705 g, 0.05 eq.) was added. Resulting reaction mixture was stirred at 80-90° C. and reaction was monitored by TLC using Ethyl acetate:hexane (1:9) as mobile phase, which shows starting material was consumed after 5 h. Reaction was quenched into ice-water slurry and compound was extracted using ethyl acetate (50 mL×3), combined organic layer were dried over anhydrous sodium sulfate and concentrated under reduce pressure to give crude compound. The crude material was subjected to column chromatography using silica 60/120 as stationary phase and ethyl acetate:n-Hexane as mobile phase. Compound was eluted in 7% ethyl acetate in Hexane. Fractions containing compound was distilled out using rotary evaporation at 40° C./250 mm Hg to obtain 2.095 g (94.51%). Mass/LCMS: LC-MS purity 92.36%, NMR: Confirmed.

Synthesis of Intermediate (3)

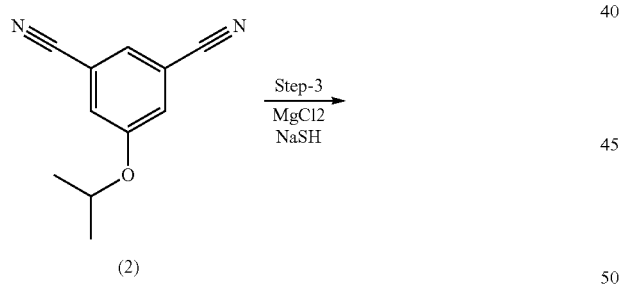

(2)
Molecular Weight: 186.21

(3)
Molecular Weight: 220.29

In a 3-neck 25 mL round-bottomed flask, Intermediate-2 (0.2 g) was mixed with sodium hydrogen sulfate (0.06 gm, 0.0017 eq.) and magnesium chloride (0.24 g, 1.1 eq.). Resulting Reaction mixture was stirred at RT. Reaction was monitored by TLC using ethyl acetate: n-hexane (5:5) as mobile phase, which shows starting material was consumed after 20 min. Reaction mixture quenched in ice-water slurry and compound was extracted by ethyl acetate (20 mL×3), combined organic layer were dried over anhydrous sodium sulfate and concentrated under reduce pressure to give crude material. Obtain crude material was subjected to column purification using silica 60/120 as a stationary phase and ethyl acetate: Hexane as mobile phase. Compound was eluted in 15% ethyl acetate in hexane. Fractions containing compound was distilled out using rotary evaporation at 40° C./250 mm Hg to obtain 0.135 g (57.06%). Mass/LCMS: LCMS purity 91.6%. NMR: Confirmed.

Synthesis of Intermediate (4)

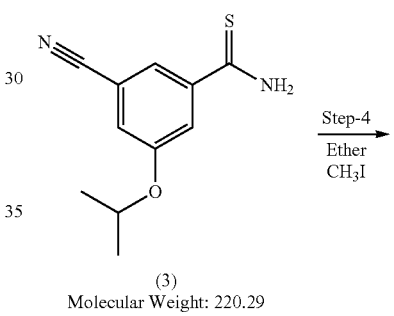

(3)
Molecular Weight: 220.29

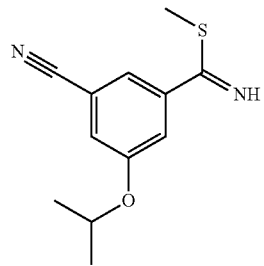

(4)
Molecular Weight: 234.32

In a 3-neck 50 mL round-bottomed flask, intermediate-3 (1.25 g) was added methyl iodide (1.8 mL, 5 eq.) drop wise. Resulting reaction mixture was stir at RT. Reaction was monitored by TLC using ethyl acetate:Hexane (1:9) as mobile phase which shows starting was consumed after 15 hours string at RT. Reaction mixture was filtered out wash with diethyl ether and dried it to give intermediate-4 (0.43 g), yield (32.34%). Mass/LCMS: Mass analysis shows 234.7 (M+1), LCMS purity 93.24%, NMR: Confirmed.

Synthesis of Intermediate (5)

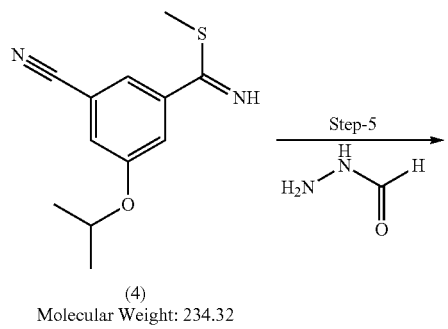

(4)
Molecular Weight: 234.32

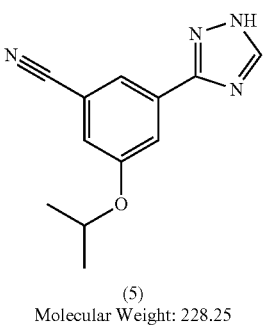

(5)
Molecular Weight: 228.25

In a 3-neck 50 mL round-bottomed flask, intermediate-4 (0.1 g, 1 eq.) was dissolved in DMF (1.5 mL, 15 Vol), to this reaction mixture formic hydrazide was added, resulting reaction mixture was stirred at RT for 5 min. then heat it at 80-90° C. Reaction was monitored by TLC using ethyl acetate:Hexane (7:3) as mobile phase. Starting was consumed after 5 hours string. Reaction mixture was quenched by ice-water, extract by ethyl acetate (10 mL×3), combined organic layer were dried over sodium sulfate and concentrate under reduce pressure to give crude material, the crude was subjected to column chromatography suing ethyl acetate:hexane as mobile phase. Compound was eluted at 25% ethyl acetate in hexane. Fractions containing compound was distilled out using rotary evaporation at 40° C./250 mm Hg to obtain 0.021 g (21.55%). Mass/LCMS: Mass analysis shows 228.7 (M+1) and 226.8 (M−1) peak. NMR: Confirmed.

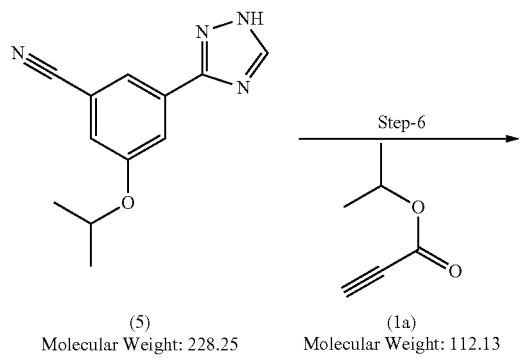

(5)
Molecular Weight: 228.25

(1a)
Molecular Weight: 112.13

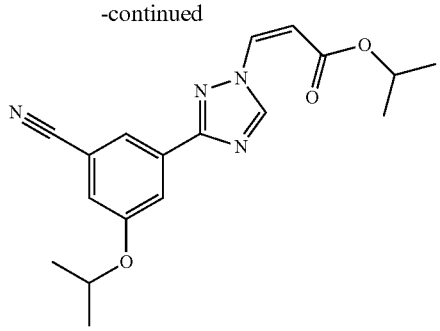

In a 3-neck 25 mL round-bottomed flask, Intermediate-5 (0.13 g) and TEA (0.08 mL, 1.0 eq.), was mixed and resulting reaction mixture was stirred at RT under photo chemical radiation for 10 min. To this reaction mixture isopropyl propiolate (1.5 eq.) was added. Resulting reaction mixture was stirred at RT under photo chemically radiation for 20-30 min. Reaction was monitored by TLC using Ethyl acetate: n-Hexane (3:7) as a mobile phase, which shows starting material was consumed. Reaction was concentrated under reduce pressure to give crude which as subjected to column chromatography followed by combi flash. Fractions containing compound was distilled out using rotary evaporation at 40° C./250 mm Hg to obtain 0.012 g (6.22%). $^1$H NMR (400 MHz, CDCl$_3$) δ 9.73 (S, 1H), 8.01 (S, 1H), 7.90 (S, 1H), 7.26-7.28 (d, J=10.8 Hz, 1H), 7.2 (S, 1H), 5.71-5.74 (d, J=11.2 Hz, 1H), 5.11-5.18 (m, 1H), 4.65-4.71 (m, 1H), 1.27-1.41 (d, 12H): LCMS for C$_{18}$H$_{20}$N$_4$O$_3$ [M+1]$^+$ 340.38 found 340.91 at 4.299 min.

Example 51

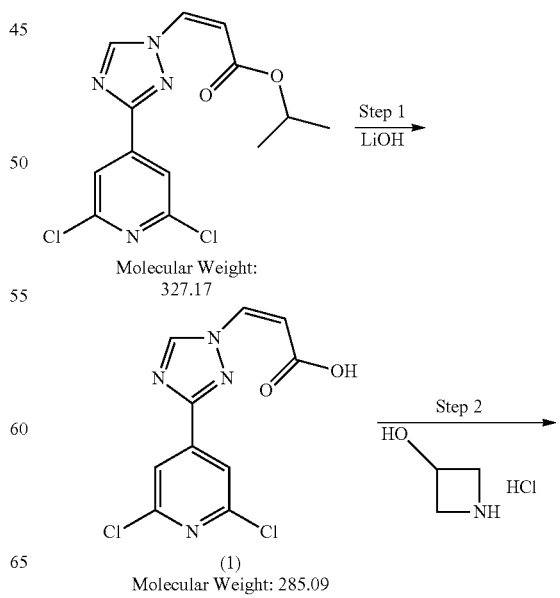

Molecular Weight: 327.17

Molecular Weight: 285.09

Synthesis of Intermediate (1)

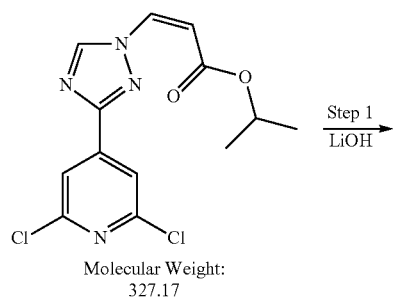
Molecular Weight: 327.17

Step 1
LiOH

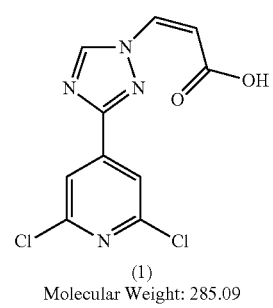
(1)
Molecular Weight: 285.09

In a 3-neck 100 mL round-bottomed flask, Example 28 (0.37, 1 .eq.) was dissolved in THF (10 mL) and Water (10 mL) (1:1) was added LiOH (0.18 g, 4 eq.) portion wise in reaction mixture. Reaction mixture was stirred at RT for 3 h. Reaction completion was monitored on TLC using DCM:MeOH (9:1) as mobile phase. Reaction mixture was quenched into the ice-water slurry (250 mL), acidified with dil. HCl and compound was extracted in the ethyl acetate (50 mL×3). Organic layer was washed with brine solution (50 mL×3) followed by drying using anhydrous sodium sulphate. Organic layer was concentrated under reduced pressure to afford 0.3 g of crude compound, Yield (93%). Mass: 285.7.

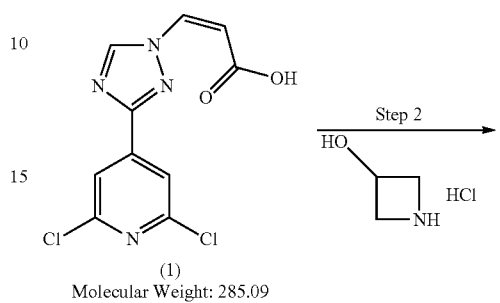
(1)
Molecular Weight: 285.09

Step 2

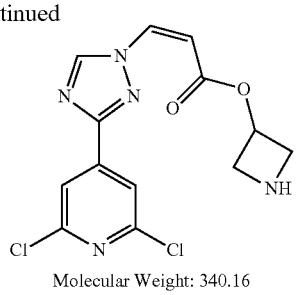
Molecular Weight: 340.16

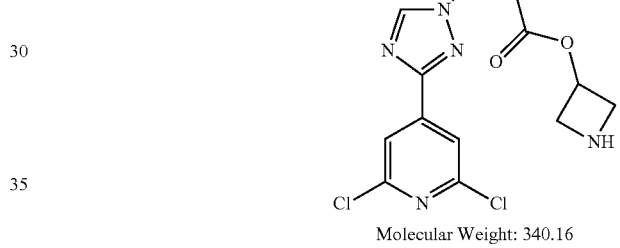
Molecular Weight: 340.16

In a 3-neck 50 mL round-bottomed flask, intermediate 1 (0.1 g, 1 eq.) was dissolved in DCM (20 mL) and DMAP (0.004 g, 0.1 eq.) was added DCC (0.093, 1.3 eq.) followed by 3-OH azitidine (0.050, 1.3 eq.) at −20° C. Reaction mixture was stirred at 0° C. for 2 h. Reaction completion was monitored on TLC using DCM:MeOH (9:1) as mobile phase. Reaction mixture was brought to room temperature and quenched into the ice-water slurry (100 mL). Compound was extracted in the Ethylacetate (100 mL×3). Organic layer was washed with brine solution (100 mL×3) followed by drying using anhydrous sodium sulphate. Organic layer was concentrated under reduced pressure to afford 0.09 g of crude compound which was purified by column to give 0.025 g of pure compound yield (21.01%). $C_{13}H_{11}Cl_2N_5O_2$. (340.16). $^1$HNMR (400 MHz, DMSO) δ 9.5 (s, 1H), 8. (s, 1H), 7.35-7.38 (d, j=10.4, 1H), 5.99-6.02 (d, j=10.4, 1H), 5.8 (d, 1H) 4.48 (s, 1H) 4.26-4.30 m, 1H). LCMS $C_{13}H_{11}Cl_2N_5O_2$ (340.16339.79) [M+1] found 331.85.

Example 52

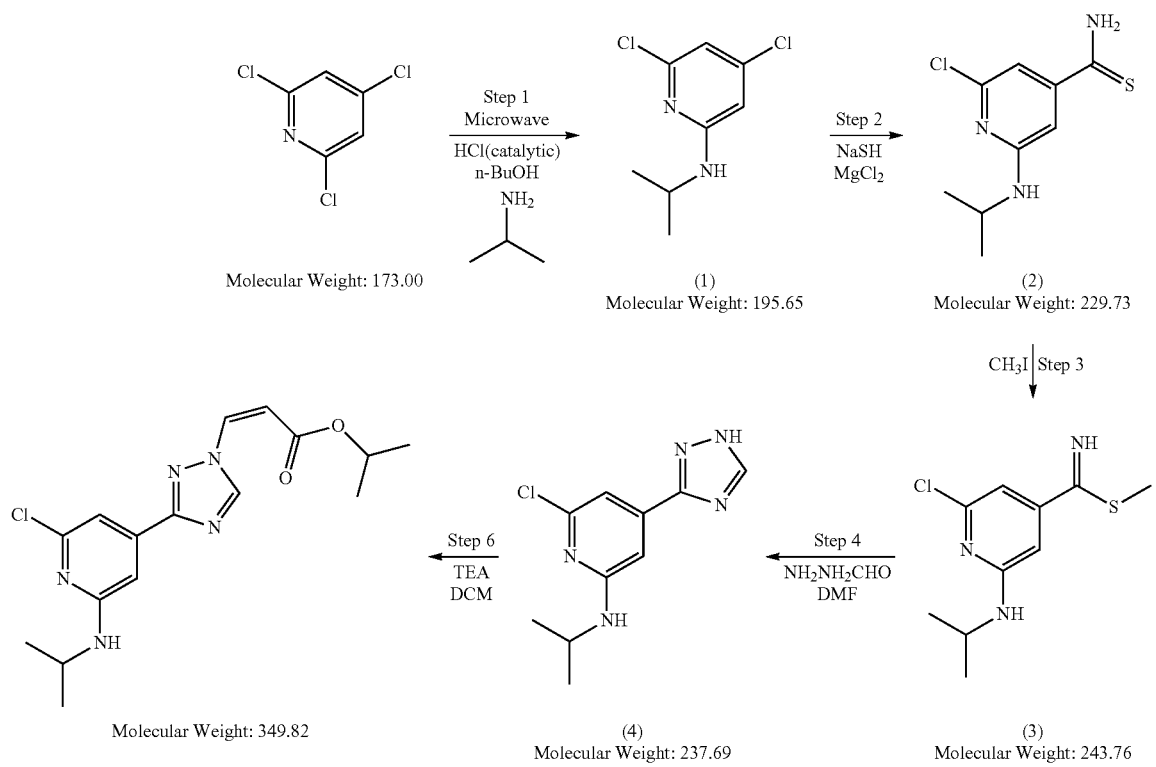

Synthesis of Intermediate (1)

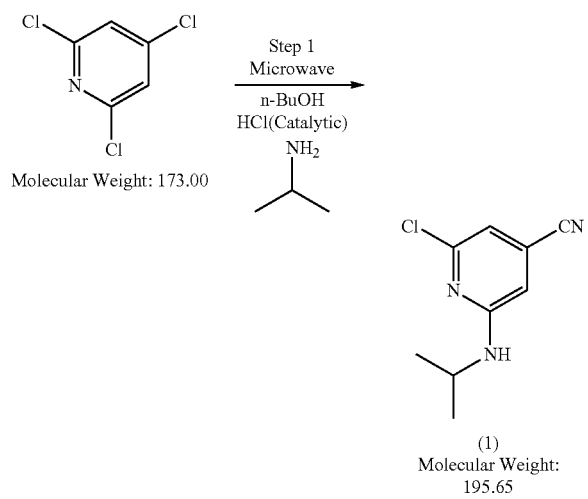

In a 25-mL microwave seal vial 2,6-dichloroisonicotinonitrile (2.5 g) and Isopropylamine (0.94 g) was dissolved in n-BuOH. Reaction was irradiated with microwave radiation at 130° C. for 20 min at 150 Watt. The Completion of the reaction was confirmed by TLC using 10% EtOAc-n-hexane as mobile phase. Reaction mixture was distilled under reduced pressure to remove n-BuOH. The crude reaction was dissolved in ethyl acetate and organic layer was washed with water (100 mL×2) & dried over anhydrous $Na_2SO_4$, filtered, and concentrated by rotary evaporation (40° C., 20 mmHg) to obtain 2.8 g of a yellow oil. The resulting crude compound (2.8 g) was subjected to column purification. The crude reaction mixture was purified by column chromatography using silica 60/120 using ethyl acetate:n-hexane as mobile phase. The column was packed in hexane and started eluting in ethyl acetate in gradient manner starting with fraction collection (25 mL fractions) from 1-3% ethyl acetate in hexane. Compound started eluting with 2% ethyl acetate in hexane. Fraction containing such TLC profile was collected together to obtain pure compound (1.5 g), Yield (53%).

Synthesis of Intermediate (2)

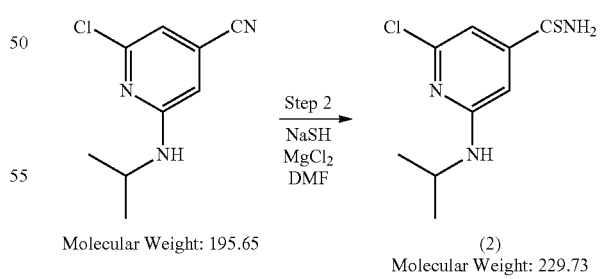

In a 100 mL 3N round-bottomed flask equipped with nitrogen bubbler on magnetic stirrer 2-chloro-6-(isopropylamino) isonicotinonitrile (1.5 g), NaSH (0.85 g), $MgCl_2$ (1.71 g) dissolved/suspended in 15 mL DMF at RT. Reaction was stirred for 1 h at the same temperature. The Completion of the reaction was confirmed by TLC with 50% EtOAc-n-hexane as mobile phase. Reaction mixture was poured into ice water slurry and compound extracted with (50×3) ethyl acetate. Organic layer dried over anhydrous Na₂SO₄, filtered, and concentrated by rotary evaporation to afford 2 .g of a yellow oil. The resulting crude compound (2.0 g) was forwarded to the next step without further purification.

Synthesis of Intermediate (3)

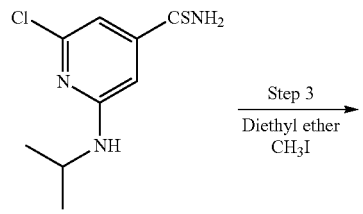

Molecular Weight: 229.73

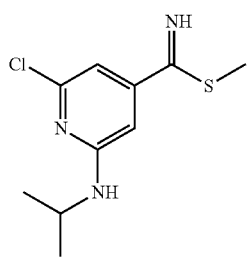

(3)
Molecular Weight: 243.76

In a 100 mL 3N round-bottomed flask attached with nitrogen bubbler on magnetic stirrer 2-chloro-6-(isopropylamino)pyridine-4-carbothioamide (2 g), CH₃I (6.17 g) was dissolved in 20 mL diethyl ether at RT. Reaction was stirred for 15 h. The Completion of the reaction was monitored by TLC using 50% EtOAc-n-hexane as mobile phase. The precipitate of intermediate-3 was filtered from ether to obtain 1.4 g compound which was carried forwarded to next step.

Synthesis of Intermediate (4)

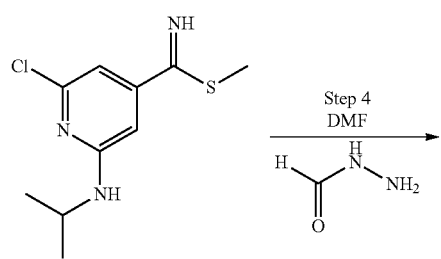

(3)
Molecular Weight: 243.76

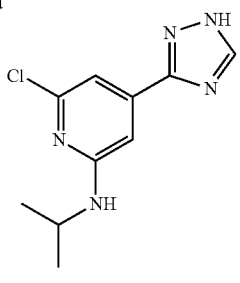

(4)
Molecular Weight: 237.69

In a 50 mL 3N round-bottomed flask equipped with nitrogen bubbler, reflux condenser on magnetic stirrer methyl-2-chloro-6-(isopropylamino)pyridine-4-carbimidothioate (1.4 g) and Formic hydrazide (0.689 g) was dissolved in 14 mL DMF at RT and stirring was continued for 1 h to form uncyclised form of intermediate-4 which was confirmed by mass and observed on TLC as a polar spot as compared to SM(3). Reaction mixture was heated at 80° C. for 6 h to obtain non polar spot as compared to uncyclised form. The Completion of the reaction was confirmed by TLC with 50% EtOAc-n-hexane as mobile phase. The reaction mixture was poured into ice water solution & compound was extracted with ethyl acetate (3×50 mL) Organic layer was dried over anhydrous Na₂SO₄ & concentrated to obtain crude product (1.5 g). The crude reaction mixture was purified by column chromatography using silica 60/120 using ethyl acetate:hexane as mobile phase. The column was packed in hexane and started eluting in ethyl acetate in gradient manner starting with fraction collection (25 mL fractions) from 5-25% ethyl acetate in hexane. Compound started eluting with 25% ethylacetate in hexane. Fraction containing such TLC profile was collected together to obtain pure compound (0.8 g), Yield (58%).

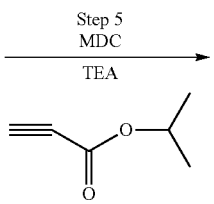

(4)
Molecular Weight: 237.69

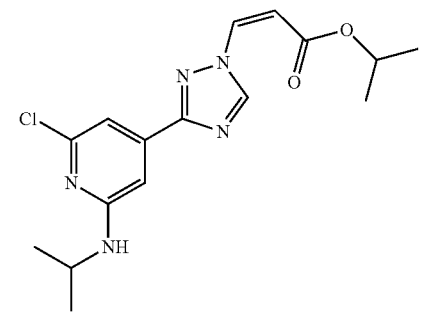

Molecular Weight: 349.82

In a 50 mL 3N round-bottomed flask attached with nitrogen bubbler, on magnetic stirrer 6-chloro-N-isopropyl-4-

(1H-1,2,4-triazol-3-yl)pyridin-2-amine (0.5 g) and TEA (0.276 g) was dissolved in 5 mL MDC at RT. Isopropyl propiolate (0.306 g) was diluted with MDC (1 mL) and added dropwise in the reaction mixture. Reaction mixture was stirred for 30 min. Completion of the reaction was confirmed on TLC in 50% ethylacetate/n-Hexane as mobile phase. Reaction confirmed two isomeric compound (Cis/Trans) compound. The reaction mixture was poured into ice water slurry & compound was extracted with MDC (3×25 mL) Organic layer dried over anhydrous $Na_2SO_4$ & concentrated to obtain crude product (1.1 g). The crude reaction mixture was purified by Preparative TLC using 30% Ethyl acetate in Hexane mobile phase. Upper spot confirmed as cis on basis of NMR which was purified by combiflash to obtain 35 mg of pure compound. $^1$H NMR (400 MHz, $CDCl_3$) δ 9.72 (s, 1H), 8.12 (s, 1H), 7.26-7.28 (d, 1H), 7.03 (s, 1H), 5.7-5.76 (d, 1H, J=10.8 Hz), 5.12-5.17 (m, 1H), 3.94-3.97 (m, 1H), 1.34-1.32 (d, 6H, J=8), 1.31-1.29 (d, 6H, J=8 Hz). LCMS for $C_{16}H_{20}ClN_5O_2$ [M+1]$^+$ 349.8 found 349.7 at 4.268 min (LCMS 97.32%).

Example 53

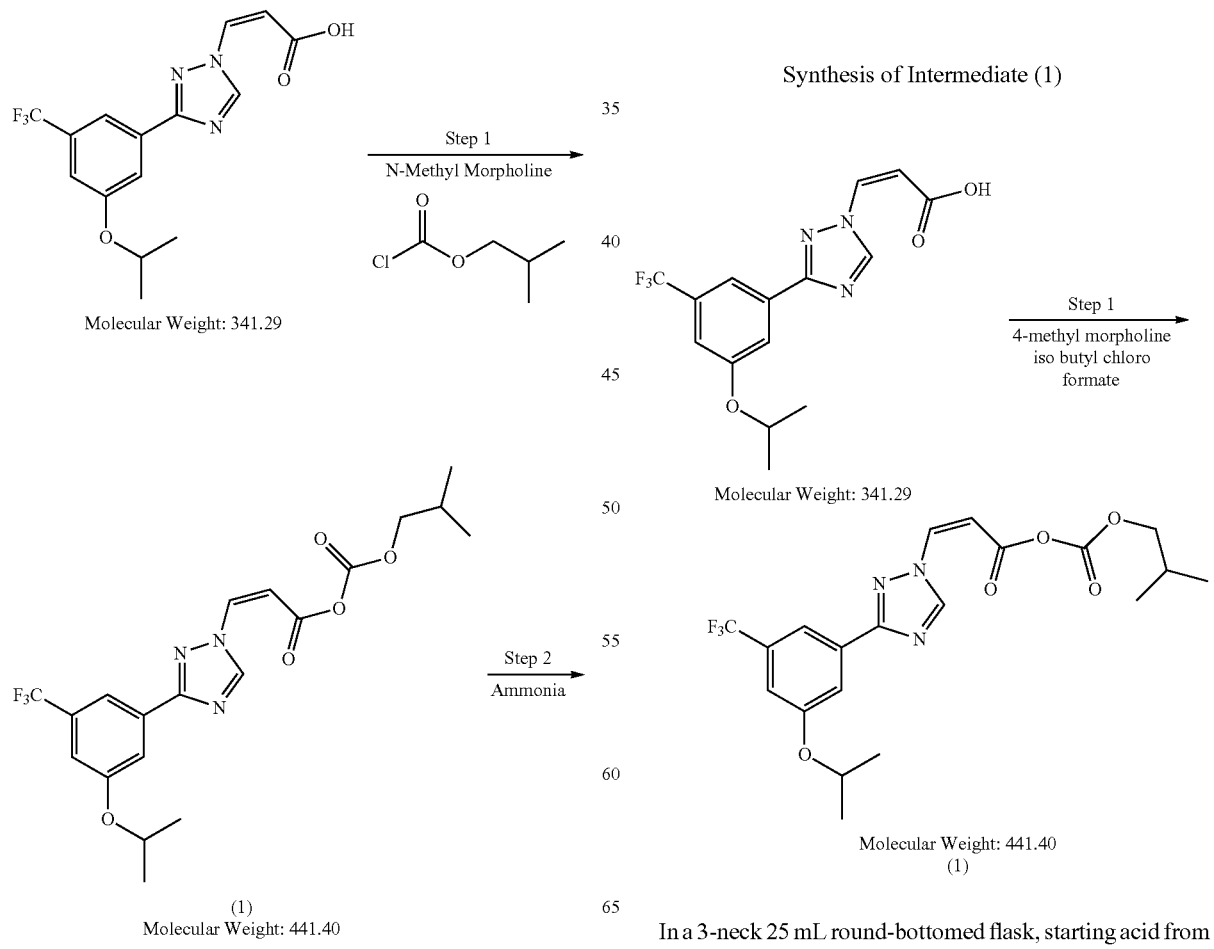

Synthesis of Intermediate (1)

In a 3-neck 25 mL round-bottomed flask, starting acid from Example 44 (0.150 g, 1.0 eq) was dissolved in 5 mL of THF at 0° C. under N$_2$ atmosphere, 4-methyl morpholine (0.067 mL, 1.4 eq) and Isobutyl chloroformate (0.088 mL, 1.5 eq) was added to this. Reaction mixture was stirred at 0° C. for 1 h. The progress of the reaction was followed by TLC analysis on silica gel with 10% methanol:DCM as mobile phase and visualization with UV, SM R$_f$=0.15 and Product R$_f$=0.40. Reaction was stirred for 1 h and white solid was separated and compound was collected by filtration and washed with THF (15 mL). The filtrate was used as such for next stage without any further purification. Mass: (ES+) 442.40 (M+1).

Synthesis of Intermediate (2)

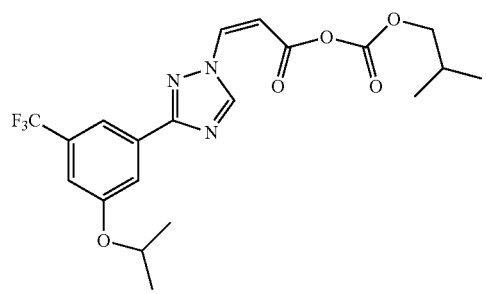

(1)
Molecular Weight: 441.40

Step 2
NH$_3$ Gas

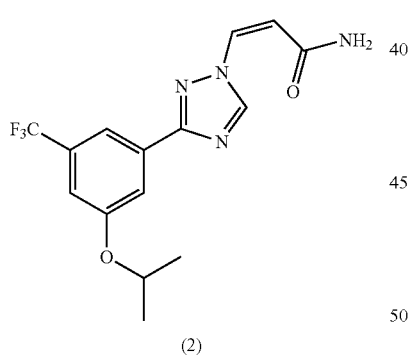

(2)
Molecular Weight: 340.30

In a 50 mL 3-neck round bottom flask equipped with septum, nitrogen bubbler and thermometer pocket, intermediate 1 (0.193 g) was dissolved in THF (10 mL). NH$_3$ gas was purged into the above reaction mixture for 5 min. The completion of reaction was monitored on TLC using Ethyl acetate:n-Hexane (5:5) as mobile phase. The reaction mixture was dumped into water (100 mL). Aqueous layer was extracted with Ethyl acetate (3×50 mL). Organic layer was dried over anhydrous sodium sulphate and solvent was evaporated to dryness under reduced pressure to obtain crude compound. Mass: Confirmed.

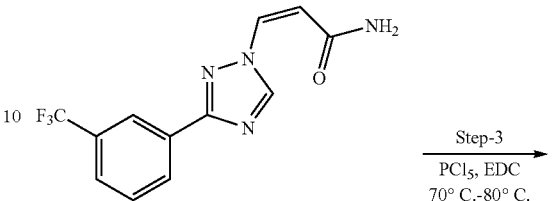

(2)
Molecular Weight: 340.30

Step-3
PCl$_5$, EDC
70° C.-80° C.

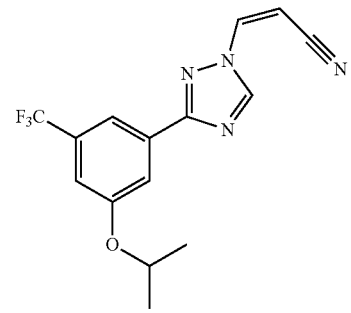

Molecular Weight: 322.29

In a 100 mL 3-neck round-bottomed flask equipped with condenser, nitrogen bubbler and thermometer pocket intermediate 2 (0.180 g, 0.00052 mol) was dissolved in EDC (7 mL). PCl$_5$ (0.121 g, 0.00058 mol) was added to the reaction mixture and reaction was refluxed for 2-3 h. The completion of reaction was monitored on TLC using Ethyl acetate:n-Hexane (4:6) as mobile phase. The reaction mixture was dumped in water (100 mL). Aqueous layer was extracted with Ethyl acetate (3×50 mL). Organic layer was dried over sodium sulphate. Solvent was evaporated to dryness under reduced pressure to obtain crude material. $^1$H NMR (400 MHz, DMSO) δ 9.04 (s, 1H), 7.98-8.00 (d, J=9.6 Hz, 1H), 7.87 (s, 1H), 7.81 (s, 1H), 7.39 (s, 1H) 5.81-5.83 (d, J=9.6 Hz, 1H) 4.79-4.85 (q, 1H) 1.34-1.32 (dd, 6H) LCMS C$_{15}$H$_{13}$F$_3$N$_4$O (322.29)[M+] found 322.86 at 4.10 min (LCMS 99.68%).

Example 54
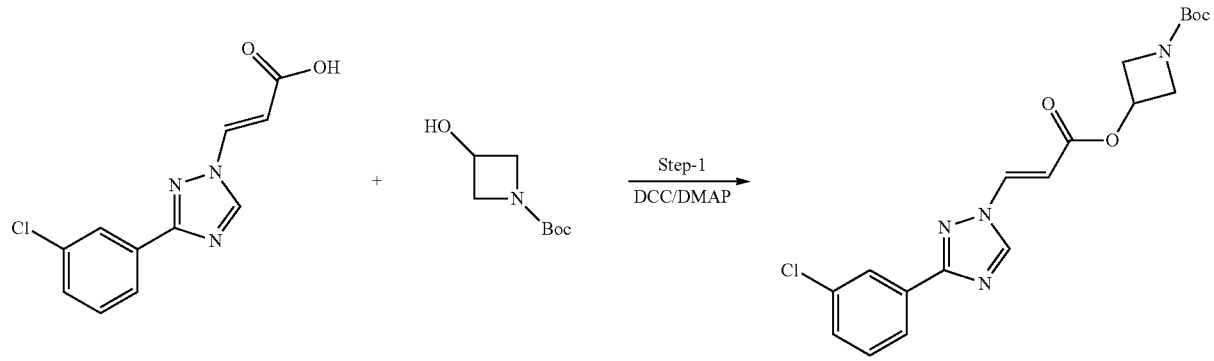
Molecular Weight: 249.65    Molecular Weight: 173.21    Molecular Weight: 404.85
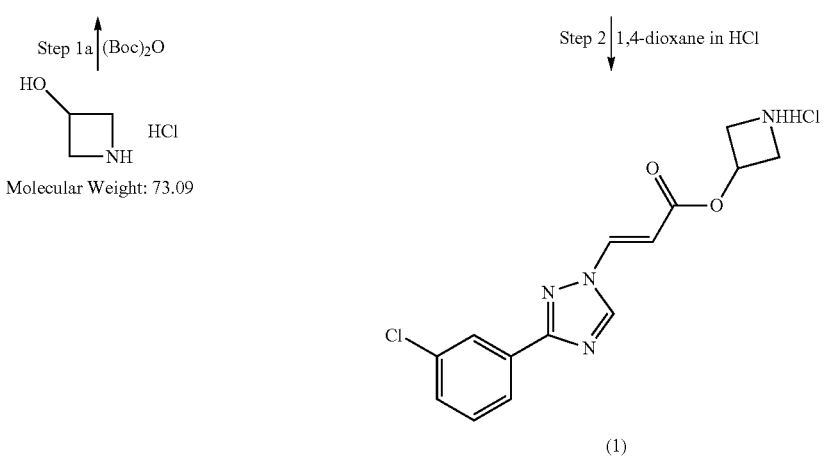
Molecular Weight: 73.09    Molecular Weight: 304.73
Synthesis of Intermediate (1)
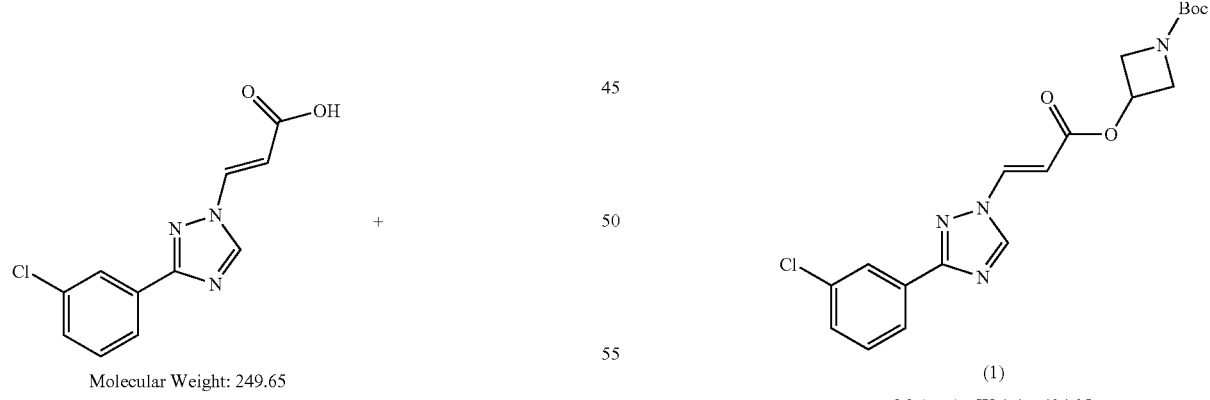
Molecular Weight: 249.65    Molecular Weight: 404.85
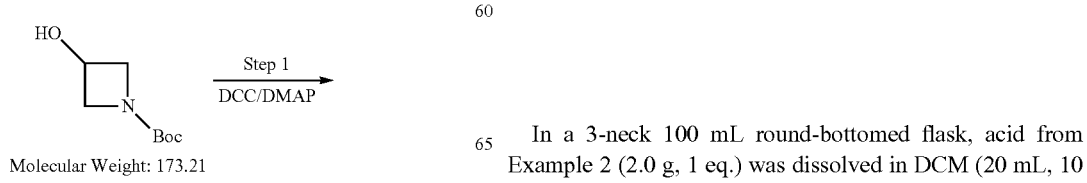
Molecular Weight: 173.21
In a 3-neck 100 mL round-bottomed flask, acid from Example 2 (2.0 g, 1 eq.) was dissolved in DCM (20 mL, 10 Vol.). DCC (2.14 g, 1.3 eq.), DMAP (0.098 g, 1.1 eq.) and tert-butyl 3-hydroxyazetidine-1-carboxylate (1.52 g, 1.1 eq.) was added to this reaction mixture and reaction mixture was stirred at 0° C. for 3-4 h. Reaction completion was monitored on TLC using ethyl acetate:hexane (3:7) mobile phase. Reaction mixture was filtered through celite bed and filtered was distilled off to get crude compound. The crude compound was purified using silica 60/120 and ethylacetate:hexane as mobile phase. Column purification was started with 5% EtOAc in hexane up to 30%. Compound started eluting in 10% ethyl acetate and continued till 12% EtOAc. Fractions containing compound was distilled out using rotary evaporation at 45° C./250 mm Hg to obtain 1.87 g of pure compound, Yield (57.7%). Mass: 404.9. LCMS: Confirmed.

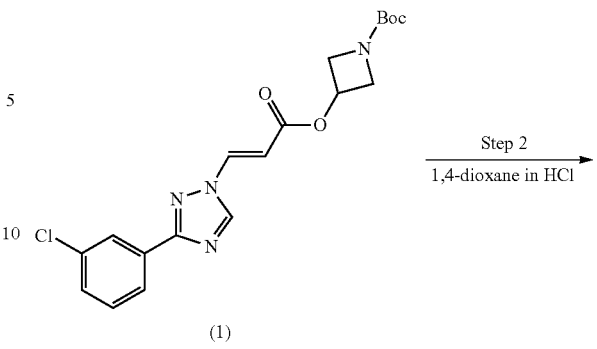

(1)
Molecular Weight: 404.85

Synthesis of Intermediate (1a)

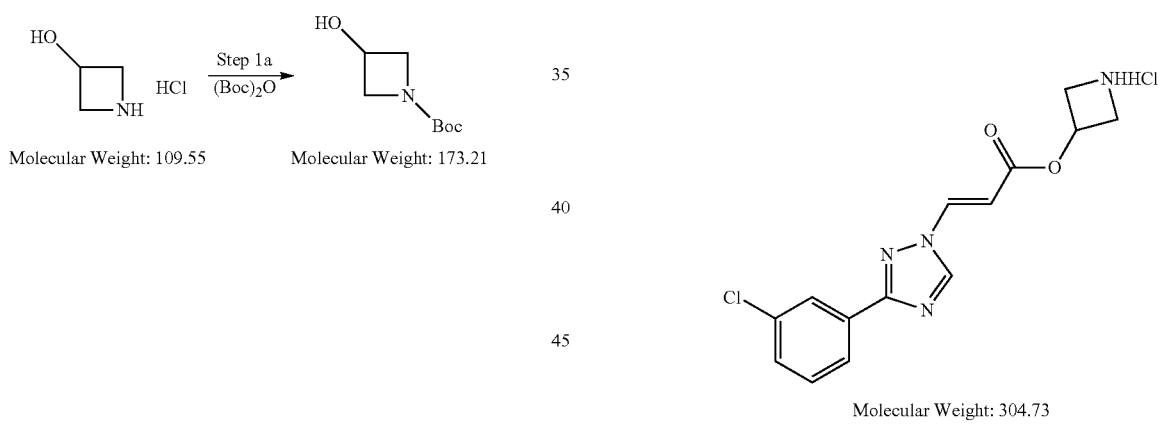

Molecular Weight: 304.73

In a 3-neck 50 mL round-bottomed flask, azetidin-3-ol (5.0 g, 1 eq.) was dissolved in DCM (100 mL, 20 Vol.) and cooled the reaction mixture to 0° C. TEA (6.68 g, 1.5 eq.) and Boc anhydride (10.9 g, 1.1 eq.) was added to this reaction mixture. Reaction mixture was stirred at 0° C. for 1 h. Reaction completion was monitored on TLC using ethyl acetate:hexane (5:5) mobile phase. Reaction mixture was brought to room temperature and quenched into the ice-water slurry (100 mL) and compound was extracted in the DCM (100 mL×3). Organic layer was washed with brine solution (150 mL×3) followed by drying using anhydrous sodium sulphate. Organic layer was concentrated under reduced pressure to afford 7.0 g of crude compound, yield (88.60%). Mass/LCMS: Confirmed.

In a 3-neck 50 mL round-bottomed flask, (E)-tert-butyl 3-(3-(3-(3-chlorophenyl)-1H-1,2,4-triazol-1-yl)acryloyloxy)azetidine-1-carboxylate (1.77 g, 1 eq.) was dissolved in 1,4-dioxane (10.0 mL, 5 Vol.) and added 1,4-Dioxane HCl (5.0 mL, 3 Vol.). Reaction mixture was stirred at RT for 12 h. Reaction completion was monitored on TLC using ethyl acetate:hexane (4:6) mobile phase. Reaction mixture was concentrated under reduced pressure to afford 1.14 g of compound. Yield (85.7%). $^1$H NMR (400 MHz, DMSO-$d_6$) δ 9.42 (broad s, $D_2O$ exchangeable, 1H), 9.15 (s, 1H), 7.58-8.54 (m, 4H), 8.28 (broad s, $D_2O$ exchangeable, 1H), 7.56-7.59 (d, J=14.4 Hz, 1H), 6.58-6.63 (d, J=14.0 Hz, 1H), 5.34-5.37 (m, 1H), 4.32-4.33 (m, 2H), 4.06-4.08 (m, 2H): LCMS for $C_{14}H_{14}Cl_2N_4O_2$ 341.19 found 304.88 at 2.668 min (LCMS 78.28%).

Example 55
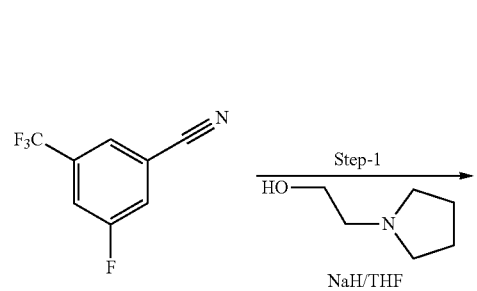
Molecular Weight: 189.1
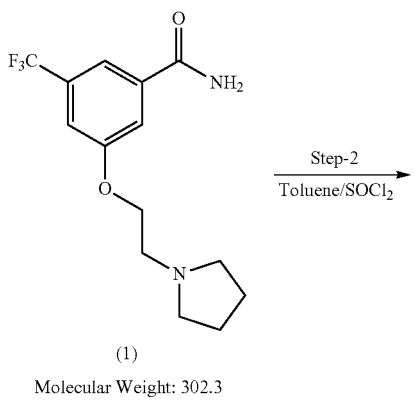
(1)
Molecular Weight: 302.3
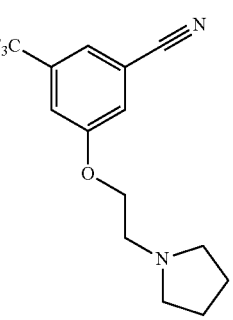
(2)
Molecular Weight: 284.3
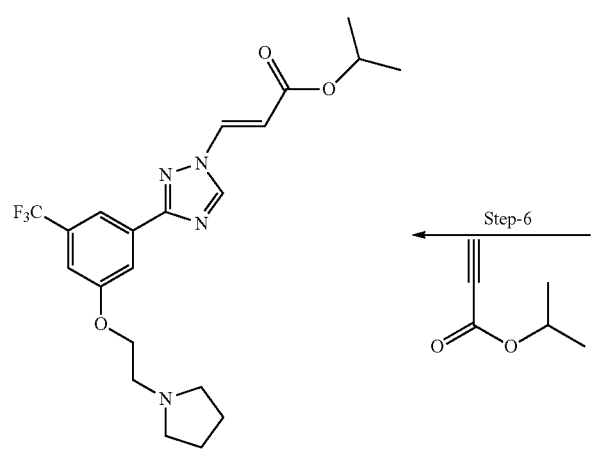
(5)
Molecular Weight: 438.44
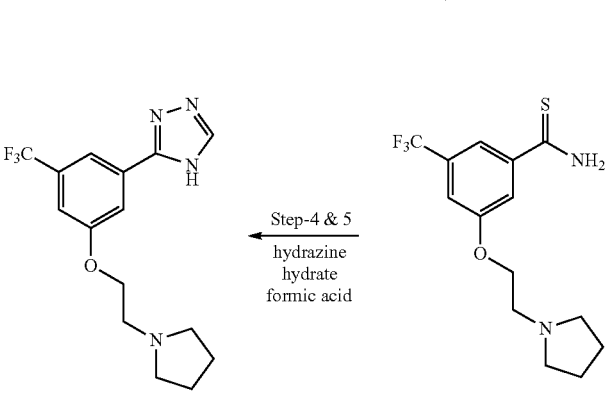
(4)
Molecular Weight: 326.3
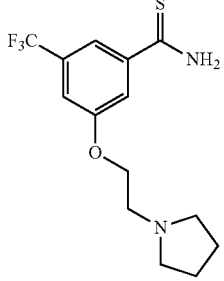
(3)
Molecular Weight: 318.4
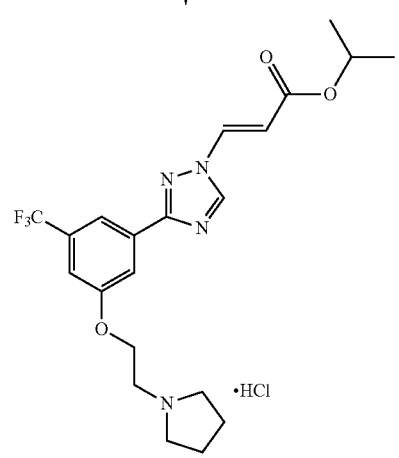
Molecular Weight: 474.9

Synthesis of Intermediate (1)

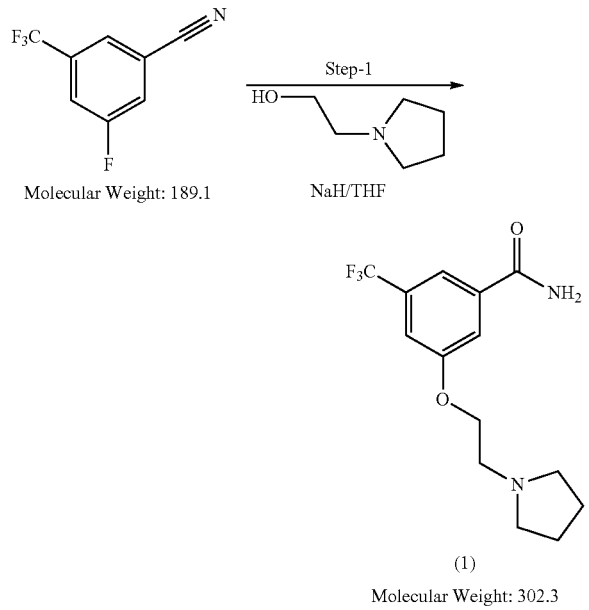

(1)
Molecular Weight: 302.3

In a 3-neck 100 mL round-bottomed flask, 2-(pyrrolidin-1-yl)ethanol (6.7, 1.1 eq.) was dissolved in THF (50 mL, 10 Vol) and NaH (2.55 g) was added portion wise in reaction mixture −25° C. Reaction mixture was stirred at −25° C. for 1 h. 3-Fluoro-5-(trifluoromethyl)benzonitrile (10.0 g, 1.0 eq.) was added portion wise in reaction mixture. Reaction mixture was stirred at this temp for 2 h and then at RT overnight. Reaction completion was monitored on TLC using ethyl acetate: n-hexane (3:7) as mobile phase. Reaction mixture was quenched into the ice-water slurry (250 mL) and compound was extracted in the ethyl acetate (50 mL×3). Organic layer was washed with brine solution (50 mL×3) followed by drying using anhydrous sodium sulphate. Organic layer was concentrated under reduced pressure to afford 14.0 g of crude compound, Yield (87.57%). This crude material was directly used for next step without purification. Mass: 303.1.

Synthesis of Intermediate (2)

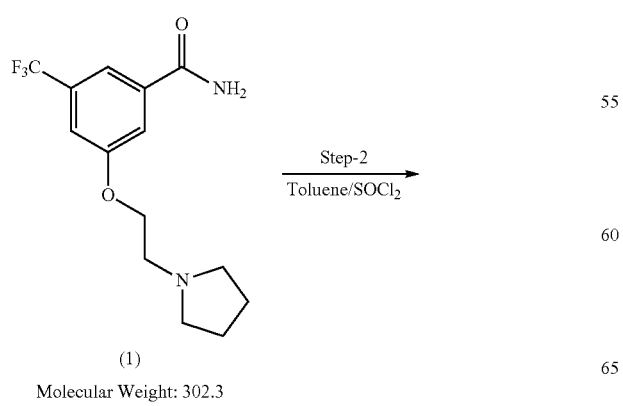

(1)
Molecular Weight: 302.3

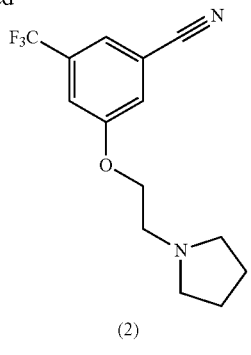

(2)
Molecular Weight: 284.3

In a 3-neck 100 mL round-bottomed flask, Intermediate 1 (14.0 g, 1 eq.) was dissolved in DMF (140 mL, 10 Vol) and $SOCl_2$ (11.01 g, 2.0 eq.) was added and reaction mixture was heated to 90° C. for 4-5 h. Reaction completion was monitored on TLC using ethyl acetate:n-hexane (2:8) as mobile phase. Reaction mixture was brought to room temperature and quenched into the ice-water slurry (140 mL) and neutralized with sodium bicarbonate solution. Compound was extracted in the Ethylacetate (200 mL×3). Organic layer was washed with brine solution (100 mL×3) followed by drying using anhydrous sodium sulphate. Organic layer was concentrated under reduced pressure to afford 12.0 g of crude compound, yield (91.15%). This crude material was directly used for next step without purification. Mass: 285.1.

Synthesis of Intermediate (3)

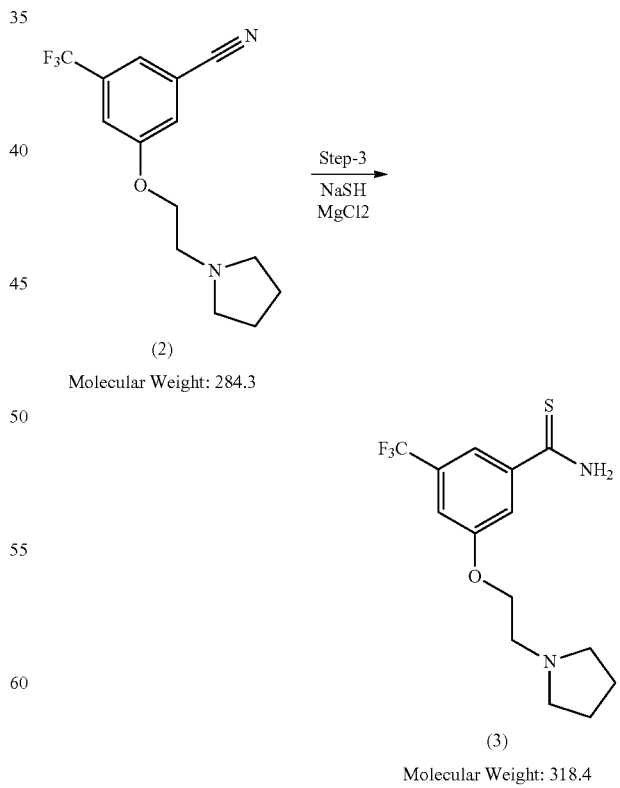

In a 1-neck 100 mL round-bottomed flask, Intermediate-2 (12 g, 1.0 eq.) was dissolved in DMF (120 mL, 10 V) and NaSH (4.73 g, 2.0 eq) followed by MgCl$_2$ (9.44 g, 1.1 eq.) was added into the reaction mixture. The reaction mixture was stirred for 6-8 h at RT. Reaction completion was monitored on TLC using ethyl acetate:n-hexane (4:6) as mobile phase. Reaction mixture was brought to room temperature and quenched into the ice-water slurry (250 mL) and compound was extracted in the Ethylacetate (100 mL×3). Organic layer was washed with brine solution (100 mL×3) and dried using anhydrous sodium sulphate. Organic layer was concentrated under reduced pressure to afford 10 g of crude compound, yield (74.39%). This crude material was directly used for next step without purification. Mass: 317.9.

Synthesis of Intermediate (4 and 5)

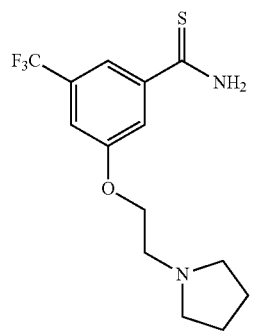

(3)
Molecular Weight: 318.4

Step-4 & 5
1. hydrazine hydrate
2. formic acid

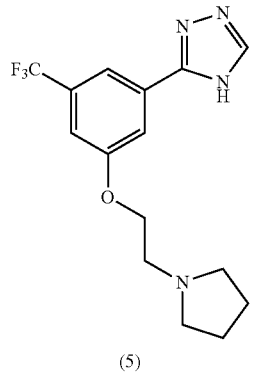

(5)
Molecular Weight: 326.3

In 1-neck 100 mL round-bottomed flask, Intermediate-3 (6.0 g, 1 eq.) was dissolved in DMF (120 mL, 10V) and Hydrazine hydrate (3.30 g, 2.0 eq.) was added and reaction mixture was stirred at RT for 2-3 h. Then Formic acid (100 mL, 5 Vol) was added and heated to 90° C. for 10-12 h. Reaction completion was monitored on TLC using methanol: DCM (1:9) as mobile phase. Reaction mixture was brought to room temperature and quenched into the ice-water slurry (1000 mL) and compound was extracted in the Ethyl acetate (200 mL×3). Organic layer was washed with brine solution (100 mL×3) followed by drying using anhydrous sodium sulphate. Organic layer was concentrated under reduced pressure to afford 11.5 g of crude compound. The crude reaction mixture was purified by column chromatography using silica 60/120 using Methanol: DCM as mobile phase. The column (5×10 cm) was packed in DCM and started eluting in Methanol in gradient manner starting with fraction collection (25 mL fractions) from 0.5-3.5% methanol in DCM. Compound started eluting with 2.5% methanol in DCM. Fraction containing such TLC profile was collected together to obtain pure compound (6.0 g), Yield (58.54%). Mass: 326.3.

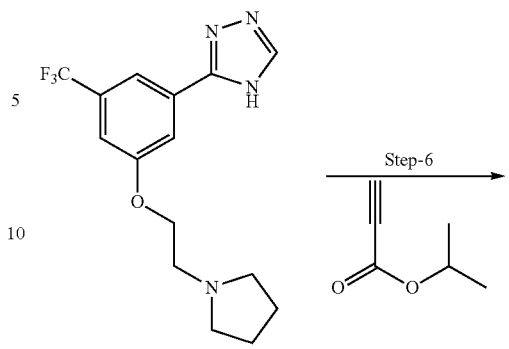

(5)
Molecular Weight: 326.32

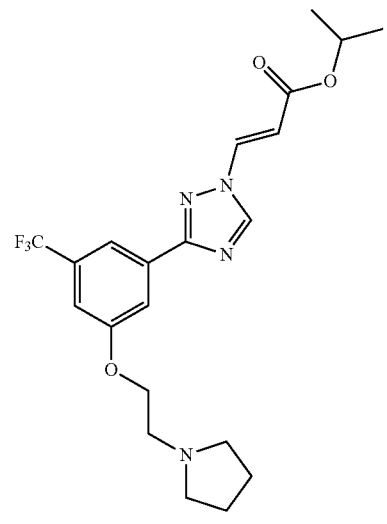

Molecular Weight: 438.44

In a 1-neck 25 mL round-bottomed flask, intermediate-5 (1.0 g, 1.0 eq.), was dissolved in DCM (10 mL, 10 vol.), TEA (0.400 g, 13 eq.) was added and Isopropyl propionate (0.446 g, 1.3 eq.) was added. Reaction mixture was stirred under photochemical 100 Watt lamp at 0° C. for 2-3 h. Reaction completion was monitored on TLC using Ethyl acetate:n-Hexane (2:8) as mobile phase. Reaction mixture was concentrated under reduced pressure to afford 1.2 g of crude compound. The crude reaction mixture was purified by column chromatography using silica 60/120 using ethyl acetate: n-hexane as mobile phase. The column (5×10 cm) was packed in hexane and started eluting in ethyl acetate in gradient manner starting with fraction collection (25 mL fractions) from 5-10% ethyl acetate in hexane. Compound started eluting with 5% ethylacetate in hexane. Fraction containing such TLC profile was collected together to obtain pure compound (200 mg), Yield (14.88%). Further Purified Cis compound was taken in 1-neck 25 ml, round-bottomed flask and dissolved in dioxane (2 mL, 10 vol.), added Dioxane/HCl (1.0 mL, 5 Vol) at 15-20° C. and stirred 2-3 h. Reaction completion was monitored on TLC using Ethyl acetate:n-Hexane (2:8) as mobile phase. Reaction mixture was concentrated under reduced pressure to afford 0.175 g of crude compound. Product was purified by Trituration with diethyl ether to afford 140 g pure compound.

Trans Isomer: $^1$H NMR (400 MHz, DMSO) δ 9.124 (s, 1H), 8.34-8.39 (d, 1H, J=14), 7.907-7.859 (d, 2H), 7.41 (S, 1H), 6.56-6.64 (d, 1H, J=14 Hz), 5.02-5.08 (m, 1H), 4.24 (m, 2H), 2.84 (m, 2H), 2.54 (m, 4H), 1.69 (Broad S, 4H), 1.13-1.17 (d, 6H). $C_{21}H_{25}F_3N_4O_3$ [M+1] 438.44 found 438.98 at 8.120 min (LCMS 98.27%).

Example 56

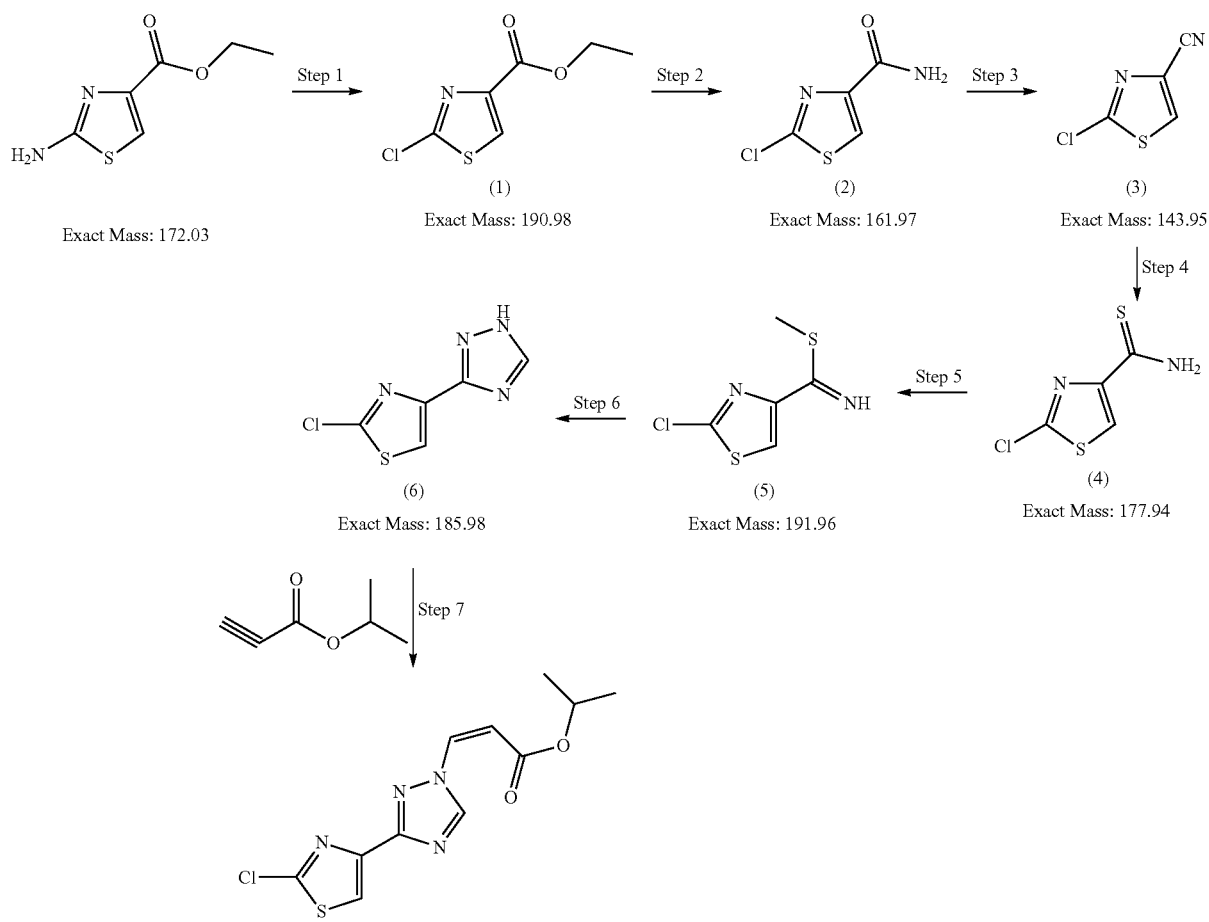

Synthesis of Intermediate (1)

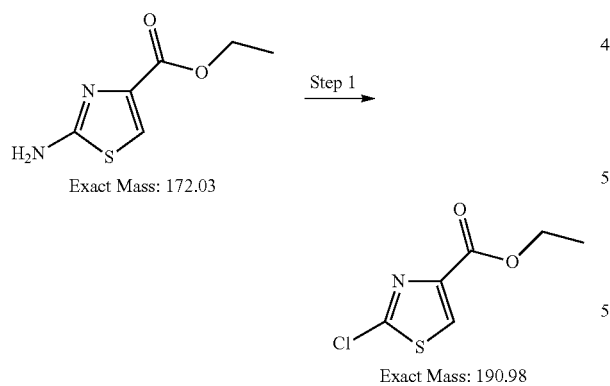

In a 3-neck 500 mL round-bottomed flask, Ethyl 2-amino thiazole 4-carboxylate (20.0 g, 1 eq.) was mixed with acetonitrile (300 mL, 15 Vol.), Cupric chloride (25.74 g, 1.3 eq.) and Isoamylnitrile (23.4 g, 1.5 eq.) was added dropwise in the reaction mixture and reaction mixture was stirred at room temperature for 1 h. Reaction remained dark green colored clear solution throughout the reaction. Reaction completion was monitored on TLC using ethyl acetate:hexane (3:7) mobile phase. After 1 h reaction was completed and worked up. Reaction mixture was poured into water (600 mL) and solid emulsion was filtered through celite. Compound was extracted in the ethyl acetate (200 mL×3). Organic layer was again washed with water (200 mL×3) followed by drying using anhydrous sodium sulphate. Organic layer was concentrated under reduced pressure to afford 22.0 g of crude compound. Crude compound was carry forward in next step. Yield (98.9%). Mass/LCMS: 192.0 Confirmed, NMR: Confirmed.

Synthesis of Intermediate (2)

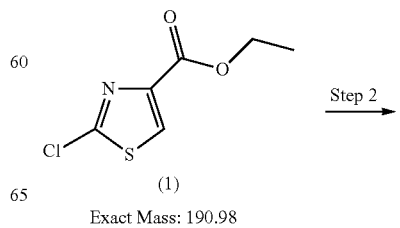

274

Synthesis of Intermediate (4)

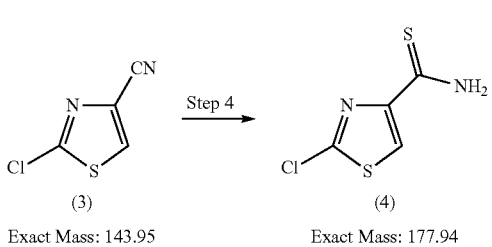

(3)           (4)

Exact Mass: 143.95     Exact Mass: 177.94

In a 3-neck 100 mL round-bottomed flask, Int-3 (3.7 g, 1 eq.) was mixed with DMF (56 mL, 15 Vol.), MgCl$_2$6H$_2$O (5.2 g, 1.0 eq.) and sodium thiol (3.79 g, 2.0 eq.) and reaction mixture was sired at room temperature for 15 min. Reaction remained green colored clear solution throughout the reaction. Reaction completion was monitored on TLC using ethyl MDC:Hexane (8.5:1.5) mobile phase. After 15 minutes reaction was completed and worked up. Reaction mixture was brought to room temperature and poured into water (300 mL) and compound was extracted in the ethyl acetate (100 mL×3). Organic layer was again washed with water (200 mL×3) followed by drying using anhydrous sodium sulphate. Organic layer was concentrated under reduced pressure to afford 2.32 g of crude compound. Crude compound was purified by column chromatography using ethyl acetate and hexane as mobile phase. Wt of pure product 3.0 g. yield (64.37%). Mass/LCMS: Confirmed, NMR: Confirmed.

Synthesis of Intermediate (5)

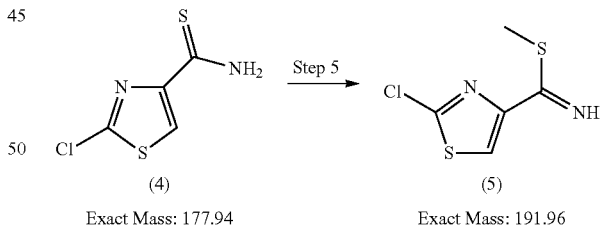

(4)           (5)

Exact Mass: 177.94     Exact Mass: 191.96

In a 3-neck 100 mL round-bottomed flask, Int-4 (3.0 g, 1 eq.) was dissolved in acetone (50 mL, 17 Vol) and reaction mixture was cooled at 0° C. and methyl iodide was dropwise added in reaction mixture and reaction mixture was heated to reflux for 1 hour. Reaction completion was monitored on TLC using ethyl acetate:hexane (3:7) mobile phase. Product was filtered and washed with diethyl ether (3×50 mL). Product was dried under reduced pressure to afford 3.86 g of crude compound. Mass/LCMS: Confirmed, NMR: confirmed.

273

-continued

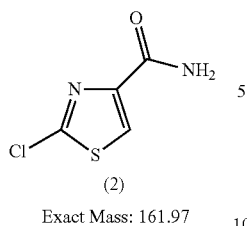

(2)

Exact Mass: 161.97

In a 3-neck 500 mL round-bottomed flask, intermediate 1 (21.0 g, 1 eq.) was dissolved in Liq. NH$_3$ (300 mL, 15 Vol) and reaction mixture was stirred at RT for 3 h. Reaction completion was monitored on TLC using ethyl acetate:hexane (3:7) as mobile phase. Product was filtered and washed with water (3×100 mL). Product was dissolved in ethyl acetate (500 mL) followed by drying using anhydrous sodium sulfate. Organic layer was concentrated under reduced pressure to afford 13.4 g of crude compound. Crude compound was carry forward in next step. Yield (74.0%), NMR: confirmed.

Synthesis of Intermediate (3)

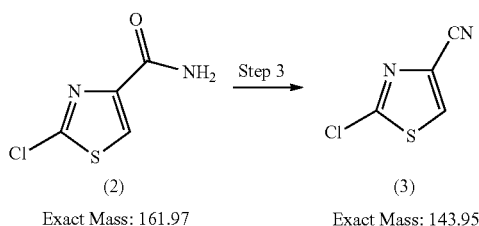 [SMILES: NC(=O)c1csc(Cl)n1 ; N#Cc1csc(Cl)n1]

(2)           (3)

Exact Mass: 161.97     Exact Mass: 143.95

In a 3-neck 250 mL round-bottomed flask, Intermediate 2 (10.8 g, 1 eq.) was dissolved in DMF (100 mL, 10 Vol) and reaction mixture was cooled to 0° C. and POCl$_3$ (24.3 mL, 4 eq.) was dropwise added in reaction mixture at 0° C. and reaction mixture was stirred at 60° C. for 30 min. Reaction completion was monitored on TLC using ethyl acetate:Hexane (3:7) mobile phase. Reaction mixture was brought to room temperature and poured into the ice water (500 mL) and adjust P$^H$ 7 using sodium bicarbonate. Compound was extracted in the Ethyl acetate (200 mL×3). Organic layer was again washed with water (200 mL×3) followed by drying using anhydrous sodium sulphate. Organic layer was concentrated under reduced pressure to afford 9.0 g of crude compound. Crude product was purified by flash chromatography using ethyl acetate and hexane as mobile phase. Wt of pure product 7.2 g, Yield (75.7%). Mass/LCMS: Not Confirmed, NMR: Confirmed, CMR: Confirmed.

Synthesis of Intermediate (6)

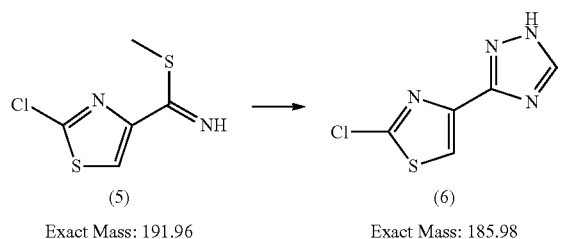

(5)  Exact Mass: 191.96

(6)  Exact Mass: 185.98

In a 3-neck 100 mL round-bottomed flask, Intermediate 5 (3.68 g, 1 eq.) and formic hydrazide (2.3 g, 2 eq) were dissolved in DMF (37 mL, 10 Vol) and reaction mixture was stirred at reflux temperature for 2 h. Reaction completion was monitored on TLC using ethyl acetate: n-Hexane (5:5) as mobile phase. Reaction mixture was brought to room temperature and poured into the water (100 mL) and compound was extracted in the Ethylacetate (100 mL×3). Organic layer was again washed with water (100 mL×3) followed by drying using anhydrous sodium sulphate. Organic layer was concentrated under reduced pressure to afford 2.0 g of crude compound. Crude product was purified by flash chromatography using ethyl acetate and hexane as mobile phase to obtain as pure product 0.6 g. Yield (16.83%). Mass/LCMS: Confirmed, NMR: Confirmed.

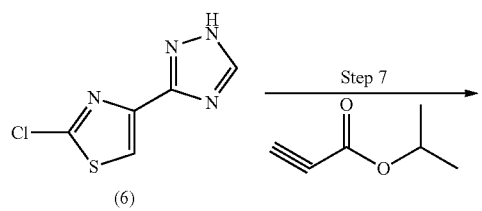

(6)  Exact Mass: 185.98

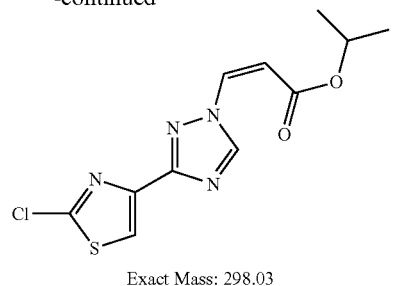

Exact Mass: 298.03

In a 1-neck 50 mL round-bottomed flask, Intermediate (6) (0.400 g, 1 eq.) and TEA (0.36 mL, 1.2 eq.) was dissolved in MDC (20 mL, 50 vol.) and reaction mixture was cooled to 15-20° C. and isopropyl propiolate (0.288 g, 1.2 eq.) was added dropwise and reaction mixture was stirred at 15-20° C. for 30 min. Reaction completion was monitored on TLC using Ethyl acetate: n-Hexane (5:5) as mobile phase. Reaction mixture was brought to room temperature and poured into the water (100 mL) and compound was extracted in the Ethyl acetate (50 mL×3). Organic layer was again washed with water (50 mL×3) followed by drying using anhydrous sodium sulphate. Organic layer was concentrated under reduced pressure to afford 0.250 g of crude compound, Product was purified by flash chromatography using ethyl acetate and Hexane to afford 0.006 g pure compound. Yield (0.93%). $^1$H NMR (400 MHz, DMSO-$d_6$) δ 9.2 (S, 1H), 8.22 (S, 1H), 7.45-7.48 (d, J=10.4 Hz, 1H), 5.94-5.96 (d, J=10.0 Hz, 1H), 5.02-5.05 (m, 1H), 1.23-1.24 (d, 6H): LCMS for $C_{11}H_{11}ClN_4O_2S$ [M+1]$^+$ 298.03 found 298.79 at 3.552 min.

Example 57

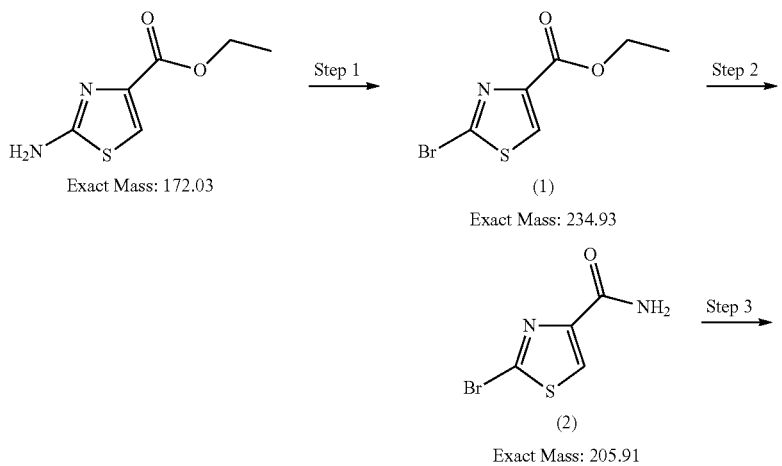

-continued

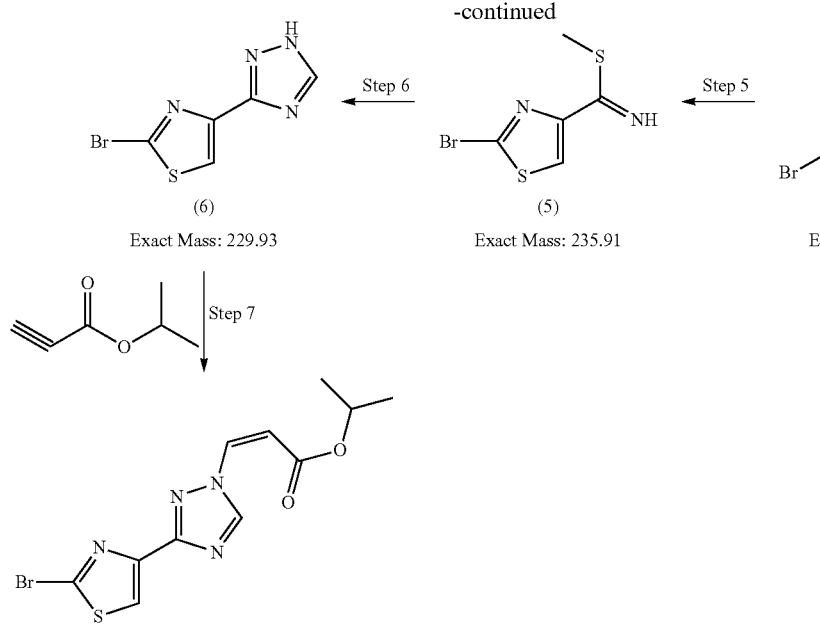

Synthesis of Intermediate (1)

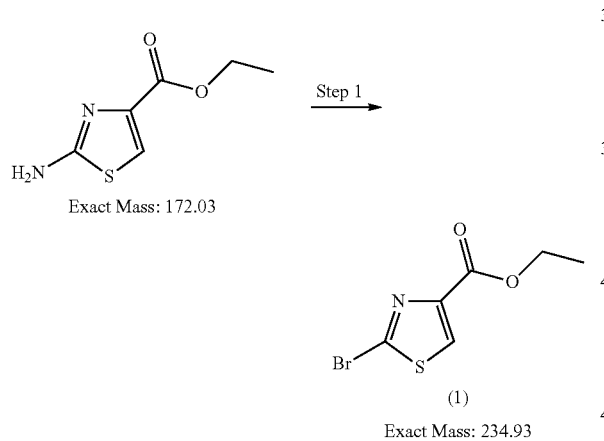

In a 3-neck 500 mL round-bottomed flask, Ethyl 2-amino thiazole 4-carboxylate (10.0 g, 1 eq.) was mixed with acetonitrile (100 mL, 10 Vol.), Cupric bromide (16.9 g, 1.3 eq.) and Isoamyl nitrile (11.7 mL, 1.5 eq.) was dropwise added in the reaction mixture and reaction mixture was stirred at room temperature for 1 h. Reaction completion was monitored on TLC using ethyl acetate:hexane (3:7) mobile phase. After 1 h reaction was completed and worked up. Reaction mixture was poured into water (600 mL) and solid emulsion was filtered through celite. Compound was extracted in the ethyl acetate (200 mL×3). Organic layer was again washed with water (200 mL×3) followed by drying using anhydrous sodium sulphate. Organic layer was concentrated under reduced pressure to afford 8.0 g of crude compound. Crude compound was carried forwarded in next step without purification Yield (58.6%). Mass/LCMS: 236.0 Confirmed.

Synthesis of Intermediate (2)

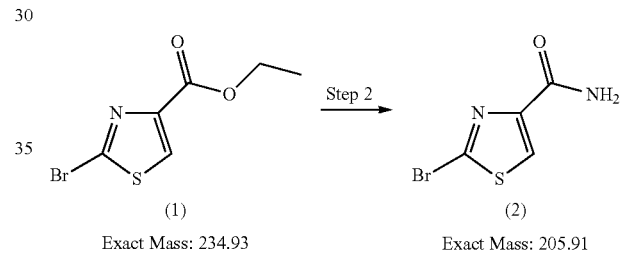

In a 3-neck 500 mL round-bottomed flask, Int-1 (8.0 g, 1 eq.) was dissolved in Liq. $NH_3$ (120 mL, 15 Vol) and reaction mixture was stirred at RT for 3 hrs. Reaction completion was monitored on TLC using ethyl acetate:hexane (3:7) mobile phase. Product was filtered and washed with water (3×100 mL). Product was dissolved in ethyl acetate (500 mL) followed by drying using anhydrous sodium sulfate. Organic layer was concentrated under reduced pressure to afford 5.0 g of crude compound. Crude compound was carry forward in next step Yield (71.3%).

Synthesis of Intermediate (3)

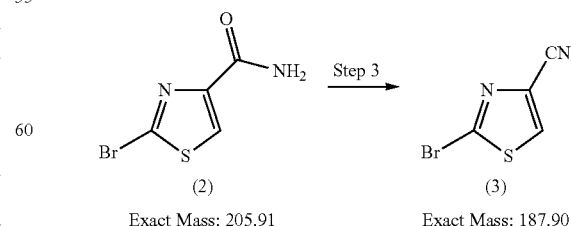

In a 3-neck 100 mL round-bottomed flask, Intermediate 2 (4.8 g, 1 eq.) was dissolved in DMF (20 mL, 5 Vol) and reaction mixture was cooled at 0° C. and POCl₃ (8.5 mL, 4 eq.) was added dropwise in reaction mixture and reaction mixture was stirred at 60° C. for 30 min. Reaction completion was monitored on TLC using ethyl acetate: n-hexane (3:7) as mobile phase. Reaction mixture was brought to room temperature and poured into the ice water (500 mL) and adjusted $P^H$ 7 using sodium bicarbonate. Compound was extracted in the Ethylacetate (200 mL×3). Organic layer was again washed with water (200 mL×3) followed by drying using anhydrous sodium sulphate. Organic layer was concentrated under reduced pressure to afford 3.0 g of crude compound. Crude product was purified by flash chromatography using ethyl acetate and hexane as mobile phase to obtain 2.88 g pure compound Yield (65.74%).

Synthesis of Intermediate (4)

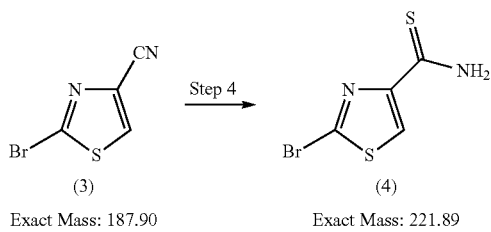 [SMILES: N#Cc1csc(Br)n1 ; NC(=S)c1csc(Br)n1]

(3)
Exact Mass: 187.90

(4)
Exact Mass: 221.89

In a 3-neck 100 mL round-bottomed flask, Intermediate 3 (2.87 g, 1 eq.) was mixed with DMF (43 mL, 15 Vol.), MgCl₂6H₂O (2.25 g, 1.0 eq.) and sodium thiol (3.08 g, 2.0 eq.) and reaction mixture was stirred at room temperature for 15 min. Reaction remained green colored clear solution throughout the reaction. Reaction completion was monitored on TLC using ethyl MDC: Hexane (8.5:1.5) mobile phase. After 15 minutes reaction was completed and worked up. Reaction mixture was brought to room temperature and poured into water (300 mL) and compound was extracted in the ethyl acetate (100 mL×3). Organic layer was again washed with water (200 mL×3) followed by drying using anhydrous sodium sulphate. Organic layer was concentrated under reduced pressure to afford 2.32 g of crude compound. Crude compound was purified by column chromatography using ethyl acetate and hexane as mobile phase to obtain 2.81 g of pure product yield (82.95%). Mass/LCMS: Confirmed, NMR: Confirmed.

Synthesis of Intermediate (5)

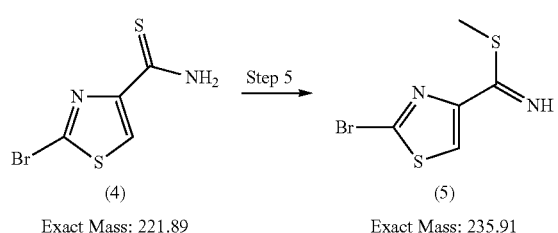

(4)
Exact Mass: 221.89

(5)
Exact Mass: 235.91

In a 3-neck 100 mL round-bottomed flask, Intermediate 4 (1.2 g, 1 eq.) was dissolved in acetone (50 mL, 42 Vol) and reaction mixture was cooled at 0° C. and methyl iodide was added dropwise in reaction mixture and reaction mixture was heated to reflux for 1 h. Reaction completion was monitored on TLC using ethyl acetate:hexane (3:7) mobile phase. Compound was filtered and washed with diethyl ether (3×50 mL). Compound was dried under reduced pressure to afford 1.38 g of crude compound. NMR: confirmed.

Synthesis of Intermediate (6)

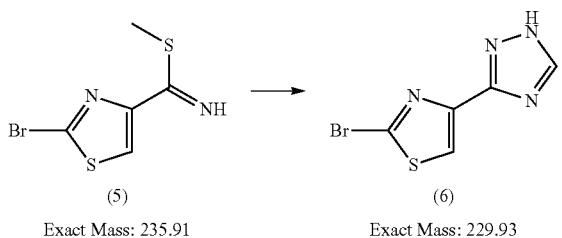

(5)
Exact Mass: 235.91

(6)
Exact Mass: 229.93

In a 3-neck 100 mL round-bottomed flask, Intermediate 5 (1.38 g, 1 eq.) and Formic hydrazide (0.7 g, 2 eq) were dissolved in DMF (15 mL, 10 Vol) and reaction mixture was stirred at reflux temperature for 2 h. Reaction completion was monitored on TLC using ethyl acetate:Hexane (5:5) as mobile phase. Reaction mixture was brought to room temperature and poured into the water (100 mL) and compound was extracted in the Ethyl acetate (100 mL×3). Organic layer was again washed with water (100 mL×3) followed by drying using anhydrous sodium sulphate. Organic layer was concentrated under reduced pressure to afford 2.0 g of crude compound. Crude product was purified by flash chromatography using ethyl acetate and hexane as mobile phase to obtain 0.303 g of pure product Yield (22.3%). Mass/LCMS: Confirmed, NMR: Confirmed.

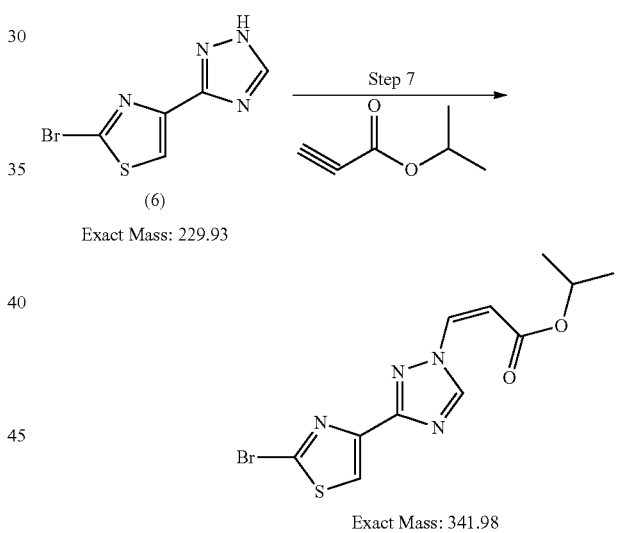

(6)
Exact Mass: 229.93

Exact Mass: 341.98

In a 1-neck 50 mL round-bottomed flask, Intermediate 6 (0.300 g, 1 eq.) and TEA (0.22 mL, 1.2 eq.) was dissolved in MDC (20 mL, 55 vol.) and Reaction mixture was cool at 15-20° C. and isopropyl propiolate (0.175 g, 1.2 eq.) was added dropwise and reaction mixture was stirred at 15-20° C. for 30 min. Reaction completion was monitored on TLC using Ethyl acetate:n-hexane (5:5) as mobile phase. Reaction mixture was brought to room temperature and poured into the water (100 mL) and compound was extracted in the Ethyl acetate (50 mL×3). Organic layer was again washed with water (50 mL×3) followed by drying using anhydrous sodium sulphate. Organic layer was concentrated under reduced pressure to afford 0.25 g of crude compound. Compound was purified by flash chromatography using ethyl acetate and Hexane to afford 0.011 g pure compound. Yield (2.46%). ¹H NMR (400 MHz, DMSO-d₆) δ 9.2 (S, 1H), 8.25 (S, 1H), 7.45-7.48 (d, J=10.4 Hz, 1H), 5.94-5.96 (d, J=10.4 Hz, 1H), 5.04-5.06 (m, 1H), 1.23-1.25 (d, 6H): LCMS for $C_{11}H_{11}BrN_4O_2S$ [M+1]$^+$ 343.2 found 344.71 at 3.587 min (LCMS 87.20%).

Example 58

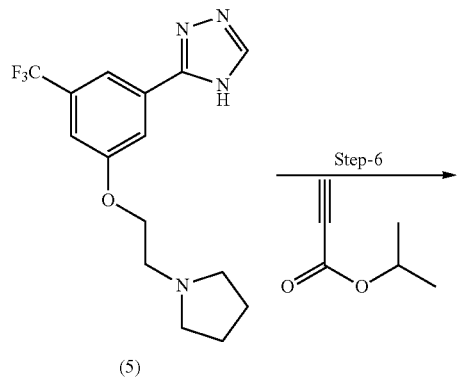

In a 1-neck 25 mL round-bottomed flask, intermediate-5 (from Example 55) (1.0 g, 1.0 eq.), was dissolved in DCM (10 mL, 10 vol.), TEA (0.400 g, 13 eq.) was added and Isopropyl propionate (0.446 g, 1.3 eq.) was added. Reaction mixture was stirred under photochemical 100 Watt lamp at 0° C. for 2-3 h. Reaction completion was monitored on TLC using Ethyl acetate:n-Hexane (2:8) as mobile phase. Reaction mixture was concentrated under reduced pressure to afford 1.2 g of crude compound. The crude reaction mixture was purified by column chromatography using silica 60/120 using ethyl acetate: n-hexane as mobile phase. The column (5×10 cm) was packed in hexane and started eluting in ethyl acetate in gradient manner starting with fraction collection (25 mL fractions) from 5-10% ethyl acetate in hexane. Compound started eluting with 5% ethylacetate in hexane. Fraction containing such TLC profile was collected together to obtain pure compound (200 mg), Yield (14.88%). Further Purified Cis compound was taken in 1-neck 25 mL round-bottomed flask and dissolved in dioxane (2 mL, 10 vol.), added Dioxane/HCl (1.0 mL, 5 Vol) at 15-20° C. and stirred 2-3 h. Reaction completion was monitored on TLC using Ethyl acetate:n-Hexane (2:8) as mobile phase. Reaction mixture was concentrated under reduced pressure to afford 0.175 g of crude compound. Product was purified by Trituration with diethyl ether to afford 140 mg pure compound. $^1$H NMR (400 MHz, DMSO-d$_6$) δ 12.97 (broad 1H, D$_2$O exchangeable), 9.75 (S, 1H), 7.38-8.09 (m, 3H), 7.21-7.24 (d, J=11.6 Hz, 1H), 5.73-5.75 (d, J=10.8 Hz, 1H), 5.12-5.18 (m, 1H), 4.68-4.71 (t, 2H), 3.85-3.94 (t, 2H), 3.55-3.60 (t, 2H), 3.01-3.08 (t, 2H), 2.28-2.33 (m, 2H), 2.13-2.18 (m, 2H), 1.32-1.34 (d, 6H): LCMS for $C_{21}H_{25}F_3N_4O_3$ [M+H]$^+$ 438.4 found 438.88 at RT 6.491 min (LCMS 96%).

Example 59

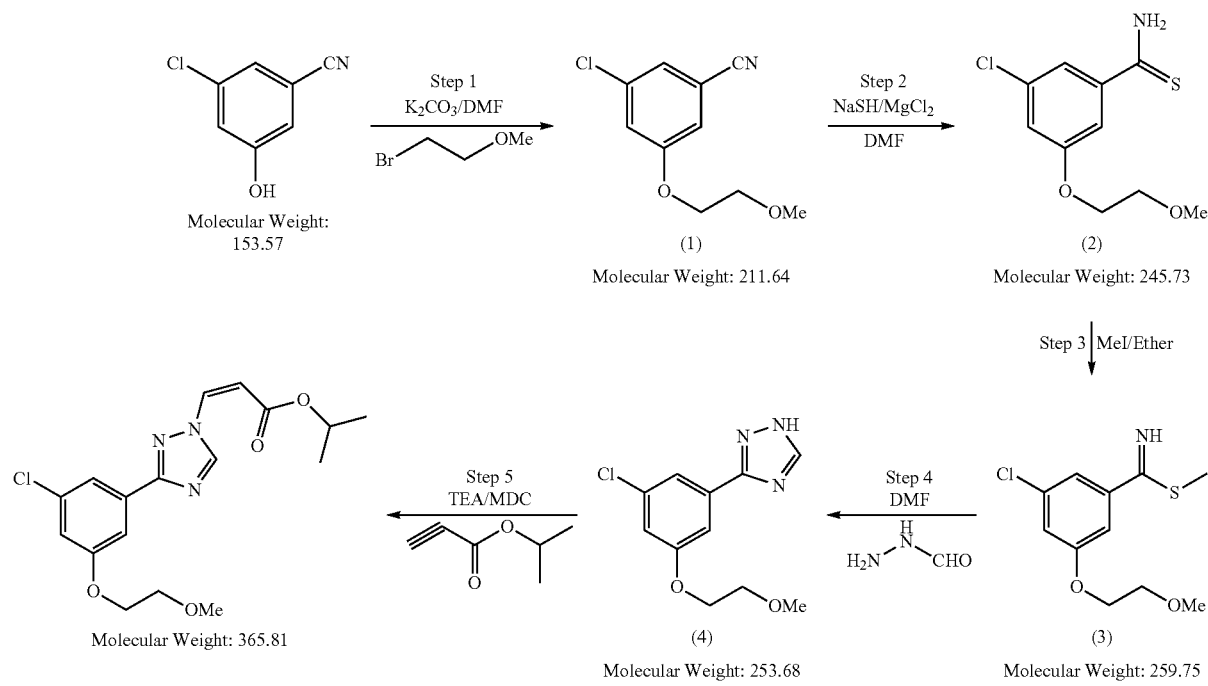

Synthesis of Intermediate (1)

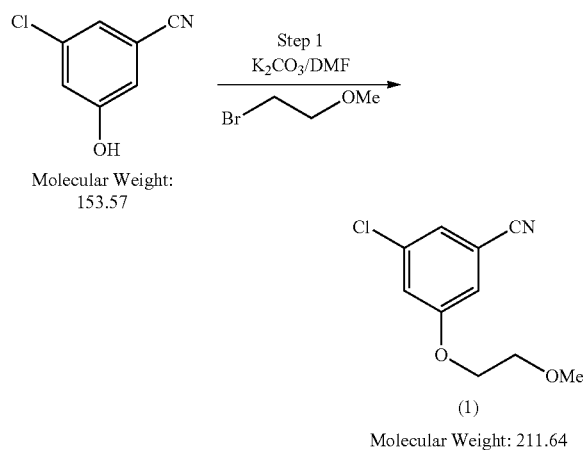

To a stirred solution of 3-chloro-5-hydroxybenzonitrile (0.500 g, 1 eq.) and potassium carbonate (0.677 g, 1.5 eq.) in DMF (5 mL, 5V) in 3 necked 100 mL round-bottomed flask equipped with refluxing condenser 1-bromo-2-methoxyethane (0.679 g, 1.5 eq.) was added dropwise at RT. Upon completion of addition, temperature of reaction mixture was slowly raised from RT to refluxing with constant stirring. Reaction mixture was refluxed for 2 h. Reaction completion was monitored on TLC using ethyl acetate:n-hexane (2:8) as mobile phase. The reaction mixture was quenched into the ice-water slurry (50 mL) and was extracted with ethyl acetate (30 mL×3). Organic layer was washed with brine solution (50 mL). The organic layer was dried using anhydrous sodium sulfate, filtered, and concentrated under reduced pressure to provide the 0.688 g crude titled compound, yield (99%). This crude material was directly used for next step without purification.

Synthesis of Intermediate (2)

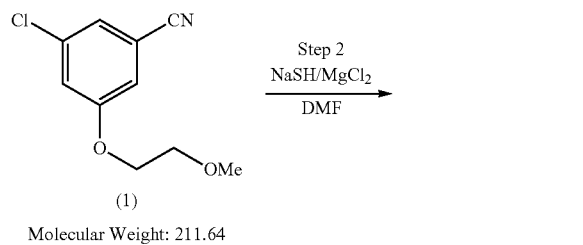

In a 1-neck 100 mL round-bottomed flask, intermediate 1 (0.688 g, 1 eq.) was dissolved in DMF (6.8 mL, 10 V) added sodium hydrogen sulfide hydrate (0.365 g, 2 eq.) and magnesium chloride hexahydrate (0.727 g, 1.1 eq.) in reaction mixture. The reaction mixture was stirred for 3-4 h at room temperature. Reaction completion was monitored on TLC using ethyl acetate:hexane (2:8) mobile phase. The reaction mixture was quenched into the ice-water slurry (50 mL) and was extracted with ethyl acetate (30 mL×3). Organic layer was washed with brine solution (50 mL). The organic layer was dried using anhydrous sodium sulfate, filtered, and concentrated under reduced pressure to provide the 0.935 g crude titled compound. This crude material was directly used for next step without purification. Mass: $[M+H]^+$ 245.7.

Synthesis of Intermediate (3)

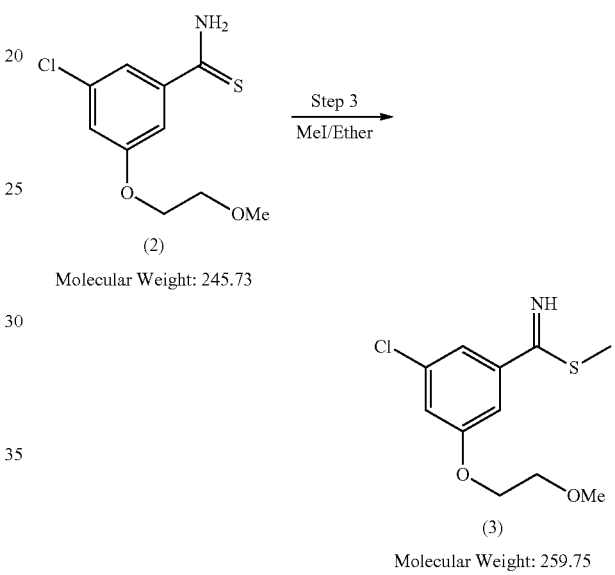

In a 3-neck 100 mL round-bottomed flask, intermediate 2 (0.935 g, 1 eq.) was dissolved in acetone (9.4 mL, 10 V) and dropwise added iodomethane (2.7 g, 5 eq.) and reaction mixture was stirred at room temperature for 1 h. Reaction completion was monitored on TLC using ethyl acetate:hexane (2:8) mobile phase. The reaction mixture was concentrated under reduced pressure to provide the 1.1 g crude titled compound. This crude material was directly used for next step without purification. Mass: $[M+H]^+$ 259.7.

Synthesis of Intermediate (4)

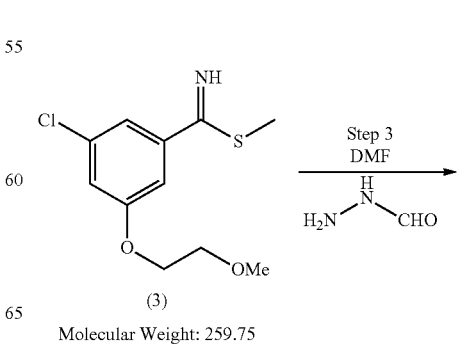

285
-continued

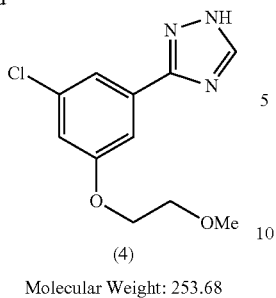

(4)
Molecular Weight: 253.68

In a 3-neck 100 mL round-bottomed flask, methyl intermediate 3 (1.1 g, 1 eq.) and formylhydrazine (0.508 g, 2.0 eq.) was dissolved in DMF (11 mL, 5 Vol) and reaction mixture was refluxed for 2 h. Reaction completion was monitored on TLC using ethyl acetate:hexane (2:8) mobile phase. The reaction mixture was quenched into the ice-water slurry (50 mL) and was extracted with ethyl acetate (30 mL×3). Organic layer was washed with brine solution (50 mL). The organic layer was dried using anhydrous sodium sulfate, filtered, and concentrated under reduced pressure to provide the 0.950 g crude compound was purified by column chromatography using ethyl acetate and hexane as mobile phase. Product was eluted in 25% ethyl acetate in hexane to afford 0.650 g of pure titled compound, yield (60.5%). Mass: [M+H]+ 253.7.

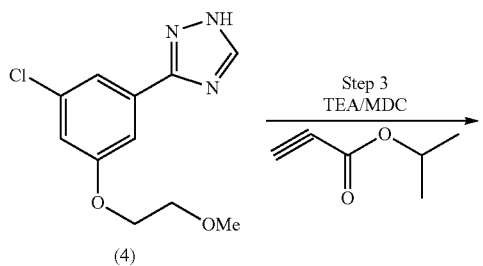

(4)
Molecular Weight: 253.68

286
-continued

VS 203
Molecular Weight: 365.81

In a 3-neck 50 mL round-bottomed flask, intermediate 4 (0.650 g, 1 eq.) and Triethylamine (0.389 g, 1.5 eq.) was dissolved in DCM (6.5 mL, 10 Vol) and added isopropyl propiolate (0.430 g, 1.5 eq.) at 15° C. and reaction mixture was stirred for 30 min at 15° C. Reaction completion was monitored on TLC using ethyl acetate:hexane (2:8) mobile phase. The reaction mixture was concentrated under reduced pressure to provide the 0.980 g crude compound was purified by column chromatography using ethyl acetate and hexane as mobile phase. Product was eluted in 4% ethyl acetate in hexane to afford 0.012 g of pure titled compound, yield (1.3%). $^1$H NMR (400 MHz, CDCl$_3$) δ 9.16 (s, 1H), 7.18-7.57 (m, 4H), 5.96-5.99 (d, J=10 Hz, 1H), 5.02-5.05 (m, 1H), 4.18-4.20 (t, J=4 Hz, J'=8.4 Hz, 2H), 3.67-3.69 (t, J=4.4 Hz, J'=8.8 Hz, 2H), 3.33 (s, 3H), 1.23-1.28 (m, 6H). LCMS-ESI calcd for C$_{17}$H$_{20}$ClN$_3$O$_4$ [M+H]+ 365.81. found 365.89 at 4.14 min (LCMS 85.30%).

Example 60

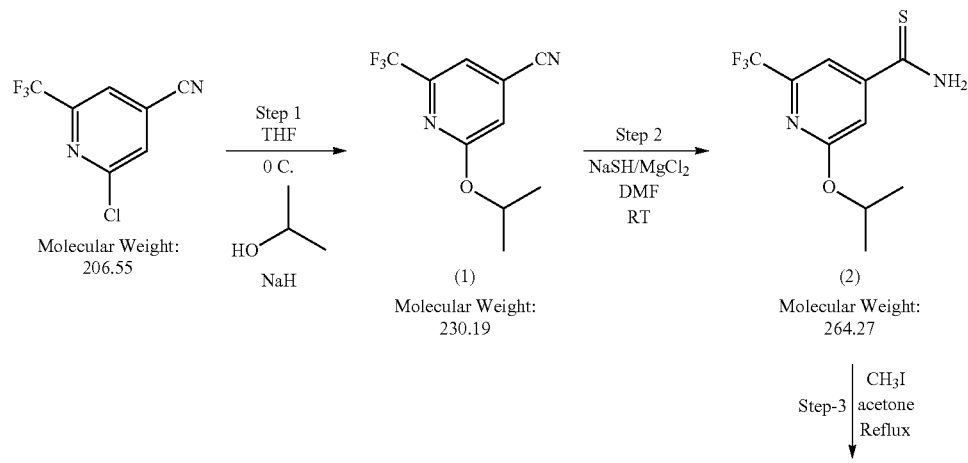

-continued

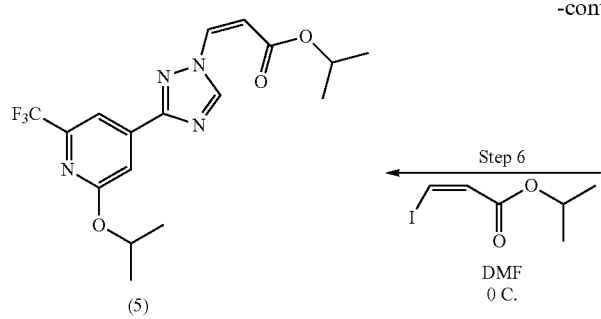

(5)
Molecular Weight: 384.35

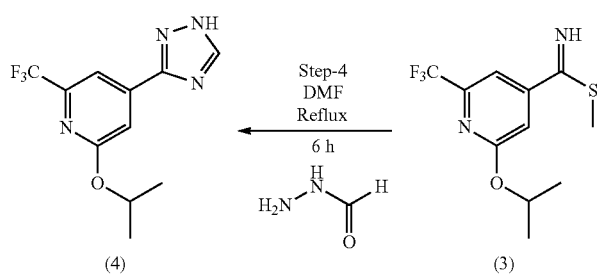

(4)
Molecular Weight: 272.23

(3)
Molecular Weight: 278.29

Synthesis of Intermediate (1)

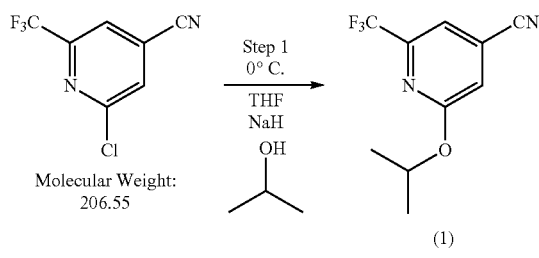

(1)
Molecular Weight: 230.19

In a 250-mL 3 neck round-bottomed flask NaH (1.39 g) suspended in THF (100 mL) at 0° C. Isopropanol (4.36 g) was added to the above reaction mixture. Reaction mixture was allowed to stirred at RT for 3 h and 2-chloro-6-trifluoromethylisonicotinonitrile (10 g) in THF (80 mL) was added dropwise at 0° C. Reaction mixture was maintained 0° C. for 30 min. Completion of reaction was monitored by TLC. Reaction mixture was quenched in ice water slurry. Compound was extracted in ethylacetate and organic layer was washed with water (100 mL×2) &dried over anhydrous $Na_2SO_4$, filtered, and concentrated under reduced pressure (40° C., 20 mmHg) to afford 8 g of a yellow oil. The resulting crude compound forwarded for next step.

Synthesis of Intermediate (2)

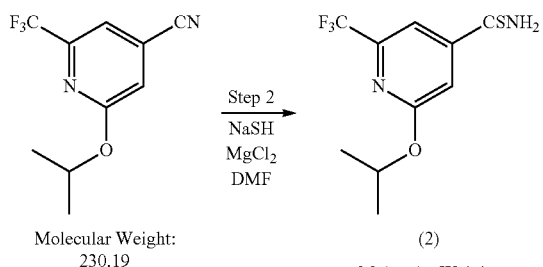

(2)
Molecular Weight: 264.27

In a 500 mL 3N round-bottomed flask equipped with nitrogen bubbler on magnetic stirrer, 2-isopropoxy-6-(trifluoromethyl)isonicotinonitrile (7.5 g), NaSH (2.73 g) and $MgCl_2$ (9.92 g) dissolved in DMF (75 mL) at RT. Reaction was stirred for 3 h and reaction completion was confirmed by TLC with 20% EtOAc-n-hexaneasmobile phase. Reaction mixture was poured into ice water and compound was extracted with ethylacetate (50×3). Organic layer was dried over anhydrous $Na_2SO_4$, filtered, and concentrated under reduced pressure to afford 7.5 g of a yellow oil. The resulting crude compound was forwarded for next step without any further purification.

Synthesis of Intermediate (3)

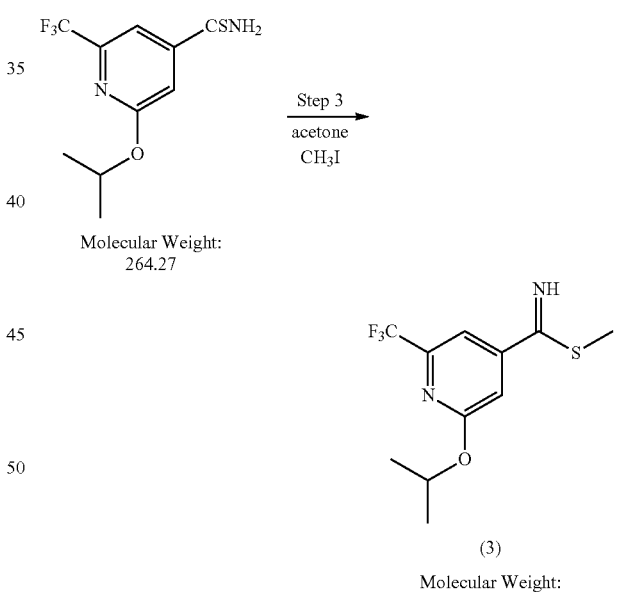

(3)
Molecular Weight: 278.29

In a 100 mL 3N round-bottomed flask equipped with nitrogen bubbler on magnetic stirrer intermediate 2 (7.5 g) and $CH_3I$ (10.18) was dissolved in acetone (75 mL) at RT. Reaction was refluxed for 2 h and progress of the reaction was followed by TLC with 20% acetone-n-hexane as mobile phase. The reaction mixture was concentrated under reduced pressure to obtain crude compound forwarded to next step.

Synthesis of Intermediate (4)

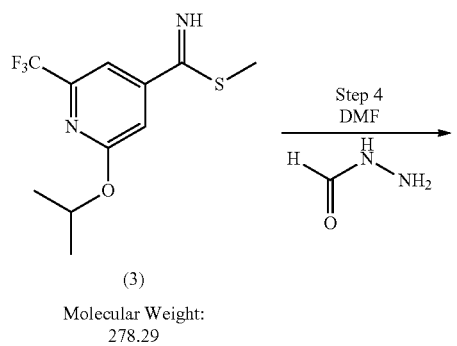

(3)
Molecular Weight:
278.29

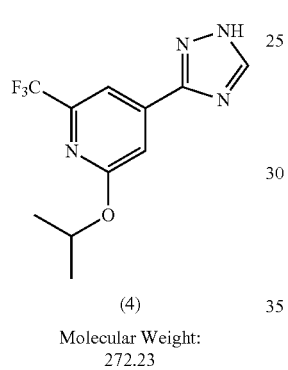

(4)
Molecular Weight:
272.23

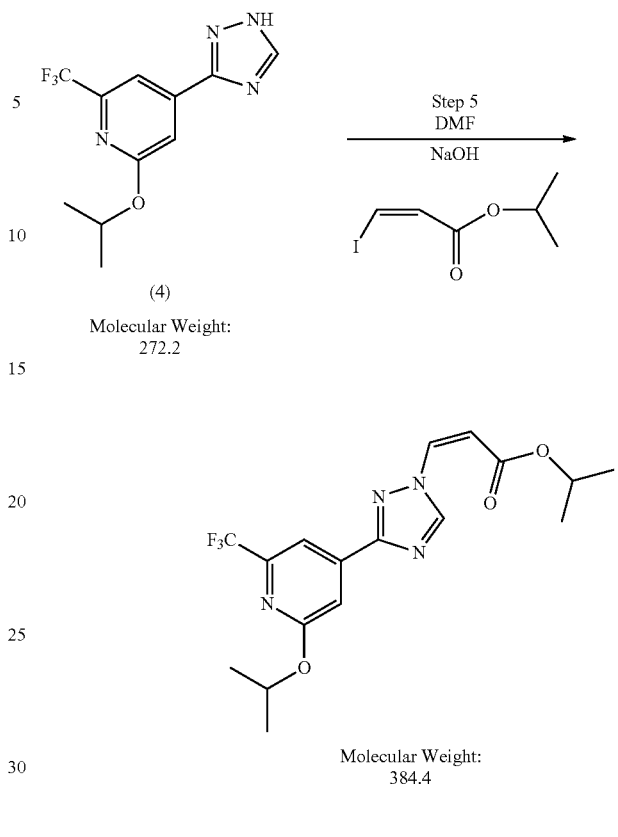

(4)
Molecular Weight:
272.2

Molecular Weight:
384.4

In a 50 mL 3N round-bottomed flask equipped with nitrogen bubbler, reflux condenser on magnetic stirrer, Intermediate 3 (5 g), Formic hydrazide (0.431 g), dissolved in DMF (50 mL) at RT for 20 min to form uncyclised form of intermediate-4 which was confirmed by mass & on TLC as a polar spot as compared to SM(3). Reaction mixture was heated at 80-90° C. for 6 h to obtain little non-polar spot as compared to uncyclised form. The Completion of the reaction was confirmed by TLC with 50% EtOAc-hexane as mobile phase. The reaction mixture was poured into ice water solution & extracted with ethyl acetate (200 mL×3). Organic layer was dried over $Na_2SO_4$ & concentrated to give crude product (5 g). The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 5% to 25% ethyl acetate in hexane. Compound started eluting with 25% ethyl acetate in hexane. Fraction containing such TLC profile was collected together to obtain pure compound (3.5 g).

In a 50 mL 3N round-bottomed flask equipped with nitrogen bubbler on magnetic stirrer intermediate 4 (1 g) was dissolved in DMF (10 mL) at RT. Isopropyl iodo acrylate (1.310 g) in DMF (1 mL) was dropwise added in the reaction mixture. To this reaction mixture was added NaOH (0.291 g) and reaction mixture was stirred for 12 h at 0° C. Completion of the reaction confirmed on TLC in 30% ethylacetate/n-Hexane as mobile phase. Reaction gives two isomeric compound (Cis/Trans). The reaction mixture was poured into ice water solution & compound was extracted with ethylacetate (3×50 mL) Organic layer was dried over anhydrous $Na_2SO_4$ & concentrated to give crude product (1.1 g). The crude reaction mixture was purified by column chromatography using silica 60/120 using ethyl acetate:hexane as mobile phase. The column was packed in hexane and started eluting in ethyl acetate in gradient manner starting with fraction collection (25 mL fractions) from 1-5% ethyl acetate in hexane. Compound started eluting with 5% ethylacetate in hexane. Fraction containing such TLC profile was collected together to obtain pure compound (500 mg). $^1$H NMR (400 MHz, $CDCl_3$): δ 9.79 (s, 1H), 8.46-8.44 (d, 1H, J=8 Hz), 7.32-7.35 (m, 1H), 7.28 (s, 1H), 5.69-5.71 (d, 1H, J=11.2 Hz), 5.47-5.53 (m, 1H), 5.11-5.17 (m, 1H), 1.46-1.49 (d, 6H, J=12 Hz), 1.29-1.31 (d, 6H, J=8) $C_{17}H_{19}F_3N_4O_3$ 384.35 at 7.90 min (LCMS 99.48%).

Example 61

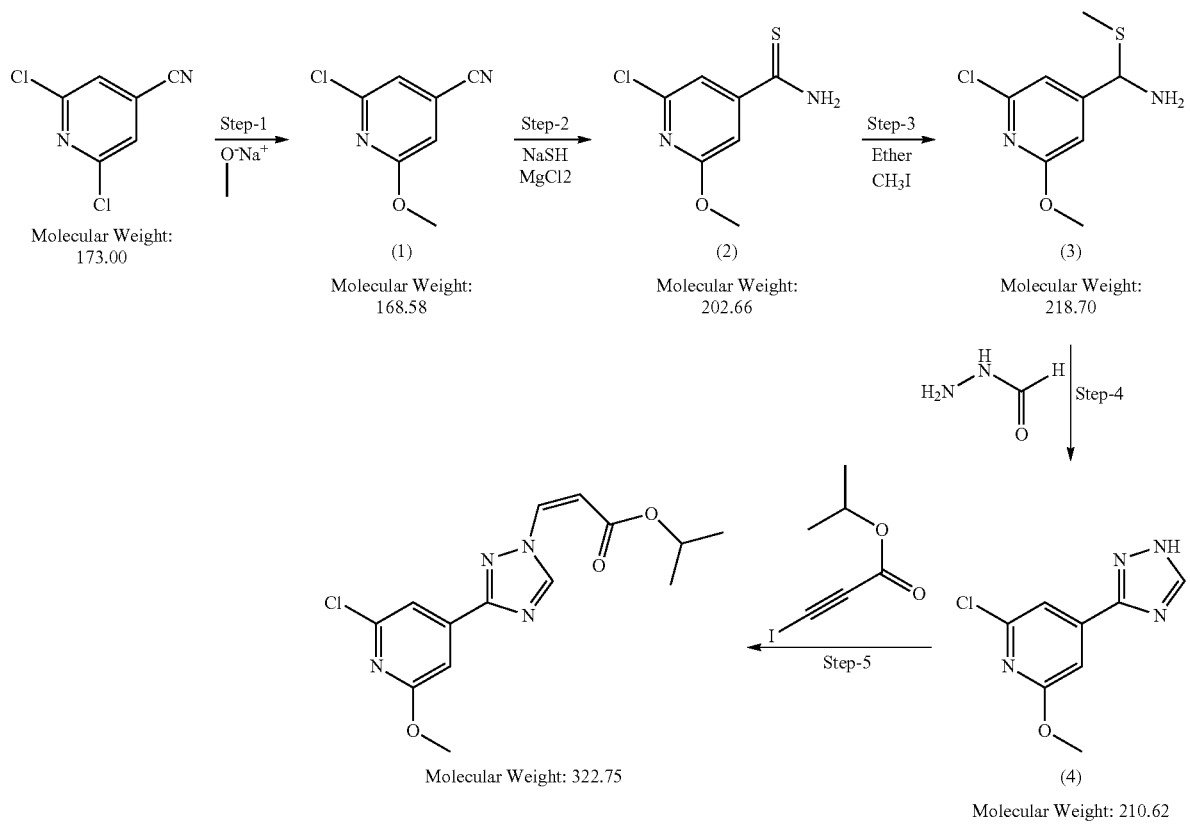

Synthesis of Intermediate (1)

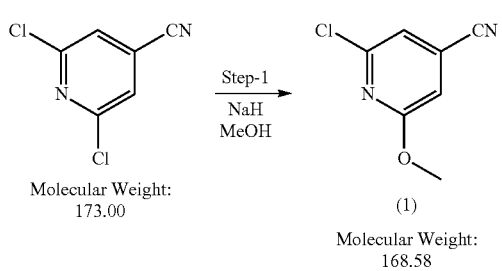

In a 25-mL, 3N round-bottomed flask equipped with thermometer pocket fitted with a nitrogen inlet and a rubber septum, NaH (0.112 g, 1.0 eq.), methanol (0.11 mL, 1.0 eq.), suspended in N-Methyl pyrrolidine (5 mL). The reaction mixture was stirred at 25-30° C. for 30 min. To this reaction mixture 2,6-Dichloro,4-cyano-pyridine was added at 0-5° C. The progress of the reaction was followed by TLC analysis on silica gel with 10% EtOAc-hexane as mobile phase which shows completion after 2 h staring at 0-5° C. Reaction was quenched by water and precipitate was observed which was filtered and wash with hexane to give required compound (0.51 g, Crude). Reaction was stirred for 20 min with water and solid was separated and compound was collected by filtration and washed with hexane (30 mL). Yield: 0.51 g Crude.

Synthesis of Intermediate (2)

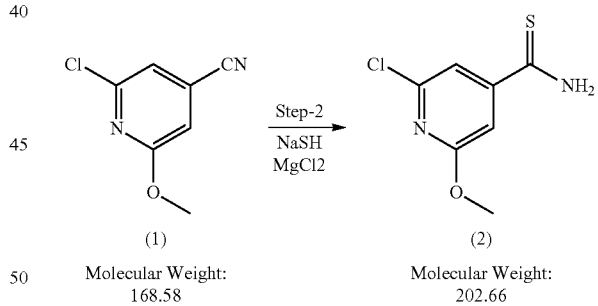

In a 25-mL, 3N round-bottomed flask equipped with thermometer pocket fitted with a nitrogen inlet and a rubber septum, Intermediate-1 (0.25 g, 1.0 eq.), MgCl$_2$ 6H$_2$O (0.3616 g, 1.2 eq.), NaSH (0.099 g) was dissolved in DMF (3 mL). The reaction mixture was stirred at 25-30° C. The progress of the reaction was followed by TLC analysis on silica gel with 30% EtOAc-hexane as mobile phase which shows that starting material was consumed after 30 minutes staring at 25-30° C. Reaction was quenched in water, precipitate was filtered by filter paper and wash with hexane to give required compound. Reaction was stirred for 10 min with water solid were separated and compound was collected and washed with hexane (30 mL). Yield: 0.180 g (60%). Mass: (ES+) 202.7 (M+1), 200.8 (M−1).

Synthesis of Intermediate (3)

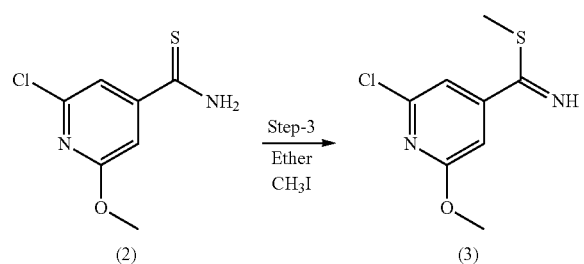

(2)
Molecular Weight: 202.66

(3)
Molecular Weight: 216.69

In a 100-mL, 3N round-bottomed flask equipped with thermometer pocket fitted with condenser, a nitrogen inlet and a rubber septum, Intermediate-2 (0.58 g, 1.0 eq.) and methyl iodide (0.89 mL, 5.0 eq.) was dissolved in diethyl ether (60 mL) resulting reaction mixture was stirred at RT. The progress of the reaction was followed by TLC analysis on silica gel with 20% acetone:hexane as mobile phase which shows that starting material was consumed after 15 h. Compound was filtered and purified as follows. Solid were separated and compound was collected by filtration and washed with hexane (100 mL). Yield: 0.257 g (41.44%) LCMS (%): 27.07% [M+H]$^+$ 217.92 RT: 4.216 min (Crude). NMR: Confirmed the structure.

Synthesis of Intermediate (4)

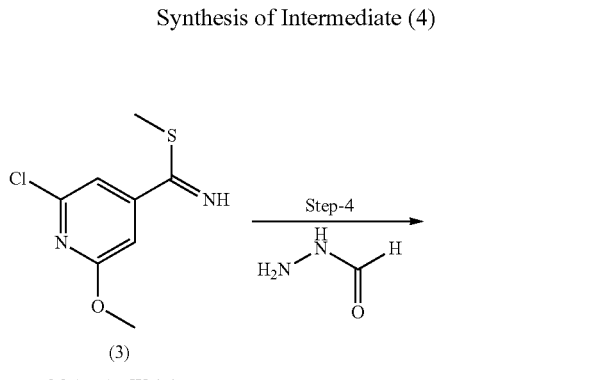

(3)
Molecular Weight: 216.69

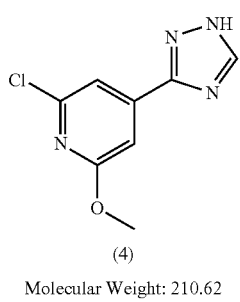

(4)
Molecular Weight: 210.62

In a 50 mL, 3N round-bottomed flask equipped with thermometer pocket fitted with a nitrogen inlet and a rubber septum, Intermediate-3 (2.2 g, 1.0 eq.), formyl hydrazide (1.22 g, 2.0 eq.) was dissolved in DMF (25 mL) resulting reaction mixture was stirred at 25-30° C. for 15-20 min and heated at 80-90° C. The progress of the reaction was followed by TLC analysis on silica gel with 50% EtOAc-hexane as mobile phase which shows that starting material was consumed after 5 h. Reaction was quenched into water. Solid material was separated out that was collected by filtration to give crude material. The solid compound was washed with hexane and ether to give pure compound. Remaining quantities was purifying by column chromatography using ethyl acetate:hexane as mobile phase. Compound was eluted in 15% ethyl acetate in hexane. Yield: 0.32 g (14.96%). LCMS (%): 86.61% [M+H]$^+$ 210.9 RT: 2.821 min.

Synthesis of Intermediate (5)

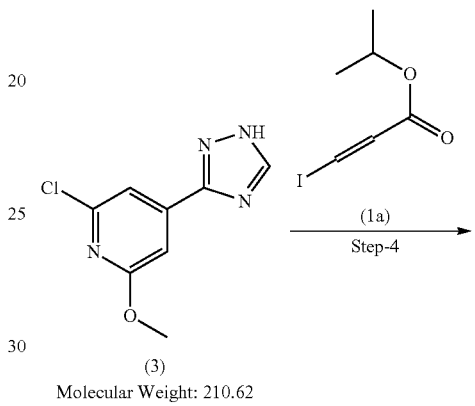

(3)
Molecular Weight: 210.62

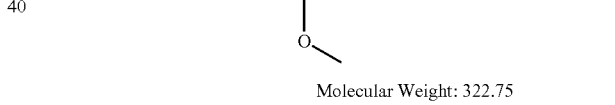

Molecular Weight: 322.75

In a 25-mL, 3N round-bottomed flask equipped with thermometer pocket fitted with a nitrogen inlet and a rubber septum, Intermediate-3 (0.4 g, 1.0 eq.), isopropyl 3-iodo acrylate (1.0285 g, 1.5 eq.) and NaOH (0.2285 g, 3 eq) was dissolved in DMF (4 mL) resulting reaction mixture was stirred at 0-5° C. The progress of the reaction was followed by TLC analysis on silica gel with 20% EtOAc-hexane as mobile phase which shows that starting material was consumed after 3 h. Reaction was quenched by water, extracted by ethyl acetate (20*3 mL), combined organic layer were dried over sodium sulfate and concentrated under reduce pressure to give crude material (0.6 g). The crude material was subjected to column chromatography using ethyl acetate hexane as mobile phase. The crude material was subjected to column chromatography using ethyl acetate:hexane as mobile phase. Compound was eluted in 4% ethyl acetate in hexane. Yield: 0.38 g (61.99%). LCMS (%): 99.82% [M+H]$^+$ 322.84 RT: 4.269; $^1$HNMR (CDCl$_3$, 400 Hz) δ=9.73 (s, 1H), 7.65 (s, 1H), 7.40 (s, 1H), 7.26-7.29 (d, J=10.4 Hz, 1H), 5.74-5.77 (d, J=10.8 Hz, 1H), 5.12-5.18 (m, 1H), 4.01 (s, 3H), 1.32-1.34 (d, 6H). LC-MS: Calculated for C$_{14}$H$_{15}$ClN$_4$O$_3$ (M+1)+322.7 found 322.87 at 4.371 min (LCMS 98.01%).

Example 62

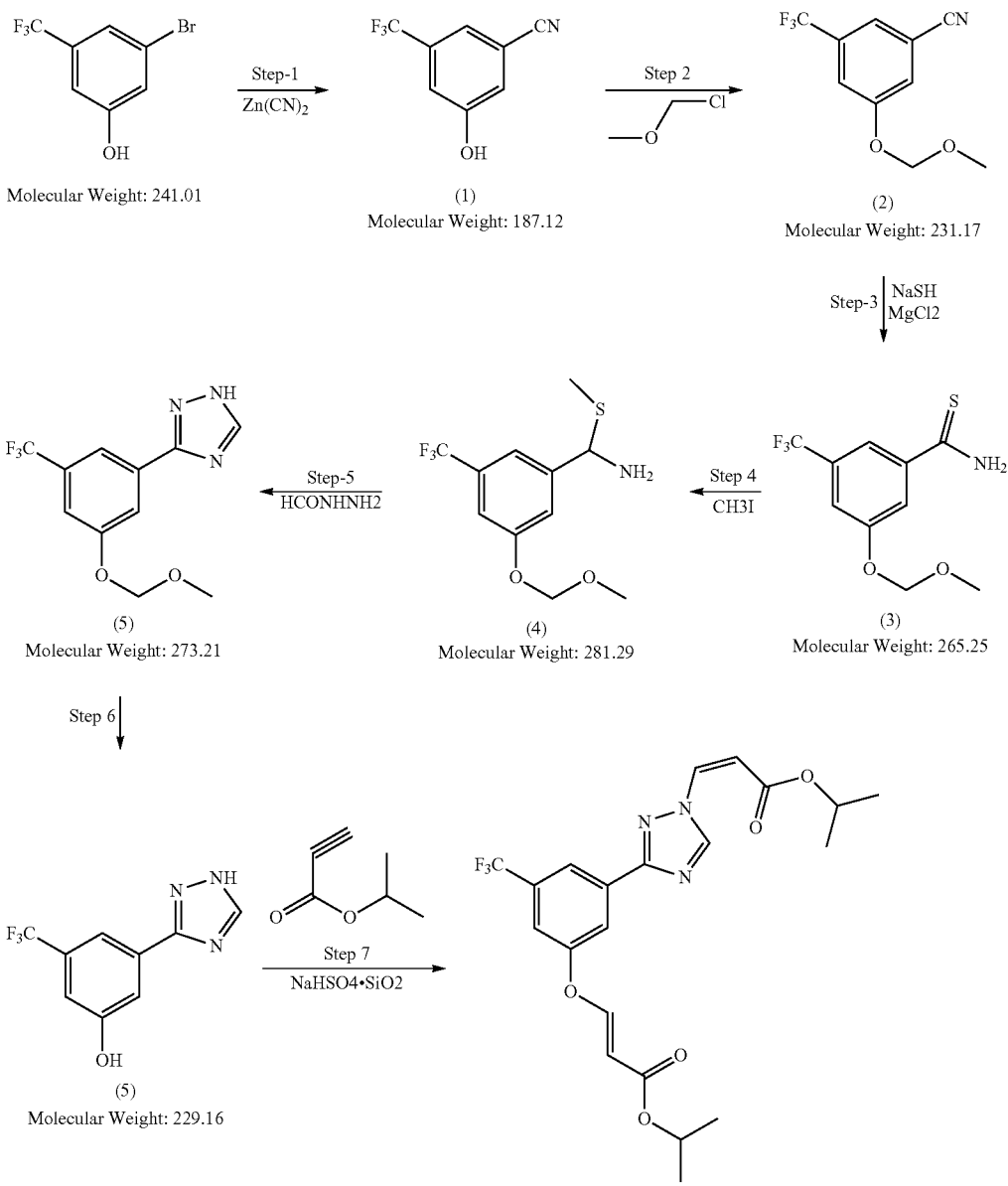

Synthesis of Intermediate (1)

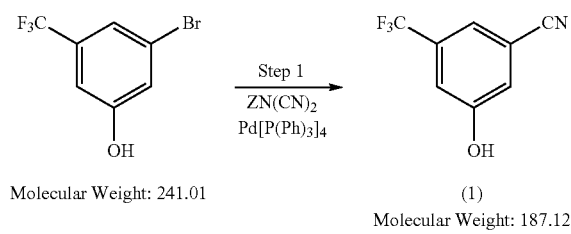 [SMILES: Oc1cc(Br)cc(C(F)(F)F)c1 ; N#Cc1cc(O)cc(C(F)(F)F)c1]

In a 3-neck 100 mL round-bottomed flask, stirred solution of 3-bromo-5-(trifluoromethyl)phenol (2 g, 1 eq.) in DMF (25 mL, 25 Vol) was degassed. ZN(CN)$_2$ (0.68 g, 0.7 eq.) and Pd[P(Ph)$_3$]$_4$ (1.9 g, 0.2 eq.) was added in reaction and heat at 90° C. for 2 h. Reaction completion was monitored on TLC using ethyl acetate:hexane (2:8) mobile phase. Reaction mixture was brought to room temperature and quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 1.5 g of crude compound which was purified by column chromatography using ethyl acetate and Hexane as mobile phase. Product was eluted in 6% ethyl acetate in Hexane to afford 1.5 g of pure compound. Yield (96.7%). Mass: 187.9.

Synthesis of Intermediate (2)

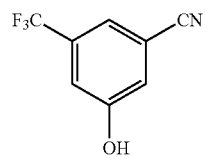 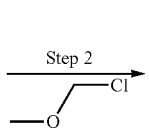

(1)
Molecular Weight: 187.12

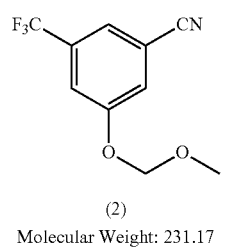

(2)
Molecular Weight: 231.17

In a 3-neck 50 mL round-bottomed flask, intermediate 1 (0.5 g, 1 eq.) was dissolved in THF (10 mL, 20 Vol). DIPEA (0.38 g, 1.1 eq.) and chloromethylmethylether (0.23 g, 1.1 eq.) was added dropwise at 0° C. and reaction mixture was stirred at room temperature for overnight. Reaction completion was monitored on TLC using ethyl acetate:hexane (2:8) as mobile phase. Reaction mixture was quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 0.5 g of crude compound. Mass: 231.4. NMR: Confirmed.

Synthesis of Intermediate (3)

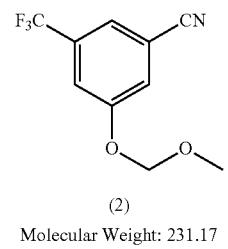  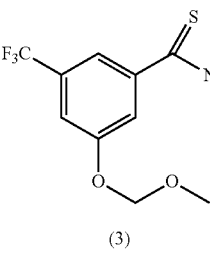

(2)
Molecular Weight: 231.17

(3)
Molecular Weight: 265.25

In a 3-neck 50 mL round-bottomed flask, 3-(methoxymethoxy)-5-(trifluoromethyl)benzonitrile (0.5 g, 1 eq.), NaSH H$_2$O (0.32 g, 2.0 eq.) and MgCl$_2$6H$_2$O (0.43 g, 1.0 eq.) was dissolved in DMF (10 mL, 20 Vol) and reaction mixture was stirred at room temperature for 2 h. Reaction completion was monitored on TLC using ethyl acetate:hexane (4:6) as mobile phase. Reaction mixture was brought to room temperature and quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 0.6 g of crude compound. Mass: 265.31.

Synthesis of Intermediate (4)

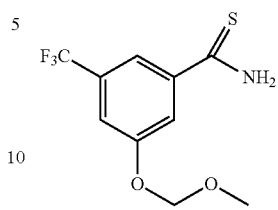 

(3)
Molecular Weight: 265.25

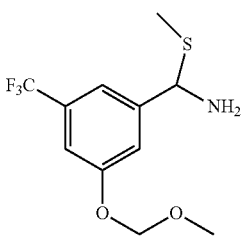

(4)
Molecular Weight: 281.29

In a 3-neck 50 mL round-bottomed flask, intermediate 3 (0.6 g, 1 eq.) was dissolved in Diethyl ether (15 mL, 10 Vol) and methyl iodide (1.58 g, 5.0 eq.) was added dropwise in reaction mixture and reaction mixture was stirred at RT for overnight. Reaction completion was monitored on TLC using ethyl acetate: n-hexane (5:5) as mobile phase. Product was filtered and washed with diethyl ether (3×50 mL). Product was dried under reduced pressure to afford 0.6 g of crude compound. Mass: 281.41.

Synthesis of Intermediate (5)

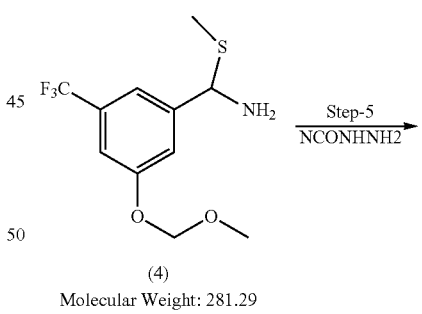

(4)
Molecular Weight: 281.29

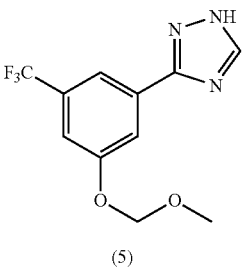

(5)
Molecular Weight: 273.21

In a 3-neck 100 mL round-bottomed flask, intermediate 4 (0.6 g, 1 eq.) and Formic hydrazide (0.25 g, 2 eq) was dissolved in DMF (20 mL1) and reaction mixture was stirred at reflux temperature for 2 h. Reaction completion was monitored on TLC using ethyl acetate:n-hexane (5:5) as mobile phase. Reaction mixture was brought to room temperature and poured into the water (100 mL) and compound was extracted in the Ethyl acetate (100 mL×3). Organic layer was again washed with water (100 mL×3) followed by drying using anhydrous sodium sulphate. Organic layer was concentrated under reduced pressure to afford 0.9 g of crude compound which is purified by column to give 0.25 gm of pure Compound. Mass: 273.4.

column chromatography using ethyl acetate and Hexane as mobile phase. Product was eluted in 8% ethyl acetate in Hexane to afford 0.06 g of pure compound, Yield (3%). $^1$H NMR (400 MHz, CDCl$_3$): δ 8.38 (s, 1H), 8.28 (s, 1H), 8.07 (s, 1H), 7.98-8.01 (d, J=13.6 Hz, 1H), 7.83-7.86 (d, J=12 Hz, 1H), 7.42 (s, 1H), 6.70-6.74 (d, J=14 Hz, 1H), 5.66-5.69 (d, J=12 Hz, 1H), 5.11-5.20 (m, 2H), 1.18-1.40 (m, 12H): LCMS for C$_{21}$H$_{22}$F$_3$N$_3$O$_5$ M.W. 453.41 found 453.83 at 4.853 min.

Example 63

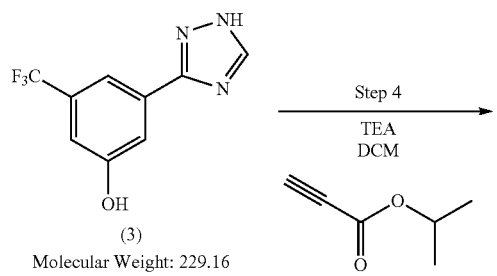

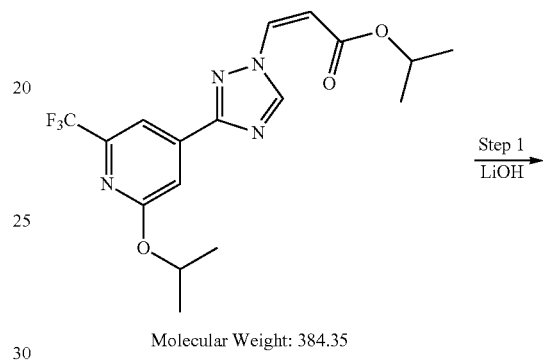

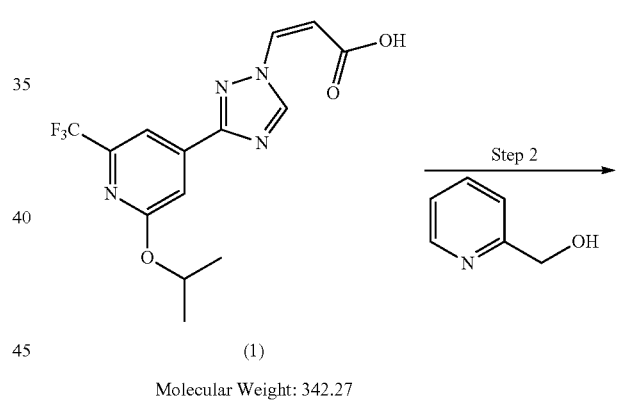

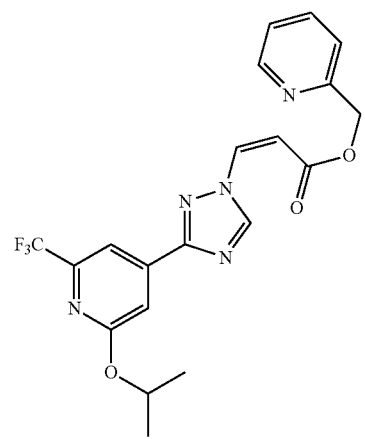

In a 3-neck 50 mL round-bottomed flask, 3-(1H-1,2,4-triazol-3-yl)-5-(trifluoromethyl)phenol (1 g, 1 eq.) was dissolved in DCM (15 mL, 15 Vol) and TEA (0.574 g, 1.3 eq) was added and Propiolic ester (0.636 g, 1.3 eq.) was stirred at 15° C. for 30 min. Reaction completion was monitored on TLC using ethyl acetate: n-hexane (2:8) as mobile phase. Reaction mixture was concentrated under reduced pressure to afford 1.5 g of crude compound and the compound was purified by

Synthesis of Intermediate (1)

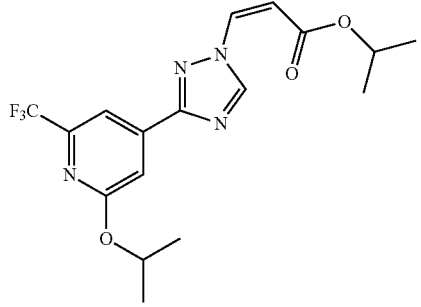

Molecular Weight: 384.35

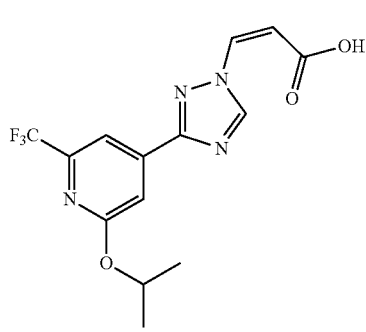

(1)
Molecular Weight: 342.27

In a 250 mL, 3N round-bottomed flask equipped with nitrogen inlet, and a rubber septum, Example 60 (0.75 g, 1.0 eq.) was dissolved in THF:water (7.5 mL)(1:1). To this reaction mixture LiOH (0.164 g) was added. The reaction mixture was stirred at RT for 2 hr. The progress of the reaction was followed by TLC analysis on silica gel with 50% Ethyl acetate-n-Hexane as mobile phase. Reaction mixture was poured into ice-water (100 mL) and acidified with dilute HCl. White product was obtained. The compound was filtered through vacuum and concentrated by rotary evaporation (25° C., 20 mmHg) to afford 0.6 g of pure compound. Mass: 342.27.

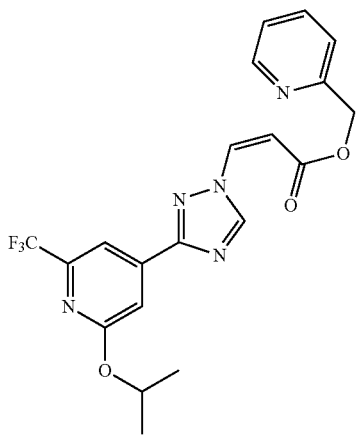

Molecular Weight: 433.38

In a 10 mL, 3N round-bottomed flask equipped with nitrogen inlet, and a rubber septum, Intermediate-1 (0.150 g, 1.0 eq.) was dissolved in DCM (2.5 mL, 25 V). The reaction mixture was cooled at 0° C. To this reaction mixture was added DCC (0.099 g, 1.1 eq), 4-DMAP (0.0053 g, 0.1 eq) and pyridine-2-methanol (0.052 g, 1.1 eq.). The reaction mixture was maintained at 0° C. for 1-2 h. The progress of the reaction was followed by TLC analysis on silica gel with 50% Ethyl acetate-Hexane as mobile phase. Reaction mixture was filtered through celite bed and concentrated by rotary evaporation (25° C., 20 mmHg) to afford 0.132 g of crude compound. The crude reaction mixture was purified by column chromatography using silica 60/120 using ethyl acetate: n-hexane as mobile phase. The column (5×10 cm) was packed in hexane and started eluting in ethyl acetate in gradient manner starting with fraction collection (25 mL fractions) from 25-30% ethyl acetate in hexane. Compound started eluting with 30% ethyl acetate in hexane. Fraction containing such TLC profile was collected together to obtain pure compound (25 mg), Yield (13.22%). $^1$HNMR [400 MHz DMSO-d6] δ 9.27 (s, 1H), 8.51-8.52 (d, 1H), 8.42-8.44 (d, 1H), 7.70-7.72 (m, 1H), 7.57-7.60 (m, 2H), 7.35-7.37 (m, 1H), 7.28-7.31 (m, 1H), 6.09-6.12 (d, J=10, 1H), 5.33-5.37 (s, 2H), 5.29 (m, 1H), 1.34-1.35 (d, 6H): LCMS for $C_{20}H_{18}F_3N_5O_3$ [M]$^+$ 433.4 found 433.83 at 4.00 min (LCMS 94%).

Example 64

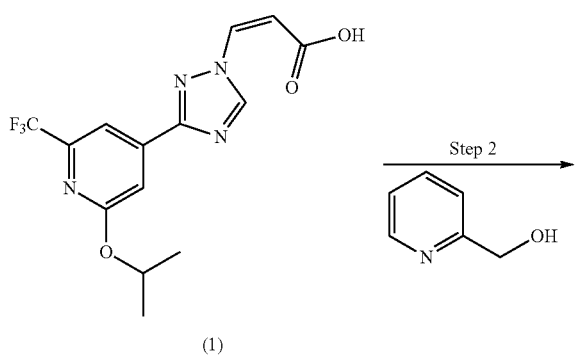

(1)
Molecular Weight: 342.27

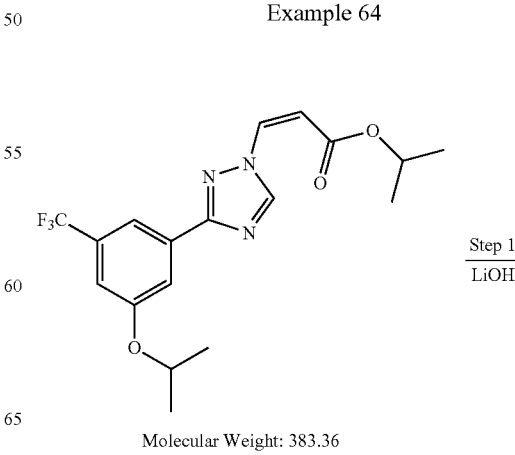

Molecular Weight: 383.36

303

-continued

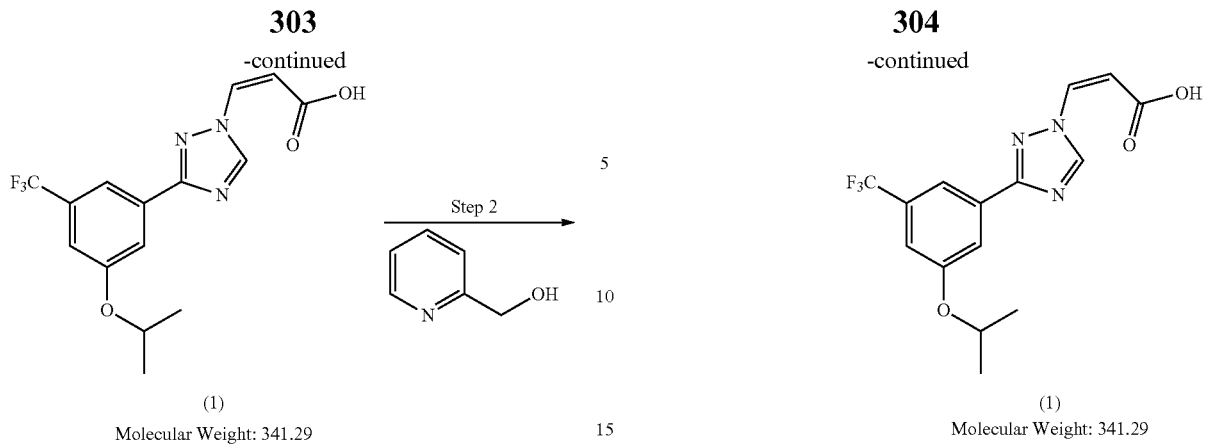

(1)
Molecular Weight: 341.29

Synthesis of Intermediate (1)

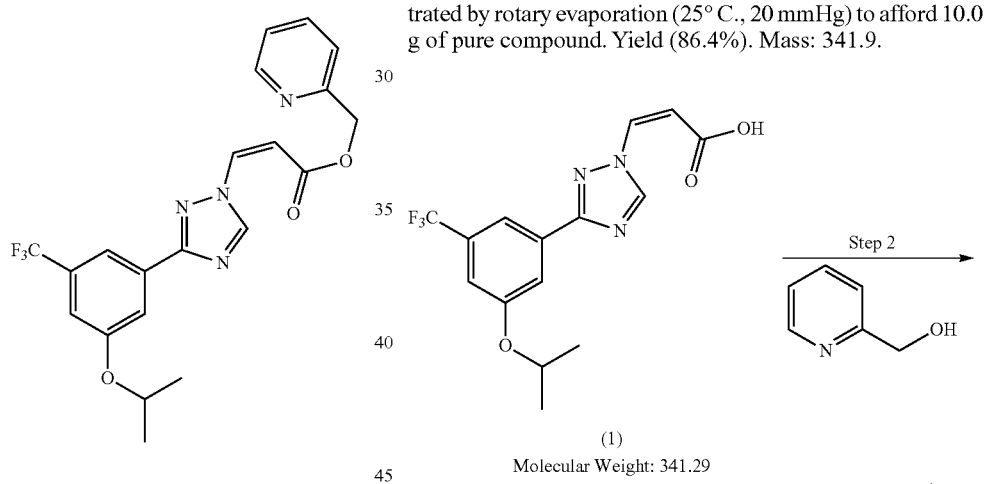

Molecular Weight: 383.36

304

-continued (1)
Molecular Weight: 341.29

In a 250-mL, 3N round-bottomed flask equipped with nitrogen inlet, and a rubber septum, Example 44 (13.0 g, 1.0 eq.) was dissolved in THF:Water (1:1) (40 mL:40 mL) and LiOH (2.85 g, 2.0 eq.) was added. The reaction mixture was stirred at RT for 3-4 h. The progress of the reaction was followed by TLC analysis on silica gel with 20% Ethyl acetate-n-Hexane as mobile phase. SM $R_f$=0.60 and Product $R_f$=0.1. Reaction mixture was poured in to water (100 mL) and acidify with Dilute HCl. White product was obtained. The compound was filtered through Vacuum and concentrated by rotary evaporation (25° C., 20 mmHg) to afford 10.0 g of pure compound. Yield (86.4%). Mass: 341.9.

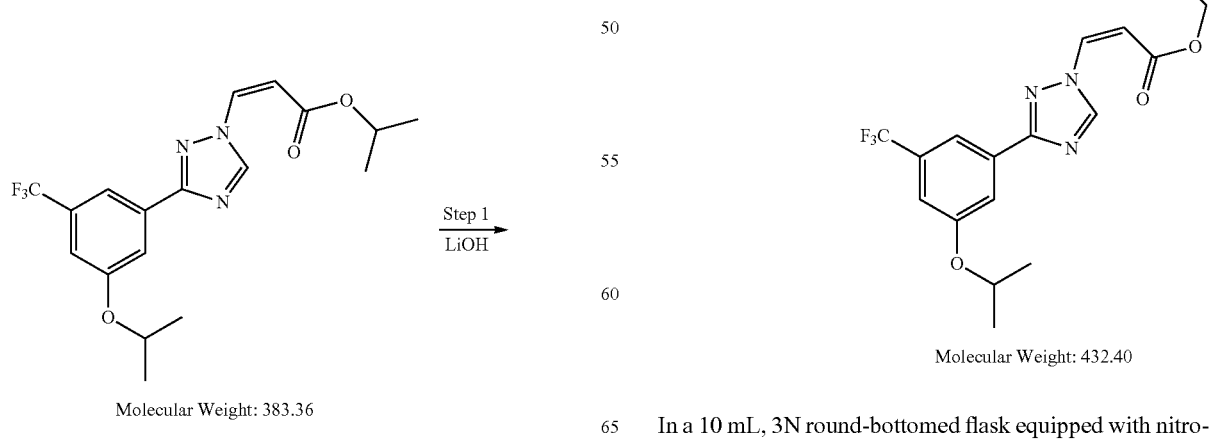

(1)
Molecular Weight: 341.29

Molecular Weight: 432.40

In a 10 mL, 3N round-bottomed flask equipped with nitrogen inlet, and a rubber septum, Intermediate-1 (0.1 g, 1.0 eq.) was dissolved in DCM (2.5 mL, 25 V). The reaction mixture was cooled to 0° C. To this reaction mixture was added DIPEA (0.042 g, 1.1 eq.), HATU (0.122 g, 1.1 eq.) and pyridine-2-methanol (0.035 g, 1.1 eq.). The reaction mixture was maintained at 0° C. for 1-2 h. The progress of the reaction was followed by TLC analysis on silica gel with 50% Ethyl acetate-Hexane as mobile phase. SM $R_f$=0.20 and Product $R_f$=0.4. Reaction mixture was filtered through celite bed and concentrated under reduced pressure by rotary evaporation (25° C., 20 mmHg) to afford 0.132 g of Crude compound. The crude reaction mixture was purified by column chromatography using silica 60/120 using ethyl acetate: n-hexane as mobile phase. The column (5×10 cm) was packed in hexane and started eluting in ethyl acetate in gradient manner starting with fraction collection (25 mL fractions each) from 25-30% ethyl acetate in hexane. Compound started eluting with 30% ethyl acetate in hexane. Fraction containing such TLC profile was collected together to obtain pure compound (10 mg), Yield (7.93%). ($^1$HNMR [400 MHz CDCl$_3$] δ 9.76 (s, 1H), 8.65-8.66 (d, 1H), 7.98 (s, 1H), 7.84 (s, 1H), 7.73-7.76 (m, 1H), 7.36-7.41 (m, 2H), 7.20 (s, 1H), 5.85-5.88 (d, J=11.2, 1H), 5.39 (s, 2H), 4.70-4.73 (m, 1H), 1.35-1.39 (m, 6H): LCMS for $C_{21}H_{19}F_3N_4O_3$ [M+1]$^+$ 432.4 found 432.96 at 4.21 min (LCMS 90%).

Example 65

Synthesis of Intermediate (1)

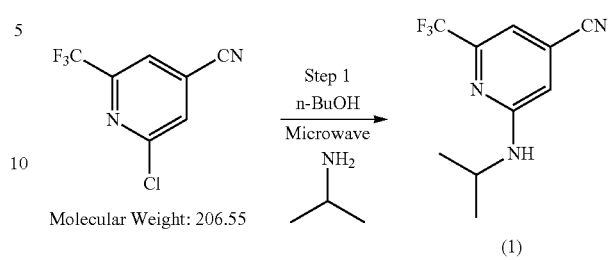

In a 25-mL capacity microwave seal tube 2-chloro-6-trifluoromethylisonicotinonitrile (1 g) & Isopropyl amine (0.571 g) dissolved in n-Butanol (10 mL) with one drop of Con HCl. Reaction mixture was irradiated with microwave radiation at 130° C. for 30 min in 150 Watt. The Completion of the reaction was confirmed by TLC with 10% EtOAc-n-hexane as mobile phase. Reaction mixture was quenched into ice water slurry. Compound was extracted in ethyl acetate (100

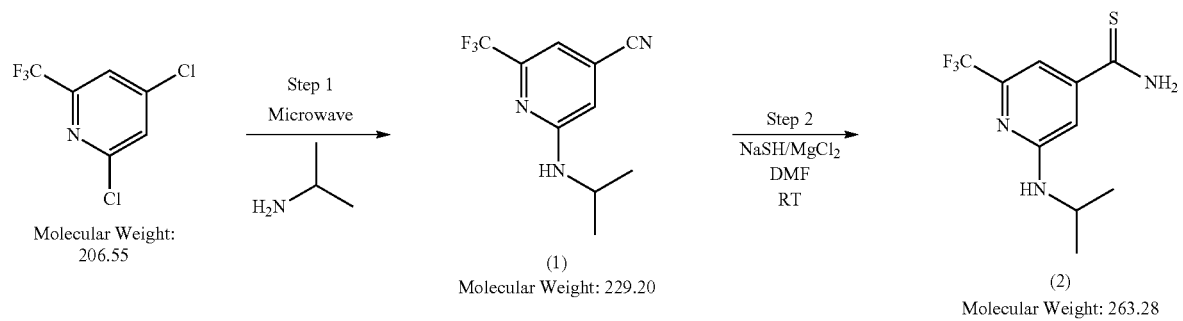

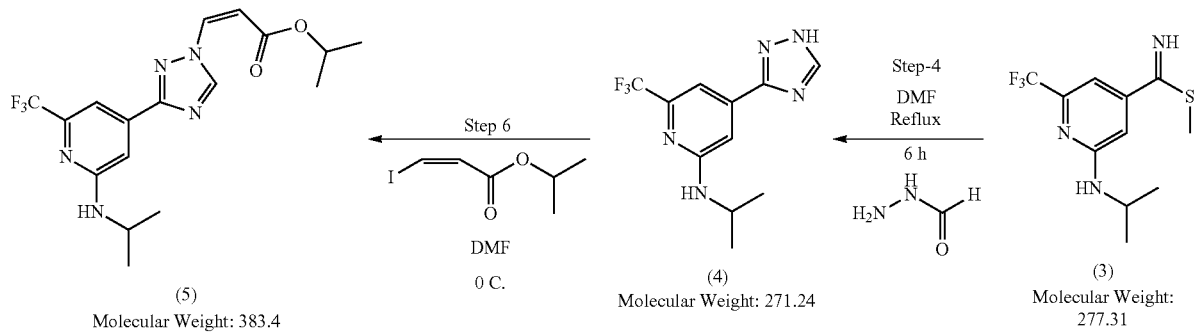

mL×2) and organic layer washed with water (100 mL×2) & dried over Na$_2$SO$_4$, filtered, and concentrated under reduced by rotary evaporation (40° C., 20 mmHg) to afford 8 g of a yellow oil. The resulting crude compound was used as such without any further purification.

The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 1% to 3% ethyl acetate in hexane. Compound started eluting with 2% ethylacetate in hexane. Fractions containing such TLC profile was collected together to obtain pure compound (0.8 g).

Synthesis of Intermediate (2)

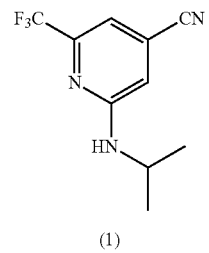 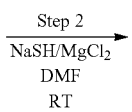 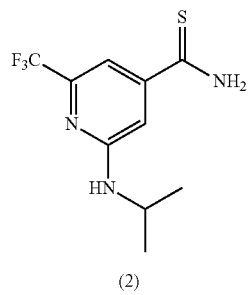

In a 100 mL 3N round-bottomed flask equipped with nitrogen bubbler & magnetic stirrer, intermediate 1 (0.750 g, 3.27 mmol), NaSH (0.275 g, 4.91 mmol), MgCl$_2$ (0.996 g, 4.91 mmol) was dissolved in 7.5 mL of DMF at RT. Reaction mixture was stirred for 3 h. The Completion of the reaction was confirmed by TLC using 20% EtOAc-n-hexane as mobile phase. Reaction mixture was poured into ice water slurry and compound extracted with ethylacetate (50×3). Organic layer was dried over anhydrous Na$_2$SO$_4$, filtered, and concentrated by rotary evaporation to afford 0.750 g of as yellow oil. The resulting crude compound was forwarded to next step without further purification.

Synthesis of Intermediate (3)

 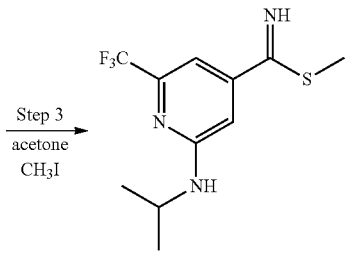

In a 50 mL 3N round-bottomed flask equipped with nitrogen bubbler & magnetic stirrer intermediate 2 (0.750 g, 2.85 mmol), CH$_3$I (2.02 g, 14.25 mmol), was dissolved in acetone (7.5 mL) at RT. Reaction mixture was refluxed for 2 h. The Completion of the reaction was confirmed by TLC with 20% acetone-n-hexane as mobile phase. The reaction mixture was distilled & crude compound forwarded to next step without further purification.

Synthesis of Intermediate (4)

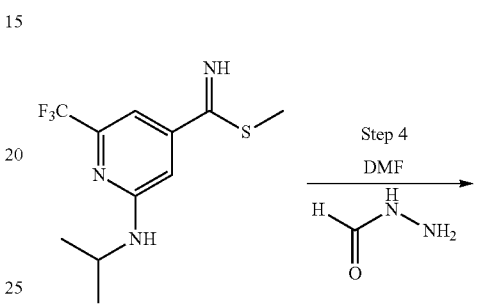

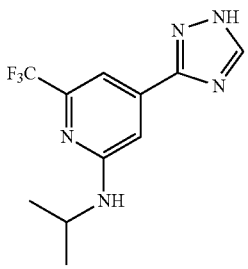

In a 50 mL 3N round-bottomed flask equipped with nitrogen bubbler, reflux condenser & magnetic stirrer intermediate 3 (0.5 g), Formic hydrazide (0.216), dissolved in DMF (5 mL) at RT for 20 min to form uncyclised form of intermediate-4 which was confirmed by mass & on TLC as a polar spot as compared to SM. Reaction mixture was refluxed at 80-90° C. for 6 h, which drives the reaction for the cyclization as nonpolar spot as compared to uncyclised form. The Completion of the reaction was confirmed by TLC with 50% EtOAc-n-hexane as mobile phase. The reaction mixture was poured into ice water slurry & compound was extracted with ethyl acetate (3×200 mL) Organic layer dried over anhydrous Na$_2$SO$_4$ & concentrated to give crude product (0.5 g). The crude reaction mixture was purified by column chromatography using silica 60/120 using ethyl acetate:hexane as mobile phase. The column was packed in hexane and started eluting in ethyl acetate in gradient manner starting with fraction collection (25 mL fractions) from 5%-25% ethyl acetate in hexane. Compound started eluting with 25% ethyl acetate in hexane. Fraction containing such TLC profile was collected together to obtain pure compound (0.350 g).

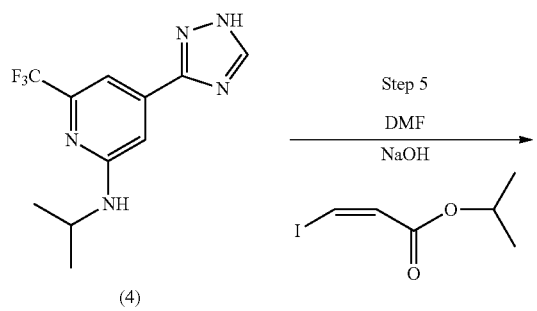

In a 50 mL 3N round-bottomed flask equipped with nitrogen bubbler, & magnetic stirrer intermediate 4 (0.250 g) was dissolved in 4 mL DMF at RT. Ethyl iodoacrylate (0.331 g) in was added dropwise dissolved in DMF (1 mL) in the reaction mixture. Then NaOH (0.073 g) was added & reaction mixture was stirred for 6 h at 0° C. Completion of the reaction was confirmed on TLC in 30% ethylacetate/n-Hexane as mobile phase. Reaction gave two isomeric compound (Cis/Trans) as expected. The reaction mixture was poured into ice water solution & compound was extracted with ethylacetate (3×50 mL) Organic layer dried over anhydrous $Na_2SO_4$ & concentrated to give crude product (0.3 g). The crude reaction mixture was purified by column chromatography using silica 60/120 using ethyl acetate:hexane as mobile phase. The column was packed in hexane and started eluting in ethyl acetate in gradient manner starting from 1% to 5% and fractions were collected (25 mL each). Compound started eluting with 5% ethylacetate in hexane. Fraction containing such TLC profile was collected together to obtain pure compound (cis) (80 mg). Compound was further purified by combiflash if required to remove little aliphatic impurity. $^1$H NMR [400 MHz DMSO-$d_6$] δ 9.24 (s, 1H), 8.45-8.47 (d, 1H), 7.89-7.91 (d, 1H), 7.54-7.56 (d, J=10.4, 1H), 7.10-7.12 (d, 1H), 6.00-6.03 (d, J=10, 1H), 5.06-5.10 (m, 1H), 4.28-4.33 (m, 1H), 1.27-1.29 (d, 6H), 1.18-1.20 (d, 6H): LCMS for $C_{17}H_{20}F_3N_5O_2$ [M+1]$^+$ 383.37 found 383.83 at 8.44 min (LCMS 99.89%).

Example 66

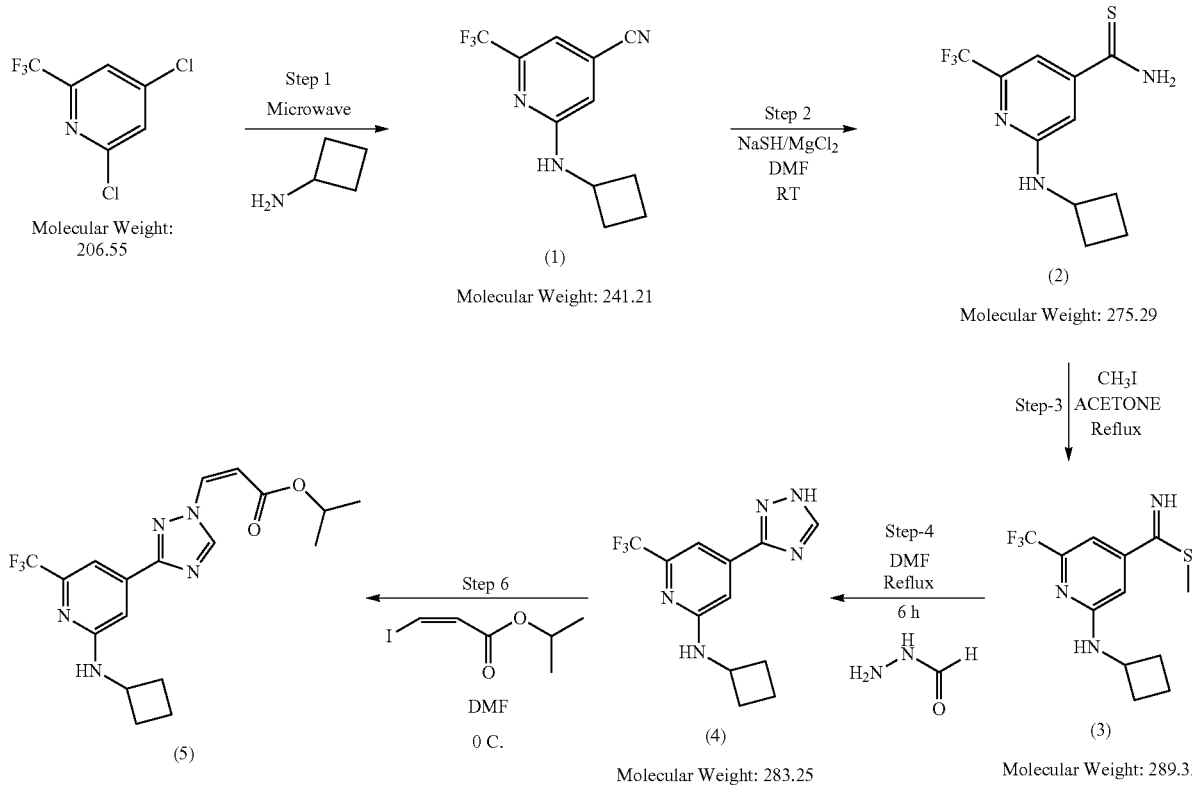

Synthesis of Intermediate (1)

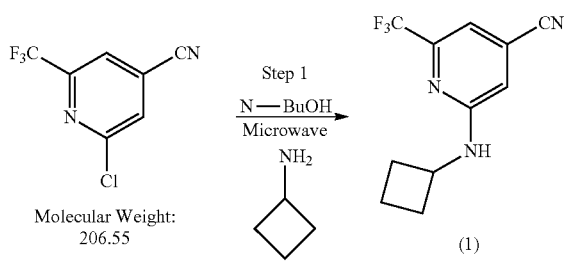

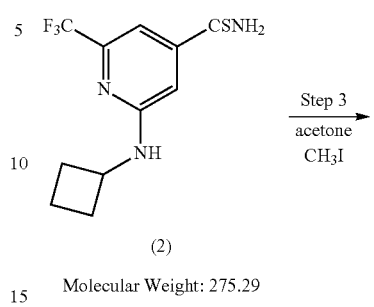

In a 25-mL microwave seal tube 2-chloro-6-trifluoromethylisonicotinonitrile (1 g) & Isopropyl amine (0.517 g) was dissolved in n-butanol (10 mL) and one drop of con. HCl was added. Reaction mixture was irradiated at 130° C. for 30 min in Microwave. The Completion of the reaction was confirmed by TLC using 10% EtOAc-n-hexane as mobile phase. Reaction mixture was quenched into ice water slurry. Extract compound in ethyl acetate. organic layer washed with water two times & dried over $Na_2SO_4$, filtered, and concentrated by rotary evaporation (40° C., 20 mmHg) to afford 8 g of a yellow oil. The resulting crude compound was purified by column chromatography. The crude reaction mixture was purified by column chromatography using silica 60/120 using ethyl acetate:n-hexane as mobile phase. The column was packed in hexane and started eluting in ethyl acetate in gradient manner starting with fraction collection (25-mL fractions) from 1-3% ethyl acetate in hexane. Compound started eluting with 2% ethylacetate in hexane. Fraction containing such TLC profile was collected together to obtain pure compound (0.8 g).

Synthesis of Intermediate (2)

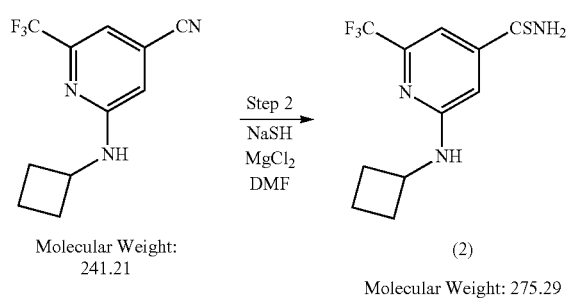

In a 100 mL 3N round-bottomed flask equipped with nitrogen bubbler & magnetic stirrer intermediate 1 (0.750 g), NaSH (0.260 g), $MgCl_2$ (0.945 g) was dissolved in DMF (7.5 mL) at RT. Reaction was stirred at RT for 3 h and completion of the reaction was confirmed by TLC with 20% EtOAc-n-hexane as mobile phase. Reaction mixture was poured into ice water and compound was extracted with (50×3) ethyl acetate. Organic layer was dried over anhydrous $Na_2SO_4$, filtered, and concentrated under reduced pressure to afford 0.750 g of a yellow oil. The resulting crude compound was forwarded to next step without any analysis.

Synthesis of Intermediate (3)

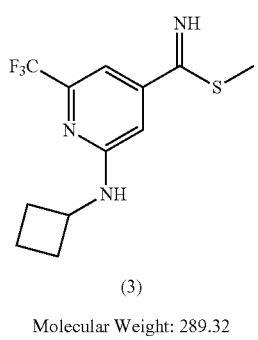

In a 50 mL 3N round-bottomed flask attached with nitrogen bubbler & magnetic stirrer intermediate 2 (0.75 g), $CH_3I$ (1.93 g) was dissolved in 7.5 mL acetone at RT. Reaction was refluxed for 2 h and completion of was of the reaction was followed by TLC with 20% acetone-n-hexane as mobile phase. The reaction mixture was distilled & crude compound forwarded to next step.

Synthesis of Intermediate (4)

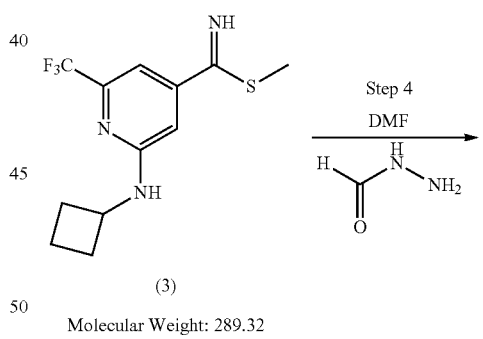

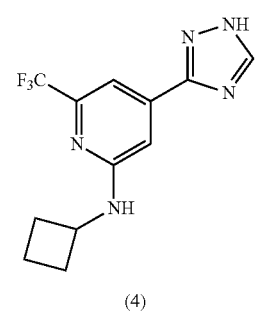

In a 50 mL capacity 3N round-bottomed flask attached with nitrogen bubbler, reflux condenser & magnetic stirrer intermediate 3 (0.5 g), Formic hydrazide (0.207) was dissolved in 5 mL DMF at RT within 20 min to form uncyclised form of intermediate-4 which was confirmed by mass & confirmed on TLC as a polar spot as compared to SM(3). Reaction mixture was heated at 80-90° C. for 6 h, which gave non polar spot as compared to uncyclised form. The Completion of the reaction was confirmed by TLC with 50% EtOAc-hexane as mobile phase. The reaction mixture was poured into ice water solution & compound was extracted with ethyl acetate (3×200 mL) Organic layer was dried over anhydrous Na$_2$SO$_4$& concentrated to give crude compound (0.5 g). The crude reaction mixture was purified by column chromatography using silica 60/120 using ethyl acetate:hexane as mobile phase. The column was packed in hexane and started eluting in ethyl acetate in gradient manner starting with fraction collection (25 mL fractions) from 5% to 25% ethyl acetate in hexane. Compound started eluting with 25% ethyl acetate in hexane. Fraction containing such TLC profile was collected together to obtain pure compound (0.350 g).

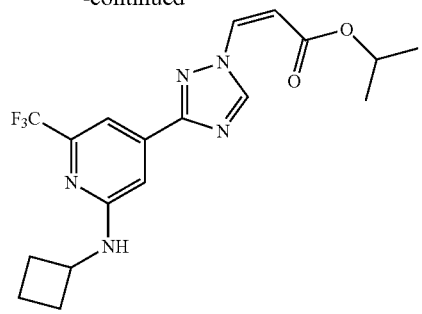

Molecular Weight: 395.38

In a 50 mL 3N round-bottomed flask equipped with nitrogen bubbler on magnetic stirrer intermediate 4 (0.250 g) was dissolved in 4 mL DMF at RT. Ethyl iodo acrylate (0.317 g) was dissolved in DMF (1 mL) and added dropwise in the above reaction mixture. To this reaction mixture was added NaOH (0.07 g) and reaction stirred for 6 h at 0° C. Completion of the reaction was confirmed on TLC in 30% ethylacetate/n-Hexane as mobile phase. Reaction yielded two isomeric compound (Cis/Trans). The reaction mixture was poured in ice water solution & extract with ethylacetate (3×50) mL Organic layer was dried over Na$_2$SO$_4$& concentrated to give crude product (0.30 g). The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 1% to 5% ethyl acetate in hexane. Compound started eluting with 5% ethylacetate in hexane. Fraction containing such TLC profile was collected together to obtain pure compound (cis) (70 mg). $^1$H NMR [400 MHz DMSO-d$_6$] δ 9.47 (s, 1H), 8.45-8.47 (d, 1H), 8.15-8.17 (d, 1H), 7.56-7.58 (d, J=10, 1H), 7.12-7.14 (d, 1H), 6.01-6.03 (d, J=10.4, 1H), 5.07-5.10 (m, 1H), 4.57-4.59 (m, 1H), 2.50-2.51 (m, 2H), 2.09-2.10 (m, 2H), 1.76-1.78 (m, 2H), 1.35-1.37 (m, 6H): LCMS for C$_{18}$H$_{20}$F$_3$N$_5$O$_2$ [M+1]$^+$ 395.4 found 395.9 at 8.62 min (LCMS 98.61%).

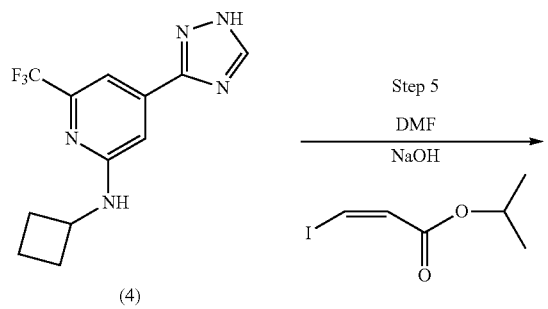

Example 67

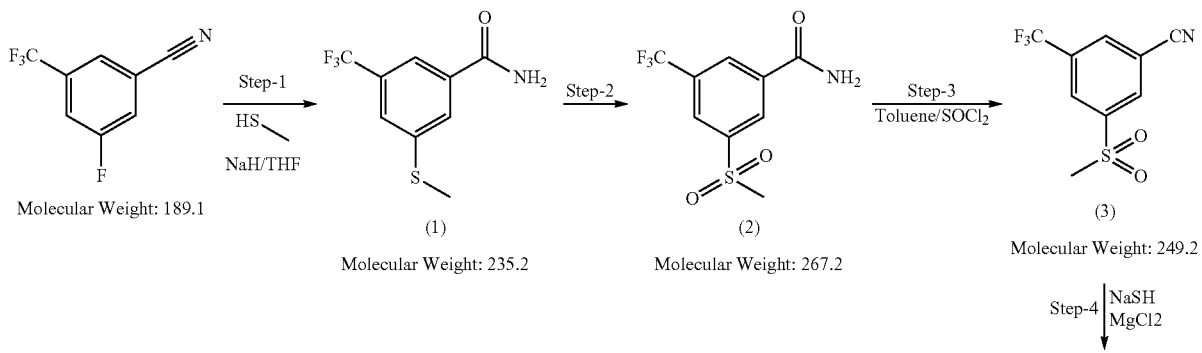

-continued

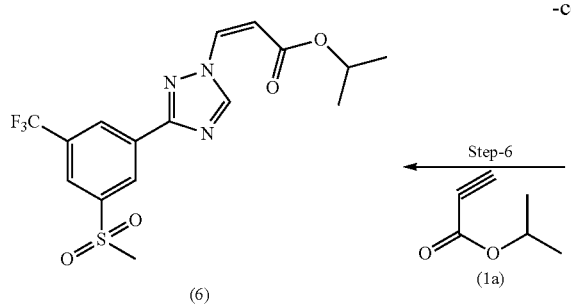

(6)
Molecular Weight: 403.4

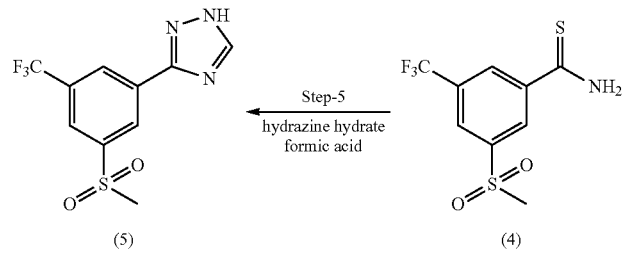

(1a)

(5)
Molecular Weight: 291.2

(4)
Molecular Weight: 283.3

Synthesis of Intermediate (1)

Synthesis of Intermediate (2)

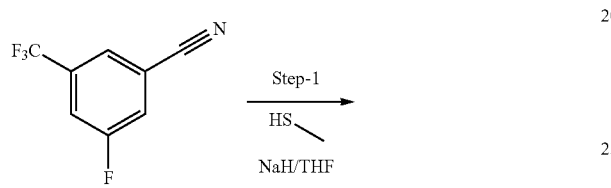

Molecular Weight: 189.1

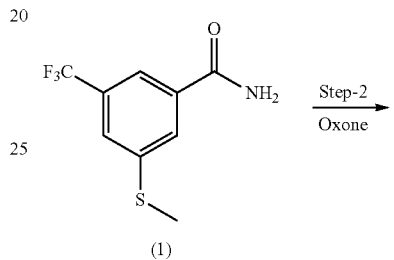

(1)
Molecular Weight: 235.2

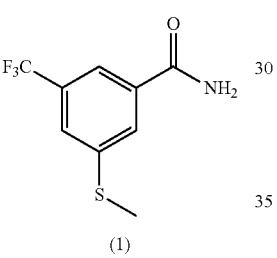

(1)
Molecular Weight: 235.2

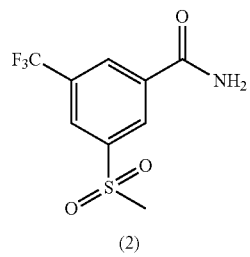

(2)
Molecular Weight: 267.2

In a 500-mL, 3N round-bottomed flask equipped with an 100-mL pressure-equalizing addition funnel fitted with a nitrogen inlet, and a rubber septum, 3-fluoro-5-(trifluoromethyl)benzonitrile (8.0 g, 1.0 eq.), in acetone (40 mL). Sodium thiomethoxide (3.42 g, 1.15 eq) was dissolved in water to make 21% aqueous solution and was added dropwise in 30 min at 5° C. temperature. The temperature of the reaction was slowly raised to RT and stirred for 3 h. Then temperature was raised to 50-60° C. and maintained for further 4-6 h. The progress of the reaction was followed by TLC analysis on silica gel with 10% MeOH-DCM as mobile phase and visualization with UV, SM $R_f$=0.40 and Product $R_f$=0.25. Reaction was stirred for 3 hr at 25° C. and 4-6 Hrs at 50-60° C. and reaction mixture was transparent. The reaction mass was quench by water and extracted by ethyl acetate (3×100 mL). The combined organic layer was washed with brine 50 mL and dried over sodium sulphate and evaporated on buchi rotaevaporator. The resulting crude compound White (8 g) was subjected to further stage Yield (80.9%). Mass: (ES+) 235.94 (M+1).

In a 500-mL, 3N round-bottomed flask equipped with an 100-mL pressure-equalizing addition funnel fitted with an nitrogen inlet, and a rubber septum, intermediate (1) (8.0 g, 1.0 eq.), in acetone (70 mL). Oxone (36.5 g, 2 eq) was added at RT. The reaction was stirred for 12 h. The progress of the reaction was followed by TLC analysis on silica gel with 30% EA-Hexane as mobile phase and visualization with UV, SM $R_f$=0.30 and Product $R_f$=0.20. Reaction was stirred for 12 h and white solid (Oxone salts) was separated by filtration on a Büchner funnel and washed with acetone (100 mL). The combined acetone layer was concentrated by rotary evaporation (40° C., 20 mmHg) to afford 7.0 g of off white solid. The resulting crude compound off white (7 g) was subjected to further stage Yield (90.4%). Mass: (ES+) 267.89 (M+1).

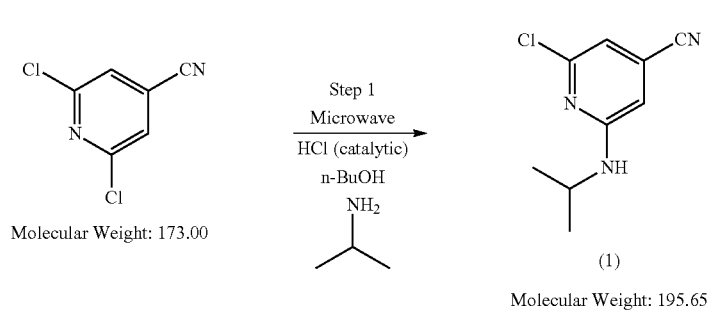

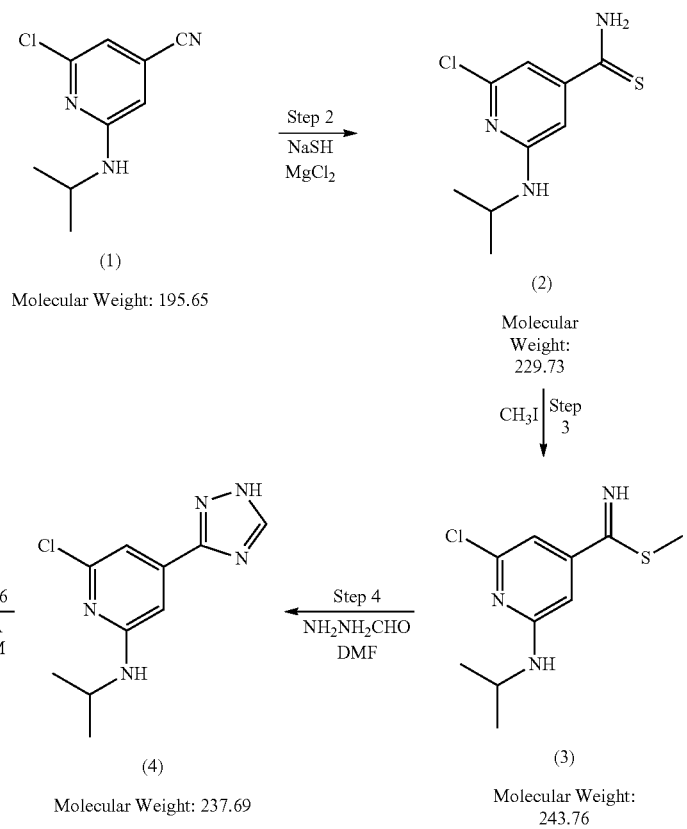

Synthesis of Intermediate (3)

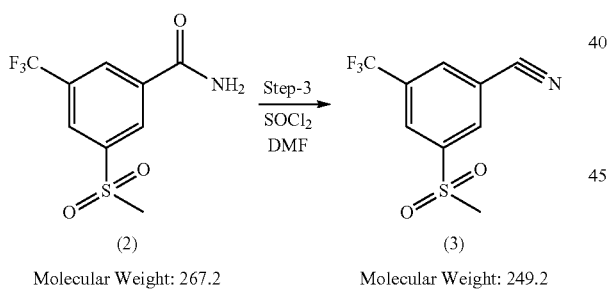

In a 3-neck 500 mL round-bottomed flask, intermediate 2 (7 g, 1 eq.) was dissolved in DMF (70 mL, 10 Vol) and added thionyl chloride (3.8 mL, 2.0 eq.) and reaction mixture was refluxed to 90° C. for 12 h. The progress of the reaction was followed by TLC analysis on silica gel with 30% EA—Hexane as mobile phase and visualization with UV, SM $R_f$=0.20 and Product $R_f$=0.35. Reaction mixture was brought to room temperature and quenched into the ice-water slurry (300 mL) and neutralized with sodium bi carbonate solution. Compound was extracted in the ethyl acetate (100 mL×3). Organic layer was washed with brine solution (100 mL) followed by drying using anhydrous sodium sulphate. Organic layer was concentrated under reduced pressure to afford 5.0 g of crude compound, yield (95.0%). The crude reaction mixture was purified by column chromatography using silica 60/120 using ethyl acetate:hexane as mobile phase. The column (5×20 cm) was packed in hexane and started eluting in ethyl acetate in gradient manner starting with fraction collection (25-mL fractions) from 15% to 20% ethyl acetate in hexane. Compound started eluting with 15% ethyl acetate in hexane. Fraction containing such TLC profile was collected together to obtain pure compound (4 g), Yield (62%). Mass: (ES−) 247.97 (M−1).

Synthesis of Intermediate (4)

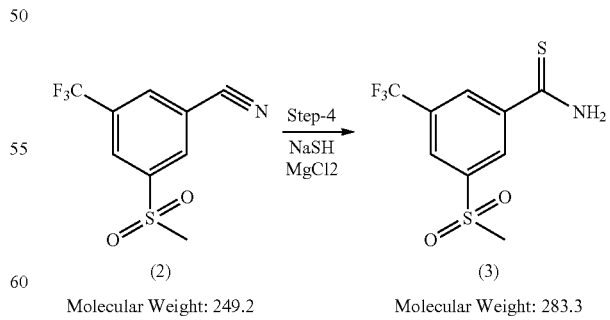

In a 1-neck 250 mL round-bottomed flask, Intermediate-3 (4.0 g, 1.0 eq.) was dissolved in DMF (40 mL, 10 V) added (1.80 g, 2.0 eq.) and MgCl$_2$ (3.58 g, 1.1 eq.). in reaction mixture. The reaction mixture was stirred for 6-8 h at RT. The progress of the reaction was followed by TLC analysis on silica gel with 40% ethyl acetate:hexane as mobile phase and visualization with UV, SM $R_f$=0.30 and Product $R_f$=0.20. Reaction mixture was quenched into the ice-water slurry (300 mL) and extracted in the ethyl acetate (100 mL×3). Organic layer was washed with brine solution (100 mL) followed by drying using anhydrous sodium sulphate. Organic layer was concentrated under reduced pressure to afford 4.0 g of crude compound, yield (88%). This crude material was directly used for next step without purification. Mass: (ES−) 281.9 (M−1).

Synthesis of Intermediate (5)

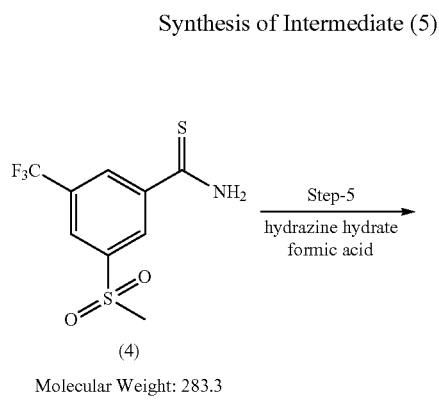

In a 1-neck 250 mL round-bottomed flask, Intermediate-4 (4.0 g, 1.0 eq.) was dissolved in DMF (40 mL, 10 V) added hydrazine hydrate (1.60 g, 2.0 eq) and stirred reaction mixture for 3 h. Then formic acid (20 mL, 5 vol) was added and stirred for 1 h at the same temperature. Then temperature increased to 90° C. and maintained for 10-12 hrs. The progress of the reaction was followed by TLC analysis on silica gel with 10% methanol: DCM as mobile phase and visualization with UV, SM $R_f$=0.30 and Product $R_f$=0.20. Reaction mixture was quenched into the ice-water slurry (300 mL) and extracted in the ethyl acetate (100 mL×3). Organic layer was washed with sodium bicarbonate solution (100×3 mL) followed by drying using anhydrous sodium sulphate. Organic layer was concentrated under reduced pressure to afford 3.0 g of crude compound. The resulting crude compound (4.0 g) was subjected to column purification. The crude reaction mixture was purified by column chromatography using silica 60/120 using methanol: DCM as mobile phase. The column (5×10 cm) was packed in DCM and started eluting in Methanol in gradient manner starting with fraction collection (25 mL fractions) from 3-5% methanol in DCM. Compound started eluting with 3% methanol in DCM. Fraction containing such TLC profile was collected together to obtain pure compound (3.0 g), Yield (73.6%).

Synthesis of Intermediate (6)

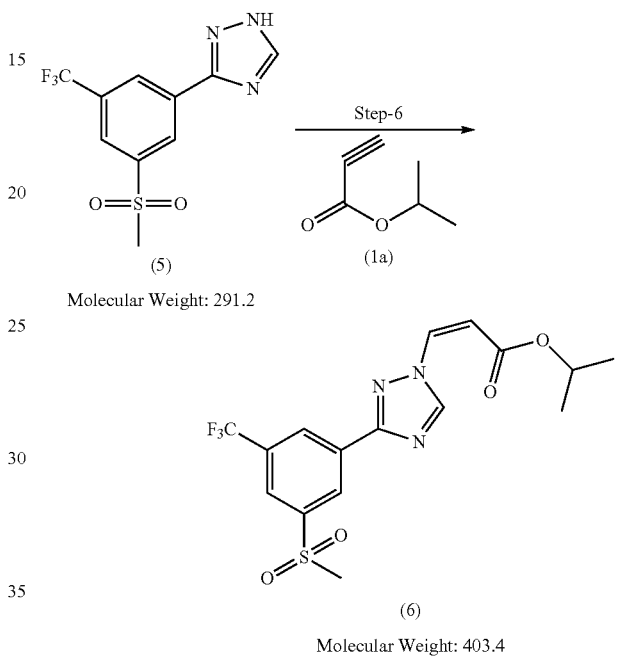

In a 1-neck 25 mL round-bottomed flask, Intermediate-5 (0.10 g, 1.0 eq.), was dissolved in DCM (5 mL, 50 vol.), added TEA (0.052 g, 1.2 eq) and added Isopropyl propionate (0.056 g, 1.2 eq.). Reaction mixture was stirred at 0° C. for 2-3 h. The progress of reaction was followed by TLC analysis on silica gel with 10% Methanol:DCM as mobile phase and visualization with UV, SM $R_f$=0.20 and Product $R_f$=0.35. Reaction mixture was concentrated under reduced pressure to afford 0.250 g of crude compound. The resulting crude compound (0.250 g) was subjected to column purification. The crude reaction mixture was purified by column chromatography using silica 60/120 using methanol:DCM as mobile phase. The column (2×10 cm) was packed in DCM and started eluting in Methanol in gradient manner starting with fraction collection (25-mL fractions) from 1.5% to 2.5% methanol in DCM. Compound started eluting with 1.5% methanol in DCM. Fraction containing such TLC profile was collected together to obtain pure compound (0.025 g), Yield (18%); $^1$H NMR (400 MHz, CDCl$_3$) δ 9.76 (S, 1H), 8.28-8.92 (m, 3H), 7.28-7.31 (d, J=10.8, 1H), 5.77-5.80 (d, J=10.8 Hz, 1H), 5.13-5.19 (m, 1H), 3.17 (S, 3H), 1.34-1.41 (d, 6H): LCMS for C$_{16}$H$_{16}$F$_3$N$_3$O$_4$S [M+Acetonitrile]$^+$ 403.4 found 444.71 at 6.653 min.

Example 68

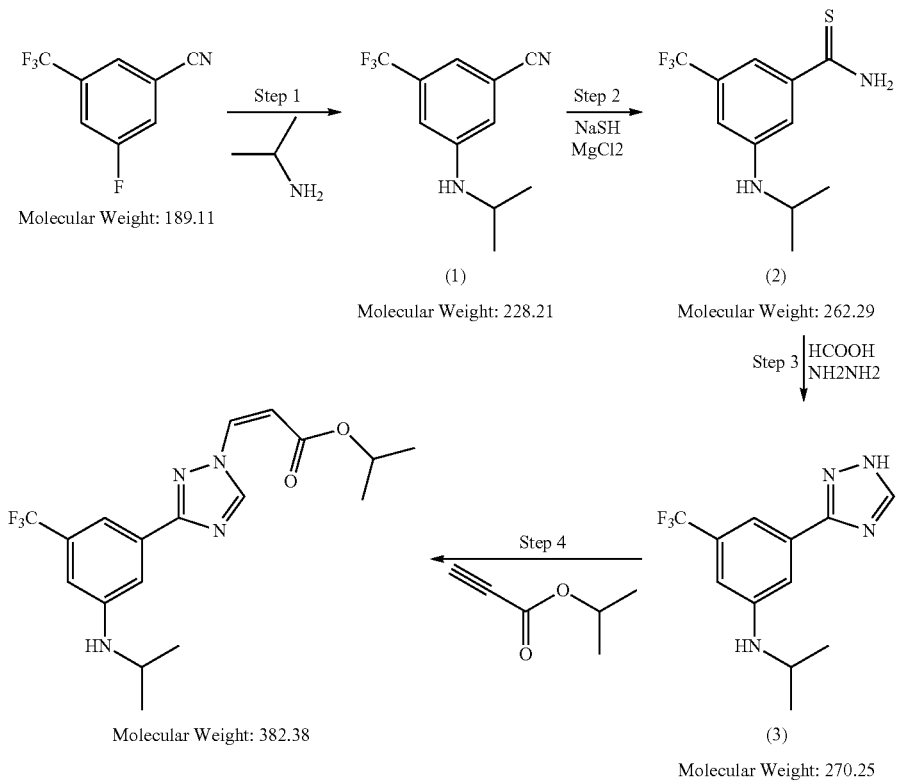

Synthesis of Intermediate (1)

Synthesis of Intermediate (2)

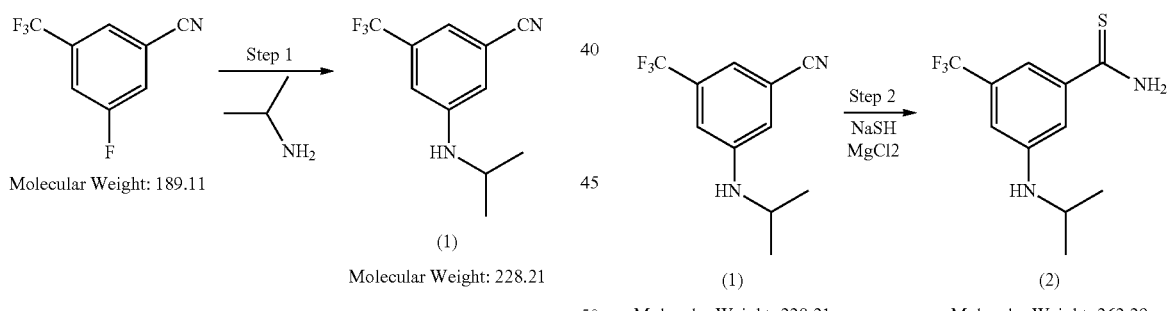

In a 50-mL, 3N round-bottomed flask equipped with nitrogen inlet, and a rubber septum, 3-fluoro-5-trifluorobenzonitrile (1.25 g, 1.0 eq.) was dissolved in DMSO (25 mL). Isopropylamine (0.781 g, 2.0 eq.) and potassium carbonate (3.18 g, 3.5 eq.) was added to this reaction mixture. The reaction mixture was heated at 100° C. for 4-5 h. The progress of reaction was followed by TLC analysis on silica gel with 20% Ethyl acetate-n-hexane as mobile phase, SM $R_f$=0.6 and Product $R_f$=0.4. Reaction mixture was poured into ice water (100 mL) and extracted with EtOAc (3×50 mL). The combined organic layers were washed with brine solution (3×50 mL), dried over MgSO$_4$, filtered, and concentrated by rotary evaporation (25° C., 20 mmHg) to afford 1.0 g of crude compound which was used for next step without any purification, Yield (66.7%). Mass: 228.70.

In a 25-mL, 3N round-bottomed flask equipped with nitrogen inlet, and a rubber septum, Intermediate-1 (1.0 g, 1.0 eq.) was dissolved in DMF (10 mL, 10V), NaSH (0.648 g, 2.0 eq.) was added to this reaction mixture followed by MgCl$_2$ (0.982 g, 1.1 eq.). Reaction mixture was stirred at RT for 2-3 h. The progress of reaction was followed by TLC analysis on silica gel with 40% EtOAc-n-hexane as mobile phase, SM $R_f$=0.5 and Product $R_f$=0.3. Reaction mixture was poured into ice-water (50 mL) and compound was extracted with EtOAc (3×25 mL). The combined organic layers were washed with brine solution (3×25 mL), dried over MgSO$_4$, filtered, and concentrated by rotary evaporation (25° C., 20 mmHg) to afford 1.0 g of crude compound which was used for next step without any purification, Yield (87.03%). Mass: 262.4.

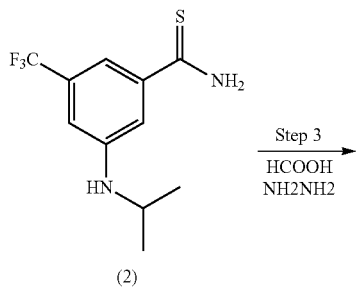

(2)
Molecular Weight: 262.29

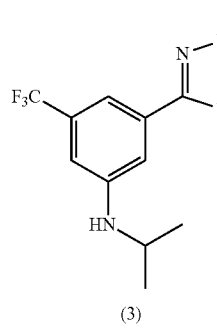

(3)
Molecular Weight: 270.25

In a 50-mL, 3N round-bottomed flask equipped with nitrogen inlet, and a rubber septum, intermediate-2 (1.0 g, 1.0 eq.) was dissolved in DMF (20 mL, 20V) and added NH$_2$NH$_2$.H$_2$O (5.0 mL, 5V). The reaction mixture was stirred at RT for 1 h. To this reaction mixture was added HCOOH (5.0 mL, 5V) and reaction mixture was refluxed at 90° C. for 2-3 h. The progress of reaction was followed by TLC analysis on silica gel with 50% Ethyl acetate-n-Hexane as mobile phase. SM R$_f$=0.50 and Product R$_f$=0.3. Reaction mixture was poured into ice water (100 mL) and neutralized with Saturated sodium bicarbonate solution. The reaction mixture was extracted with EtOAc (3×50 mL) and combined organic layers were washed with brine solution. (3×50 mL), dried over MgSO$_4$, filtered, and concentrated by rotary evaporation (25° C., 20 mmHg) to afford 0.5 g of Crude compound. Yield (48.54%). Mass: 270.40.

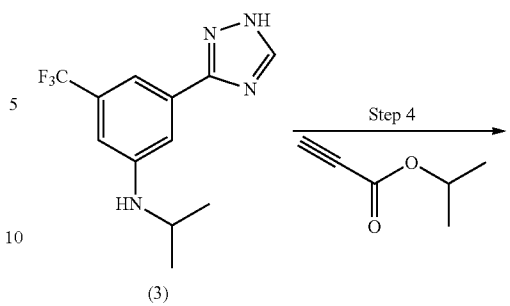

In a 10-mL, 3N round-bottomed flask equipped with nitrogen inlet, and a rubber septum, Intermediate-3 (0.250 g, 1.0 eq.) was dissolved in DCM (5.0 mL, 20V), added TEA (0.122 g, 1.3 eq.) and isopropyl propiolate (0.134 g, 1.3 eq.). The Reaction mixture was stirred at RT for 30 mins. The progress of the reaction was followed by TLC analysis on silica gel with 50% ethylacetate-hexane as mobile phase (SM; R$_f$=0.30 and product R$_f$=0.5). Reaction mixture was concentrated by rotary evaporation (25° C., 20 mmHg) to afford 0.3 g of Crude compound. The crude reaction mixture was purified by column chromatography using silica 60/120 using Ethyl acetate: Hexane as mobile phase. The column (5×10 cm) was packed in Hexane and started eluting in Ethyl acetate in gradient manner starting with fraction collection (50-mL fractions) from 5% to 20% Ethyl acetate in hexane. Compound started eluting with 20% Ethyl acetate in Hexane. Fraction containing such TLC profile was collected together to obtain pure compound (10 mg), Yield (2.86%). ($^1$H NMR: 400 MHz, CDCl$_3$) δ 9.70 (s, 1H), δ 7.69 (s, 1H), δ 7.51 (s, 1H), δ 7.27-7.29 (d: 10.8 Hz, 1H), 66.84 (s, 1H), δ 5.68-5.71 (d, J: 10.8 Hz, 1H), δ 5.11-5.18 (m, 1H), δ 3.57-3.64 (m, 1H), 61.33-1.34 (d, 6H), δ 1.26-1.28 (d, 6H). LCMS of C$_{18}$H$_{21}$F$_3$N$_4$O$_2$(M+1)$^+$: 382.38 found: 382.89 at 4.481 min (LCMS 95.57%).

Example 69
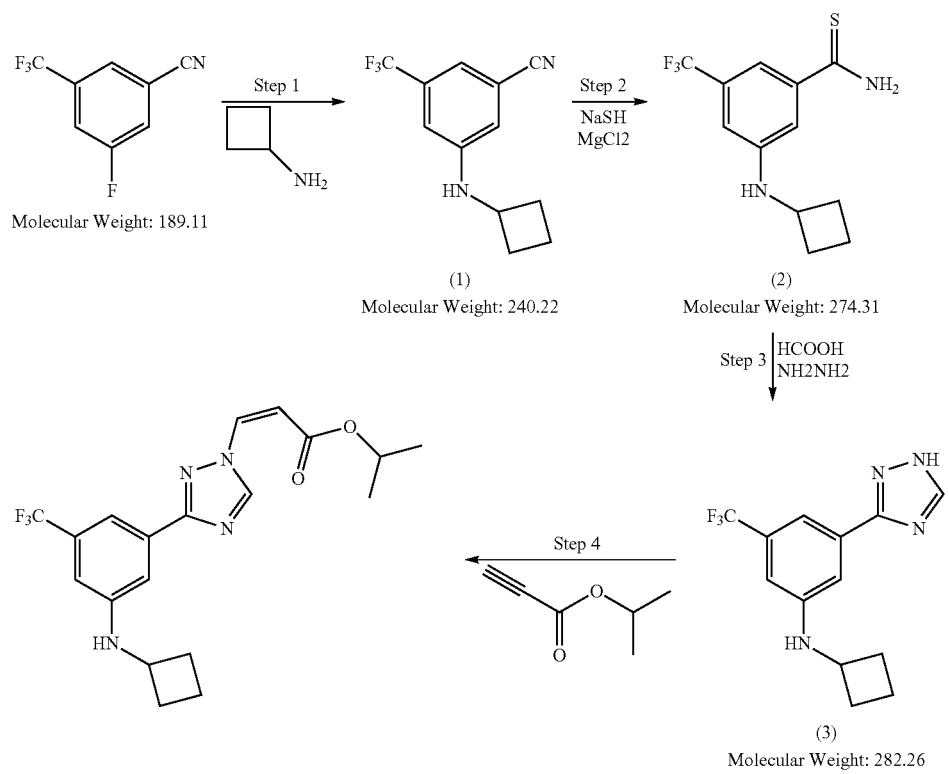
Synthesis of Intermediate (1)
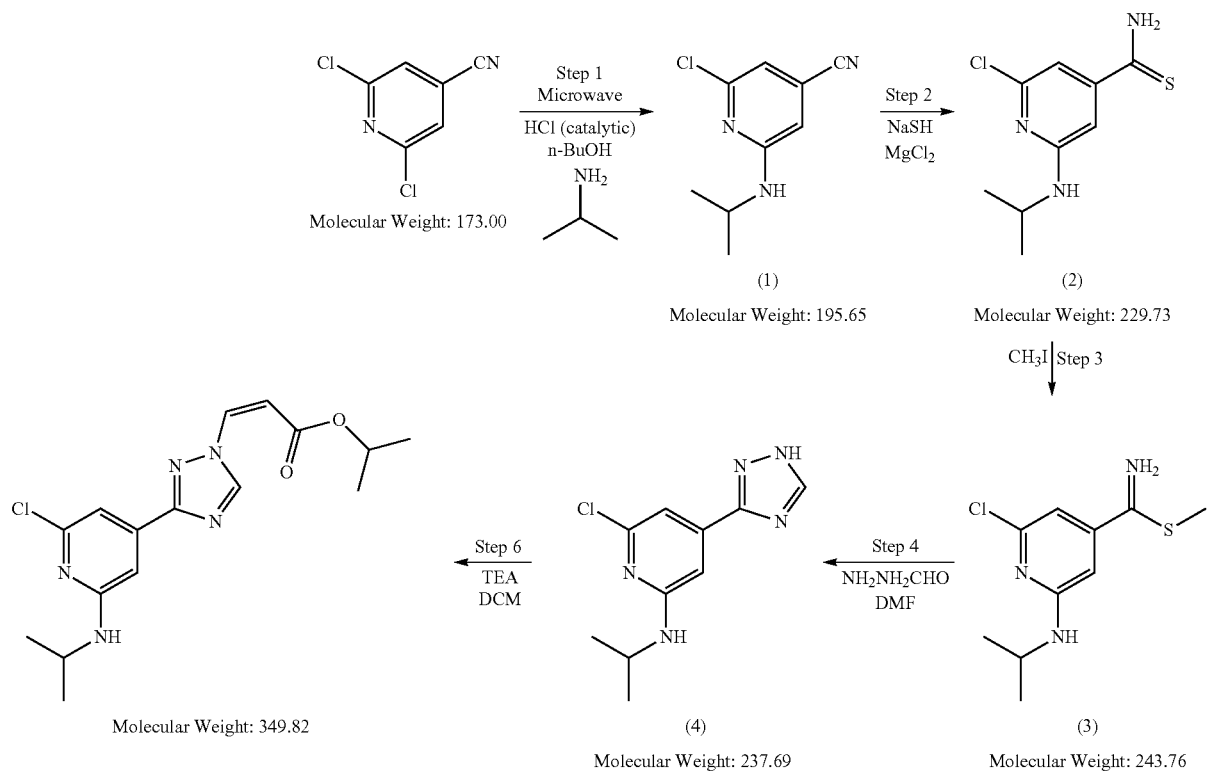

Synthesis of Intermediate (1)

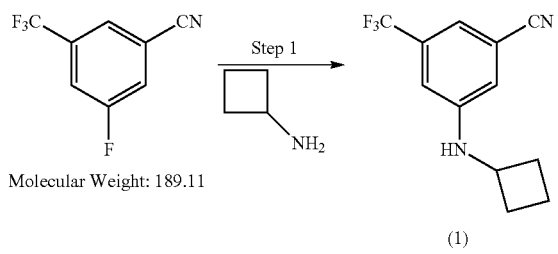

(1)
Molecular Weight: 240.22

In a 50-mL, 3N round-bottomed flask equipped with nitrogen inlet and a rubber septum, 3-fluoro-5-trifluorobenzonitrile (1.5 g, 1.0 eq.) was dissolved in DMSO (30 mL) and cyclobutanamine (1.128 g, 2.0 eq.) and potassium carbonate (3.81 g, 3.5 eq.) was added. The reaction mixture was heated at 100° C. for 4-5 h. The progress of reaction was followed by TLC analysis on silica gel with 20% Ethyl acetate-hexane as mobile phase. SM $R_f$=0.6 and Product $R_f$=0.4. Reaction mixture was poured into ice water (150 mL) and extracted with EtOAc (3×50 mL). The combined organic layers were washed with brine solution (3×50 mL) and dried over anhydrous MgSO$_4$, filtered, and concentrated by rotary evaporation (25° C., 20 mmHg) to afford 1.8 g of crude compound which was used for next step without any purification. Yield (94.7%). Mass: 240.90.

Synthesis of Intermediate (2)

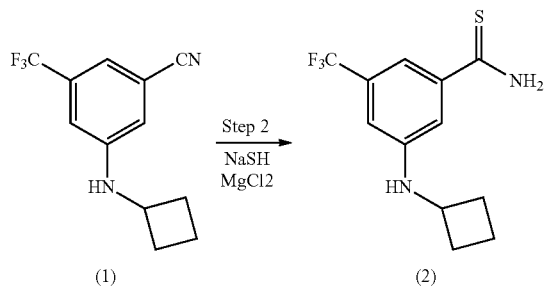

In a 50-mL, 3N round-bottomed flask equipped with nitrogen inlet and a rubber septum, intermediate-1 (1.8 g, 1.0 eq.) was dissolved in DMF (18 mL, 10V) and NaSH (1.11 g, 2.0 eq.) was added along with MgCl$_2$ (1.67 g, 1.1 eq.). Reaction mixture was stirred at RT for 2-3 h. The progress of reaction was followed by TLC analysis on silica gel with 40% EtOAc-n-hexane as mobile phase. SM $R_f$=0.5 and Product $R_f$=0.3. Reaction mixture was poured into ice water (100 mL) and extracted with EtOAc (3×50 mL). The combined organic layers were washed with brine solution (3×50 mL), dried over anhydrous Na$_2$SO$_4$, filtered, and concentrated by rotary evaporation (25° C., 20 mmHg) to afford 2.0 g of crude compound which was used for next step without any purification, Yield (97.5%). Mass: 274.82.

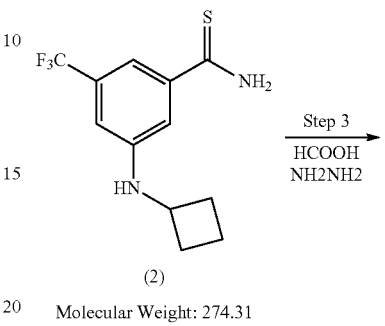

(2)
Molecular Weight: 274.31

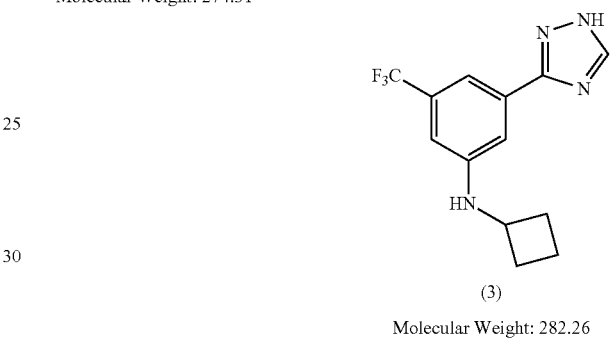

(3)
Molecular Weight: 282.26

In a 100-mL, 3N round-bottomed flask equipped with nitrogen inlet and a rubber septum, Intermediate-2 (2.0 g, 1.0 eq.) was dissolved in DMF (250 mL, 20V) NH$_2$NH$_2$.H$_2$O (10.0 mL, 5V) was added. The reaction mixture was stirred at RT for 1 h and HCOOH (10.0 mL, 5V) was added. Reaction mixture was refluxed at 90° C. for 2-3 h. The progress of reaction was followed by TLC analysis on silica gel with 50% Ethyl acetate-n-Hexane as mobile phase. SM $R_f$=0.50 and Product $R_f$=0.3. Reaction mixture was poured into ice water (150 mL) and neutralized with saturated sodium bicarbonate solution. The reaction mixture was extracted with EtOAc (3×100 mL). The combined organic layers were washed with Brine solution. (3×100 mL), dried over MgSO$_4$, filtered, and concentrated by rotary evaporation (25° C., 20 mmHg) to afford 1.9 g of crude compound, Yield (92.7%). Mass: 282.92.

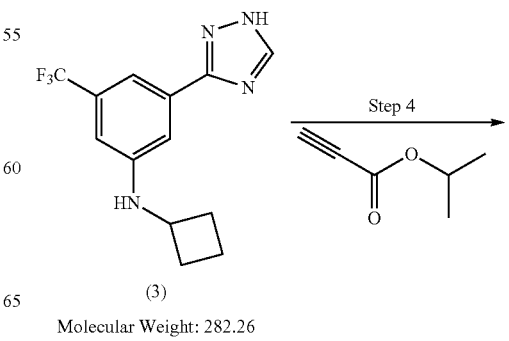

(3)
Molecular Weight: 282.26

-continued

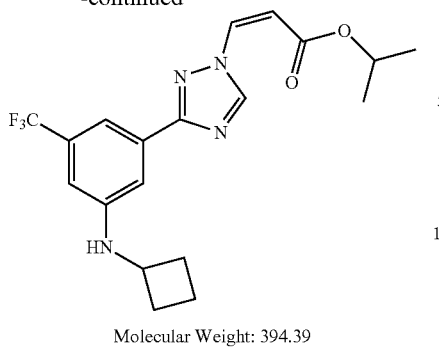

Molecular Weight: 394.39

In a 100-mL, 3N round-bottomed flask equipped with nitrogen inlet and a rubber septum, intermediate-3 (12.5 g, 1.0 eq.) was dissolved in DCM (40 mL, 20V) and TEA (0.932 g, 1.3 eq.) was added. To this reaction mixture isopropyl propiolate (1.03 g, 1.3 eq.) was added and reaction was stirred at RT for 30 min. The progress of reaction was followed by TLC analysis on silica gel with 50% Ethyl acetate-n-Hexane as mobile phase. SM $R_f$=0.30 and Product $R_f$=0.5. Reaction mixture was concentrated by rotary evaporation (25° C., 20 mmHg) to afford 2.0 g of Crude compound. The crude reaction mixture was purified by column chromatography using silica 60/120 using Ethyl acetate:Hexane as mobile phase. The column (5×10 cm) was packed in Hexane and started eluting in Ethyl acetate in gradient manner starting with fraction collection (50-mL fractions) from 5% to 20% Ethyl acetate in hexane. Compound started eluting with 20% Ethyl acetate in Hexane. Fraction containing such TLC profile was collected together to obtain pure compound (50 mg), Yield (1.79%). $^1$H NMR (400 MHz, CDCl$_3$) δ 9.71 (s, 1H), 7.71 (s, 1H), 7.47 (s, 1H), 7.27-7.30 (d, J=10.8 Hz, 1H), 6.80 (s, 1H), 5.68-5.71 (d, J=10.8 Hz, 1H), 5.11-5.18 (m, 1H), 4.17 (broad s, D$_2$O exchangeable, 1H), 4.02-4.04 (m, 1H), 2.50-2.54 (m, 2H), 1.83-1.91 (m, 4H), 1.27-1.34 (d, 6H): LCMS for C$_{19}$H$_{21}$F$_3$N$_4$O$_2$ 394.39 found 394.93 at R.T. 4.631 min (LCMS 98.28%).

Example 70

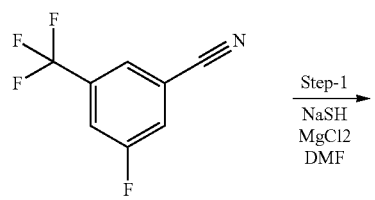

Molecular Weight: 189.11

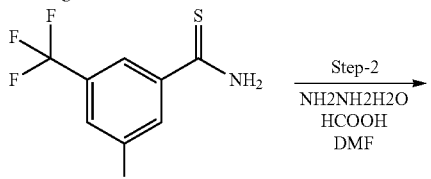

(1)
Molecular Weight: 223.19

-continued

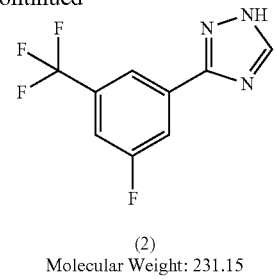

(2)
Molecular Weight: 231.15

Step-3

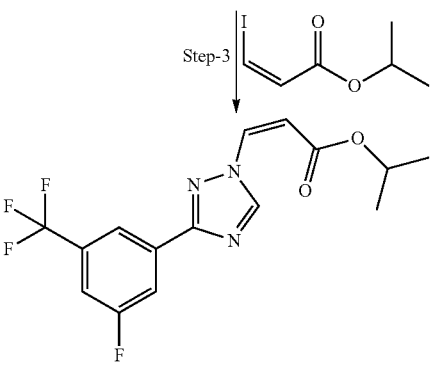

Molecular Weight: 343.28

Synthesis of Intermediate (1)

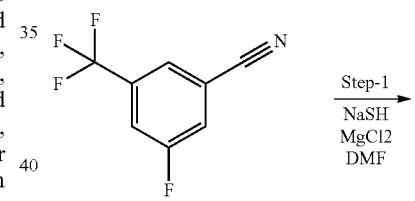

Molecular Weight: 189.11

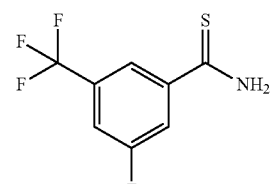

(1)
Molecular Weight: 223.19

In a 25-mL, 3N round-bottomed flask equipped with nitrogen inlet and a rubber septum, 3-fluoro-5-(trifluoromethyl) benzonitrile (3.0 g, 1.0 eq.), MgCl$_2$ 6H$_2$O (3.87 g, 1.2 eq.), NaSH (1.07 g) was dissolved in DMF (30 mL). The reaction mixture was stirred at 25-30° C. The progress of reaction was followed by TLC analysis on silica gel with 20% EtOAc-n-hexane as mobile phase which shows that starting material was consumed after 30 min. Reaction was quenched by ice cold water, precipitate was observed that was filter on Buchner funnel and washed with hexane to give required compound. Reaction was stirred for 10 min with ice cold water, solid were separated and compound was collected by filtration and washed with hexane (30 mL). Yield: 4.08 g (crude).

Synthesis of Intermediate (2)

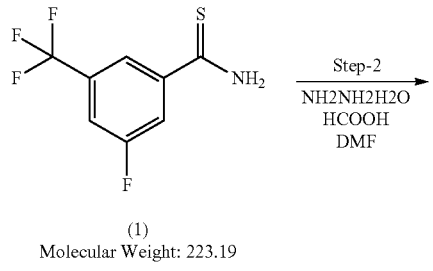

(1)
Molecular Weight: 223.19

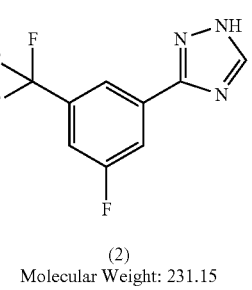

(2)
Molecular Weight: 231.15

In a 100-mL, 3N round-bottomed flask equipped with thermometer pocket fitted with water condenser, nitrogen inlet and a rubber septum, intermediate-1 (4.0 g, 1.0 eq.) dissolved in DMF (40 mL) and hydrazine hydrate (4.4 mL, 5.0 eq.) was added dropwise. The resulting reaction mixture was stirred at RT for 15-20 min. To this reaction mixture formic acid (3.4 mL, 5.0 eq.) was added dropwise. The reaction mixture was stirred at 85-90° C. The progress of reaction was followed by TLC analysis on silica gel with 50% EtOAc-hexane as mobile phase which shows that starting material was consumed after 3 h. Reaction was quenched into ice cold water, precipitate was observed that was filtered and washed with hexane to give required compound. Reaction was stirred for 10 min with ice cold water solid were separated and compound was collected by filtration on a Buchner funnel and washed with hexane (100 mL) Yield: 0.07 g. LCMS (%): Retention time: 3.122 min, (5.08%), (M+H)$^+$ 231.9. NMR: Confirmed.

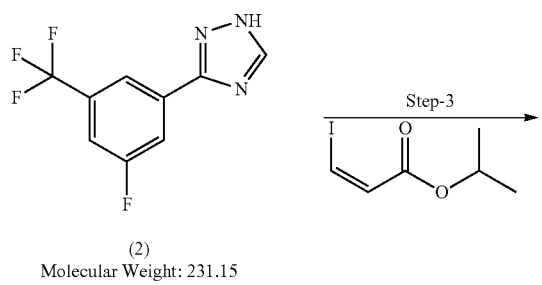

(2)
Molecular Weight: 231.15

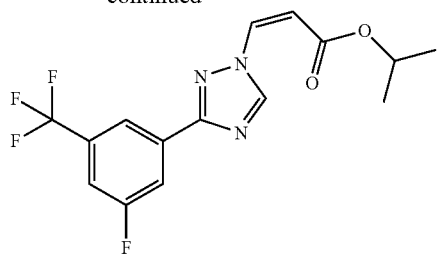

Molecular Weight: 343.28

In a 25-mL, 3N round-bottomed flask equipped with thermometer pocket fitted with water condenser, nitrogen inlet and a rubber septum, intermediate-2 (0.07 g, 1.0 eq.), isopropyl-3-iodoacrylate (0.109 g, 1.5 eq.) and NaOH (0.036 g, 3 eq) was dissolved in DMF (2 mL), resulting reaction mixture was stirred at 0-5° C. The progress of reaction was followed by TLC analysis on silica gel with 20% EtOAc-n-hexane as mobile phase which shows that starting material was consumed after 3 h. Reaction was quenched into ice cold water and extracted by ethyl acetate (10*3 mL), combined organic layer were dried over anhydrous sodium sulfate and concentrated under reduce pressure to obtain crude material (0.10 g), crude compound was subjected to column chromatography using ethyl acetate hexane as mobile phase. The crude material was subjected to column chromatography using ethyl acetate:hexane as mobile phase. Compound was eluted in 4% ethyl acetate in hexane it was not enough pure, so it was followed by combiflash purification. Yield: 0.03 g (28.86%). $^1$H NMR: δ=9.19 (s, 1H), 8.10 (s, 1H), 8.02-8.04 (d, J=8 Hz, 1H), 7.86-7.88 (d, J=8 Hz, 1H), 7.47-7.50 (d, J=12 Hz, 1H), 6.02-6.05 (d, J=12 Hz, 1H), 5.00-5.07 (m, 1H), 1.23-1.25 (d, 6H). LCMS: Calculated for $C_{15}H_{13}F_4N_3O_2$ (M+H)$^+$ 343.28 Found: 343.85 at 4.451 min (LCMS 96.77%).

Example 71

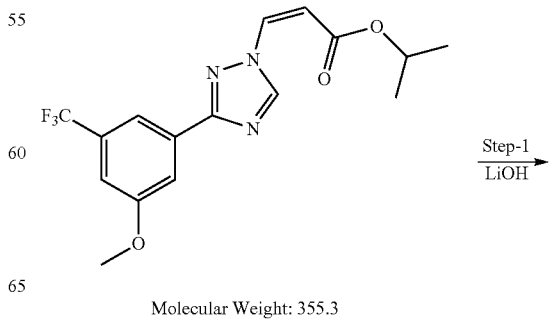

Molecular Weight: 355.3

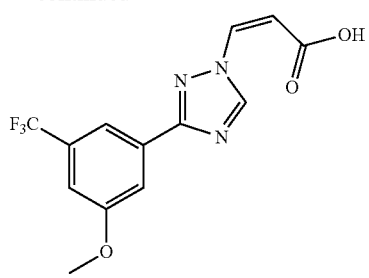

(1)
Molecular Weight: 313.2

HOBt/EDC•HCl
DIPEA
3,3-difluoroazetidine hydrochloride | Step-2

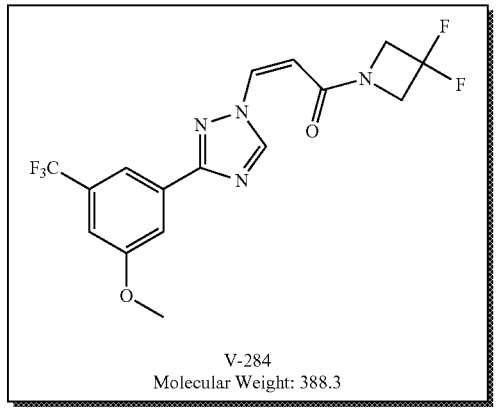

V-284
Molecular Weight: 388.3

Synthesis of Intermediate (1)

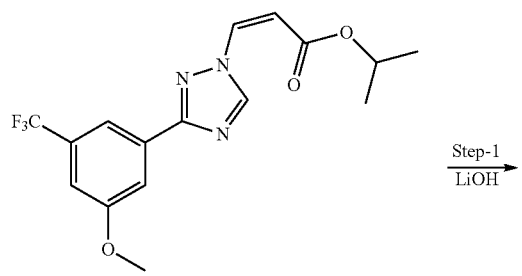

Molecular Weight: 355.3

Step-1
LiOH (1)
Molecular Weight: 313.2

In a 1-neck 25 mL round-bottomed flask, Example 26 (0.200 g, 1.0 eq.), was dissolved in THF (5 mL, 5 vol.) and water (5 mL, 3.5 Vol) and LiOH (0.035 g, 1.5 eq.) was added to it. Reaction mixture was stirred at RT for 2-3 hrs. The progress of reaction was followed by TLC analysis on silica gel with 10% methanol:DCM as mobile phase and visualization with UV, SM $R_f$=0.35 and Product $R_f$=0.15. Reaction mixture was quenched into the acidic ice-water slurry (30 mL) and extracted in the ethyl acetate (25 mL×3). Organic layer was washed with dil HCl solution (50 mL) followed by drying using anhydrous sodium sulphate. Organic layer was concentrated under reduced pressure to afford 150 mg of crude compound. The resulting crude compound off white was used for further stage, yield (85.5%). Mass: (ES+) 313.9 (M+1).

(1)
Molecular Weight: 313.2

Step-2
HOBt/EDC•HCl
DIPEA
3,3-difluoroazetidine hydrochloride

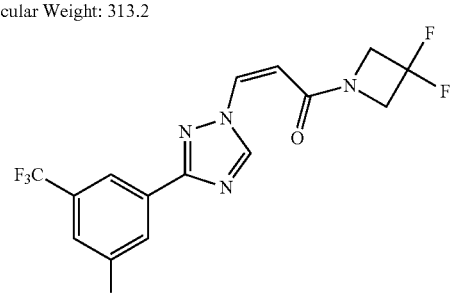

VS-199
Molecular Weight: 388.3

In a 3-neck 25 mL round-bottomed flask, intermediate 1 (0.145 g, 1.0 eq.) was dissolved in 10 ml of DCM at 0° C. under $N_2$ atmosphere, added DIPEA (0.075 g, 1.2 eq.) and EDC.HCl (0.138 g, 1.5 eq.) and 3,3-difluoroazetidine hydrochloride (0.075 g, 1.2 eq.) and finally HOBt (0.087 g, 1.2 eq.). Reaction mixture was stirred at 0° C. for 3-4 hrs. The progress of reaction was followed by TLC analysis on silica gel with 10% methanol: DCM as mobile phase and visualization with UV, SM $R_f$=0.15 and Product $R_f$=0.40. Reaction was stirred for 3-4 h and yellow reaction mixture was evaporated on rotary evaporator under reduced pressure to afford 0.150 g of crude compound. The crude reaction mixture was purified by column chromatography using silica 60/120 using methanol: DCM as mobile phase. The column (2×10 cm) was packed in DCM and started eluting in Methanol in gradient manner starting with fraction collection (25-mL fractions) from 1.5% to 2.5% methanol in DCM. Compound started eluting with 1.5% methanol in DCM. Fraction containing such TLC profile was collected together to obtain pure compound (0.060 g), Yield (40.6%). $^1$H NMR (400 MHz, CDCl$_3$) δ 9.58 (S, 1H), 7.28-8.35 (m, 3H), 7.22-7.25 (d, J=11.2, 1H), 5.61-5.64 (d, J=10.8 Hz, 1H), 4.45-4.58 (m, 4H); LCMS for $C_{16}H_{13}F_5N_4O_2$ [M+H]$^+$ 388.3 found 388.85 at RT 6.190 min.

Example 72

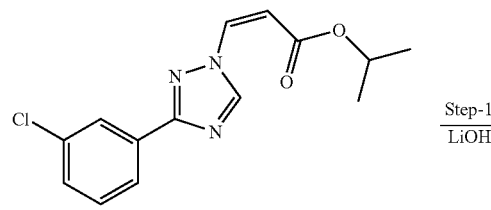

Molecular Weight: 291.7

Step-1
LiOH

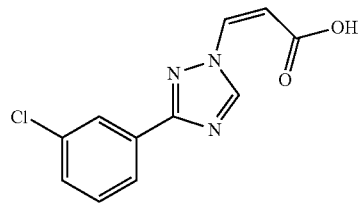

(1)
Molecular Weight: 249.7

HOBt/EDC•HCl
DIPEA
3,3-difluoroazetidine hydrochloride
Step-2

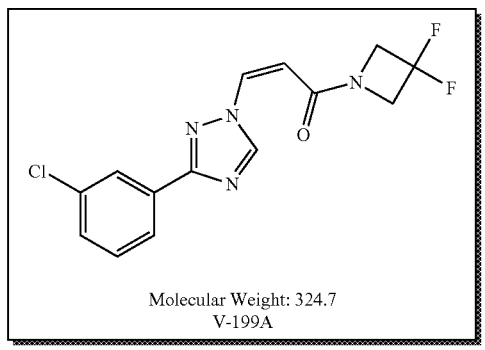

Molecular Weight: 324.7
V-199A

Synthesis of Intermediate (1)

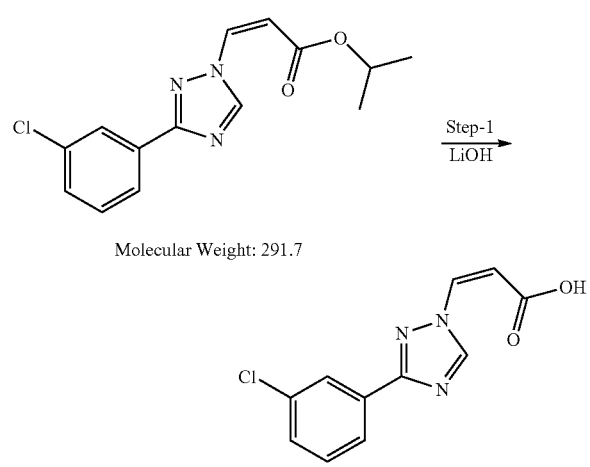

Molecular Weight: 291.7

Step-1
LiOH

Molecular Weight: 249.7

In a 1-neck 25 mL round-bottomed flask, Example 1 (0.2 g, 1.0 eq.), was dissolved in THF (5 mL, 5 vol.), added water (5 mL, 3.5 Vol) followed by LiOH (0.043 g, 1.5 eq.). Reaction mixture was stirred at RT for 2-3 h. The progress of reaction was followed by TLC analysis on silica gel with 10% methanol:DCM as mobile phase and visualization with UV, SM $R_f$=0.35 and Product $R_f$=0.15. Reaction mixture was quenched into the acidic ice-water slurry (30 mL) and compound was extracted in the ethyl acetate (25 mL×3). Organic layer was washed with dil HCl solution (50 mL) followed by drying using anhydrous sodium sulphate. Organic layer was concentrated under reduced pressure to afford 145 mg of crude compound. The resulting crude compound off white was used for further stage, yield (85%). Mass: (ES−) 247.9 (M−1).

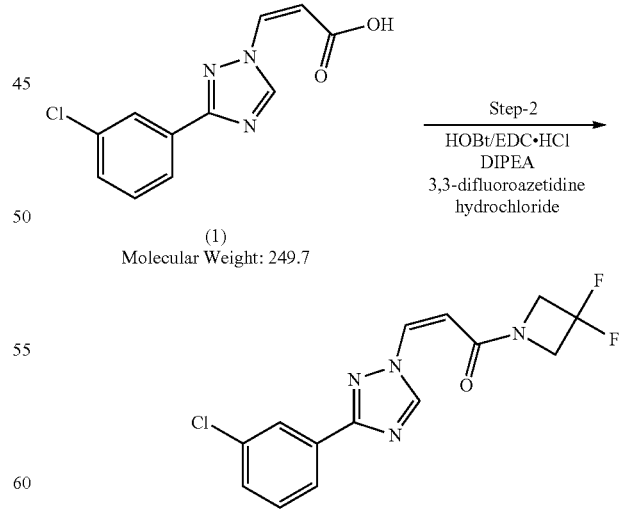

(1)
Molecular Weight: 249.7

Step-2
HOBt/EDC•HCl
DIPEA
3,3-difluoroazetidine hydrochloride

Molecular Weight: 324.7
V-199A

In a 3-neck 25 mL round-bottomed flask, intermediate 1 (0.145 g, 1.0 eq.) was dissolved in 10 mL of DCM at 0° C.

under N₂ atmosphere, added DIPEA (0.089 g, 1.2 eq.), EDC HCl (0.167 g, 1.5 eq.), 3,3-difluoroazetidine hydrochloride (0.075 g, 1.2 eq.) and HOBt (0.105 g, 1.2 eq.) was added. Reaction mixture was stirred at 0° C. for 3-4 hrs. The progress of reaction was followed by TLC analysis on silica gel with 10% methanol: DCM as mobile phase and visualization with UV, SM $R_f$=0.15 and Product $R_f$=0.40. Reaction was stirred for 3-4 h and yellow reaction mixture was evaporated on rotary evaporator under reduced pressure to afford 0.2 g of crude compound. The crude reaction mixture was purified by column chromatography using silica 60/120 using methanol: DCM as mobile phase. The column (2×10 cm) was packed in DCM and started eluting in Methanol in gradient manner starting with fraction collection (25 mL fractions) from 1.5% to 2.5% methanol in DCM. Compound started eluting with 1.5% methanol in DCM. Fraction containing such TLC profile was collected together to obtain pure compound (0.080 g), Yield (42.4%). ¹H NMR (400 MHz, CDCl₃) δ 9.55 (S, 1H), 7.38-8.15 (m, 4H), 7.21-7.24 (d, J=10.8, 1H), 5.60-5.63 (d, J=10.8 Hz, 1H), 4.45-4.57 (m, 4H); LCMS for $C_{14}H_{11}ClF_2N_4O$ [M+H]⁺ 324.7 found 324.77 at RT 5.899 min.

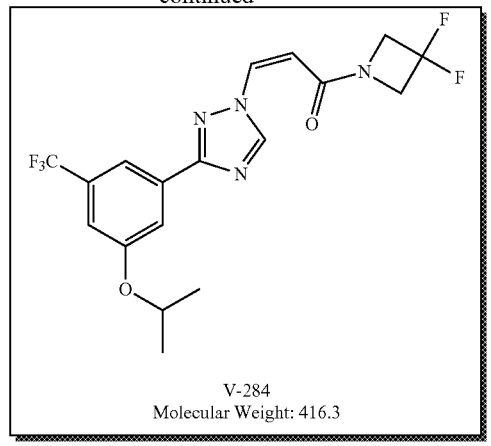

V-284
Molecular Weight: 416.3

Synthesis of Intermediate (1)

Example 73

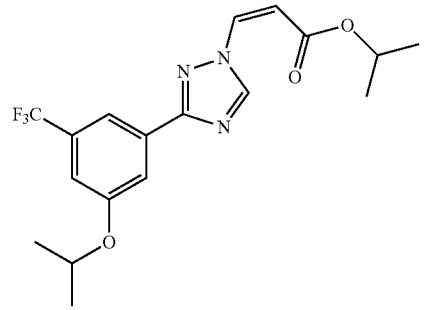

Molecular Weight: 383.4

| Step-1
LiOH

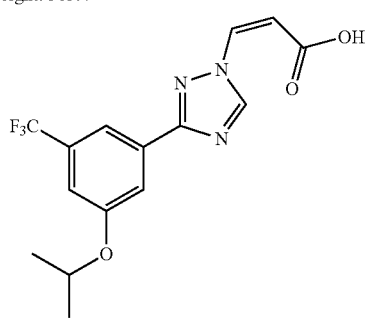

(1)
Molecular Weight: 341.3

HOBt/EDC•HCl
DIPEA
3,3-difluoroazetidine
hydrochloride | Step-2

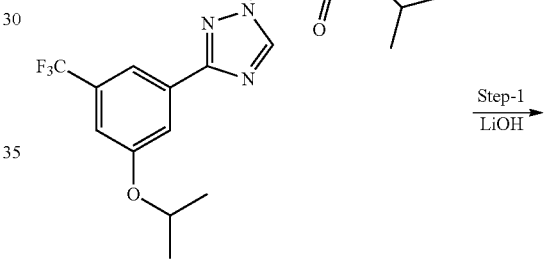

Molecular Weight: 383.4

| Step-1
LiOH

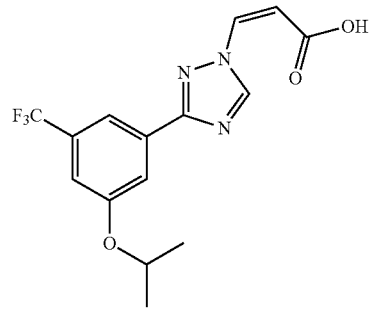

(1)
Molecular Weight: 341.3

In a 1-neck 25 mL round-bottomed flask, Example 44 (0.190 g, 1.0 eq.), was dissolved in THF (5 mL, 5 vol.) added water (5 mL, 3.5 Vol) and added LiOH (0.035 g, 1.5 eq.). Reaction mixture was stirred at RT for 2-3 hrs. The progress of reaction was followed by TLC analysis on silica gel with 10% methanol:DCM as mobile phase and visualization with UV, SM $R_f$=0.35 and Product $R_f$=0.15. Reaction mixture was quenched into the acidic ice-water slurry (30 mL) and extracted in the ethyl acetate (25 mL×3). Organic layer was washed with dil HCl solution (50 mL) followed by drying using anhydrous sodium sulphate. Organic layer was concentrated under reduced pressure to afford 165 mg of crude compound. The resulting crude compound off white was used for further stage, yield (86.3%). Mass: (ES+) 341.9 (M+1).

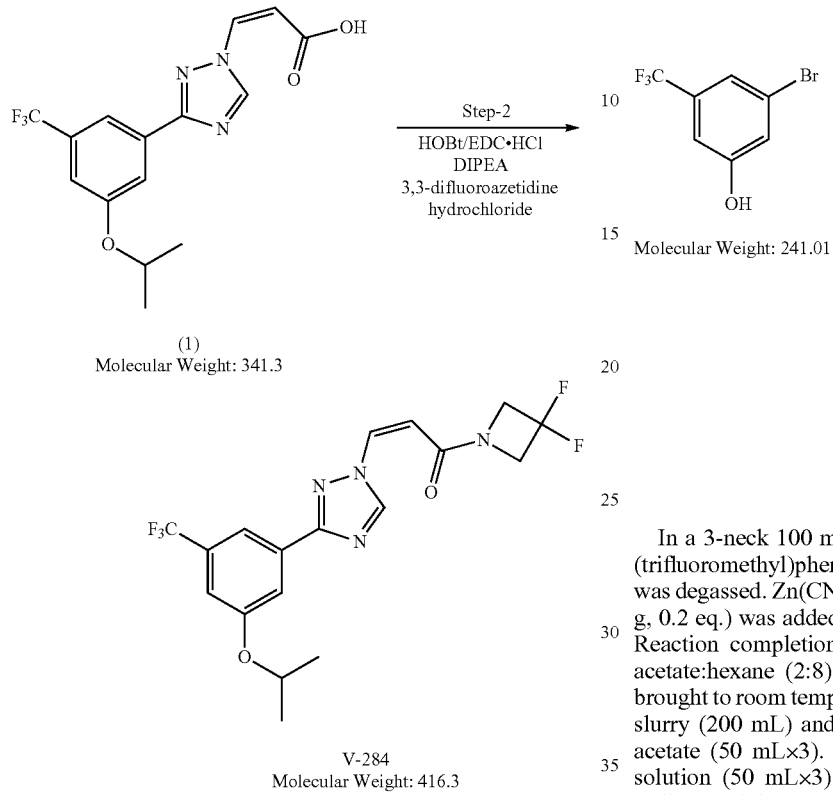

In a 3-neck 25 mL round-bottomed flask, intermediate 1 (0.145 g, 1.0 eq.) was dissolved in 10 mL of DCM at 0° C. under $N_2$ atmosphere, DIPEA (0.075 g, 1.2 eq.) was added followed by EDC.HCl (0.138 g, 1.5 eq.) and 3,3-difluoroazetidine hydrochloride (0.075 g, 1.2 eq.) and HOBt (0.087 g, 1.2 eq.). Reaction mixture was stirred at 0° C. for 3-4 h. The progress of reaction was followed by TLC analysis on silica gel with 10% methanol:DCM as mobile phase and visualization with UV, SM $R_f$=0.15 and Product $R_f$=0.40. Reaction was stirred for 3-4 h and yellow reaction mixture was evaporated on rotary evaporator under reduced pressure to afford 0.150 g of crude compound. The crude reaction mixture was purified by column chromatography using silica 60/120 using methanol:DCM as mobile phase. The column (2×10 cm) was packed in DCM and started eluting in methanol in gradient manner starting with fraction collection (25 mL fractions) from 1.5-2.5% methanol in DCM. Compound started eluting with 1.5% methanol in DCM. Fraction containing such TLC profile was collected together to obtain pure compound (0.010 g), Yield (5.6%). $^1$H NMR (400 MHz, CDCl$_3$) δ 9.57 (s, 1H), 7.97 (s, 1H), 7.83 (s, 1H), 7.22-7.25 (d, J=10.8 Hz, 1H), 7.20 (s, 1H), 5.61-5.63 (d, J=10.8 Hz, 1H), 4.68-4.74 (m, 1H), 4.45-4.57 (m, 4H), 1.30-1.32 (d, 6H): LCMS for $C_{18}H_{17}F_5N_4O_2$ 416.3 found 416.83 at 6.884 min (LCMS 96.82%).

Example 74

Example 74

Synthesis of Intermediate (1)

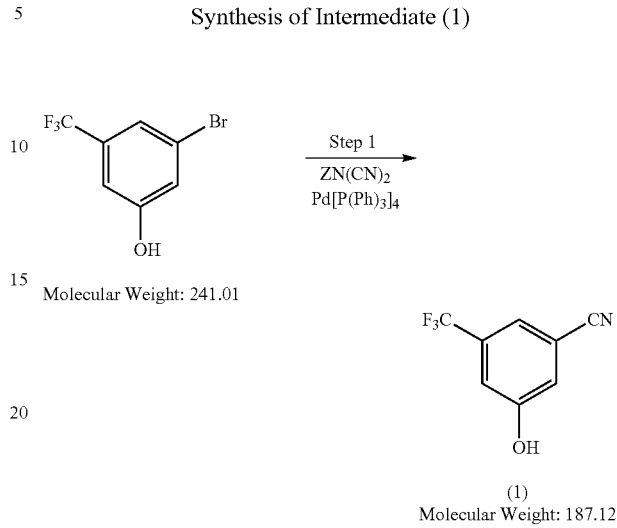

In a 3-neck 100 mL RBF, stirred solution of 3-bromo-5-(trifluoromethyl)phenol (2 g, 1 eq.) in DMF (25 mL, 25 Vol) was degassed. Zn(CN)$_2$ (0.68 g, 0.7 eq.) and Pd[P(Ph)$_3$]$_4$ (1.9 g, 0.2 eq.) was added in reaction and heat at 90° C. for 2 h. Reaction completion was monitored on TLC using ethyl acetate:hexane (2:8) mobile phase. Reaction mixture was brought to room temperature and quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 1.5 g of crude compound which was purified by column chromatography using ethyl acetate and Hexane as mobile phase. Product was eluted in 6% ethyl acetate in Hexane to afford 1.5 g of pure compound. Yield (96.7%). Mass: 187.9.

Synthesis of Intermediate (2)

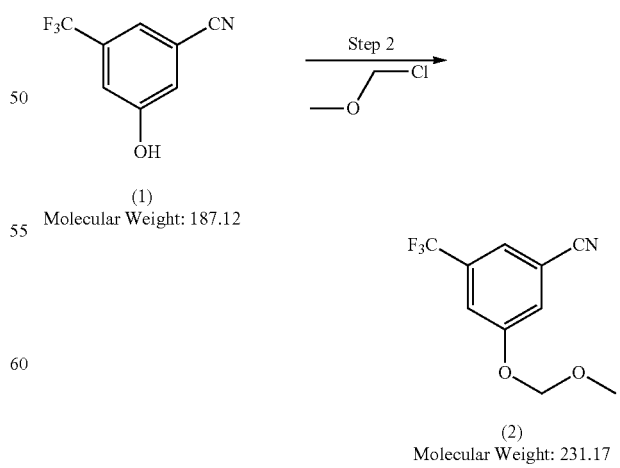

In a 3-neck 50 mL RBF, 3-hydroxy-5-(trifluoromethyl)benzonitrile (0.5 g, 1 eq.) was dissolved in THF (10 mL, 20

Vol). DIPEA (0.38 g, 1.1 eq.) and chloromethylmethylether (0.23 g, 1.1 eq.) was added dropwise at 0° C. and reaction mixture was stirred at room temperature for overnight. Reaction completion was monitored on TLC using ethyl acetate: hexane (2:8) as mobile phase. Reaction mixture was quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 0.5 g of crude compound. Mass: 231.4.

Synthesis of Intermediate (3)

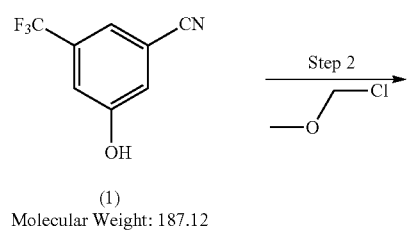

(1)
Molecular Weight: 187.12

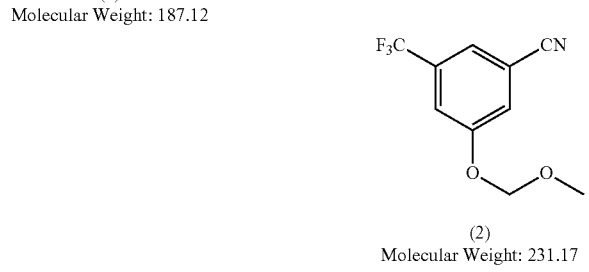

(2)
Molecular Weight: 231.17

In a 3-neck 50 mL RBF, 3-hydroxy-5-(trifluoromethyl)benzonitrile (0.5 g, 1 eq.) was dissolved in THF (10 mL, 20 Vol). DIPEA (0.38 g, 1.1 eq.) and chloromethylmethylether (0.23 g, 1.1 eq.) was added dropwise at 0° C. and reaction mixture was stirred at room temperature for overnight. Reaction completion was monitored on TLC using ethyl acetate: hexane (2:8) as mobile phase. Reaction mixture was quenched into the ice-water slurry (200 mL) and compound was extracted in the ethyl acetate (50 mL×3). Organic layer was washed with brine solution (50 mL×3) followed by drying using anhydrous sodium sulphate. Organic layer was concentrated under reduced pressure to afford 0.5 g of crude compound. Mass: 231.4. NMR: Confirmed.

Synthesis of Intermediate (4)

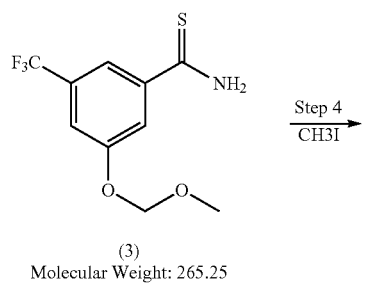

(3)
Molecular Weight: 265.25

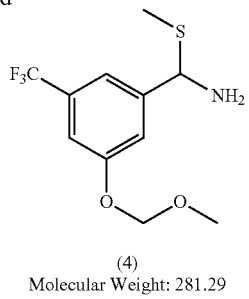

(4)
Molecular Weight: 281.29

In a 3-neck 50 mL RBF, 3-(methoxymethoxy)-5-(trifluoromethyl)benzothioamide (0.6 g, 1 eq.) was dissolved in diethyl ether (15 mL, 10 Vol) and methyl iodide (1.58 g, 5.0 eq.) was added dropwise in reaction mixture and reaction mixture was stirred at RT for overnight. Reaction completion was monitored on TLC using ethyl acetate: n-hexane (5:5) as mobile phase. Product was filtered and washed with diethyl ether (3×50 mL). Product was dried under reduced pressure to afford 0.6 g of crude compound. Mass: 281.41.

Synthesis of Intermediate (5)

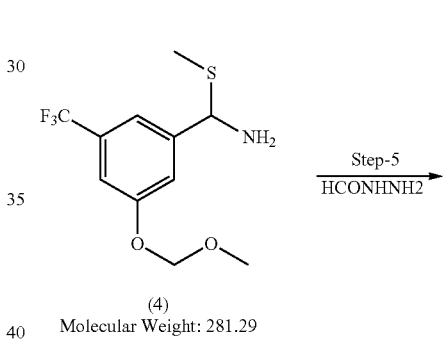

(4)
Molecular Weight: 281.29

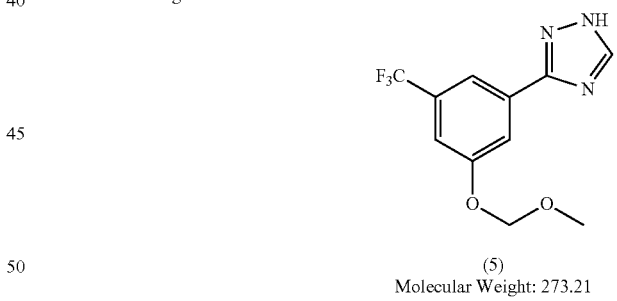

(5)
Molecular Weight: 273.21

In a 3-neck 100 mL RBF, (3-(methoxymethoxy)-5-(trifluoromethyl)phenyl)(methylthio)methanamine (0.6 g, 1 eq.) and Formic hydrazide (0.25 g, 2 eq) was dissolved in DMF (20 mL) and reaction mixture was stirred at reflux temperature for 2 h. Reaction completion was monitored on TLC using ethylacetate:n-hexane (5:5) as mobile phase. Reaction mixture was brought to room temperature and poured into the water (100 mL) and compound was extracted in the Ethyl acetate (100 mL×3). Organic layer was again washed with water (100 mL×3) followed by drying using anhydrous sodium sulphate. Organic layer was concentrated under reduced pressure to afford 0.9 g of crude compound which is purified by column to give 0.25 gm of pure Compound. Mass: 273.4.

Synthesis of Intermediate (6)

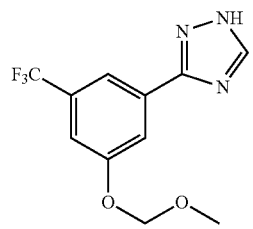

(5)
Molecular Weight: 273.21

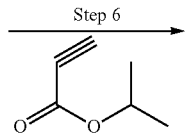 Step 6

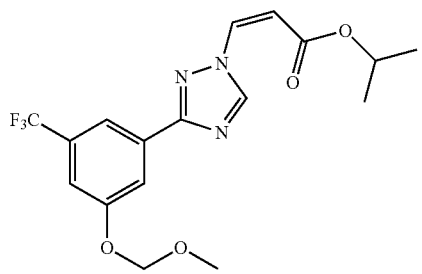

(6)
Molecular Weight: 385.34

In a 3-neck 50 mL RBF, 3-(3-(methoxymethoxy)-5-(trifluoromethyl)phenyl)-1H-1,2,4-triazole (0.25 g, 1 eq.) was dissolved in DCM (15 mL) and TEA (0.10 g, 1.1 eq) was added followed by isopropyl propiolate (0.13 g, 1.3 eq.). The reaction mixture was stirred at 15° C. for 30 min. Reaction completion was monitored on TLC using ethyl acetate:n-hexane (2:8) as mobile phase. Reaction mixture was concentrated under reduced pressure to afford 0.5 g of crude compound and the compound was purified by column chromatography using ethyl acetate and Hexane as mobile phase. Product was eluted in 4% ethyl acetate in Hexane to afford 0.05 g of pure compound Yield (8.0%). LCMS: 92%, NMR: Confirmed

Synthesis of (E)-isopropyl 3-(3-(1-((Z)-3-isopropoxy-3-oxoprop-1-enyl)-1H-1,2,4-triazol-3-yl)-5-(trifluoromethyl)phenoxy)acrylate

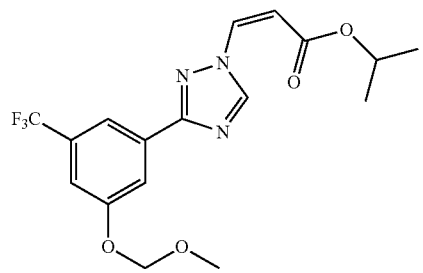

(6)
Molecular Weight: 385.34

Step 7
NaHSO4•SiO2

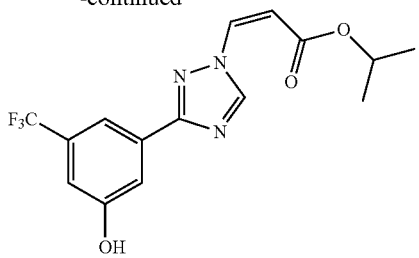

Molecular Weight: 341.29

In a 3-neck 50 mL RBF, (Z)-isopropyl 3-(3-(3-(methoxymethoxy)-5-(trifluoromethyl)phenyl)-1H-1,2,4-triazol-1-yl)acrylate (0.05 g, 1 eq.) was dissolved in DCM (5 mL) and activated NaHSO$_4$.SiO$_2$ (0.050 g) was added and reaction mixture was stirred at RT for 30 min. Reaction completion was monitored on TLC using ethyl acetate:hexane (3:7) mobile phase. Reaction mixture was filtered and concentrates under reduced pressure to afford 0.02 g of pure compound, Yield (45%). $^1$H NMR (400 MHz, CDCl$_3$): δ 10.5 (s, 1H, D$_2$O Exchangeable), 9.14 (s, 1H), 7.703-7.707 (d, 2H), 7.45-7.48 (d, J=10 Hz, 1H), 7.14 (s, 1H), 5.973-5.998 (d, J=10 Hz, 1H), 5.02-5.08 (m, 1H), δ 1.22-1.24 (s, 6H): LCMS for C$_{15}$H$_{14}$F$_3$N$_3$O$_3$ MW 341.3 found 341.8 at 3.812 min (LCMS 98.66%).

Example 75

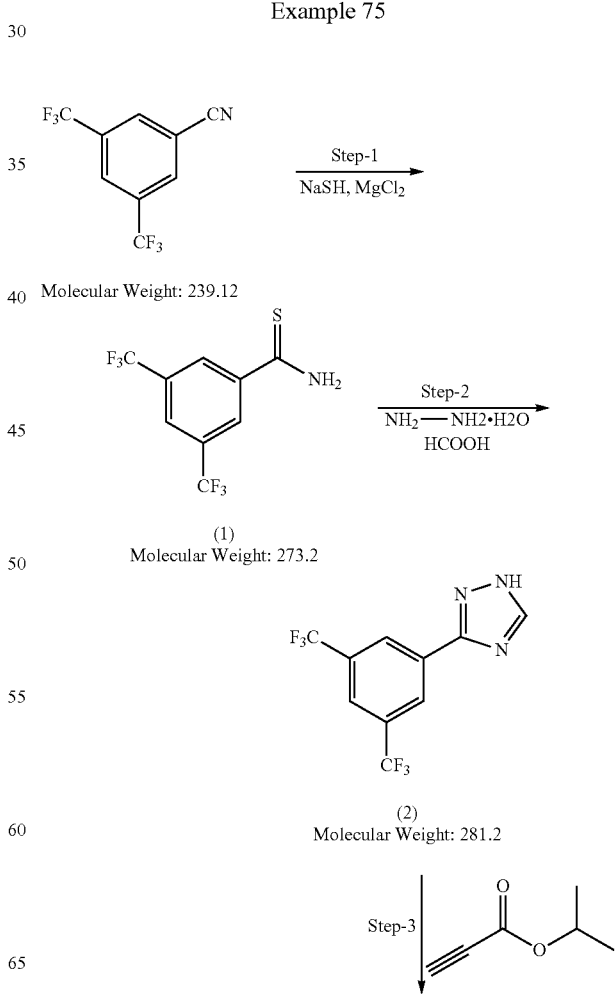

345

-continued

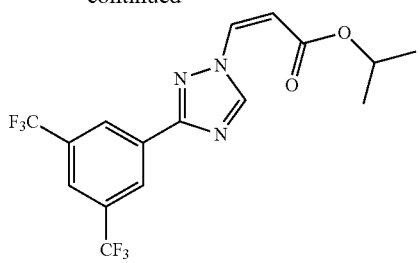

Molecular Weight: 393.3

Synthesis of Intermediate (1)

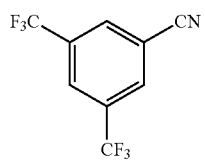

Molecular Weight: 239.12

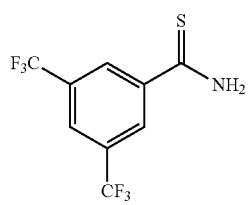

(1)
Molecular Weight: 273.2

In a 100-mL, 3N round-bottomed flask equipped with nitrogen inlet, and a rubber septum, 3,5-bis(trifluoromethyl) benzonitrile (5.0 g, 1.0 eq) dissolved in DMF (50 mL, 10V), Added NaSH (3.09 g, 2.0 eq) and MgCl2 (4.24 g, 1 eq). Reaction mixture was stirred at RT for 2-3 h. The progress of reaction was followed by TLC analysis on silica gel with 40% EtOAc-hexane as mobile phase. SM $R_f$=0.5 and Product $R_f$=0.3. Reaction mixture was poured in to ice water (250 mL) and extracted with EtOAc (3×100 mL). The combined organic layers were washed with brine solution (3×100 mL), dried over MgSO₄, filtered, and concentrated by rotary evaporation (25° C., 20 mmHg) to afford 5.0 g of Crude compound which was used for next step without any purification, Yield (87.5%). Mass [M+1]⁺: 273.8

346

Synthesis of Intermediate-2

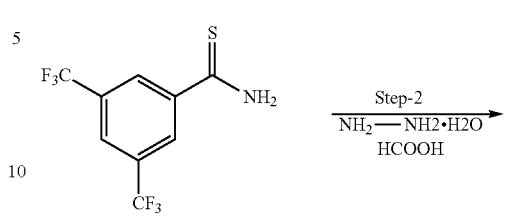

(1)
Molecular Weight: 273.20

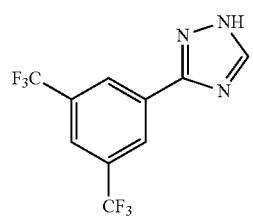

(2)
Molecular Weight: 281.16

In a 250-mL, 3N round-bottomed flask equipped with nitrogen inlet, and a rubber septum, Intermediate-1 (5.0 g, 1.0 eq.) was dissolved in DMF (50 mL, 10V), added NH₂NH₂.H₂O (25.0 mL, 5V). The reaction mixture was stirred at RT for 1 h. To this reaction mixture HCOOH (25.0 mL, 5V) was added and reaction mixture was refluxed at 90° for 2-3 h. The progress of reaction was followed by TLC analysis on silica gel with 50% Ethyl acetate-n-Hexane as mobile phase. SM $R_f$=0.50 and Product $R_f$=0.3. Reaction mixture was poured into ice water (500 mL) and neutralized with saturated sodium bicarbonate solution. The reaction mixture was extracted with EtOAc (3×100 mL). The combined organic layers were washed with brine solution, (3×100 mL), dried over MgSO₄, filtered, and concentrated by rotary evaporation (25° C., 20 mmHg) to afford 4.6 g of crude compound, yield (89.49%). Mass: 279.6 (-ve mode).

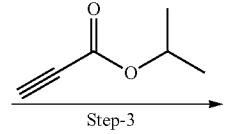

Molecular Weight: 281.2

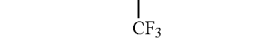
Step-3

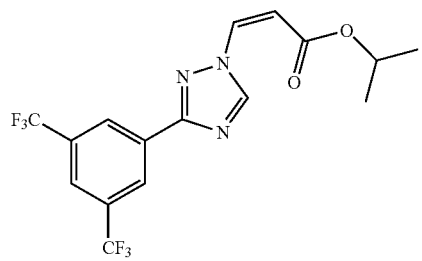

Molecular Weight: 393.3

In a 100-mL, 3N round-bottomed flask equipped with nitrogen inlet, and a rubber septum, Intermediate-2 (4.5 g, 1.0 eq.) was dissolved in DCM (45 mL, 10V), added TEA (2.10 g, 1.3 eq) and isopropyl propiolate (2.33 g, 1.3 eq). The Reaction mixture was stirred at RT for 30 min. The progress of reaction was followed by TLC analysis on silica gel with 50% Ethyl acetate-Hexane as mobile phase, SM $R_f$=0.30 and Product $R_f$=0.5. Reaction mixture was concentrated by rotary evaporation (25° C., 20 mmHg) to afford 5.8 g of Crude compound. The crude reaction mixture was purified by column chromatography using silica 60/120 using Ethyl acetate:Hexane as mobile phase. The column (5×10 cm) was packed in Hexane and started eluting in Ethyl acetate in gradient manner starting with fraction collection (50-mL fractions) from 5% to 20% Ethyl acetate in hexane. Compound started eluting with 20% Ethyl acetate in Hexane. Fraction containing such TLC profile was collected together to obtain pure compound (1.4 g), Yield (22.26%). $^1$H NMR: CDCl$_3$, 400 MHz) δ 9.74 (s, 1H), δ 8.63 (s, 2H), δ 7.95 (s, 1H), δ 7.28-7.31 (d, J: 12.0 Hz, 1H), 65.75-5.78 (d, J: 11.2 Hz, 1H) δ 5.14-5.17 (m, 1H), δ 1.27-1.35 (m, 6H). LCMS of $C_{16}H_{13}F_6N_3O_2$(M+1)$^+$: 393.28 found 393.77 at 4.707 min (LCMS 99.25%).

General method for Example 76, Example 77, Example 78, Example 79, Example 83

A mixture of 5-(3-Chlorophenyl)-1,2,4-triazole (0.50 g, 3.4 mmol), respective propiolate (0.52 ml, 5.1 mmol) and some drops of triethylamine in acetonitrile under nitrogen was stirred at room temperature for 12-16 h. Acetonitrile was removed under reduced pressure to give a residual oil, which was purified by flash chromatography (3-5% EtOAc/hexanes) to afford the both cis and trans isomers. Cis isomer was isolated 10-30% and trans was isolated in 30-50% with overall yield of 50-80%.

Example 76

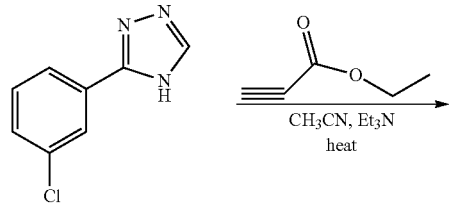

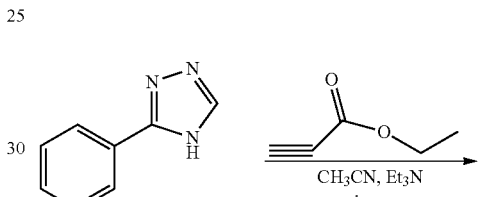

Cis-isomer: $^1$H NMR (CDCl$_3$, 300 MHz): 1.34 (2d, 6H), 5.15 (m, 1H), 5.72 (d, 1H), 7.21 (d, 1H), 7.42 (m, 2H), 8.0 (m, 1H), 8.19 (s, 1H), 9.72 (s, 1H). Mass (ESI): 291.90 (M+H).

Example 77

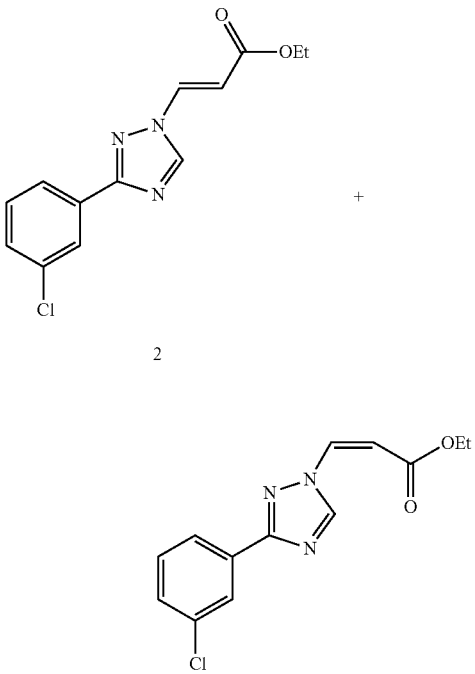

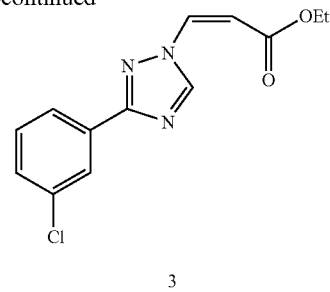

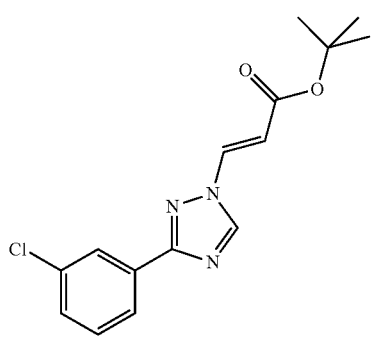 [SMILES: CC(C)(C)OC(=O)/C=C/n1cnc(-c2cccc(Cl)c2)n1]
Example 78
From Example 21 preparation: Cis-isomer: $^1$H NMR (CDCl$_3$, 300 MHz): 1.58 (s, 9H), 5.64 (d, 1H), 7.22 (d, 1H), 7.43 (m, 2H), 8.0 (m, 1H), 9.62 (s, 1H), 8.22 (s, 1H). Mass (ESI): 306.3 (M+H).
Trans-isomer: $^1$H NMR (CDCl$_3$, 300 MHz): 1.59 (s, 9H), 6.61 (d, 1H), 7.41 (m, 2H), 7.89 (d, 1H), 8.05 (d, 1H), 8.15 (s, 1H), 8.31 (s, 1H). Mass (ESI): 306.3 (M+H).
Example 79
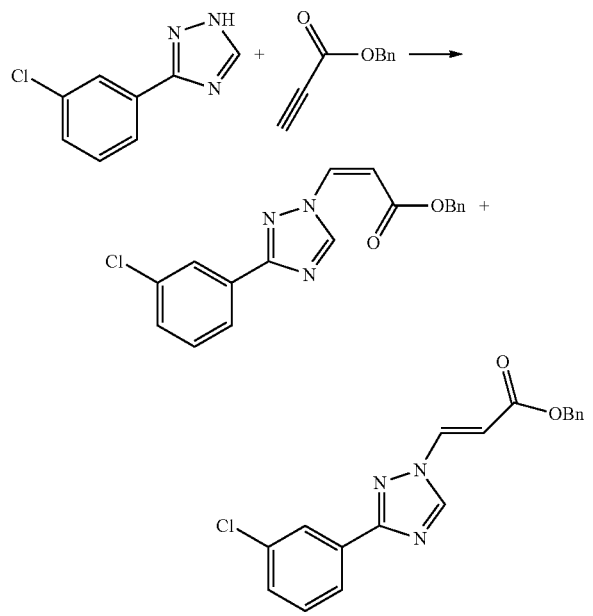
Cis-isomer: $^1$H NMR (CDCl$_3$, 300 MHz): 5.27 (s, 2H), 5.85 (d, 1H), 7.28-7.42 (m, 7H), 8.05 (m, 1H), 8.19 (s, 1H), 9.72 (s, 1H). Mass (ESI): 340.3 (M+H).
Example 80
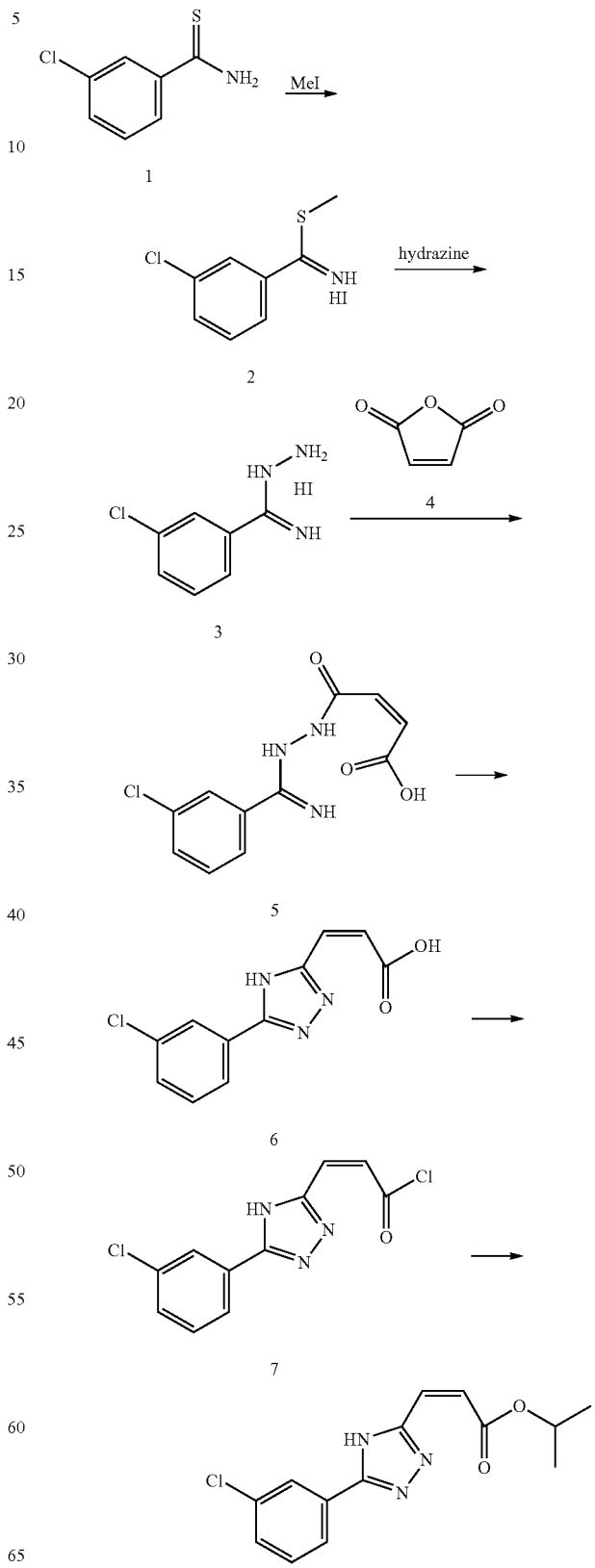

Step 1. Treatment of 1 (1.6 g) with MeI (871 uL) in acetone at 65 C for overnight. The reaction mixture was concentrated and the residue was added into CH3CN. The solid formed was filtrated to get the product 2.

Step 2. The 2 (1.2 g) was dissolved in the anhydrous MeOH and treated with NH2NH2 (123 mg). The reaction mixture was stirred at room temperature until the reaction went to completion. The reaction mixture was then concentrated and the residue was purified by prep-HPLC to get the pure product 3.

Step 3. Treatment of 3 (1.05 g) in DCM with 4 (346 mg) at room temperature with triethyl amine until the reaction went to completion afforded crude 5. The purified product 5 (706 mg) was obtained by prep-HPLC.

Step 4. To 5 (600 mg, 3.23 mmol) in HOAc (2 mL) was heated at 120 C for 10 min on MW. After the mixture was cooled to room temperature and concentrated, the residue was purified by prep-HPLC to give product 6 (520 mg).

Step 5. The mixture of 6 (125 mg) and SOCl2 (1 mL) in DCE (5 mL) was reflux until the reaction was completed. The mixture was cooled to room temperature and concentrated. The residue was added toluene and concentrated. The crude mixture of 7 was used for next step.

Step 6. Treatment of 7 in DCM (5 mL) in the presence of triethyl amine (100 uL) with isopropanol at room temperature for 3 h resulted in the formation of products with mass of [M+1]=292 monitored by LC-MS. The reaction mixture was concentrated and purified by prep-HPLC to give KPT-0132 (55 mg). LC-MS: [M+1]=292.

NMR (CDCl3) 8.14 (1H, S), 8.00-8.03 (1H, m), 7.37-7.39 (2H, m), 7.09 (1H, d, J=12.9 Hz), 6.24 (1H, d, J=12.9 Hz), 5.12-5.20 (1H, m), 1.35 (6H, d=6.1 Hz).

Example 83

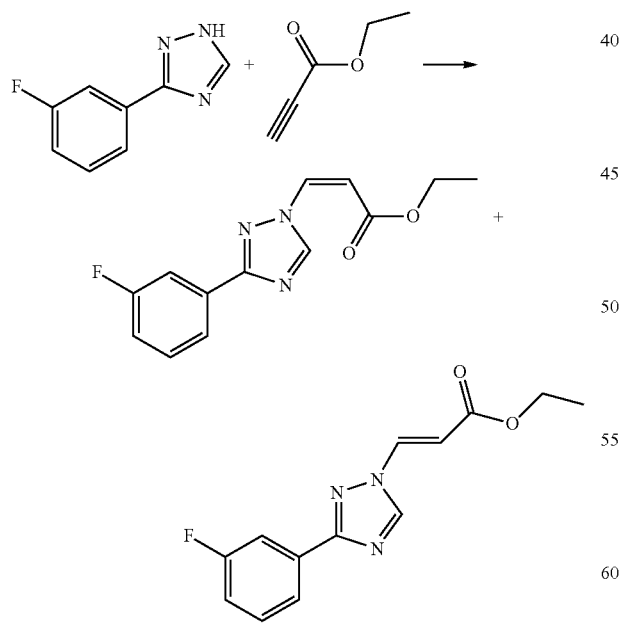

Cis-isomer: ¹H NMR (CDCl3, 300 MHz): 1.31 (t, 3H), 4.26 (q, 2H), 5.70 (d, 1H), 7.11 (m, 1H), 72.4 (d, 1H), 7.41 (m, 1H), 7.79 (d, 1H), 78.3 (d, 1H), 9.68 (s, 1H). Mass (ESI): 262.1 (M+H).

Trans-isomer: ¹H NMR (CDCl3, 300 MHz): 1.34 (t, 3H), 4.25 (q, 2H), 6.63 (d, 1H), 7.36 (s, 1H), 7.90 (d, 1H), 7.99 (s, 1H), 8.27 (s, 1H). Mass (ESI): 262.1 (M+H).

Example 84

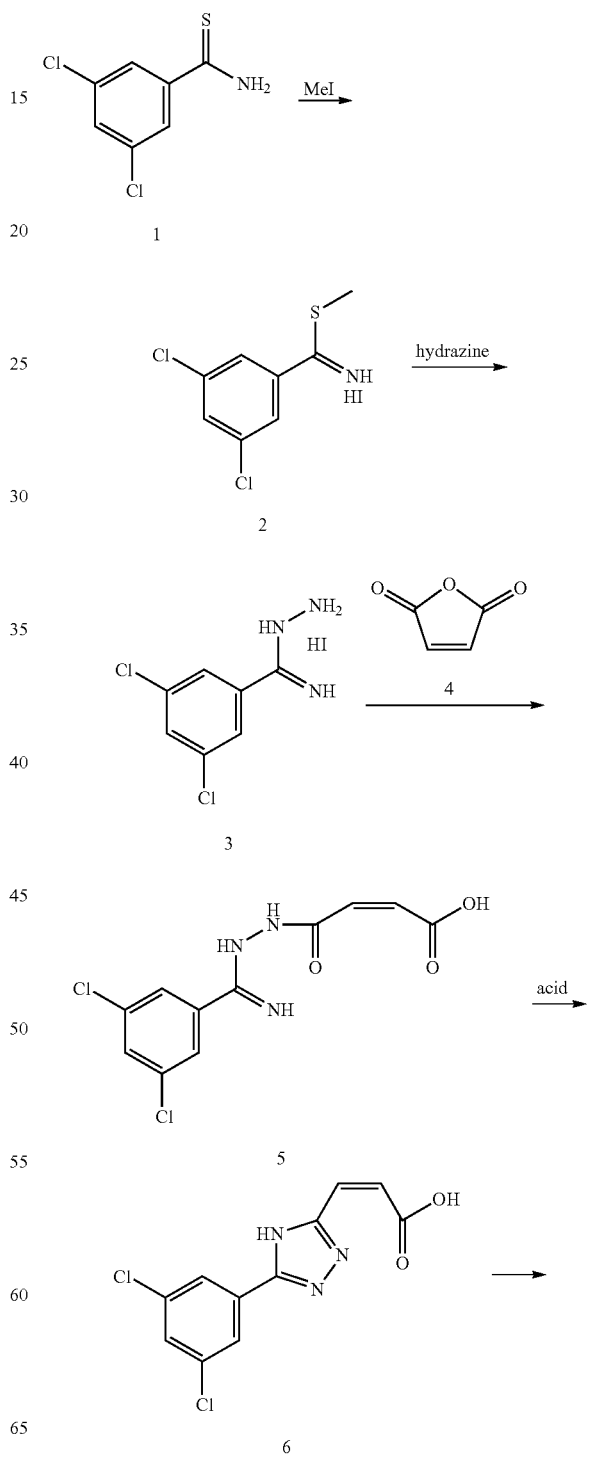

-continued

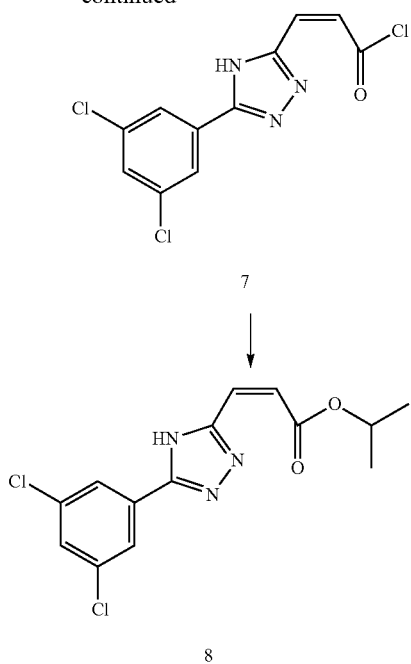

Step 1. Treatment of 1 (0.6 g) with MeI (871 uL) in acetone at 65 C for overnight. The reaction mixture was concentrated and the residue was added into CH3CN. The solid formed was filtrated to get the product 2.

Step 2. 2 (0.98 g) was dissolved in the anhydrous MeOH and treated with NH2NH2 (90 mg). The reaction mixture was stirred at room temperature until the reaction went to completion. The reaction mixture was then concentrated and the residue was purified by prep-HPLC to get the pure product 3.

Step 3. To a solution of 3 (664 mg) in DCM (30 mL) was added 4 (196 mg) and Et3N (545 uL) and stirred at room temperature for over night. The reaction mixture was concentrated and purified by prep-HPLC to give product 5 (798 mg).

Step 4. The compound 5 (798 mg) was treated with the acid with microwave at 150 C for 10 min. The reaction mixture was concentrated and purified by prep-HPLC to give product 6 (430 mg).

Step 5. The compound 6 (170 mg) was treated with the SOCl2 at 80 C for 30 min. The reaction mixture was concentrated to give crude product 7 used for next step without further purification.

Step 6. To a solution of 7 in DCM was added isopropanol (1 mL) and Et3N (167 uL) and stirred at room temperature for over night. The reaction mixture was concentrated and purified by prep-HPLC to give Example 84 (87 mg).). LC-MS: [M+1]=326. $^1$H NMR (DMSO) 7.92 (2H, S), 7.69 (1H, s), 6.88 (1H, d, J=11.4 Hz), 6.41 (1H, d, J=11.4 Hz), 4.98-5.06 (1H, m), 1.22 (6H, d=6.0 Hz).

Example 85

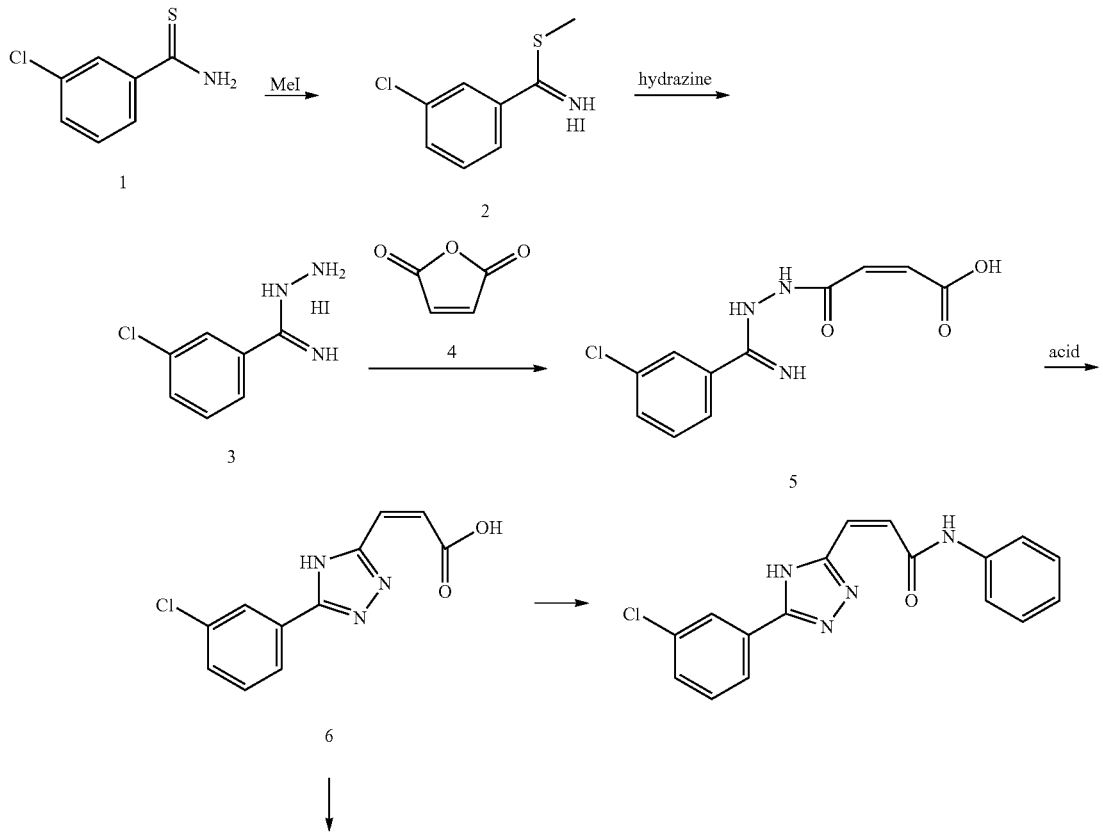

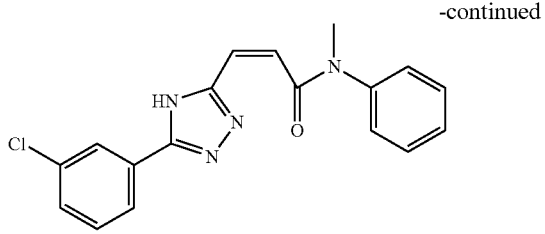

Step 1. Treatment of 1 (1.6 g) with MeI (871 uL) in acetone at 65 C for overnight. The reaction mixture was concentrated and the residue was added into CH3CN. The solid formed was filtrated to get the product 2.

Step 2. 2 (1.2 g) was dissolved in the anhydrous MeOH and treated with NH2NH2 (123 mg). The reaction mixture was stirred at room temperature until the reaction went to completion. The reaction mixture was then concentrated and the residue was purified by prep-HPLC to get the pure product 3.

Step 3. To a solution of 3 (200 mg) in DCM (10 mL) was added 4 (75 mg) and Et3N (217 uL) and stirred at room temperature for over night. The reaction mixture was concentrated and purified by prep-HPLC to give product 5 (198 mg).

Step 4. The compound 5 (198 mg) was treated with the acid with microwave at 150 C for 10 min. The reaction mixture was concentrated and purified by prep-HPLC to give product 6 (126 mg).

Step 5. The compound 6 (100 mg), HATU (264 mg), DIPEA (242 uL) was dissolved in DMF and then aniline (50 uL) was added. The reaction mixture was stirred at room temperature for 24 h. After reaction completion, the mixture was added H2O, extracted with DCM. The organic layer was fried over Na$_2$SO$_4$, concentrated. The residue was purified by prep-HPLC to give Example 85 (64 mg). LC-MS: [M+1]=325. $^1$H NMR (CDCl3+DMSO) 10.28 (1H, s), 7.93-8.06 (3H, m), 7.63 (1H, d, J=8.1 Hz), 7.21-7.32 (4H, m), 7.08 (1H, d, J=7.2 Hz), 6.86 (1H, d, J=13.2 Hz), 6.41 (1H, m).

Example 86

The compound 5 (100 mg), HATU (264 mg), DIPEA (242 uL) was dissolved in DMF and then N-methylaniline (60 uL) was added. The reaction mixture was stirred at room temperature for 24 h. After reaction completion, the mixture was added H2O, extracted with DCM. The organic layer was fried over Na$_2$SO$_4$, concentrated. The residue was purified by prep-HPLC to give Example 86 (68 mg). LC-MS: [M+1]=339. $^1$H NMR (CDCl$_3$) 8.00-8.14 (2H, m), 7.17-7.50 (7H, d, J=8.1 Hz), 6.77 (1H, d, J=12.9 Hz), 6.10 (1H, d, J=12.9 Hz), 3.41 (3H, s).

Example 87

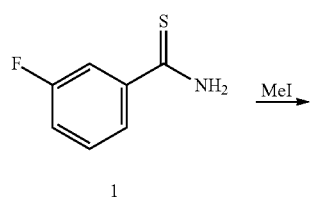

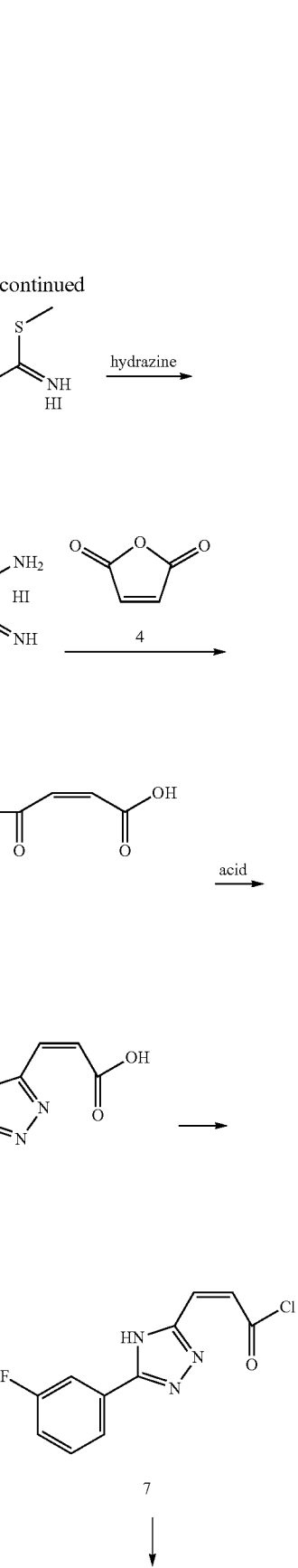

-continued

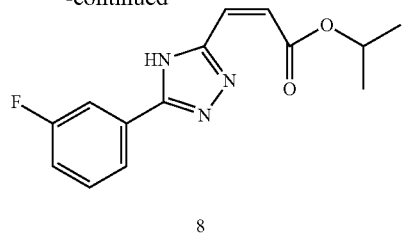

Step 1. Treatment of 1 (1.5 g) with MeI (900 uL) in acetone at 65 C for overnight. The reaction mixture was concentrated and the residue was added into CH3CN. The solid formed was filtrated to get the product 2.

Step 2. 2 (1 g) was dissolved in the anhydrous MeOH and treated with NH2NH2 (107 mg). The reaction mixture was stirred at room temperature until the reaction went to completion. The reaction mixture was then concentrated and the residue was purified by prep-HPLC to get the pure product 3.

Step 3. To a solution of 3 (843 mg) in DCM (30 mL) was added 4 (294 mg) and Et3N (817 uL) and stirred at room temperature for over night. The reaction mixture was concentrated and purified by prep-HPLC to give product 5 (1034 mg).

Step 4. The compound 5 (1034 mg) was treated with the acid with microwave at 150 C for 10 min. The reaction mixture was concentrated and purified by prep-HPLC to give product 6 (600 mg).

Step 5. The compound 6 (233 mg) was treated with the SOCl2 at 80 C for 30 min. The reaction mixture was concentrated to give crude product 7 used for next step without further purification.

Step 6. To a solution of 7 in DCM was added isopropanol (1 mL) and Et3N (408 uL) and stirred at room temperature for over night. The reaction mixture was concentrated and purified by prep-HPLC to give Example 87 (70 mg).). LC-MS: [M+1]=276. $^1$H NMR (CDCl$_3$) 7.92 (1H, d, J=7.8 Hz), 7.84 (1H, d, J=9.9 Hz), 7.38-7.45 (1H, m), 7.07-7.12 (2H, m), 7.25 (1H, d, J=12.6 Hz), 5.14-5.20 (1H, m), 1.38 (6H, d=6.1 Hz).

Example 88

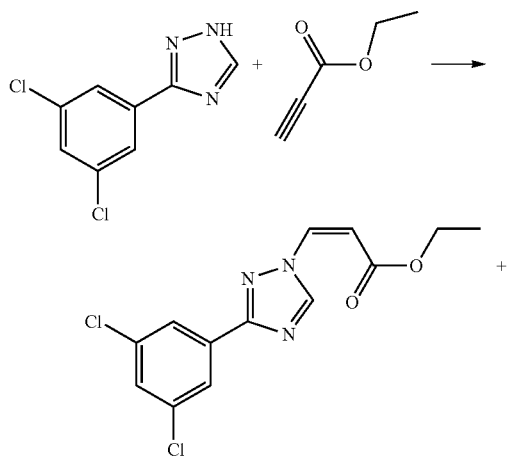

-continued

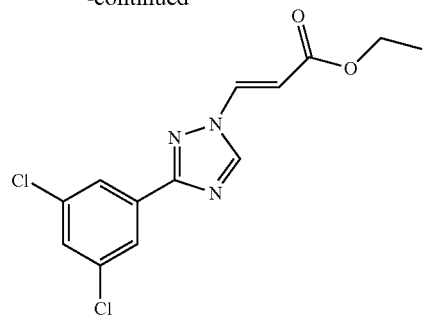

Following same procedure as Example 84. Cis-isomer: $^1$H NMR (CDCl$_3$, 300 MHz): 1.31 (t, 3H), 4.26 (q, 2H), 5.73 (d, 1H), 7.24 (m, 3H), 7.38 (s, 1H), 8.01 (s, 1H), 9.66 (s, 1H). Mass (ESI): 312.1 (M+H).

Trans-isomer: $^1$H NMR (CDCl$_3$, 300 MHz): 1.34 (t, 3H), 4.25 (q, 2H), 6.63 (d, 1H), 7.24 (m, 3H), 7.38 (s, 1H), 7.99 (s, 1H), 8.27 (s, 1H). Mass (ESI): 312.1 (M+H).

Example 89

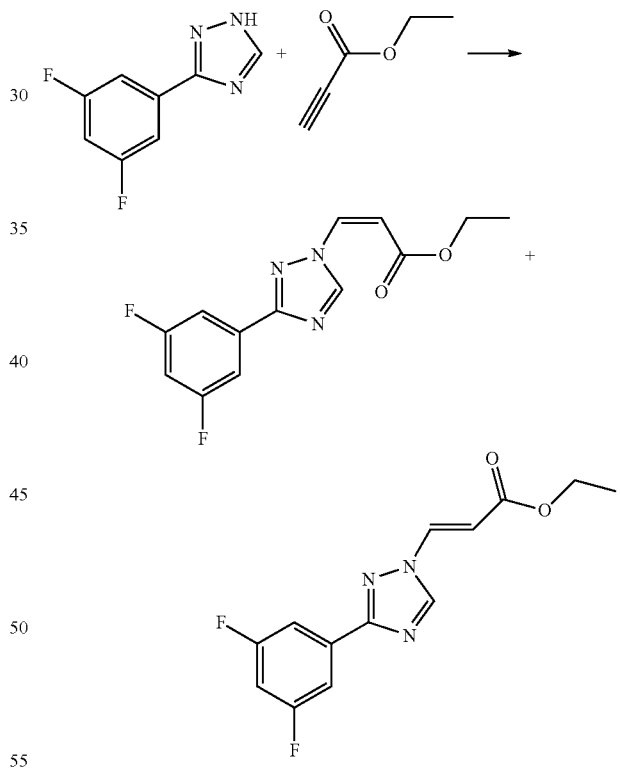

Following same procedure as Example 84. Cis-isomer: $^1$H NMR (CDCl$_3$, 300 MHz): 1.34 (t, 3H), 4.29 (q, 2H), 5.72 (d, 1H), 6.85 (m, 1H), 7.24 (m, 2H), 7.63 (m, 2H), 9.67 (s, 1H). Mass (ESI): 280.3 (M+H).

Trans-isomer: $^1$H NMR (CDCl$_3$, 300 MHz): 1.34 (t, 3H), 4.25 (q, 2H), 6.63 (d, 1H), 6.85 (m, 1H), 7.63 (m, 2H), 7.91 (d, 1H), 8.27 (s, 1H). Mass (ESI): 280.3 (M+H).

Inhibition of Nuclear Export

The inhibition of Crm1 induced nuclear export of compounds of the invention were determined and are shown in Table 1. The evaluation of the affinity of compounds for the Crm1 protein was determined in the RevGFP assay. Compounds of the invention are active in Rev-GFP assay with IC50 less than <10 μM with the most preferred compounds having activities less than an IC50 of 1 μM.

Experimental protocol: Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/Crm1 pathway (Neville et al, 1997). Nuclear accumulation of Rev can be observed in cells treated with specific inhibitors of Crm1, such as LMB (Kau et al, 2003). In this assay, U2OS-RevGFP cells are seeded onto clear-bottom, black, 384-well plates the day before the experiment. Compounds are serially diluted 1:2 starting from 40 μM in a separate 384-well plate in DMEM, and then transferred onto cells. Cells are incubated with compound for ~1 hr before fixation with 3.7% formaldehyde and nuclei staining with Hoechst 33258. The amount of GFP in cell nuclei will be measured and compound IC50s determined (Kau et al, 2003).

MTT Cell Proliferation Assay

The MTT cell proliferation assay was used to study the cytotoxic properties of the compounds. The assay was performed according to the method described by Roche Molecular Biochemicals with minor modifications. The assay is based on the cleavage of the tetrazolium salt, MTT, in the presence of an electron-coupling reagent. The water-insoluble formazan salt produced must be solubilized in an additional step. Cells, grown in a 96-well tissue culture plate, are incubated with the MTT solution for approximately 4 hours. After this incubation period, a water-insoluble formazan dye is formed. After solubilization, the formazan dye is quantitated using a scanning multi-well spectrophotometer (ELISA reader). The absorbance revealed directly correlates to the cell number. The cells were seeded at $1.5 \times 10^4$ cells in each well of 96-well plate in 200 μL of fresh culture medium and were allowed to attach for overnight. The stock solutions of the compounds were diluted in cell culture medium to obtain eight concentrations of each drug, ranging from 1 nM to 20 μM. After 72 h of treatment the medium was aspirated and the cells were washed once with sterile 1×PBS. Each plate contained the samples, negative control and blank. The DMSO at less than 1% v/v was used as a negative control. In most cases the assay was performed in triplicates and the results were presented as a mean percent inhibition to the negative control±SE. The following formula was used to calculate the percent of inhibition: Inhibition (%)=(1−(ODo/OD))×100.

Tumor cells were assayed for viability in the absence or presence of drug/control treatments, and drug combination dose response studies were analyzed graphically by correlating the fraction of surviving cells with drug concentrations for each drug.r Combinations studies with doxorubicin. Human myeloma cell lines (H929) grown at 2×10^6 cells/mL (high density) were incubated with and without Example 1 for 16 h followed by doxorubicin (2 umol/L; Sigma) for 4 h and assayed for apoptosis by anti-caspase-3 assay (BD Pharmingen). The results of this assay are set forth in FIG. 1.

Cytotoxicity Assay (CellTiter 96® AQueous One Solution Cell Proliferation Assay)

Cells were seeded into 96-well plates and compounds at the indicated concentrations were added to the cells after overnight incubation. Seventy two hrs later the proliferation assay was done in the following way: Twenty microliters of CellTiter 96® AQueous One Solution Reagent was added into each well. After 1 hour at 37° C. in a humidified, 5% CO2 atmosphere, the absorbance at 490 nm was recorded using an ELISA plate reader.

Test compound was assayed in numerous cancer cell lines using the above assay protocol. Results are depicted in FIG. 3.

BIBLIOGRAPHY

1. Cronshaw J M and Matunis M J. 2004. The nuclear pore complex: disease associations and functional correlations TRENDS Endocrin Metab. 15:34-39
2. Falini B et al. 2006. Both carboxy-terminus NES motif and mutated tryptophan(s) are crucial for aberrant nuclear export of nucleophosmin leukemic mutants in NPMc+ AML Blood. 107:4514-4523
3. Cai X and Liu X. 2008. Inhibition of Thr-55 phosphorylation restores p53 nuclear localization and sensitizes cancer cells to DNA damage. PNAS. 105:16958-16963.
4. Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517
5. Davis J R et al. 2007. Controlling protein compartmentalization to overcome disease Pharmaceut Res. 24:17-27
6. Freundt E, Yu L, Park E, et al 2009 Molecular determinants for subcellular localization of the severe acute respiratory syndrome coronavirus open reading frame 3b protein. J Virol 83(13):6631-40
7. Ghildyal R, Ho A, Dias M, et al 2009 The respiratory syncytial virus matrix protein possesses a Crm1-mediated nuclear export mechanism. J Virol 83(11):5353-62
8. Ghosh C C et al 2008 Analysis of nucleocytoplasmic shuttling of NF kappa B proteins in human leukocytes. Methods Mol. Biol. 457:279-92.
9. Gupta N et al 2008 Retinal tau pathology in human glaucomas Can J Ophthalmol. 2008 February; 43(1):53-60
10. HoshinoL et al. 2008. Combined effects of p53 gene therapy and leptomycin B in human esophageal squamous cell carcinoma. Oncology. 75:113-119.
11. Lain S et al. 1999a An inhibitor of nuclear export activates the p53 response and induces the localization of HDM2 and p53 to U1A-positive nuclear bodies associated with the PODs Exp Cell Res. 248:457-472.
12. Lain S et al. 1999b. Accumulating active p53 in the nucleus by inhibition of nuclear export: a novel strategy to promote the p53 tumor suppressor function Exp Cell Res. 253:315.
13. Muller P A et al. 2009 Nuclear-cytosolic transport of COMMD1 regulates NF-kappaB and HIF-1 activity. Traffic on-line publication
14. Mutka S 2007 Nuclear Export Inhibitors (NEIs) as novel cancer therapies AACR Annual Meeting. Poster 5609.
15. Mutka S, Yang W, Dong S, et al. 2009. Identification of nuclear export inhibitors with potent anticancer activity in vivo. Cancer Res. 69: 510-7.

16. Nakahara J et al. 2009. Abnormal expression of TIP30 and arrested nucleocytoplasmic transport within oligodendrocyte precursor cells in multiple sclerosis J Clin Invest. 119:169-181
17. Noske A et al. 2008. Expression of the nuclear export protein chromosomal region maintenance/exportin 1/Xpo1 is a prognostic factor in human ovarian cancer
18. Cancer. 112:1733-1743
19. Pollard V & Malim M. 1998 The HIV-1 Rev protein 52:491-532.
20. Rawlinson S, Pryor M, Wright P, Jans D 2009 CRM1-mediated nuclear export of dengue virus RNA polymerase NS5 modulates interleukin-8 induction and virus production J Biol Chem 284(23):15589-97
21. Sanchez V, Mahr J, Orazio N, et al 2007 Nuclear export of the human cytomegalovirus tegument protein pp 65 requires cyclin-dependent kinase activity and the Crm1 exporter J Virol 81(21):11730-6.
22. Sorokin A V et al. 2007. Nucleocytoplasmic transport of proteins Biochemistry. 72:1439-1457.
23. Terry U et al. 2007. Crossing the nuclear envelope: hierarchical regulation of nucleocytoplasmic transport Science. 318:1412-1416
24. Van der Watt P J et al. 2008. The Karyopherin proteins, Crm1 and Karyopherin beta1, are overexpressed in cervical cancer and are critical for cancer cell survival and proliferation Int J Canc. 124:1829-1840
25. Walsh M D et al. 2008 Exportin 1 inhibition attenuates nuclear factor-kappaB-dependent gene expression. Shock 29:160-166
26. Williams P, Verhagen J, Elliott G 2008 Characterization of a CRM1-dependent nuclear export signal in the C terminus of herpes simplex virus type 1 tegument protein UL47 J Virol 82(21):10946-52.
27. Yang W 2007 Anti-tumor activity of novel nuclear export inhibitors (NEIs) in multiple murine leukemia models AACR Annual Meeting. Poster 5597.
28. Yao Y et al. 2009. The expression of CRM1 is associated with prognosis in human osteosarcoma Oncol Rep. 21:229-35.
29. Zimmerman T L et al 2006 Nuclear export of retinoid X receptor alpha in response to interleukin-1beta-mediated cell signaling: roles for JNK and SER260J Biol Chem 281:15434-15440

We claim:

1. A compound of formula III':

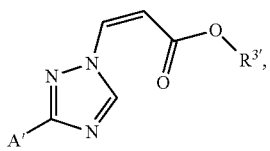

or a pharmaceutically acceptable salt thereof, wherein:
A' is phenyl substituted with one or more $R^{1''}$;
each $R^{1''}$ is independently selected from the group consisting of halogen, —$NO_2$, —CN, —$OR^a$, —$SR^a$, —$N(R^a)_2$, —$N_3$, or -$L^1$-R;
each $R^a$ is independently —H, —R or —C(O)R;
$L^1$ is a covalent bond or an optionally substituted bivalent $C_{1-6}$ hydrocarbon chain, wherein one or more methylene units of $L^1$ is optionally and independently replaced by —Cy—, —O—, —S—, —$N(R^a)$—, —C(O)—, —C(S)—, —C(O)N($R^a$)—, —N($R^a$)C(O)N($R^a$)—, —N($R^a$)C(O)—, —N($R^a$)C(O)O—, —OC(O)N($R^a$)—, —S(O)—, —$S(O)_2$—, —$S(O)_2$N($R^a$)—, —N($R^a$)$S(O)_2$—, —OC(O)—, or —C(O)O—;

—Cy— is an optionally substituted bivalent ring selected from a 3-7 membered saturated or partially unsaturated cycloalkylene ring, a 4-7 membered saturated or partially unsaturated heterocycloalkylene ring having 1-4 heteroatoms independently selected from nitrogen, oxygen and sulfur, phenylene, a 5-6 membered monocyclic heteroarylene having 1-3 heteroatoms independently selected from nitrogen, oxygen and sulfur, an 8-10 membered bicyclic arylene, or an 8-10 membered bicyclic heteroarylene having 1-4 heteroatoms independently selected from nitrogen, oxygen and sulfur;

each R is independently optionally substituted $C_{1-8}$ alkyl; $C_{2-8}$ alkenyl; $C_{2-8}$ alkynyl; haloalkyl; phenyl; a 3-7 membered saturated or partially unsaturated cycloalkyl ring; an 8-10 membered bicyclic saturated, partially unsaturated or aryl carbocyclic ring; a 4-7 membered saturated or partially unsaturated heterocycloalkyl ring having 1-4 heteroatoms independently selected from nitrogen, oxygen, and sulfur; a 5-6 membered monocyclic heteroaryl ring having 1-3 heteroatoms independently selected from nitrogen, oxygen, and sulfur; or an 8-10 membered bicyclic heteroaryl ring having 1-4 heteroatoms independently selected from nitrogen, oxygen, and sulfur; or:

two R on the same nitrogen are taken together with their intervening atoms to form a 4-7 membered heterocyclic ring having 1-2 heteroatoms independently selected from nitrogen, oxygen and sulfur; and $R^{3'}$ is -$L^1$-R, wherein $L^1$ is —$CH_2$— and R is a 5-6 membered monocyclic heterocyclic ring having 1-3 heteroatoms independently selected from nitrogen, oxygen and sulfur.

2. The compound according to claim 1, wherein $R^{3'}$ is wherein $L^1$ is —$CH_2$— and R is a 6-membered monocyclic heterocyclic ring having 1-3 nitrogens.

3. The compound according to claim 1, selected from the group consisting of:

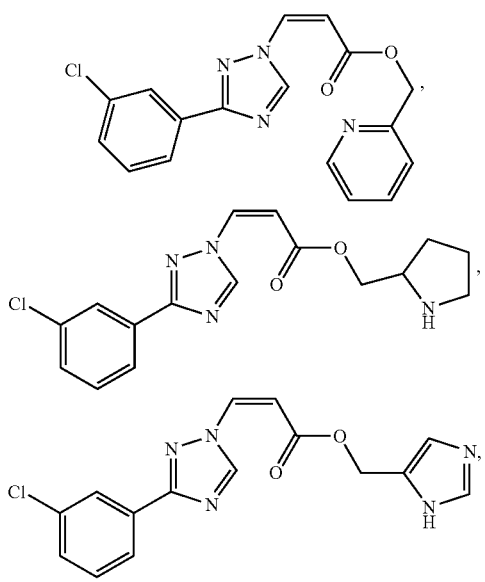

-continued

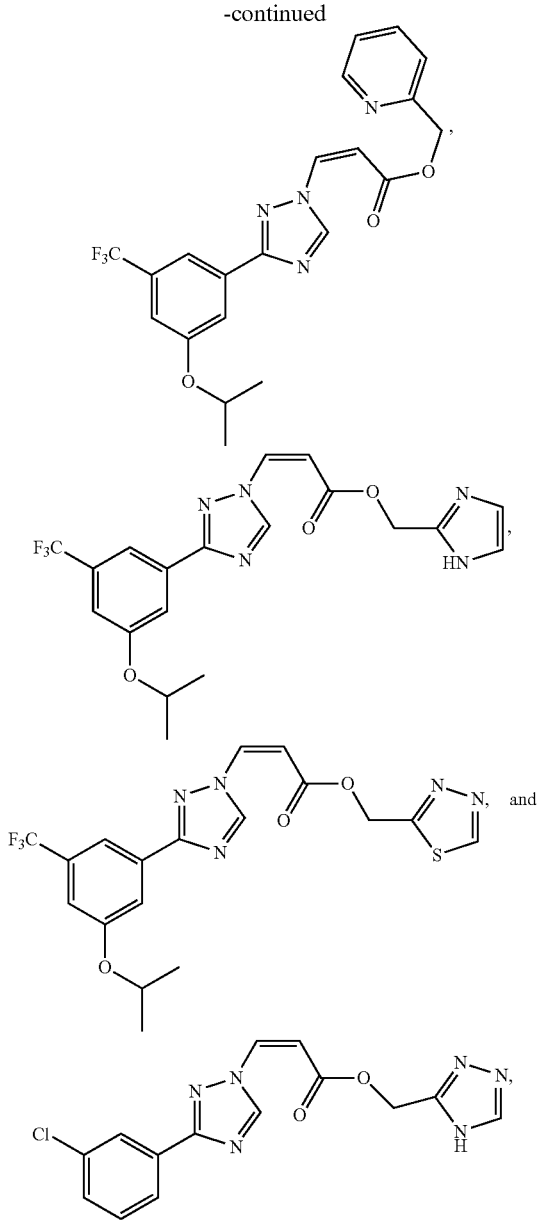

or a pharmaceutically acceptable salt thereof.

4. A compound of formula III':

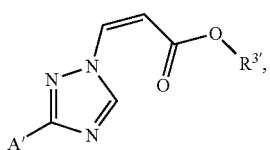

or a pharmaceutically acceptable salt thereof, wherein:

A' is phenyl substituted with one or more R$^{1'}$;

each R$^{1'}$ is independently selected from the group consisting of halogen, —NO$_2$, —CN, —OR$^a$, —SR$^a$, —N(R$^a$)$_2$, —N$_3$, or -L$^1$-R;

each R$^a$ is independently —H, —R or —C(O)R;

L$^1$ is a covalent bond or an optionally substituted bivalent C$_{1-6}$ hydrocarbon chain, wherein one or more methylene units of L$^1$ is optionally and independently replaced by —Cy—, —O—, —S—, —N(R$^a$)—, —C(O)—, —C(S)—, —C(O)N(R$^a$)—, —N(R$^a$)C(O)N(R$^a$)—, —N(R$^a$)C(O)—, —N(R$^a$)C(O)O—, —OC(O)N(R$^a$)—, —S(O)—, —S(O)$_2$—, —S(O)$_2$N(R$^a$)—, —N(R$^a$)S(O)$_2$—, —OC(O)—, or —C(O)O—;

—Cy— is an optionally substituted bivalent ring selected from a 3-7 membered saturated or partially unsaturated cycloalkylene ring, a 4-7 membered saturated or partially unsaturated heterocycloalkylene ring having 1-4 heteroatoms independently selected from nitrogen, oxygen and sulfur, phenylene, a 5-6 membered monocyclic heteroarylene having 1-3 heteroatoms independently selected from nitrogen, oxygen and sulfur, an 8-10 membered bicyclic arylene, or an 8-10 membered bicyclic heteroarylene having 1-4 heteroatoms independently selected from nitrogen, oxygen and sulfur;

each R is independently optionally substituted C$_{1-8}$ alkyl; C$_{2-8}$ alkenyl; C$_{2-8}$ alkynyl; haloalkyl; phenyl; 3-7 membered saturated or partially unsaturated cycloalkyl ring; 8-10 membered bicyclic saturated, partially unsaturated or aryl carbocyclic ring; 4-7 membered saturated or partially unsaturated heterocycloalkyl ring having 1-4 heteroatoms independently selected from nitrogen, oxygen, and sulfur; 5-6 membered monocyclic heteroaryl ring having 1-3 heteroatoms independently selected from nitrogen, oxygen, and sulfur; or 8-10 membered bicyclic heteroaryl ring having 1-4 heteroatoms independently selected from nitrogen, oxygen, and sulfur; or:

two R on the same nitrogen are taken together with their intervening atoms to form a 4-7 membered heterocyclic ring having 1-2 heteroatoms independently selected from nitrogen, oxygen and sulfur; and R$^{3'}$ is —CH(CH$_3$)$_2$.

5. The compound according to claim 4, selected from the group consisting of:

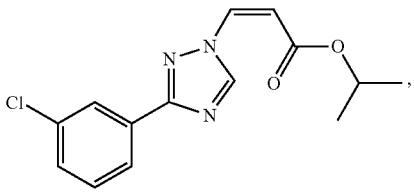

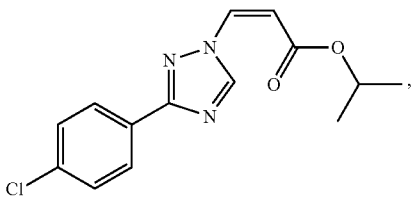

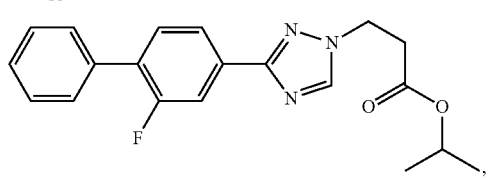

365
-continued
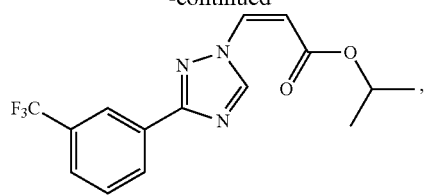
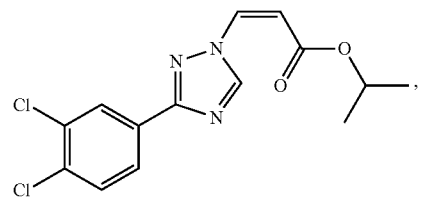
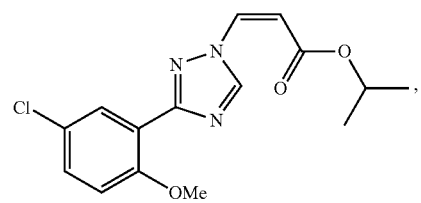
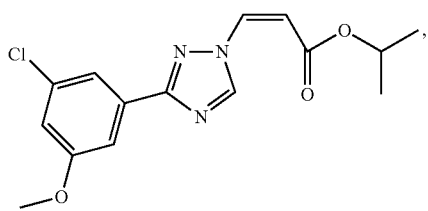
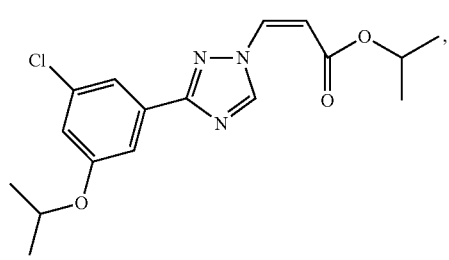
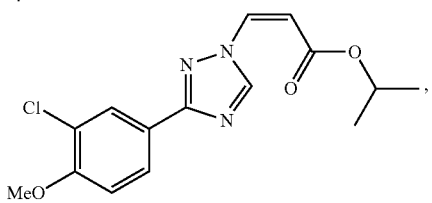
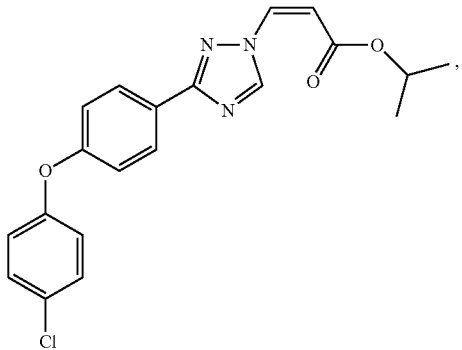
366
-continued
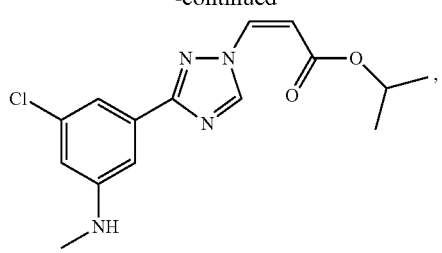
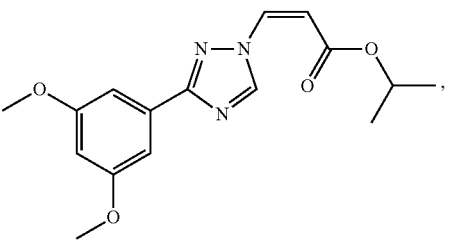
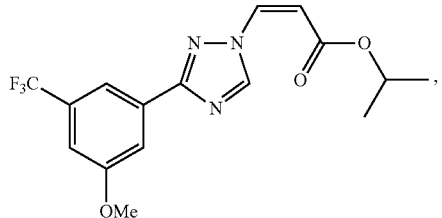
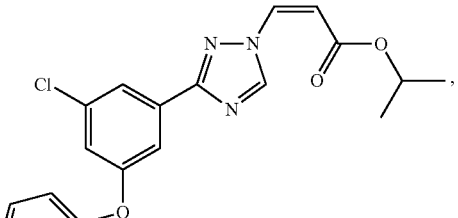
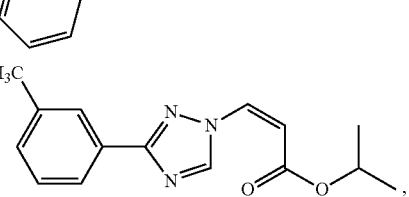
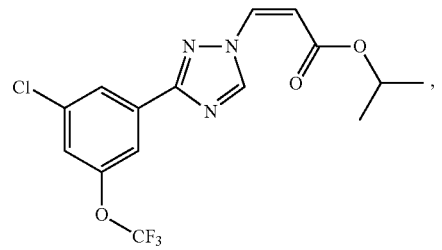
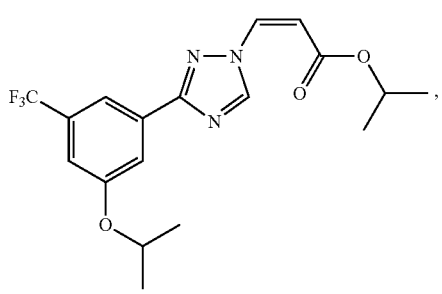

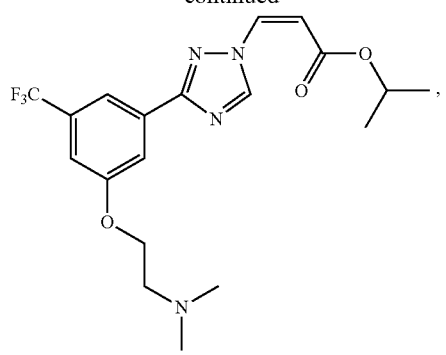
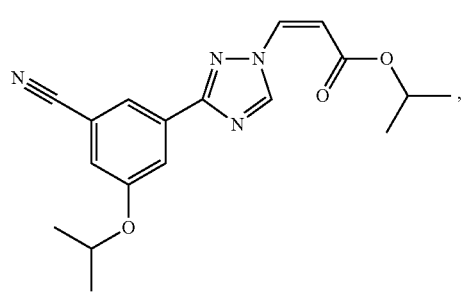
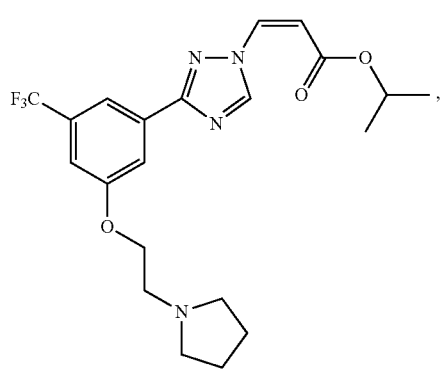
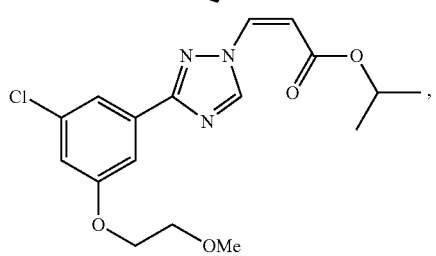
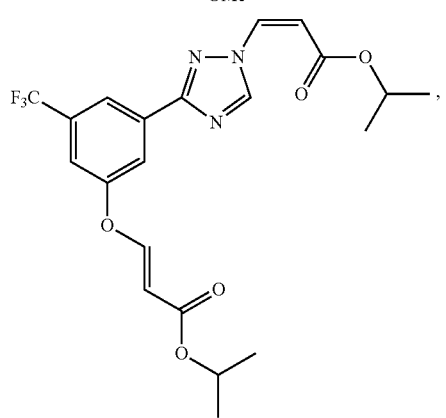
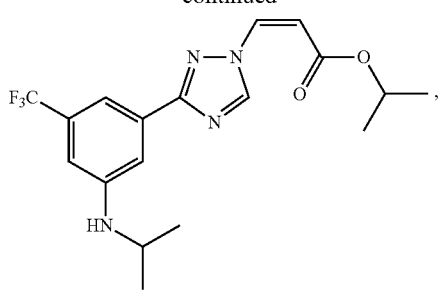
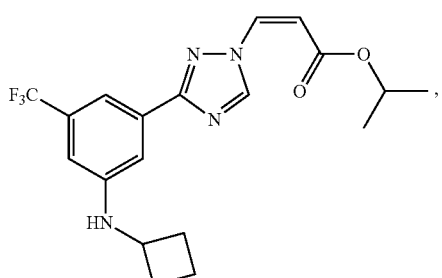
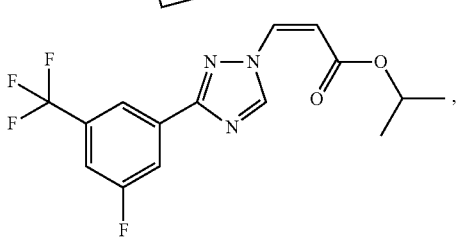
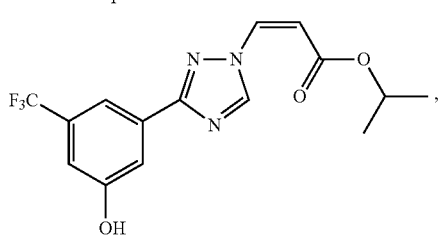
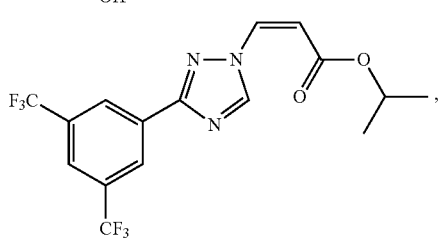
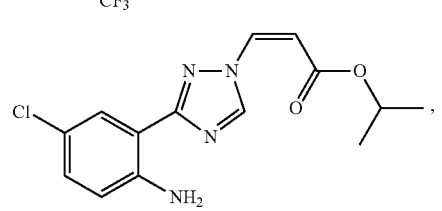
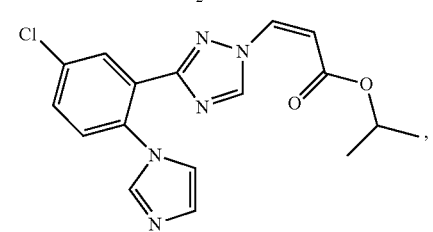

-continued
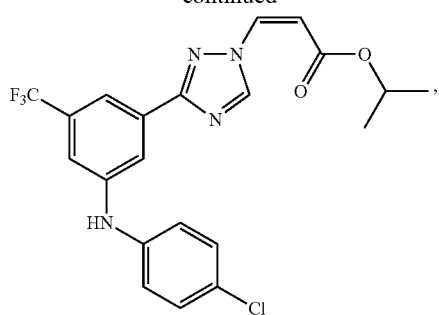
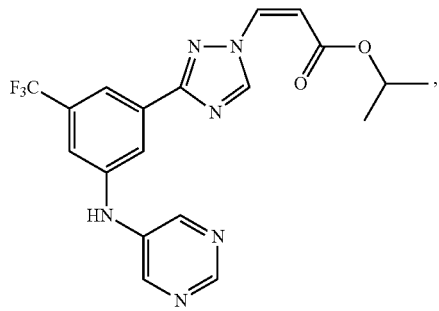
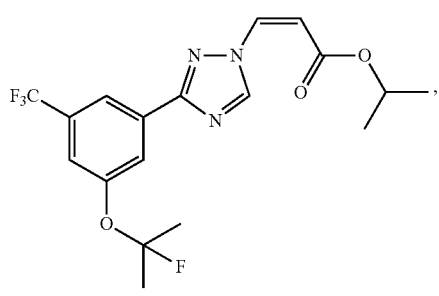
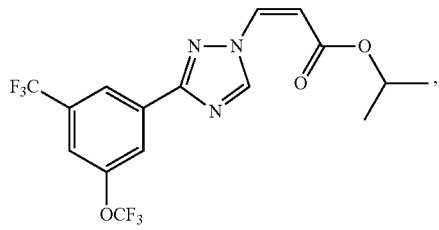
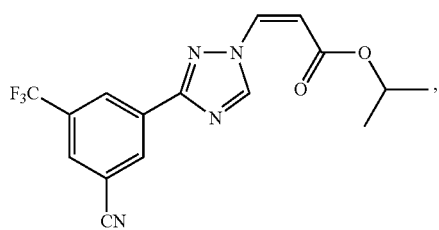
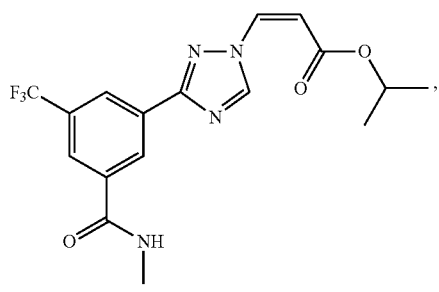
-continued
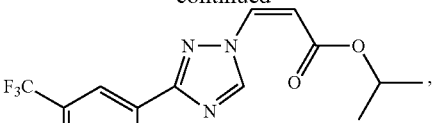
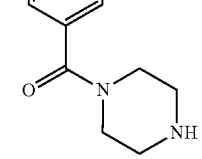
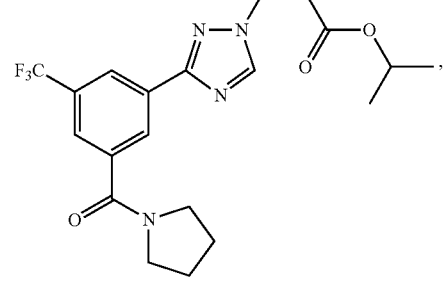
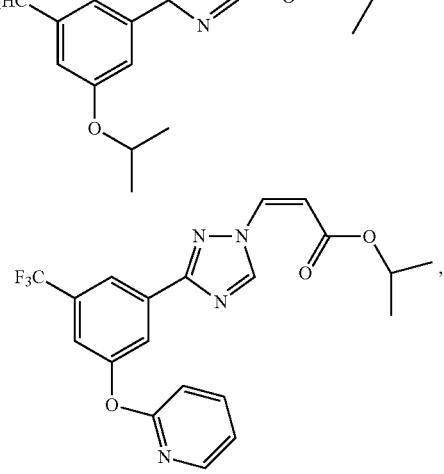
or a pharmaceutically acceptable salt thereof.
6. The compound according to claim 5, selected from the group consisting of:
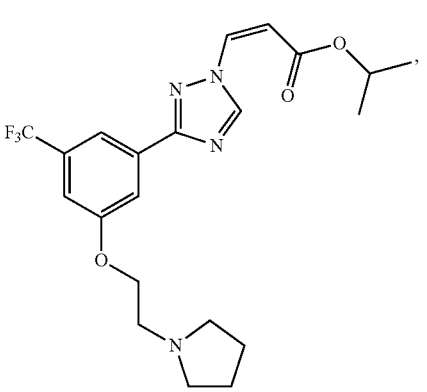 [SMILES: CC(C)OC(=O)/C=C\n1cnc(-c2cc(OCCN3CCCC3)cc(C(F)(F)F)c2)n1]
or a pharmaceutically acceptable salt thereof.

7. A compound selected from the group consisting of:
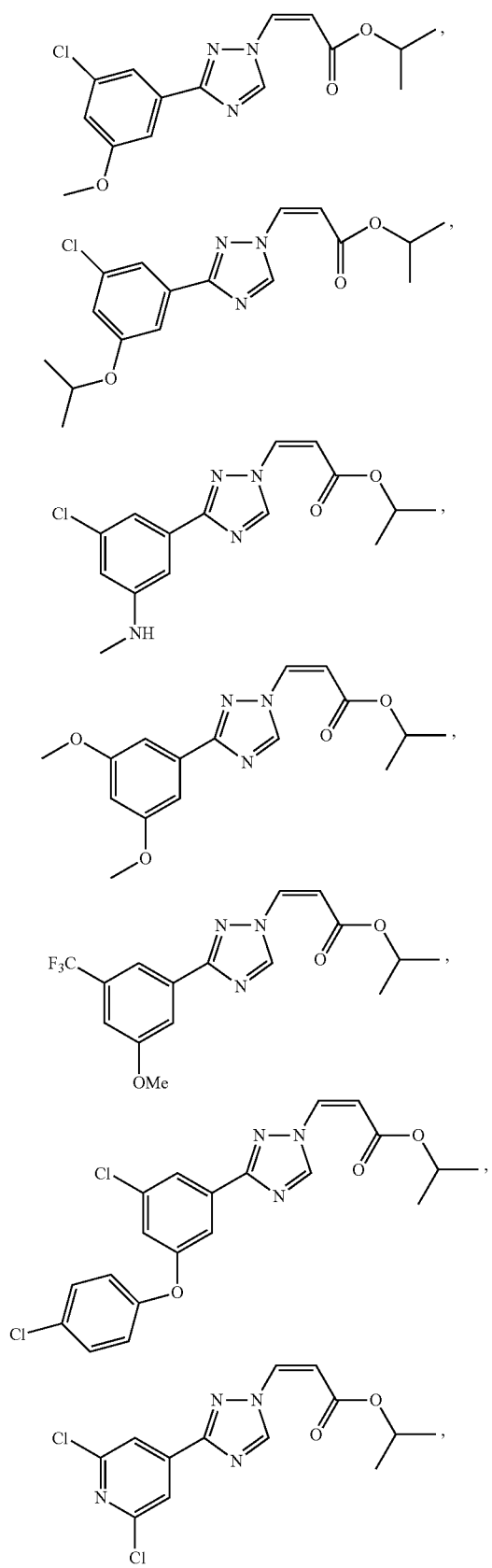
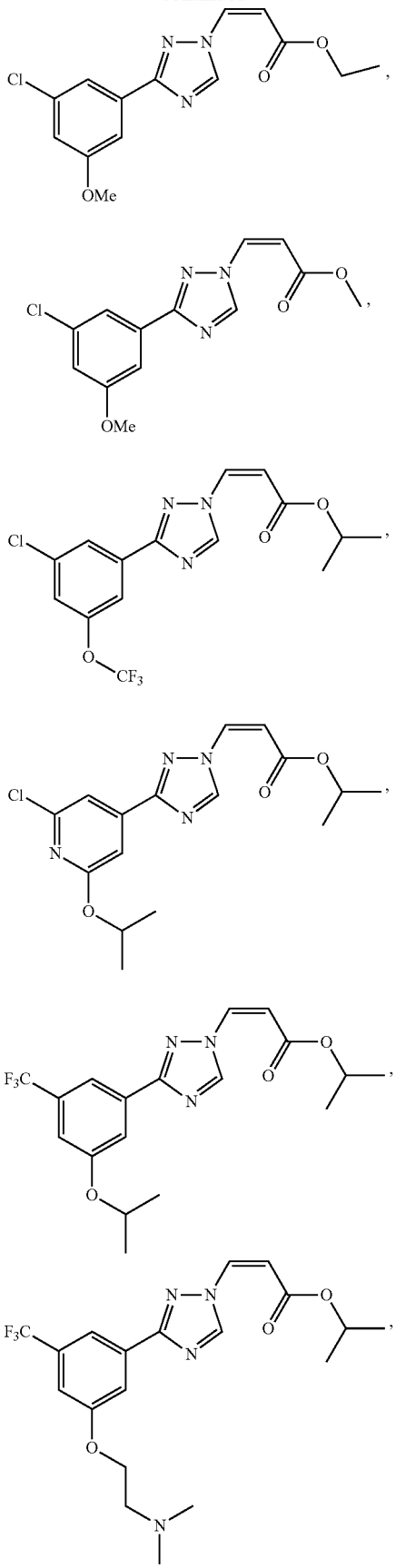

373
-continued
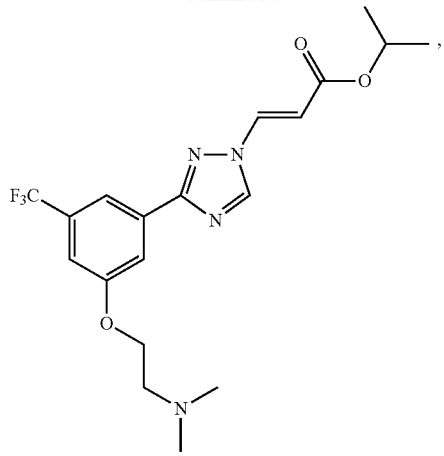
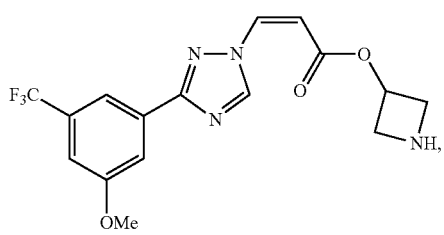
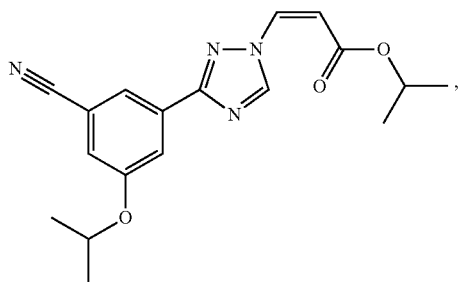
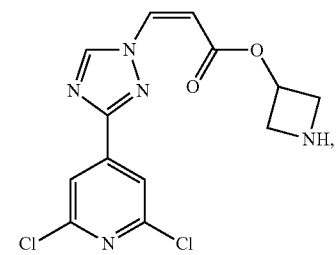
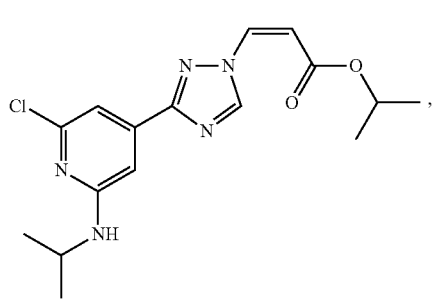
374
-continued
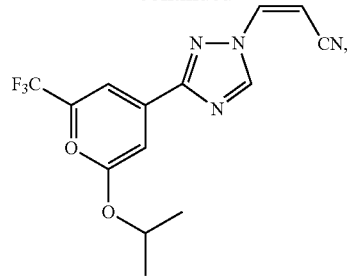
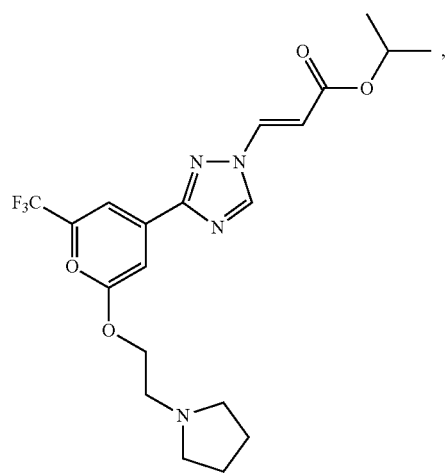
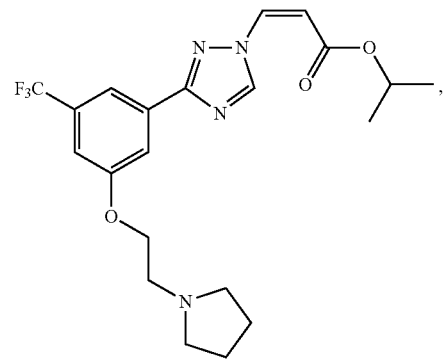
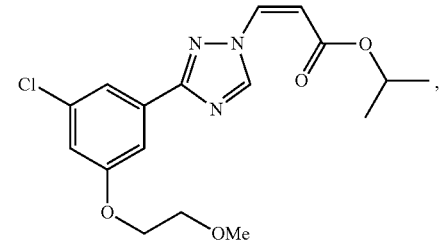
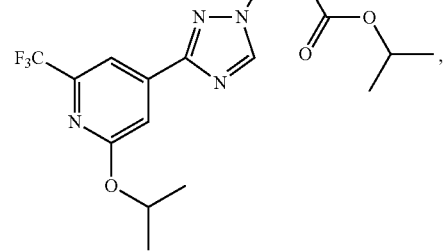

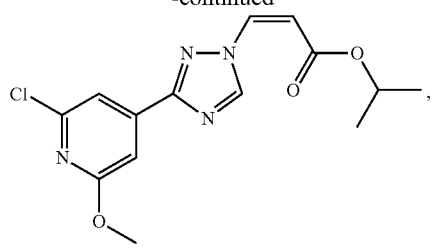
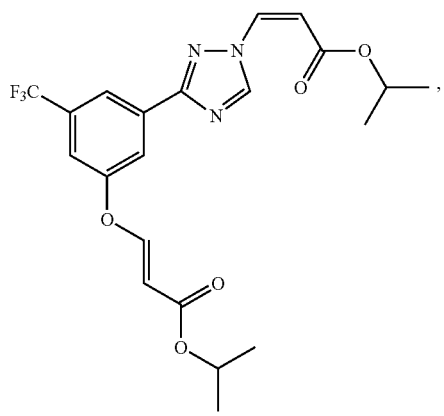
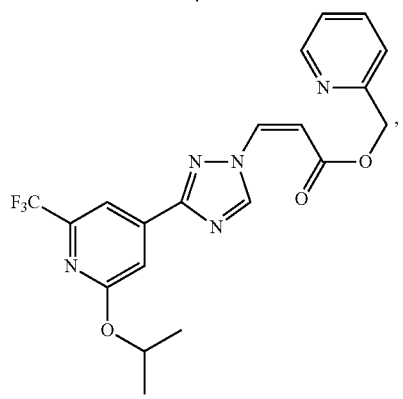
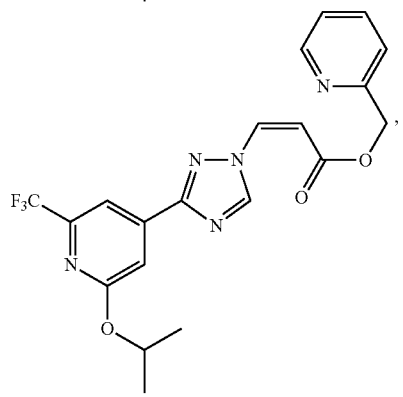
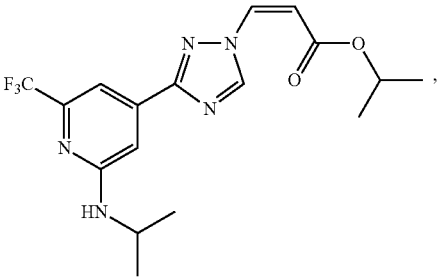
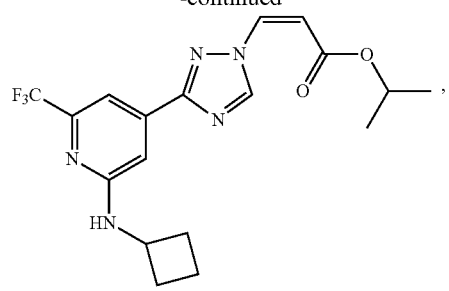
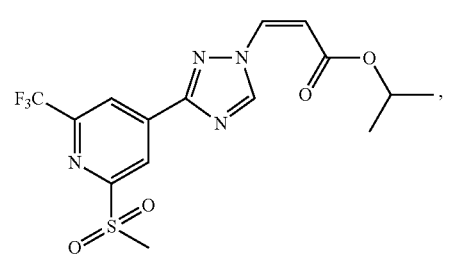
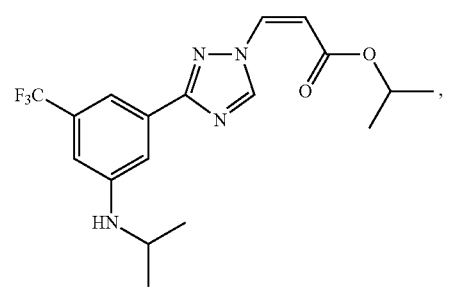
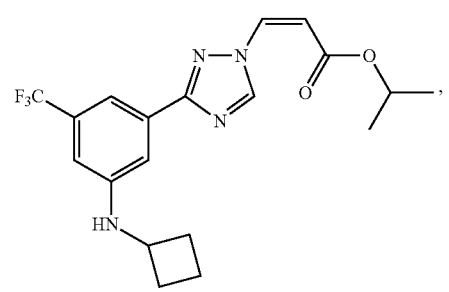
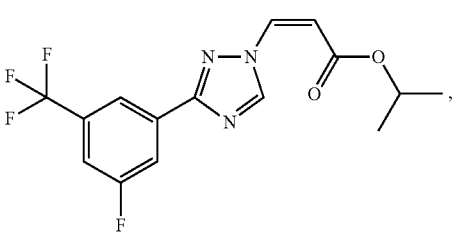
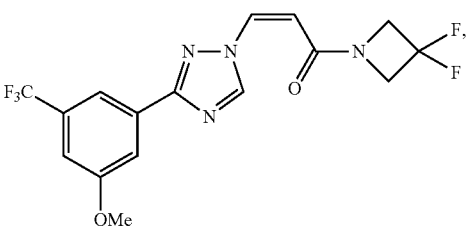

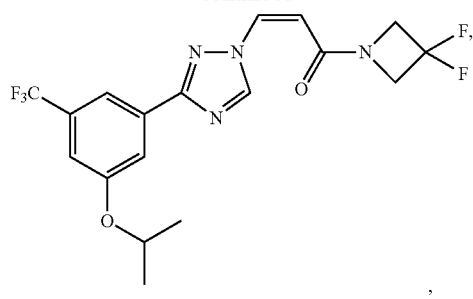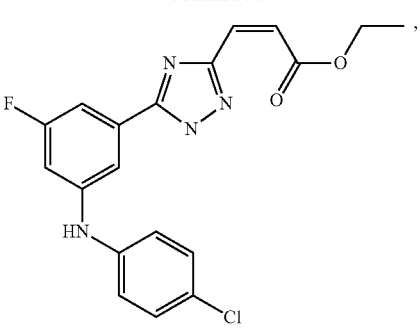

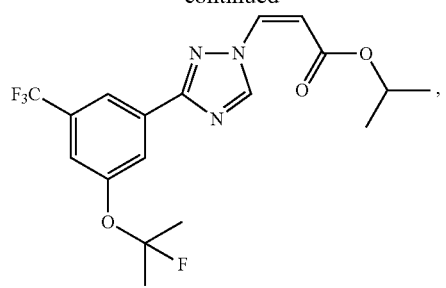
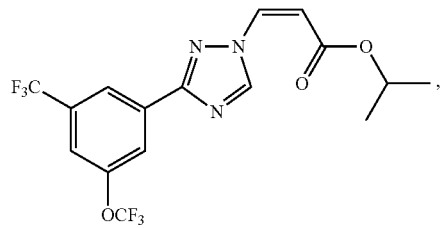
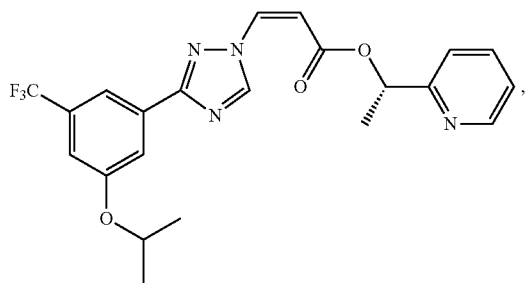
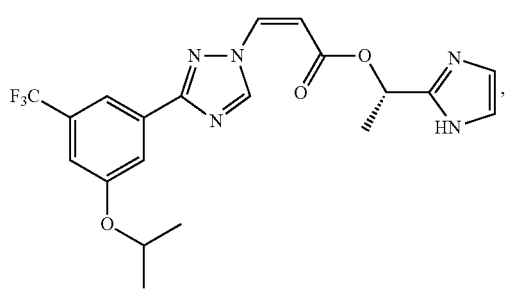
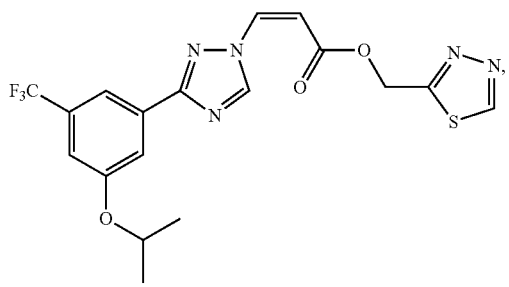
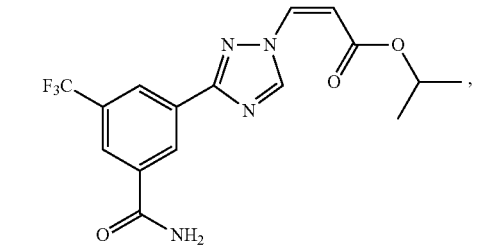
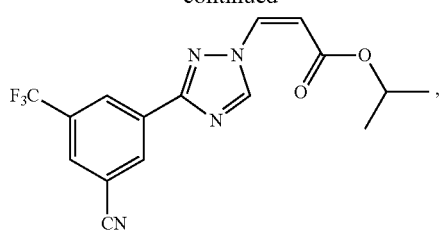
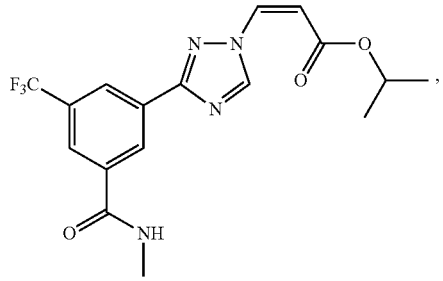
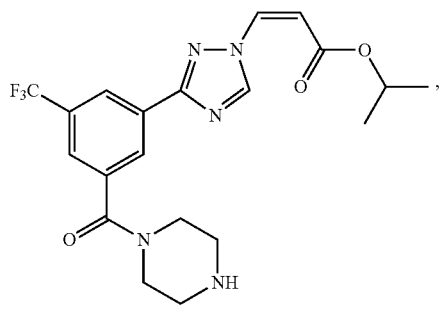
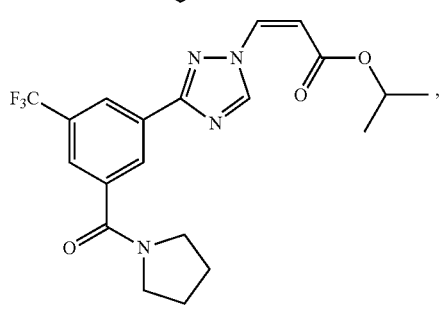
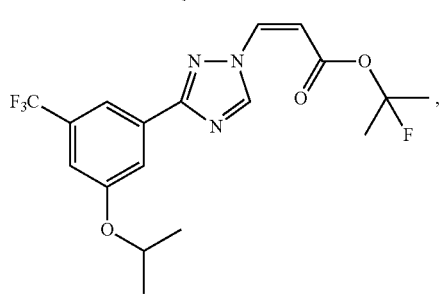
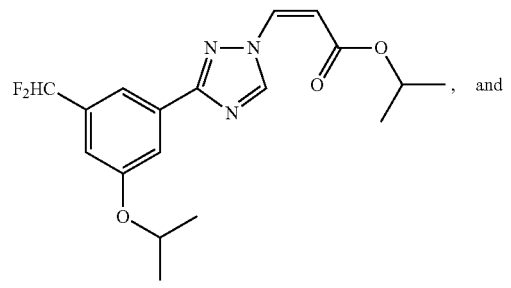

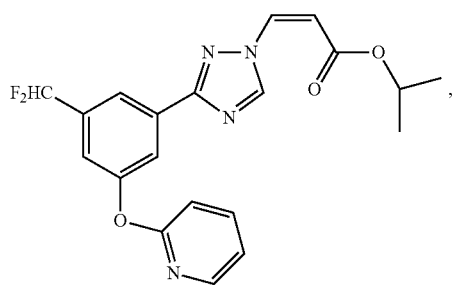
or a pharmaceutically acceptable salt thereof.
* * * * *

UNITED STATES PATENT AND TRADEMARK OFFICE
CERTIFICATE OF CORRECTION

PATENT NO. : 8,513,230 B2
APPLICATION NO. : 13/041377
DATED : August 20, 2013
INVENTOR(S) : Sharon Shacham et al.

Page 1 of 5

It is certified that error appears in the above-identified patent and that said Letters Patent is hereby corrected as shown below:

In the Claims:

In Column 361, Claim 1, line 58, delete "$R^{1}$" and insert -- $R^{1'}$ --.

In Column 362, Claim 2, line 38, after "$R^{3'}$ is" insert -- $L^{1}$-R, --.

In Column 364, Claim 5, beginning at line 60 and ending at line 67, delete

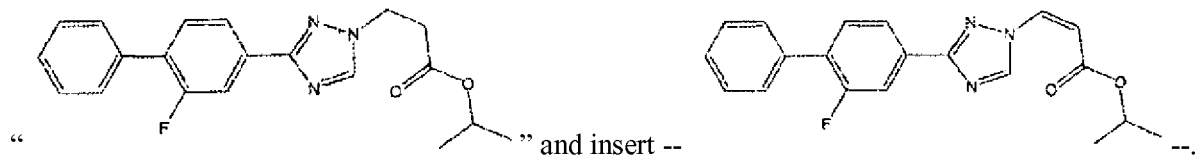

" and insert --

In Column 369, Claim 5, beginning at line 15 and ending at line 25, delete

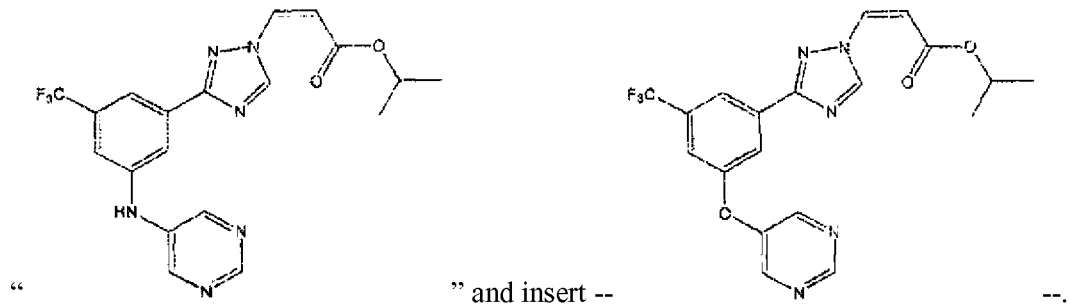

" and insert --                                     --.

Signed and Sealed this
Second Day of September, 2014

Michelle K. Lee
*Deputy Director of the United States Patent and Trademark Office*

In Column 370, Claim 6, line 52 to end of claim, should read
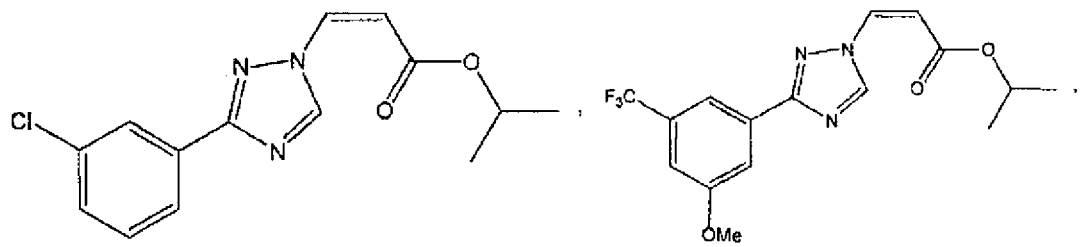
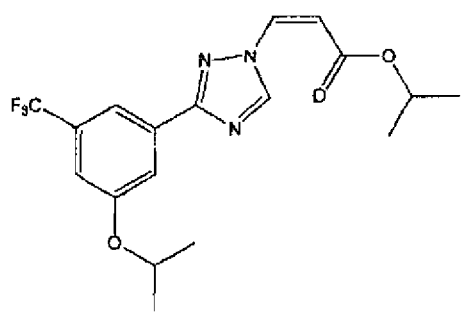
and
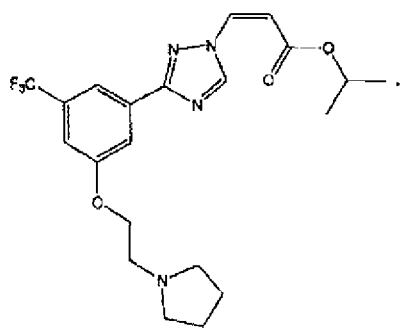
, or a pharmaceutically acceptable salt thereof.
In Column 374, Claim 7, beginning at line 1 and ending at line 13, delete
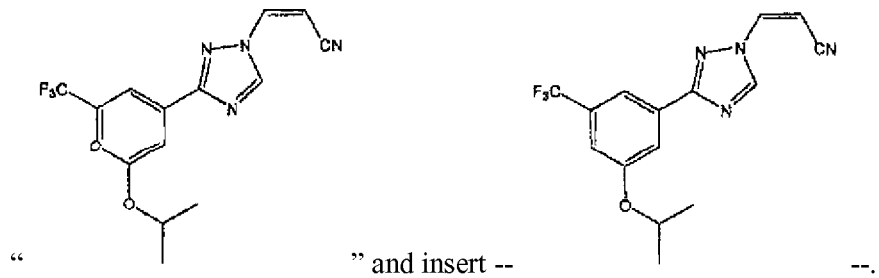
" and insert -- --.

CERTIFICATE OF CORRECTION (continued)
U.S. Pat. No. 8,513,230 B2

In Column 374, Claim 7, beginning at line 14 and ending at line 32, delete

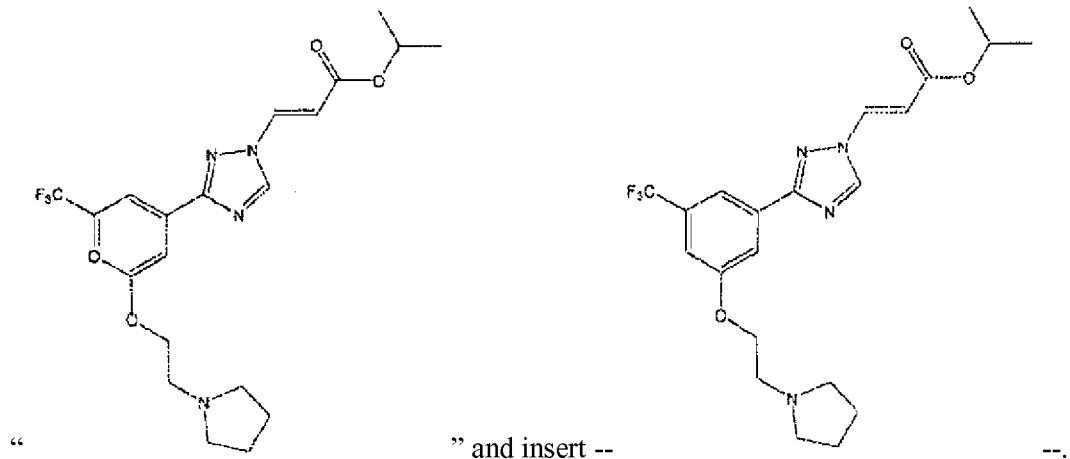

" and insert -- --.

In Column 375, Claim 7, beginning at line 40 and ending at line 55, delete

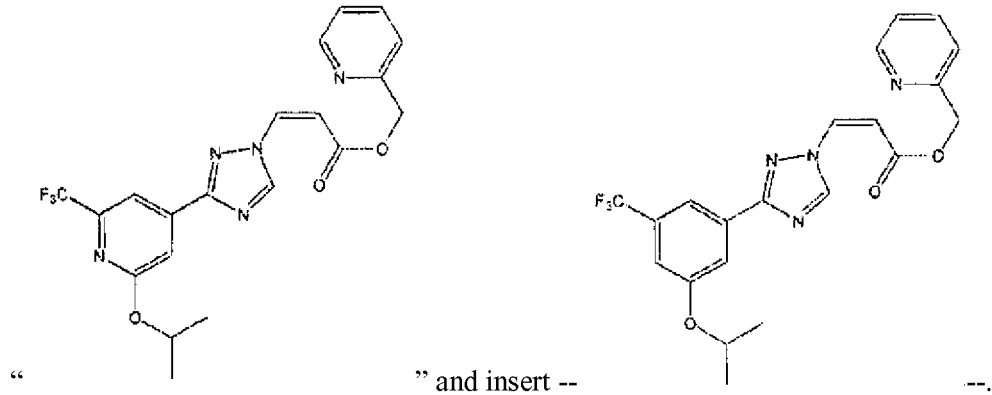

" and insert -- --.

In Column 376, Claim 7, beginning at line 14 and ending at line 24, delete

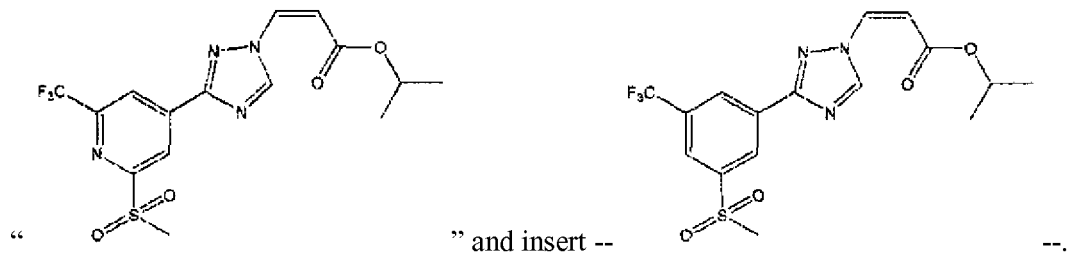

" and insert -- --.

In Column 377, Claim 7, beginning at line 48 and ending at line 57, delete

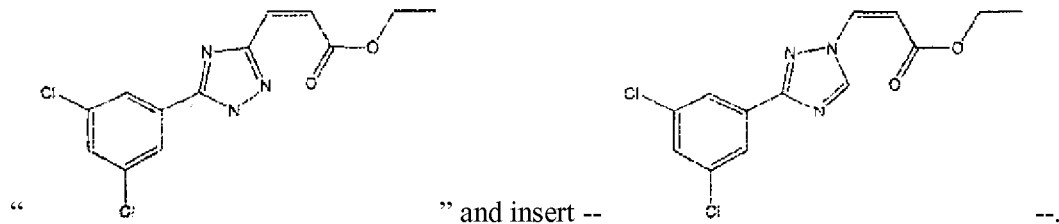

" and insert -- --.

CERTIFICATE OF CORRECTION (continued)
U.S. Pat. No. 8,513,230 B2

Page 4 of 5

In Column 377, Claim 7, beginning at line 58 and ending at line 68, delete

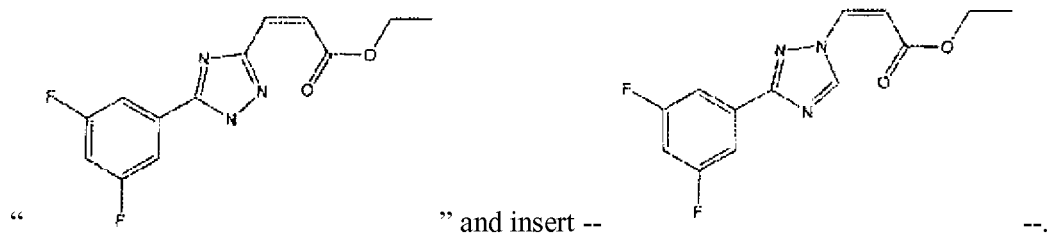

" and insert -- --.

In Column 378, Claim 7, beginning at line 1 and ending at line 15, delete

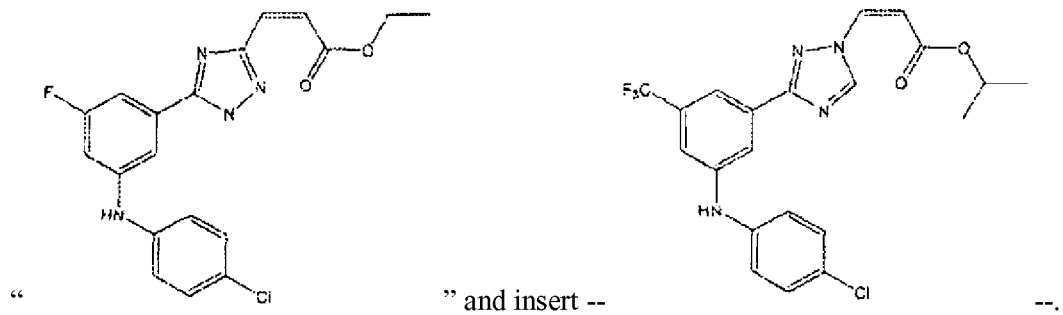

" and insert -- --.

In Column 378, Claim 7, beginning at line 58 and ending at line 68, delete

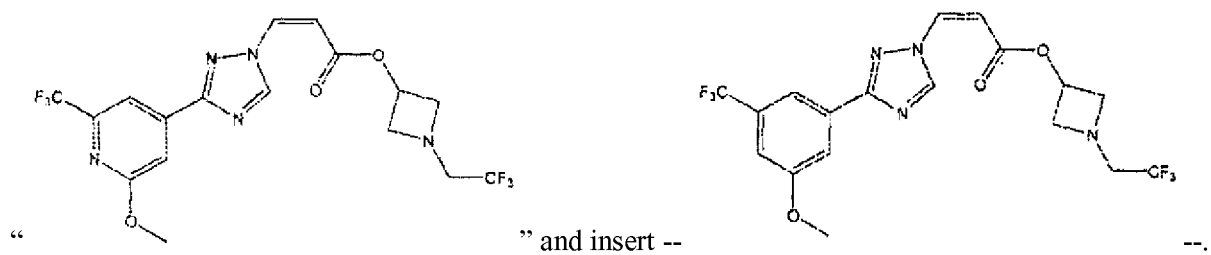

" and insert -- --.

In Column 379, Claim 7, beginning at line 35 and ending at line 46, delete

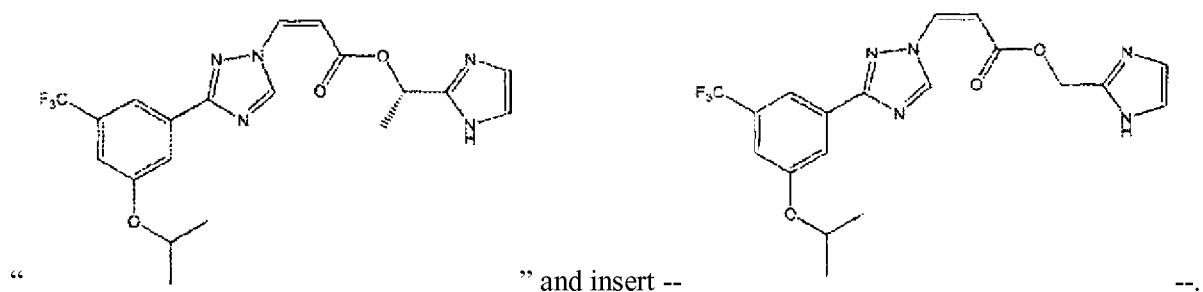

" and insert -- --.

CERTIFICATE OF CORRECTION (continued)
U.S. Pat. No. 8,513,230 B2

In Column 381, Claim 7, beginning at line 1 and ending at line 15, delete

" 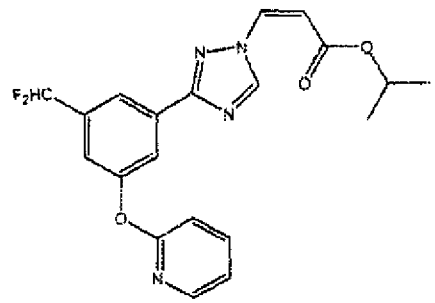 " and insert -- 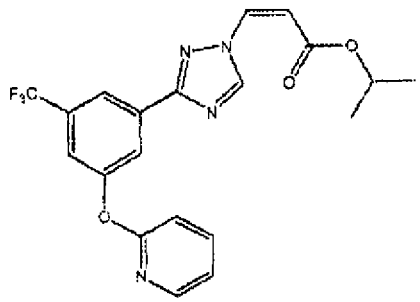 --.